US009604984B2

(12) United States Patent
Zak et al.

(10) Patent No.: US 9,604,984 B2
(45) Date of Patent: Mar. 28, 2017

(54) 5-CHLORO-2-DIFLUOROMETHOXYPHENYL PYRAZOLOPYRIMIDINE COMPOUNDS, COMPOSITIONS AND METHODS OF USE THEREOF

(71) Applicant: Genentech, Inc., South San Francisco, CA (US)

(72) Inventors: Mark Edward Zak, San Mateo, CA (US); Nicholas Charles Ray, Harlow (GB); Simon Charles Goodacre, Harlow (GB); Rohan Mendonca, Pleasanton, CA (US); Terry Kellar, Burlingame, CA (US); Yun-Xing Cheng, Beijing (CN); Wei Li, Beijing (CN); Po-Wei Yuen, Ann Arbor, MI (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/139,164

(22) Filed: Apr. 26, 2016

(65) Prior Publication Data

US 2016/0237086 A1 Aug. 18, 2016

Related U.S. Application Data

(63) Continuation of application No. 14/720,323, filed on May 22, 2015, now Pat. No. 9,346,815.

(60) Provisional application No. 62/002,547, filed on May 23, 2014, provisional application No. 62/101,234, filed on Jan. 8, 2015, provisional application No. 62/130,098, filed on Mar. 9, 2015.

(30) Foreign Application Priority Data

Apr. 22, 2015 (WO) ................ PCT/CN2015/077176

(51) Int. Cl.

| | |
|---|---|
| *C07D 487/04* | (2006.01) |
| *A61K 31/519* | (2006.01) |
| *A61P 11/06* | (2006.01) |
| *C07D 471/04* | (2006.01) |
| *C07D 519/00* | (2006.01) |

(52) U.S. Cl.

CPC .......... *C07D 471/04* (2013.01); *A61K 31/519* (2013.01); *C07D 487/04* (2013.01); *C07D 519/00* (2013.01)

(58) Field of Classification Search

CPC ............................ C07D 487/04; A61K 31/519
USPC ........................................ 544/281; 514/259.3
See application file for complete search history.

(56) References Cited

U.S. PATENT DOCUMENTS

| | | | |
|---|---|---|---|
| 4,603,139 | A | 7/1986 | King |
| 4,847,256 | A | 7/1989 | Tseng et al. |
| 5,705,625 | A | 1/1998 | Civin et al. |
| 6,136,595 | A | 10/2000 | Ihle et al. |
| 6,210,654 | B1 | 4/2001 | Ihle et al. |
| 6,235,741 | B1 | 5/2001 | Bilodeau et al. |
| 7,070,972 | B1 | 7/2006 | O'Shea et al. |
| 7,161,003 | B1 | 1/2007 | Guzi et al. |
| 7,306,631 | B2 | 12/2007 | Glenn et al. |
| 8,999,998 | B2 | 4/2015 | Gibbons et al. |
| 9,255,110 | B2 | 2/2016 | Arora et al. |
| 2004/0097485 | A1 | 5/2004 | Burkitt et al. |
| 2005/0245546 | A1 | 11/2005 | Cristalli |
| 2005/0288502 | A1 | 12/2005 | Andersen et al. |
| 2006/0089362 | A1 | 4/2006 | Seno et al. |
| 2006/0142612 | A1 | 6/2006 | Anthony et al. |
| 2006/0153852 | A1 | 7/2006 | Coleman et al. |
| 2007/0082902 | A1 | 4/2007 | Paruch et al. |
| 2007/0270408 | A1 | 11/2007 | Andersen et al. |
| 2007/0281951 | A1 | 12/2007 | Guzi et al. |
| 2009/0054410 | A1 | 2/2009 | Griffioen et al. |
| 2009/0163545 | A1 | 6/2009 | Goldfarb |
| 2012/0015962 | A1 | 1/2012 | Arora et al. |

FOREIGN PATENT DOCUMENTS

| | | | |
|---|---|---|---|
| EP | 1 040 817 | A1 | 10/2000 |
| EP | 1 221 444 | A1 | 7/2002 |
| WO | 98/14451 | A1 | 4/1998 |
| WO | 01/42246 | A2 | 6/2001 |
| WO | 01/42246 | A3 | 6/2001 |
| WO | 2004/037823 | A1 | 5/2004 |
| WO | 2004/052315 | A2 | 6/2004 |
| WO | 2004/089415 | A2 | 10/2004 |
| WO | 2004/089415 | A3 | 10/2004 |
| WO | 2004/089416 | A2 | 10/2004 |
| WO | 2004/089416 | A3 | 10/2004 |
| WO | 2004/089471 | A2 | 10/2004 |
| WO | 2004/089471 | A3 | 10/2004 |
| WO | 2005/002552 | A2 | 1/2005 |
| WO | 2005/002552 | A3 | 1/2005 |
| WO | 2005/058837 | A1 | 6/2005 |
| WO | 2005/110477 | A2 | 11/2005 |
| WO | 2005/110477 | A3 | 11/2005 |
| WO | 2006/052913 | | 5/2006 |
| WO | 2007/013673 | A1 | 2/2007 |
| WO | 2007/039797 | A1 | 4/2007 |

(Continued)

OTHER PUBLICATIONS

U.S. Appl. No. 61/224,196, filed Jul. 9, 2009, Andrews, S. et al.
(Applicant's Response in U.S. Appl. No. 13/099,179 dated Nov. 13, 2012).
(File Registry RN 1252132-61-8 Entered STN: Nov. 9, 2010).
(File Registry RN 1316553-50-0 Entered STN: Aug. 12, 2011).
(File Registry RN 1319894-27-3, Entered STN: Aug. 19, 2011).
(International Preliminary Report on Patentability for International Patent Application No. PCT/US2009/063014), (May 3, 2011).
(Non-Final Rejection of U.S. Appl. No. 13/099,179 dated Mar. 22, 2012).
(Notice of Allowance in U.S. Appl. No. 13/099,179 dated Feb. 5, 2013).
(Notice of Allowance in U.S. Appl. No. 13/099,179 dated Jun. 14, 2013).

(Continued)

*Primary Examiner* — Venkataraman Balasubramanian
(74) *Attorney, Agent, or Firm* — Tamara A. Kale

(57) ABSTRACT

Compounds of Formula (00A) and methods of use as Janus kinase inhibitors are described herein.

21 Claims, 1 Drawing Sheet

(56) References Cited

FOREIGN PATENT DOCUMENTS

| | | |
|---|---|---|
| WO | 2007/048066 A2 | 4/2007 |
| WO | 2007/048066 A3 | 4/2007 |
| WO | 2007/065664 A2 | 6/2007 |
| WO | 2007/065664 A3 | 6/2007 |
| WO | 2007/108750 A1 | 9/2007 |
| WO | 2008/004698 A2 | 1/2008 |
| WO | 2008/004698 A3 | 1/2008 |
| WO | 2008/008539 A2 | 1/2008 |
| WO | 2008/008539 A3 | 1/2008 |
| WO | 2008/052734 A1 | 5/2008 |
| WO | 2008/063671 A2 | 5/2008 |
| WO | 2008/063671 A3 | 5/2008 |
| WO | 2009/017954 A1 | 2/2009 |
| WO | 2009/047359 A1 | 4/2009 |
| WO | 2009/073153 A2 | 6/2009 |
| WO | 2009/073153 A3 | 6/2009 |
| WO | 2009/091374 A2 | 7/2009 |
| WO | 2009/091374 A3 | 7/2009 |
| WO | 2010/001184 A1 | 1/2010 |
| WO | 2010/019762 A1 | 2/2010 |
| WO | 2010/051549 A1 | 5/2010 |
| WO | 2010/063487 A1 | 6/2010 |
| WO | 2010/089292 A1 | 8/2010 |
| WO | 2010/094647 A1 | 8/2010 |
| WO | 2011/003065 A2 | 1/2011 |
| WO | 2011/003065 A3 | 1/2011 |
| WO | 2011/006074 A1 | 1/2011 |
| WO | 2011/048082 A1 | 4/2011 |
| WO | 2011/113802 A2 | 9/2011 |
| WO | 2011/134831 A1 | 11/2011 |
| WO | 2012/007375 A1 | 1/2012 |
| WO | 2012/075393 A2 | 6/2012 |
| WO | 2012/075393 A3 | 6/2012 |
| WO | 2012/129258 A1 | 9/2012 |
| WO | 2015/073267 A1 | 5/2015 |
| WO | 2016/144844 A1 | 9/2016 |
| WO | 2016/144846 A1 | 9/2016 |
| WO | 2016/144847 A1 | 9/2016 |
| WO | 2016/144848 A1 | 9/2016 |

OTHER PUBLICATIONS (Notice of Allowance in U.S. Appl. No. 13/099,179 dated Sep. 18, 2013).

(PCT ISR and the Written Opinion for PCT/EP2011/070313).

(PCT ISR and Written Opinion for PCT/EP2011/053826).

(Rule 114(2) Communication from EPO dated Nov. 14, 2013).

Anderson et al., "Chemistry of the adenosine monophosphate site of rabbit muscle glycogen phosphorylase. I. Hydrophobic nature and affinity labeling of the allosteric site" Biochem 12(10):1895-900 (1973).

Barraclough et al., "Inotropic 'A' ring substituted sulmazole and isomazole analogues" J Med Chem 33(8):2231-9 (1990).

Baslund et al., "Targeting interleukin-15 in patients with rheumatoid arthritis: a proof-of-concept study" Arthritis Rheum 52(9):2686-92 (Sep. 2005).

Borrmann et al., "Structure-activity relationships of adenine and deazaadenine derivatives as ligands for adenine receptors, a new purinergic receptor family" J Med Chem 52:5974-89 (2009).

Cartwright et al., "Imidazopyridine and pyrimidinopyridine systems from perfluorinated pyridine derivatives" Tetrahedron 63(30) (Jun. 13, 2007).

CAS Registry Database, 1089652-06-1, (downloaded Jun. 30, 2010, Publication Date Feb. 8, 2010).

CAS Registry Database, 1147525-55-0, (downloaded Jun. 30, 2010, Publication Date Feb. 8, 2010).

CAS Registry Database, 1214490-10-4, (downloaded Jun. 30, 2010, Publication Date Feb. 16, 2010).

CAS Registry Database, 1223183-38-7, (downloaded Jun. 30, 2010, Publication Date May 7, 2010).

Cecil Textbook of Medicine Bennet, J.C. and Plum F., 20th edition, vol. 1:1004-1010 (1996).

Changelian et al., "Prevention of organ allograft rejection by a specific Janus kinase 3 inhibitor" Science 302:875-8 (Oct. 2003).

Cohen et al., "The development and therapeutic potential of protein kinase inhibitors" Curr Opin Chem Biol 3:459-465 (1999).

Cornejo et al., "JAK3: A two-faced player in hematological disorders" Int J Biochem Cell Biol 41(12):2376-2379 (2009).

Dameshek, "Editorial: Some Speculations on the Myeloproliferative Syndromes" Blood 6(4):372-375 (1951).

Database Registry [Online] Chemical Abstracts Service, Columbus, Ohio, US; Jun. 13, 2008 (Jun. 13, 2008), 'Not yet assigned', Database accession No. 1027914-11-9 the whole document.

Database Registry [Online] Chemical Abstracts Service, Columbus, Ohio, US; Aug. 29, 2004 (Aug. 29, 2004), '9H-Purine, 9-(4-cholorphenyl)-8-(2-fluorophenyl)-6-(1 -pyrrolidinyl)-', Database accession No. 734532-63-9 the whole document.

Database Registry [Online] Chemical Abstracts Service, Columbus, Ohio, US; Jun. 8, 2008 (Jun. 8, 2008), 'Not yet assigned', Database accession No. 1026421-43-1 the whole document.

Database Registry [Online] Chemical Abstracts Service, Columbus, Ohio, US; Jun. 10, 2008 (Jun. 10, 2008), 'Not yet assigned', Database accession No. 1026925-65-4 the whole document.

Database Registry [Online] Chemical Abstracts Service, Columbus, Ohio, US; Nov. 10, 2004 (Nov. 10, 2004), '-Azabicyclo[3.1. 0]hexan-6-amine, 3-[9-(4-chlorophenyl)-8-(2,3-dichloropheny 1)-9H-purin-6-yl]-N,N-dimethyl-, (1.alpha.-5.alpha.,6.beta.)-', Database accession No. 777853-55-1 the whole document.

Database Registry [Online] Chemical Abstracts Service, Columbus, Ohio, US; Apr. 4, 2003 (2003-84-84), '9H-Purin-6-amine, 8-(2,4-dichlorophenyl)-', Database accession No. 501657-71-2 the whole document.

Database Registry [Online] Chemical Abstracts Service, Columbus, Ohio, US; Jun. 10, 2008 (Jun. 10, 2008), 'Not yet assigned', Database accession No. 1027012-36-7 the whole document.

Database Registry [Online] Chemical Abstracts Service, Columbus, Ohio, US; Sep. 14, 2010 (Sep. 14, 2010), '1H-Imidazo[4,5-c]pyridin-4-amine, 2-(2-clorophenyl)-N-[3-methoxy-4-(3-methyl-1H-1,2,4-triazol-1-yl]phenyl]-1-(methylethyl=-', Database accession No. 1240783-28-1 the whole document.

Database Registry [Online] Chemical Abstracts Service, Columbus, Ohio, US; Sep. 8, 2004 (Sep. 8, 2004), '3-Azabicyclo[3.1.0]hexan-6-amine, 3-[9-(4-chlorophenyl)-8-(2,3-dichloropheny 1)-9H-purin-6-yl]-N,N-dimethyl-, (1. alpha.- 5. alpha. , 6. beta. ) -, Database accession No. 741249-27-4 the whole document.

Database Registry [Online] Chemical Abstracts Service, Columbus, Ohio, US; Jul. 12, 2010 (Jul. 12, 2010), '9H-Purine, 8-(2-chlorophenyl)-6-(4-methyl-1-piperazin yl)-9-[(tetrahydro-2H-piran-4-yl)methyl]-' Database accession No. 1231299-64-1 the whole document.

Dermer et al., Bio/Technol 12:320 (1994).

EP Office Action dated Aug. 13, 2013 for EP Application No. 10 794 815.0.

Firmbach-Kraft et al., "tyk2, prototype of a novel class of non-receptor tyrosine kinase genes" Oncogene 5:1329-36 (1990).

Freshney et al. Culture of Animal Cells, A Manual of Basic Technique New York:Alan R. Liss, Inc., (1983).

Gausterer et al., "In Vivo Target Validation: Methodology and Case Studies on the Janus Kinase Tyk2" Anti-Inflammatory & Anti-Allergy Agents in Medicinal Chemistry (Cited in Office Action U.S. Appl. No. 13/099,179), 6:29-45 (2007).

Gavrin et al., "Synthesis of Pyrazolo [1,5-a] Pyrimidinone Regioisomers" J Org Chem (Cited in Office Action U.S. Appl. No. 13/099,179), 72(3):1043-1046 (2007).

Geldenhuys et al., "Virtual screening to identify novel antagonists for the G protein-coupled NK3 receptor" J Med Chem 53:8080-8 (Nov. 2010).

Golub et al., "Molecular Classification of Cancer: Class Discovery and Class Prediction by Gene Expression Monitoring" Science 286:531-537 (1999).

Griffith et al., "Discovery of 1-]9-(4-chlorophenyl)-8-(2-chlorophenyl)-9H-purin-6-yl]-4-ethylaminopiperidine-4-carboxylic acid amide hydrochloride (CP-945, 598), a novel, potent, and selective cannabinoid type 1 receptor antagonist" J Med Chem 52(2):234-7 (Jan. 22, 2009).

(56) References Cited

OTHER PUBLICATIONS

Hasnik et al., "Cross-Coupling reactions of Halopurines with Aryl- and alkyltrifluoroborates; The Scope and Limitations in the Synthesis of Modified Purines" Synthesis 9:1309-17 (Mar. 25, 2009).
International Search Report on Patentability for International Patent Application No. PCT/EP2015/061350.
IUPAC Ed—MacNaught Alan D et al. Compendium of Chemical Terminology: IUPAC Recommendations; ]IUPAC Chemical Data Series], [ISBN: 978-0-86542-684-9] "cycloalkyl groups, [retrieved on Apr. 20, 2012; http://goldbook.iupac.org/about.html/]" Oxford [U.A.]:Blackwell Science, Oxford [U.A.].
IUPAC Ed—MacNaught Alan D et al. Compendium of Chemical Terminology: IUPAC Recommendations; [IUPAC Chemical Data Series], [ISBN: 978-0-86542-684-9]"alkyl groups, [retrieved on Apr. 20, 2012; http://goldbook.iupac.org/about.html/]"Blackwell Science, Oxford [U.A.].
Jacob, "Resolution of (+/−)-5-Bromonornicitine. Synthesis of (R)- and (S)-Nornicotine of High Enantiomeric Purity", J Org Chem 47:4165-67 (1982).
Kisseleva et al., "Signaling through the JAK/STAT pathway, recent advances and future challenges" Gene 285:1-24 (Feb. 2002).
Krueger et al., "A human interleukin-12/23 monoclonal antibody for the treatment of psoriasis" New Engl J Med 356(6):580-92 (Feb. 2007).
Levy et al., "Stats: transcriptional control and biological impact" Nat Rev Mol Cell Biol 3(9):651-62 (2002).
Lim et al., "Discovery of 5-amino-N-(1H-pyrazolo[1,5-a]pyrimidine-3-carboxamide inhibitors of IRAK4" ACS Med Chem Lett 6:683-688 (2015).
Mannon et al., "Anti-interleukin-12 antibody for active Crohn's disease" New Engl J Med 351(20):2069-79 (Nov. 2004).
McCloskey et al., "New insights into the design of inhibitors of human S-adenosylmethionine decarboxylase: studies of adenine C8 substitution in structural analogues of S-adenosylmethionine" J Med Chem 52(5):1388-407 (2009).
Medebielle et al., "Electrochemically induced SRNI substitution of fluorinated aryl halides. Application to the synthesis of fluorinated-aryl heterocycles" Electrochimica Acta 42(13):2049-55 (1997).
Meyer et al., "Molecular Pathways: Molecular Pathways: Molecular basis for sensitivity and resistance to JAK kinase inhibitors" Clin Cancer Res 20(8);2051-2059 (2014).
Morgan et al., "A Role for JAK2 Mutations in Myeloproliferative Diseases" Annu Rev Med 59:213-222 (2008).
O'Shea et al., "Cytokine Signaling in 2002: New Surprises in the Jak/Stat Pathway" Cell 109:S121-S131 (Apr. 2002).
Ragan et al., "Development of a practical and Efficient Synthesis of CP-945,598-02, a CBI Antagonist for the Treatment of Obesity" Organic Process Res Dev 13(2):186-197 (Dec. 22, 2008).
Reich et al., "Ustekinumab" Nat Rev Drug Discov 8(5):355-6 (May 2009).
Sahnoun et al., "A site selective C-H arylation of free-(NH2) adenines with aryl chlorides: application to teh synthesis of 6,8-disubstituted adenines" Org Biomol Chem 7(20):4271-8 (Aug. 14, 2009).
Sahnoun et al., "Microwave-assisted Pd(OH)2-catalyzed direct C-H arylation of free-(NH2) adenines with aryl halides" Tetrahedron Letters 49(51):7279-83 (Dec. 15, 2008).
Saltzmann et al., "Cloning and characterization of human Jak-2 kinase: high mRNA expression in immune cells and muscle tissue" Biochem Bioph Res Co 246:627-33 (May 1998).
Sasaki et al., "Syntheses of Fused Heterocycles via cycloaddition of Hetaryne Studies on Heteroaromaticity, Part XL VII" Bulletin of the Chemical Society of Japan 44(3) (Jan. 1, 1971).
Scheinecker et al., "Tocilizumab" Nat Rev Drug Discov 8(4):273-4 (Apr. 2009).
Schindler, "JAK-STAT signaling: from intereferons to cytokines" J Biol Chem 282(28):20059-63 (Jul. 2007).
STN Structure Search, Supplier Ambinter, download Jan. 24, 2014, p. 1.
Storr et al., "Pd(0)/Cu(I)-mediated direct arylation of 2'-deoxyadenosines: mechanistic role of Cu(I) and reactivity comparisons with related purine nuclosides" J Org Chem 74(16):5810-21 (2009).
Verstovsek, S., "Therapeutic potential of JAK2 inhibitors" Am Soc Hematol, The Education Program:636-642 (2009).
Watford et al., "Human tyk2 kinase deficiency: another primary immunodeficiency syndrome" Immunity 25:695-7 (Nov. 2006).
Wilks et al., "The JAK Kinases: Not just another kinase drug discovery target" Seminar in Cell & Developmental Biol 19(4):319-328 (Aug. 1, 2008).
Wilks et al., "Two novel protein-tyrosine kinases, each with a second phosphotransferase-related catalytic domain, define a new class o protein kinase" Mol Cell Biol 11:2057-2065 (1991).
Wilks, "Two putative protein-tyrosine kinases identified by application of the polymerase chain reaction" P Natl Acad Sci USA 86:1603-1607 (1989).
Yang et al., "Use of N-(thiofuran-2) pyrazolo [1, 5-a] pyrimidine-3-methanamide compound for preparing the antineoplastic medicine" (Abstract Patent/Publication: CN101537007A), (Oct. 12, 2011).
Young et al., "Purine derivatives re competitive inhibitors of human erythrocyte membrane phosphatidylinositol 4-kinase" J Med Chem 33(8):2073-80 (Aug. 1990).

(i)

(ii)

5-CHLORO-2-DIFLUOROMETHOXYPHENYL PYRAZOLOPYRIMIDINE COMPOUNDS, COMPOSITIONS AND METHODS OF USE THEREOF

CROSS-REFERENCE TO RELATED APPLICATIONS

This application is a continuation of U.S. application Ser. No. 14/720,323, filed May 22, 2015, which claims the benefit of: U.S. Provisional Application No. 62/002,547, filed May 23, 2014; U.S. Provisional Application No. 62/101,234, filed Jan. 8, 2015; U.S. Provisional Application No. 62/130,098, filed Mar. 9, 2015; and International Application No. PCT/CN2015/077176, filed Apr. 22, 2015, each of which is incorporated herein by reference in its entirety.

FIELD OF THE INVENTION

The field of the invention pertains to compounds of Formula (00A), and subformulas thereof, which are inhibitors of a Janus kinase, such as JAK1, as well as compositions containing these compounds, and methods of use including, but not limited to, diagnosis or treatment of patients suffering from a condition responsive to the inhibition of a JAK kinase.

BACKGROUND OF INVENTION

Cytokine pathways mediate a broad range of biological functions, including many aspects of inflammation and immunity. Janus kinases (JAK), including JAK1, JAK2, JAK3 and TYK2, are cytoplasmic protein kinases that associate with type I and type II cytokine receptors and regulate cytokine signal transduction. Cytokine engagement with cognate receptors triggers activation of receptor associated JAKs and this leads to JAK-mediated tyrosine phosphorylation of signal transducer and activator of transcription (STAT) proteins and ultimately transcriptional activation of specific gene sets (Schindler et al., 2007, J. Biol. Chem. 282: 20059-63). JAK1, JAK2 and TYK2 exhibit broad patterns of gene expression, while JAK3 expression is limited to leukocytes. Cytokine receptors are typically functional as heterodimers, and as a result, more than one type of JAK kinase is usually associated with cytokine receptor complexes. The specific JAKs associated with different cytokine receptor complexes have been determined in many cases through genetic studies and corroborated by other experimental evidence. Exemplary therapeutic benefits of the inhibition of JAK enzymes are discussed, for example, in International Application No. WO 2013/014567.

JAK1 was initially identified in a screen for novel kinases (Wilks A. F., 1989, Proc. Natl. Acad. Sci. U.S.A. 86:1603-1607). Genetic and biochemical studies have shown that JAK1 is functionally and physically associated with the type I interferon (e.g., IFNalpha), type II interferon (e.g., IFNgamma), and IL-2 and IL-6 cytokine receptor complexes (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). JAK1 knockout mice die perinatally due to defects in LIF receptor signaling (Kisseleva et al., 2002, Gene 285:1-24; O'Shea et al., 2002, Cell, 109 (suppl.): S121-S131). Characterization of tissues derived from JAK1 knockout mice demonstrated critical roles for this kinase in the IFN, IL-10, IL-2/IL-4 and IL-6 pathways. A humanized monoclonal antibody targeting the IL-6 pathway (Tocilizumab) was approved by the European Commission for the treatment of moderate-to-severe rheumatoid arthritis (Scheinecker et al., 2009, Nat. Rev. Drug Discov. 8:273-274).

CD4 T cells play an important role in asthma pathogenesis through the production of TH2 cytokines within the lung, including IL-4, IL-9 and IL-13 (Cohn et al., 2004, Annu. Rev. Immunol. 22:789-815). IL-4 and IL-13 induce increased mucus production, recruitment of eosinophils to the lung, and increased production of IgE (Kasaian et al., 2008, Biochem. Pharmacol. 76(2): 147-155). IL-9 leads to mast cell activation, which exacerbates the asthma symptoms (Kearley et al., 2011, Am. J. Resp. Crit. Care Med., 183(7): 865-875). The IL-4Rα chain activates JAK1 and binds to either IL-4 or IL-13 when combined with the common gamma chain or the IL-13Rα1 chain respectively (Pernis et al., 2002, J. Clin. Invest. 109(10):1279-1283). The common gamma chain can also combine with IL-9Rα to bind to IL-9, and IL-9Rα activates JAK1 as well (Demoulin et al., 1996, Mol. Cell Biol. 16(9):4710-4716). While the common gamma chain activates JAK3, it has been shown that JAK1 is dominant over JAK3, and inhibition of JAK1 is sufficient to inactivate signaling through the common gamma chain despite JAK3 activity (Haan et al., 2011, Chem. Biol. 18(3):314-323). Inhibition of IL-4, IL-13 and IL-9 signaling by blocking the JAK/STAT signaling pathway can alleviate asthmatic symptoms in pre-clinical lung inflammation models (Mathew et al., 2001, J. Exp. Med. 193(9): 1087-1096; Kudlacz et. al., 2008, Eur. J. Pharmacol. 582(1-3): 154-161).

Biochemical and genetic studies have shown an association between JAK2 and single-chain (e.g., EPO), IL-3 and interferon gamma cytokine receptor families (Kisseleva et al., 2002, Gene 285:1-24; Levy et al., 2005, Nat. Rev. Mol. Cell Biol. 3:651-662; O'Shea et al., 2002, Cell, 109 (suppl.): S121-S131). Consistent with this, JAK2 knockout mice die of anemia (O'Shea et al., 2002, Cell, 109 (suppl.): S121-S131). Kinase activating mutations in JAK2 (e.g., JAK2 V617F) are associated with myeloproliferative disorders in humans.

JAK3 associates exclusively with the gamma common cytokine receptor chain, which is present in the IL-2, IL-4, IL-7, IL-9, IL-15 and IL-21 cytokine receptor complexes. JAK3 is critical for lymphoid cell development and proliferation and mutations in JAK3 result in severe combined immunodeficiency (SCID) (O'Shea et al., 2002, Cell, 109 (suppl.): S121-S131). Based on its role in regulating lymphocytes, JAK3 and JAK3-mediated pathways have been targeted for immunosuppressive indications (e.g., transplantation rejection and rheumatoid arthritis) (Baslund et al., 2005, Arthritis & Rheumatism 52:2686-2692; Changelian et al., 2003, Science 302: 875-878).

TYK2 associates with the type I interferon (e.g., IFNalpha), IL-6, IL-10, IL-12 and IL-23 cytokine receptor complexes (Kisseleva et al., 2002, Gene 285:1-24; Watford, W. T. & O'Shea, J. J., 2006, Immunity 25:695-697). Consistent with this, primary cells derived from a TYK2 deficient human are defective in type I interferon, IL-6, IL-10, IL-12 and IL-23 signaling. A fully human monoclonal antibody targeting the shared p40 subunit of the IL-12 and IL-23 cytokines (Ustekinumab) was recently approved by the European Commission for the treatment of moderate-to-severe plaque psoriasis (Krueger et al., 2007, N. Engl. J. Med. 356:580-92; Reich et al., 2009, Nat. Rev. Drug Discov. 8:355-356). In addition, an antibody targeting the IL-12 and IL-23 pathways underwent clinical trials for treating Crohn's Disease (Mannon et al., 2004, N. Engl. J. Med. 351:2069-79).

There exists a need in the art for additional or alternative treatments of conditions mediated by JAK kinases, such as those described above.

SUMMARY OF INVENTION

Provided herein are 5-chloro-2-difluoromethoxyphenyl pyrazolopyrimidine compounds that inhibit one or more JAK kinases.

Accordingly, one aspect of the invention includes a compound of Formula (00A):

(00A)

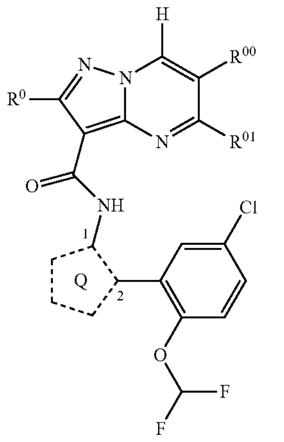

and stereoisomers and salts thereof, wherein: $R^{00}$ is H or $CH_3$; $R^{01}$ is H or $NH_2$; $R^0$ is H or $NH_2$; and Ring Q is either (i) or (ii):

(i)

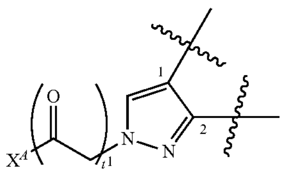

(ii)

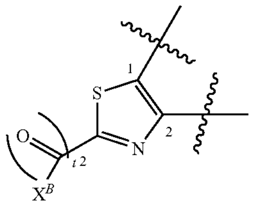

wherein: $t^1$ and $t^2$ are each independently 0 or 1; $X^A$ and $X^B$ are independently selected from the group consisting of H, $C_1$-$C_6$ alkyl, $C_2$-$C_4$ alkenyl, —$NR^aR^b$, $C_2$-$C_5$ alkynyl, 3-6-membered cycloalkyl, 6-10 membered aryl, 3-11 membered heterocycloalkyl, 5-6 membered heterocycloalkenyl, and 5-10 membered heteroaryl; wherein when either of $X^A$ and $X^B$ are independently $C_1$-$C_6$ alkyl, $C_2$-$C_4$ alkenyl, $C_2$-$C_5$ alkynyl, 3-6-membered cycloalkyl, 6-10 membered aryl, 3-11 membered heterocycloalkyl, 5-6 membered heterocycloalkenyl, and 5-10 membered heteroaryl, each of $X^A$ and $X^B$ is independently optionally substituted by $Y^1$, wherein $Y^1$ is selected from:

(a) $C_1$-$C_6$ alkyl optionally substituted by $T^1$, wherein $T^1$ is selected from the group consisting of OH, halo, CN, imino, 3-6 membered cycloalkyl, 3-11 membered heterocycloalkyl, 3-11 membered heterocycloalkenyl, 5-10 membered heteroaryl, —O—($C_1$-$C_6$ alkyl), C(O)OH, oxetan-3-ylmethyl, —C(O)O—($C_1$-$C_6$ alkyl), —S—($C_1$-$C_6$ alkyl), —$SO_2$—($C_1$-$C_6$ alkyl), —$NR^aR^b$, —N(+)$R^aR^bR^c$ wherein $R^c$ is methyl, —C(O)$NR^aR^b$, -(2-oxoindolin-1-yl), —OC(O)-3-6 membered cycloalkyl, and phenyl, wherein each alkyl, cycloalkyl, heterocycloalkyl, heterocycloalkenyl, heteroaryl, and phenyl of $T^1$ is optionally substituted by OH, —C(O)O—($C_1$-$C_6$ alkyl), $C_1$-$C_6$ alkyl, halo, CN, oxo, —($C_1$-$C_6$ alkyl)CON$R^aR^b$, —$NR^aR^b$, phenyl, or —O—($C_1$-$C_6$ alkyl) optionally substituted by OH;

(b) 3-11 membered heterocycloalkyl, —($C_1$-$C_6$ alkylene)-3-11 membered heterocycloalkyl, —C(O)-3-11 membered heterocycloalkyl, —($C_1$-$C_6$ alkylene)C(O)-3-11 membered heterocycloalkyl, or —OC(O)-4-6 membered heterocycloalkyl; wherein the heterocycloalkyl is optionally substituted by OH, halo, CN, $C_1$-$C_6$ alkyl, —($C_1$-$C_6$ alkylene)-$CF_3$, oxo, —C(O)—($C_1$-$C_6$ alkyl), —C(O)O—($C_1$-$C_6$ alkyl), —C(O)O—($C_1$-$C_6$ alkylene)-phenyl, —$SO_2$—($C_1$-$C_6$ alkyl), —C(O)$NR^aR^b$, —$NR^aR^b$, —($C_1$-$C_6$ alkylene)-phenyl, or —C(O)-4-6 membered heterocycloalkyl optionally substituted by —$NR^aR^b$;

(c) N(+)$(AA)_3$, wherein each AA is independently $C_1$-$C_6$ alkyl optionally substituted by phenyl;

(d) 3-6 membered cycloalkyl optionally substituted by OH, halo, $NR^aR^b$, or CN;

(e) CN, halo, or oxo;

(f) —C(O)—($C_1$-$C_6$ alkyl), —C(O)OH, —C(O)O—($C_1$-$C_6$ alkylene)-phenyl, —$SO_2$—($C_1$-$C_6$ alkyl), —C(O)$NR^aR^b$, or —C(O)-4-6 membered heterocycloalkyl optionally substituted by —($C_1$-$C_6$ alkyl) or —$NR^aR^b$, or —C(O)O—($C_1$-$C_6$ alkyl) optionally substituted by OH, $NR^aR^b$, or 3-11 membered heterocycloalkyl wherein said heterocycloalkyl is optionally substituted by $C_1$-$C_6$ alkyl;

(g) OH, —O-phenyl, or —O—($C_1$-$C_6$ alkyl), wherein the alkyl is optionally substituted by OH or —$NR^aR^b$;

(h) phenyl optionally substituted by OH, halo, $C_1$-$C_6$ alkyl, $CF_3$, or CN;

(i) 5-6 membered heteroaryl optionally substituted by OH, halo, $C_1$-$C_6$ alkyl, $CF_3$, CN, or 3-11 membered heterocycloalkyl optionally substituted by $C_1$-$C_6$ alkyl or 3-11 membered heterocycloalkyl;

(j) isoindolin-2-yl optionally substituted by halo;

(k) —$NR^aR^b$, and (l) —O—$CH_2$C(O)-3-11 membered heterocycloalkyl;

wherein $R^a$ and $R^b$ are independently selected from:

(a) H, (b) $C_1$-$C_6$ alkyl optionally substituted by OH, halo, CN, —C(O)OH, —C(O)O—($C_1$-$C_6$alkyl), —C(O)O-(3-11 membered heterocycloalkyl), —C(O)O—($C_1$-$C_6$ alkyl)-S—($C_1$-$C_6$ alkyl), —S—($C_1$-$C_6$ alkyl), naphthylenyl, —$NR^{az}R^{bz}$, —C(O)$NR^{az}R^{bz}$, oxo, —O—($C_1$-$C_6$ alkyl), 5-6 membered heteroaryl optionally substituted by $C_1$-$C_6$ alkyl or halo, or benzo[1,3]dioxol-2-yl, or 3-11 membered heterocycloalkenyl optionally substituted by oxo;

(c) —($C_1$-$C_6$ alkylene)-3-6 membered cycloalkyl wherein the alkylene is optionally substituted by OH, halo, or CN;

(d) —($C_1$-$C_6$ alkylene)-phenyl wherein alkylene is optionally substituted by halo and the phenyl is optionally substituted by OH, halo, $CF_3$, $C_1$-$C_6$ alkyl, —O—($C_1$-$C_6$ alkyl), —S—($C_1$-$C_6$ alkyl, or —O-phenyl;

(e) —($C_1$-$C_6$ alkylene)-4-6 membered heterocycloalkyl wherein the heterocycloalkyl is optionally substituted by halo, oxo, or $C_1$-$C_6$ alkyl;

(f) —($C_1$-$C_6$ alkylene)-O-phenyl wherein the phenyl is optionally substituted by halo, $C_1$-$C_6$ alkyl, or —O-phenyl;

(g) —($C_1$-$C_6$ alkyl)3-6 membered cycloalkyl optionally substituted by OH, halo, CN, or $C_1$-$C_6$ alkyl optionally substituted by OH or CN;

(h) $C_2$-$C_5$ alkenyl;

(i) 4-6 membered heterocycloalkyl optionally substituted by halo, (j) —($C_1$-$C_6$ alkylene)-3-6 membered cycloalkyl substituted by hydroxymethyl, (k) phenyl, (l) —C(O)($C_1$-$C_6$ alkyl), (m) —C(O)O($C_1$-$C_6$ alkyl), (n) —C(O)O(3-6 membered cycloalkyl), and (o) —C(O)-phenyl, wherein $R^{az}$ and $R^{bz}$ are each independently selected from (a) H, (b) $C_1$-$C_6$ alkyl optionally substituted by OH, halo, CN, —C(O)OH, —C(O)O—($C_1$-$C_6$alkyl), —C(O)O-(3-11 membered heterocycloalkyl), —C(O)O—($C_1$-$C_6$ alkyl)-S—($C_1$-$C_6$ alkyl), —S—($C_1$-$C_6$ alkyl), naphthylenyl, -oxo, —O—($C_1$-$C_6$ alkyl), 5-6 membered heteroaryl optionally substituted by $C_1$-$C_6$ alkyl or halo, or benzo[1,3]dioxol-2-yl, or 3-11 membered heterocycloalkenyl optionally substituted by oxo;

(c) —($C_1$-$C_6$ alkylene)-3-6 membered cycloalkyl wherein the alkylene is optionally substituted by OH, halo, or CN;

(d) —($C_1$-$C_6$ alkylene)-phenyl wherein alkylene is optionally substituted by halo and the phenyl is optionally substituted by OH, halo, $CF_3$, $C_1$-$C_6$ alkyl, —O—($C_1$-$C_6$ alkyl), —S—($C_1$-$C_6$ alkyl, or —O-phenyl;

(e) —($C_1$-$C_6$ alkylene)-4-6 membered heterocycloalkyl wherein the heterocycloalkyl is optionally substituted by halo, oxo, or $C_1$-$C_6$ alkyl;

(f) —($C_1$-$C_6$ alkylene)-O-phenyl wherein the phenyl is optionally substituted by halo, $C_1$-$C_6$ alkyl, or —O-phenyl;

(g) —($C_1$-$C_6$ alkyl)3-6 membered cycloalkyl optionally substituted by OH, halo, CN, or $C_1$-$C_6$ alkyl optionally substituted by OH or CN;

(h) $C_2$-$C_5$ alkenyl;

(i) 4-6 membered heterocycloalkyl optionally substituted by halo, (j) —($C_1$-$C_6$ alkylene)-3-6 membered cycloalkyl substituted by hydroxymethyl, (k) phenyl, (l) —C(O)($C_1$-$C_6$ alkyl), (m) —C(O)O($C_1$-$C_6$ alkyl), (n) —C(O)O(3-6 membered cycloalkyl), and (o) —C(O)-phenyl, with the following provisos: when $R^0$, $R^{00}$, and $R^{01}$ are each H and Ring Q is

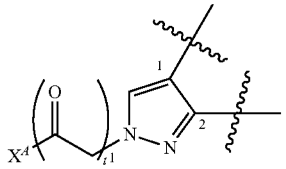

where $t^1$ is 0, then $X^A$ is not methyl, 2-methylpropan-2-ol, or tetrahydropyranyl; and, in some embodiments, when Ring Q is (i) and $t^1$ is 0, then $X^A$ cannot be —$NR^aR^b$.

Further, another aspect of the invention includes a compound of Formula (00A), further defined as a compound of Formula (0A):

(0A)

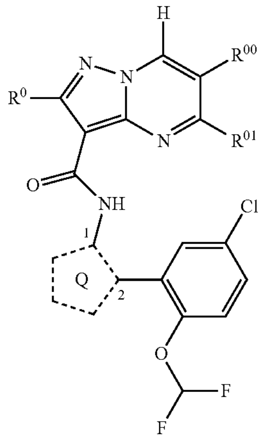

and stereoisomers and salts thereof, wherein: $R^{00}$ is H or $CH_3$; $R^{01}$ is H or $NH_2$; $R^0$ is H or $NH_2$; and Ring Q is either (i) or (ii):

(i)

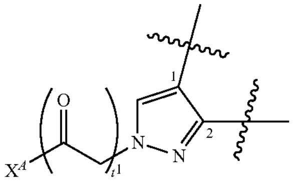

(ii)

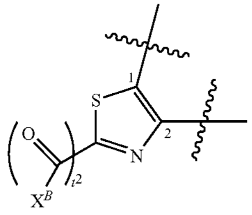

wherein: $t^1$ and $t^2$ are each independently 0 or 1; $X^A$ and $X^B$ are independently selected from the group consisting of H, $C_1$-$C_6$ alkyl, $C_2$-$C_4$ alkenyl, —$NR^aR^b$, $C_2$-$C_5$ alkynyl, 3-6-membered cycloalkyl, 6-10 membered aryl, 3-11 membered heterocycloalkyl, 5-6 membered heterocycloalkenyl, and 5-10 membered heteroaryl; wherein when either of $X^A$ and $X^B$ are independently $C_1$-$C_6$ alkyl, $C_2$-$C_5$ alkynyl, 3-6-membered cycloalkyl, 6-10 membered aryl, 3-11 membered heterocycloalkyl, 5-6 membered heterocycloalkenyl, and 5-10 membered heteroaryl, each of $X^A$ and $X^B$ are independently optionally substituted by $Y^1$, wherein $Y^1$ is selected from:

(a) $C_1$-$C_6$ alkyl optionally substituted by $T^1$, wherein $T^1$ is selected from the group consisting of OH, halo, CN, imino, 3-6 membered cycloalkyl, 3-11 membered heterocycloalkyl, 3-11 membered heterocycloalkenyl, 5-10 membered heteroaryl, —O—($C_1$-$C_6$ alkyl), C(O)OH, oxetan-3-ylmethyl, —C(O)O—($C_1$-$C_6$ alkyl), —S—($C_1$-$C_6$ alkyl), —$SO_2$—($C_1$-$C_6$ alkyl), —$NR^aR^b$, —N(+)$R^aR^bR^c$ wherein $R^c$ is methyl, —C(O)$NR^aR^b$, -(2-oxoindolin-1-yl), —OC(O)-3-6 membered cycloalkyl, and phenyl, wherein each alkyl, cycloalkyl, heterocycloalkyl, heterocycloalkenyl, heteroaryl, and phenyl of $T^1$ is optionally substituted by OH, —C(O)O—($C_1$-$C_6$ alkyl), $C_1$-$C_6$ alkyl, halo, CN, oxo, —$NR^aR^b$, phenyl, or —O—($C_1$-$C_6$ alkyl) optionally substituted by OH;

(b) 3-11 membered heterocycloalkyl, —($C_1$-$C_6$ alkylene)-3-11 membered heterocycloalkyl, —C(O)-3-11 membered heterocycloalkyl, —($C_1$-$C_6$ alkylene)C(O)-3-11 membered heterocycloalkyl, or —OC(O)-4-6 membered heterocycloalkyl; wherein the heterocycloalkyl is optionally substituted by OH, halo, CN, $C_1$-$C_6$ alkyl, —($C_1$-$C_6$ alkylene)-$CF_3$, oxo, —C(O)—($C_1$-$C_6$ alkyl), —C(O)O—($C_1$-$C_6$ alkyl), —C(O)O—($C_1$-$C_6$ alkylene)-phenyl, —$SO_2$—($C_1$-$C_6$ alkyl), —C(O)$NR^aR^b$, —$NR^aR^b$, —($C_1$-$C_6$ alkylene)-phenyl, or —C(O)-4-6 membered heterocycloalkyl optionally substituted by —$NR^aR^b$;

(c) N(+)$(AA)_3$, wherein each AA is independently $C_1$-$C_6$ alkyl optionally substituted by phenyl;

(d) 3-6 membered cycloalkyl optionally substituted by OH, halo, or CN;

(e) CN, halo, or oxo;

(f) —C(O)—($C_1$-$C_6$ alkyl), —C(O)OH, —C(O)O—($C_1$-$C_6$ alkylene)-phenyl, —$SO_2$—($C_1$-$C_6$ alkyl), —C(O)$NR^aR^b$, or —C(O)-4-6 membered heterocycloalkyl optionally substituted by —$NR^aR^b$, or —C(O)O—($C_1$-$C_6$ alkyl) optionally substituted by OH, $NR^aR^b$, or 3-11 membered heterocycloalkyl wherein said heterocycloalkyl is optionally substituted by C1-C6 alkyl;

(g) OH, —O-phenyl, or —O—($C_1$-$C_6$ alkyl), wherein the alkyl is optionally substituted by OH or —$NR^aR^b$;

(h) phenyl optionally substituted by OH, halo, $C_1$-$C_6$ alkyl, $CF_3$, or CN;

(i) 5-6 membered heteroaryl optionally substituted by OH, halo, $C_1$-$C_6$ alkyl, $CF_3$, or CN;

(j) isoindolin-2-yl optionally substituted by halo; and (k) —$NR^aR^b$, wherein $R^a$ and $R^b$ are independently selected from:

(a) H, (b) $C_1$-$C_6$ alkyl optionally substituted by OH, halo, CN, —C(O)OH, —C(O)O—($C_1$-$C_6$alkyl), —C(O)O-(3-11 membered heterocycloalkyl), —C(O)O—($C_1$-$C_6$ alkyl)-S—($C_1$-$C_6$ alkyl), —S—($C_1$-$C_6$ alkyl), naphthylenyl, —$NR^{az}R^{bz}$, —C(O)$NR^{az}R^{bz}$, oxo, —O—($C_1$-$C_6$ alkyl), 5-6 membered heteroaryl optionally substituted by $C_1$-$C_6$ alkyl or halo, or benzo[1,3]dioxol-2-yl, or 3-11 membered heterocycloalkenyl optionally substituted by oxo;

(c) —($C_1$-$C_6$ alkylene)-3-6 membered cycloalkyl wherein the alkylene is optionally substituted by OH, halo, or CN;

(d) —($C_1$-$C_6$ alkylene)-phenyl wherein alkylene is optionally substituted by halo and the phenyl is optionally substituted by OH, halo, $CF_3$, $C_1$-$C_6$ alkyl, —O—($C_1$-$C_6$ alkyl), —S—($C_1$-$C_6$ alkyl, or —O-phenyl;

(e) —($C_1$-$C_6$ alkylene)-4-6 membered heterocycloalkyl wherein the heterocycloalkyl is optionally substituted by halo, oxo, or $C_1$-$C_6$ alkyl;

(f) —($C_1$-$C_6$ alkylene)-O-phenyl wherein the phenyl is optionally substituted by halo, $C_1$-$C_6$ alkyl, or —O-phenyl;

(g) 3-6 membered cycloalkyl optionally substituted by OH, halo, CN, or $C_1$-$C_6$ alkyl optionally substituted by OH;

(h) $C_2$-$C_5$ alkenyl;

(i) 4-6 membered heterocycloalkyl optionally substituted by halo, (j) —($C_1$-$C_6$ alkylene)-3-6 membered cycloalkyl substituted by hydroxymethyl, (k) phenyl, (l) —C(O)($C_1$-$C_6$ alkyl), (m) —C(O)O($C_1$-$C_6$ alkyl), (n) —C(O)O(3-6 membered cycloalkyl), and (o) —C(O)-phenyl, wherein $R^{az}$ and $R^{bz}$ are each independently selected from (a) H, (b) $C_1$-$C_6$ alkyl optionally substituted by OH, halo, CN, —C(O)OH, —C(O)O—($C_1$-$C_6$alkyl), —C(O)O-(3-11 membered heterocycloalkyl), —C(O)O—($C_1$-$C_6$ alkyl)-S—($C_1$-$C_6$ alkyl), —S—($C_1$-$C_6$ alkyl), naphthylenyl, -oxo, —O—($C_1$-$C_6$ alkyl), 5-6 membered heteroaryl optionally substituted by $C_1$-$C_6$ alkyl or halo, or benzo[1,3]dioxol-2-yl, or 3-11 membered heterocycloalkenyl optionally substituted by oxo;

(c) —($C_1$-$C_6$ alkylene)-3-6 membered cycloalkyl wherein the alkylene is optionally substituted by OH, halo, or CN;

(d) —($C_1$-$C_6$ alkylene)-phenyl wherein alkylene is optionally substituted by halo and the phenyl is optionally substituted by OH, halo, $CF_3$, $C_1$-$C_6$ alkyl, —O—($C_1$-$C_6$ alkyl), —S—($C_1$-$C_6$ alkyl, or —O-phenyl;

(e) —($C_1$-$C_6$ alkylene)-4-6 membered heterocycloalkyl wherein the heterocycloalkyl is optionally substituted by halo, oxo, or $C_1$-$C_6$ alkyl;

(f) —($C_1$-$C_6$ alkylene)-O-phenyl wherein the phenyl is optionally substituted by halo, $C_1$-$C_6$ alkyl, or —O-phenyl;

(g) —($C_1$-$C_6$ alkyl)3-6 membered cycloalkyl optionally substituted by OH, halo, CN, or $C_1$-$C_6$ alkyl optionally substituted by OH or CN;

(h) $C_2$-$C_5$ alkenyl;

(i) 4-6 membered heterocycloalkyl optionally substituted by halo, (j) —($C_1$-$C_6$ alkylene)-3-6 membered cycloalkyl substituted by hydroxymethyl, (k) phenyl, (l) —C(O)($C_1$-$C_6$ alkyl), (m) —C(O)O($C_1$-$C_6$ alkyl), (n) —C(O)O(3-6 membered cycloalkyl), and (o) —C(O)-phenyl, with the following provisos: when $R^0$, $R^{00}$, and $R^{01}$ are each H and Ring Q is

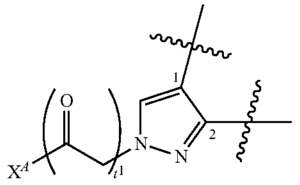

where $t^1$ is 0, then $X^A$ is not methyl, 2-methylpropan-2-ol, or tetrahydropyranyl; and, in some embodiments, when Ring Q is (i) and $t^1$ is 0, then $X^A$ cannot be —$NR^aR^b$.

Another aspect of the invention includes a compound of Formula (00A), further defined as a compound of Formula (A):

(A)

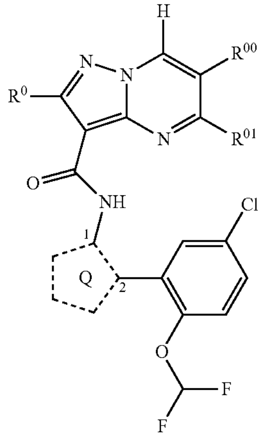

and stereoisomers and salts thereof, wherein: $R^{00}$ is H or $CH_3$; $R^{01}$ is H or $NH_2$; $R^0$ is H or $NH_2$; and Ring Q is either (i) or (ii):

(i)

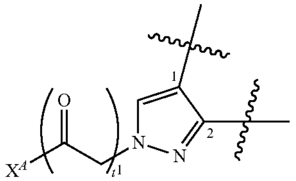

(ii)

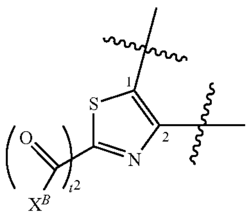

wherein: $t^1$ and $t^2$ are each independently 0 or 1; $X^A$ and $X^B$ are independently selected from the group consisting of H, $C_1$-$C_6$ alkyl, —$NR^aR^b$, $C_2$-$C_5$ alkynyl, 3-6-membered cycloalkyl, 6-10 membered aryl, 3-11 membered heterocycloalkyl, 5-6 membered heterocycloalkenyl, and 5-10 membered heteroaryl; wherein when either of $X^A$ and $X^B$ are independently $C_1$-$C_6$ alkyl, $C_2$-$C_5$ alkynyl, 3-6-membered cycloalkyl, 6-10 membered aryl, 3-11 membered heterocycloalkyl, 5-6 membered heterocycloalkenyl, and 5-10 membered heteroaryl, each of $X^A$ and $X^B$ are independently optionally substituted by $Y^1$, wherein $Y^1$ is selected from:

(a) $C_1$-$C_6$ alkyl optionally substituted by $T^1$, wherein $T^1$ is selected from the group consisting of OH, halo, CN, imino, 3-6 membered cycloalkyl, —O—($C_1$-$C_6$ alkyl), —C(O)O—($C_1$-$C_6$ alkyl), —$SO_2$—($C_1$-$C_6$ alkyl), —$NR^aR^b$, —N(+)$R^aR^bR^c$ wherein $R^c$ is methyl, —C(O)$NR^aR^b$, -(2-oxoindolin-1-yl), —OC(O)-3-6 membered cycloalkyl, and phenyl, wherein each alkyl, cycloalkyl, and phenyl of $T^1$ is optionally substituted by OH, $C_1$-$C_6$ alkyl, halo, CN, oxo, —$NR^aR^b$, phenyl, or —O—($C_1$-$C_6$ alkyl) optionally substituted by OH;

(b) 3-11 membered heterocycloalkyl, —($C_1$-$C_6$ alkylene)-3-11 membered heterocycloalkyl, —C(O)-3-11 membered heterocycloalkyl, —($C_1$-$C_6$ alkylene)C(O)-3-11 membered heterocycloalkyl, or —OC(O)-4-6 membered heterocycloalkyl; wherein the heterocycloalkyl is optionally substituted by OH, halo, CN, $C_1$-$C_6$ alkyl, —($C_1$-$C_6$ alkylene)-$CF_3$, oxo, —C(O)—($C_1$-$C_6$ alkyl), —C(O)O—($C_1$-$C_6$ alkyl), —C(O)O—($C_1$-$C_6$ alkylene)-phenyl, —$SO_2$—($C_1$-$C_6$ alkyl), —C(O)$NR^aR^b$, —$NR^aR^b$, —($C_1$-$C_6$ alkylene)-phenyl, or —C(O)-4-6 membered heterocycloalkyl optionally substituted by —$NR^aR^b$;

(c) N(+)$(AA)_3$, wherein each AA is independently $C_1$-$C_6$ alkyl optionally substituted by phenyl;

(d) 3-6 membered cycloalkyl optionally substituted by OH, halo, or CN;

(e) CN, halo, or oxo;

(f) —C(O)—($C_1$-$C_6$ alkyl), —C(O)O—($C_1$-$C_6$ alkyl) optionally substituted by OH, —C(O)OH, —C(O)O—($C_1$-$C_6$ alkylene)-phenyl, —$SO_2$—($C_1$-$C_6$ alkyl), —C(O)$NR^aR^b$, or —C(O)-4-6 membered heterocycloalkyl optionally substituted by —$NR^aR^b$, (g) OH, —O-phenyl, or —O—($C_1$-$C_6$ alkyl), wherein the alkyl is optionally substituted by OH or —$NR^aR^b$;

(h) phenyl optionally substituted by OH, halo, $C_1$-$C_6$ alkyl, $CF_3$, or CN;

(i) 5-6 membered heteroaryl optionally substituted by OH, halo, $C_1$-$C_6$ alkyl, $CF_3$, or CN;

(j) isoindolin-2-yl optionally substituted by halo; and (k) —$NR^aR^b$, wherein $R^a$ and $R^b$ are independently selected from:

(a) H, (b) $C_1$-$C_6$ alkyl optionally substituted by OH, halo, CN, naphthylenyl, —$NR^{az}R^{bz}$, —C(O)$NR^{az}R^{bz}$, oxo, —O—($C_1$-$C_6$ alkyl), phenyl, 5-6 membered heteroaryl optionally substituted by $C_1$-$C_6$ alkyl or halo, or benzo[1,3]dioxol-2-yl;

(c) —($C_1$-$C_6$ alkylene)-3-6 membered cycloalkyl wherein the alkylene is optionally substituted by OH, halo, or CN;

(d) —($C_1$-$C_6$ alkylene)-phenyl wherein alkylene is optionally substituted by halo and the phenyl is optionally substituted by OH, halo, $CF_3$, $C_1$-$C_6$ alkyl, —O—($C_1$-$C_6$ alkyl), or —O-phenyl;

(e) —($C_1$-$C_6$ alkylene)-4-6 membered heterocycloalkyl wherein the heterocycloalkyl is optionally substituted by halo or $C_1$-$C_6$ alkyl;

(f) —($C_1$-$C_6$ alkylene)-O-phenyl wherein the phenyl is optionally substituted by halo, $C_1$-$C_6$ alkyl, or —O-phenyl;

(g) 3-6 membered cycloalkyl optionally substituted by OH, halo, CN, or $C_1$-$C_6$ alkyl optionally substituted by OH;

(h) $C_2$-$C_5$ alkenyl;

(i) 4-6 membered heterocycloalkyl optionally substituted by halo, (j) —($C_1$-$C_6$ alkylene)-3-6 membered cycloalkyl substituted by hydroxymethyl, (k) phenyl, (l) —C(O)($C_1$-$C_6$ alkyl), (m) —C(O)O($C_1$-$C_6$ alkyl), (n) —C(O)O(3-6 membered cycloalkyl), and (o) —C(O)-phenyl, wherein $R^{az}$ and $R^{bz}$ are each independently selected from (a) H, (b) $C_1$-$C_6$ alkyl optionally substituted by OH, halo, CN, —C(O)OH, —C(O)O—($C_1$-$C_6$alkyl), —C(O)O-(3-11 membered heterocycloalkyl), —C(O)O—($C_1$-$C_6$ alkyl)-S—($C_1$-$C_6$ alkyl), —S—($C_1$-$C_6$ alkyl), naphthylenyl, -oxo, —O—($C_1$-$C_6$ alkyl), 5-6 membered heteroaryl optionally substituted by $C_1$-$C_6$ alkyl or halo, or benzo[1,3]dioxol-2-yl, or 3-11 membered heterocycloalkenyl optionally substituted by oxo;

(c) —($C_1$-$C_6$ alkylene)-3-6 membered cycloalkyl wherein the alkylene is optionally substituted by OH, halo, or CN;

(d) —($C_1$-$C_6$ alkylene)-phenyl wherein alkylene is optionally substituted by halo and the phenyl is optionally substituted by OH, halo, $CF_3$, $C_1$-$C_6$ alkyl, —O—($C_1$-$C_6$ alkyl), —S—($C_1$-$C_6$ alkyl, or —O-phenyl;

(e) —($C_1$-$C_6$ alkylene)-4-6 membered heterocycloalkyl wherein the heterocycloalkyl is optionally substituted by halo, oxo, or $C_1$-$C_6$ alkyl;

(f) —($C_1$-$C_6$ alkylene)-O-phenyl wherein the phenyl is optionally substituted by halo, $C_1$-$C_6$ alkyl, or —O-phenyl;

(g) —($C_1$-$C_6$ alkyl)3-6 membered cycloalkyl optionally substituted by OH, halo, CN, or $C_1$-$C_6$ alkyl optionally substituted by OH or CN;

(h) $C_2$-$C_5$ alkenyl;

(i) 4-6 membered heterocycloalkyl optionally substituted by halo, (j) —($C_1$-$C_6$ alkylene)-3-6 membered cycloalkyl substituted by hydroxymethyl, (k) phenyl, (l) —C(O)($C_1$-$C_6$ alkyl), (m) —C(O)O($C_1$-$C_6$ alkyl), (n) —C(O)O(3-6 membered cycloalkyl), and (o) —C(O)-phenyl, with the following provisos: when $R^0$, $R^{00}$, and $R^{01}$ are each H and Ring Q is

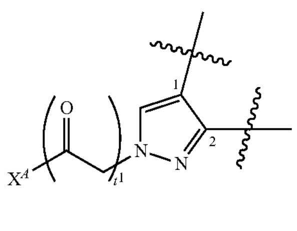

where $t^1$ is 0, then $X^A$ is not methyl, 2-methylpropan-2-ol, or tetrahydropyranyl; and, in some embodiments, when Ring Q is (i) and $t^1$ is 0, then $X^A$ cannot be —$NR^aR^b$.

Also provided are pharmaceutical compositions comprising a 5-chloro-2-difluoromethoxyphenyl pyrazolopyrimidine as described herein, such as a compound of Formula (00A) and a pharmaceutically acceptable carrier, dilient or excipient.

The present invention also provides, in some embodiments, use of a 5-chloro-2-difluoromethoxyphenyl pyrazolopyrimidine compound as described herein, such as a compound of Formula (00A), in therapy, such as in the treatment of an inflammatory disease. Also provided are uses of a 5-chloro-2-difluoromethoxyphenyl pyrazolopyrimidine compound as described herein, such as a compound of Formula (00A), for the preparation of a medicament for the treatment of an inflammatory disease. Also provided is a method of preventing, treating or lessening the severity of a disease or condition responsive to the inhibition of a Janus kinase activity in a patient, comprising administering to the patient a therapeutically effective amount of a 5-chloro-2-difluoromethoxyphenyl pyrazolopyrimidine compound as described herein, such as a compound of Formula (00A).

DESCRIPTION OF THE DRAWINGS

The foregoing aspects and many of the attendant advantages will become more readily appreciated as the same become better understood by reference to the following detailed description, when taken in conjunction with the accompanying drawings, where.

DETAILED DESCRIPTION OF THE INVENTION

Definitions

Figure 1:
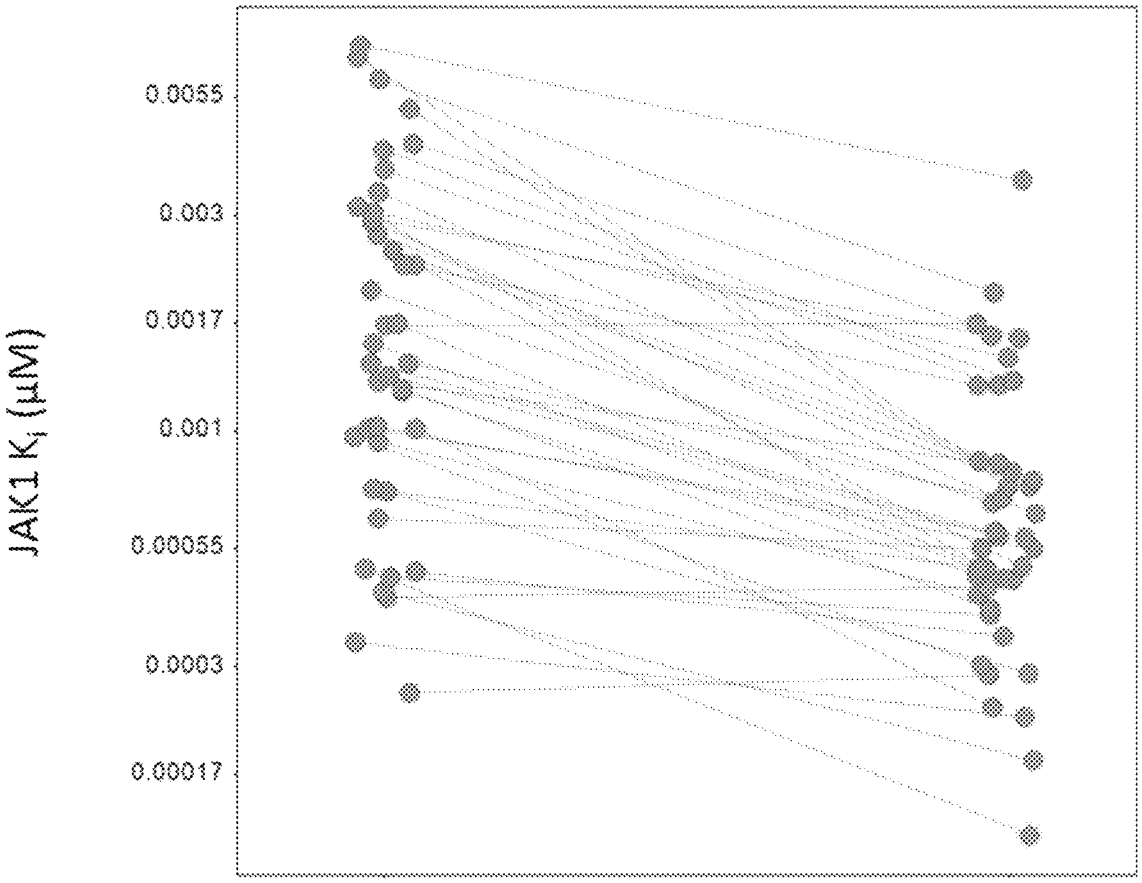
FIG. 1 depicts a matched pair analysis of certain compounds of the present invention containing either an OMe (i) or $OCHF_2$ (ii) group at the indicated position.
Figure 1:
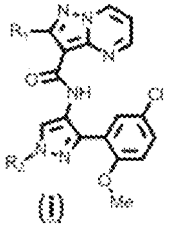
Figure 1:
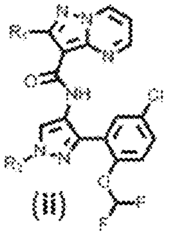

"Halogen" or "halo" refers to F, Cl, Br or I. Additionally, terms such as "haloalkyl," are meant to include monohaloalkyl and polyhaloalkyl.

The term "alkyl" refers to a saturated linear or branched-chain monovalent hydrocarbon radical, wherein the alkyl radical may be optionally substituted. In one example, the alkyl radical is one to eighteen carbon atoms ($C_1$-$C_{18}$). In other examples, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. $C_0$ alkyl refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH$(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)$ $CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)$ $CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)$ $CH_2CH_2CH_2CH_3$), 3-hexyl (—$CH(CH_2CH_3)$ $(CH_2CH_2CH_3)$), 2-methyl-2-pentyl (—$C(CH_3)_2$ $CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—C$(CH_3)_2CH(CH_3)_2$), 3,3-dimethyl-2-butyl (—$CH(CH_3)C$ $(CH_3)_3$, 1-heptyl and 1-octyl. In some embodiments, substituents for "optionally substituted alkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

The term "alkenyl" refers to linear or branched-chain monovalent hydrocarbon radical with at least one site of unsaturation, i.e., a carbon-carbon double bond, wherein the alkenyl radical may be optionally substituted, and includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl ($-CH{=}CH_2$), prop-1-enyl ($-CH{=}CHCH_3$), prop-2-enyl ($-CH_2CH{=}CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl. In some embodiments, substituents for "optionally substituted alkenyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

The term "alkynyl" refers to a linear or branched monovalent hydrocarbon radical with at least one site of unsaturation, i.e., a carbon-carbon, triple bond, wherein the alkynyl radical may be optionally substituted. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl ($-C{\equiv}CH$), prop-1-ynyl ($-C{\equiv}CCH_3$), prop-2-ynyl (propargyl, $-CH_2C{\equiv}CH$), but-1-ynyl, but-2-ynyl and but-3-ynyl. In some embodiments, substituents for "optionally substituted alkynyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

"Alkylene" refers to a saturated, branched or straight chain hydrocarbon group having two monovalent radical centers derived by the removal of two hydrogen atoms from the same or two different carbon atoms of a parent alkane. In one example, the divalent alkylene group is one to eighteen carbon atoms ($C_1$-$C_{18}$). In other examples, the divalent alkylene group is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$, or $C_1$-$C_3$. The group $C_0$ alkylene refers to a bond. Example alkylene groups include methylene ($-CH_2-$), 1,1-ethyl ($-CH(CH_3)-$), (1,2-ethyl ($-CH_2CH_2-$), 1,1-propyl ($-CH(CH_2CH_3)-$), 2,2-propyl ($-C(CH_3)_2-$), 1,2-propyl ($-CH(CH_3)CH_2-$), 1,3-propyl ($-CH_2CH_2CH_2-$), 1,1-dimethyleth-1,2-yl ($-C(CH_3)_2CH_2-$), 1,4-butyl ($-CH_2CH_2CH_2CH_2-$), and the like.

The term "heteroalkyl" refers to a straight or branched chain monovalent hydrocarbon radical, consisting of the stated number of carbon atoms, or, if none are stated, up to 18 carbon atoms, and from one to five heteroatoms selected from the group consisting of O, N, Si and S, and wherein the nitrogen and sulfur atoms can optionally be oxidized and the nitrogen heteroatom can optionally be quaternized. In some embodiments, the heteroatom is selected from O, N and S, wherein the nitrogen and sulfur atoms can optionally be oxidized and the nitrogen heteroatom can optionally be quaternized. The heteroatom(s) can be placed at any interior position of the heteroalkyl group, including the position at which the alkyl group is attached to the remainder of the molecule (e.g., $-O-CH_2-CH_3$). Examples include $-CH_2-CH_2-O-CH_3$, $-CH_2-CH_2-NH-CH_3$, $-CH_2-CH_2-N(CH_3)-CH_3$, $-CH_2-S-CH_2-CH_3$, $-S(O)-CH_3$, $-CH_2-CH_2-S(O)_2-CH_3$, $-Si(CH_3)_3$ and $-CH_2-CH{=}N-OCH_3$. Up to two heteroatoms can be consecutive, such as, for example, $-CH_2-NH-OCH_3$ and $-CH_2-O-Si(CH_3)_3$. Heteroalkyl groups can be optionally substituted. In some embodiments, substituents for "optionally substituted heteroalkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

"Amino" means primary (i.e., $-NH_2$), secondary (i.e., $-NRH$), tertiary (i.e., $-NRR$) and quaternary (i.e., $-N(+)RRR$) amines, that are optionally substituted, in which each R is the same or different and selected from alkyl, cycloalkyl, aryl, and heterocyclyl, wherein the alkyl, cycloalkyl, aryl and heterocyclyl groups are as defined herein. Particular secondary and tertiary amines are alkylamine, dialkylamine, arylamine, diarylamine, aralkylamine and diaralkylamine, wherein the alkyl and aryl portions can be optionally substituted. Particular secondary and tertiary amines are methylamine, ethylamine, propylamine, isopropylamine, phenylamine, benzylamine, dimethylamine, diethylamine, dipropylamine and diisopropylamine. In some embodiments, R groups of a quarternary amine are each independently optionally substituted alkyl groups.

"Aryl" refers to a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see, e.g., Lang's Handbook of Chemistry (Dean, J. A., ed.) $13^{th}$ ed. Table 7-2 [1985]). A particular aryl is phenyl. Substituted phenyl or substituted aryl means a phenyl group or aryl group substituted with one, two, three, four or five substituents, for example, 1-2, 1-3 or 1-4 substituents, such as chosen from groups specified herein (see "optionally substituted" definition), such as F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 2,4-difluorophenyl and the like; a mono- or di(hydroxy) phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl) phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methyl sulfonylamino))phenyl such as 3-(N-methyl sulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, 2-chloro-5-difluoromethoxy and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. In some embodiments, a substituent of an aryl, such as phenyl, comprises an amide. For example, an aryl (e.g., phenyl) substituent may be $-(CH_2)_{0-4}CONR'R''$, wherein R' and R'' each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R''; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R''; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R''; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R''; or R' and R'' can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R''.

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1] heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane. In some embodiments, substituents for "optionally substituted cycloalkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonyl amino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list. In some embodiments, a substituent of a cycloalkyl comprises an amide. For example, a cycloalkyl substituent may be $-(CH_2)_{0-4}CONR'R''$, wherein R' and R'' each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R''; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R''; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R''; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R''; or R' and R'' can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R''.

"Guanidine" or "guanidinyl" means the group —NH—C(NH)—NHR in which R is hydrogen, alkyl, cycloalkyl, aryl or heterocyclyl, wherein the alkyl, cycloalkyl, aryl and heterocyclyl groups are as defined herein. A particular guanidine is the group $—NH—C(NH)—NH_2$.

"Heterocyclic group", "heterocyclic", "heterocycle", "heterocyclyl", or "heterocyclo" are used interchangeably and refer to any mono-, bi-, tricyclic or spiro, saturated or unsaturated, aromatic (heteroaryl) or non-aromatic (e.g., heterocycloalkyl), ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-11 ring atoms ("members") and includes monocycles, bicycles, tricycles and spiro ring systems, wherein the ring atoms are carbon, where at least one atom in the ring or ring system is a heteroatom selected from nitrogen, sulfur or oxygen. In one example, heterocyclyl includes 1 to 4 heteroatoms. In one example, heterocyclyl includes 1 to 3 heteroatoms. In another example, heterocyclyl includes 3- to 7-membered monocycles having 1-2, 1-3 or 1-4 heteroatoms selected from nitrogen, sulfur or oxygen. In another example, heterocyclyl includes 4- to 6-membered monocycles having 1-2, 1-3 or 1-4 heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles, e.g., 5-6 membered heteroaryl. In another example, heterocyclyl includes 3-11 membered heterocycloyalkyls, such as 4-11 membered heterocycloalkyls. In some embodiments, a heterocycloalkyl includes at least one nitrogen. In one example, the heterocyclyl group includes 0 to 3 double bonds. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocycles containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocycles are benzoxazol-2-yl, benzthiazol-2-yl and benzimidazol-2-yl. Example 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocycle groups. Heterocycles may be optionally substituted. For example, substituents for "optionally substituted heterocycles" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonyl amino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list. In some embodiments, a substituent of a heterocyclic group, such as a heteroaryl or heterocycloalkyl, comprises an amide. For example, a heterocyclic (e.g., heteroaryl or heterocycloalkyl) substituent may be $-(CH_2)_{0-4}CONR'R''$, wherein R' and R'' each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R''; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R''; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R''; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R''; or R' and R'' can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R''.

"Heteroaryl" refers to any mono-, bi-, or tricyclic ring system where at least one ring is a 5- or 6-membered aromatic ring containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.) $13^{th}$ ed. Table 7-2 [1985]. Included in the definition are any bicyclic groups where any of the above heteroaryl rings are fused to an aryl ring, wherein the aryl ring or the heteroaryl ring is joined to the remainder of the molecule. In one embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b] pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl and indolyl. Heteroaryl groups can be optionally substituted. In some embodiments, substituents for "optionally substituted heteroaryls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list. In some embodiments, a substituent of a heteroaryl comprises an amide. For example, a heteroaryl substituent may be $—(CH_2)_{0-4}CONR'R''$, wherein R' and R'' each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R''; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R''; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R''; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R''; or R' and R'' can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R''.

In particular embodiments, a heterocyclyl group is attached at a carbon atom of the heterocyclyl group. By way of example, carbon bonded heterocyclyl groups include bonding arrangements at position 2, 3, 4, 5, or 6 of a pyridine ring, position 3, 4, 5, or 6 of a pyridazine ring, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group is N-attached. By way of example, nitrogen bonded heterocyclyl or heteroaryl groups include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "alkoxy" refers to a linear or branched monovalent radical represented by the formula —OR in which R is alkyl, as defined herein. Alkoxy groups include methoxy, ethoxy, propoxy, isopropoxy, mono-, di- and tri-fluoromethoxy and cyclopropoxy.

"Acyl" means a carbonyl containing substituent represented by the formula —C(O)—R in which R is hydrogen, alkyl, cycloalkyl, aryl or heterocyclyl, wherein the alkyl, cycloalkyl, aryl and heterocyclyl are as defined herein. Acyl groups include alkanoyl (e.g., acetyl), aroyl (e.g., benzoyl), and heteroaroyl (e.g., pyridinoyl).

"Optionally substituted" unless otherwise specified means that a group may be unsubstituted or substituted by one or more (e.g., 0, 1, 2, 3, 4, or 5 or more, or any range derivable therein) of the substituents listed for that group in which said substituents may be the same or different. In an embodiment, an optionally substituted group has 1 substituent. In another embodiment an optionally substituted group has 2 substituents. In another embodiment an optionally substituted group has 3 substituents. In another embodiment an optionally substituted group has 4 substituents. In another embodiment an optionally substituted group has 5 substituents.

Optional substituents for alkyl radicals, alone or as part of another substituent (e.g., alkoxy), as well as alkylenyl, alkenyl, alkynyl, heteroalkyl, heterocycloalkyl, and cycloalkyl, also each alone or as part of another substituent, can be a variety of groups, such as those described herein, as well as selected from the group consisting of halogen; oxo; CN; NO; $N_3$; —OR'; perfluoro-$C_1$-$C_4$ alkoxy; unsubstituted $C_3$-$C_7$ cycloalkyl; $C_3$-$C_7$ cycloalkyl substituted by halogen, OH, CN, unsubstituted $C_1$-$C_6$ alkyl, unsubstituted $C_1$-$C_6$ alkoxy, oxo or NR'R''; unsubstituted $C_6$-$C_{10}$ aryl (e.g., phenyl); $C_6$-$C_{10}$ aryl substituted by halogen, OH, CN, unsubstituted $C_1$-$C_6$ alkyl, unsubstituted $C_1$-$C_6$ alkoxy, or NR'R''; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R''; —NR'R''; —SR'; —SiR'R''R'''; —OC(O)R'; —C(O)R'; $—CO_2R'$; —CONR'R''; —OC(O)NR'R''; —NR''C(O)R'; —NR'''C(O)NR'R''; $—NR''C(O)_2R'$; $—S(O)_2$ R'; $—S(O)_2NR'R''$; $—NR'S(O)_2R''$; $—NR'''S(O)_2$ NR'R''; amidinyl; guanidinyl; $—(CH_2)_{1-4}—OR'$; $—(CH_2)_{1-4}$ —NR'R''; $—(CH_2)_{1-4}—SR'$; $—(CH_2)_{1-4}—SiR'R''R'''$; $—(CH_2)_{1-4}—OC(O)R'$; $—(CH_2)_{1-4}—C(O)R'$; $—(CH_2)_{1-4}—CO_2R'$; and $—(CH_2)_{1-4}CONR'R''$, or combinations thereof, in a number ranging from zero to (2m'+1), where m' is the total number of carbon atoms in such radical. R', R'' and R''' each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R''; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R''; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R''; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R". When R' and R" are attached to the same nitrogen atom, they can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R". For example, —NR'R" is meant to include 1-pyrrolidinyl and 4-morpholinyl.

Similarly, optional substituents for the aryl and heteroaryl groups are varied. In some embodiments, substituents for aryl and heteroaryl groups are selected from the group consisting of halogen; CN; NO; $N_3$; —OR'; perfluoro-$C_1$-$C_4$ alkoxy; unsubstituted $C_3$-$C_7$ cycloalkyl; $C_3$-$C_7$ cycloalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl (e.g., phenyl); $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R"; —NR'R"; —SR'; —SiR'R"R'"; —OC(O)R'; —C(O)R'; —$CO_2$R'; —CONR'R"; —OC(O)NR'R"; —NR"C(O)R'; —NR'"C(O)NR'R"; —NR"C(O)$_2$R'; —S(O)$_2$R'; —S(O)$_2$NR'R"; —NR'S(O)$_2$R"; —NR'"S(O)$_2$NR'R"; amidinyl; guanidinyl; —$(CH_2)_{1-4}$ —OR'; —$(CH_2)_{1-4}$—NR'R"; —$(CH_2)_{1-4}$—SR'; —$(CH_2)_{1-4}$ —SiR'R"R'"; —$(CH_2)_{1-4}$—OC(O)R'; —$(CH_2)_{1-4}$ —C(O)R'; —$(CH_2)_{1-4}$—$CO_2$R'; and —$(CH_2)_{1-4}$ CONR'R", or combinations thereof, in a number ranging from zero to (2m'+1), where m' is the total number of carbon atoms in such radical. R', R" and R'" each independently refer to groups including, for example, hydrogen; unsubstituted $C_1$-$C_6$ alkyl; $C_1$-$C_6$ alkyl substituted by halogen, OH, CN, unsubstituted $C_1$-$C_6$ alkyl, unsubstituted $C_1$-$C_6$ alkoxy, oxo or NR'R"; unsubstituted $C_1$-$C_6$ heteroalkyl; $C_1$-$C_6$ heteroalkyl substituted by halogen, OH, CN, unsubstituted $C_1$-$C_6$ alkyl, unsubstituted $C_1$-$C_6$ alkoxy, oxo or NR'R"; unsubstituted $C_6$-$C_{10}$ aryl; $C_6$-$C_{10}$ aryl substituted by halogen, OH, CN, unsubstituted $C_1$-$C_6$ alkyl, unsubstituted $C_1$-$C_6$ alkoxy, or NR'R"; unsubstituted 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S); and 3-11 membered heterocyclyl (e.g., 5-6 membered heteroaryl containing 1 to 4 heteroatoms selected from O, N and S or 4-11 membered heterocycloalkyl containing 1 to 4 heteroatoms selected from O, N and S) substituted by halogen, OH, CN, unsubstituted $C_1$-$C_6$ alkyl, unsubstituted $C_1$-$C_6$ alkoxy, oxo or NR'R". When R' and R" are attached to the same nitrogen atom, they can be combined with the nitrogen atom to form a 3-, 4-, 5-, 6-, or 7-membered ring wherein a ring atom is optionally substituted with N, O or S and wherein the ring is optionally substituted with halogen, OH, CN, unsubstituted $C_1$-$C_6$ alkyl, unsubstituted $C_1$-$C_6$ alkoxy, oxo or NR'R". For example, —NR'R" is meant to include 1-pyrrolidinyl and 4-morpholinyl.

The term "oxo" refers to ═O or (═O)$_2$.

As used herein a wavy line "∿∿" that intersects a bond in a chemical structure indicate the point of attachment of the atom to which the wavy bond is connected in the chemical structure to the remainder of a molecule, or to the remainder of a fragment of a molecule. In some embodiments, an arrow together with an asterisk is used in the manner of a wavy line to indicate a point of attachment.

In certain embodiments, divalent groups are described generically without specific bonding configurations. It is understood that the generic description is meant to include both bonding configurations, unless specified otherwise. For example, in the group $R^1$—$R^2$—$R^3$, if the group $R^2$ is described as —$CH_2$C(O)—, then it is understood that this group can be bonded both as $R^1$—$CH_2$C(O)—$R^3$, and as $R^1$—C(O)$CH_2$—$R^3$, unless specified otherwise.

The phrase "pharmaceutically acceptable" refers to molecular entities and compositions that do not produce an adverse, allergic or other untoward reaction when administered to an animal, such as, for example, a human, as appropriate.

Compounds of the present invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulphate, phosphate, acetate, fumarate, maleate, tartrate, lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), 2-mesitylenesulphonate, 2-naphthalenesulphonate, 2,5-dichlorobenzenesulphonate, D-mandelate, L-mandelate, cinnamate, benzoate, adipate, esylate, malonate, mesitylate (2-mesitylenesulphonate), napsylate (2-naphthalenesulfonate), camsylate (camphor-10-sulphonate, for example (1S)-(+)-10-camphorsulfonic acid salt), glutamate, glutarate, hippurate (2-(benzoylamino)acetate), orotate, xylate (p-xylene-2-sulphonate), and pamoic (2,2'-dihydroxy-1,1'-dinaphthylmethane-3,3'-dicarboxylate).

A “sterile” formulation is aseptic or free from all living microorganisms and their spores.

“Stereoisomers” refer to compounds that have identical chemical constitution, but differ with regard to the arrangement of the atoms or groups in space. Stereoisomers include diastereomers, enantiomers, conformers and the like.

“Chiral” refers to molecules which have the property of non-superimposability of the mirror image partner, while the term “achiral” refers to molecules which are superimposable on their mirror image partner.

“Diastereomer” refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

“Enantiomers” refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., “Stereochemistry of Organic Compounds”, John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms “racemic mixture” and “racemate” refer to an equimolar mixture of two enantiomeric species, devoid of optical activity.

The term “tautomer” or “tautomeric form” refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Certain compounds of the present invention can exist in unsolvated forms as well as solvated forms, including hydrated forms. A “solvate” refers to an association or complex of one or more solvent molecules and a compound of the present invention. Examples of solvents that form solvates include water, isopropanol, ethanol, methanol, DMSO, ethyl acetate, acetic acid, and ethanolamine. Certain compounds of the present invention can exist in multiple crystalline or amorphous forms. In general, all physical forms are intended to be within the scope of the present invention. The term “hydrate” refers to the complex where the solvent molecule is water.

A “metabolite” refers to a product produced through metabolism in the body of a specified compound or salt thereof. Such products can result, for example, from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

“Amino-protecting group” as used herein refers to a derivative of the groups commonly employed to block or protect an amino group while reactions are carried out on other functional groups on the compound. Examples of such protecting groups include carbamates, amides, alkyl and aryl groups, and imines, as well as many N-heteroatom derivatives which can be removed to regenerate the desired amine group. Particular amino protecting groups are Pmb (p-Methoxybenzyl), Boc (tert-Butyloxycarbonyl), Fmoc (9-Fluorenylmethyl oxycarbonyl) and Cbz (Carbobenzyloxy). Further examples of these groups are found in T. W. Greene and P. G. M. Wuts, “Protecting Groups in Organic Synthesis, 3rd ed., John Wiley & Sons, Inc., 1999. The term “protected amino” refers to an amino group substituted with one of the above amino-protecting groups.

“Carboxy-protecting group” as used herein refers to those groups that are stable to the conditions of subsequent reaction(s) at other positions of the molecule, which may be removed at the appropriate point without disrupting the remainder of the molecule, to give the unprotected carboxy-group. Examples of carboxy protecting groups include, ester groups and heterocyclyl groups. Ester derivatives of the carboxylic acid group may be employed to block or protect the carboxylic acid group while reactions are carried out on other functional groups on the compound. Examples of such ester groups include substituted arylalkyl, including substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl or substituted alkyl esters such as methyl, ethyl, t-butyl allyl or t-amyl, triphenylmethyl (trityl), 4-methoxytrityl, 4,4'-dimethoxytrityl, 4,4',4"-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl)methylsilyl)ethyl, p-toluenesulfonylethyl, 4-nitrobenzyl sulfonylethyl, allyl, cinnamyl, 1-(trimethylsilylmethyl)prop-1-en-3-yl, and like moieties. Another example of carboxy-protecting groups are heterocyclyl groups such as 1,3-oxazolinyl. Further examples of these groups are found in T. W. Greene and P. G. M. Wuts, "Protecting Groups in Organic Synthesis, 3$^{rd}$ ed., John Wiley & Sons, Inc., 1999. The term "protected carboxy" refers to a carboxy group substituted with one of the above carboxy-protecting groups.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g., TBS, TBDPS) groups. Further examples of these groups are found in T. W. Greene and P. G. M. Wuts, "Protecting Groups in Organic Synthesis, 3$^{rd}$ ed., John Wiley & Sons, Inc., 1999. The term "protected hydroxy" refers to a hydroxy group substituted with one of the above hydroxy-protecting groups.

A "subject," "individual," or "patient" is a vertebrate. In certain embodiments, the vertebrate is a mammal. Mammals include, but are not limited to, farm animals (such as cows), sport animals, pets (such as guinea pigs, cats, dogs, rabbits and horses), primates, mice and rats. In certain embodiments, a mammal is a human. In embodiments comprising administration of a compound of Formula (00A), (0A), (A), (Ia), (Ib), (II), (III), (IV), (V), (VI), (VII), (VIII), (IX), or (X), or a compound of Table 1 or of Examples 1-468, to a patient, the patient is typically in need thereof.

The term "Janus kinase" refers to JAK1, JAK2, JAK3 and TYK2 protein kinases. In some embodiments, a Janus kinase may be further defined as one of JAK1, JAK2, JAK3 or TYK2. In any embodiment, any one of JAK1, JAK2, JAK3 and TYK2 may be specifically excluded as a Janus kinase. In some embodiments, a Janus kinase is JAK1. In some embodiments, a Janus kinase is a combination of JAK1 and JAK2.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., JAK1 activity) compared to normal.

In some embodiments, a compound of Formula (00A), (0A), (A), (Ia), (Ib), (II), (III), (IV), (V), (VI), (VII), (VIII), (IX), or (X), or a compound of Table 1 or of Examples 1-468, is selective for inhibition of JAK1 over JAK3 and TYK2. In some embodiments, a compound of Formula (00A), (0A), (A), (Ia), (Ib), (II), (III), (IV), (V), (VI), (VII), (VIII), (IX), or (X), or a compound of Table 1 or of Examples 1-468, is selective for inhibition of JAK1 over JAK2, JAK3, or TYK2, or any combination of JAK2, JAK3, or TYK2. In some embodiments, a compound of Formula (00A), (0A), (A), (Ia), (Ib), (II), (III), (IV), (V), (VI), (VII), (VIII), (IX), or (X), or a compound of Table 1 or of Examples 1-468, is selective for inhibition of JAK1 and JAK2 over JAK3 and TYK2. In some embodiments, a compound of Formula (00A), (0A), (A), (Ia), (Ib), (II), (III), (IV), (V), (VI), (VII), (VIII), (IX), or (X), or a compound of Table 1 or of Examples 1-468, is selective for inhibition of JAK1 over JAK3. By "selective for inhibition" it is meant that the compound is at least a 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, better inhibitor of a particular Janus kinase (e.g., JAK1) activity compared to another particular Janus kinase (e.g., JAK1) activity, or is at least a 2-, 3-, 4-, 5-, 10-, 25-, 50-, 100-, 250-, or 500-fold better inhibitor of a particular Janus kinase (e.g., JAK1) activity compared to another particular Janus kinase (e.g., JAK1) activity.

"Therapeutically effective amount" means an amount of a compound of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, that (i) treats or prevents the particular disease, condition or disorder, or (ii) attenuates, ameliorates or eliminates one or more symptoms of the particular disease, condition, or disorder, and optionally (iii) prevents or delays the onset of one or more symptoms of the particular disease, condition or disorder described herein. In some embodiments, the therapeutically effective amount is an amount sufficient to decrease or alleviate the symptoms of an autoimmune or inflammatory disease (e.g., asthma). In some embodiments, a therapeutically effective amount is an amount of a chemical entity described herein sufficient to significantly decrease the activity or number of B-cells. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; or relieve to some extent one or more of the symptoms associated with the cancer. To the extent the drug may prevent growth or kill existing cancer cells, it may be cytostatic or cytotoxic. For cancer therapy, efficacy can, for example, be measured by assessing the time to disease progression (TTP) or determining the response rate (RR).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, compounds of the invention, such as a compound of Formula (00A), (0A), (A), (Ia), (Ib), (II), (III), (IV), (V), (VI), (VII), (VIII), (IX), or (X), or a compound of Table 1 or of Examples 1-468, are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented.

"Inflammatory disorder" refers to any disease, disorder or syndrome in which an excessive or unregulated inflammatory response leads to excessive inflammatory symptoms, host tissue damage, or loss of tissue function. "Inflammatory disorder" also refers to a pathological state mediated by influx of leukocytes or neutrophil chemotaxis.

"Inflammation" refers to a localized, protective response elicited by injury or destruction of tissues, which serves to destroy, dilute, or wall off (sequester) both the injurious agent and the injured tissue. Inflammation is notably associated with influx of leukocytes or neutrophil chemotaxis. Inflammation can result from infection with pathogenic organisms and viruses and from noninfectious means such as trauma or reperfusion following myocardial infarction or stroke, immune responses to foreign antigens, and autoimmune responses. Accordingly, inflammatory disorders amenable to treatment with a compound of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity responses mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" refers to any group of disorders in which tissue injury is associated with humoral or cell-mediated responses to the body's own constituents. Non-limiting examples of autoimmune diseases include rheumatoid arthritis, lupus and multiple sclerosis.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

In some embodiments, inflammatory disorders which can be treated according to the methods of this invention include, but are not limited to, asthma, rhinitis (e.g., allergic rhinitis), allergic airway syndrome, atopic dermatitis, bronchitis, rheumatoid arthritis, psoriasis, contact dermatitis, chronic obstructive pulmonary disease and delayed hypersensitivity reactions.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

"Package insert" is used to refer to instructions customarily included in commercial packages of therapeutic products that contain information about the indications, usage, dosage, administration, contraindications or warnings concerning the use of such therapeutic products.

The terms "compound(s) of this invention," and "compound(s) of the present invention" and the like, unless otherwise indicated, include compounds of Formula (00A), (0A), (A), (Ia), (Ib), (II), (III), (IV), (V), (VI), (VII), (VIII), (IX), or (X), or a compound of Table 1 or of Examples 1-468, and stereoisomers (including atropisomers), geometric isomers, tautomers, solvates, metabolites, isotopes, salts (e.g., pharmaceutically acceptable salts), and prodrugs thereof. In some embodiments, solvates, metabolites, isotopes or prodrugs are excluded, or any combination thereof.

Unless otherwise stated, structures depicted herein are also meant to include compounds that differ only in the presence of one or more isotopically enriched atoms. Exemplary isotopes that can be incorporated into compounds of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}$, $^{18}F$, $^{36}Cl$, $^{123}I$, and $^{125}$, respectively. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds of Formula (00A), (0A), (A), (Ia), (Ib), (II), (III), (IV), (V), (VI), (VII), (VIII), (IX), or (X), or a compound of Table 1 or of Examples 1-468, one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

The use of the term "or" is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used herein, "a" or "an" means one or more, unless clearly indicated otherwise. As used herein, "another" means at least a second or more.

Headings used herein are intended only for organizational purposes.

Inhibitors of Janus Kinases

Accordingly, one aspect of the invention includes a compound of Formula (00A):

(00A)

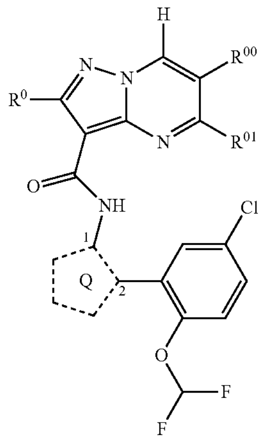

and stereoisomers and salts thereof, wherein: $R^{00}$ is H or $CH_3$; $R^{01}$ is H or $NH_2$; $R^0$ is H or $NH_2$; and Ring Q is either (i) or (ii):

(i)

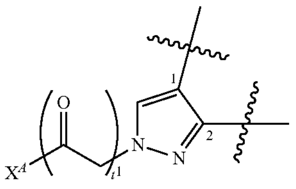

(ii)

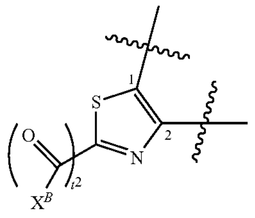

wherein: $t^1$ and $t^2$ are each independently 0 or 1; $X^A$ and $X^B$ are independently selected from the group consisting of H, $C_1$-$C_6$ alkyl, $C_2$-$C_4$ alkenyl, —$NR^aR^b$, $C_2$-$C_5$ alkynyl, 3-6-membered cycloalkyl, 6-10 membered aryl, 3-11 membered heterocycloalkyl, 5-6 membered heterocycloalkenyl, and 5-10 membered heteroaryl; wherein when either of $X^A$ and $X^B$ are independently $C_1$-$C_6$ alkyl, $C_2$-$C_4$ alkenyl, $C_2$-$C_5$ alkynyl, 3-6-membered cycloalkyl, 6-10 membered aryl, 3-11 membered heterocycloalkyl, 5-6 membered heterocycloalkenyl, and 5-10 membered heteroaryl, each of $X^A$ and $X^B$ is independently optionally substituted by $Y^1$, wherein $Y^1$ is selected from:

(a) $C_1$-$C_6$ alkyl optionally substituted by $T^1$, wherein $T^1$ is selected from the group consisting of OH, halo, CN, imino, 3-6 membered cycloalkyl, 3-11 membered heterocycloalkyl, 3-11 membered heterocycloalkenyl, 5-10 membered heteroaryl, —O—($C_1$-$C_6$ alkyl), C(O)OH, oxetan-3-ylmethyl, —C(O)O—($C_1$-$C_6$ alkyl), —S—($C_1$-$C_6$ alkyl), —$SO_2$—($C_1$-$C_6$ alkyl), —$NR^aR^b$, —N(+)$R^aR^bR^c$ wherein $R^c$ is methyl, —C(O)$NR^aR^b$, -(2-oxoindolin-1-yl), —OC(O)-3-6 membered cycloalkyl, and phenyl, wherein each alkyl, cycloalkyl, heterocycloalkyl, heterocycloalkenyl, heteroaryl, and phenyl of $T^1$ is optionally substituted by OH, —C(O)O—($C_1$-$C_6$ alkyl), $C_1$-$C_6$ alkyl, halo, CN, oxo, —($C_1$-$C_6$ alkyl)CONR$^a$R$^b$, —NR$^a$R$^b$, phenyl, or —O—($C_1$-$C_6$ alkyl) optionally substituted by OH;

(b) 3-11 membered heterocycloalkyl, —($C_1$-$C_6$ alkylene)-3-11 membered heterocycloalkyl, —C(O)-3-11 membered heterocycloalkyl, —($C_1$-$C_6$ alkylene)C(O)-3-11 membered heterocycloalkyl, or —OC(O)-4-6 membered heterocycloalkyl; wherein the heterocycloalkyl is optionally substituted by OH, halo, CN, $C_1$-$C_6$ alkyl, —($C_1$-$C_6$ alkylene)-$CF_3$, oxo, —C(O)—($C_1$-$C_6$ alkyl), —C(O)O—($C_1$-$C_6$ alkyl), —C(O)O—($C_1$-$C_6$ alkylene)-phenyl, —$SO_2$—($C_1$-$C_6$ alkyl), —C(O)NR$^a$R$^b$, —NR$^a$R$^b$, —($C_1$-$C_6$ alkylene)-phenyl, or —C(O)-4-6 membered heterocycloalkyl optionally substituted by —NR$^a$R$^b$;

(c) N(+)(AA)$_3$, wherein each AA is independently $C_1$-$C_6$ alkyl optionally substituted by phenyl;

(d) 3-6 membered cycloalkyl optionally substituted by OH, halo, NR$^a$R$^b$, or CN;

(e) CN, halo, or oxo;

(f) —C(O)—($C_1$-$C_6$ alkyl), —C(O)OH, —C(O)O—($C_1$-$C_6$ alkylene)-phenyl, —$SO_2$—($C_1$-$C_6$ alkyl), —C(O)NR$^a$R$^b$, or —C(O)-4-6 membered heterocycloalkyl optionally substituted by —($C_1$-$C_6$ alkyl) or —NR$^a$R$^b$, or —C(O)O—($C_1$-$C_6$ alkyl) optionally substituted by OH, NR$^a$R$^b$, or 3-11 membered heterocycloalkyl wherein said heterocycloalkyl is optionally substituted by $C_1$-$C_6$ alkyl;

(g) OH, —O-phenyl, or —O—($C_1$-$C_6$ alkyl), wherein the alkyl is optionally substituted by OH or —NR$^a$R$^b$;

(h) phenyl optionally substituted by OH, halo, $C_1$-$C_6$ alkyl, $CF_3$, or CN;

(i) 5-6 membered heteroaryl optionally substituted by OH, halo, $C_1$-$C_6$ alkyl, $CF_3$, CN, or 3-11 membered heterocycloalkyl optionally substituted by $C_1$-$C_6$ alkyl or 3-11 membered heterocycloalkyl;

(j) isoindolin-2-yl optionally substituted by halo;

(k) —NR$^a$R$^b$, and (l) —O—$CH_2$C(O)-3-11 membered heterocycloalkyl;

wherein R$^a$ and R$^b$ are independently selected from:

(p) H, (a) $C_1$-$C_6$ alkyl optionally substituted by OH, halo, CN, —C(O)OH, —C(O)O—($C_1$-$C_6$alkyl), —C(O)O-(3-11 membered heterocycloalkyl), —C(O)O—($C_1$-$C_6$ alkyl)-S—($C_1$-$C_6$ alkyl), —S—($C_1$-$C_6$ alkyl), naphthylenyl, —NR$^{az}$R$^{bz}$, —C(O)NR$^{az}$R$^{bz}$, oxo, —O—($C_1$-$C_6$ alkyl), 5-6 membered heteroaryl optionally substituted by $C_1$-$C_6$ alkyl or halo, or benzo[1,3]dioxol-2-yl, or 3-11 membered heterocycloalkenyl optionally substituted by oxo;

(b) —($C_1$-$C_6$ alkylene)-3-6 membered cycloalkyl wherein the alkylene is optionally substituted by OH, halo, or CN;

(c) —($C_1$-$C_6$ alkylene)-phenyl wherein alkylene is optionally substituted by halo and the phenyl is optionally substituted by OH, halo, $CF_3$, $C_1$-$C_6$ alkyl, —O—($C_1$-$C_6$ alkyl), —S—($C_1$-$C_6$ alkyl, or —O-phenyl;

(d) —($C_1$-$C_6$ alkylene)-4-6 membered heterocycloalkyl wherein the heterocycloalkyl is optionally substituted by halo, oxo, or $C_1$-$C_6$ alkyl;

(e) —($C_1$-$C_6$ alkylene)-O-phenyl wherein the phenyl is optionally substituted by halo, $C_1$-$C_6$ alkyl, or —O-phenyl;

(f) —($C_1$-$C_6$ alkyl)3-6 membered cycloalkyl optionally substituted by OH, halo, CN, or $C_1$-$C_6$ alkyl optionally substituted by OH or CN;

(g) $C_2$-$C_5$ alkenyl;

(h) 4-6 membered heterocycloalkyl optionally substituted by halo, (i) —($C_1$-$C_6$ alkylene)-3-6 membered cycloalkyl substituted by hydroxymethyl, (j) phenyl, (k) —C(O)($C_1$-$C_6$ alkyl), (l) —C(O)O($C_1$-$C_6$ alkyl), (m) —C(O)O(3-6 membered cycloalkyl), and (n) —C(O)-phenyl, wherein R$^{az}$ and R$^{bz}$ are each independently selected from (a) H, (b) $C_1$-$C_6$ alkyl optionally substituted by OH, halo, CN, —C(O)OH, —C(O)O—($C_1$-$C_6$alkyl), —C(O)O-(3-11 membered heterocycloalkyl), —C(O)O—($C_1$-$C_6$ alkyl)-S—($C_1$-$C_6$ alkyl), —S—($C_1$-$C_6$ alkyl), naphthylenyl, -oxo, —O—($C_1$-$C_6$ alkyl), 5-6 membered heteroaryl optionally substituted by $C_1$-$C_6$ alkyl or halo, or benzo[1,3]dioxol-2-yl, or 3-11 membered heterocycloalkenyl optionally substituted by oxo;

(c) —($C_1$-$C_6$ alkylene)-3-6 membered cycloalkyl wherein the alkylene is optionally substituted by OH, halo, or CN;

(d) —($C_1$-$C_6$ alkylene)-phenyl wherein alkylene is optionally substituted by halo and the phenyl is optionally substituted by OH, halo, $CF_3$, $C_1$-$C_6$ alkyl, —O—($C_1$-$C_6$ alkyl), —S—($C_1$-$C_6$ alkyl, or —O-phenyl;

(e) —($C_1$-$C_6$ alkylene)-4-6 membered heterocycloalkyl wherein the heterocycloalkyl is optionally substituted by halo, oxo, or $C_1$-$C_6$ alkyl;

(f) —($C_1$-$C_6$ alkylene)-O-phenyl wherein the phenyl is optionally substituted by halo, $C_1$-$C_6$ alkyl, or —O-phenyl;

(g) —($C_1$-$C_6$ alkyl)3-6 membered cycloalkyl optionally substituted by OH, halo, CN, or $C_1$-$C_6$ alkyl optionally substituted by OH or CN;

(h) $C_2$-$C_5$ alkenyl;

(i) 4-6 membered heterocycloalkyl optionally substituted by halo, (j) —($C_1$-$C_6$ alkylene)-3-6 membered cycloalkyl substituted by hydroxymethyl, (k) phenyl, (l) —C(O)($C_1$-$C_6$ alkyl), (m) —C(O)O($C_1$-$C_6$ alkyl), (n) —C(O)O(3-6 membered cycloalkyl), and (o) —C(O)-phenyl, with the following provisos: when R$^0$, R$^{00}$, and R$^{01}$ are each H and Ring Q is

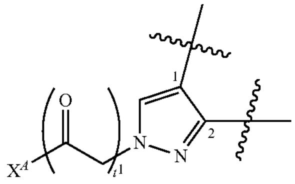

where $t^1$ is 0, then X$^A$ is not methyl, 2-methylpropan-2-ol, or tetrahydropyranyl; and, in some embodiments, when Ring Q is (i) and $t^1$ is 0, then X$^A$ cannot be —NR$^a$R$^b$.

Further, another aspect of the invention includes a compound of Formula (00A), further defined as a compound of Formula (0A):

(0A)

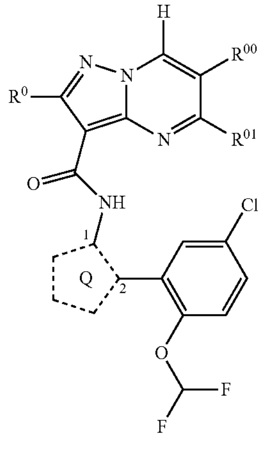

and stereoisomers and salts thereof, wherein: $R^{00}$ is H or $CH_3$; $R^{01}$ is H or $NH_2$; $R^0$ is H or $NH_2$; and Ring Q is either (i) or (ii):

(i)

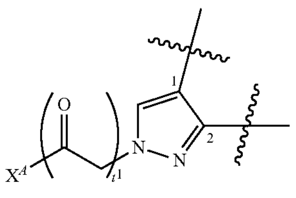

(ii)

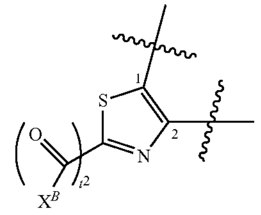

wherein: $t^1$ and $t^2$ are each independently 0 or 1; $X^A$ and $X^B$ are independently selected from the group consisting of H, $C_1$-$C_6$ alkyl, $C_2$-$C_4$ alkenyl, —$NR^aR^b$, $C_2$-$C_5$ alkynyl, 3-6-membered cycloalkyl, 6-10 membered aryl, 3-11 membered heterocycloalkyl, 5-6 membered heterocycloalkenyl, and 5-10 membered heteroaryl; wherein when either of $X^A$ and $X^B$ are independently $C_1$-$C_6$ alkyl, $C_2$-$C_5$ alkynyl, 3-6-membered cycloalkyl, 6-10 membered aryl, 3-11 membered heterocycloalkyl, 5-6 membered heterocycloalkenyl, and 5-10 membered heteroaryl, each of $X^A$ and $X^B$ are independently optionally substituted by $Y^1$, wherein $Y^1$ is selected from:

(a) $C_1$-$C_6$ alkyl optionally substituted by $T^1$, wherein $T^1$ is selected from the group consisting of OH, halo, CN, imino, 3-6 membered cycloalkyl, 3-11 membered heterocycloalkyl, 3-11 membered heterocycloalkenyl, 5-10 membered heteroaryl, —O—($C_1$-$C_6$ alkyl), C(O)OH, oxetan-3-ylmethyl, —C(O)O—($C_1$-$C_6$ alkyl), —S—($C_1$-$C_6$ alkyl), —$SO_2$—($C_1$-$C_6$ alkyl), —$NR^aR^b$, —N(+)$R^aR^bR^c$ wherein $R^c$ is methyl, —C(O)$NR^aR^b$, -(2-oxoindolin-1-yl), —OC(O)-3-6 membered cycloalkyl, and phenyl, wherein each alkyl, cycloalkyl, heterocycloalkyl, heterocycloalkenyl, heteroaryl, and phenyl of $T^1$ is optionally substituted by OH, —C(O)O—($C_1$-$C_6$ alkyl), $C_1$-$C_6$ alkyl, halo, CN, oxo, —$NR^aR^b$, phenyl, or —O—($C_1$-$C_6$ alkyl) optionally substituted by OH;

(b) 3-11 membered heterocycloalkyl, —($C_1$-$C_6$ alkylene)-3-11 membered heterocycloalkyl, —C(O)-3-11 membered heterocycloalkyl, —($C_1$-$C_6$ alkylene)C(O)-3-11 membered heterocycloalkyl, or —OC(O)-4-6 membered heterocycloalkyl; wherein the heterocycloalkyl is optionally substituted by OH, halo, CN, $C_1$-$C_6$ alkyl, —($C_1$-$C_6$ alkylene)-$CF_3$, oxo, —C(O)—($C_1$-$C_6$ alkyl), —C(O)O—($C_1$-$C_6$ alkyl), —C(O)O—($C_1$-$C_6$ alkylene)-phenyl, —$SO_2$—($C_1$-$C_6$ alkyl), —C(O)$NR^aR^b$, —$NR^aR^b$, —($C_1$-$C_6$ alkylene)-phenyl, or —C(O)-4-6 membered heterocycloalkyl optionally substituted by —$NR^aR^b$;

(c) N(+)$(AA)_3$, wherein each AA is independently $C_1$-$C_6$ alkyl optionally substituted by phenyl;

(d) 3-6 membered cycloalkyl optionally substituted by OH, halo, or CN;

(e) CN, halo, or oxo;

(f) —C(O)—($C_1$-$C_6$ alkyl), —C(O)OH, —C(O)O—($C_1$-$C_6$ alkylene)-phenyl, —$SO_2$—($C_1$-$C_6$ alkyl), —C(O)$NR^aR^b$, or —C(O)-4-6 membered heterocycloalkyl optionally substituted by —$NR^aR^b$, or —C(O)O—($C_1$-$C_6$ alkyl) optionally substituted by OH, $NR^aR^b$, or 3-11 membered heterocycloalkyl wherein said heterocycloalkyl is optionally substituted by $C_1$-$C_6$ alkyl;

(g) OH, —O-phenyl, or —O—($C_1$-$C_6$ alkyl), wherein the alkyl is optionally substituted by OH or —$NR^aR^b$;

(h) phenyl optionally substituted by OH, halo, $C_1$-$C_6$ alkyl, $CF_3$, or CN;

(i) 5-6 membered heteroaryl optionally substituted by OH, halo, $C_1$-$C_6$ alkyl, $CF_3$, or CN;

(j) isoindolin-2-yl optionally substituted by halo; and (k) —$NR^aR^b$, wherein $R^a$ and $R^b$ are independently selected from:

(a) H, (b) $C_1$-$C_6$ alkyl optionally substituted by OH, halo, CN, —C(O)OH, —C(O)O—($C_1$-$C_6$alkyl), —C(O)O-(3-11 membered heterocycloalkyl), —C(O)O—($C_1$-$C_6$ alkyl)-S—($C_1$-$C_6$ alkyl), —S—($C_1$-$C_6$ alkyl), naphthylenyl, —$NR^{az}R^{bz}$, —C(O)$NR^{az}R^{bz}$, oxo, —O—($C_1$-$C_6$ alkyl), 5-6 membered heteroaryl optionally substituted by $C_1$-$C_6$ alkyl or halo, or benzo[1,3]dioxol-2-yl, or 3-11 membered heterocycloalkenyl optionally substituted by oxo;

(c) —($C_1$-$C_6$ alkylene)-3-6 membered cycloalkyl wherein the alkylene is optionally substituted by OH, halo, or CN;

(d) —($C_1$-$C_6$ alkylene)-phenyl wherein alkylene is optionally substituted by halo and the phenyl is optionally substituted by OH, halo, $CF_3$, $C_1$-$C_6$ alkyl, —O—($C_1$-$C_6$ alkyl), —S—($C_1$-$C_6$ alkyl, or —O-phenyl;

(e) —($C_1$-$C_6$ alkylene)-4-6 membered heterocycloalkyl wherein the heterocycloalkyl is optionally substituted by halo, oxo, or $C_1$-$C_6$ alkyl;

(f) —($C_1$-$C_6$ alkylene)-O-phenyl wherein the phenyl is optionally substituted by halo, $C_1$-$C_6$ alkyl, or —O-phenyl;

(g) 3-6 membered cycloalkyl optionally substituted by OH, halo, CN, or $C_1$-$C_6$ alkyl optionally substituted by OH;

(h) $C_2$-$C_5$ alkenyl;

(i) 4-6 membered heterocycloalkyl optionally substituted by halo, (j) —($C_1$-$C_6$ alkylene)-3-6 membered cycloalkyl substituted by hydroxymethyl, (k) phenyl, (l) —$C(O)(C_1$-$C_6$ alkyl), (m) —$C(O)O(C_1$-$C_6$ alkyl), (n) —C(O)O(3-6 membered cycloalkyl), and (o) —C(O)-phenyl, wherein $R^{az}$ and $R^{bz}$ are each independently selected from (a) H, (b) $C_1$-$C_6$ alkyl optionally substituted by OH, halo, CN, —C(O)OH, —C(O)O—($C_1$-$C_6$alkyl), —C(O)O-(3-11 membered heterocycloalkyl), —C(O)O—($C_1$-$C_6$ alkyl)-S—($C_1$-$C_6$ alkyl), —S—($C_1$-$C_6$ alkyl), naphthylenyl, -oxo, —O—($C_1$-$C_6$ alkyl), 5-6 membered heteroaryl optionally substituted by $C_1$-$C_6$ alkyl or halo, or benzo[1,3]dioxol-2-yl, or 3-11 membered heterocycloalkenyl optionally substituted by oxo;

(c) —($C_1$-$C_6$ alkylene)-3-6 membered cycloalkyl wherein the alkylene is optionally substituted by OH, halo, or CN;

(d) —($C_1$-$C_6$ alkylene)-phenyl wherein alkylene is optionally substituted by halo and the phenyl is optionally substituted by OH, halo, $CF_3$, $C_1$-$C_6$ alkyl, —O—($C_1$-$C_6$ alkyl), —S—($C_1$-$C_6$ alkyl, or —O-phenyl;

(e) —($C_1$-$C_6$ alkylene)-4-6 membered heterocycloalkyl wherein the heterocycloalkyl is optionally substituted by halo, oxo, or $C_1$-$C_6$ alkyl;

(f) —($C_1$-$C_6$ alkylene)-O-phenyl wherein the phenyl is optionally substituted by halo, $C_1$-$C_6$ alkyl, or —O-phenyl;

(g) —($C_1$-$C_6$ alkyl)3-6 membered cycloalkyl optionally substituted by OH, halo, CN, or $C_1$-$C_6$ alkyl optionally substituted by OH or CN;

(h) $C_2$-$C_5$ alkenyl;

(i) 4-6 membered heterocycloalkyl optionally substituted by halo, (j) —($C_1$-$C_6$ alkylene)-3-6 membered cycloalkyl substituted by hydroxymethyl, (k) phenyl, (l) —$C(O)(C_1$-$C_6$ alkyl), (m) —$C(O)O(C_1$-$C_6$ alkyl), (n) —C(O)O(3-6 membered cycloalkyl), and (o) —C(O)-phenyl, with the following provisos: when $R^0$, $R^{00}$, and $R^{01}$ are each H and Ring Q is

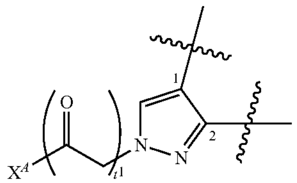

where $t^1$ is 0, then $X^A$ is not methyl, 2-methylpropan-2-ol, or tetrahydropyranyl; and, in some embodiments, when Ring Q is (i) and $t^1$ is 0, then $X^A$ cannot be —$NR^aR^b$.

In some embodiments of any formula herein, when Ring Q is

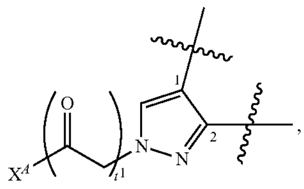
, and $t^1$ is 0, the pyrazole is not N-linked to a nitrogen of $X^A$.

Another aspect of the invention provides compounds of Formula (00A), further defined as a compound of Formula (A):

(A)

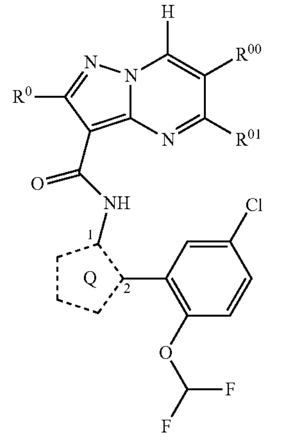

and stereoisomers and salts thereof, wherein:

$R^{00}$ is H or $CH_3$;

$R^{01}$ is H or $NH_2$;

$R^0$ is H or $NH_2$; and

Ring Q is either (i) or (ii):

(i)

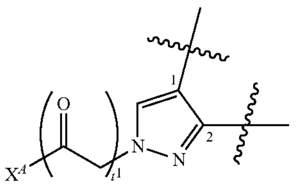

(ii)

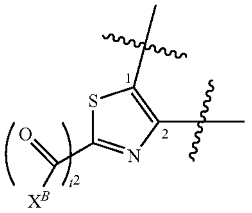

wherein:

$t^1$ and $t^2$ are each independently 0 or 1;

$X^A$ and $X^B$ are independently selected from the group consisting of H, $C_1$-$C_6$ alkyl, —$NR^aR^b$, $C_2$-$C_5$ alkynyl, 3-6-membered cycloalkyl, 6-10 membered aryl, 3-11 membered heterocycloalkyl, 5-6 membered heterocycloalkenyl, and 5-10 membered heteroaryl;

wherein when either of $X^A$ and $X^B$ are independently $C_1$-$C_6$ alkyl, $C_2$-$C_5$ alkynyl, 3-6-membered cycloalkyl, 6-10 membered aryl, 3-11 membered heterocycloalkyl, 5-6 membered heterocycloalkenyl, and 5-10 membered heteroaryl, each of $X^A$ and $X^B$ are independently optionally substituted by $Y^1$, wherein $Y^1$ is selected from:

(a) $C_1$-$C_6$ alkyl optionally substituted by $T^1$, wherein $T^1$ is selected from the group consisting of OH, halo, CN, imino, 3-6 membered cycloalkyl, —O—($C_1$-$C_6$ alkyl), —C(O)O—($C_1$-$C_6$ alkyl), —$SO_2$—($C_1$-$C_6$ alkyl), —$NR^aR^b$, —N(+)$R^aR^bR^c$ wherein $R^c$ is methyl, —C(O)$NR^aR^b$, -(2-oxoindolin-1-yl), —OC(O)-3-6 membered cycloalkyl, and phenyl, wherein each alkyl, cycloalkyl, and phenyl of $T^1$ is optionally substituted by OH, $C_1$-$C_6$ alkyl, halo, CN, oxo, —$NR^aR^b$, phenyl, or —O—($C_1$-$C_6$ alkyl) optionally substituted by OH;

(b) 3-11 membered heterocycloalkyl, —($C_1$-$C_6$ alkylene)-3-11 membered heterocycloalkyl, —C(O)-3-11 membered heterocycloalkyl, —($C_1$-$C_6$ alkylene)C(O)-3-11 membered heterocycloalkyl, or —OC(O)-4-6 membered heterocycloalkyl;

wherein heterocycloalkyl is optionally substituted by OH, halo, CN, $C_1$-$C_6$ alkyl, —($C_1$-$C_6$ alkylene)-$CF_3$, oxo, —C(O)—($C_1$-$C_6$ alkyl), —C(O)O—($C_1$-$C_6$ alkyl), —C(O)O—($C_1$-$C_6$ alkylene)-phenyl, —$SO_2$—($C_1$-$C_6$ alkyl), —C(O)$NR^aR^b$, —$NR^aR^b$, —($C_1$-$C_6$ alkylene)-phenyl, or —C(O)-4-6 membered heterocycloalkyl optionally substituted by —$NR^aR^b$;

(c) N(+)$(AA)_3$, wherein each AA is independently $C_1$-$C_6$ alkyl optionally substituted by phenyl;

(d) 3-6 membered cycloalkyl optionally substituted by OH, halo, or CN;

(e) CN, halo, or oxo;

(f) —C(O)—($C_1$-$C_6$ alkyl), —C(O)O—($C_1$-$C_6$ alkyl) optionally substituted by OH, —C(O)O—($C_1$-$C_6$ alkylene)-phenyl, —$SO_2$—($C_1$-$C_6$ alkyl), —C(O)$NR^aR^b$, or —C(O)-4-6 membered heterocycloalkyl optionally substituted by —$NR^aR^b$, (g) OH, —O-phenyl, or —O—($C_1$-$C_6$ alkyl), wherein the alkyl is optionally substituted by OH or —$NR^aR^b$;

(h) phenyl optionally substituted by OH, halo, $C_1$-$C_6$ alkyl, $CF_3$, or CN;

(i) 5-6 membered heteroaryl optionally substituted by OH, halo, $C_1$-$C_6$ alkyl, $CF_3$, or CN;

(j) isoindolin-2-yl optionally substituted by halo; and (k) —$NR^aR^b$, wherein $R^a$ and $R^b$ are independently selected from:

(a) H, (b) $C_1$-$C_6$ alkyl optionally substituted by OH, halo, CN, naphthylenyl, —$NR^{az}R^{bz}$, —C(O)$NR^{az}R^{bz}$, oxo, —O—($C_1$-$C_6$ alkyl), phenyl, 5-6 membered heteroaryl optionally substituted by $C_1$-$C_6$ alkyl or halo, or benzo[1,3]dioxol-2-yl;

(c) —($C_1$-$C_6$ alkylene)-3-6 membered cycloalkyl wherein the alkylene is optionally substituted by OH, halo, or CN;

(d) —($C_1$-$C_6$ alkylene)-phenyl wherein alkylene is optionally substituted by halo and the phenyl is optionally substituted by OH, halo, $CF_3$, $C_1$-$C_6$ alkyl, —O—($C_1$-$C_6$ alkyl), or —O-phenyl;

(e) —($C_1$-$C_6$ alkylene)-4-6 membered heterocycloalkyl wherein the heterocycloalkyl is optionally substituted by halo or $C_1$-$C_6$ alkyl;

(f) —($C_1$-$C_6$ alkylene)-O-phenyl wherein the phenyl is optionally substituted by halo, $C_1$-$C_6$ alkyl, or —O-phenyl;

(g) 3-6 membered cycloalkyl optionally substituted by OH, halo, CN, or $C_1$-$C_6$ alkyl optionally substituted by OH;

(h) $C_2$-$C_5$ alkenyl;

(i) 4-6 membered heterocycloalkyl optionally substituted by halo, (j) —($C_1$-$C_6$ alkylene)-3-6 membered cycloalkyl substituted by hydroxymethyl, (k) phenyl, (l) —C(O)($C_1$-$C_6$ alkyl), (m) —C(O)O($C_1$-$C_6$ alkyl), (n) —C(O)O(3-6 membered cycloalkyl), and (o) —C(O)-phenyl, wherein $R^{az}$ and $R^{bz}$ are each independently selected from (a) H, (b) $C_1$-$C_6$ alkyl optionally substituted by OH, halo, CN, —C(O)OH, —C(O)O—($C_1$-$C_6$alkyl), —C(O)O-(3-11 membered heterocycloalkyl), —C(O)O—($C_1$-$C_6$ alkyl)-S—($C_1$-$C_6$ alkyl), —S—($C_1$-$C_6$ alkyl), naphthylenyl, -oxo, —O—($C_1$-$C_6$ alkyl), 5-6 membered heteroaryl optionally substituted by $C_1$-$C_6$ alkyl or halo, or benzo[1,3]dioxol-2-yl, or 3-11 membered heterocycloalkenyl optionally substituted by oxo;

(c) —($C_1$-$C_6$ alkylene)-3-6 membered cycloalkyl wherein the alkylene is optionally substituted by OH, halo, or CN;

(d) —($C_1$-$C_6$ alkylene)-phenyl wherein alkylene is optionally substituted by halo and the phenyl is optionally substituted by OH, halo, $CF_3$, $C_1$-$C_6$ alkyl, —O—($C_1$-$C_6$ alkyl), —S—($C_1$-$C_6$ alkyl, or —O-phenyl;

(e) —($C_1$-$C_6$ alkylene)-4-6 membered heterocycloalkyl wherein the heterocycloalkyl is optionally substituted by halo, oxo, or $C_1$-$C_6$ alkyl;

(f) —($C_1$-$C_6$ alkylene)-O-phenyl wherein the phenyl is optionally substituted by halo, $C_1$-$C_6$ alkyl, or —O-phenyl;

(g) —($C_1$-$C_6$ alkyl)3-6 membered cycloalkyl optionally substituted by OH, halo, CN, or $C_1$-$C_6$ alkyl optionally substituted by OH or CN;

(h) $C_2$-$C_5$ alkenyl;

(i) 4-6 membered heterocycloalkyl optionally substituted by halo, (j) —($C_1$-$C_6$ alkylene)-3-6 membered cycloalkyl substituted by hydroxymethyl, (k) phenyl, (l) —C(O)($C_1$-$C_6$ alkyl), (m) —C(O)O($C_1$-$C_6$ alkyl), (n) —C(O)O(3-6 membered cycloalkyl), and (o) —C(O)-phenyl, with the following provisos:

when $R^0$, $R^{00}$, and $R^{01}$ are each H and Ring Q is

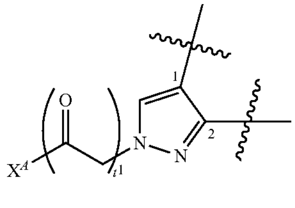

where $t^1$ is 0, then $X^A$ is not methyl, 2-methylpropan-2-ol, or tetrahydropyranyl; and, in some embodiments, when Ring Q is (i) and $t^1$ is 0, then $X^A$ cannot be —$NR^aR^b$.

In some embodiments, a compound of Formula (00A), (0A) or (A) is further defined as a compound of Formula (II):

(II)

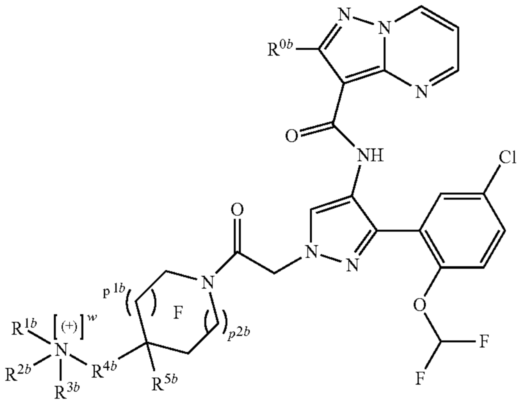

wherein:

w is 0 or 1;

$R^{0b}$ is H or $NH_2$;

$R^{1b}$ is selected from the group consisting of a. H, b. $C_1$-$C_6$ alkyl optionally substituted by OH, halo, CN, —O—($C_1$-$C_6$ alkyl), naphthylenyl, 5-6 membered heteroaryl, or —C(O)NR$^v$R$^w$, wherein R$^v$ and R$^w$ are independently H or $C_1$-$C_6$ alkyl optionally substituted by halo, c. —($C_1$-$C_6$ alkylene)-3-6 membered cycloalkyl wherein the cycloalkyl is optionally substituted by CN, d. —($C_1$-$C_6$ alkylene)-phenyl wherein the alkyl is optionally substituted by halo and wherein the phenyl is optionally substituted by OH, halo, $CF_3$, $C_1$-$C_6$ alkyl, —O—($C_1$-$C_6$ alkyl) or —O-phenyl, e. —($C_1$-$C_6$ alkylene)-4-6 membered heterocycloalkyl wherein the heterocycloalkyl is optionally substituted by halo or $C_1$-$C_6$ alkyl, f. —($C_1$-$C_6$ alkylene)-O-phenyl wherein the phenyl is optionally substituted by halo or $C_1$-$C_6$ alkyl, or g. 3-6 membered cycloalkyl;

$R^{2b}$ is selected from the group consisting of H, $C_1$-$C_6$ alkyl optionally substituted by halo, or $C_2$-$C_5$ alkenyl;

or $R^{1b}$ and $R^{2b}$ together form a 3-11 membered heterocycloalkyl optionally substituted by OH;

$R^{3b}$ is absent or methyl, wherein when $R^{3b}$ is methyl, the nitrogen to which it is attached is N+ and w is 1;

$R^{4b}$ is a bond or $C_1$-$C_6$ alkylene;

$R^{5b}$ is selected from the group consisting of H, OH, and phenyl; and

Ring F is a 3-7 membered heterocycloalkyl wherein $p^{1b}$ is 0, 1 or 2 and $p^{2b}$ is 0, 1 or 2;

wherein w is equal to 1 only when $R^{3b}$ is methyl.

In some embodiments, a compound of Formula (00A), (0A) or (A) is further defined as a compound of Formula (Ia) or Formula (Ib):

(Ia)

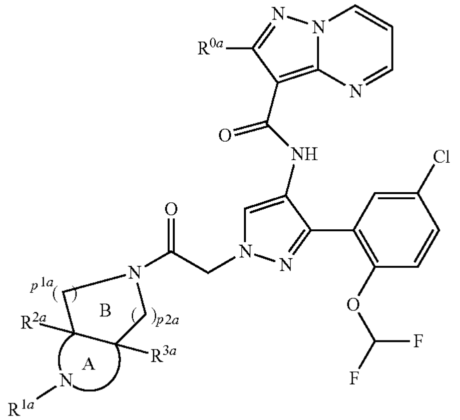

(Ib)

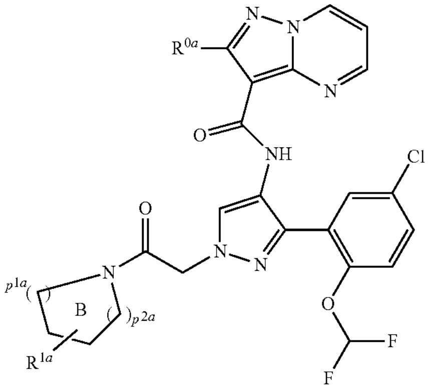

wherein:

$R^{0a}$ is H or $NH_2$;

$R^{1a}$ is bound to a nitrogen atom of Ring A in (Ia) or is bound to a carbon atom of Ring B in (Ib), and is selected from the group consisting of:

a. H, b. $C_1$-$C_6$ alkyl optionally substituted by OH, halo, —O—($C_1$-$C_6$ alkyl), —$SO_2$—($C_1$-$C_6$ alkyl), -(2-oxoindolin-1-yl), —OC(O)-3-6 membered cycloalkyl, —OC(O)-4-6 membered heterocycloalkyl, or phenyl;

c. —($C_1$-$C_6$ alkylene)-O—($C_1$-$C_6$ alkylene)-phenyl wherein the phenyl is optionally substituted by halo;

d. —($C_1$-$C_6$ alkylene)-3-6 membered cycloalkyl wherein the cycloalkyl is optionally substituted by halo, OH, or CN;

e. —($C_1$-$C_6$ alkylene)-4-6 membered heterocycloalkyl, wherein the heterocycloalkyl is optionally substituted by oxo, $C_1$-$C_6$ alkyl, —C(O)—($C_1$-$C_6$ alkyl), —C(O)O—($C_1$-$C_6$ alkyl), —$SO_2$—($C_1$-$C_6$ alkyl), —C(O)-4-6 membered heterocycloalkyl, or —C(O)N($C_1$-$C_6$ alkyl)($C_1$-$C_6$ alkyl);

f. 4-6 membered heterocycloalkyl, wherein the heterocycloalkyl is optionally substituted by oxo, $C_1$-$C_6$ alkyl, —C(O)—($C_1$-$C_6$ alkyl), —C(O)O—($C_1$-$C_6$ alkyl), —$SO_2$—($C_1$-$C_6$ alkyl), —C(O)-4-6 membered heterocycloalkyl, or —C(O)N($C_1$-$C_6$ alkyl)($C_1$-$C_6$ alkyl);

g. —C(O)O—($C_1$-$C_6$ alkylene)-OH; and h. —C(O)O—($C_1$-$C_6$ alkylene)-phenyl;

i. —NR$^a$R$^b$, wherein R$^a$ and R$^b$ are independently selected from the group consisting of H and $C_1$-$C_6$ alkyl optionally substituted by OH, halo, CN, —C(O)OH, phenyl, and 3-7 membered heterocycloalkyl;

$R^{2a}$ is selected from the group consisting of H, $C_1$-$C_6$ alkyl optionally substituted by OH, and phenyl;

$R^{3a}$ is selected from the group consisting of H, $C_1$-$C_6$ alkyl optionally substituted by OH, and phenyl;

Ring A is a 3-7 membered heterocycloalkyl; and

Ring B is a 3-7 membered heterocycloalkyl or a 3-7 membered heterocyclyalkenyl, wherein $p^{1a}$ is 0, 1 or 2 and $p^{2a}$ is 0, 1 or 2, provided that Ring A and Ring B together form a 6-11 membered bicyclic heterocycloalkyl.

In some embodiments, a compound of Formula (00A), (0A) or (A) is further defined as a compound of Formula (III):

(III)

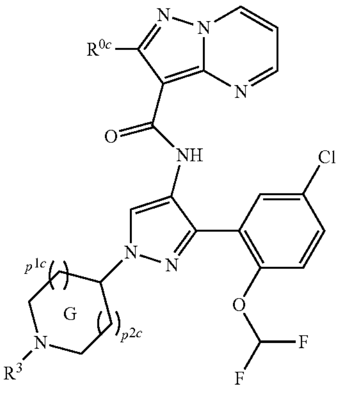

wherein:

$R^{0c}$ is H or $NH_2$;

$R^3$ is (i) or (ii):

(i)

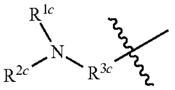

wherein:

$R^{1c}$ is selected from the group consisting of H, $C_1$-$C_6$ alkyl, —($C_1$-$C_6$ alkyl)-phenyl, —C(O)—($C_1$-$C_6$ alkyl), —C(O)-phenyl, and 4-6 membered heterocycloalkyl;

$R^{2c}$ is H or $C_1$-$C_6$ alkyl; and $R^{3c}$ is a bond or $C_1$-$C_6$ alkylene optionally substituted by oxo; or $R^{1c}$ and $R^{2c}$ together form a 3-11 membered heterocycloalkyl optionally substituted by $C_1$-$C_6$ alkyl, oxo, or —($C_1$-$C_6$ alkylene)-phenyl; or $R^{1c}$ and $R^{3c}$ together form a 3-7 membered heterocycloalkyl;

(ii) H; $C_1$-$C_6$ alkyl optionally substituted by OH, —$SO_2$—($C_1$-$C_6$ alkyl), phenyl, or —O—($C_1$-$C_6$ alkylene)-phenyl; —($C_1$-$C_6$ alkylene)-C(O)O($C_1$-$C_6$ alkyl); or 4-6 membered heterocycloalkyl optionally substituted by —C(O)($C_1$-$C_6$ alkyl); and Ring G is a 3-7 membered heterocycloalkyl wherein $p^{1c}$ is 0, 1 or 2 and $p^{2c}$ is 0, 1 or 2.

In some embodiments, a compound of Formula (00A), (0A) or (A) is further defined as a compound of Formula (IV):

(IV)

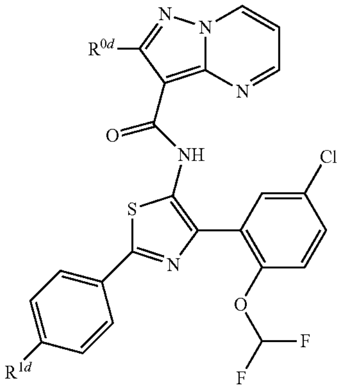

wherein:

$R^{0d}$ is H or $NH_2$;

$R^{1d}$ is 3-11 membered heterocycloalkyl or —C(O)-3-11 membered heterocycloalkyl, wherein the heterocycloalkyl is optionally substituted $C_1$-$C_6$ alkyl, $CF_3$, or fluoro, or $R^{1d}$ is —($C_1$-$C_6$ alkylene)-$NR^vR^w$, wherein $R^v$ and $R^w$ are independently H or $C_1$-$C_6$ alkyl optionally substituted by halo.

In some embodiments, a compound of Formula (00A), (0A) or (A) is further defined as a compound of Formula (V):

(V)

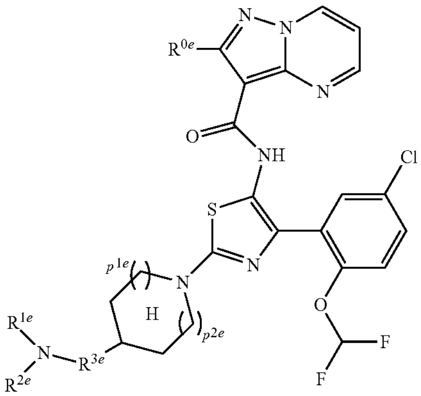

wherein:

$R^{0e}$ is H or $NH_2$;

$R^{1e}$ is selected from the group consisting of a. H, b. $C_1$-$C_6$ alkyl optionally substituted by halo, CN, or phenyl, c. —($C_1$-$C_6$ alkylene)-3-6 membered cycloalkyl wherein the cycloalkyl is optionally substituted by CN, d. —($C_1$-$C_6$ alkylene)-4-6 membered heterocycloalkyl wherein the heterocycloalkyl is optionally substituted by $C_1$-$C_6$ alkyl;

$R^{2e}$ is H or $C_1$-$C_6$ alkyl;

or $R^{1e}$ and $R^{2e}$ together form a 3-11 membered heterocycloalkyl optionally substituted by halo or —$NR^vR^w$, wherein $R^v$ and $R^w$ are independently H or $C_1$-$C_6$ alkyl optionally substituted by halo;

$R^{3e}$ is a bond or $C_1$-$C_6$ alkylene optionally substituted by oxo; and

Ring H is a 3-7 membered heterocycloalkyl wherein $p^{1e}$ is 0, 1 or 2 and $p^{2e}$ is 0, 1 or 2.

In some embodiments, a compound of Formula (00A), (0A) or (A) is further defined as a compound of Formula (VI):

(VI)

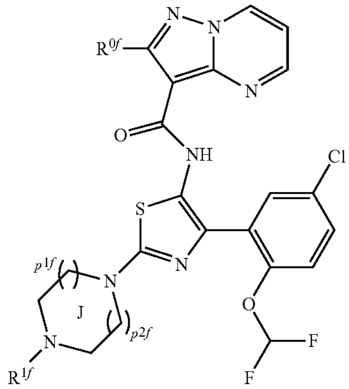

wherein:

$R^{0f}$ is H or $NH_2$;

$R^{1f}$ is selected from the group consisting of $C_1$-$C_6$ alkyl optionally substituted by halo, —C(O)OH, oxetan-3-ylmethyl, 3-6 membered cycloalkyl, 3-11 membered heterocycloalkyl, —S—($C_1$-$C_6$ alkyl), 5-10 membered heteroaryl or phenyl, or 3-11 membered heterocycloalkenyl optionally substituted by oxo; and Ring J is a 6-7 membered heterocycloalkyl wherein $p^{1f}$ is 1 or 2 and $p^{2f}$ is 1 or 2.

In some embodiments, a compound of Formula (00A), (0A) or (A) is further defined as a compound of Formula (VII):

(VII)

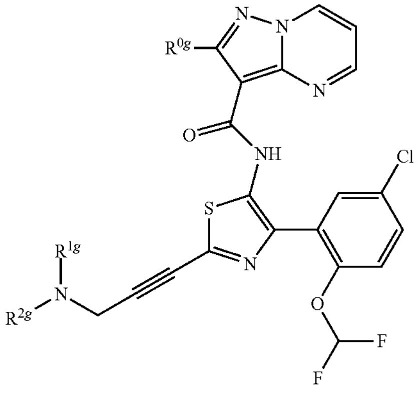

wherein:

$R^{0g}$ is H or $NH_2$;

$R^{1g}$ is selected from the group consisting of $C_1$-$C_6$ alkyl;

$R^{2g}$ is selected from the group consisting of $C_1$-$C_6$ alkyl.

In some embodiments, a compound of Formula (00A), (0A) or (A) is further defined as a compound of Formula (VIII):

(VIII)

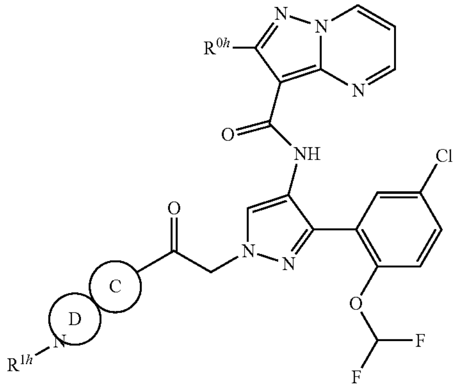

wherein:

$R^{0h}$ is H or $NH_2$;

$R^{1h}$ is selected from the group consisting of H and $C_1$-$C_6$ alkyl optionally substituted by CN, 3-6 membered cycloalkyl, or 4-6 membered heterocycloalkylene-C(O)O—($C_1$-$C_6$ alkylene)-phenyl;

Ring C is 3-7 membered cycloalkyl or 3-7 membered heterocycloalkyl; and

Ring D is a 3-7 membered heterocycloalkyl substituted at the sole nitrogen by $R^{1h}$; and provided Rings C and D together form a 3-11 membered spiro heterocycloalkyl.

In some embodiments, a compound of Formula (00A), (0A) or (A) is further defined as a compound of Formula (IX):

(IX)

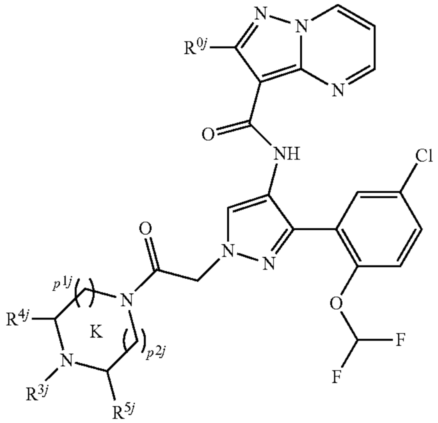

wherein:

$R^{0j}$ is H or $NH_2$;

$R^{3j}$ is selected from the group consisting of H and $C_1$-$C_6$ alkyl optionally substituted by OH, 3-6 membered cycloalkyl, —O—($C_1$-$C_6$ alkyl), —O—($C_1$-$C_6$ alkyl)-OH, —$SO_2$—($C_1$-$C_6$ alkyl) and phenyl, wherein the phenyl is optionally substituted by CN;

$R^{4j}$ is selected from the group consisting of H and $C_1$-$C_6$ alkyl optionally substituted by OH;

or $R^{3j}$ and $R^{4j}$ together form a 4-6-membered heterocycloalkyl;

$R^{5j}$ is selected from the group consisting of H and $C_1$-$C_6$ alkyl; and

Ring K is a 6-7 membered heterocycloalkyl wherein $p^{1j}$ is 1 or 2 and $p^{2j}$ is 1 or 2.

In some embodiments, a compound of Formula (00A), (0A) or (A) is further defined as a compound of Formula (X):

(X)

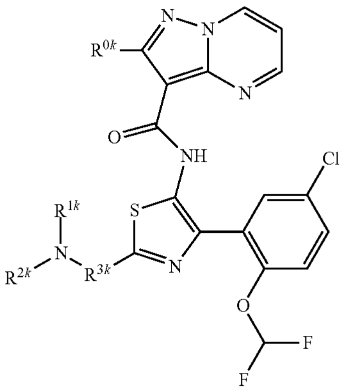

wherein:

$R^{0k}$ is H or $NH_2$;

$R^{1k}$ is selected from the group consisting of a. H, b. $C_1$-$C_6$ alkyl optionally substituted by halo, CN, or phenyl, c. —($C_1$-$C_6$ alkylene)-3-6 membered cycloalkyl wherein the cycloalkyl is optionally substituted by CN, d. —($C_1$-$C_6$ alkylene)-4-6 membered heterocycloalkyl wherein the heterocycloalkyl is optionally substituted by $C_1$-$C_6$ alkyl;

$R^{2k}$ is selected from the group consisting of H and $C_1$-$C_6$ alkyl;

or $R^{1k}$ and $R^{2k}$ together form a 3-11 membered heterocycloalkyl optionally substituted by halo; $C_1$-$C_6$ alkyl optionally substituted by OH; or —$NR^vR^w$, wherein $R^v$ and $R^w$ are independently H or $C_1$-$C_6$ alkyl optionally substituted by halo; and $R^{3k}$ is a bond, methylene, or —C(=O)—.

In some embodiments, $X^A$ and $X^B$ are independently selected from the group consisting of 3-6-membered cycloalkyl, 6-10 membered aryl, 5-6 membered heterocycloalkenyl, and 5-10 membered heteroaryl, wherein each of $X^A$ and $X^B$ are independently optionally substituted by $Y^1$.

In some embodiments, either $X^A$ or $X^B$ is a 3-11 membered heterocycloalkyl optionally substituted by $Y^1$.

In some embodiments, Ring Q is (i). In some embodiments Ring Q is (ii).

In some embodiments, $t^1$ is 0. In some embodiments, $t^1$ is 1.

In some embodiments, $R^0$, $R^{00}$ and $R^1$ are each H.

In some embodiments, $R^0$ is $NH_2$.

In some embodiments, Ring Q is (i), $t^1$ is 0 or 1, and $R^0$, $R^{00}$ and $R^{01}$ are each H.

In some embodiments, Ring Q is (ii), $t^2$ is 0 or 1, and $R^0$, $R^{00}$ and $R^1$ are each H.

In some embodiments, Ring Q is (i), $t^1$ is 1, and $X^A$ is $NR^aR^b$, wherein $R^a$ and $R^b$ are each independently H, $C_1$-$C_6$ alkyl optionally substituted with 5-6 membered heteroaryl, or 3-6 membered cycloalkyl optionally substituted by OH, halo, CN, or $C_1$-$C_6$ alkyl optionally substituted by OH.

In some embodiments, Ring Q is (i), $t^1$ is 0, and $X^A$ is $C_1$-$C_6$ alkyl or 3-6 membered cycloalkyl, wherein $X^A$ is optionally substituted by —$NR^aR^b$, wherein $R^a$ and $R^b$ are independently H or $C_1$-$C_6$ alkyl.

In some embodiments, a compound is selected from Table 1 or of Examples 1-468.

Also provided is a pharmaceutical composition comprising a 5-chloro-2-difluoromethoxyphenyl pyrazolopyrimidine compound as described herein, such as a compound of Formula (00A), (0A) or (A), or a subformula thereof, and a pharmaceutically acceptable carrier, diluent or excipient.

Use of a 5-chloro-2-difluoromethoxyphenyl pyrazolopyrimidine compound as described herein, such as a compound of Formula (00A), (0A) or (A), or a subformula thereof, in therapy is also provided.

Use of a 5-chloro-2-difluoromethoxyphenyl pyrazolopyrimidine compound as described herein, such as a compound of Formula (00A), (0A) or (A), or a subformula thereof, in the treatment of an inflammatory disease, such as asthma, is also provided.

Use of a 5-chloro-2-difluoromethoxyphenyl pyrazolopyrimidine compound as described herein, such as a compound of Formula (00A), (0A) or (A), or a subformula thereof, for the preparation of a medicament for the treatment of an inflammatory disease, such as asthma, is also provided.

Also provided is a 5-chloro-2-difluoromethoxyphenyl pyrazolopyrimidine compound as described herein, such as a compound of Formula (00A), (0A) or (A), or a subformula thereof, for use in the treatment of an inflammatory disease, such as asthma.

Also provided is a method of preventing, treating or lessening the severity of a disease or condition responsive to the inhibition of a Janus kinase activity in a patient, comprising administering to the patient a therapeutically effective amount of a 5-chloro-2-difluoromethoxyphenyl pyrazolopyrimidine compound as described herein, such as a compound of Formula (00A), (0A) or (A), or a subformula thereof. In some embodiments, the disease or condition is asthma. In some embodiments, the Janus kinase is JAK1. In some embodiments, a compound is administered via inhalation.

In some embodiments, such as a compound of Formula (00A), (0A) or (A), $R^{00}$ is H or $CH_3$; $R^{01}$ is H or $NH_2$; $R^0$ is H or $NH_2$; and Ring Q is either (i) or (ii):

(i)

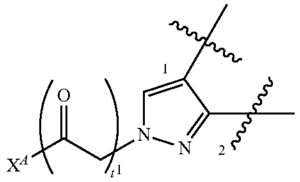

(ii)

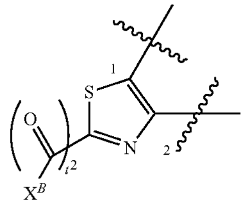

, wherein $t^1$ and $t^2$ are each independently 0 or 1, and $X^A$ and $X^B$ are each independently selected from the group consisting of:

-continued
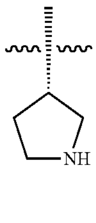
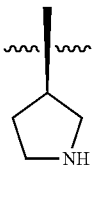
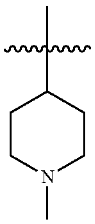
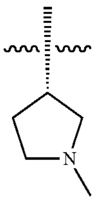
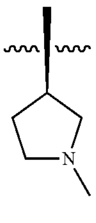
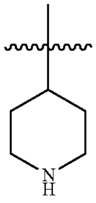
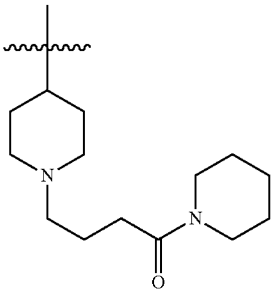
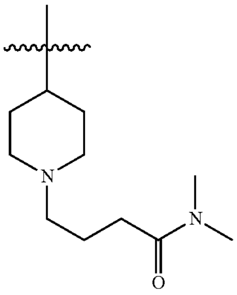
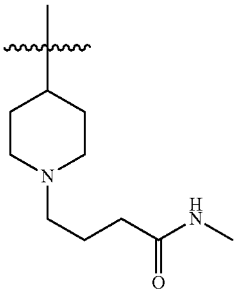
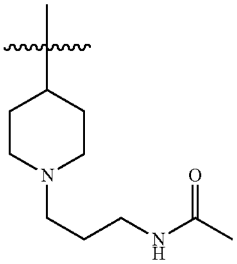
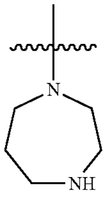
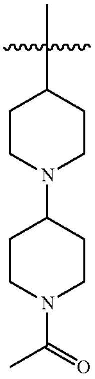
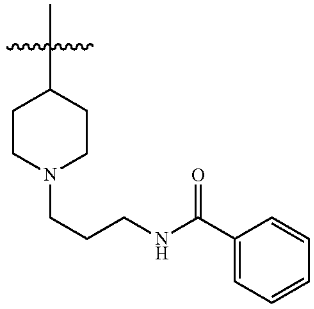
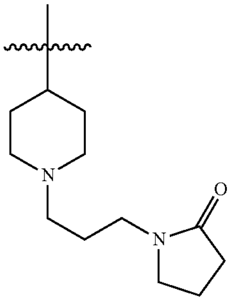
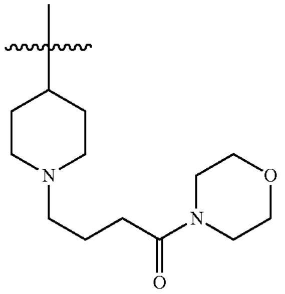
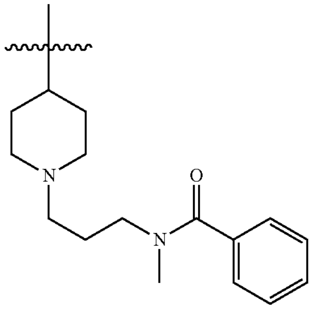
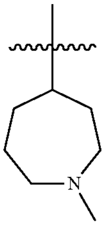
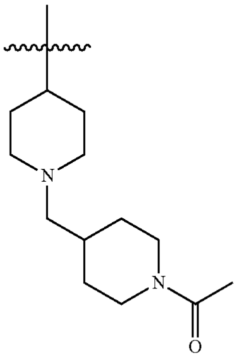
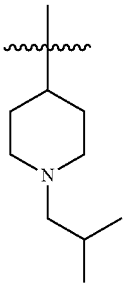
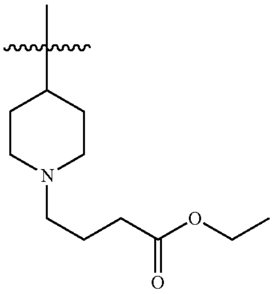
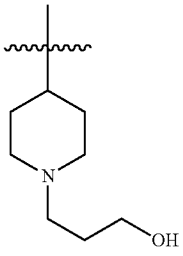
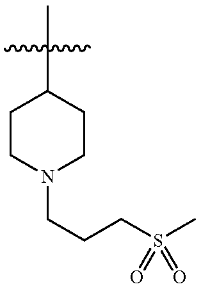
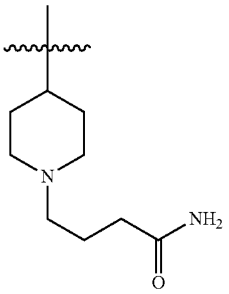

-continued
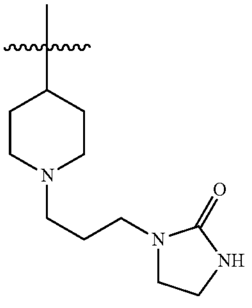
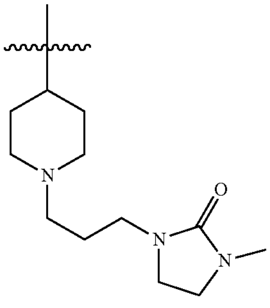
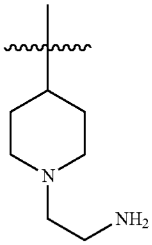
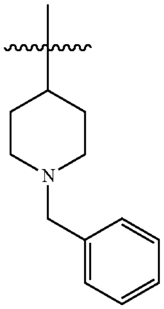
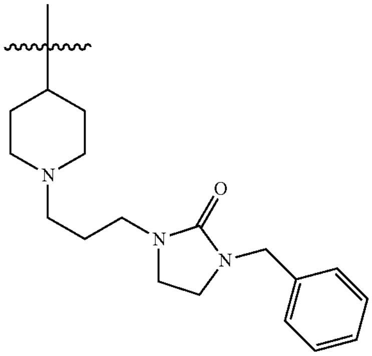
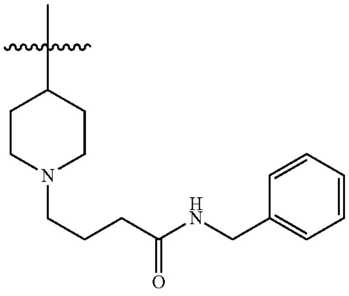
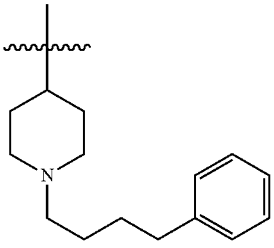
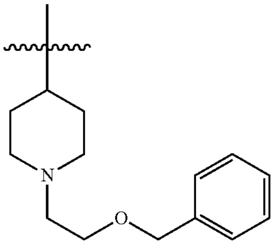
-continued
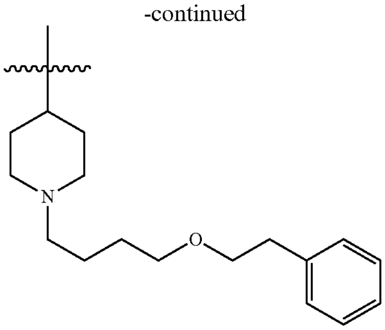
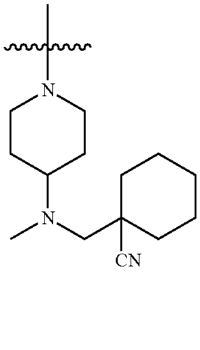
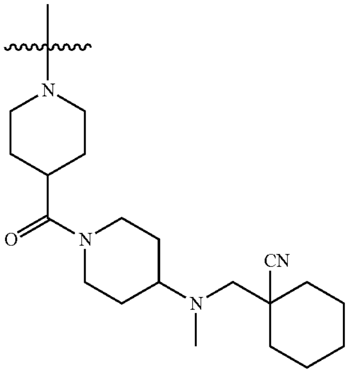
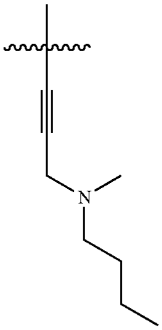
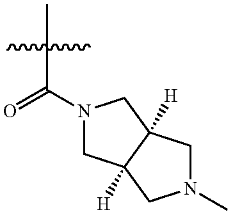
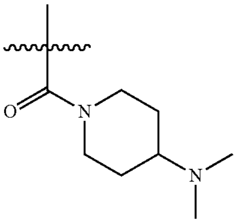
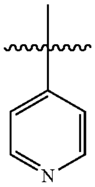
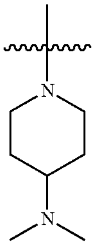
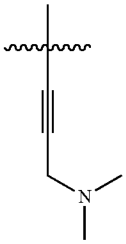
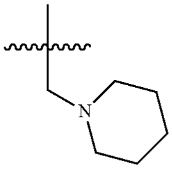
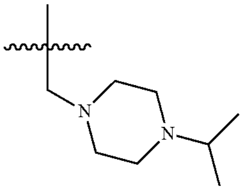
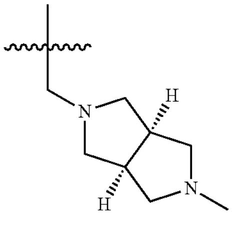
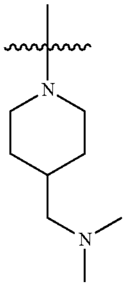
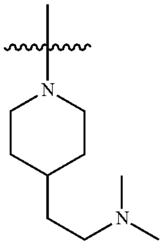

-continued
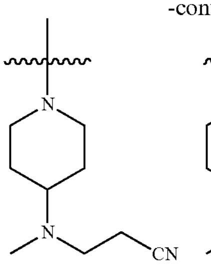
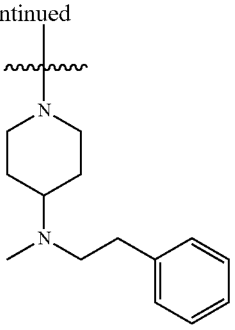
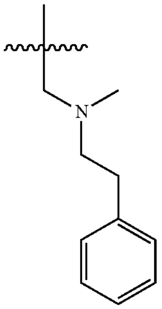
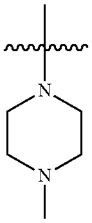
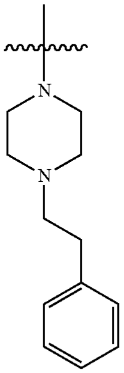
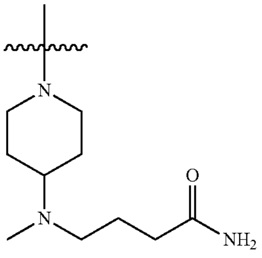
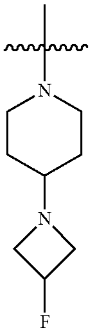
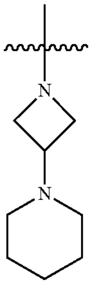
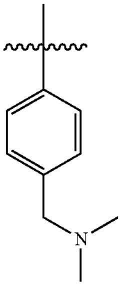
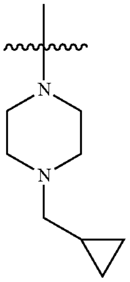
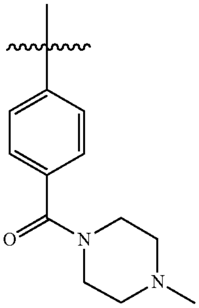
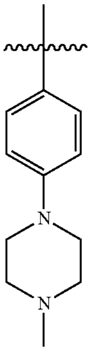
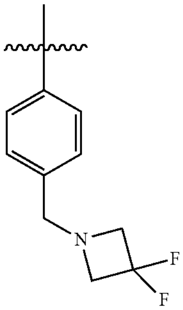
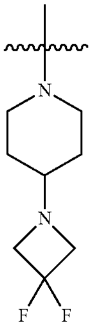
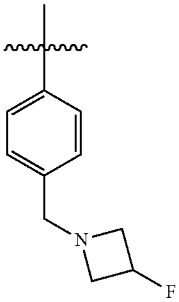
-continued
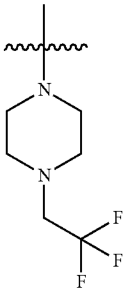
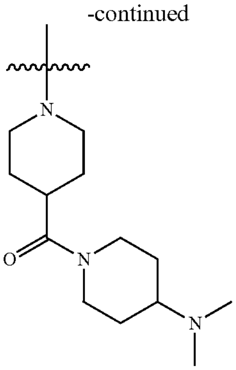
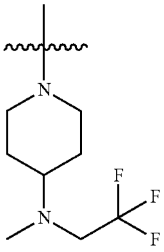
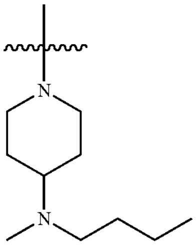
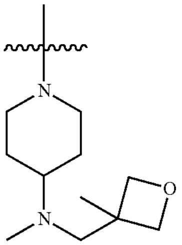
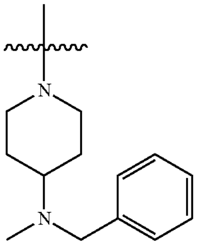
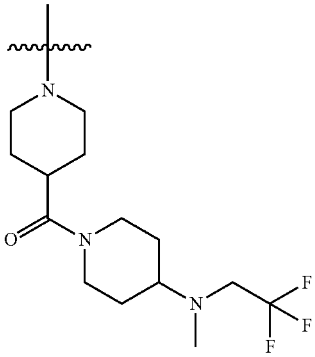
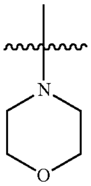
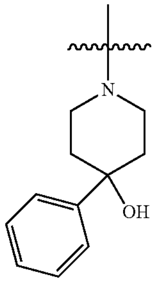
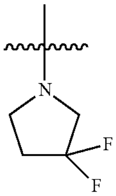
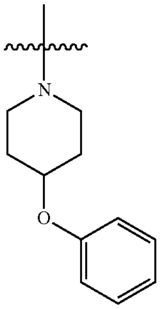
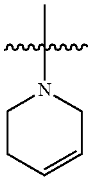
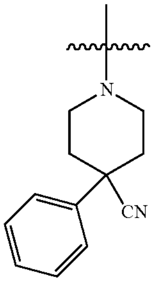
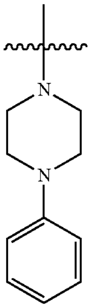

-continued
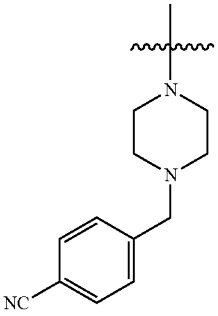
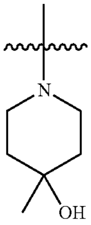
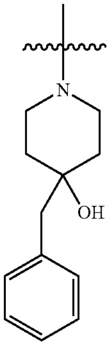
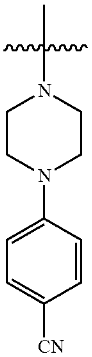
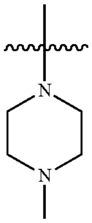
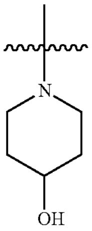
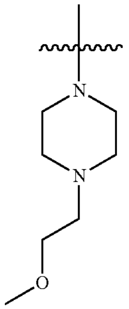
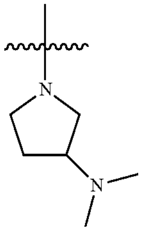
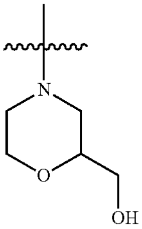
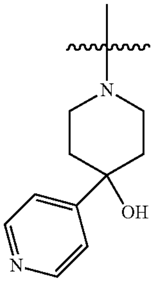
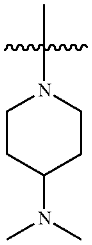
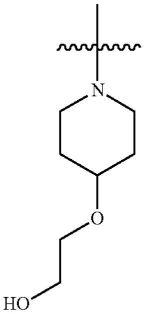
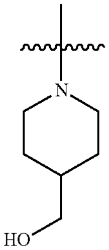
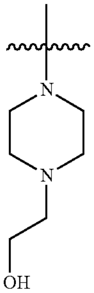
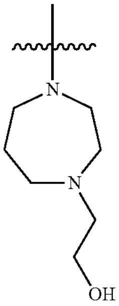
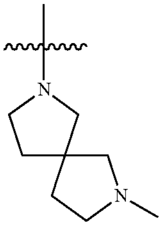
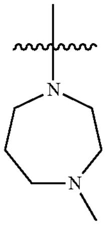
-continued
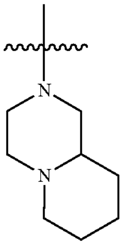
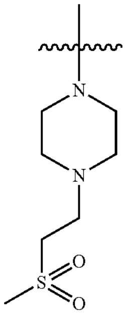
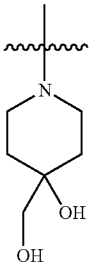
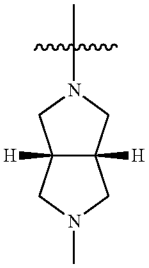
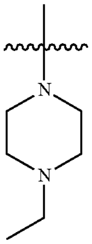
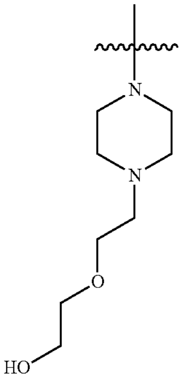
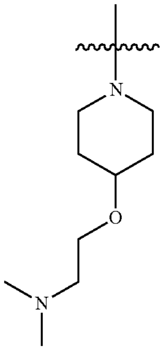
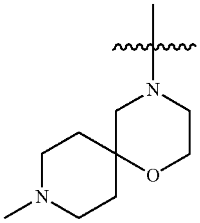
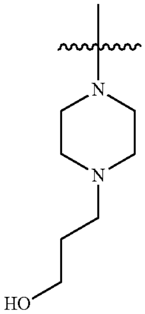
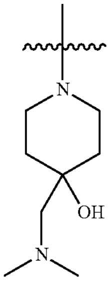
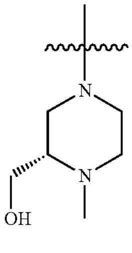
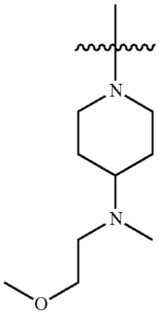
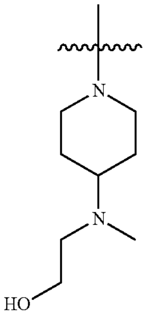
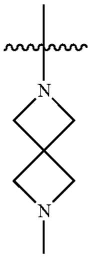
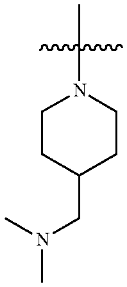
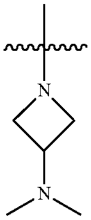
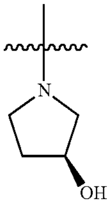
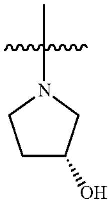

-continued
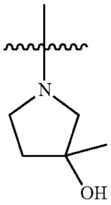 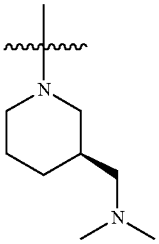 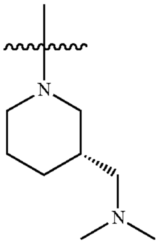
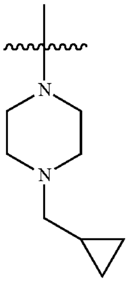 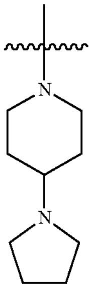 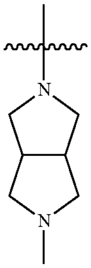 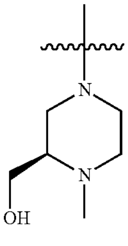
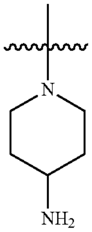 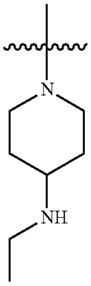 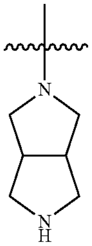 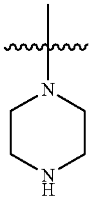 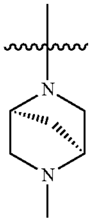
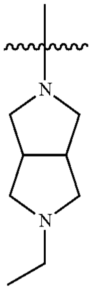 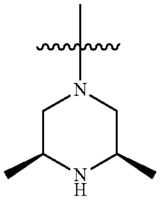 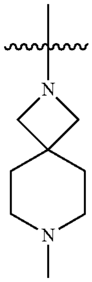 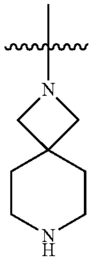
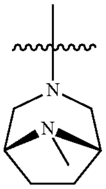 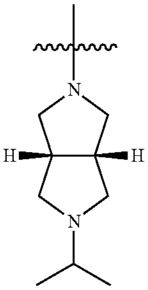 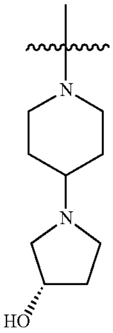 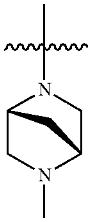
-continued
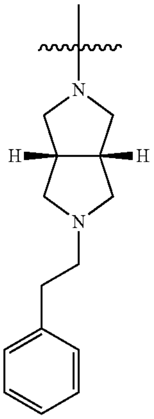 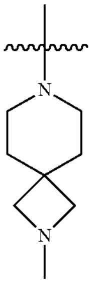 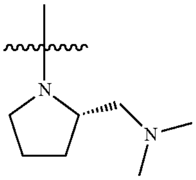
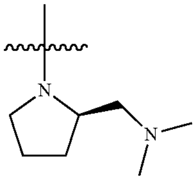 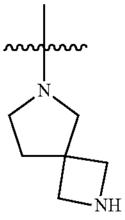 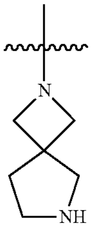 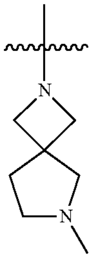
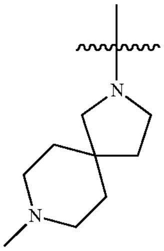 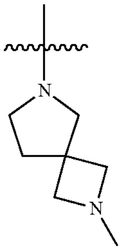 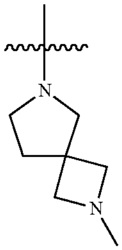 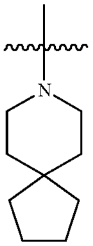
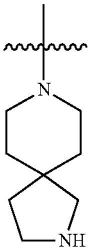 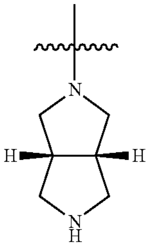 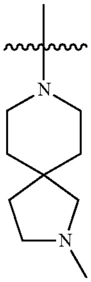 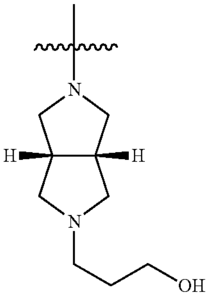
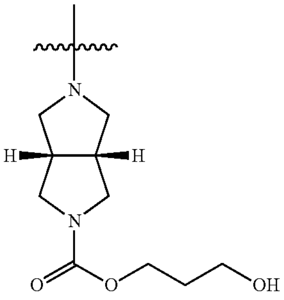 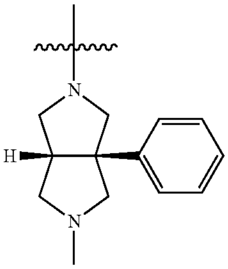

-continued
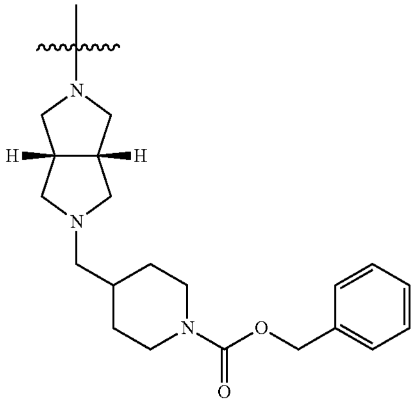
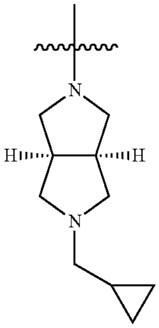
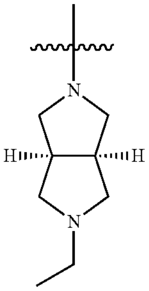
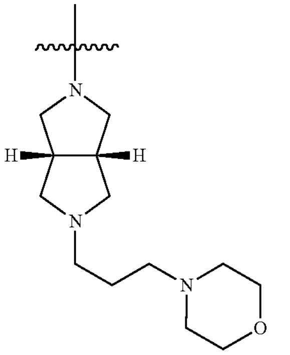
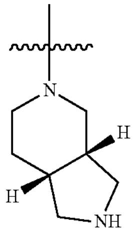
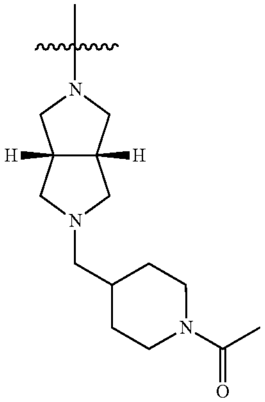
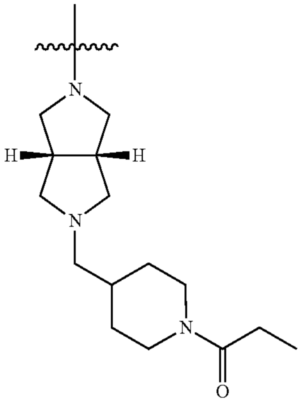
-continued
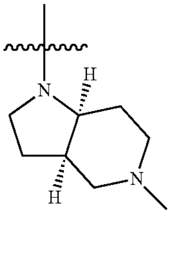
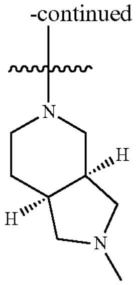
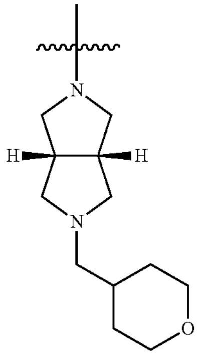
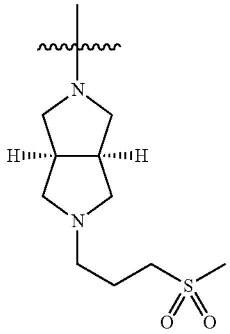
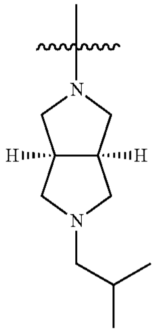
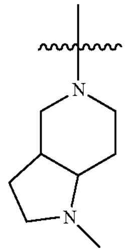
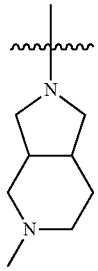
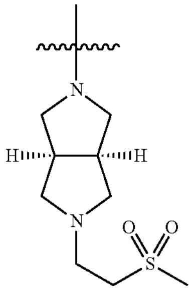
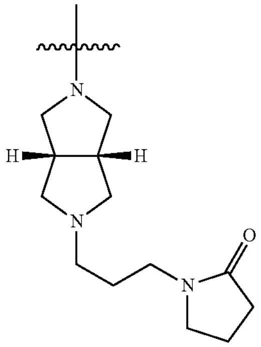
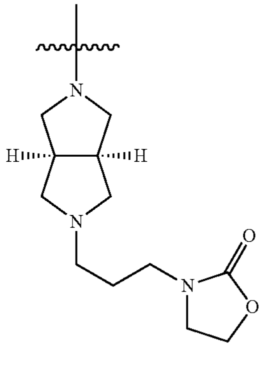
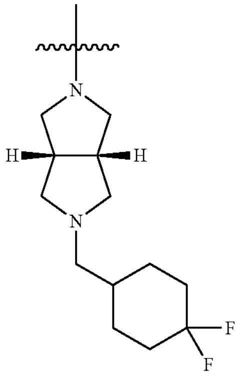

-continued
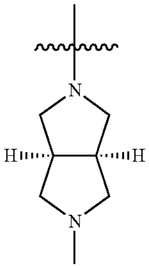
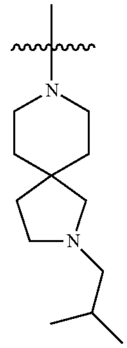
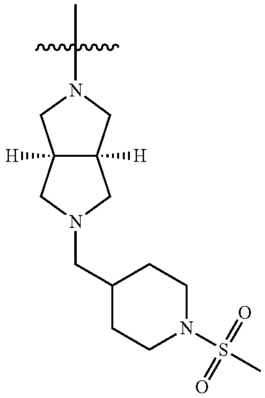
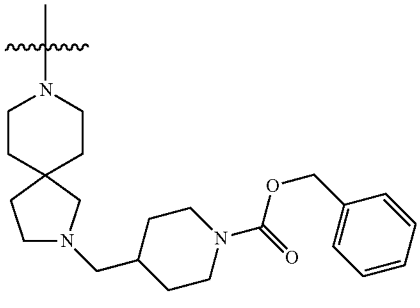
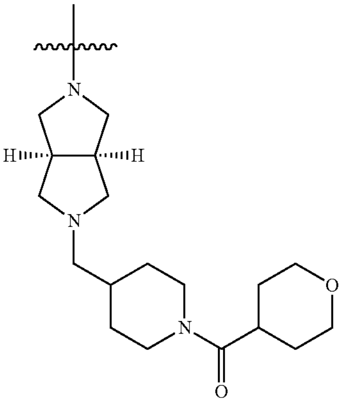
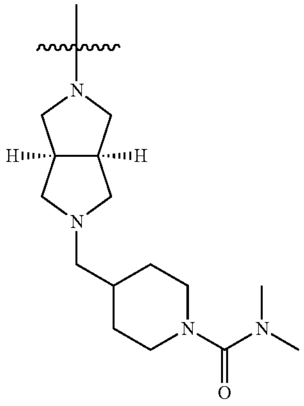
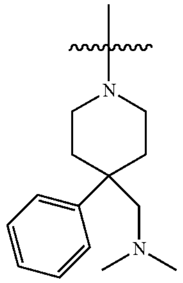
-continued
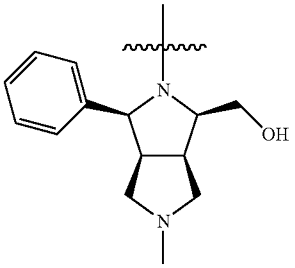
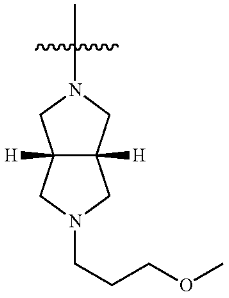
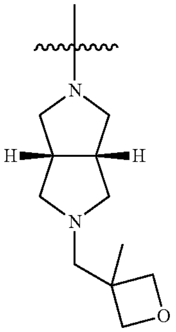
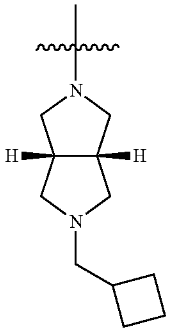
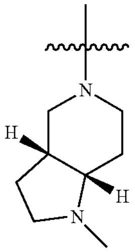
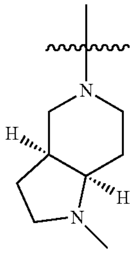
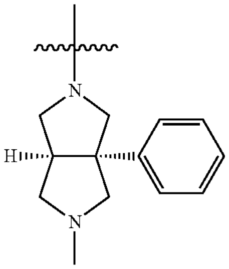
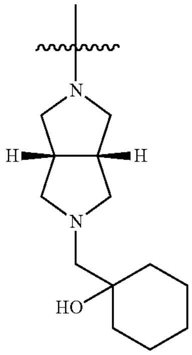
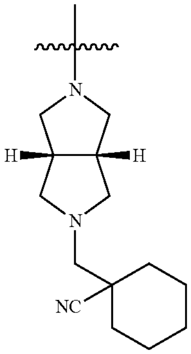
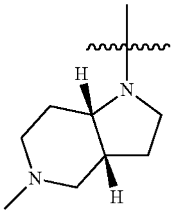
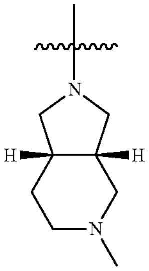
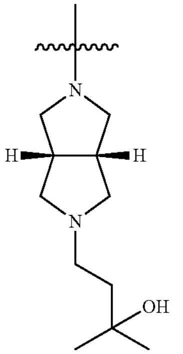
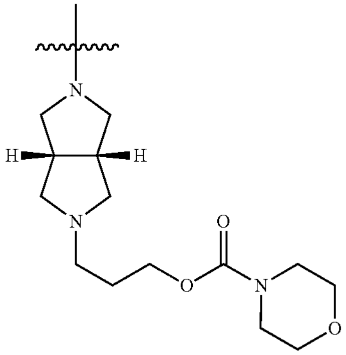

-continued
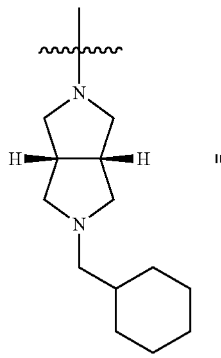
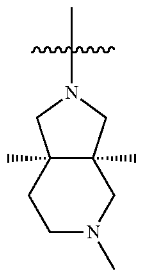
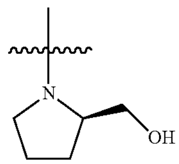
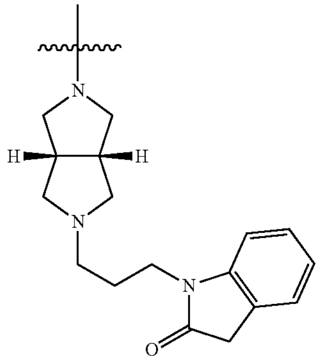
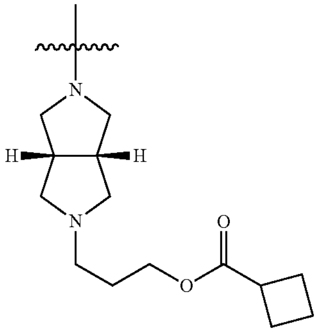
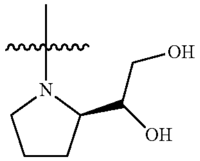
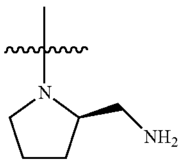
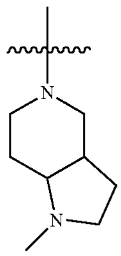
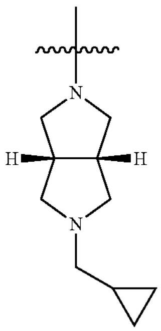
-continued
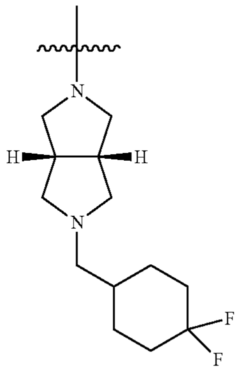
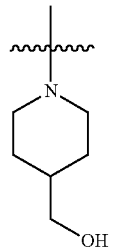
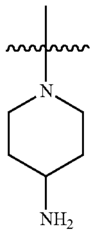
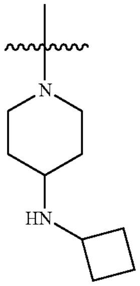
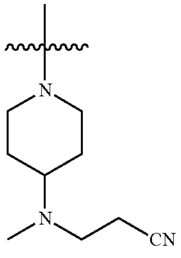
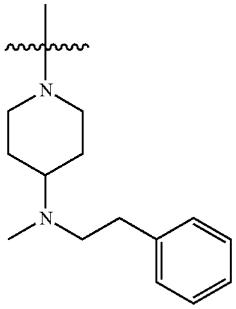
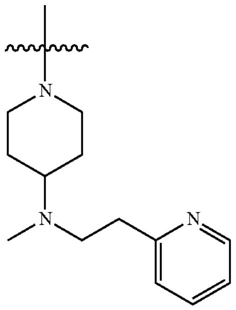
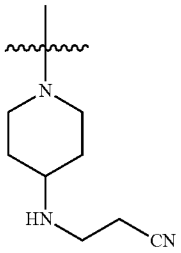
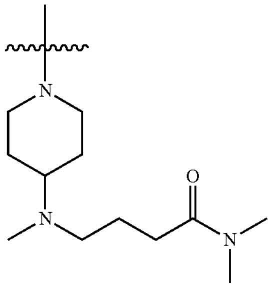
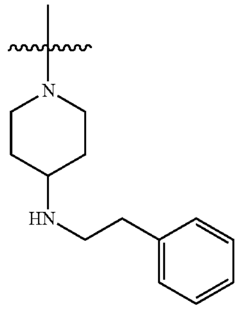
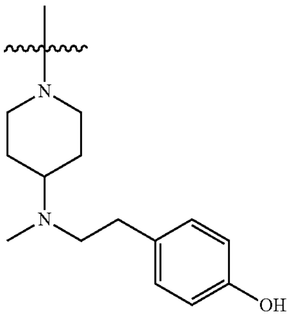

-continued
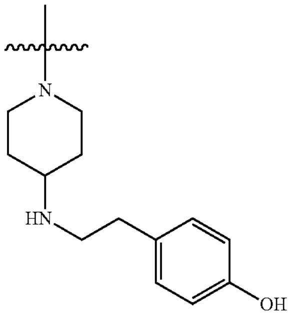
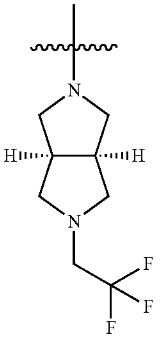
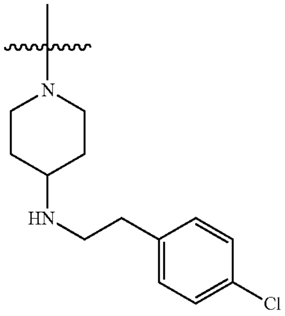
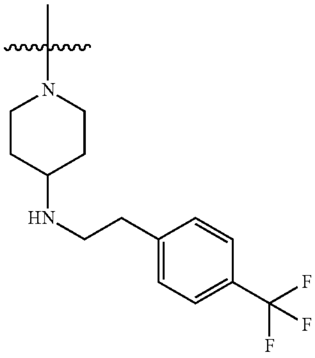
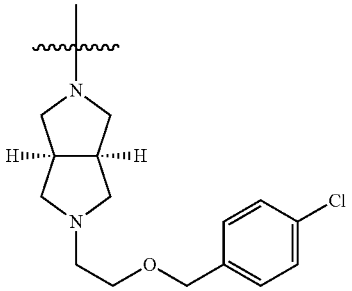
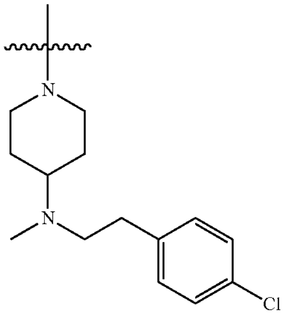
-continued
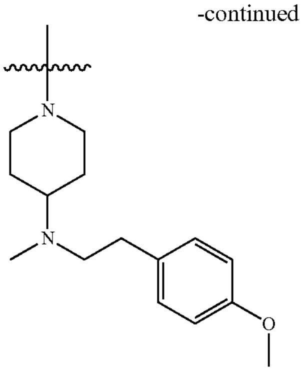
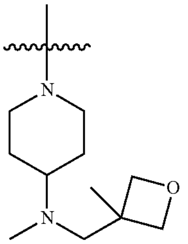
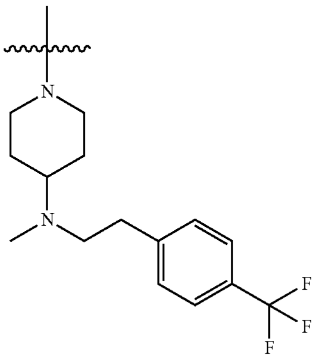
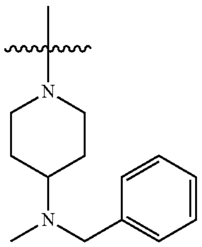
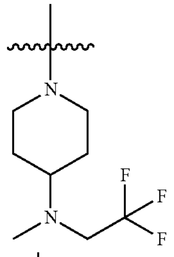
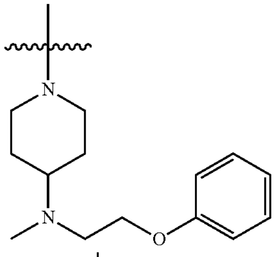
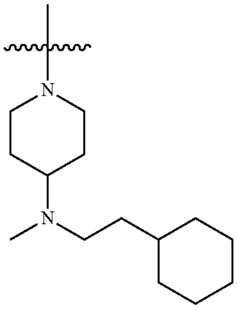
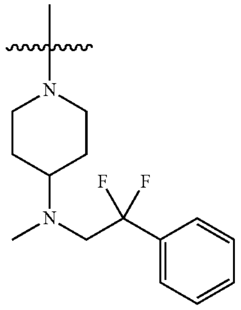
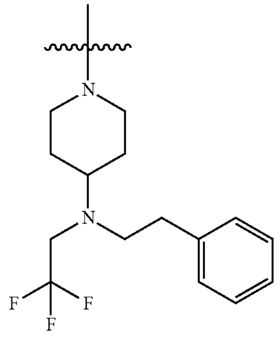

-continued
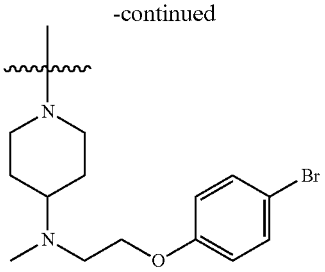
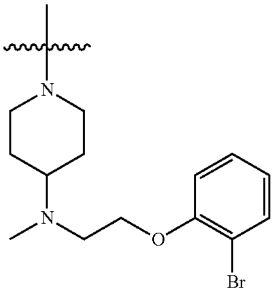
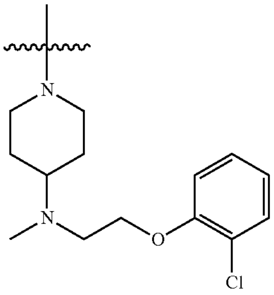
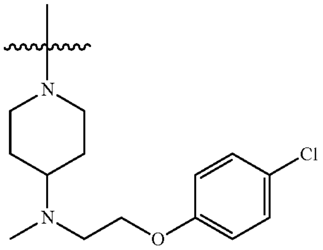
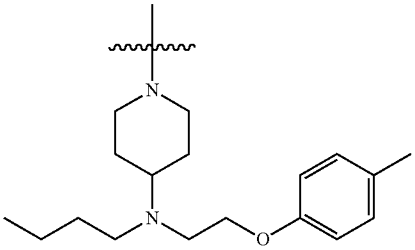
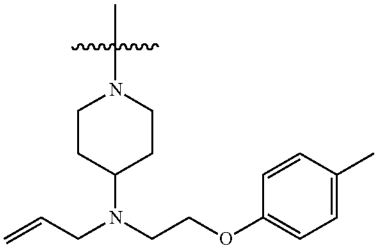
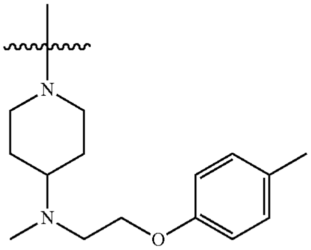
-continued
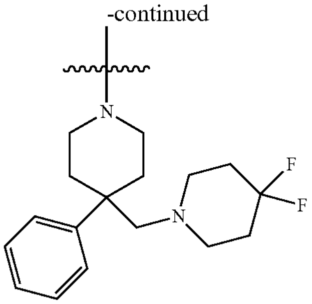
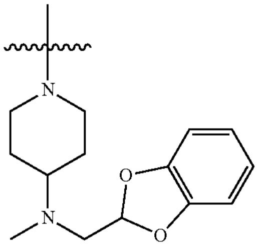
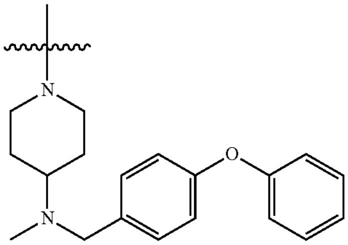
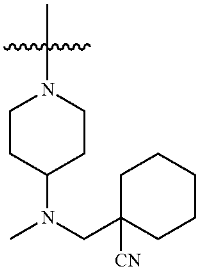
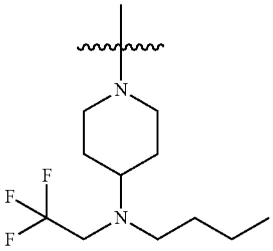
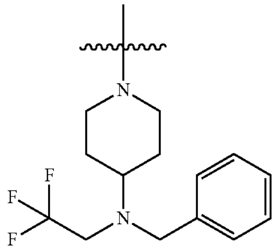
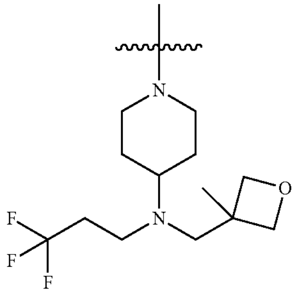

-continued
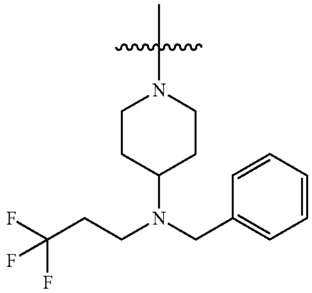
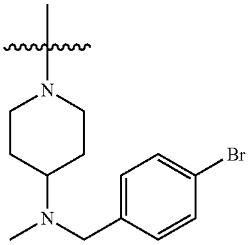
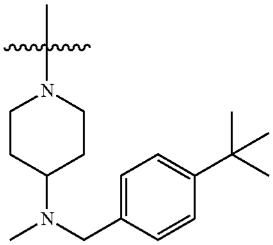
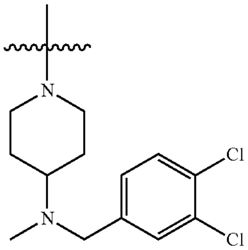
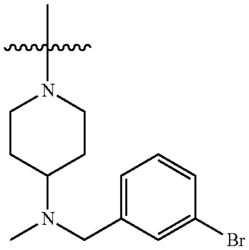
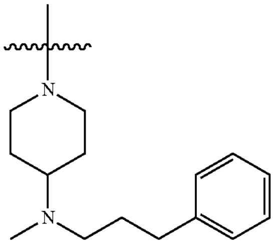
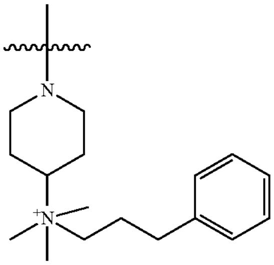
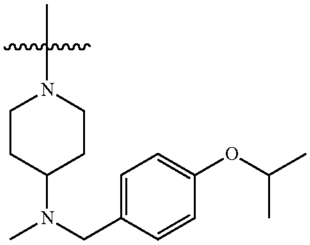
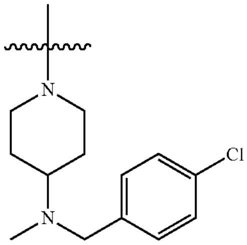
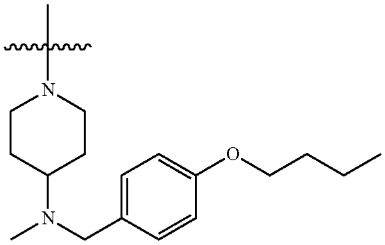
-continued
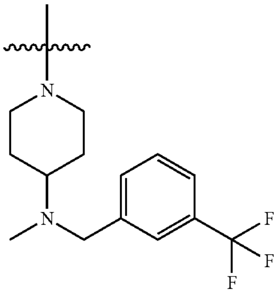
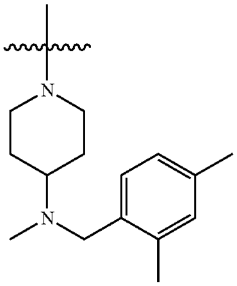
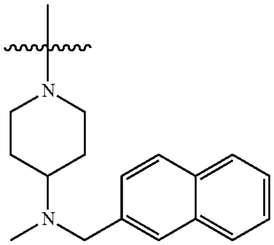
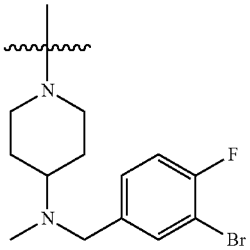
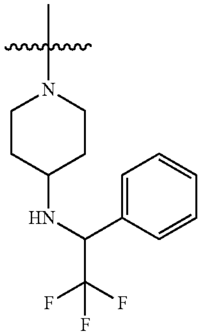
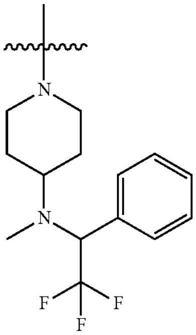
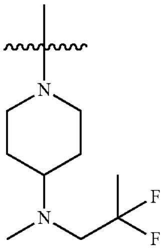
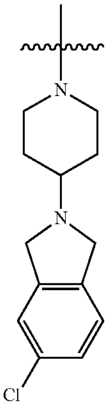
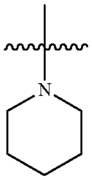
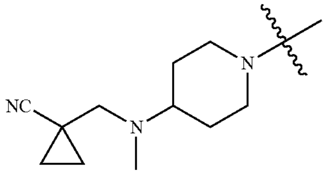
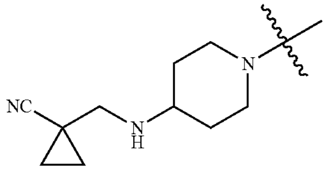
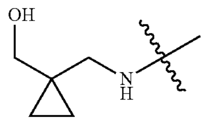

-continued
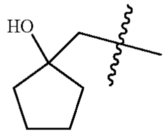
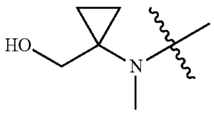
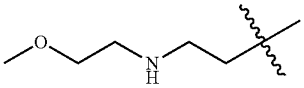
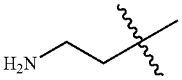
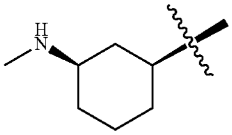
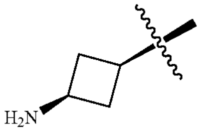
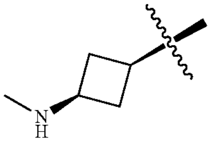
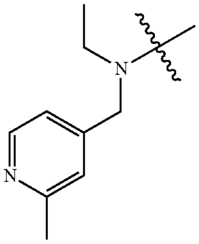
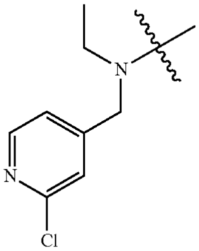
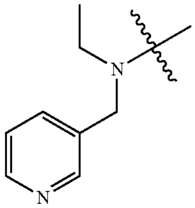
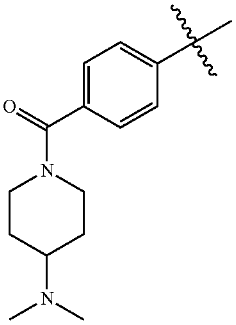
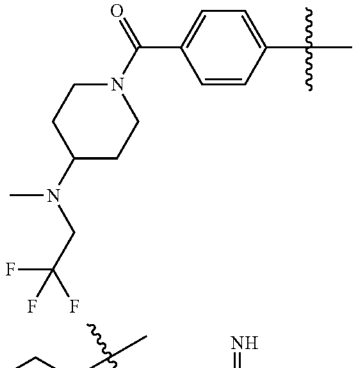
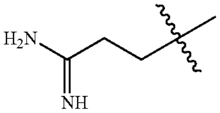
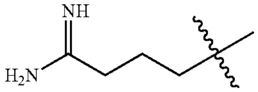
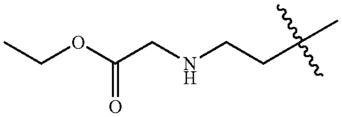
-continued
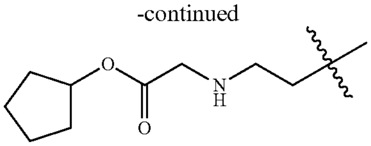
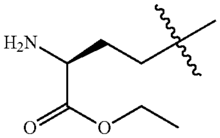
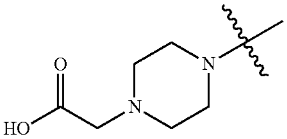
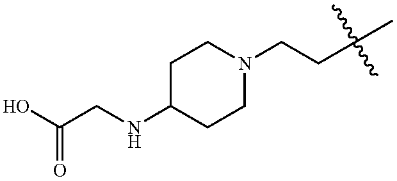
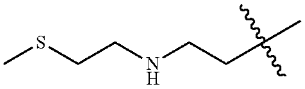
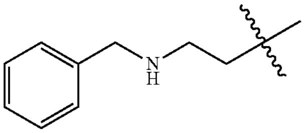
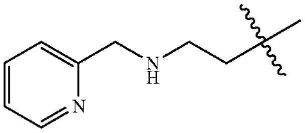
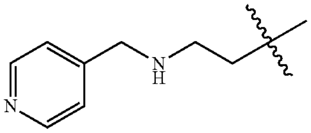
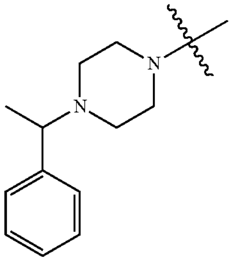
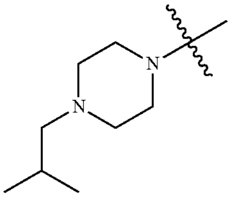
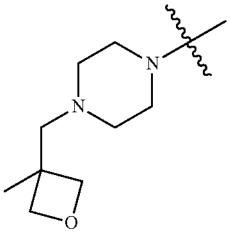
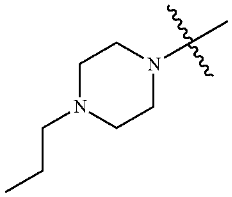
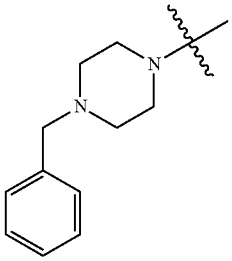

-continued
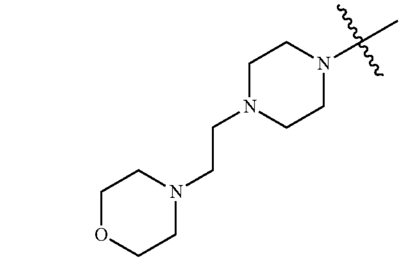
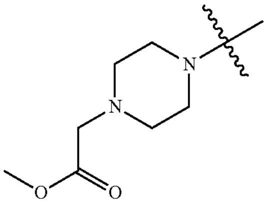
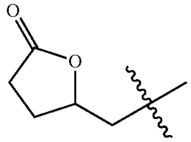
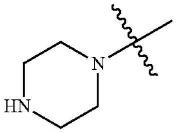
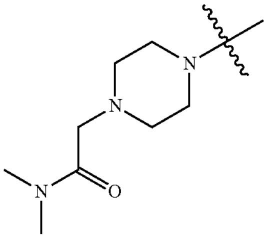
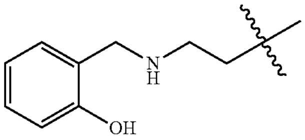
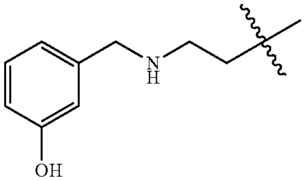
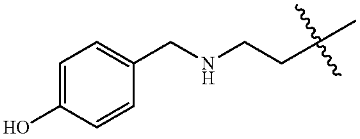
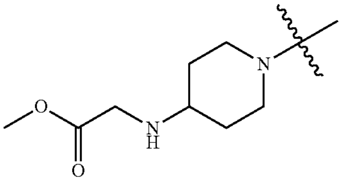
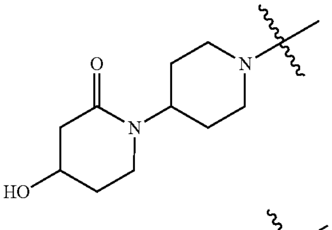
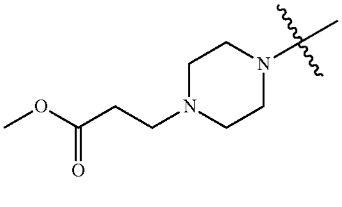
-continued
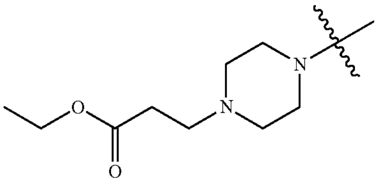
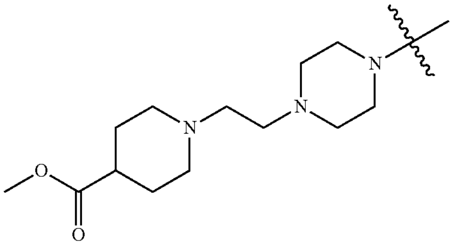
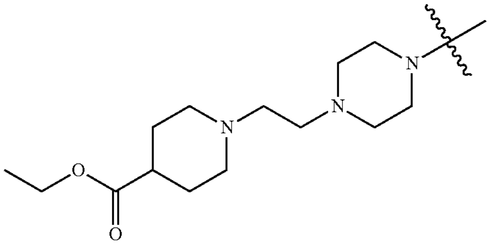
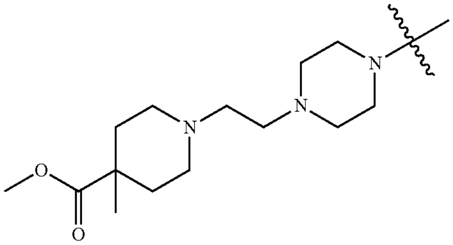
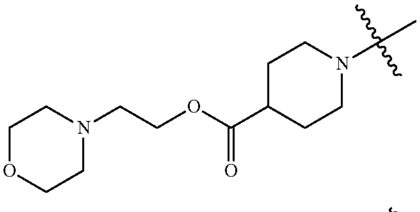
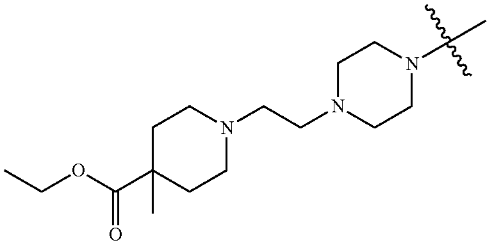
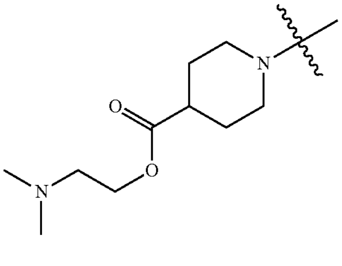

-continued
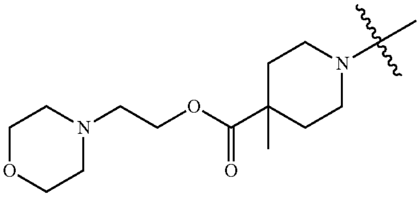
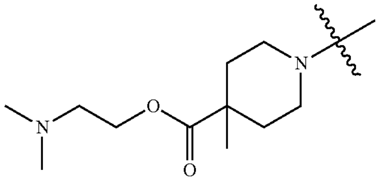
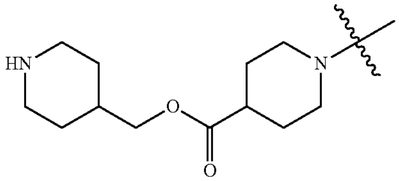
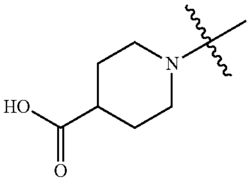
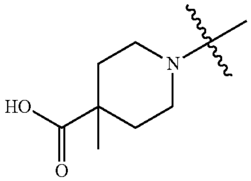
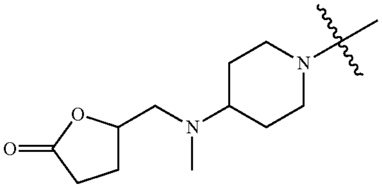
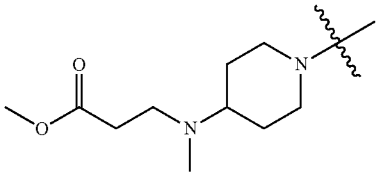
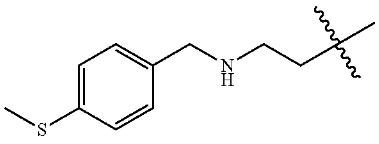
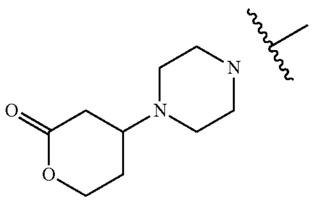
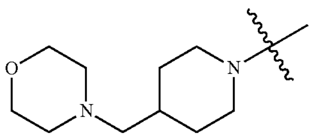
-continued
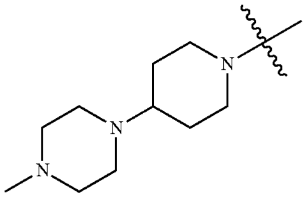
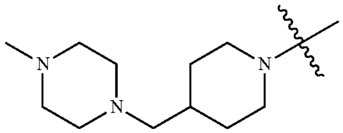
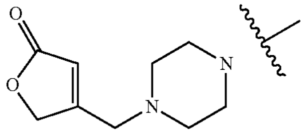
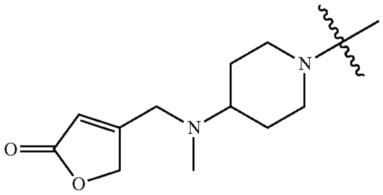
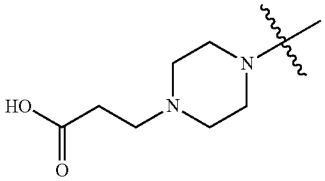
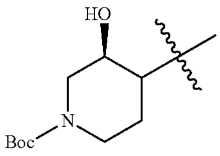
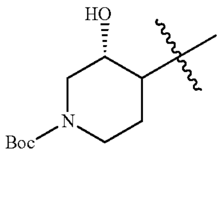
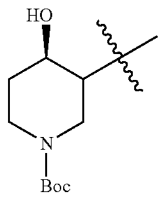
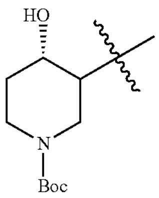
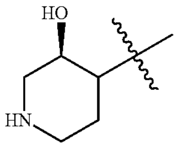
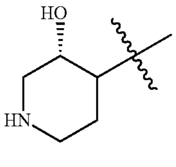
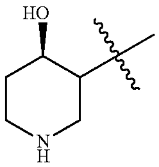
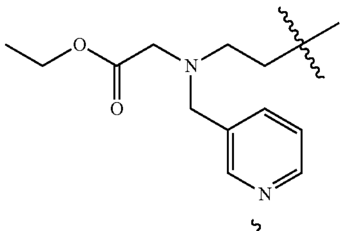
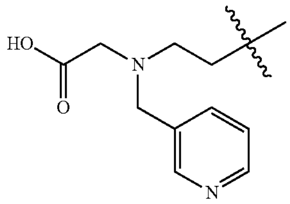

-continued
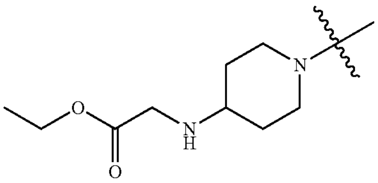
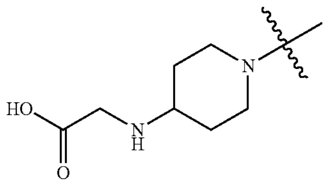
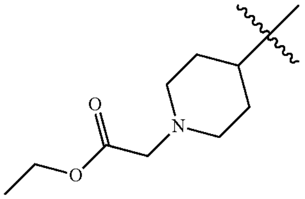
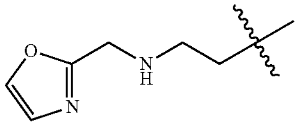
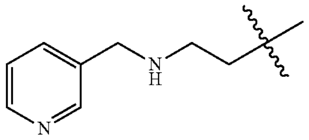
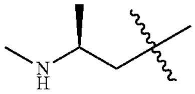
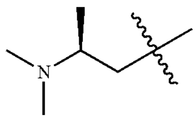
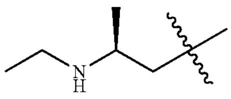
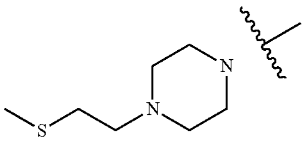
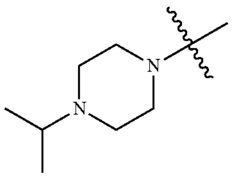
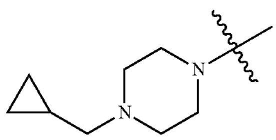
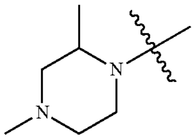
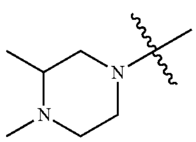
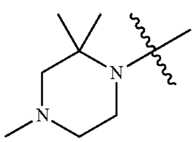
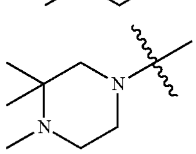
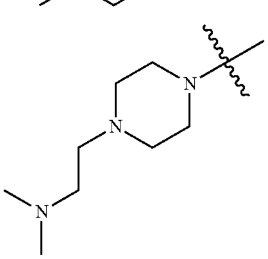
-continued
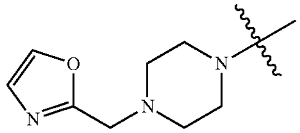
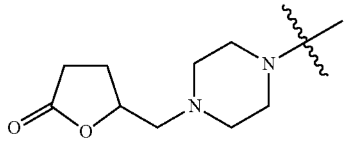
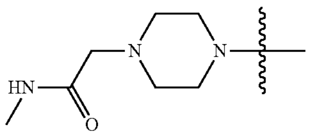
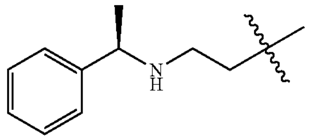
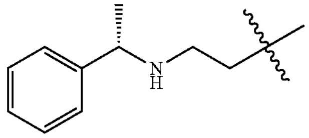
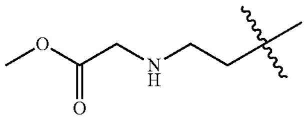
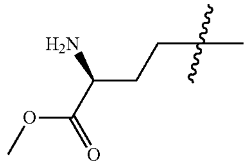
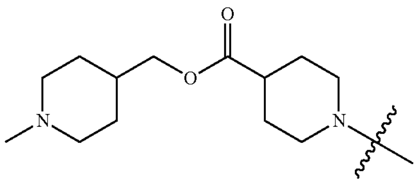
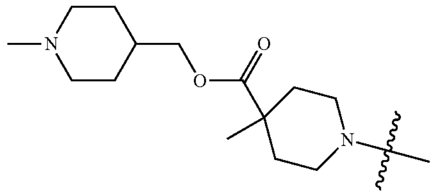
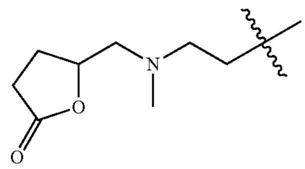
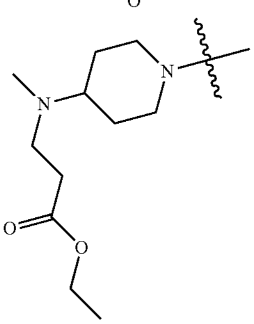
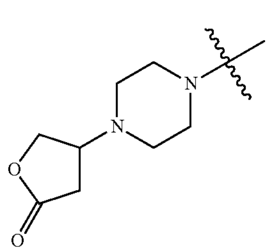

-continued
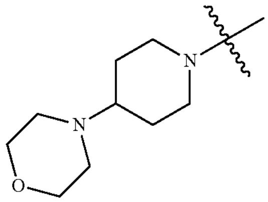
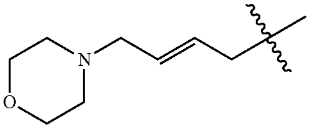
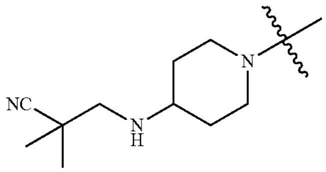
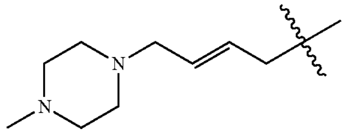
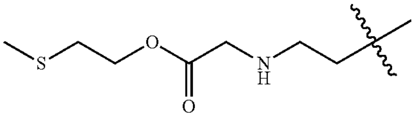
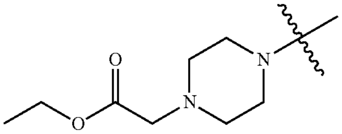
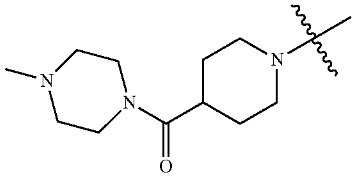
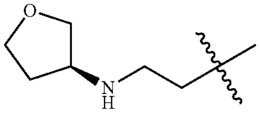
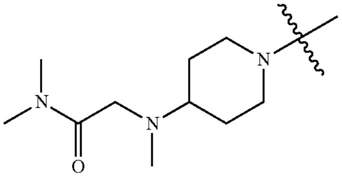
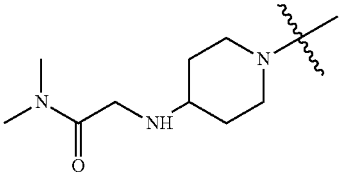
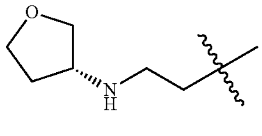
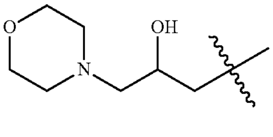
-continued
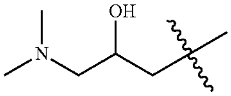
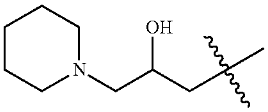
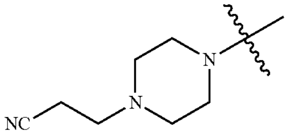
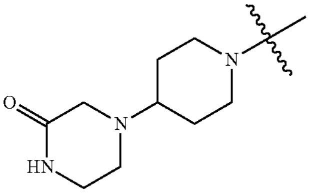
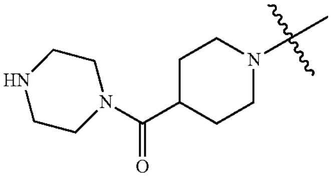
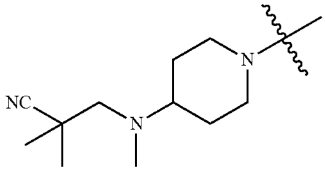
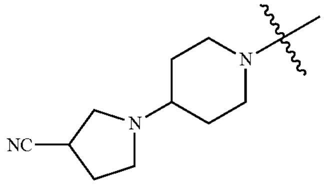
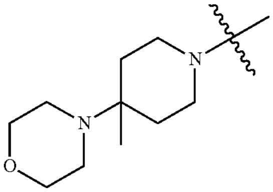
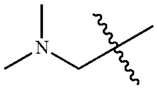
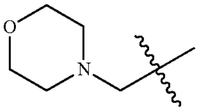
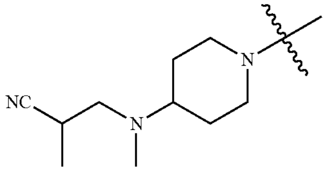
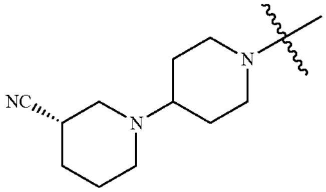

-continued
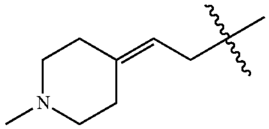
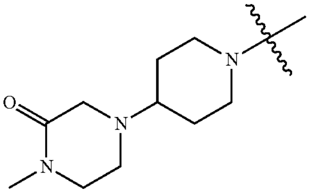
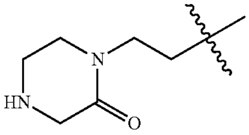
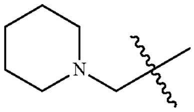
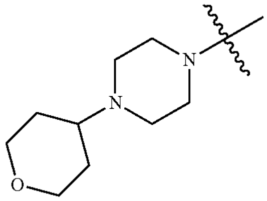
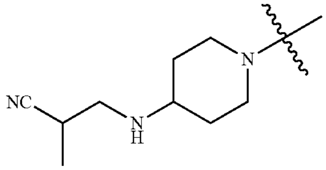
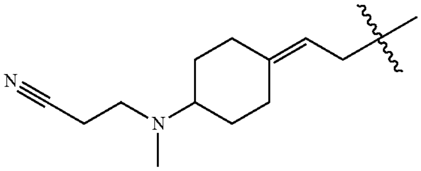
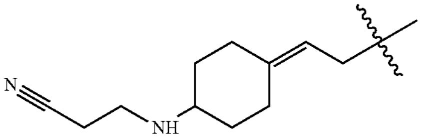
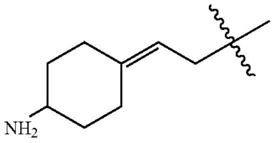
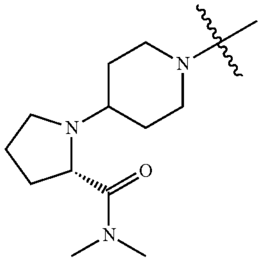
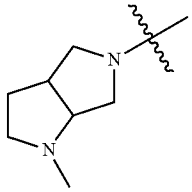
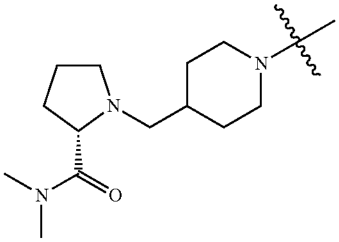
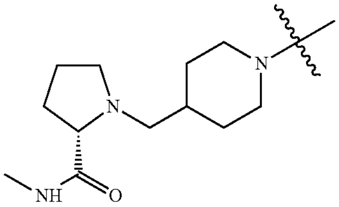
-continued
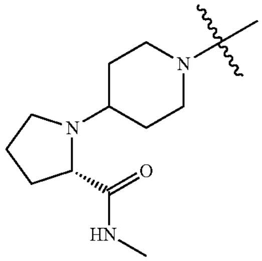
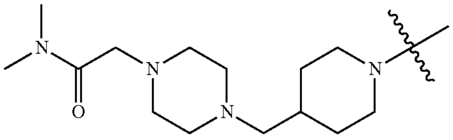
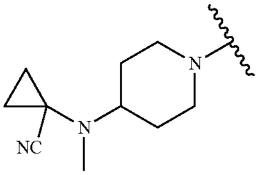
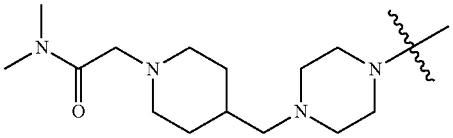
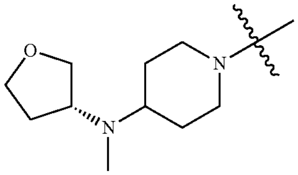
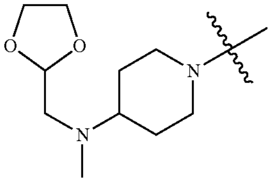
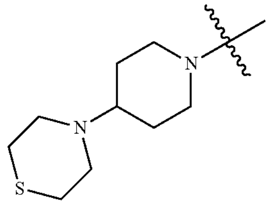
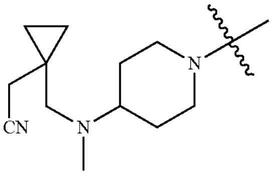
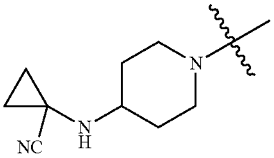
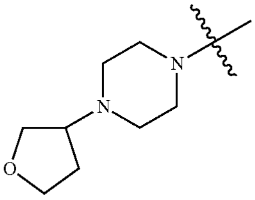
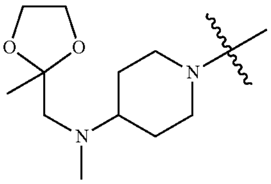
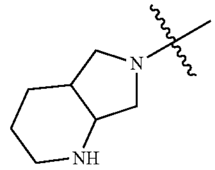
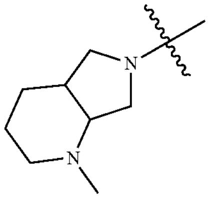

-continued
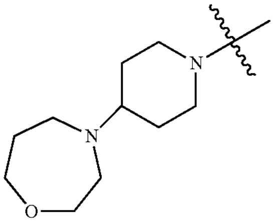
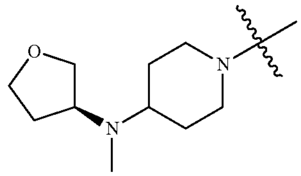
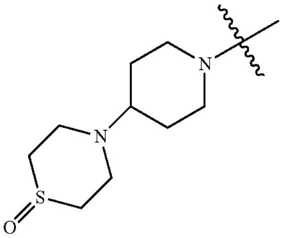
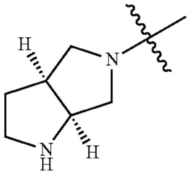
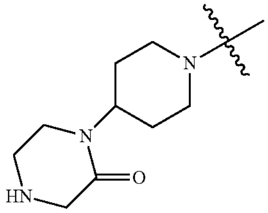
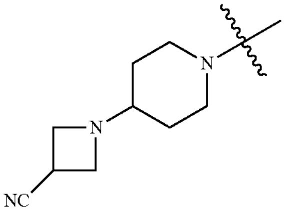
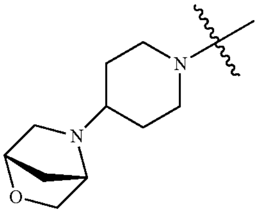
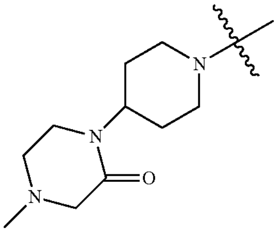
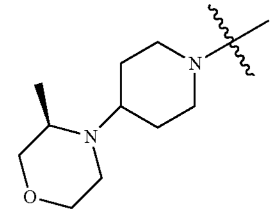
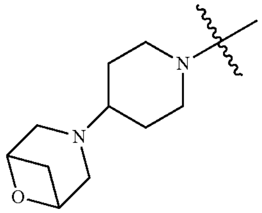
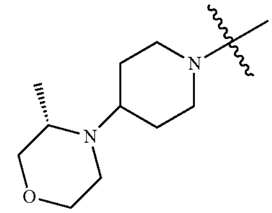
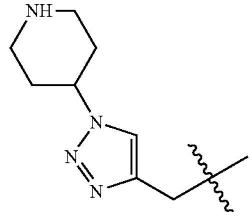
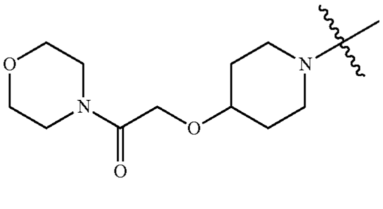
-continued
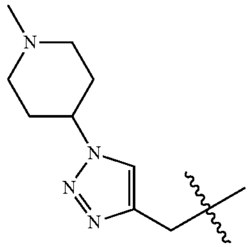
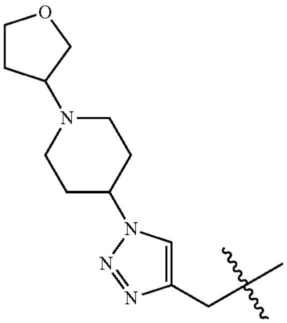
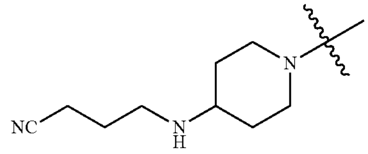
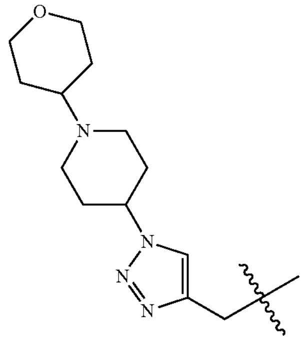
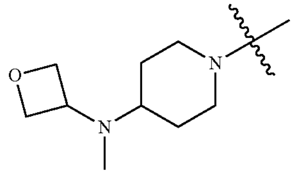
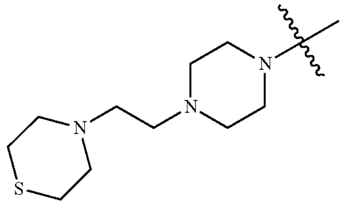
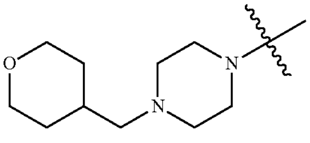
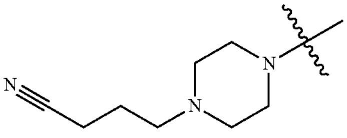
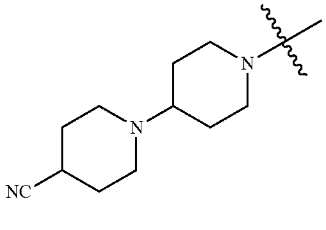

-continued
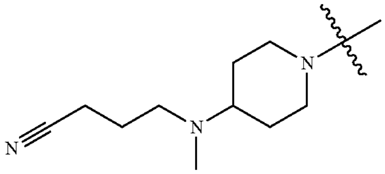
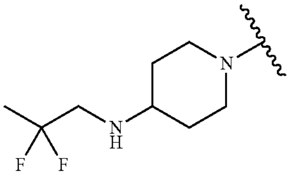
In some embodiments, such as a compound of Formula (00A), (0A) or (A), $R^{00}$ is H or $CH_3$; $R^{01}$ is H or $NH_2$; $R^0$ is H or $NH_2$; and Ring Q is either (i) or (ii):
(i)
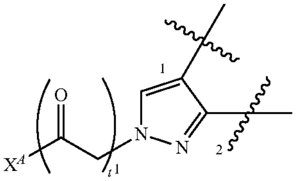
(ii)
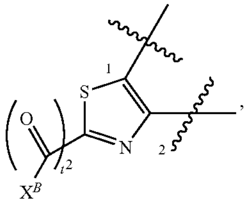
,
wherein $t^1$ and $t^2$ are each independently 0 or 1, and $X^A$ and $X^B$ are each independently selected from the group consisting of:
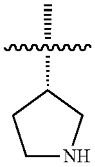
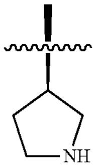
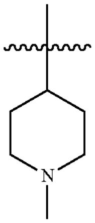
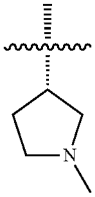
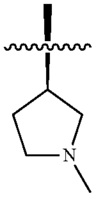
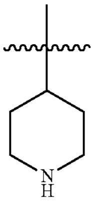
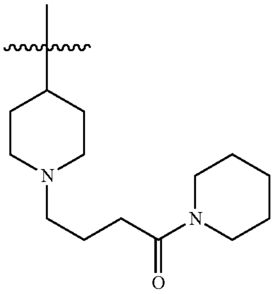
-continued
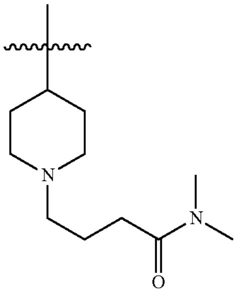
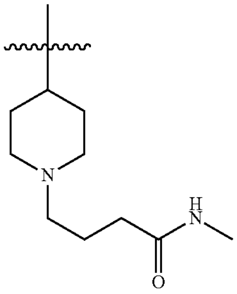
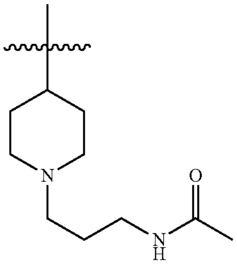
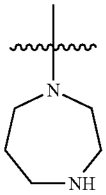
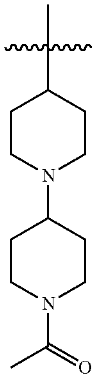
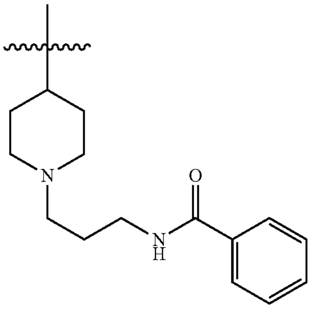
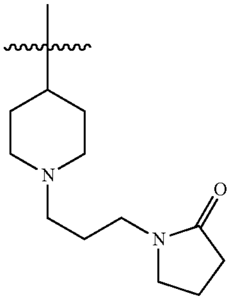
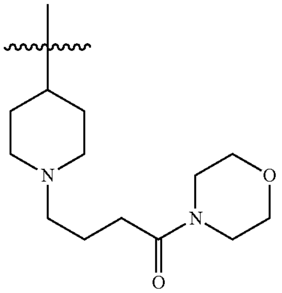
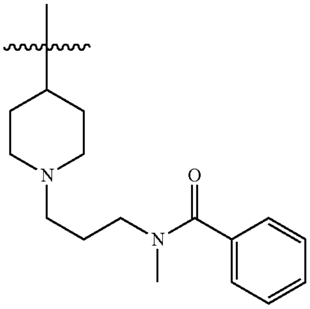
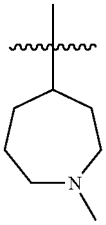

-continued
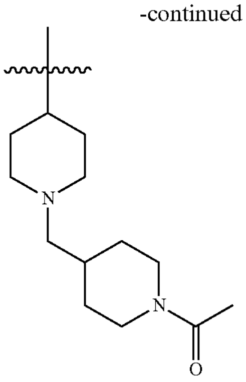
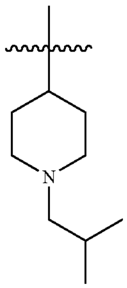
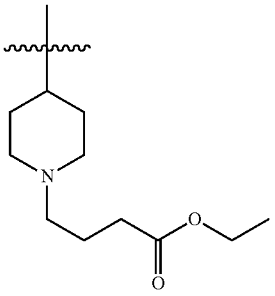
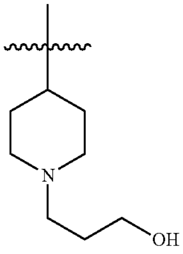
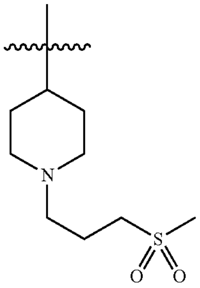
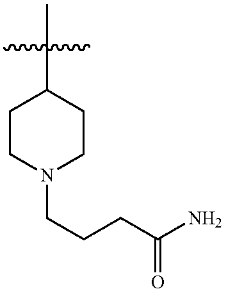
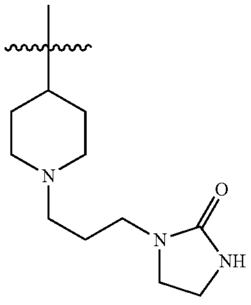
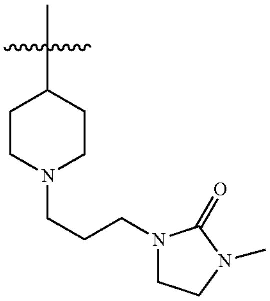
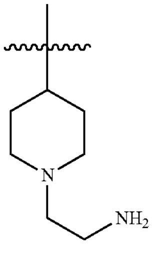
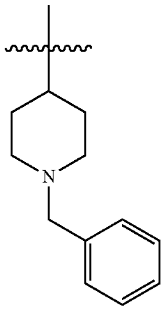
-continued
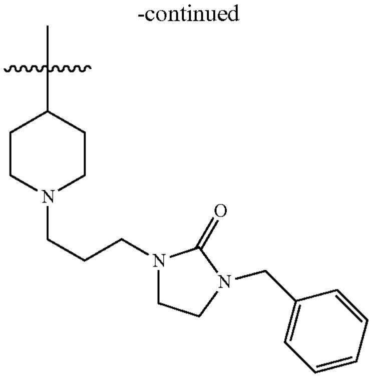
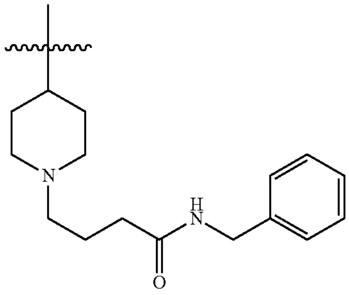
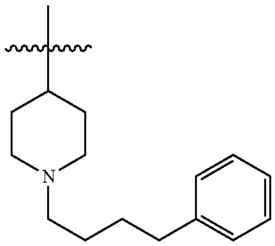
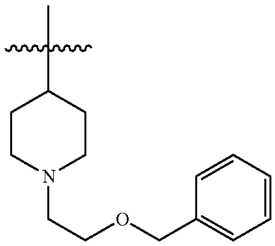
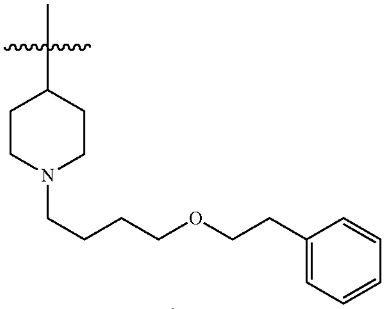
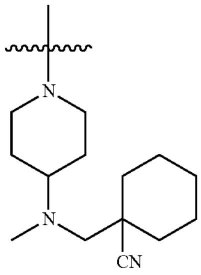
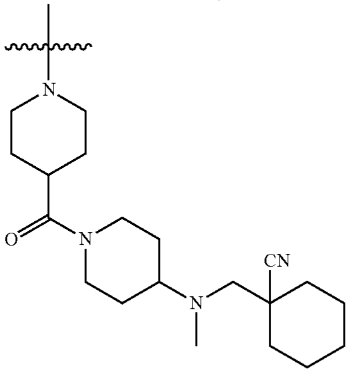

-continued
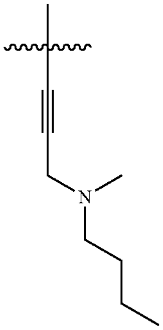
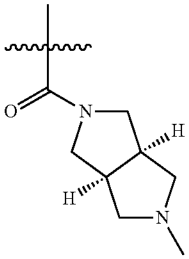
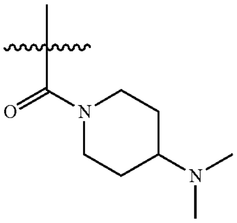
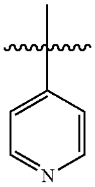
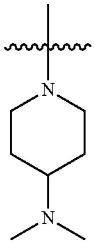
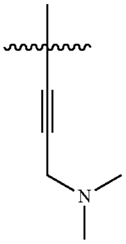
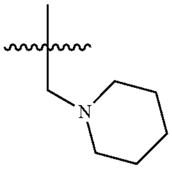
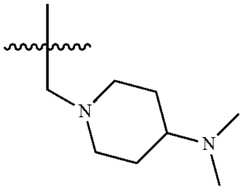
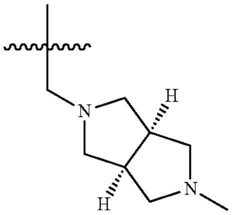
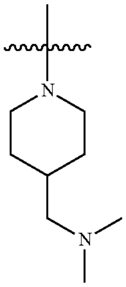
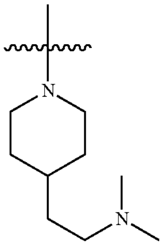
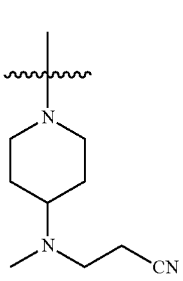
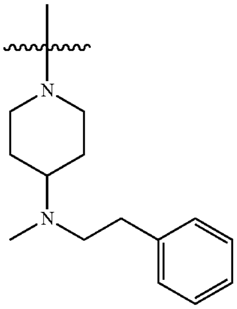
-continued
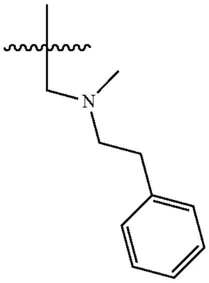
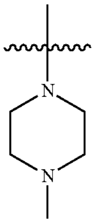
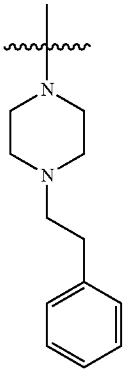
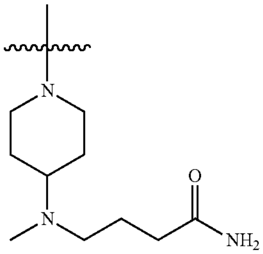
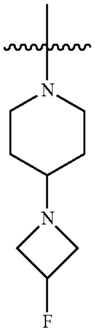
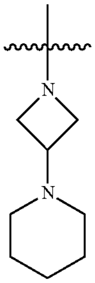
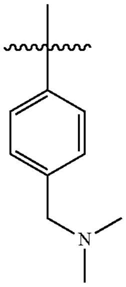
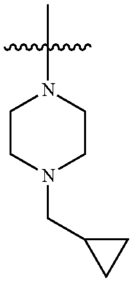
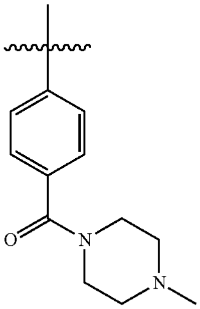
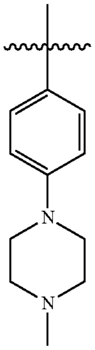
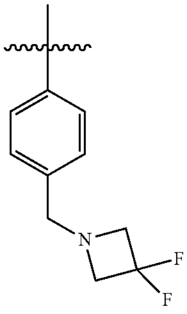
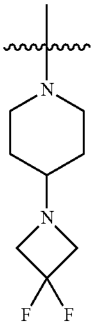
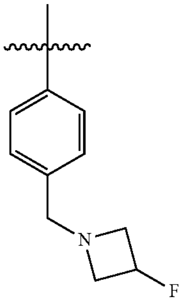
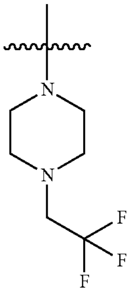

-continued
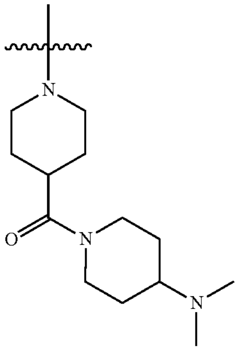 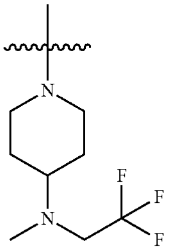
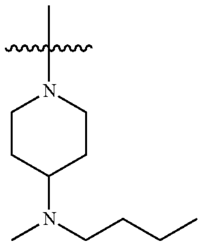 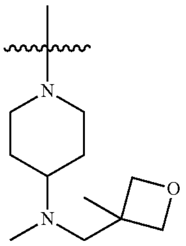
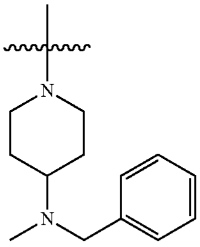 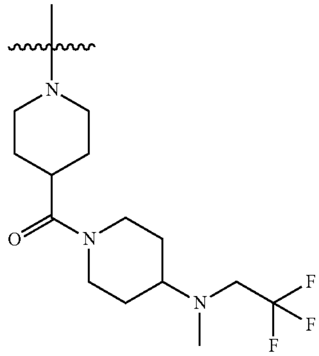
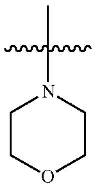 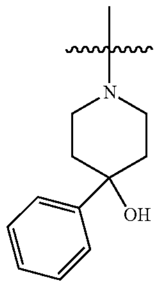 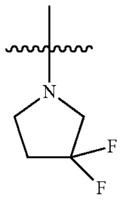 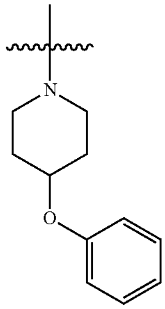
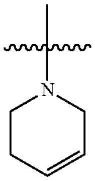 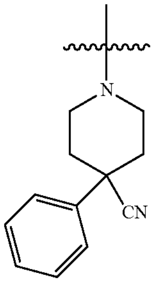 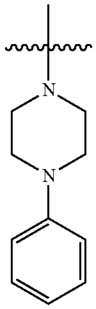
-continued
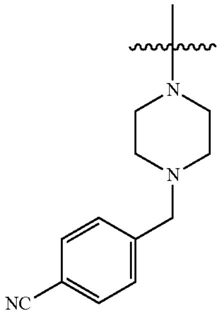 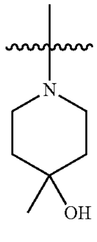 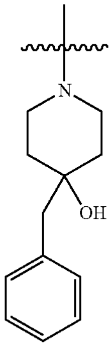 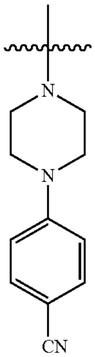
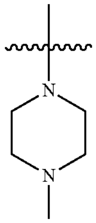 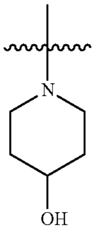 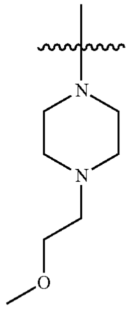 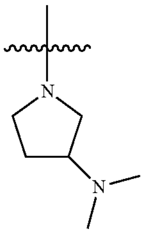
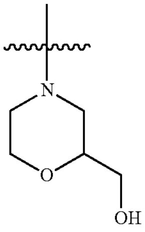 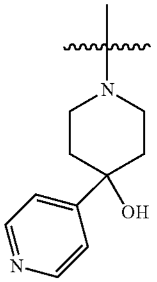 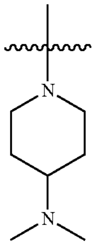 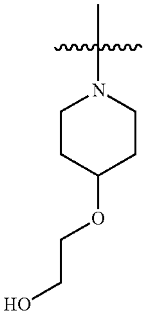
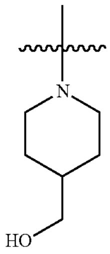 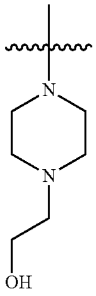 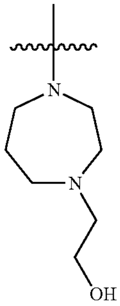 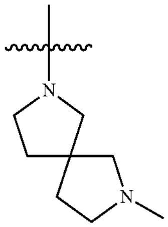
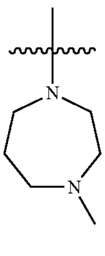 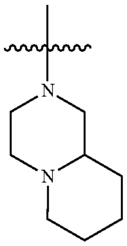 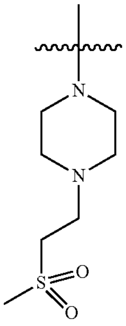 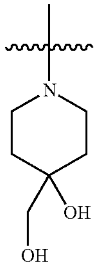

-continued
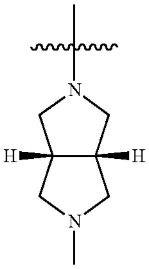
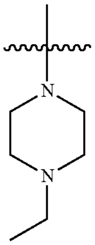
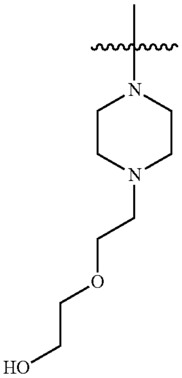
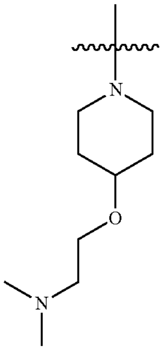
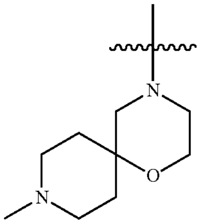
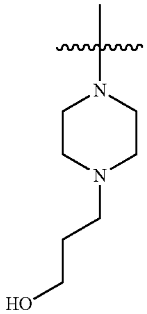
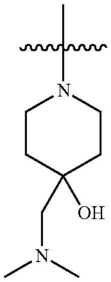
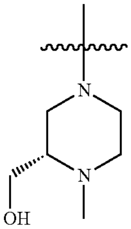
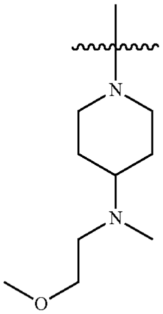
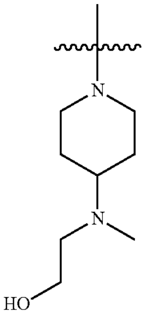
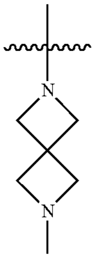
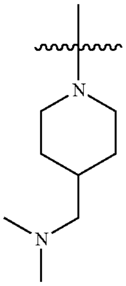
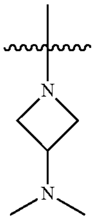
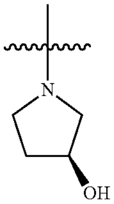
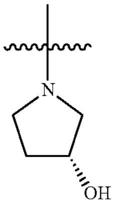
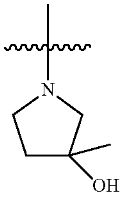
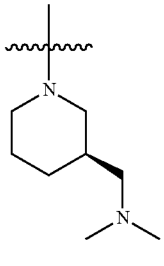
-continued
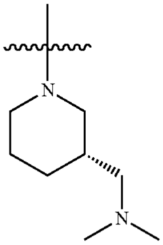
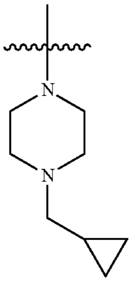
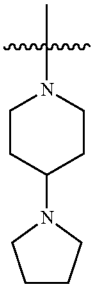
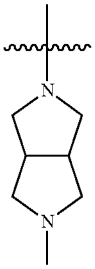
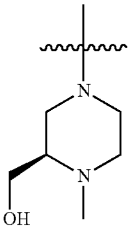
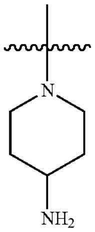
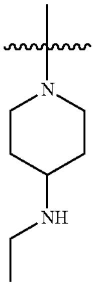
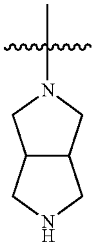
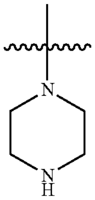
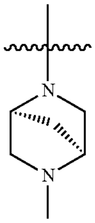
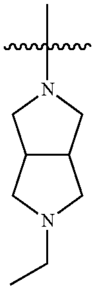
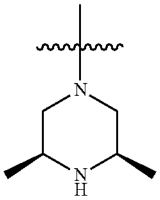
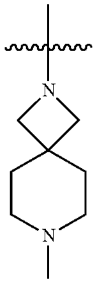
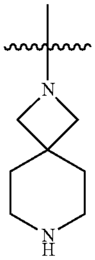
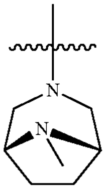
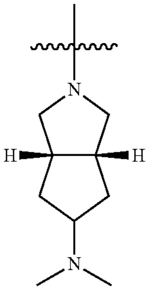
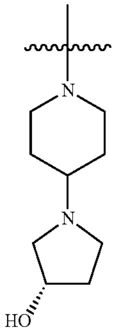
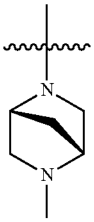
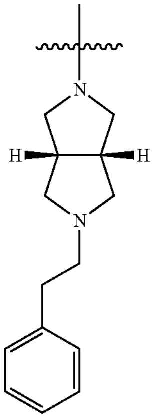
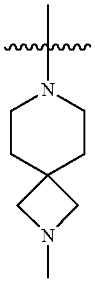
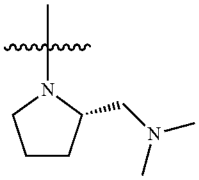

-continued
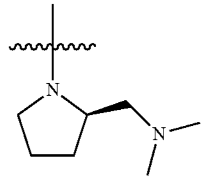
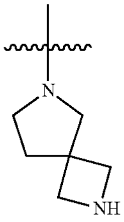
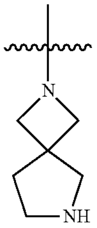
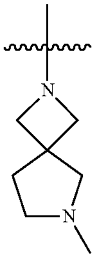
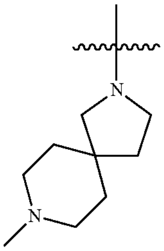
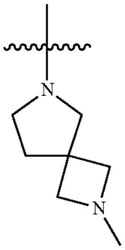
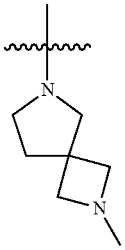
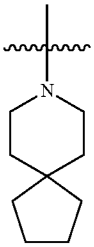
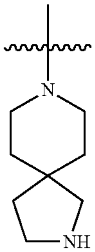
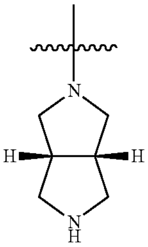
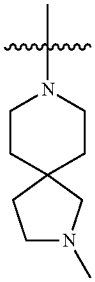
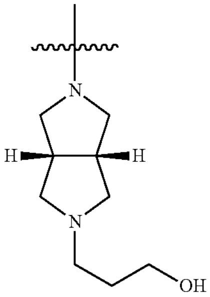
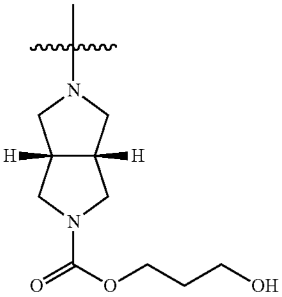
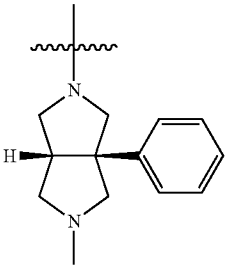
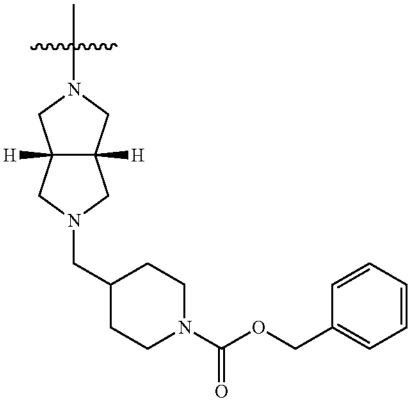
-continued
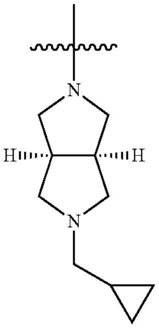
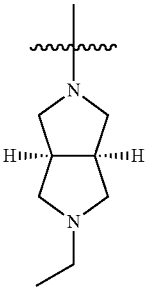
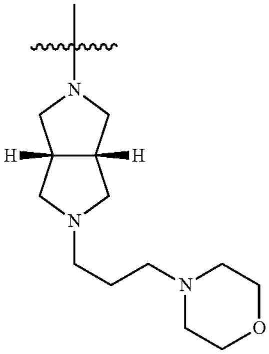
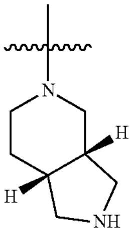
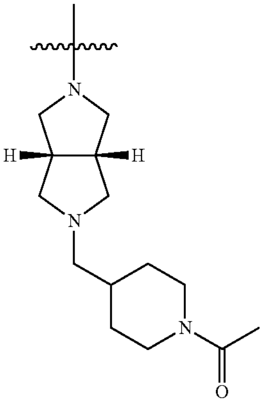
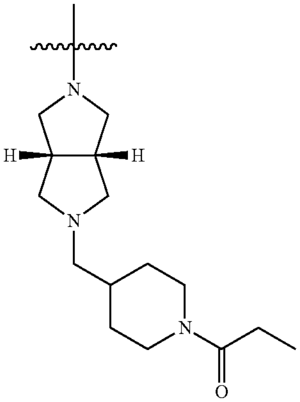
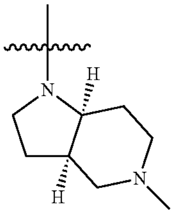
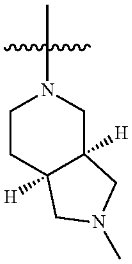
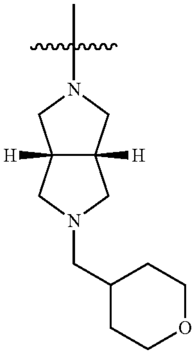

-continued
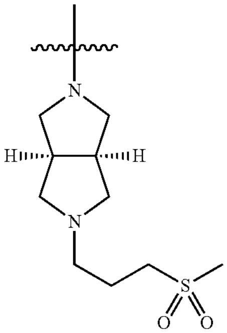
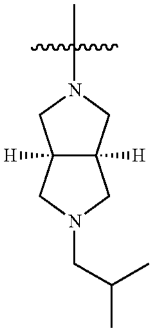
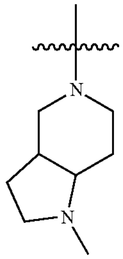
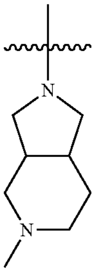
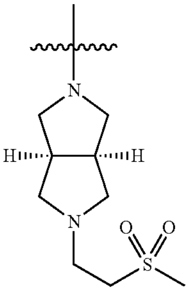
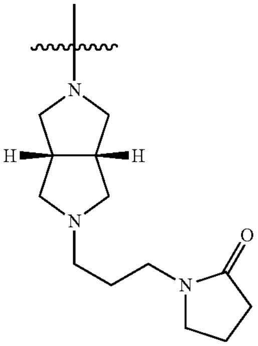
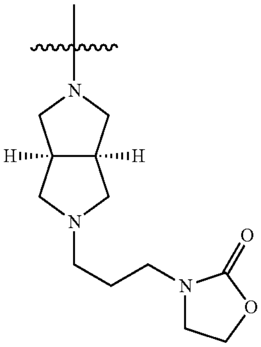
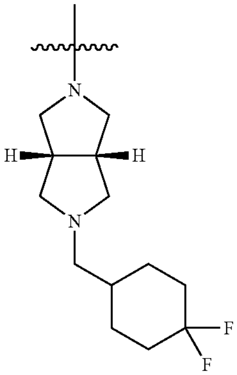
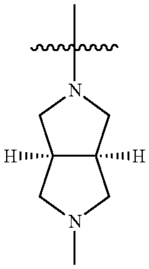
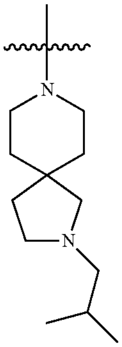
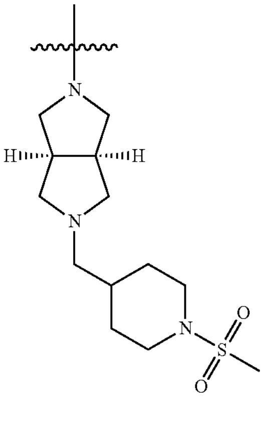
-continued
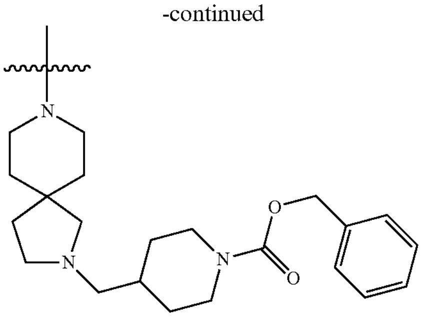
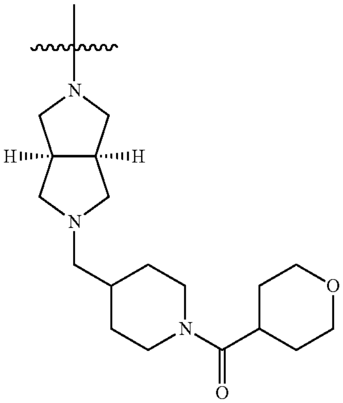
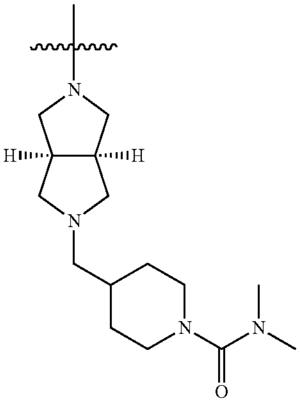
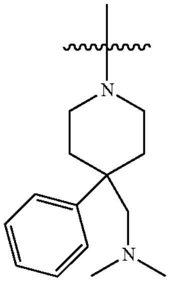
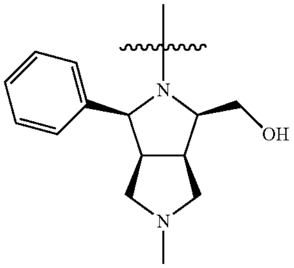
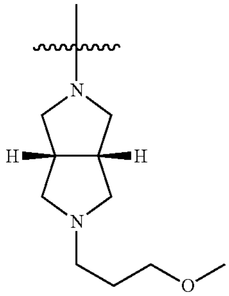
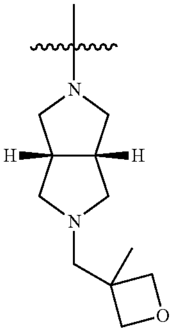
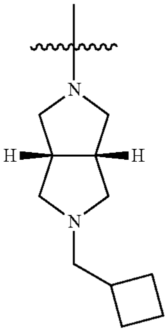
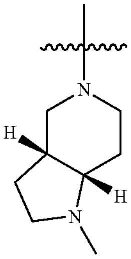

-continued
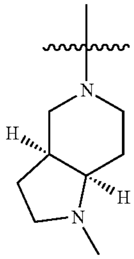
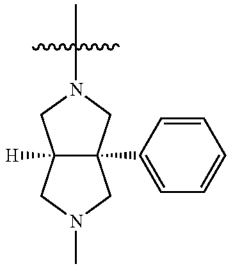
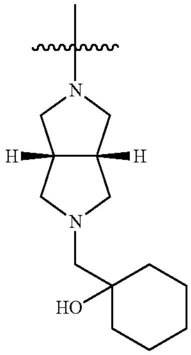
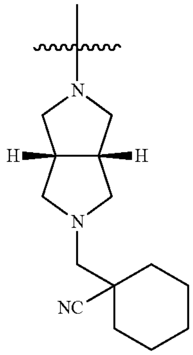
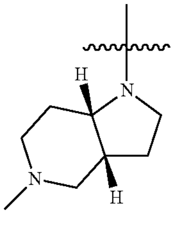
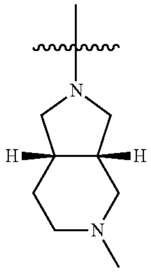
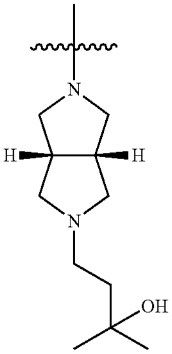
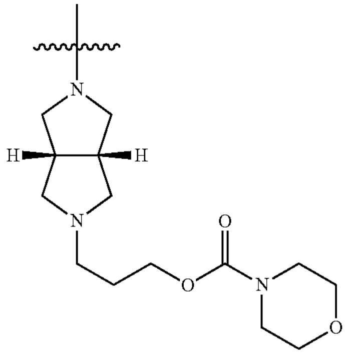
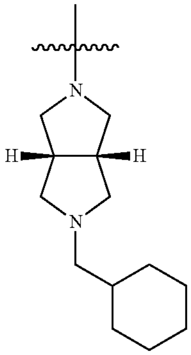
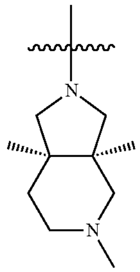
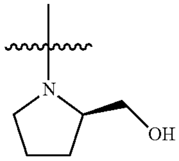
-continued
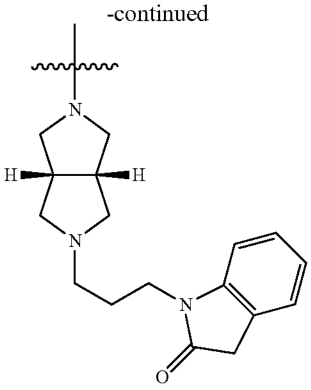
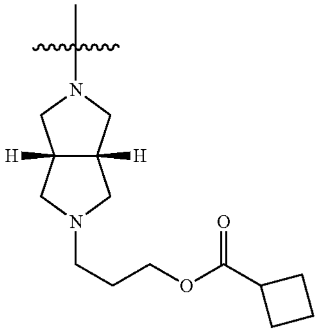
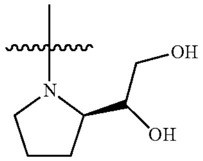
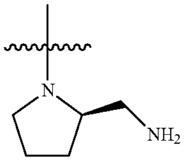
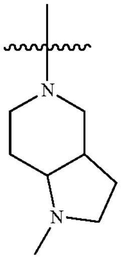
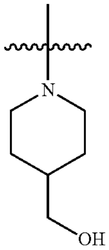
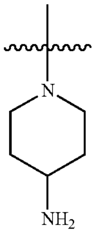
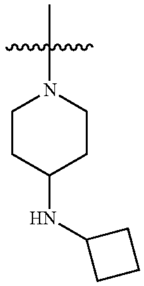
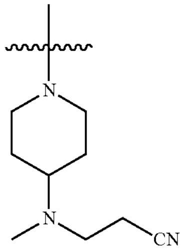
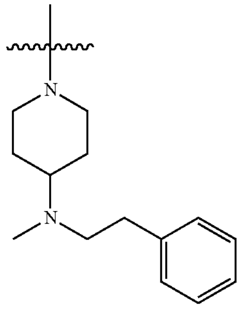
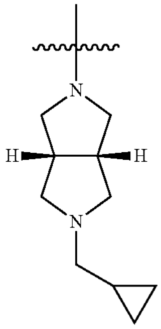

-continued
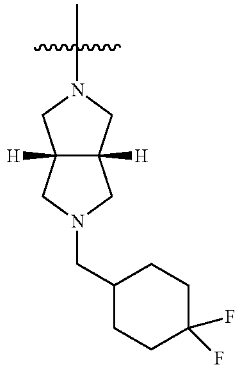
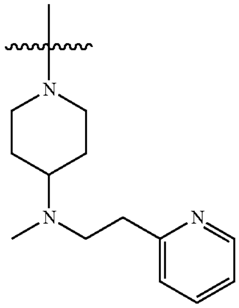
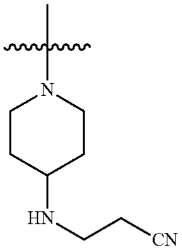
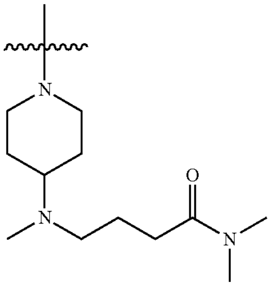
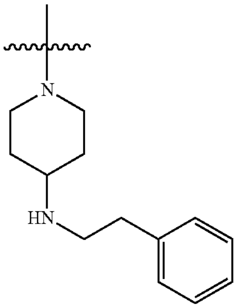
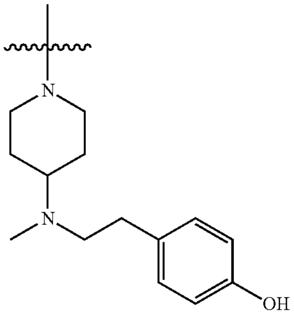
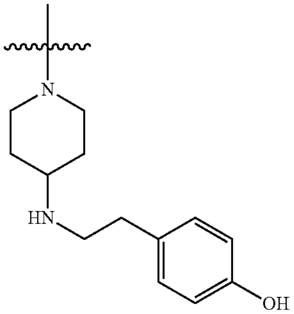
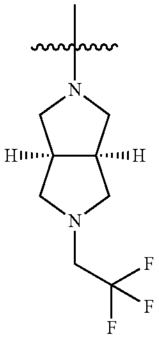
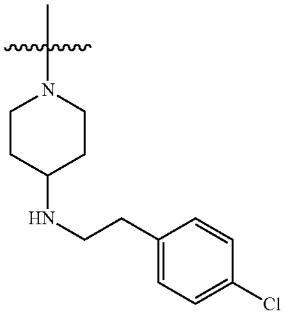
-continued
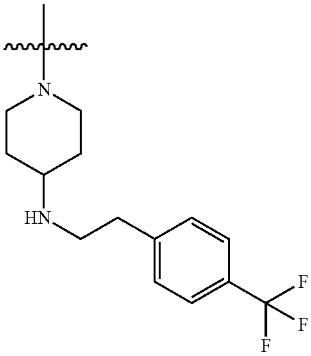
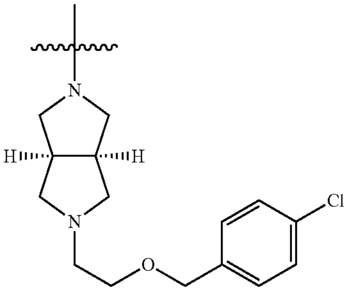
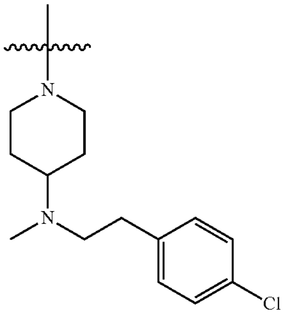
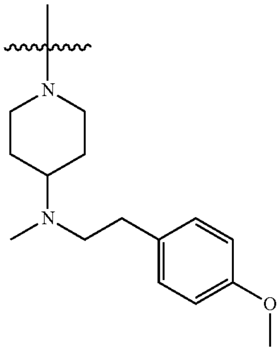
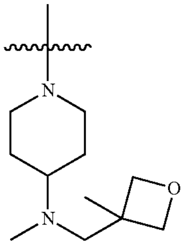
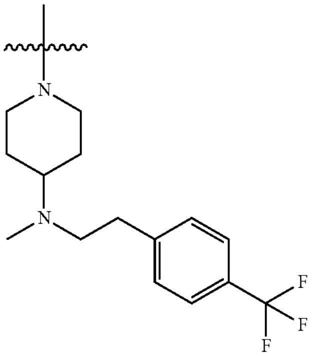
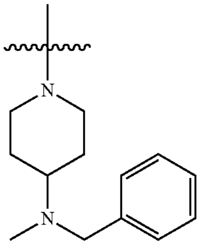
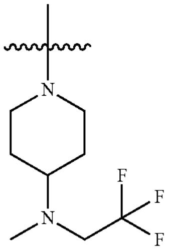

-continued
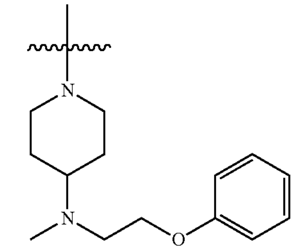
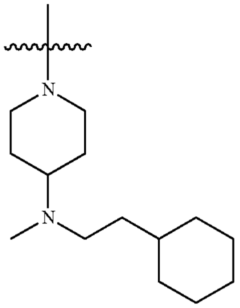
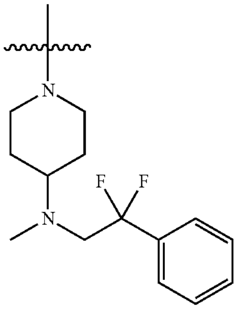
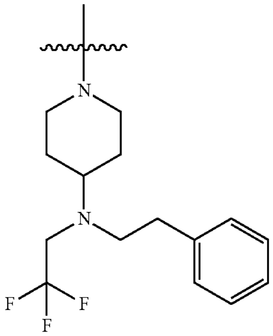
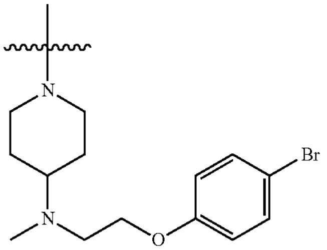
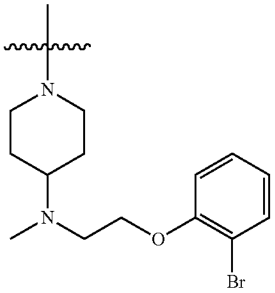
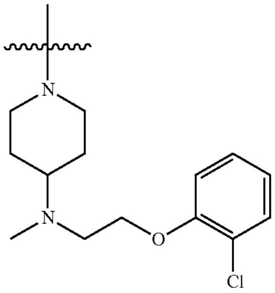
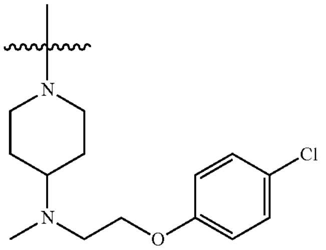
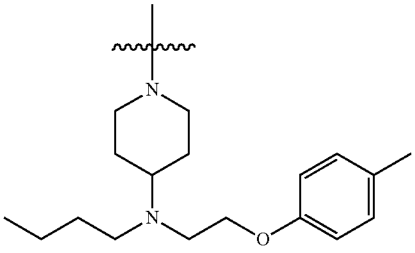
-continued
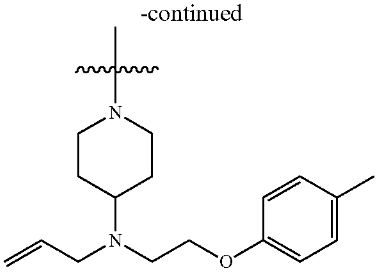
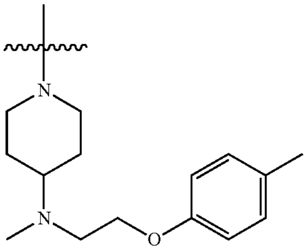
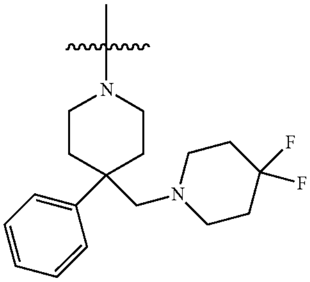
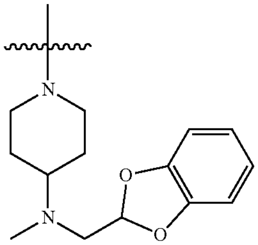
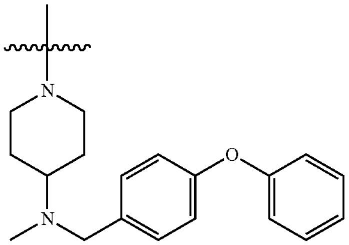
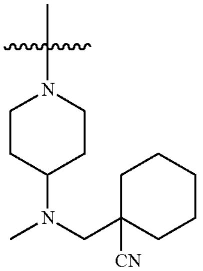
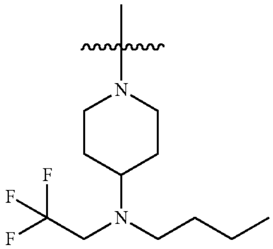
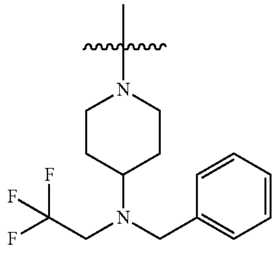

-continued
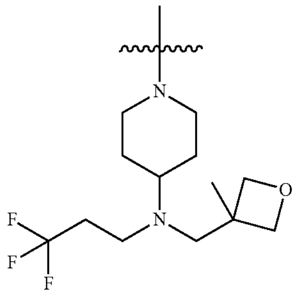
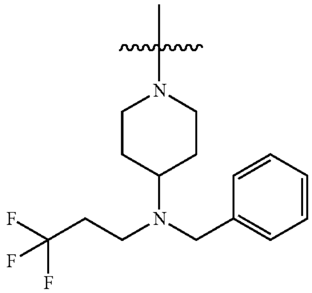
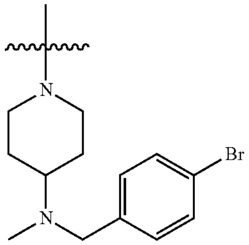
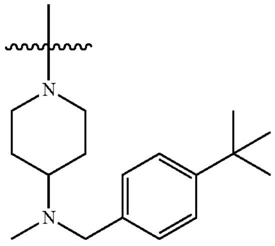
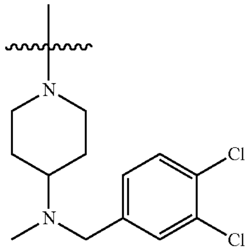
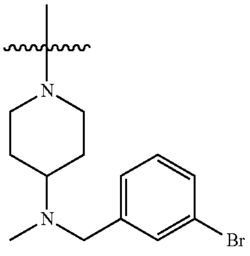
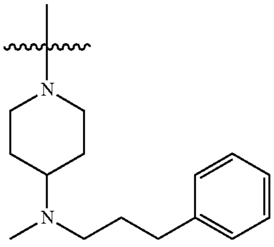
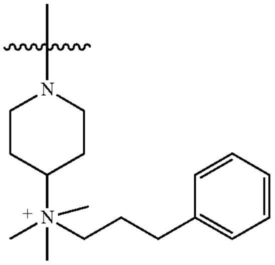
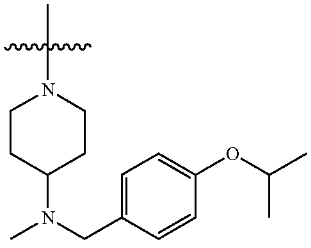
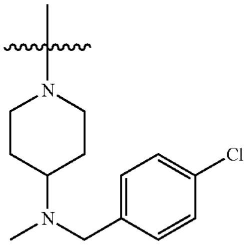
-continued
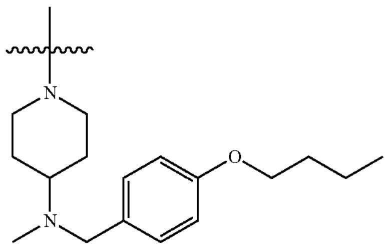
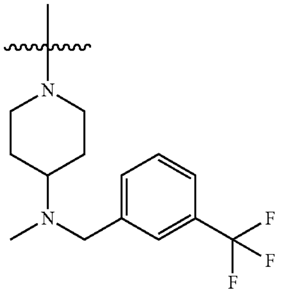
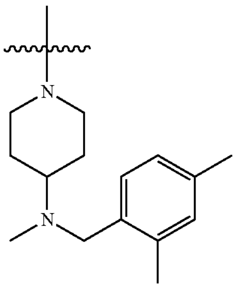
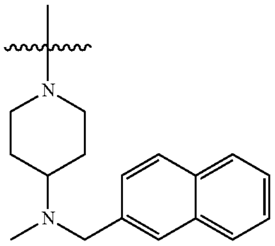
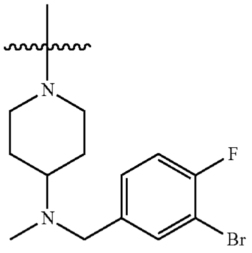
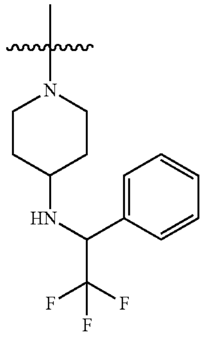
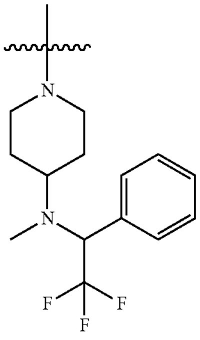
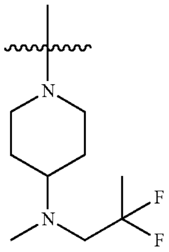
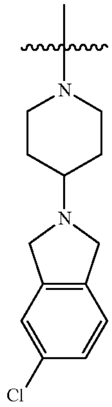
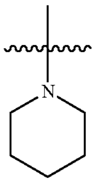
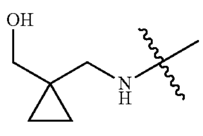
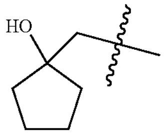

-continued
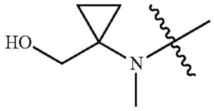
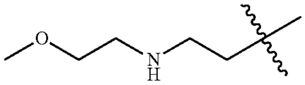
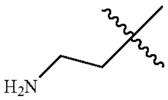
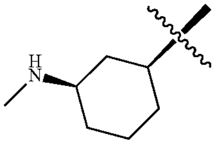
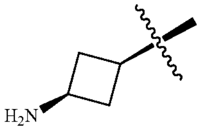
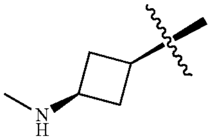
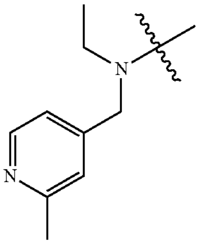
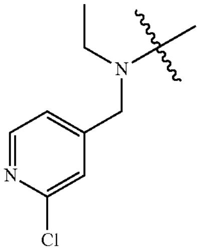
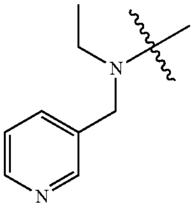
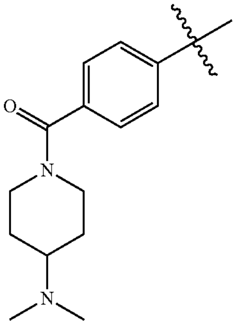
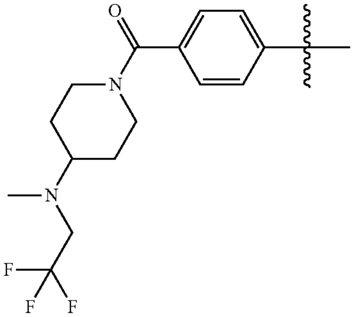
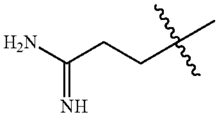
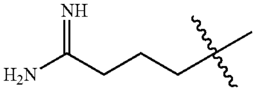
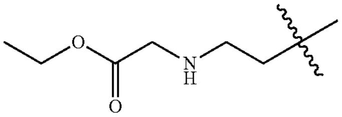
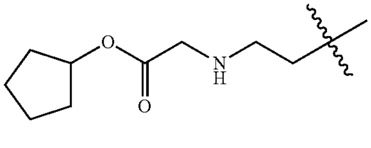
-continued
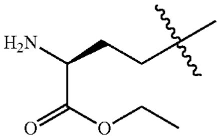
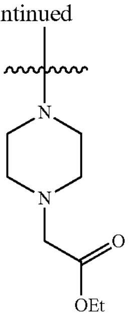
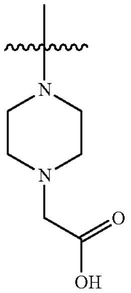
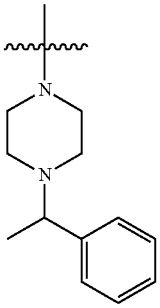
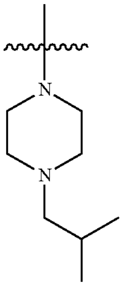
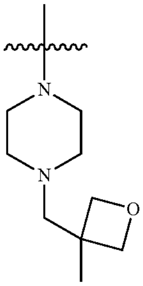
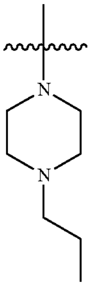
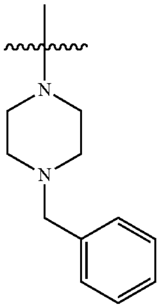
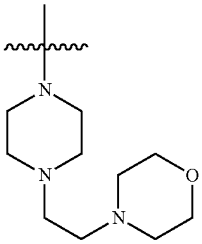
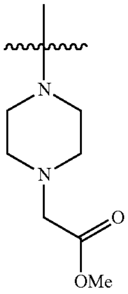
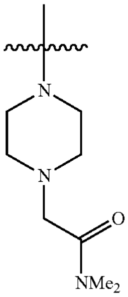
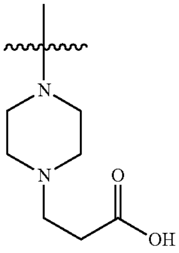
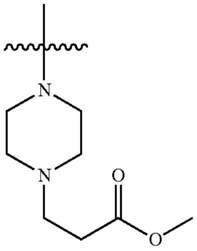
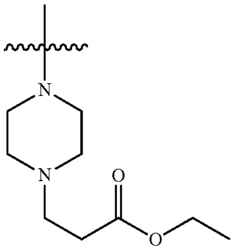
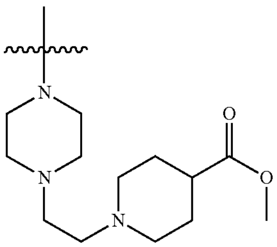

-continued
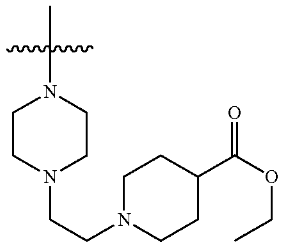
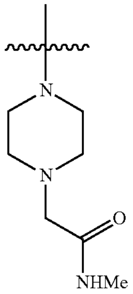
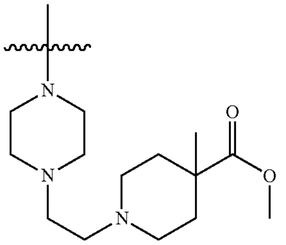
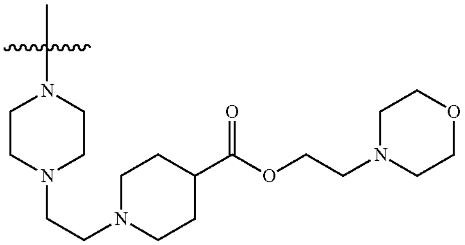
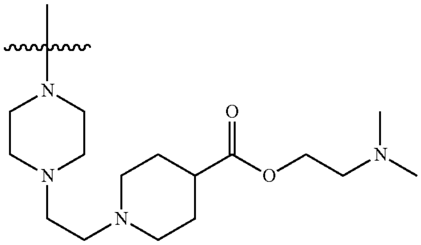
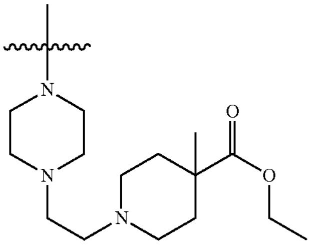
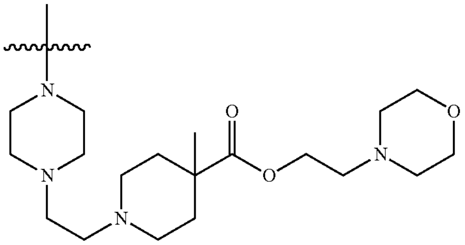
-continued
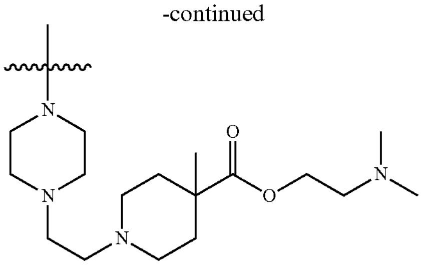
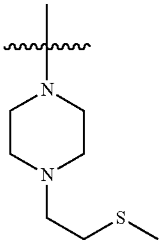
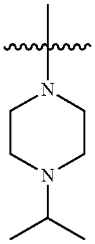
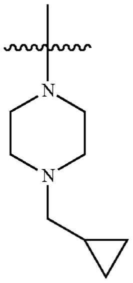
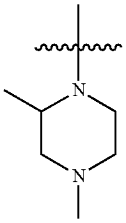
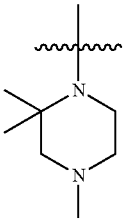
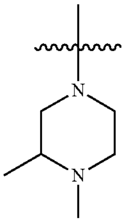
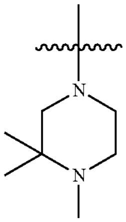
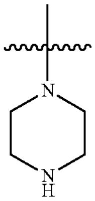
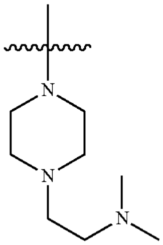
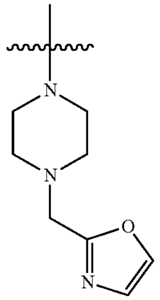
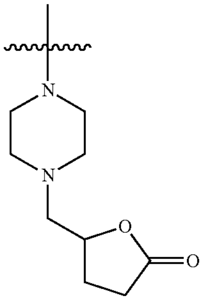
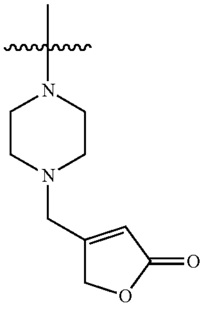
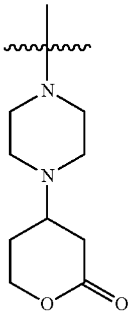
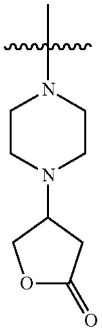
In any embodiment herein, one or more compounds of WO 2011/003065 is/are excluded.
Also provided is a compound selected from Examples 1-468 or Table 1, or any combination thereof. If any discrepancy exists between a structure and its chemical name, the structure prevails.

TABLE 1

Exemplary Compounds of the Present Invention

| Ex. | Structure | Name |
| --- | --- | --- |
| 1 | 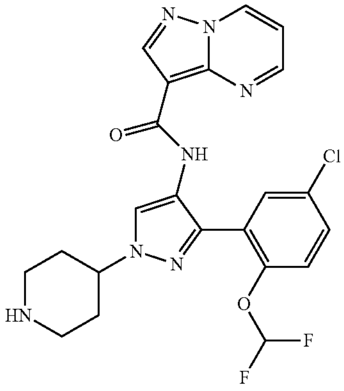 [SMILES: O=C(Nc1cn(C2CCNCC2)nc1-c1cc(Cl)ccc1OC(F)F)c1cnn2cccnc12] | N-[3-[5-chloro-2-(difluoromethoxy)phenyl]-1-(4-piperidyl)pyrazol-4-yl]pyrazolo[1,5-a]pyrimidine-3-carboxamide |
| 2 | 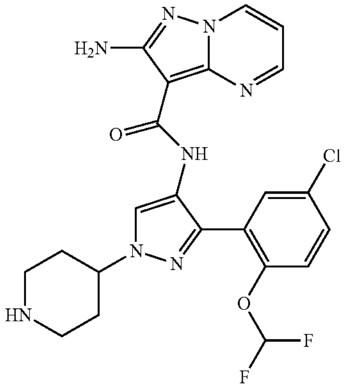 [SMILES: Nc1nn2cccnc2c1C(=O)Nc1cn(C2CCNCC2)nc1-c1cc(Cl)ccc1OC(F)F] | 2-amino-N-[3-[5-chloro-2-(difluoromethoxy)phenyl]-1-(4-piperidyl)pyrazol-4-yl]pyrazolo[1,5-a]pyrimidine-3-carboxamide |
| 3 | 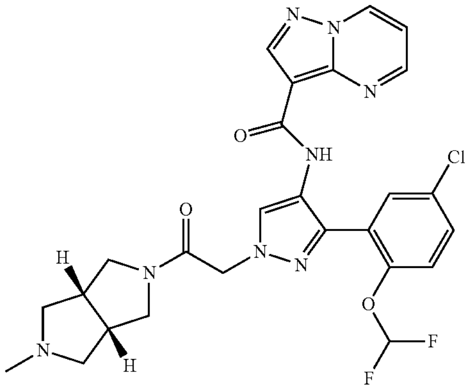 [SMILES: CN1C[C@@H]2CN(C(=O)Cn3cc(NC(=O)c4cnn5cccnc45)c(-c4cc(Cl)ccc4OC(F)F)n3)C[C@@H]2C1] | N-[1-[2-[(3aS,6aR)-2-methyl-1,3,3a,4,6,6a-hexahydropyrrolo[3,4-c]pyrrol-5-yl]-2-oxo-ethyl]-3-[5-chloro-2-(difluoromethoxy)phenyl] pyrazol-4-yl]pyrazolo[1,5-a]pyrimidine-3-carboxamide |
| 4 | 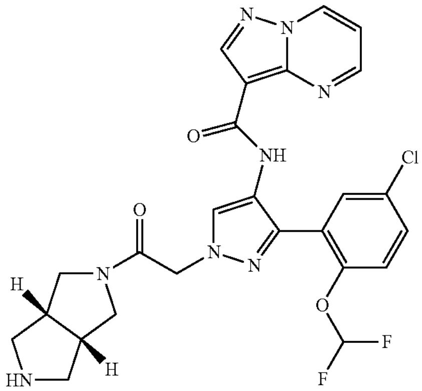 [SMILES: O=C(Nc1cn(CC(=O)N2C[C@H]3CNC[C@H]3C2)nc1-c1cc(Cl)ccc1OC(F)F)c1cnn2cccnc12] | N-[1-[2-[(3aR,6aS)-2,3,3a,4,6,6a-hexahydro-1H-pyrrolo[3,4-c]pyrrol-5-yl]-2-oxo-ethyl]-3-[5-chloro-2-(difluoromethoxy)phenyl] pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 5 | 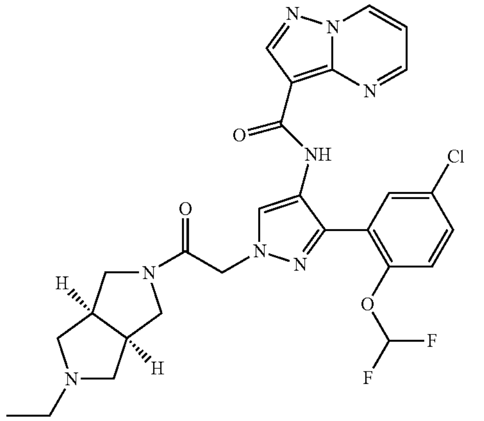 [SMILES: CCN1C[C@@H]2CN(C(=O)Cn3cc(NC(=O)c4cnn5cccnc45)c(-c4cc(Cl)ccc4OC(F)F)n3)C[C@@H]2C1] | N-[1-[2-[(3aS,6aR)-2-ethyl-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |
| 6 | 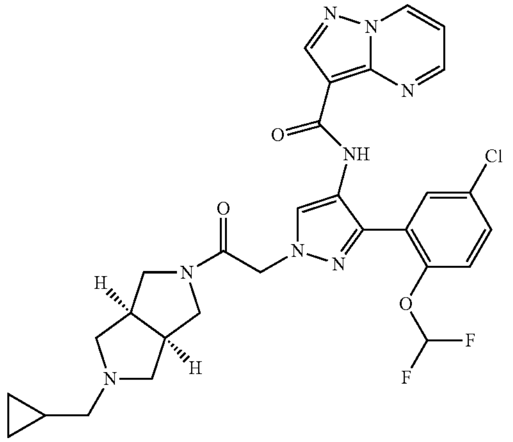 [SMILES: O=C(Nc1cn(CC(=O)N2C[C@H]3CN(CC4CC4)C[C@H]3C2)nc1-c1cc(Cl)ccc1OC(F)F)c1cnn2cccnc12] | N-[1-[2-[(3aS,6aR)-2-(cyclopropylmethyl)-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |
| 7 | 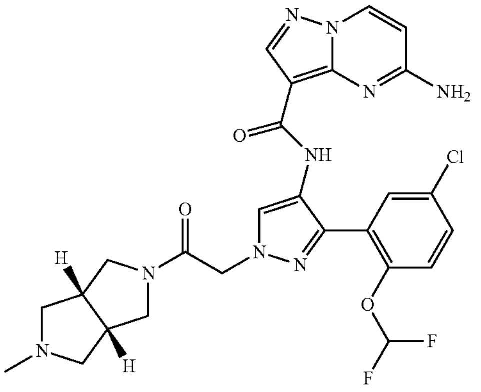 [SMILES: CN1C[C@@H]2CN(C(=O)Cn3cc(NC(=O)c4cnn5ccc(N)nc45)c(-c4cc(Cl)ccc4OC(F)F)n3)C[C@@H]2C1] | N-[1-[2-[(3aS,6aR)-2-methyl-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]-5-amino-pyrazolo[1,5-a]pyrimidine-3-carboxamide |

TABLE 1-continued

| Ex. | Structure | Name |
|---|---|---|
| | Exemplary Compounds of the Present Invention | |
| 8 | 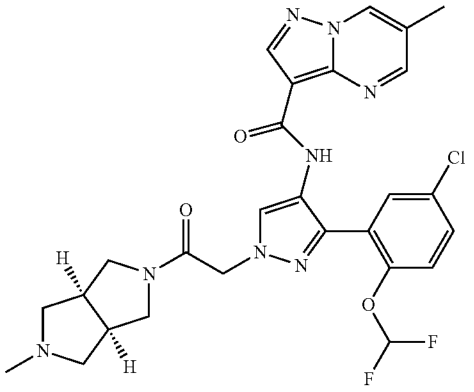 [SMILES: Cc1cnc2c(C(=O)Nc3cn(CC(=O)N4C[C@H]5CN(C)C[C@H]5C4)nc3-c3cc(Cl)ccc3OC(F)F)cnn2c1] | N-[1-[2-[(3aR,6aS)-2-methyl-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]-6-methyl-pyrazolo[1,5-a]pyrimidine-3-carboxamide |
| 9 | 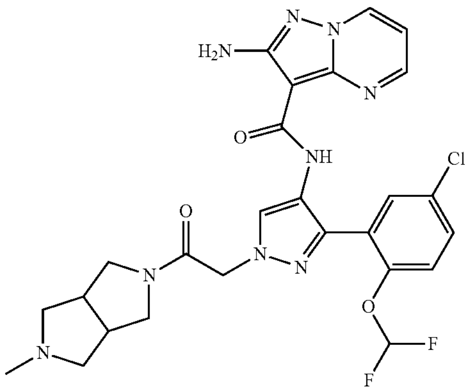 [SMILES: CN1CC2CN(C(=O)Cn3cc(NC(=O)c4c(N)nn5cccnc45)c(-c4cc(Cl)ccc4OC(F)F)n3)CC2C1] | 2-amino-N-[3-[5-chloro-2-(difluoromethoxy)phenyl]-1-[2-(2-methyl-1,3,3a,4,6,6a-hexahydropyrrolo[3,4-c]pyrrol-5-yl)-2-oxo-ethyl]pyrazol-4-yl]pyrazolo[1,5-a]pyrimidine-3-carboxamide |
| 10 | 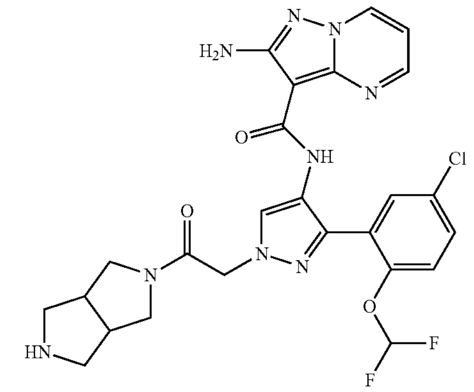 [SMILES: Nc1nn2cccnc2c1C(=O)Nc1cn(CC(=O)N2CC3CNCC3C2)nc1-c1cc(Cl)ccc1OC(F)F] | N-[1-[2-(2,3,3a,4,6,6a-hexahydro-1H-pyrrolo[3,4-c]pyrrol-5-yl)-2-oxo-ethyl]-3-[5-chloro-2-(difluoromethoxy)phenyl]pyrazol-4-yl]-2-amino-pyrazolo[1,5-a]pyrimidine-3-carboxamide |

TABLE 1-continued

| Ex. | Structure | Name |
|---|---|---|
| Exemplary Compounds of the Present Invention | | |
| 11 | 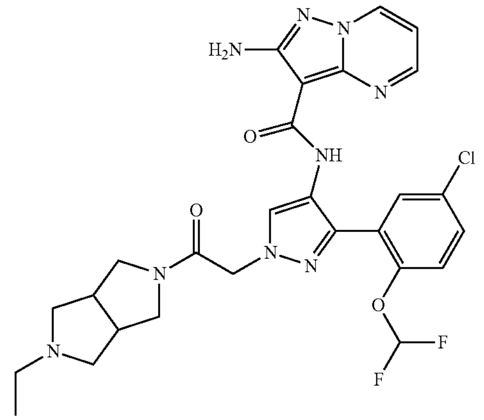 [SMILES: CCN1CC2CN(C(=O)Cn3cc(NC(=O)c4c(N)nn5cccnc45)c(-c4cc(Cl)ccc4OC(F)F)n3)CC2C1] | 2-amino-N-[3-[5-chloro-2-(difluoromethoxy)phenyl]-1-[2-(2-ethyl-1,3,3a,4,6,6a-hexahydropyrrolo[3,4-c]pyrrol-5-yl)-2-oxo-ethyl]pyrazol-4-yl]pyrazolo[1,5-a]pyrimidine-3-carboxamide |
| 12 | 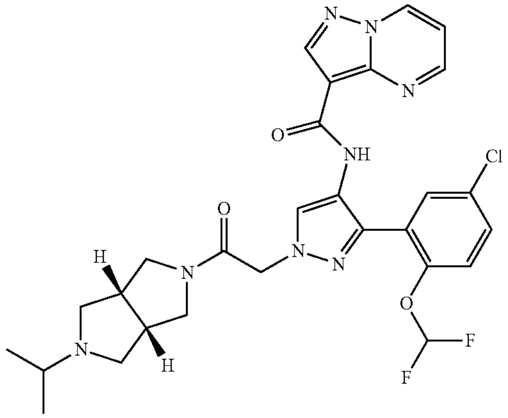 [SMILES: CC(C)N1C[C@H]2CN(C(=O)Cn3cc(NC(=O)c4cnn5cccnc45)c(-c4cc(Cl)ccc4OC(F)F)n3)C[C@H]2C1] | N-[1-[2-[(3aS,6aR)-2-isopropyl-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |
| 13 | 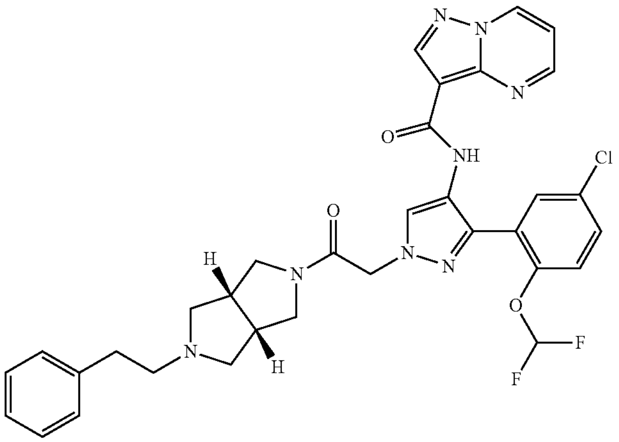 [SMILES: O=C(Nc1cn(CC(=O)N2C[C@H]3CN(CCc4ccccc4)C[C@H]3C2)nc1-c1cc(Cl)ccc1OC(F)F)c1cnn2cccnc12] | N-[1-[2-[(3aS,6aR)-2-(2-phenylethyl)-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 14 | 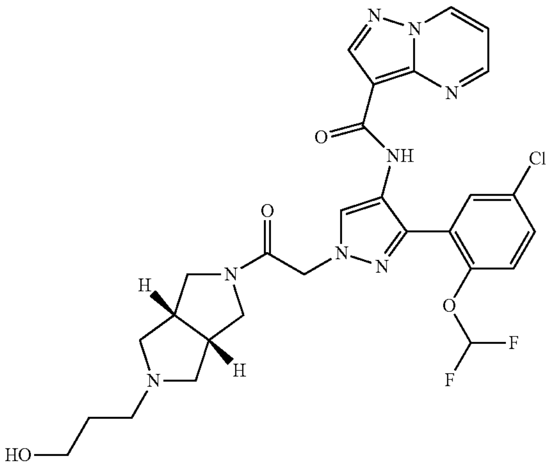 [SMILES: O=C(Nc1cn(CC(=O)N2C[C@H]3CN(CCCO)C[C@H]3C2)nc1-c1cc(Cl)ccc1OC(F)F)c1cnn2cccnc12] | N-[1-[2-[(3aR,6aS)-2-(3-hydroxypropyl)-1,3,3a,4,6,6a-hexahydropyrrolo[3,4-c]pyrrol-5-yl]-2-oxo-ethyl]-3-[5-chloro-2-(difluoromethoxy)phenyl] pyrazol-4-yl]pyrazolo[1,5-a]pyrimidine-3-carboxamide |
| 15 | 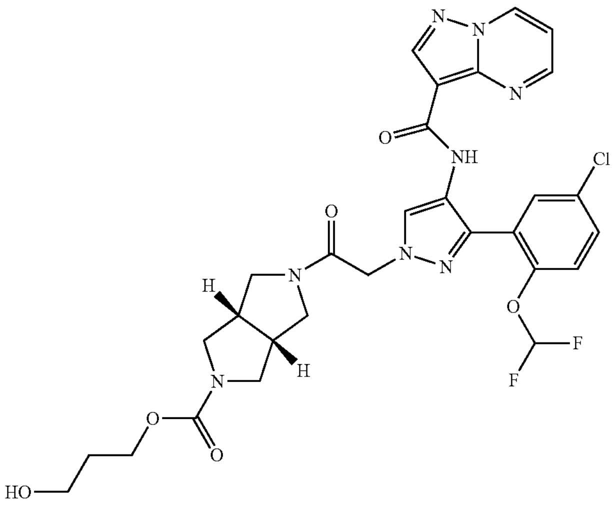 [SMILES: O=C(Nc1cn(CC(=O)N2C[C@@H]3CN(C(=O)OCCCO)C[C@@H]3C2)nc1-c1cc(Cl)ccc1OC(F)F)c1cnn2cccnc12] | 3-hydroxypropyl (3aR,6aS)-2-[2-[3-[5-chloro-2-(difluoromethoxy)phenyl]-4-(pyrazolo[1,5-a]pyrimidine-3-carbonylamino)pyrazol-1-yl]acetyl]-1,3,3a,4,6,6a-hexahydropyrrolo[3,4-c]pyrrole-5-carboxylate |
| 16 | 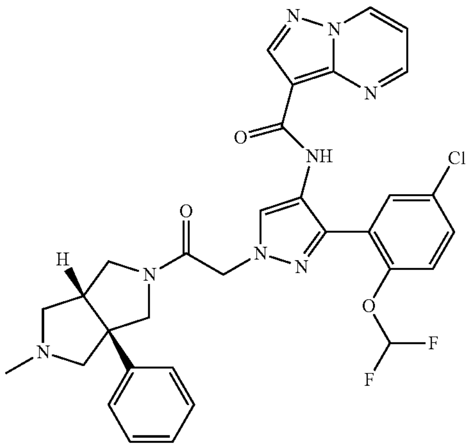 [SMILES: CN1C[C@@H]2CN(C(=O)Cn3cc(NC(=O)c4cnn5cccnc45)c(-c4cc(Cl)ccc4OC(F)F)n3)C[C@]2(c2ccccc2)C1] | N-[1-[2-[(3aR,6aR)-2-methyl-3a-phenyl-3,4,6,6a-tetrahydro-1H-pyrrolo[3,4-c]pyrrol-5-yl]-2-oxo-ethyl]-3-[5-chloro-2-(difluoromethoxy)phenyl] pyrazol-4-yl]pyrazolo[1,5-a]pyrimidine-3-carboxamide |

TABLE 1-continued

| Ex. | Structure | Name |
| --- | --- | --- |
| 17 | 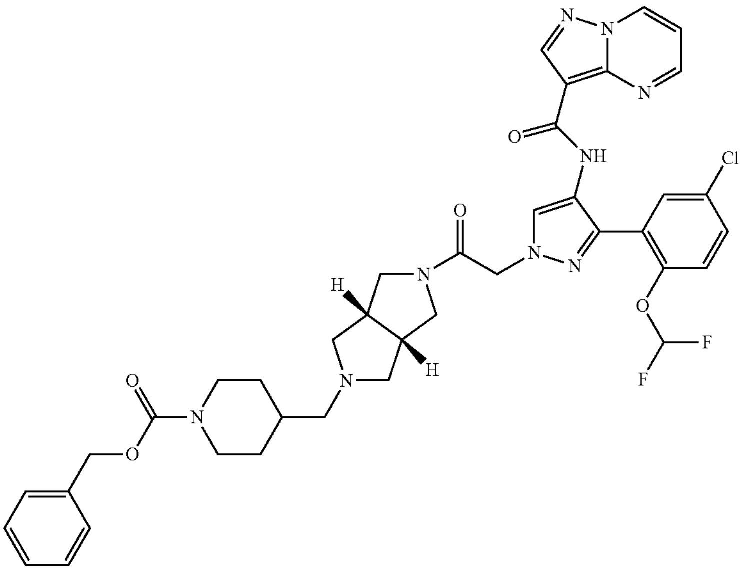 [SMILES: O=C(Nc1cn(CC(=O)N2C[C@H]3CN(CC4CCN(C(=O)OCc5ccccc5)CC4)C[C@H]3C2)nc1-c1cc(Cl)ccc1OC(F)F)c1cnn2cccnc12] | benzyl 4-[[(3aR,6aS)-5-[2-[3-[5-chloro-2-(difluoromethoxy)phenyl]-4-(pyrazolo[1,5-a]pyrimidine-3-carbonylamino)pyrazol-1-yl]acetyl]-1,3,3a,4,6,6a-hexahydropyrrolo[3,4-c]pyrrol-2-yl]methyl]piperidine-1-carboxylate |
| 18 | 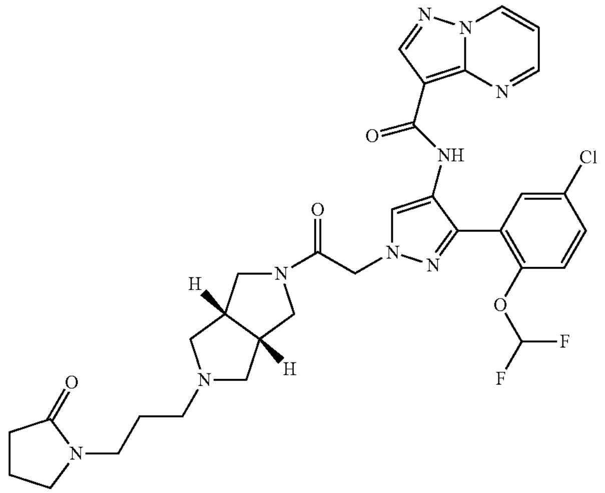 [SMILES: O=C(Nc1cn(CC(=O)N2C[C@H]3CN(CCCN4CCCC4=O)C[C@H]3C2)nc1-c1cc(Cl)ccc1OC(F)F)c1cnn2cccnc12] | N-[1-[2-[(3aR,6aS)-2-[3-(2-oxopyrrolidin-1-yl)propyl]-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |
| 19 | 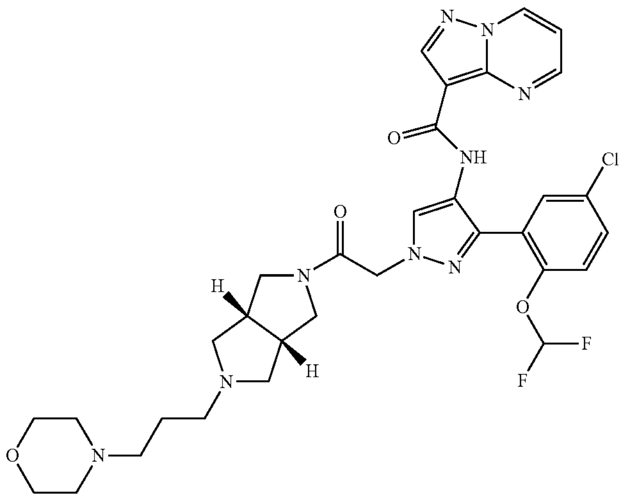 [SMILES: O=C(Nc1cn(CC(=O)N2C[C@H]3CN(CCCN4CCOCC4)C[C@H]3C2)nc1-c1cc(Cl)ccc1OC(F)F)c1cnn2cccnc12] | N-[1-[2-[(3aR,6aS)-2-(3-morpholinopropyl)-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 20 | 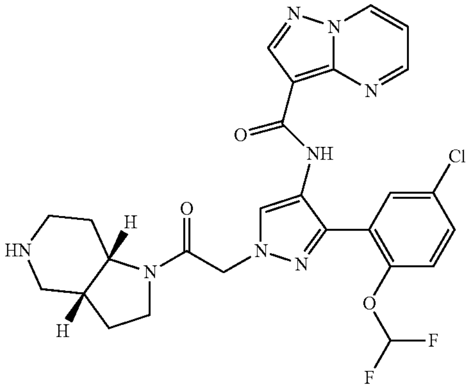 [SMILES: O=C(Nc1cn(CC(=O)N2CC[C@@H]3CNCC[C@@H]32)nc1-c1cc(Cl)ccc1OC(F)F)c1cnn2cccnc12] | N-[1-[2-[(3aR,7aS)-2,3,3a,4,5,6,7,7a-octahydropyrrolo[3,2-c]pyridin-1-yl]-2-oxo-ethyl]-3-[5-chloro-2-(difluoromethoxy)phenyl] pyrazol-4-yl]pyrazolo[1,5-a]pyrimidine-3-carboxamide |
| 21 | 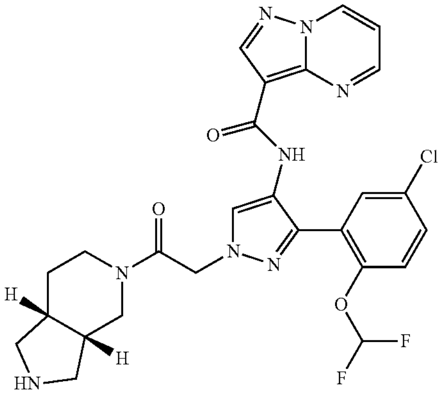 [SMILES: O=C(Nc1cn(CC(=O)N2CC[C@H]3CNC[C@H]3C2)nc1-c1cc(Cl)ccc1OC(F)F)c1cnn2cccnc12] | N-[1-[2-[(3aS,7aR)-1,2,3,3a,4,6,7,7a-octahydropyrrolo[3,4-c]pyridin-5-yl]-2-oxo-ethyl]-3-[5-chloro-2-(difluoromethoxy)phenyl] pyrazol-4-yl]pyrazolo[1,5-a]pyrimidine-3-carboxamide |
| 22 | 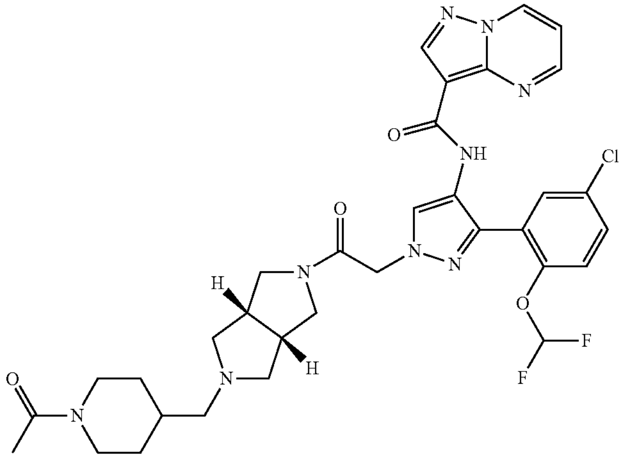 [SMILES: CC(=O)N1CCC(CN2C[C@@H]3CN(C(=O)Cn4cc(NC(=O)c5cnn6cccnc56)c(-c5cc(Cl)ccc5OC(F)F)n4)C[C@@H]3C2)CC1] | N-[1-[2-[(3aS,6aR)-2-[(1-acetyl-4-piperidyl)methyl]-1,3,3a,4,6,6a-hexahydropyrrolo[3,4-c]pyrrol-5-yl]-2-oxo-ethyl]-3-[5-chloro-2-(difluoromethoxy)phenyl] pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 23 | 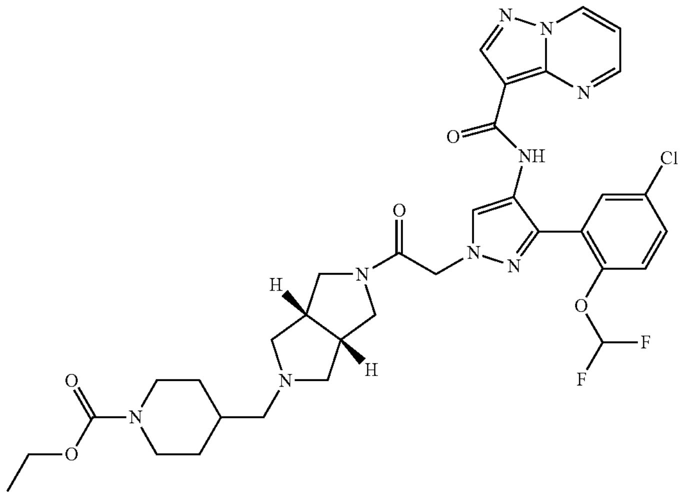 [SMILES: CCOC(=O)N1CCC(CN2C[C@@H]3CN(C(=O)Cn4cc(NC(=O)c5cnn6cccnc56)c(-c5cc(Cl)ccc5OC(F)F)n4)C[C@@H]3C2)CC1] | ethyl 4-[[(3aS,6aR)-5-[2-[3-[5-chloro-2-(difluoromethoxy)phenyl]-4-(pyrazolo[1,5-a]pyrimidine-3-carbonylamino)pyrazol-1-yl]acetyl]-1,3,3a,4,6,6a-hexahydropyrrolo[3,4-c]pyrrol-2-yl]methyl]piperidine-1-carboxylate |
| 24 | 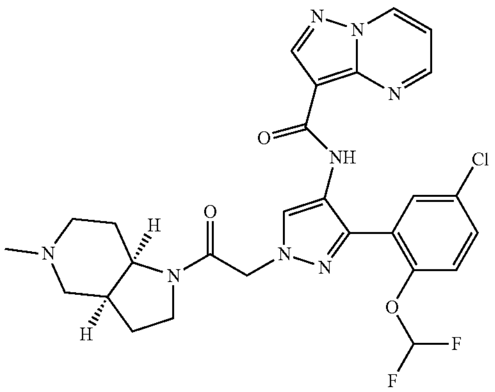 [SMILES: CN1CC[C@@H]2[C@@H](CCN2C(=O)Cn2cc(NC(=O)c3cnn4cccnc34)c(-c3cc(Cl)ccc3OC(F)F)n2)C1] | N-[1-[2-[(3aS,7aR)-5-methyl-3,3a,4,6,7,7a-hexahydro-2H-pyrrolo[3,2-c]pyridin-1-yl]-2-oxo-ethyl]-3-[5-chloro-2-(difluoromethoxy)phenyl]pyrazol-4-yl]pyrazolo[1,5-a]pyrimidine-3-carboxamide |
| 25 | 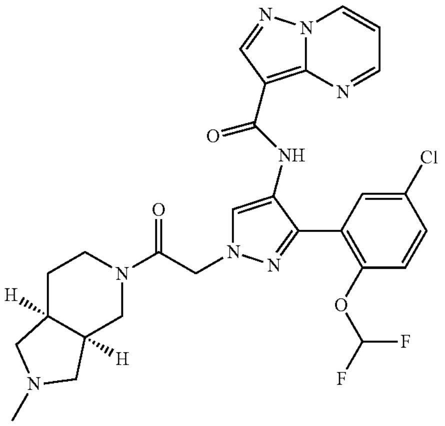 [SMILES: CN1C[C@H]2CCN(C(=O)Cn3cc(NC(=O)c4cnn5cccnc45)c(-c4cc(Cl)ccc4OC(F)F)n3)C[C@H]2C1] | N-[1-[2-[(3aR,7aS)-2-methyl-3,3a,4,6,7,7a-hexahydro-1H-pyrrolo[3,4-c]pyridin-5-yl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 26 | 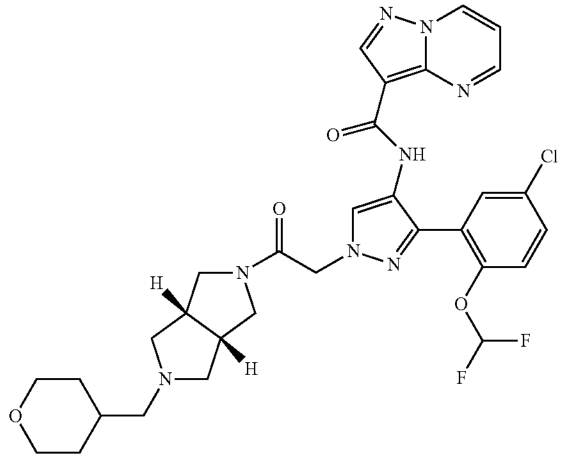 [SMILES: O=C(Nc1cn(CC(=O)N2C[C@H]3CN(CC4CCOCC4)C[C@H]3C2)nc1-c1cc(Cl)ccc1OC(F)F)c1cnn2cccnc12] | N-[1-[2-[(3aR,6aS)-2-(tetrahydropyran-4-ylmethyl)-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |
| 27 | 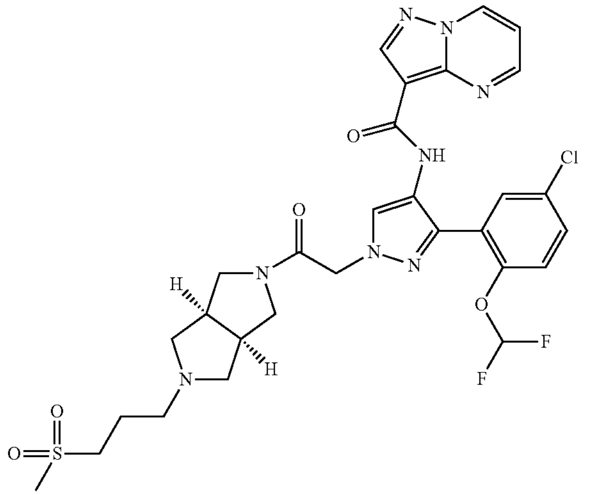 [SMILES: CS(=O)(=O)CCCN1C[C@@H]2CN(C(=O)Cn3cc(NC(=O)c4cnn5cccnc45)c(-c4cc(Cl)ccc4OC(F)F)n3)C[C@@H]2C1] | N-[1-[2-[(3aS,6aR)-2-(3-methylsulfonylpropyl)-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |
| 28 | 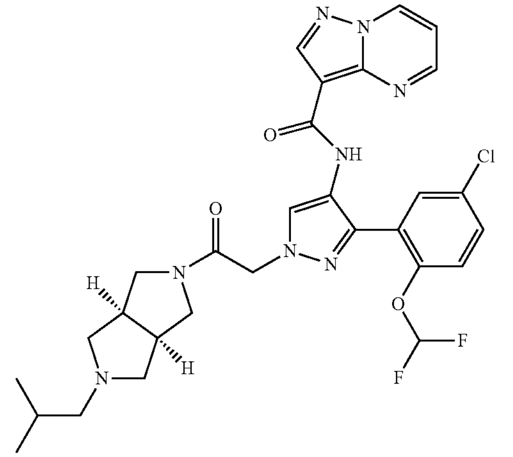 [SMILES: CC(C)CN1C[C@@H]2CN(C(=O)Cn3cc(NC(=O)c4cnn5cccnc45)c(-c4cc(Cl)ccc4OC(F)F)n3)C[C@@H]2C1] | N-[1-[2-[(3aS,6aR)-2-isobutyl-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
| --- | --- | --- |
| Ex. | Structure | Name |
| 29 | 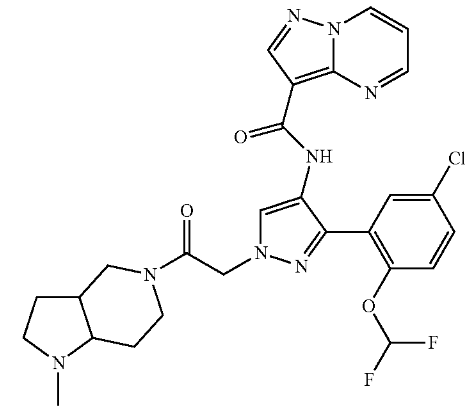 [SMILES: CN1CCC2CN(C(=O)Cn3cc(NC(=O)c4cnn5cccnc45)c(-c4cc(Cl)ccc4OC(F)F)n3)CCC21] | N-[3-[5-chloro-2-(difluoromethoxy)phenyl]-1-[2-(1-methyl-3,3a,4,6,7,7a-hexahydro-2H-pyrrolo[3,2-c]pyridin-5-yl)-2-oxo-ethyl]pyrazol-4-yl]pyrazolo[1,5-a]pyrimidine-3-carboxamide |
| 30 | 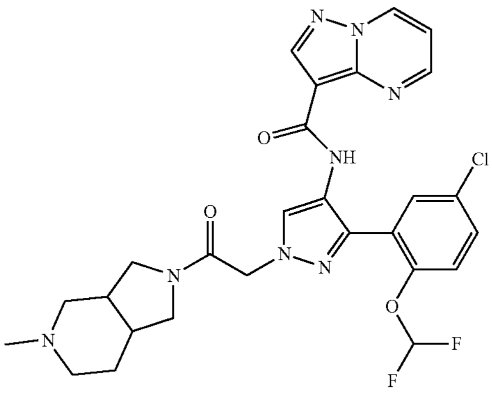 [SMILES: CN1CCC2CN(C(=O)Cn3cc(NC(=O)c4cnn5cccnc45)c(-c4cc(Cl)ccc4OC(F)F)n3)CC2C1] | N-[3-[5-chloro-2-(difluoromethoxy)phenyl]-1-[2-(5-methyl-3,3a,4,6,7,7a-hexahydro-1H-pyrrolo[3,4-c]pyridin-2-yl)-2-oxo-ethyl]pyrazol-4-yl]pyrazolo[1,5-a]pyrimidine-3-carboxamide |
| 31 | 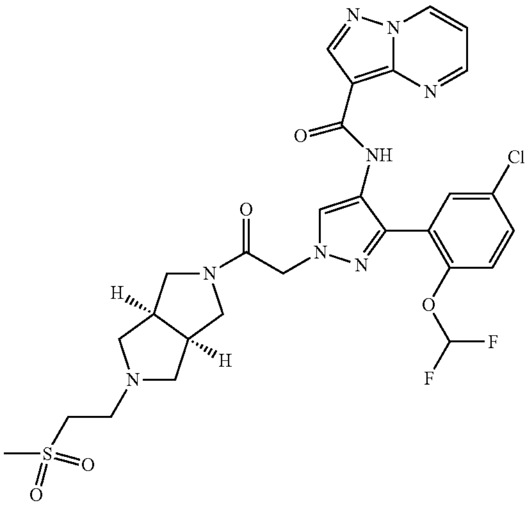 [SMILES: CS(=O)(=O)CCN1C[C@@H]2CN(C(=O)Cn3cc(NC(=O)c4cnn5cccnc45)c(-c4cc(Cl)ccc4OC(F)F)n3)C[C@@H]2C1] | N-[1-[2-[(3aS,6aR)-2-(2-methylsulfonylethyl)-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 32 | 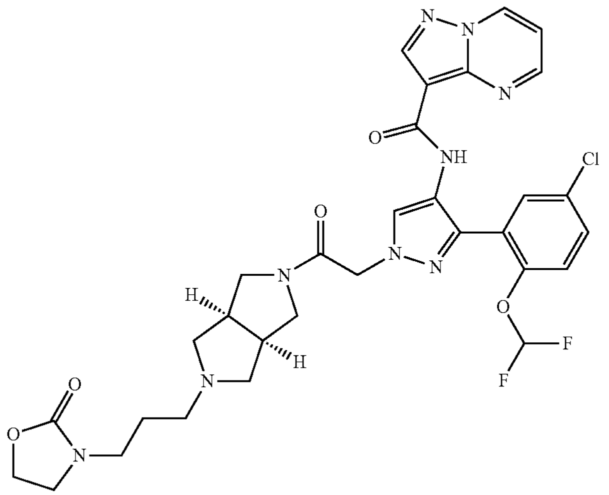 [SMILES: O=C(Nc1cn(CC(=O)N2C[C@H]3CN(CCCN4CCOC4=O)C[C@H]3C2)nc1-c1cc(Cl)ccc1OC(F)F)c1cnn2cccnc12] | N-[1-[2-[(3aS,6aR)-2-[3-(2-oxooxazolidin-3-yl)propyl]-1,3,3a,4,6,6a-hexahydropyrrolo[3,4-c]pyrrol-5-yl]-2-oxo-ethyl]-3-[5-chloro-2-(difluoromethoxy)phenyl] pyrazol-4-yl]pyrazolo[1,5-a]pyrimidine-3-carboxamide |
| 33 | 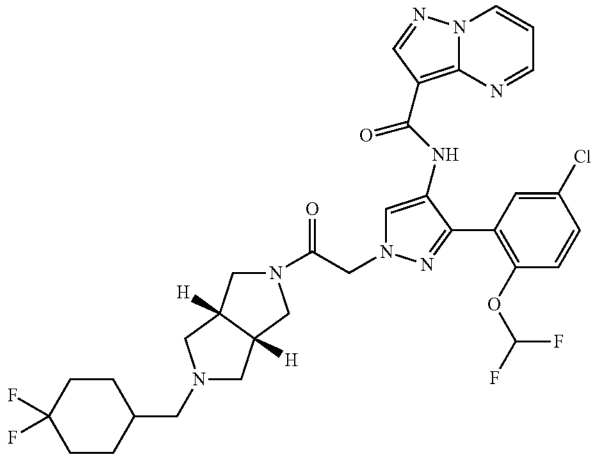 [SMILES: O=C(Nc1cn(CC(=O)N2C[C@H]3CN(CC4CCC(F)(F)CC4)C[C@H]3C2)nc1-c1cc(Cl)ccc1OC(F)F)c1cnn2cccnc12] | N-[1-[2-[(3aR,6aS)-2-[(4,4-difluorocyclohexyl)methyl]-1,3,3a,4,6,6a-hexahydropyrrolo[3,4-c]pyrrol-5-yl]-2-oxo-ethyl]-3-[5-chloro-2-(difluoromethoxy)phenyl] pyrazol-4-yl]pyrazolo[1,5-a]pyrimidine-3-carboxamide |
| 34 | 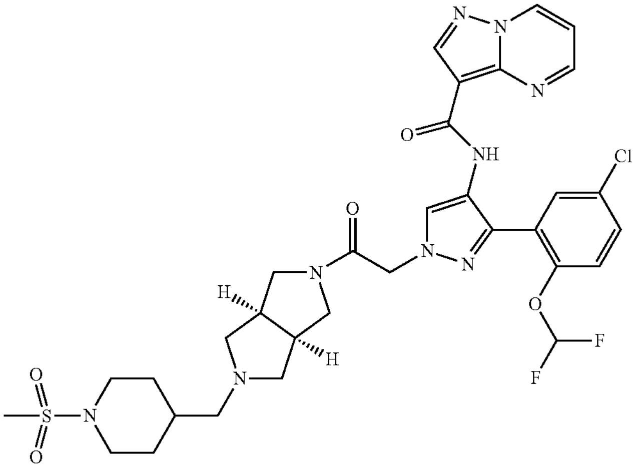 [SMILES: CS(=O)(=O)N1CCC(CN2C[C@@H]3CN(C(=O)Cn4cc(NC(=O)c5cnn6cccnc56)c(-c5cc(Cl)ccc5OC(F)F)n4)C[C@@H]3C2)CC1] | N-[1-[2-[(3aR,6aS)-2-[(1-methylsulfonyl-4-piperidyl)methyl]-1,3,3a,4,6,6a-hexahydropyrrolo[3,4-c]pyrrol-5-yl]-2-oxo-ethyl]-3-[5-chloro-2-(difluoromethoxy)phenyl] pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 35 | 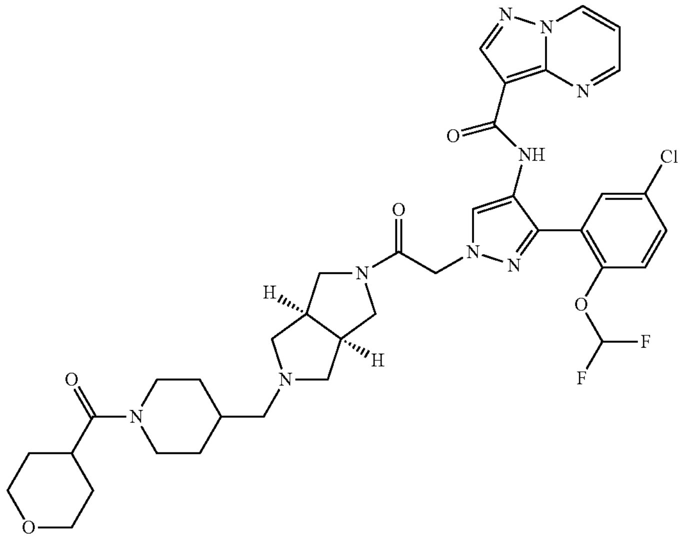 [SMILES: O=C(Nc1cn(CC(=O)N2C[C@H]3CN(CC4CCN(C(=O)C5CCOCC5)CC4)C[C@H]3C2)nc1-c1cc(Cl)ccc1OC(F)F)c1cnn2cccnc12] | N-[1-[2-[(3aR,6aS)-2-[[1-(tetrahydropyran-4-carbonyl)-4-piperidyl]methyl]-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |
| 36 | 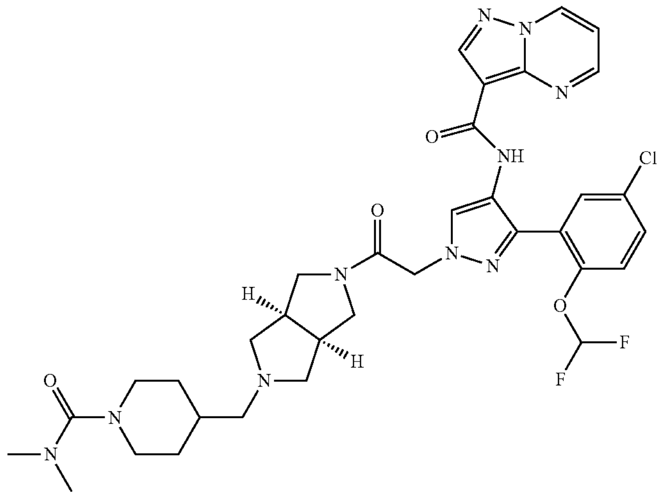 [SMILES: CN(C)C(=O)N1CCC(CN2C[C@@H]3CN(C(=O)Cn4cc(NC(=O)c5cnn6cccnc56)c(-c5cc(Cl)ccc5OC(F)F)n4)C[C@@H]3C2)CC1] | N-[1-[2-[(3aR,6aS)-2-[[1-(dimethylcarbamoyl)-4-piperidyl]methyl]-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |
| 37 | 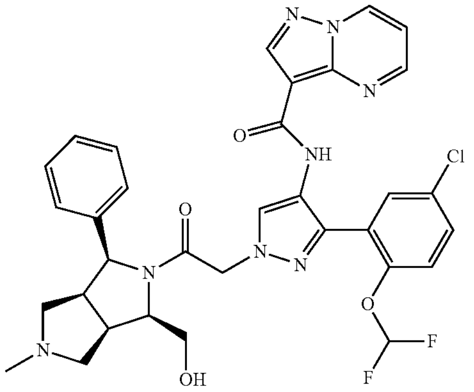 [SMILES: CN1C[C@@H]2[C@H](C1)[C@H](CO)N(C(=O)Cn1cc(NC(=O)c3cnn4cccnc34)c(-c3cc(Cl)ccc3OC(F)F)n1)[C@@H]2c1ccccc1] | N-[1-[2-[(3aS,4S,6R,6aR)-6-(hydroxymethyl)-2-methyl-4-phenyl-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 38 | 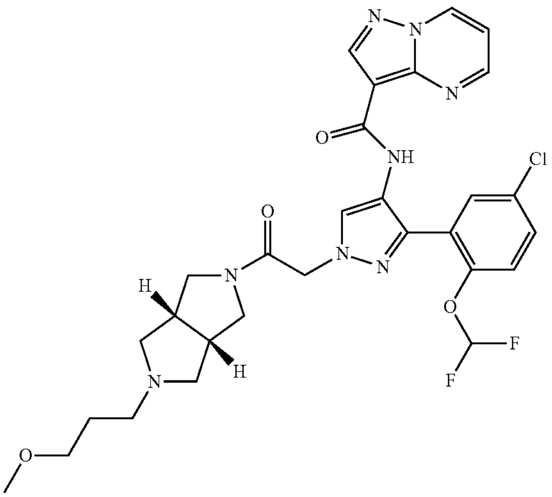 [SMILES: COCCCN1C[C@@H]2CN(C(=O)Cn3cc(NC(=O)c4cnn5cccnc45)c(-c4cc(Cl)ccc4OC(F)F)n3)C[C@@H]2C1] | N-[1-[2-[(3aR,6aS)-2-(3-methoxypropyl)-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |
| 39 | 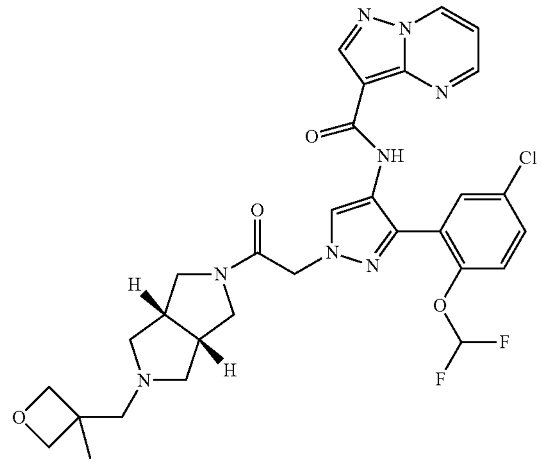 [SMILES: CC1(CN2C[C@@H]3CN(C(=O)Cn4cc(NC(=O)c5cnn6cccnc56)c(-c5cc(Cl)ccc5OC(F)F)n4)C[C@@H]3C2)COC1] | N-[1-[2-[(3aR,6aS)-2-[(3-methyloxetan-3-yl)methyl]-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |
| 40 | 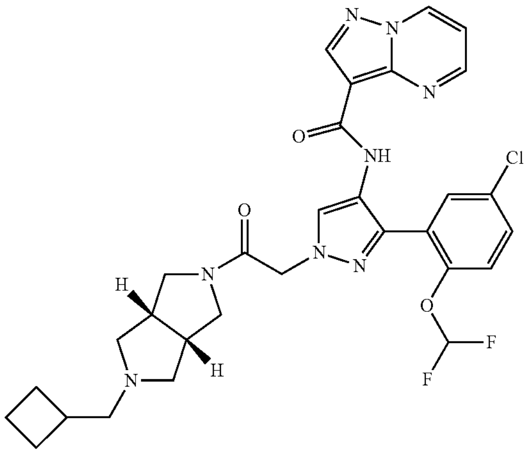 [SMILES: O=C(Nc1cn(CC(=O)N2C[C@H]3CN(CC4CCC4)C[C@H]3C2)nc1-c1cc(Cl)ccc1OC(F)F)c1cnn2cccnc12] | N-[1-[2-[(3aR,6aS)-2-(cyclobutylmethyl)-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 41 | 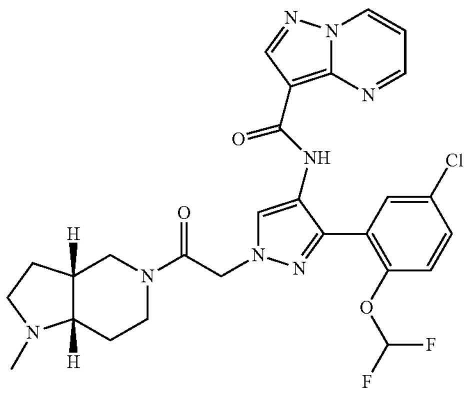 [SMILES: CN1CC[C@@H]2CN(C(=O)Cn3cc(NC(=O)c4cnn5cccnc45)c(-c4cc(Cl)ccc4OC(F)F)n3)CC[C@@H]21] | N-[1-[2-[(3aR,7aS)-1-methyl-3,3a,4,6,7,7a-hexahydro-2H-pyrrolo[3,2-c]pyridin-5-yl]-2-oxo-ethyl]-3-[5-chloro-2-(difluoromethoxy)phenyl]pyrazol-4-yl]pyrazolo[1,5-a]pyrimidine-3-carboxamide |
| 42 | 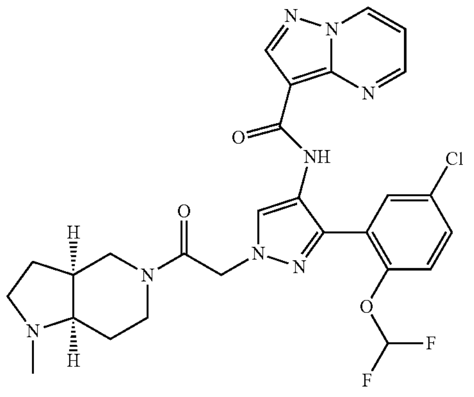 [SMILES: CN1CC[C@H]2CN(C(=O)Cn3cc(NC(=O)c4cnn5cccnc45)c(-c4cc(Cl)ccc4OC(F)F)n3)CC[C@H]21] | N-[1-[2-[(3aS,7aR)-1-methyl-3,3a,4,6,7,7a-hexahydro-2H-pyrrolo[3,2-c]pyridin-5-yl]-2-oxo-ethyl]-3-[5-chloro-2-(difluoromethoxy)phenyl]pyrazol-4-yl]pyrazolo[1,5-a]pyrimidine-3-carboxamide |
| 43 | 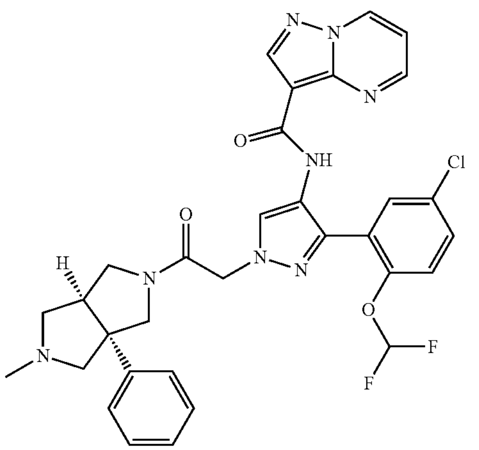 [SMILES: CN1C[C@H]2CN(C(=O)Cn3cc(NC(=O)c4cnn5cccnc45)c(-c4cc(Cl)ccc4OC(F)F)n3)C[C@@]2(c2ccccc2)C1] | N-[1-[2-[(3aS,6aS)-2-methyl-3a-phenyl-3,4,6,6a-tetrahydro-1H-pyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 44 | 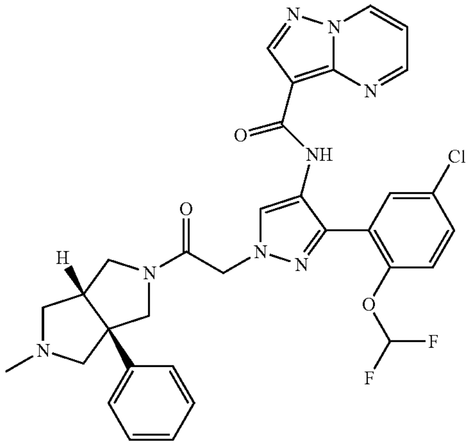 [SMILES: CN1C[C@@H]2CN(C(=O)Cn3cc(NC(=O)c4cnn5cccnc45)c(-c4cc(Cl)ccc4OC(F)F)n3)C[C@]2(c2ccccc2)C1] | N-[1-[2-[(3aR,6aR)-2-methyl-3a-phenyl-3,4,6,6a-tetrahydro-1H-pyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |
| 45 | 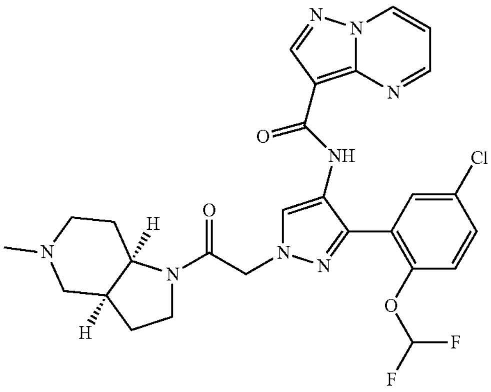 [SMILES: CN1CC[C@@H]2[C@@H](CCN2C(=O)Cn2cc(NC(=O)c3cnn4cccnc34)c(-c3cc(Cl)ccc3OC(F)F)n2)C1] | N-[1-[2-[(3aS,7aR)-5-methyl-3,3a,4,6,7,7a-hexahydro-2H-pyrrolo[3,2-c]pyridin-1-yl]-2-oxo-ethyl]-3-[5-chloro-2-(difluoromethoxy)phenyl]pyrazol-4-yl]pyrazolo[1,5-a]pyrimidine-3-carboxamide |
| 46 | 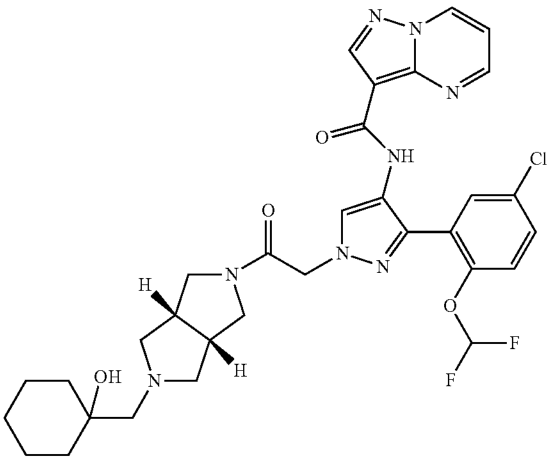 [SMILES: O=C(Nc1cn(CC(=O)N2C[C@H]3CN(CC4(O)CCCCC4)C[C@H]3C2)nc1-c1cc(Cl)ccc1OC(F)F)c1cnn2cccnc12] | N-[1-[2-[(3aS,6aR)-2-[(1-hydroxycyclohexyl)methyl]-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 47 | 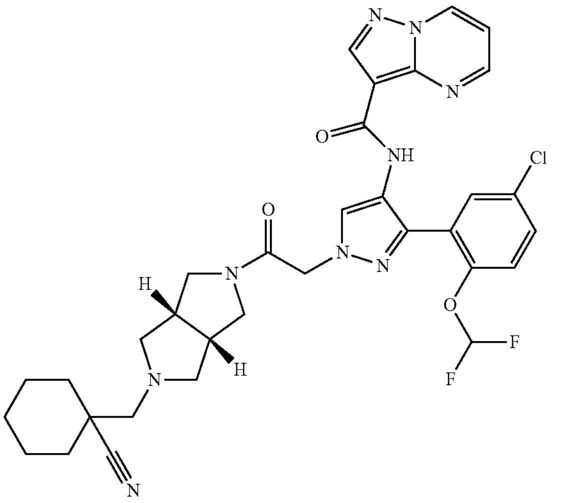 [SMILES: N#CC1(CN2C[C@@H]3CN(C(=O)Cn4cc(NC(=O)c5cnn6cccnc56)c(-c5cc(Cl)ccc5OC(F)F)n4)C[C@@H]3C2)CCCCC1] | N-[1-[2-[(3aS,6aR)-2-[(1-cyanocyclohexyl)methyl]-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |
| 48 | 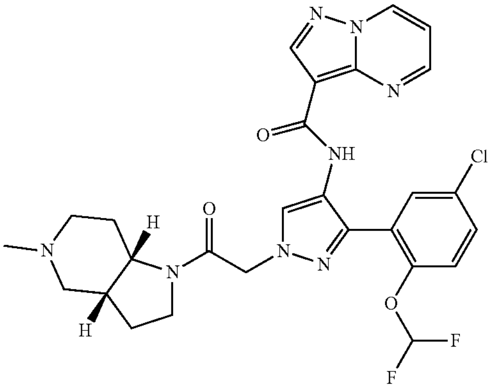 [SMILES: CN1CC[C@H]2[C@H](CCN2C(=O)Cn2cc(NC(=O)c3cnn4cccnc34)c(-c3cc(Cl)ccc3OC(F)F)n2)C1] | N-[1-[2-[(3aR,7aS)-5-methyl-3,3a,4,6,7,7a-hexahydro-2H-pyrrolo[3,2-c]pyridin-1-yl]-2-oxo-ethyl]-3-[5-chloro-2-(difluoromethoxy)phenyl]pyrazol-4-yl]pyrazolo[1,5-a]pyrimidine-3-carboxamide |
| 49 | 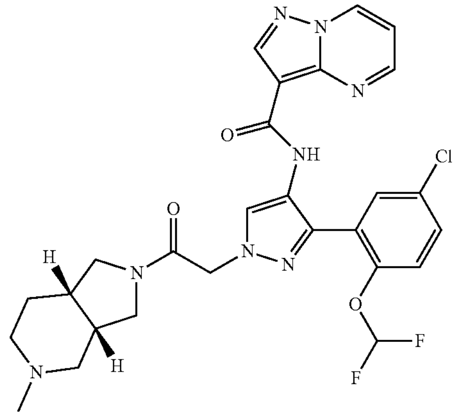 [SMILES: CN1CC[C@@H]2CN(C(=O)Cn3cc(NC(=O)c4cnn5cccnc45)c(-c4cc(Cl)ccc4OC(F)F)n3)C[C@@H]2C1] | N-[1-[2-[(3aS,7aS)-5-methyl-3,3a,4,6,7,7a-hexahydro-1H-pyrrolo[3,4-c]pyridin-2-yl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 50 | 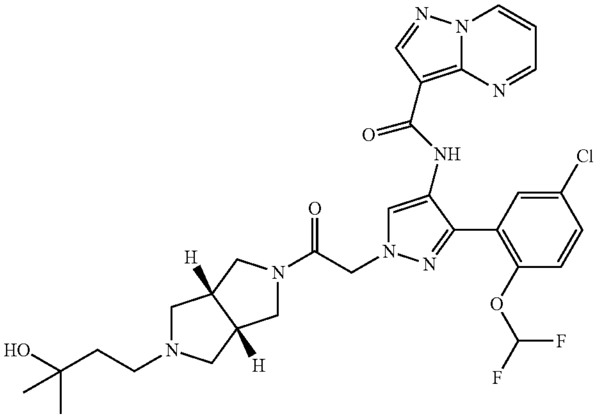 [SMILES: CC(C)(O)CCN1C[C@@H]2CN(C(=O)Cn3cc(NC(=O)c4cnn5cccnc45)c(-c4cc(Cl)ccc4OC(F)F)n3)C[C@@H]2C1] | N-[1-[2-[(3aR,6aS)-2-(3-hydroxy-3-methyl-butyl)-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |
| 51 | 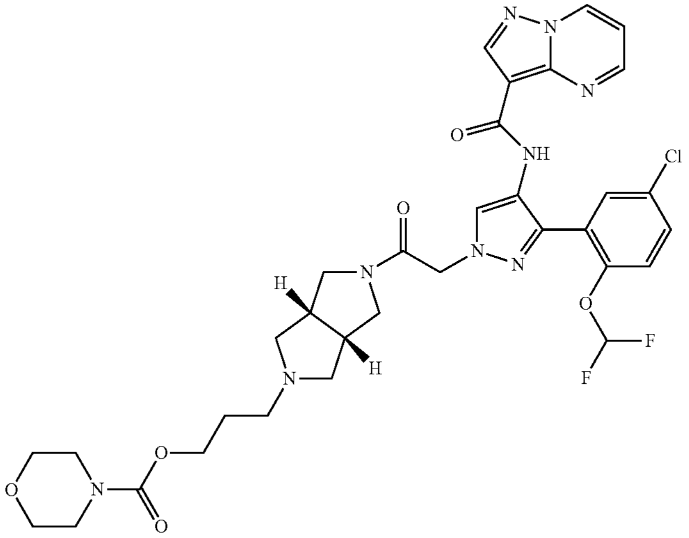 [SMILES: O=C(Nc1cn(CC(=O)N2C[C@H]3CN(CCCOC(=O)N4CCOCC4)C[C@H]3C2)nc1-c1cc(Cl)ccc1OC(F)F)c1cnn2cccnc12] | 3-[(3aR,6aS)-5-[2-[3-[5-chloro-2-(difluoromethoxy)phenyl]-4-(pyrazolo[1,5-a]pyrimidine-3-carbonylamino)pyrazol-1-yl]acetyl]-1,3,3a,4,6,6a-hexahydropyrrolo[3,4-c]pyrrol-2-yl]propyl morpholine-4-carboxylate |
| 52 | 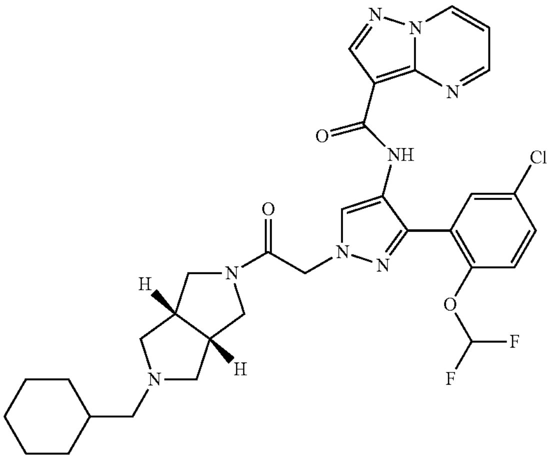 [SMILES: O=C(Nc1cn(CC(=O)N2C[C@H]3CN(CC4CCCCC4)C[C@H]3C2)nc1-c1cc(Cl)ccc1OC(F)F)c1cnn2cccnc12] | N-[1-[2-[(3aR,6aS)-2-(cyclohexylmethyl)-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 53 | 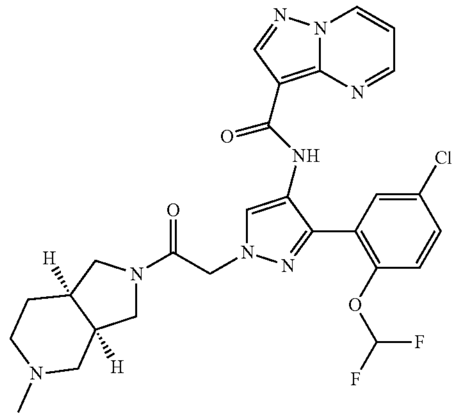 [SMILES: CN1CC[C@H]2CN(C(=O)Cn3cc(NC(=O)c4cnn5cccnc45)c(-c4cc(Cl)ccc4OC(F)F)n3)C[C@H]2C1] | N-[1-[2-[(3aR,7aR)-5-methyl-3,3a,4,6,7,7a-hexahydro-1H-pyrrolo[3,4-c]pyridin-2-yl]-2-oxo-ethyl]-3-[5-chloro-2-(difluoromethoxy)phenyl]pyrazol-4-yl]pyrazolo[1,5-a]pyrimidine-3-carboxamide |
| 54 | 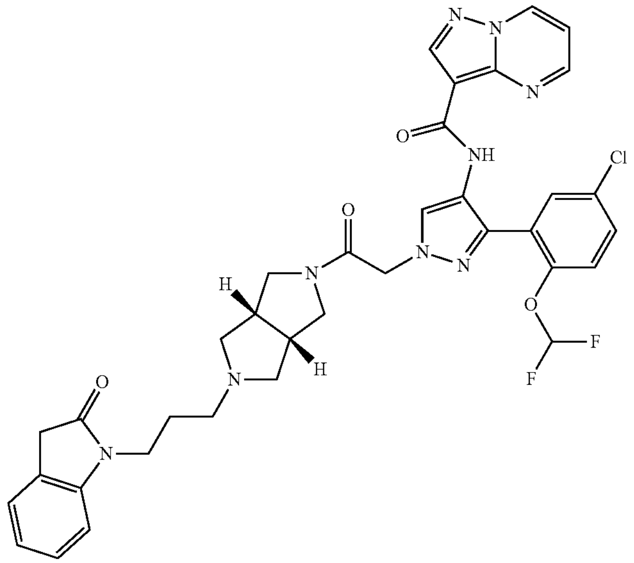 [SMILES: O=C(Nc1cn(CC(=O)N2C[C@H]3CN(CCCN4C(=O)Cc5ccccc54)C[C@H]3C2)nc1-c1cc(Cl)ccc1OC(F)F)c1cnn2cccnc12] | N-[1-[2-[(3aR,6aS)-2-[3-(2-oxoindolin-1-yl)propyl]-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |
| 55 | 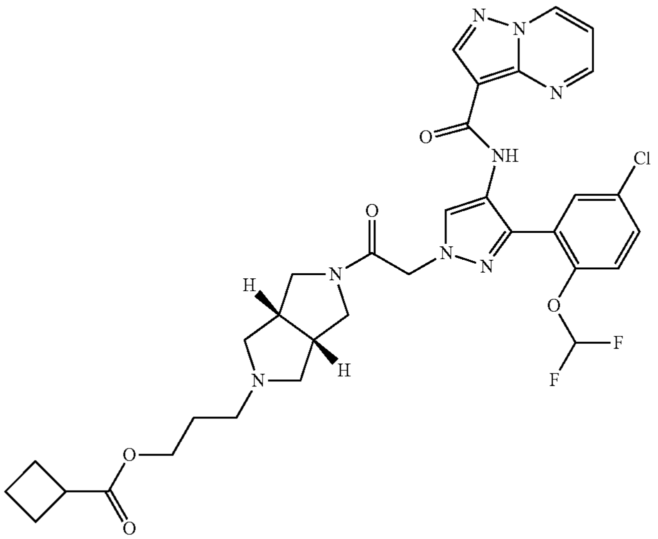 [SMILES: O=C(Nc1cn(CC(=O)N2C[C@H]3CN(CCCOC(=O)C4CCC4)C[C@H]3C2)nc1-c1cc(Cl)ccc1OC(F)F)c1cnn2cccnc12] | 3-[(3aS,6aR)-5-[2-[3-[5-chloro-2-(difluoromethoxy)phenyl]-4-(pyrazolo[1,5-a]pyrimidine-3-carbonylamino)pyrazol-1-yl]acetyl]-1,3,3a,4,6,6a-hexahydropyrrolo[3,4-c]pyrrol-2-yl]propyl cyclobutanecarboxylate |

TABLE 1-continued

| Exemplary Compounds of the Present Invention | | |
|---|---|---|
| Ex. | Structure | Name |
| 56 | 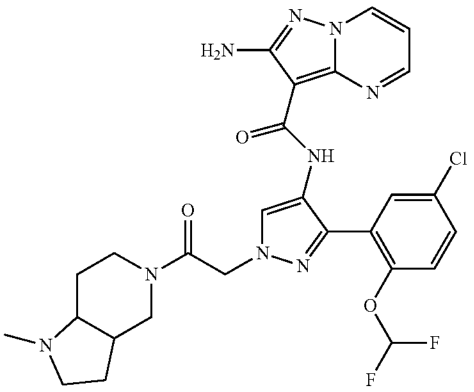 [SMILES: CN1CCC2CN(C(=O)Cn3cc(NC(=O)c4c(N)nn5cccnc45)c(-c4cc(Cl)ccc4OC(F)F)n3)CCC21] | 2-amino-N-[3-[5-chloro-2-(difluoromethoxy)phenyl]-1-[2-(1-methyl-3,3a,4,6,7,7a-hexahydro-2H-pyrrolo[3,2-c]pyridin-5-yl)-2-oxo-ethyl]pyrazol-4-yl]pyrazolo[1,5-a]pyrimidine-3-carboxamide |
| 57 | 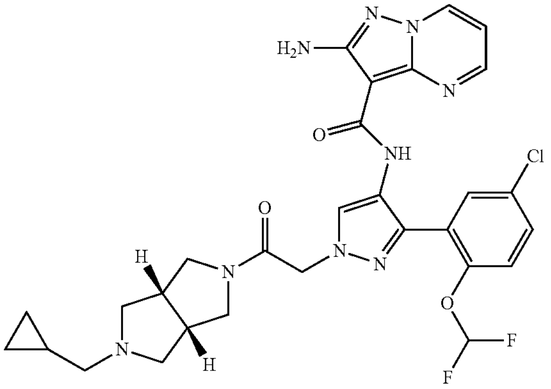 [SMILES: Nc1nn2cccnc2c1C(=O)Nc1cn(CC(=O)N2C[C@H]3CN(CC4CC4)C[C@H]3C2)nc1-c1cc(Cl)ccc1OC(F)F] | N-[1-[2-[(3aS,6aR)-2-(cyclopropylmethyl)-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]-2-amino-pyrazolo[1,5-a]pyrimidine-3-carboxamide |
| 58 | 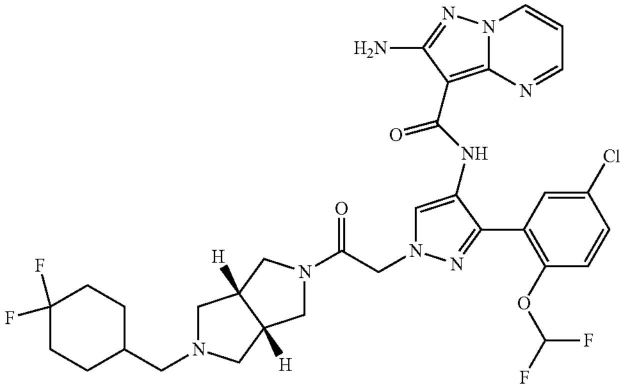 [SMILES: Nc1nn2cccnc2c1C(=O)Nc1cn(CC(=O)N2C[C@H]3CN(CC4CCC(F)(F)CC4)C[C@H]3C2)nc1-c1cc(Cl)ccc1OC(F)F] | N-[1-[2-[(3aS,6aR)-2-[(4,4-difluorocyclohexyl)methyl]-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]-2-amino-pyrazolo[1,5-a]pyrimidine-3-carboxamide |
| 59 | 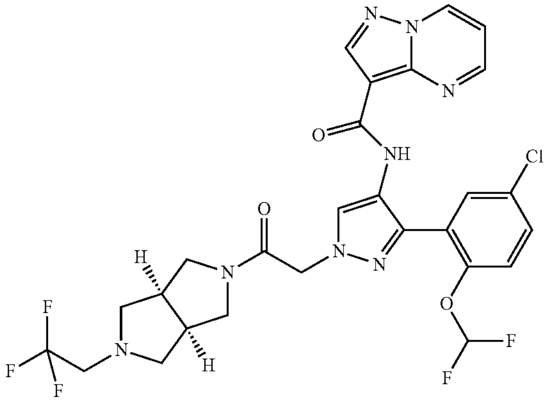 [SMILES: O=C(Nc1cn(CC(=O)N2C[C@H]3CN(CC(F)(F)F)C[C@H]3C2)nc1-c1cc(Cl)ccc1OC(F)F)c1cnn2cccnc12] | N-[1-[2-[(3aR,6aS)-2-(2,2,2-trifluoroethyl)-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Ex. | Structure | Name |
|---|---|---|
| | Exemplary Compounds of the Present Invention | |
| 60 | 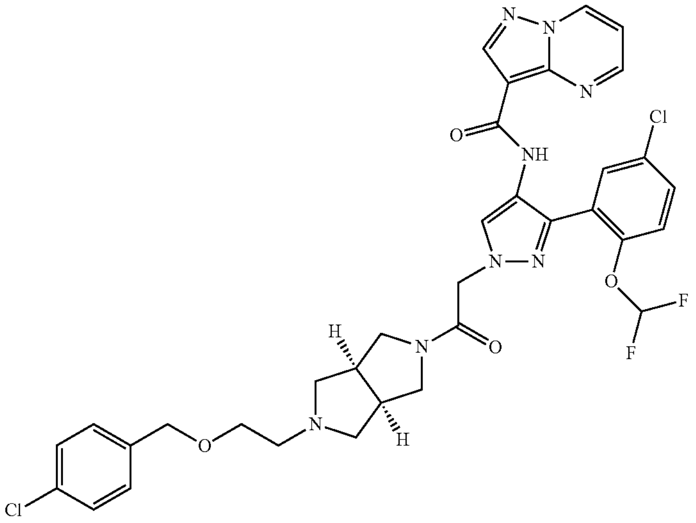 [SMILES: O=C(Nc1cn(CC(=O)N2C[C@H]3CN(CCOCc4ccc(Cl)cc4)C[C@H]3C2)nc1-c1cc(Cl)ccc1OC(F)F)c1cnn2cccnc12] | N-[1-[2-[(3aR,6aS)-2-[2-[(4-chlorophenyl)methoxy]ethyl]-1,3,3a,4,6,6a-hexahydropyrrolo[3,4-c]pyrrol-5-yl]-2-oxo-ethyl]-3-[5-chloro-2-(difluoromethoxy)phenyl]pyrazol-4-yl]pyrazolo[1,5-a]pyrimidine-3-carboxamide |
| 61 | 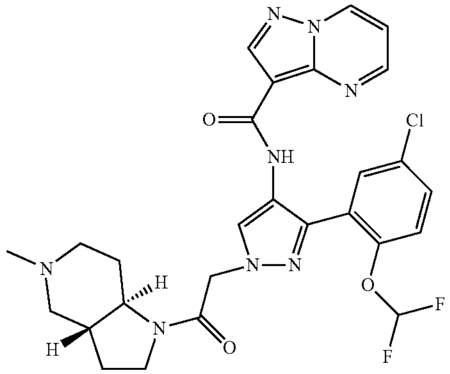 [SMILES: CN1CC[C@@H]2[C@H](CCN2C(=O)Cn2cc(NC(=O)c3cnn4cccnc34)c(-c3cc(Cl)ccc3OC(F)F)n2)C1] | N-[1-[2-[(3aR,7aR)-5-methyl-3,3a,4,6,7,7a-hexahydro-2H-pyrrolo[3,2-c]pyridin-1-yl]-2-oxo-ethyl]-3-[5-chloro-2-(difluoromethoxy)phenyl]pyrazol-4-yl]pyrazolo[1,5-a]pyrimidine-3-carboxamide |
| 62 | 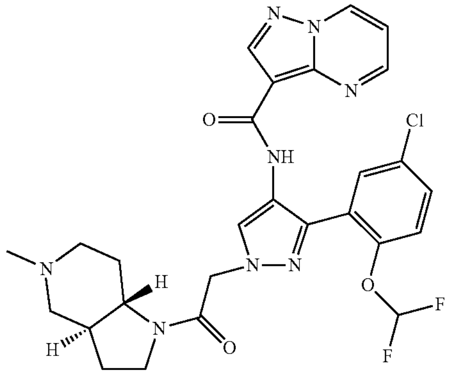 [SMILES: CN1CC[C@H]2[C@@H](CCN2C(=O)Cn2cc(NC(=O)c3cnn4cccnc34)c(-c3cc(Cl)ccc3OC(F)F)n2)C1] | N-[1-[2-[(3aS,7aS)-5-methyl-3,3a,4,6,7,7a-hexahydro-2H-pyrrolo[3,2-c]pyridin-1-yl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 63 | 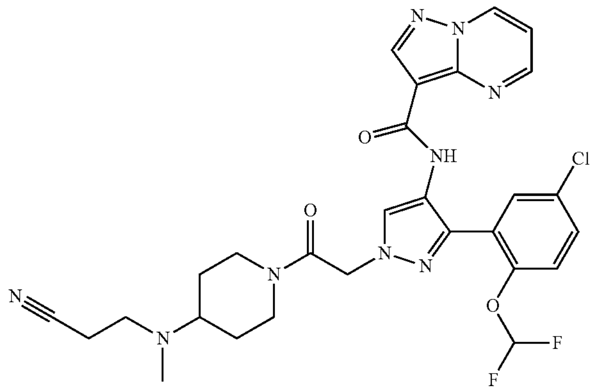 [SMILES: CN(CCC#N)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[2-cyanoethyl(methyl)amino]-1-piperidyl]-2-oxo-ethyl]pyrazol-4-yl]pyrazolo[1,5-a]pyrimidine-3-carboxamide |
| 64 | 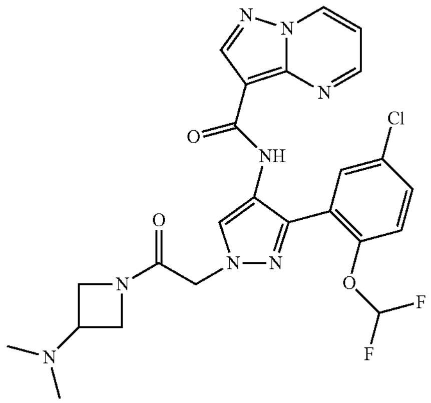 [SMILES: CN(C)C1CN(C(=O)Cn2cc(NC(=O)c3cnn4cccnc34)c(-c3cc(Cl)ccc3OC(F)F)n2)C1] | N-[3-[5-chloro-2-(difluoromethoxy)phenyl]-1-[2-[3-(dimethylamino)azetidin-1-yl]-2-oxo-ethyl]pyrazol-4-yl]pyrazolo[1,5-a]pyrimidine-3-carboxamide |
| 65 | 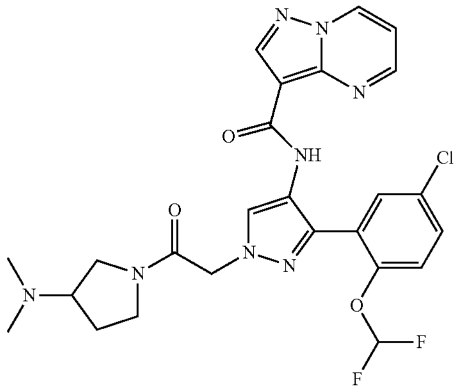 [SMILES: CN(C)C1CCN(C(=O)Cn2cc(NC(=O)c3cnn4cccnc34)c(-c3cc(Cl)ccc3OC(F)F)n2)C1] | N-[3-[5-chloro-2-(difluoromethoxy)phenyl]-1-[2-[3-(dimethylamino)pyrrolidin-1-yl]-2-oxo-ethyl]pyrazol-4-yl]pyrazolo[1,5-a]pyrimidine-3-carboxamide |
| 66 | 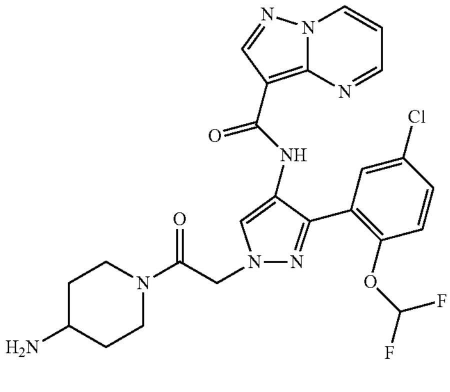 [SMILES: NC1CCN(C(=O)Cn2cc(NC(=O)c3cnn4cccnc34)c(-c3cc(Cl)ccc3OC(F)F)n2)CC1] | N-[1-[2-(4-amino-1-piperidyl)-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 67 | 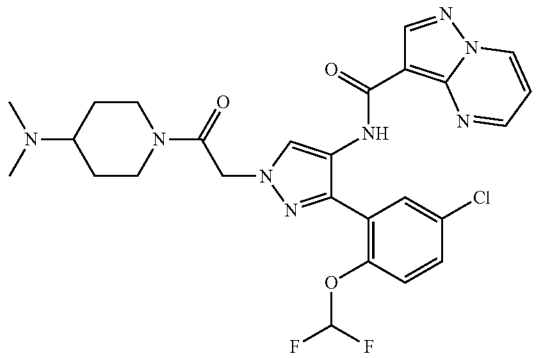 [SMILES: CN(C)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-(dimethylamino)-1-piperidyl]-2-oxo-ethyl]pyrazol-4-yl]pyrazolo[1,5-a]pyrimidine-3-carboxamide |
| 68 | 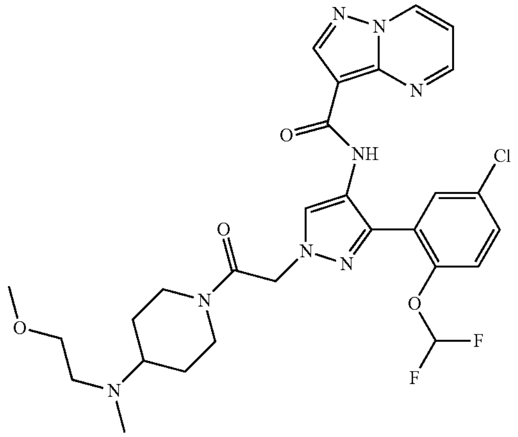 [SMILES: COCCN(C)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[2-methoxyethyl(methyl)amino]-1-piperidyl]-2-oxo-ethyl]pyrazol-4-yl]pyrazolo[1,5-a]pyrimidine-3-carboxamide |
| 69 | 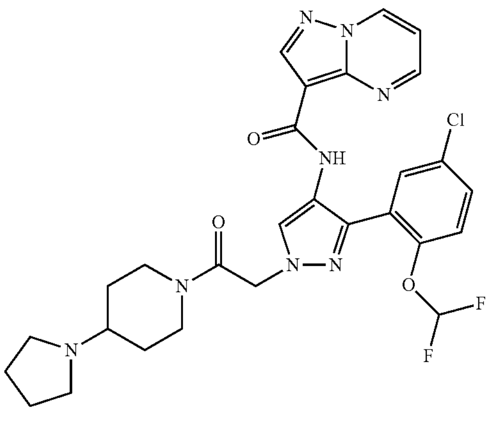 [SMILES: O=C(Nc1cn(CC(=O)N2CCC(N3CCCC3)CC2)nc1-c1cc(Cl)ccc1OC(F)F)c1cnn2cccnc12] | N-[3-[5-chloro-2-(difluoromethoxy)phenyl]-1-[2-oxo-2-(4-pyrrolidin-1-yl-1-piperidyl)ethyl]pyrazol-4-yl]pyrazolo[1,5-a]pyrimidine-3-carboxamide |

TABLE 1-continued

Exemplary Compounds of the Present Invention

| Ex. | Structure | Name |
| --- | --- | --- |
| 70 | 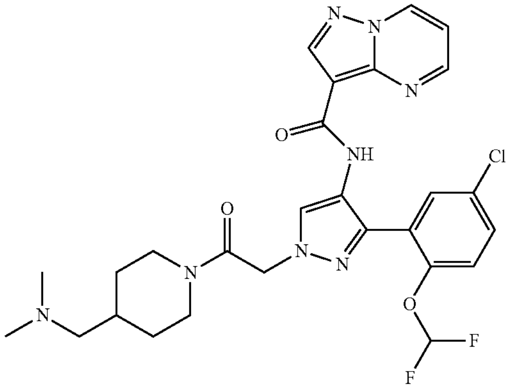 [SMILES: CN(C)CC1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[(dimethylamino)methyl]-1-piperidyl]-2-oxo-ethyl]pyrazol-4-yl]pyrazolo[1,5-a]pyrimidine-3-carboxamide |
| 71 | 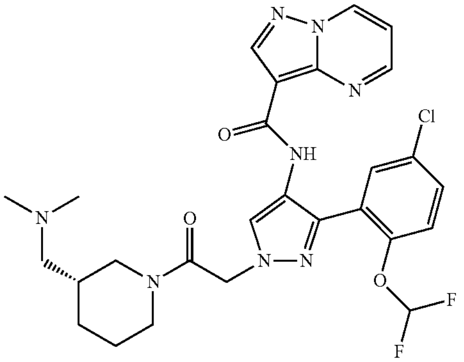 [SMILES: CN(C)C[C@H]1CCCN(C(=O)Cn2cc(NC(=O)c3cnn4cccnc34)c(-c3cc(Cl)ccc3OC(F)F)n2)C1] | N-[3-[5-chloro-2-(difluoromethoxy)phenyl]-1-[2-[(3R)-3-[(dimethylamino)methyl]-1-piperidyl]-2-oxo-ethyl]pyrazol-4-yl]pyrazolo[1,5-a]pyrimidine-3-carboxamide |
| 72 | 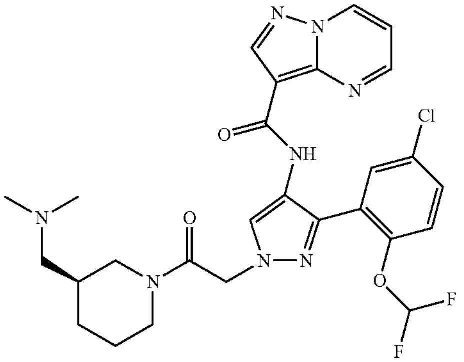 [SMILES: CN(C)C[C@@H]1CCCN(C(=O)Cn2cc(NC(=O)c3cnn4cccnc34)c(-c3cc(Cl)ccc3OC(F)F)n2)C1] | N-[3-[5-chloro-2-(difluoromethoxy)phenyl]-1-[2-[(3S)-3-[(dimethylamino)methyl]-1-piperidyl]-2-oxo-ethyl]pyrazol-4-yl]pyrazolo[1,5-a]pyrimidine-3-carboxamide |
| 73 | 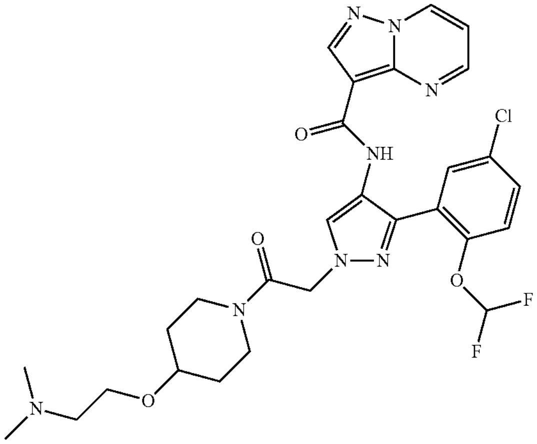 [SMILES: CN(C)CCOC1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[2-(dimethylamino)ethoxy]-1-piperidyl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 74 | 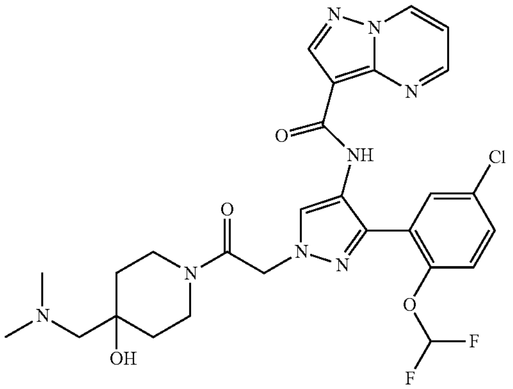 [SMILES: CN(C)CC1(O)CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[(dimethylamino)methyl]-4-hydroxy-1-piperidyl]-2-oxo-ethyl]pyrazol-4-yl]pyrazolo[1,5-a]pyrimidine-3-carboxamide |
| 75 | 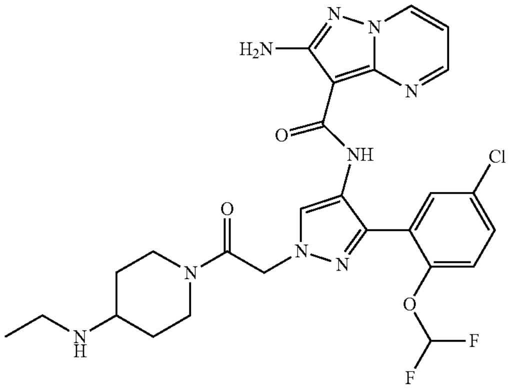 [SMILES: CCNC1CCN(C(=O)Cn2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-[2-[4-(ethylamino)-1-piperidyl]-2-oxo-ethyl]pyrazol-4-yl]pyrazolo[1,5-a]pyrimidine-3-carboxamide |
| 76 | 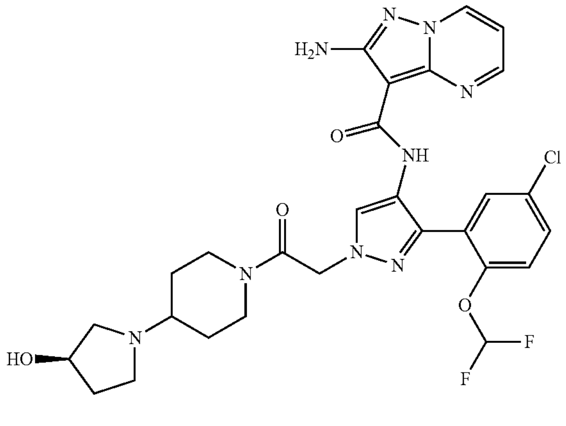 [SMILES: Nc1nn2cccnc2c1C(=O)Nc1cn(CC(=O)N2CCC(N3CC[C@@H](O)C3)CC2)nc1-c1cc(Cl)ccc1OC(F)F] | 2-amino-N-[3-[5-chloro-2-(difluoromethoxy)phenyl]-1-[2-[4-[(3R)-3-hydroxypyrrolidin-1-yl]-1-piperidyl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 77 | 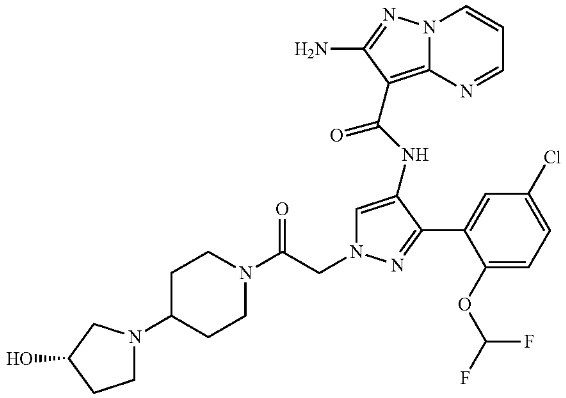 [SMILES: Nc1nn2cccnc2c1C(=O)Nc1cn(CC(=O)N2CCC(N3CC[C@H](O)C3)CC2)nc1-c1cc(Cl)ccc1OC(F)F] | 2-amino-N-[3-[5-chloro-2-(difluoromethoxy)phenyl]-1-[2-[4-[(3S)-3-hydroxypyrrolidin-1-yl]-1-piperidyl]-2-oxo-ethyl]pyrazol-4-yl]pyrazolo[1,5-a]pyrimidine-3-carboxamide |
| 78 | 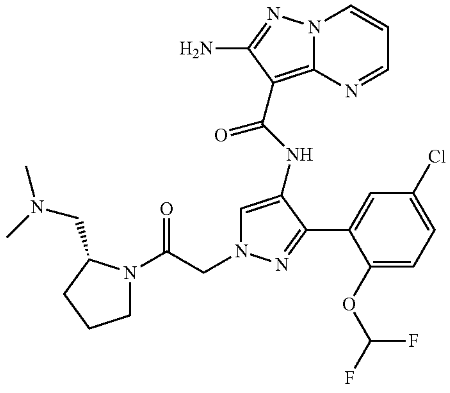 [SMILES: CN(C)C[C@H]1CCCN1C(=O)Cn1cc(NC(=O)c2c(N)nn3cccnc23)c(-c2cc(Cl)ccc2OC(F)F)n1] | 2-amino-N-[3-[5-chloro-2-(difluoromethoxy)phenyl]-1-[2-[(2R)-2-[(dimethylamino)methyl]pyrrolidin-1-yl]-2-oxo-ethyl]pyrazol-4-yl]pyrazolo[1,5-a]pyrimidine-3-carboxamide |
| 79 | 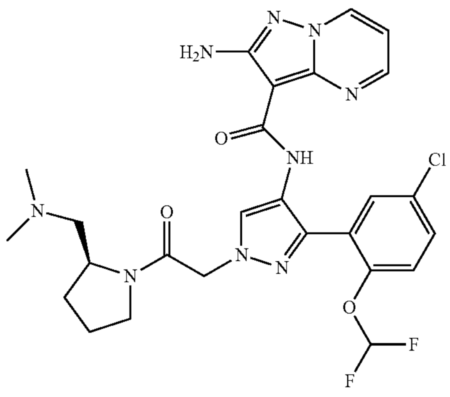 [SMILES: CN(C)C[C@@H]1CCCN1C(=O)Cn1cc(NC(=O)c2c(N)nn3cccnc23)c(-c2cc(Cl)ccc2OC(F)F)n1] | 2-amino-N-[3-[5-chloro-2-(difluoromethoxy)phenyl]-1-[2-[(2S)-2-[(dimethylamino)methyl]pyrrolidin-1-yl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 80 | 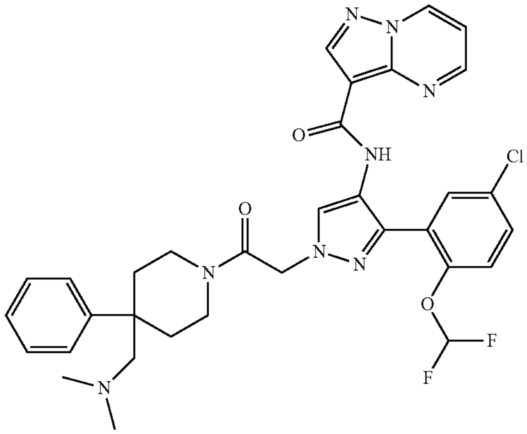 [SMILES: CN(C)CC1(c2ccccc2)CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[(dimethylamino)methyl]-4-phenyl-1-piperidyl]-2-oxo-ethyl]pyrazol-4-yl]pyrazolo[1,5-a]pyrimidine-3-carboxamide |
| 81 | 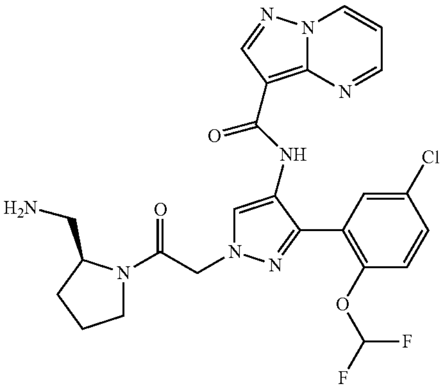 [SMILES: NC[C@@H]1CCCN1C(=O)Cn1cc(NC(=O)c2cnn3cccnc23)c(-c2cc(Cl)ccc2OC(F)F)n1] | N-[1-[2-[(2S)-2-(aminomethyl)pyrrolidin-1-yl]-2-oxo-ethyl]-3-[5-chloro-2-(difluoromethoxy)phenyl]pyrazol-4-yl]pyrazolo[1,5-a]pyrimidine-3-carboxamide |
| 82 | 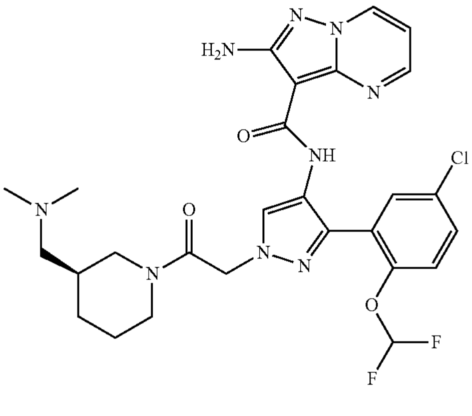 [SMILES: CN(C)C[C@@H]1CCCN(C(=O)Cn2cc(NC(=O)c3c(N)nn4cccnc34)c(-c3cc(Cl)ccc3OC(F)F)n2)C1] | 2-amino-N-[3-[5-chloro-2-(difluoromethoxy)phenyl]-1-[2-[(3S)-3-[(dimethylamino)methyl]-1-piperidyl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 83 | 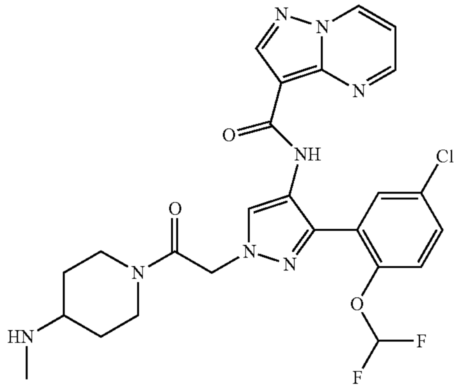 [SMILES: CNC1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-(methylamino)-1-piperidyl]-2-oxo-ethyl]pyrazol-4-yl]pyrazolo[1,5-a]pyrimidine-3-carboxamide |
| 84 | 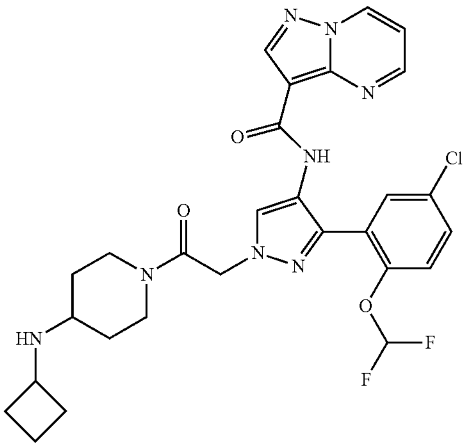 [SMILES: O=C(Nc1cn(CC(=O)N2CCC(NC3CCC3)CC2)nc1-c1cc(Cl)ccc1OC(F)F)c1cnn2cccnc12] | N-[3-[5-chloro-2-(difluoromethoxy)phenyl]-1-[2-[4-(cyclobutylamino)-1-piperidyl]-2-oxo-ethyl]pyrazol-4-yl]pyrazolo[1,5-a]pyrimidine-3-carboxamide |
| 85 | 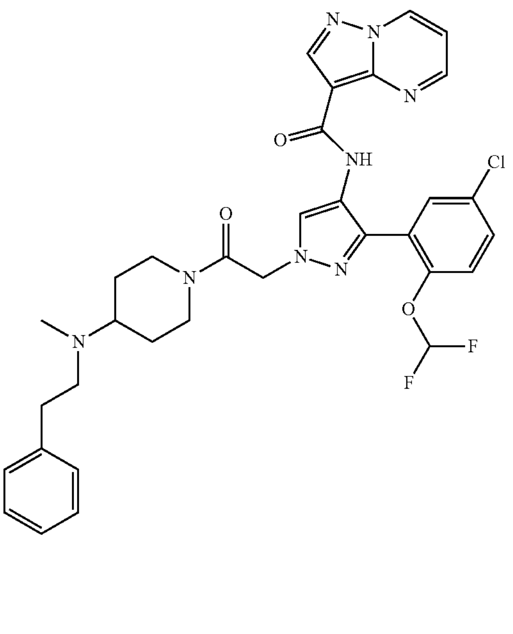 [SMILES: CN(CCc1ccccc1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[methyl(2-phenylethyl)amino]-1-piperidyl]-2-oxo-ethyl]pyrazol-4-yl]pyrazolo[1,5-a]pyrimidine-3-carboxamide |

TABLE 1-continued
| Ex. | Structure | Name |
| --- | --- | --- |
| | Exemplary Compounds of the Present Invention | |
| 86 | 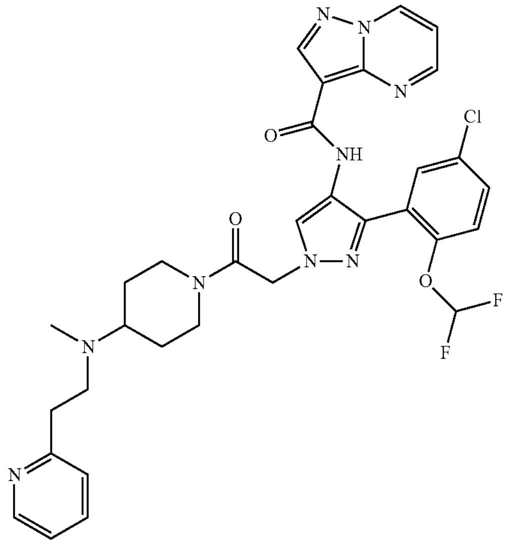 [SMILES: CN(CCc1ccccn1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[methyl-[2-(2-pyridyl)ethyl]amino]-1-piperidyl]-2-oxo-ethyl]pyrazol-4-yl]pyrazolo[1,5-a]pyrimidine-3-carboxamide |
| 87 | 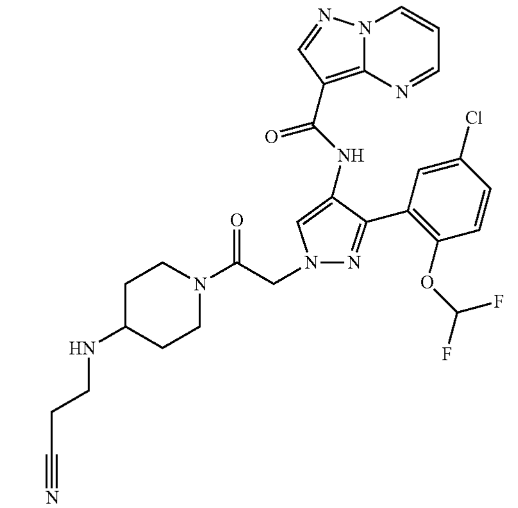 [SMILES: N#CCCNC1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-(2-cyanoethylamino)-1-piperidyl]-2-oxo-ethyl]pyrazol-4-yl]pyrazolo[1,5-a]pyrimidine-3-carboxamide |

TABLE 1-continued

| Ex. | Structure | Name |
|---|---|---|
| | Exemplary Compounds of the Present Invention | |
| 88 | 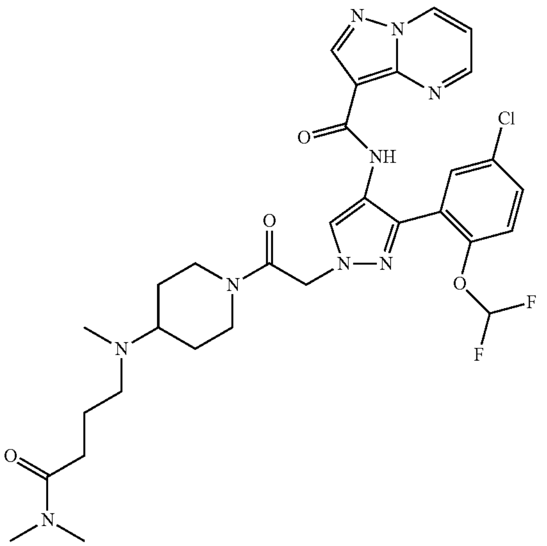 [SMILES: CN(C)C(=O)CCCN(C)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[[4-(dimethylamino)-4-oxo-butyl]-methyl-amino]-1-piperidyl]-2-oxo-ethyl]pyrazol-4-yl]pyrazolo[1,5-a]pyrimidine-3-carboxamide |
| 89 | 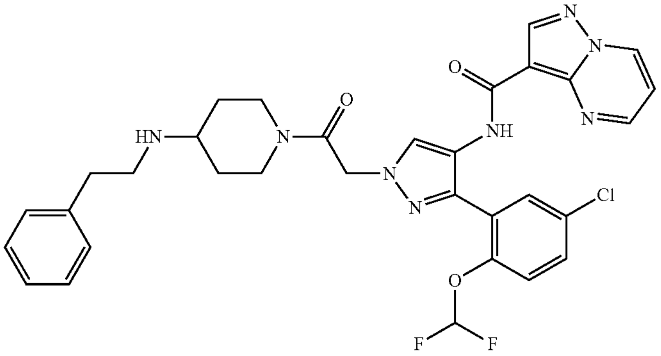 [SMILES: O=C(Nc1cn(CC(=O)N2CCC(NCCc3ccccc3)CC2)nc1-c1cc(Cl)ccc1OC(F)F)c1cnn2cccnc12] | N-[3-[5-chloro-2-(difluoromethoxy)phenyl]-1-[2-oxo-2-[4-(2-phenylethylamino)-1-piperidyl]ethyl]pyrazol-4-yl]pyrazolo[1,5-a]pyrimidine-3-carboxamide |
| 90 | 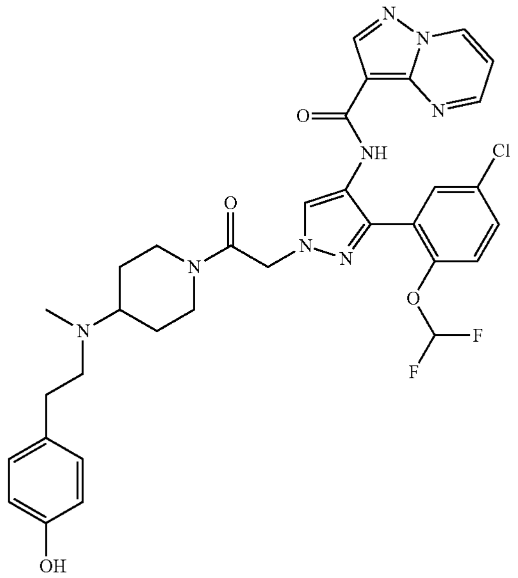 [SMILES: CN(CCc1ccc(O)cc1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[2-(4-hydroxyphenyl)ethyl-methyl-amino]-1-piperidyl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 91 | 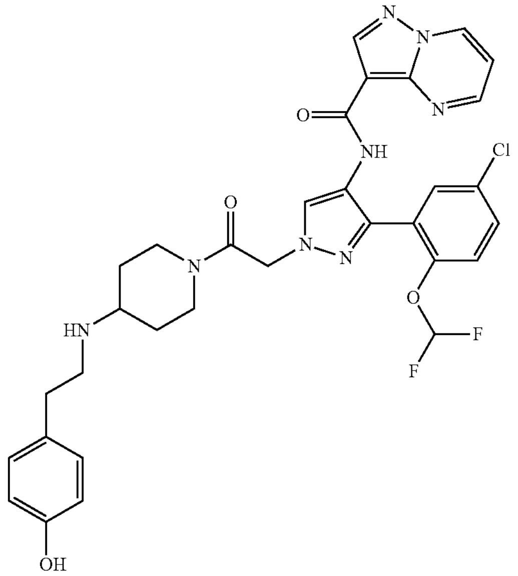 [SMILES: O=C(Nc1cn(CC(=O)N2CCC(NCCc3ccc(O)cc3)CC2)nc1-c1cc(Cl)ccc1OC(F)F)c1cnn2cccnc12] | N-[3-[5-chloro-2-(difluoromethoxy)phenyl]-1-[2-[4-[2-(4-hydroxyphenyl)ethylamino]-1-piperidyl]-2-oxo-ethyl]pyrazol-4-yl]pyrazolo[1,5-a]pyrimidine-3-carboxamide |
| 92 | 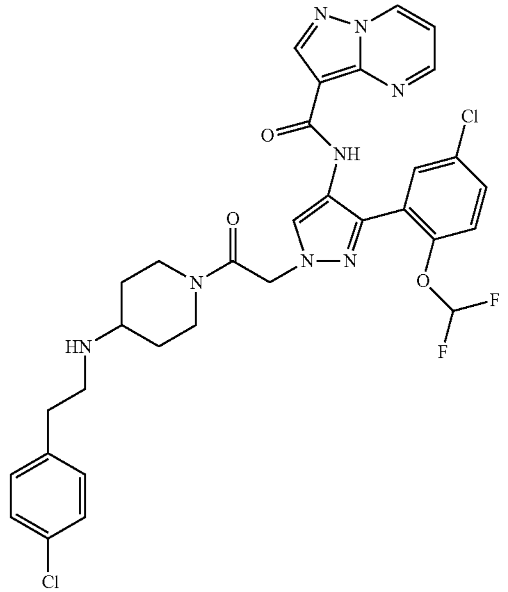 [SMILES: O=C(Nc1cn(CC(=O)N2CCC(NCCc3ccc(Cl)cc3)CC2)nc1-c1cc(Cl)ccc1OC(F)F)c1cnn2cccnc12] | N-[3-[5-chloro-2-(difluoromethoxy)phenyl]-1-[2-[4-[2-(4-chlorophenyl)ethylamino]-1-piperidyl]-2-oxo-ethyl]pyrazol-4-yl]pyrazolo[1,5-a]pyrimidine-3-carboxamide |
| 93 | 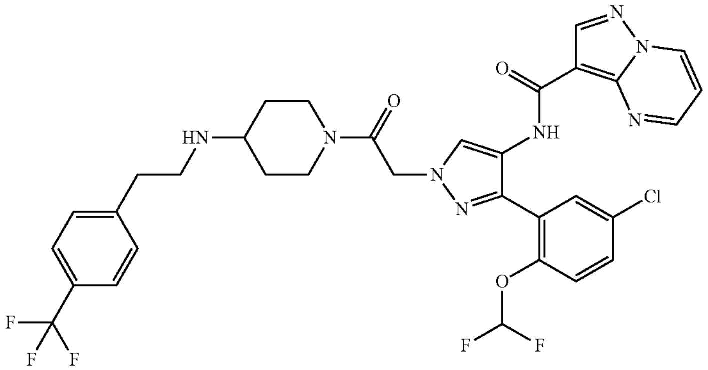 [SMILES: O=C(Nc1cn(CC(=O)N2CCC(NCCc3ccc(C(F)(F)F)cc3)CC2)nc1-c1cc(Cl)ccc1OC(F)F)c1cnn2cccnc12] | N-[3-[5-chloro-2-(difluoromethoxy)phenyl]-1-[2-oxo-2-[4-[2-[4-(trifluoromethyl)phenyl]ethylamino]-1-piperidyl]ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 94 | 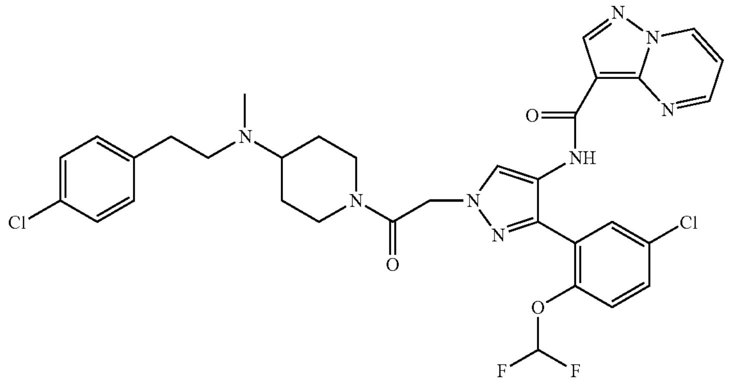 [SMILES: CN(CCc1ccc(Cl)cc1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[2-(4-chlorophenyl)ethyl-methyl-amino]-1-piperidyl]-2-oxo-ethyl]pyrazol-4-yl]pyrazolo[1,5-a]pyrimidine-3-carboxamide |
| 95 | 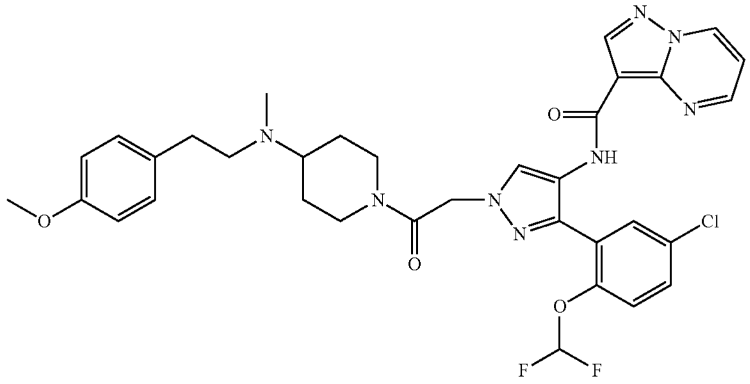 [SMILES: COc1ccc(CCN(C)C2CCN(C(=O)Cn3cc(NC(=O)c4cnn5cccnc45)c(-c4cc(Cl)ccc4OC(F)F)n3)CC2)cc1] | N-[3-[5-chloro-2-(difluoromethoxy)phenyl]-1-[2-[4-[2-(4-methoxyphenyl)ethyl-methyl-amino]-1-piperidyl]-2-oxo-ethyl]pyrazol-4-yl]pyrazolo[1,5-a]pyrimidine-3-carboxamide |
| 96 | 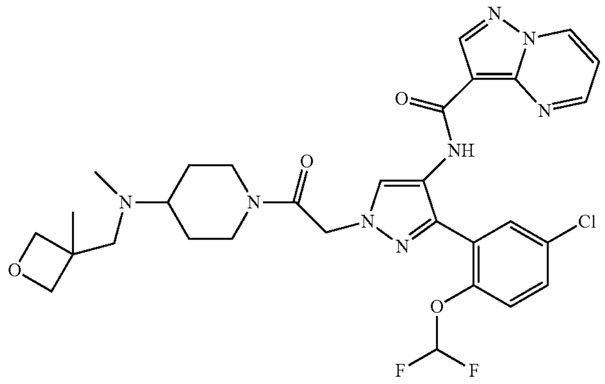 [SMILES: CN(CC1(C)COC1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[methyl-[(3-methyloxetan-3-yl)methyl]amino]-1-piperidyl]-2-oxo-ethyl]pyrazol-4-yl]pyrazolo[1,5-a]pyrimidine-3-carboxamide |
| 97 | 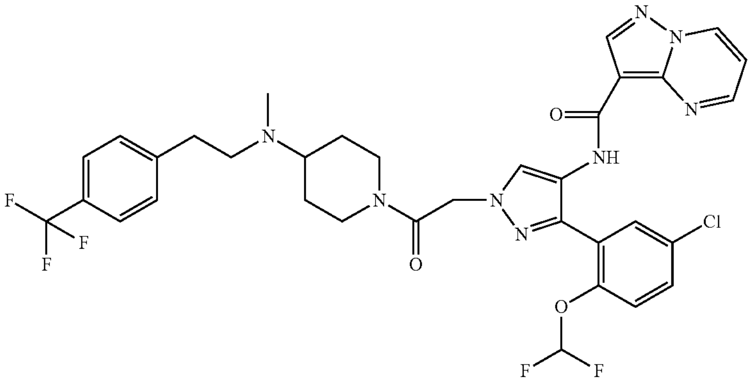 [SMILES: CN(CCc1ccc(C(F)(F)F)cc1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[methyl-[2-[4-(trifluoromethyl)phenyl] ethyl]amino]-1-piperidyl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 98 | 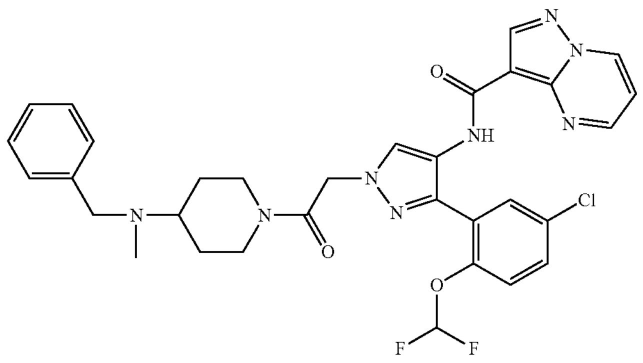 [SMILES: CN(Cc1ccccc1)C1CCN(C(=O)Cn2cc(NC(=O)c3cnn4cccnc34)c(-c3cc(Cl)ccc3OC(F)F)n2)CC1] | N-[1-[2-[4-[benzyl(methyl)amino]-1-piperidyl]-2-oxo-ethyl]-3-[5-chloro-2-(difluoromethoxy)phenyl]pyrazol-4-yl]pyrazolo[1,5-a]pyrimidine-3-carboxamide |
| 99 | 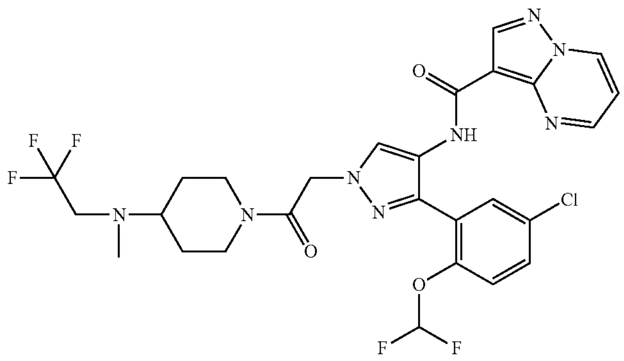 [SMILES: CN(CC(F)(F)F)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[methyl(2,2,2-trifluoroethyl)amino]-1-piperidyl]-2-oxo-ethyl]pyrazol-4-yl]pyrazolo[1,5-a]pyrimidine-3-carboxamide |
| 100 | 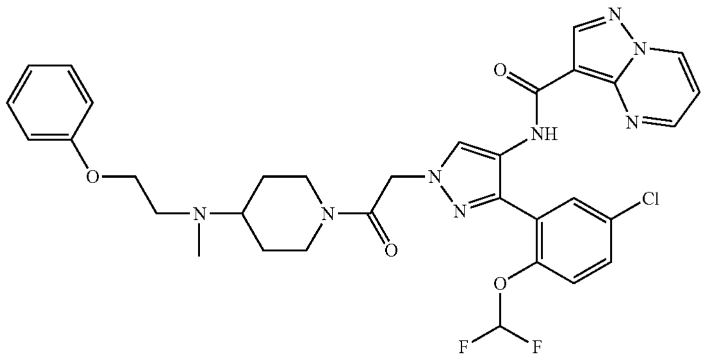 [SMILES: CN(CCOc1ccccc1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[methyl(2-phenoxyethyl)amino]-1-piperidyl]-2-oxo-ethyl]pyrazol-4-yl]pyrazolo[1,5-a]pyrimidine-3-carboxamide |
| 101 | 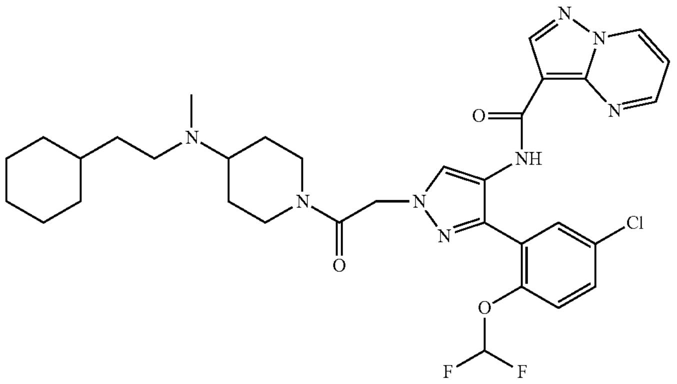 [SMILES: CN(CCC1CCCCC1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[2-cyclohexylethyl(methyl)amino]-1-piperidyl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 102 | 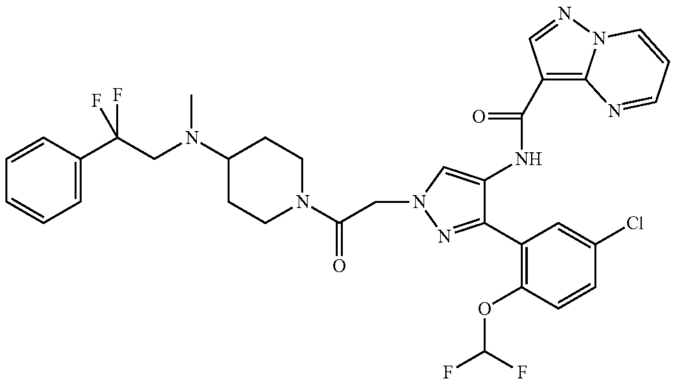 [SMILES: CN(CC(F)(F)c1ccccc1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[(2,2-difluoro-2-phenyl-ethyl)-methyl-amino]-1-piperidyl]-2-oxo-ethyl]pyrazol-4-yl]pyrazolo[1,5-a]pyrimidine-3-carboxamide |
| 103 | 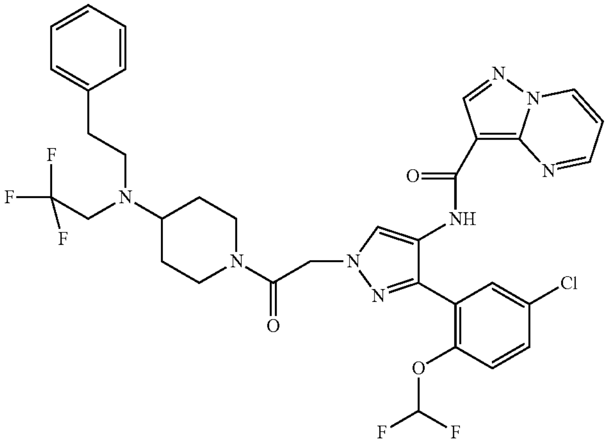 [SMILES: O=C(Nc1cn(CC(=O)N2CCC(N(CCc3ccccc3)CC(F)(F)F)CC2)nc1-c1cc(Cl)ccc1OC(F)F)c1cnn2cccnc12] | N-[3-[5-chloro-2-(difluoromethoxy)phenyl]-1-[2-oxo-2-[4-[2-phenylethyl(2,2,2-trifluoroethyl)amino]-1-piperidyl]ethyl]pyrazol-4-yl]pyrazolo[1,5-a]pyrimidine-3-carboxamide |
| 104 | 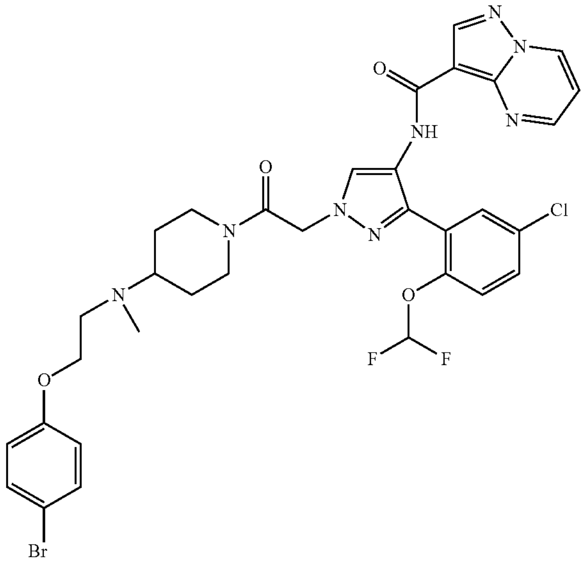 [SMILES: CN(CCOc1ccc(Br)cc1)C1CCN(C(=O)Cn2cc(NC(=O)c3cnn4cccnc34)c(-c3cc(Cl)ccc3OC(F)F)n2)CC1] | N-[1-[2-[4-[2-(4-bromophenoxy)ethyl-methyl-amino]-1-piperidyl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 105 | 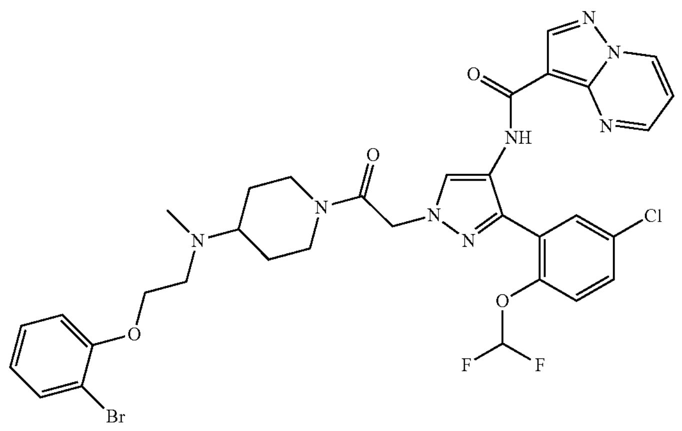 [SMILES: CN(CCOc1ccccc1Cl)C1CCN(C(=O)Cn2cc(NC(=O)c3cnn4cccnc34)c(-c3cc(Cl)ccc3OC(F)F)n2)CC1] | N-[1-[2-[4-[2-(2-bromophenoxy)ethyl-methyl-amino]-1-piperidyl]-2-oxo-ethyl]-3-[5-chloro-2-(difluoromethoxy)phenyl]pyrazol-4-yl]pyrazolo[1,5-a]pyrimidine-3-carboxamide |
| 106 | 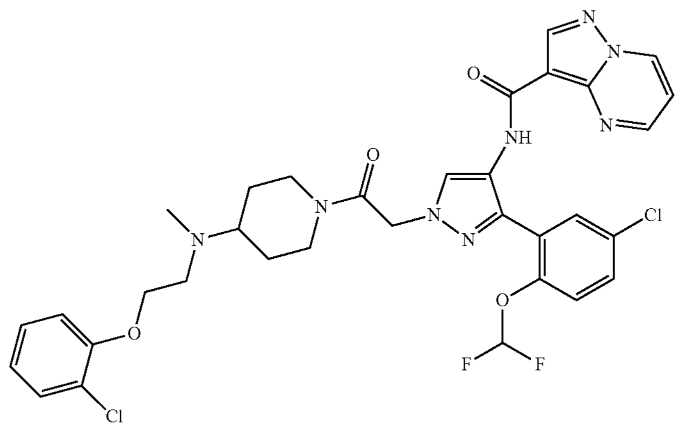 | N-[3-[5-chloro-2-(difluoromethoxy)phenyl]-1-[2-[4-[2-(2-chlorophenoxy)ethyl-methyl-amino]-1-piperidyl]-2-oxo-ethyl]pyrazol-4-yl]pyrazolo[1,5-a]pyrimidine-3-carboxamide |
| 107 | 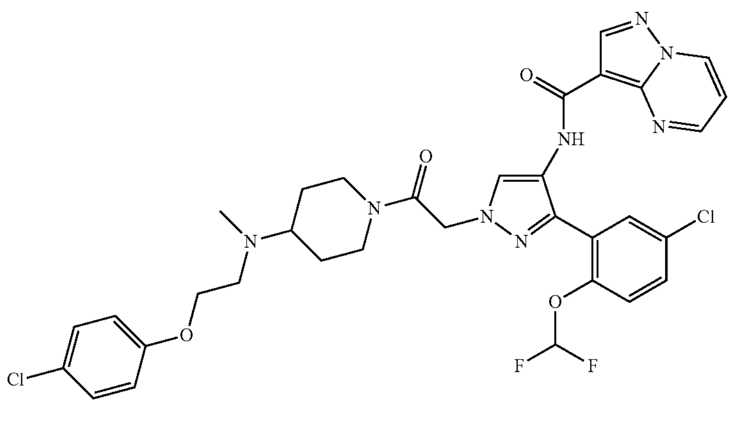 [SMILES: CN(CCOc1ccc(Cl)cc1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[2-(4-chlorophenoxy)ethyl-methyl-amino]-1-piperidyl]-2-oxo-ethyl]pyrazol-4-yl]pyrazolo[1,5-a]pyrimidine-3-carboxamide |

TABLE 1-continued
| Exemplary Compounds of the Present Invention | | |
|---|---|---|
| Ex. | Structure | Name |
| 108 | 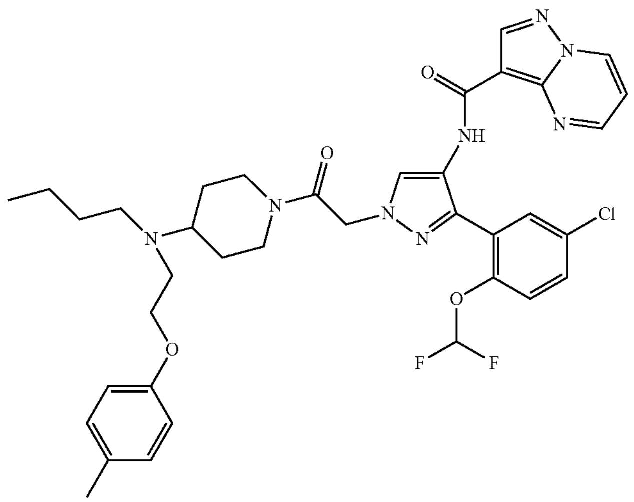 [SMILES: CCCCN(CCOc1ccc(C)cc1)C1CCN(C(=O)Cn2cc(NC(=O)c3cnn4cccnc34)c(-c3cc(Cl)ccc3OC(F)F)n2)CC1] | N-[1-[2-[4-[butyl-[2-(4-methylphenoxy)ethyl]amino]-1-piperidyl]-2-oxo-ethyl]-3-[5-chloro-2-(difluoromethoxy)phenyl]pyrazol-4-yl]pyrazolo[1,5-a]pyrimidine-3-carboxamide |
| 109 | 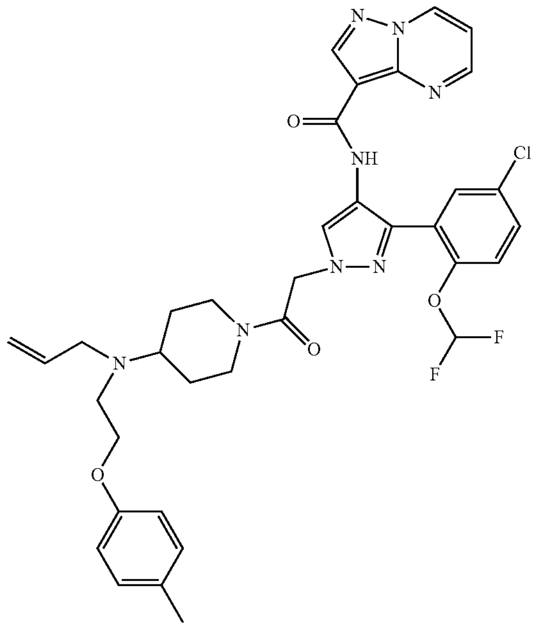 [SMILES: C=CCN(CCOc1ccc(C)cc1)C1CCN(C(=O)Cn2cc(NC(=O)c3cnn4cccnc34)c(-c3cc(Cl)ccc3OC(F)F)n2)CC1] | N-[1-[2-[4-[allyl-[2-(4-methylphenoxy)ethyl]amino]-1-piperidyl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 110 | 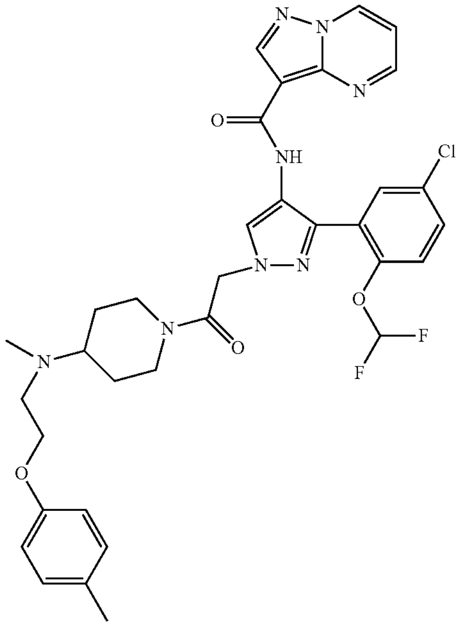 [SMILES: Cc1ccc(OCCN(C)C2CCN(C(=O)Cn3cc(NC(=O)c4cnn5cccnc45)c(-c4cc(Cl)ccc4OC(F)F)n3)CC2)cc1] | N-[3-[5-chloro-2-(difluoromethoxy)phenyl]-1-[2-[4-[methyl-[2-(4-methylphenoxy)ethyl]amino]-1-piperidyl]-2-oxo-ethyl]pyrazol-4-yl]pyrazolo[1,5-a]pyrimidine-3-carboxamide |
| 111 | 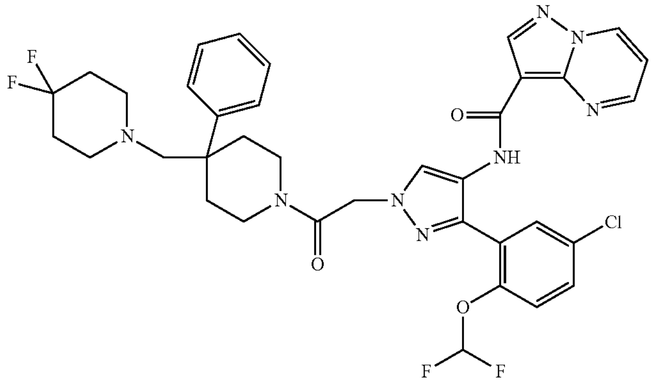 [SMILES: O=C(Nc1cn(CC(=O)N2CCC(CN3CCC(F)(F)CC3)(c3ccccc3)CC2)nc1-c1cc(Cl)ccc1OC(F)F)c1cnn2cccnc12] | N-[3-[5-chloro-2-(difluoromethoxy)phenyl]-1-[2-[4-[(4,4-difluoro-1-piperidyl)methyl]-4-phenyl-1-piperidyl]-2-oxo-ethyl]pyrazol-4-yl]pyrazolo[1,5-a]pyrimidine-3-carboxamide |
| 112 | 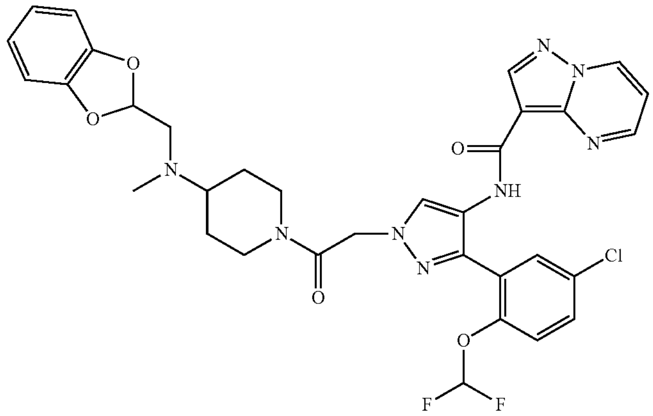 [SMILES: CN(CC1Oc2ccccc2O1)C1CCN(C(=O)Cn2cc(NC(=O)c3cnn4cccnc34)c(-c3cc(Cl)ccc3OC(F)F)n2)CC1] | N-[1-[2-[4-[1,3-benzodioxol-2-ylmethyl(methyl)amino]-1-piperidyl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 113 | 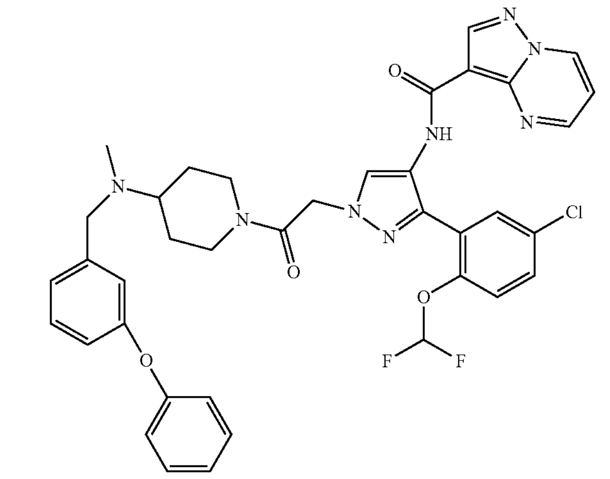 [SMILES: CN(Cc1cccc(Oc2ccccc2)c1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[methyl-[(3-phenoxyphenyl)methyl]amino]-1-piperidyl]-2-oxo-ethyl]pyrazol-4-yl]pyrazolo[1,5-a]pyrimidine-3-carboxamide |
| 114 | 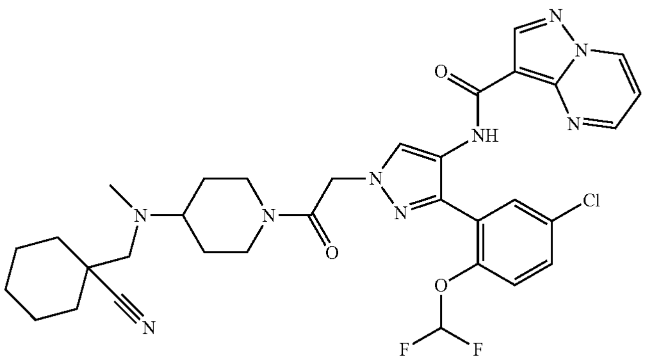 [SMILES: CN(CC1(C#N)CCCCC1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[(1-cyanocyclohexyl)methyl-methyl-amino]-1-piperidyl]-2-oxo-ethyl]pyrazol-4-yl]pyrazolo[1,5-a]pyrimidine-3-carboxamide |
| 115 | 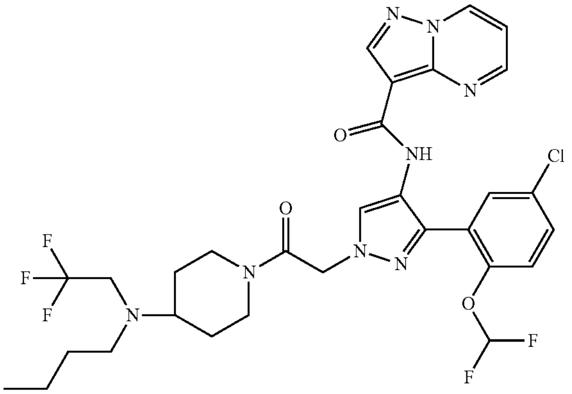 [SMILES: CCCCN(CC(F)(F)F)C1CCN(C(=O)Cn2cc(NC(=O)c3cnn4cccnc34)c(-c3cc(Cl)ccc3OC(F)F)n2)CC1] | N-[1-[2-[4-[butyl(2,2,2-trifluoroethyl)amino]-1-piperidyl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 116 | 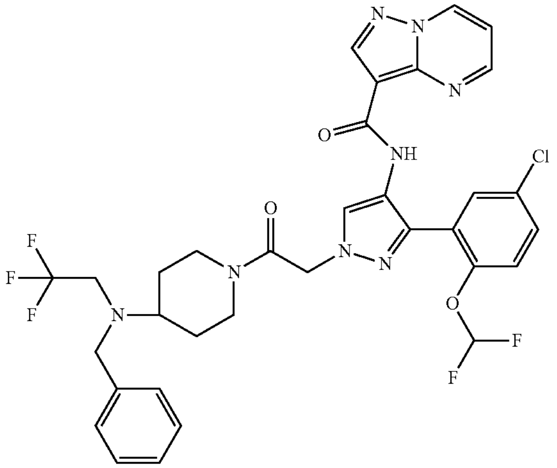 [SMILES: O=C(Nc1cn(CC(=O)N2CCC(N(Cc3ccccc3)CC(F)(F)F)CC2)nc1-c1cc(Cl)ccc1OC(F)F)c1cnn2cccnc12] | N-[1-[2-[4-[benzyl(2,2,2-trifluoroethyl)amino]-1-piperidyl]-2-oxo-ethyl]-3-[5-chloro-2-(difluoromethoxy)phenyl]pyrazol-4-yl]pyrazolo[1,5-a]pyrimidine-3-carboxamide |
| 117 | 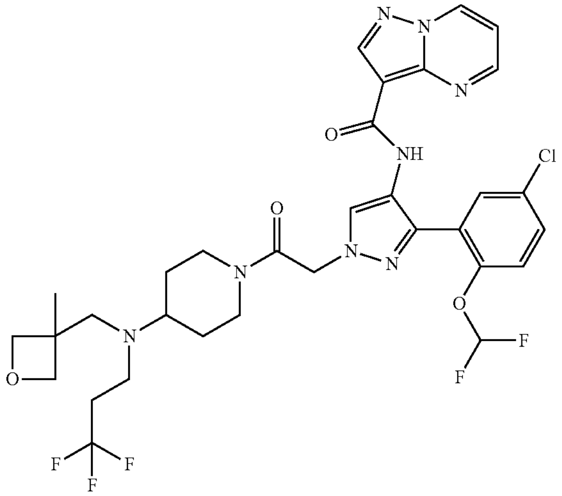 [SMILES: CC1(CN(CCC(F)(F)F)C2CCN(C(=O)Cn3cc(NC(=O)c4cnn5cccnc45)c(-c4cc(Cl)ccc4OC(F)F)n3)CC2)COC1] | N-[3-[5-chloro-2-(difluoromethoxy)phenyl]-1-[2-[4-[(3-methyloxetan-3-yl)methyl-(3,3,3-trifluoropropyl)amino]-1-piperidyl]-2-oxo-ethyl]pyrazol-4-yl]pyrazolo[1,5-a]pyrimidine-3-carboxamide |
| 118 | 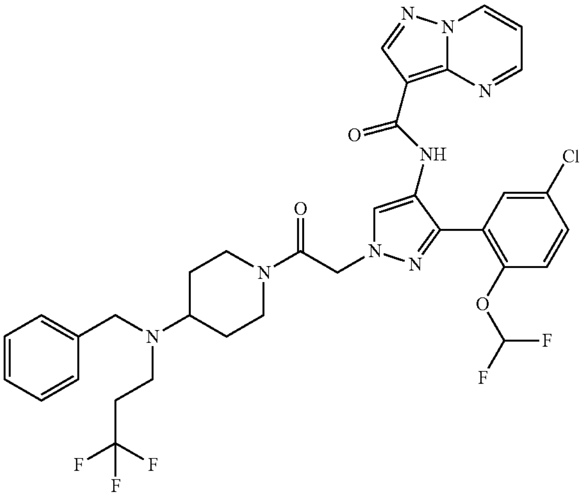 [SMILES: O=C(Nc1cn(CC(=O)N2CCC(N(CCC(F)(F)F)Cc3ccccc3)CC2)nc1-c1cc(Cl)ccc1OC(F)F)c1cnn2cccnc12] | N-[1-[2-[4-[benzyl(3,3,3-trifluoropropyl)amino]-1-piperidyl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued
| Exemplary Compounds of the Present Invention | | |
|---|---|---|
| Ex. | Structure | Name |
| 119 | 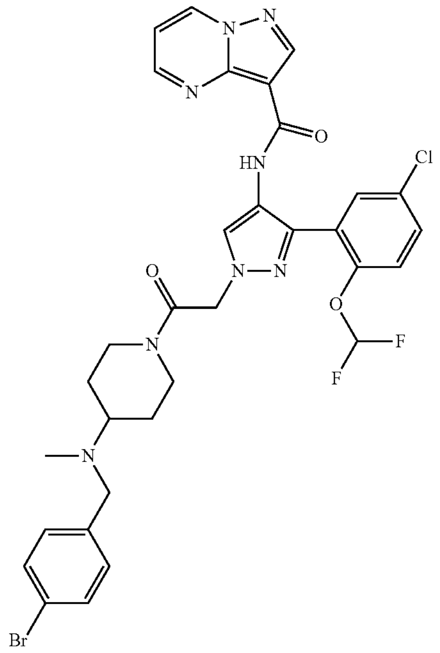 [SMILES: CN(Cc1ccc(Br)cc1)C1CCN(C(=O)Cn2cc(NC(=O)c3cnn4cccnc34)c(-c3cc(Cl)ccc3OC(F)F)n2)CC1] | N-[1-[2-[4-[(4-bromophenyl)methyl-methyl-amino]-1-piperidyl]-2-oxo-ethyl]-3-[5-chloro-2-(difluoromethoxy)phenyl]pyrazol-4-yl]pyrazolo[1,5-a]pyrimidine-3-carboxamide |
| 120 | 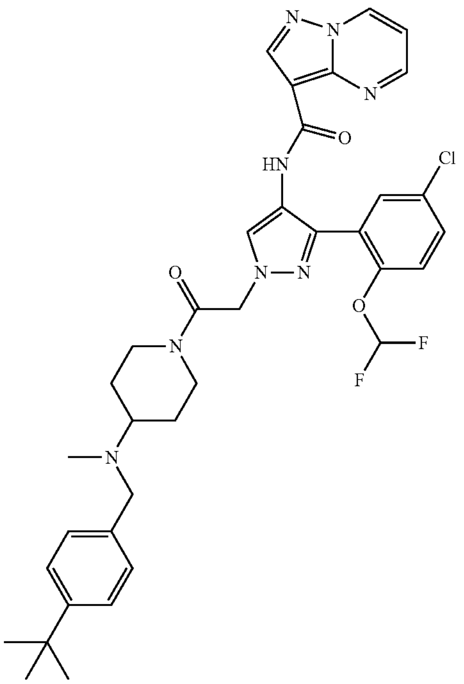 [SMILES: CN(Cc1ccc(C(C)(C)C)cc1)C1CCN(C(=O)Cn2cc(NC(=O)c3cnn4cccnc34)c(-c3cc(Cl)ccc3OC(F)F)n2)CC1] | N-[1-[2-[4-[(4-tert-butylphenyl)methyl-methyl-amino]-1-piperidyl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued
| Exemplary Compounds of the Present Invention | | |
|---|---|---|
| Ex. | Structure | Name |
| 121 | 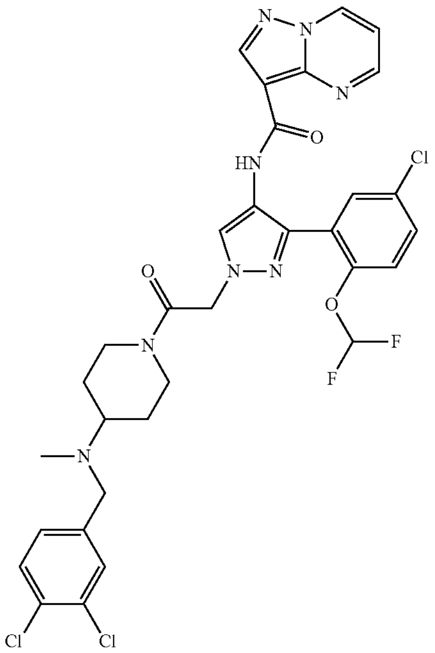 [SMILES: CN(Cc1ccc(Cl)c(Cl)c1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[(3,4-dichlorophenyl)methyl-methyl-amino]-1-piperidyl]-2-oxo-ethyl]pyrazol-4-yl]pyrazolo[1,5-a]pyrimidine-3-carboxamide |
| 122 | 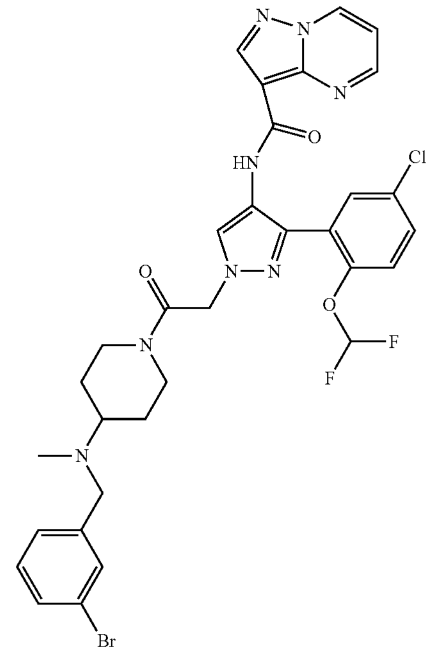 [SMILES: CN(Cc1cccc(Br)c1)C1CCN(C(=O)Cn2cc(NC(=O)c3cnn4cccnc34)c(-c3cc(Cl)ccc3OC(F)F)n2)CC1] | N-[1-[2-[4-[(3-bromophenyl)methyl-methyl-amino]-1-piperidyl]-2-oxo-ethyl]-3-[5-chloro-2-(difluoromethoxy)phenyl]pyrazol-4-yl]pyrazolo[1,5-a]pyrimidine-3-carboxamide |

TABLE 1-continued
| Exemplary Compounds of the Present Invention | | |
|---|---|---|
| Ex. | Structure | Name |
| 123 | 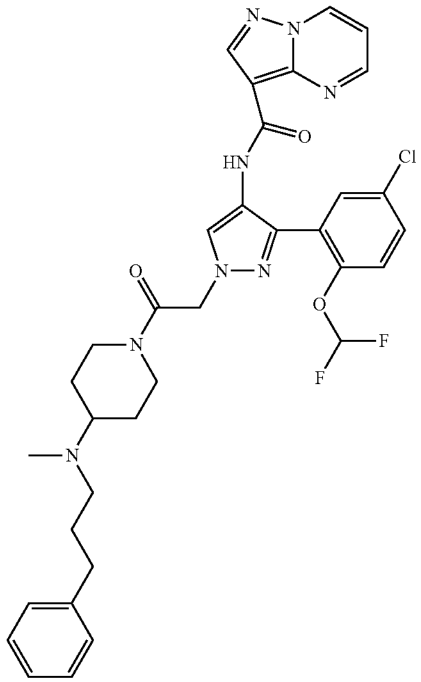 [SMILES: CN(CCCc1ccccc1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[methyl(3-phenylpropyl)amino]-1-piperidyl]-2-oxo-ethyl]pyrazol-4-yl]pyrazolo[1,5-a]pyrimidine-3-carboxamide |
| 124 | 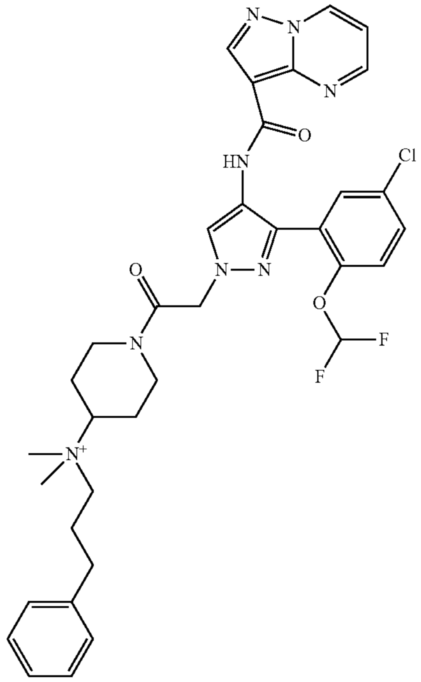 [SMILES: C[N+](C)(CCCc1ccccc1)C1CCN(C(=O)Cn2cc(NC(=O)c3cnn4cccnc34)c(-c3cc(Cl)ccc3OC(F)F)n2)CC1] | [1-[2-[3-[5-chloro-2-(difluoromethoxy)phenyl]-4-(pyrazolo[1,5-a]pyrimidine-3-carbonylamino)pyrazol-1-yl]acetyl]-4-piperidyl]-dimethyl-(3-phenylpropyl)ammonium |

TABLE 1-continued

| Ex. | Structure | Name |
|---|---|---|
| | Exemplary Compounds of the Present Invention | |
| 125 | 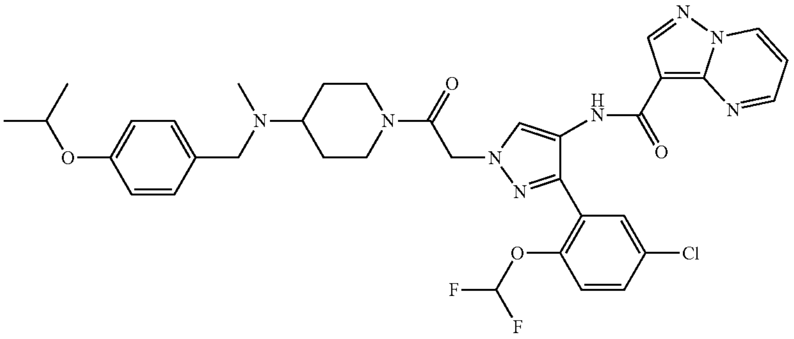 [SMILES: CC(C)Oc1ccc(CN(C)C2CCN(C(=O)Cn3cc(NC(=O)c4cnn5cccnc45)c(-c4cc(Cl)ccc4OC(F)F)n3)CC2)cc1] | N-[3-[5-chloro-2-(difluoromethoxy)phenyl]-1-[2-[4-[(4-isopropoxyphenyl)methyl-methyl-amino]-1-piperidyl]-2-oxo-ethyl]pyrazol-4-yl]pyrazolo[1,5-a]pyrimidine-3-carboxamide |
| 126 | 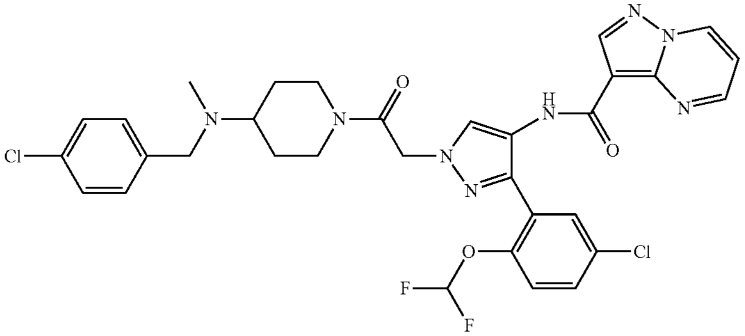 [SMILES: CN(Cc1ccc(Cl)cc1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[(4-chlorophenyl)methyl-methyl-amino]-1-piperidyl]-2-oxo-ethyl]pyrazol-4-yl]pyrazolo[1,5-a]pyrimidine-3-carboxamide |
| 127 | 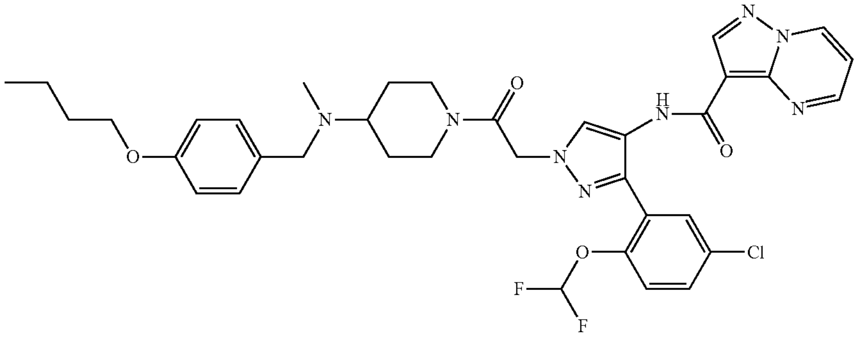 [SMILES: CCCCOc1ccc(CN(C)C2CCN(C(=O)Cn3cc(NC(=O)c4cnn5cccnc45)c(-c4cc(Cl)ccc4OC(F)F)n3)CC2)cc1] | N-[1-[2-[4-[(4-butoxyphenyl)methyl-methyl-amino]-1-piperidyl]-2-oxo-ethyl]-3-[5-chloro-2-(difluoromethoxy)phenyl]pyrazol-4-yl]pyrazolo[1,5-a]pyrimidine-3-carboxamide |
| 128 | 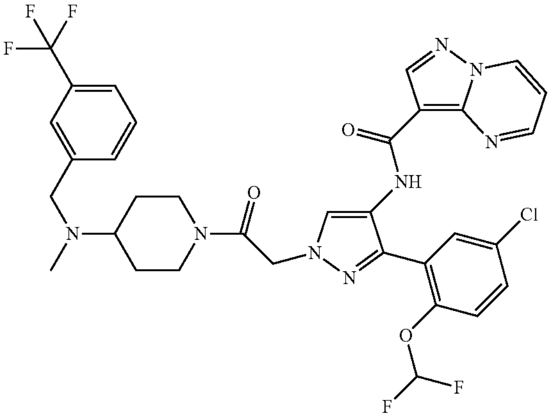 [SMILES: CN(Cc1cccc(C(F)(F)F)c1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[methyl-[[3-(trifluoromethyl)phenyl]methyl]amino]-1-piperidyl]-2-oxo-ethyl]pyrazol-4-yl]pyrazolo[1,5-a]pyrimidine-3-carboxamide |

TABLE 1-continued

| Ex. | Structure | Name |
|---|---|---|
| 129 | 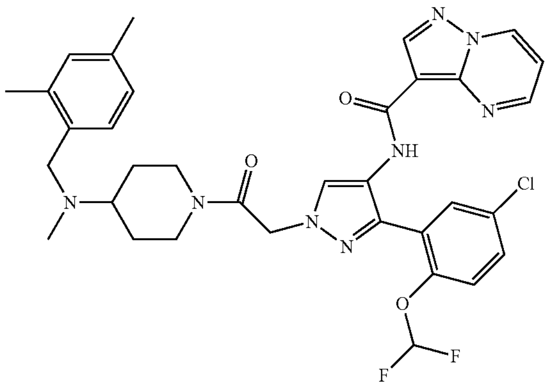 [SMILES: Cc1ccc(CN(C)C2CCN(C(=O)Cn3cc(NC(=O)c4cnn5cccnc45)c(-c4cc(Cl)ccc4OC(F)F)n3)CC2)c(C)c1] | N-[3-[5-chloro-2-(difluoromethoxy)phenyl]-1-[2-[4-[(2,4-dimethylphenyl)methyl-methyl-amino]-1-piperidyl]-2-oxo-ethyl]pyrazol-4-yl]pyrazolo[1,5-a]pyrimidine-3-carboxamide |
| 130 | 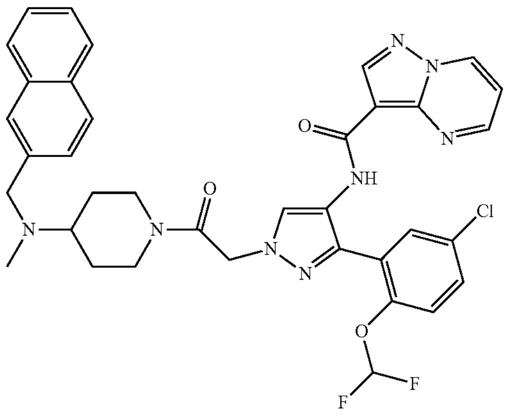 [SMILES: CN(Cc1ccc2ccccc2c1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[methyl(2-naphthylmethyl)amino]-1-piperidyl]-2-oxo-ethyl]pyrazol-4-yl]pyrazolo[1,5-a]pyrimidine-3-carboxamide |
| 131 | 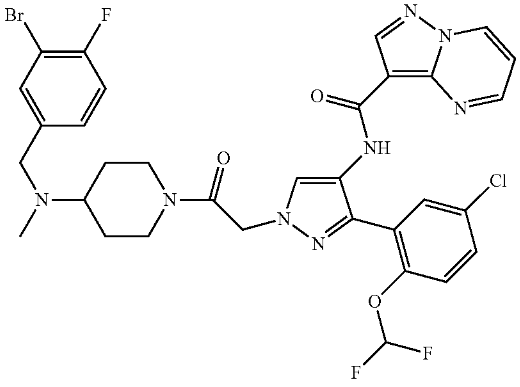 [SMILES: CN(Cc1ccc(F)c(Br)c1)C1CCN(C(=O)Cn2cc(NC(=O)c3cnn4cccnc34)c(-c3cc(Cl)ccc3OC(F)F)n2)CC1] | N-[1-[2-[4-[(3-bromo-4-fluoro-phenyl)methyl-methyl-amino]-1-piperidyl]-2-oxo-ethyl]-3-[5-chloro-2-(difluoromethoxy)phenyl]pyrazol-4-yl]pyrazolo[1,5-a]pyrimidine-3-carboxamide |

Exemplary Compounds of the Present Invention

TABLE 1-continued

| Exemplary Compounds of the Present Invention | | |
|---|---|---|
| Ex. | Structure | Name |
| 132 | 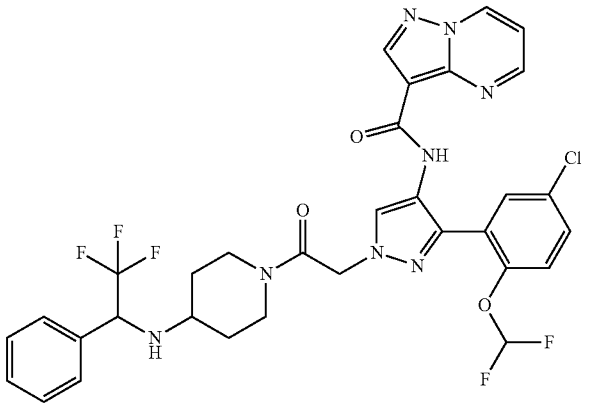 [SMILES: O=C(Nc1cn(CC(=O)N2CCC(NC(c3ccccc3)C(F)(F)F)CC2)nc1-c1cc(Cl)ccc1OC(F)F)c1cnn2cccnc12] | N-[3-[5-chloro-2-(difluoromethoxy)phenyl]-1-[2-oxo-2-[4-[(2,2,2-trifluoro-1-phenyl-ethyl)amino]-1-piperidyl]ethyl]pyrazol-4-yl]pyrazolo[1,5-a]pyrimidine-3-carboxamide |
| 133 | 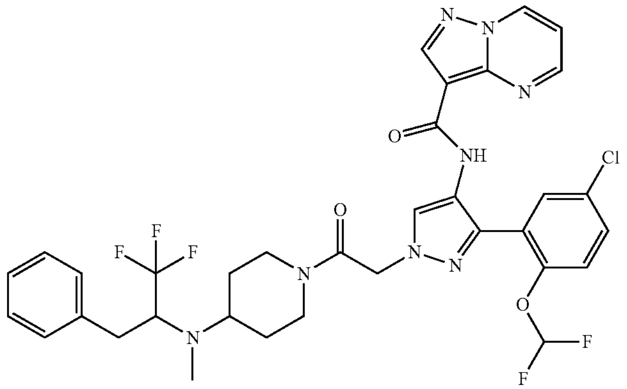 [SMILES: CN(C1CCN(C(=O)Cn2cc(NC(=O)c3cnn4cccnc34)c(-c3cc(Cl)ccc3OC(F)F)n2)CC1)C(Cc1ccccc1)C(F)(F)F] | N-[1-[2-[4-[(1-benzyl-2,2,2-trifluoro-ethyl)-methyl-amino]-1-piperidyl]-2-oxo-ethyl]-3-[5-chloro-2-(difluoromethoxy)phenyl]pyrazol-4-yl]pyrazolo[1,5-a]pyrimidine-3-carboxamide |
| 134 | 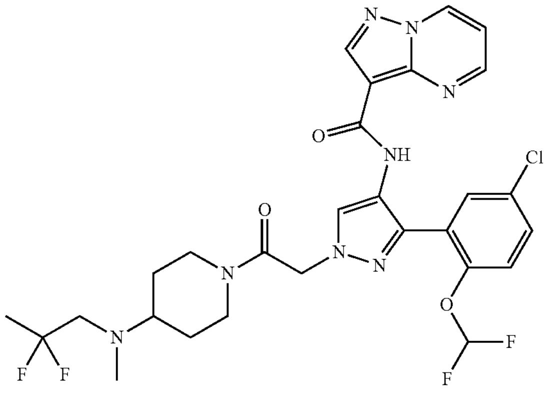 [SMILES: CN(CC(C)(F)F)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-[2,2-difluoropropyl(methyl)amino]-1-piperidyl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 135 | 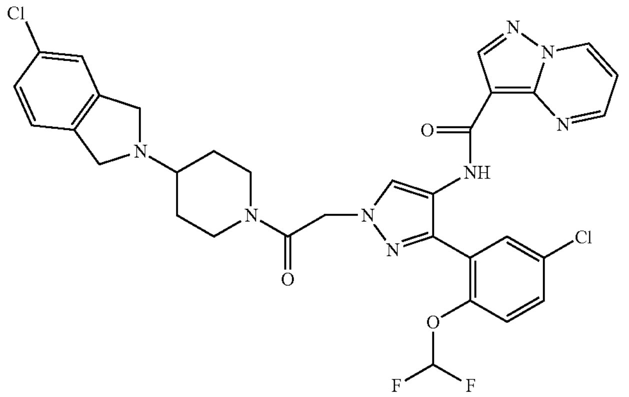 [SMILES: O=C(Nc1cn(CC(=O)N2CCC(N3Cc4ccc(Cl)cc4C3)CC2)nc1-c1cc(Cl)ccc1OC(F)F)c1cnn2cccnc12] | N-[3-[5-chloro-2-(difluoromethoxy)phenyl]-1-[2-[4-(5-chloroisoindolin-2-yl)-1-piperidyl]-2-oxo-ethyl]pyrazol-4-yl]pyrazolo[1,5-a]pyrimidine-3-carboxamide |
| 136 | 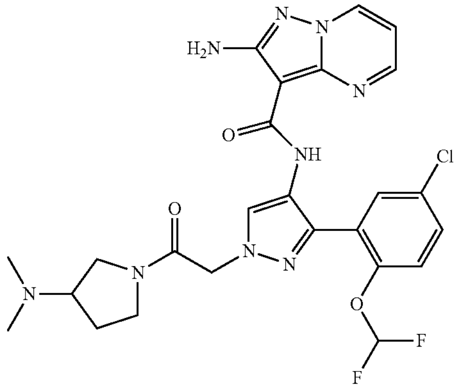 [SMILES: CN(C)C1CCN(C(=O)Cn2cc(NC(=O)c3c(N)nn4cccnc34)c(-c3cc(Cl)ccc3OC(F)F)n2)C1] | 2-amino-N-[3-[5-chloro-2-(difluoromethoxy)phenyl]-1-[2-[3-(dimethylamino)pyrrolidin-1-yl]-2-oxo-ethyl]pyrazol-4-yl]pyrazolo[1,5-a]pyrimidine-3-carboxamide |
| 137 | 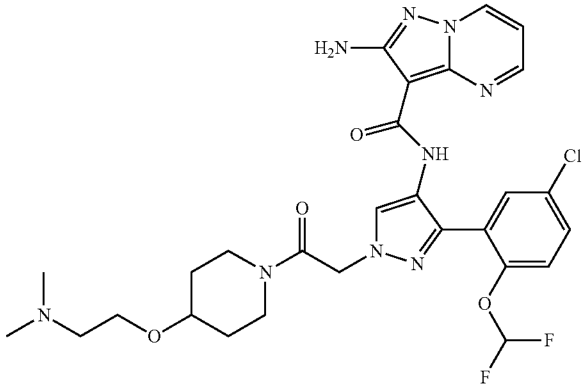 [SMILES: CN(C)CCOC1CCN(C(=O)Cn2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-[2-[4-[2-(dimethylamino)ethoxy]-1-piperidyl]-2-oxo-ethyl]pyrazol-4-yl]pyrazolo[1,5-a]pyrimidine-3-carboxamide |
| 138 | 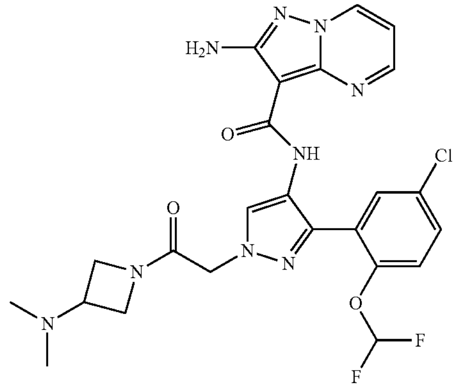 [SMILES: CN(C)C1CN(C(=O)Cn2cc(NC(=O)c3c(N)nn4cccnc34)c(-c3cc(Cl)ccc3OC(F)F)n2)C1] | 2-amino-N-[3-[5-chloro-2-(difluoromethoxy)phenyl]-1-[2-[3-(dimethylamino)azetidin-1-yl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 139 | 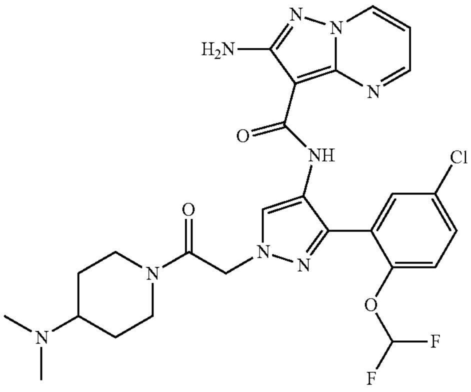 [SMILES: CN(C)C1CCN(C(=O)Cn2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-[2-[4-(dimethylamino)-1-piperidyl]-2-oxo-ethyl]pyrazol-4-yl]pyrazolo[1,5-a]pyrimidine-3-carboxamide |
| 140 | 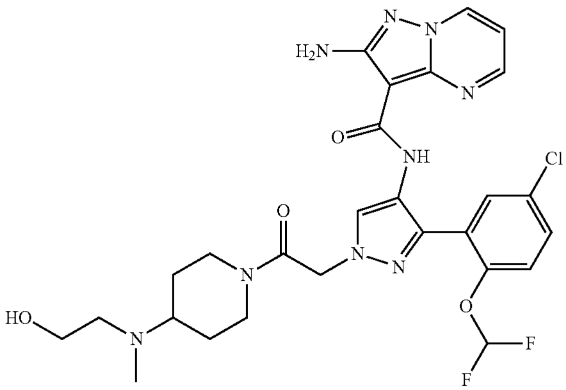 [SMILES: CN(CCO)C1CCN(C(=O)Cn2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-[2-[4-[2-hydroxyethyl (methyl)amino]-1-piperidyl]-2-oxo-ethyl]pyrazol-4-yl]pyrazolo[1,5-a]pyrimidine-3-carboxamide |
| 141 | 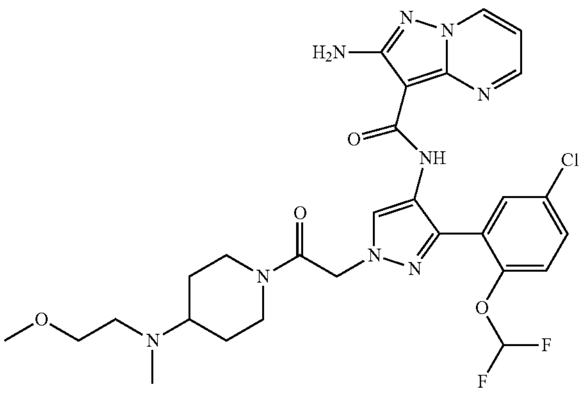 [SMILES: COCCN(C)C1CCN(C(=O)Cn2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-[2-[4-[2-methoxyethyl (methyl)amino]-1-piperidyl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 142 | 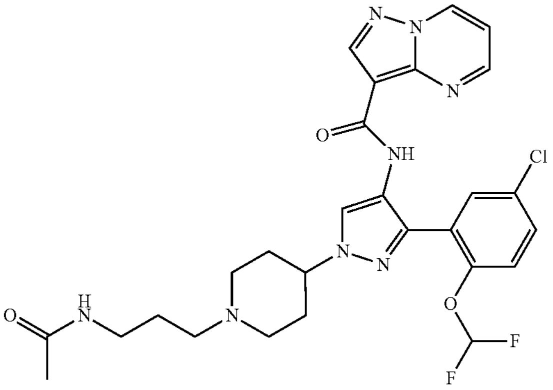 [SMILES: CC(=O)NCCCN1CCC(n2cc(NC(=O)c3cnn4cccnc34)c(-c3cc(Cl)ccc3OC(F)F)n2)CC1] | N-[1-[1-(3-acetamidopropyl)-4-piperidyl]-3-[5-chloro-2-(difluoromethoxy)phenyl]pyrazol-4-yl]pyrazolo[1,5-a]pyrimidine-3-carboxamide |
| 143 | 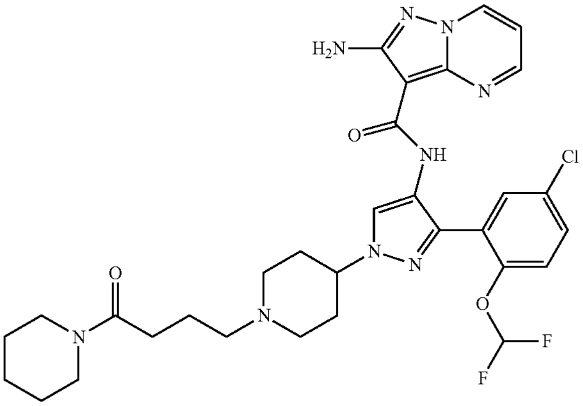 [SMILES: Nc1nn2cccnc2c1C(=O)Nc1cn(C2CCN(CCCC(=O)N3CCCCC3)CC2)nc1-c1cc(Cl)ccc1OC(F)F] | 2-amino-N-[3-[5-chloro-2-(difluoromethoxy)phenyl]-1-[1-[4-oxo-4-(1-piperidyl)butyl]-4-piperidyl]pyrazol-4-yl]pyrazolo[1,5-a]pyrimidine-3-carboxamide |
| 144 | 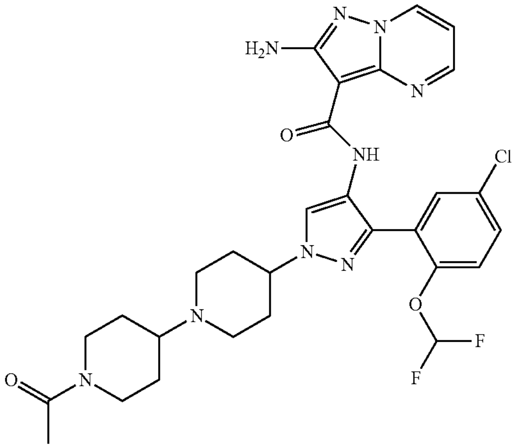 [SMILES: CC(=O)N1CCC(N2CCC(n3cc(NC(=O)c4c(N)nn5cccnc45)c(-c4cc(Cl)ccc4OC(F)F)n3)CC2)CC1] | N-[1-[1-(1-acetyl-4-piperidyl)-4-piperidyl]-3-[5-chloro-2-(difluoromethoxy)phenyl]pyrazol-4-yl]-2-amino-pyrazolo[1,5-a]pyrimidine-3-carboxamide |

TABLE 1-continued

| Exemplary Compounds of the Present Invention | | |
|---|---|---|
| Ex. | Structure | Name |
| 145 | 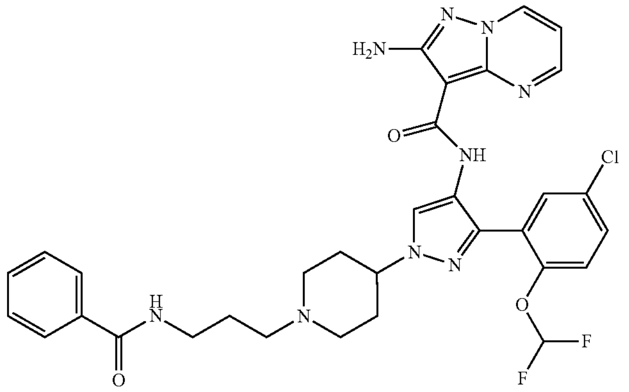 [SMILES: Nc1nn2cccnc2c1C(=O)Nc1cn(C2CCN(CCCNC(=O)c3ccccc3)CC2)nc1-c1cc(Cl)ccc1OC(F)F] | 2-amino-N-[1-[1-(3-benzamidopropyl)-4-piperidyl]-3-[5-chloro-2-(difluoromethoxy)phenyl]pyrazol-4-yl]pyrazolo[1,5-a]pyrimidine-3-carboxamide |
| 146 | 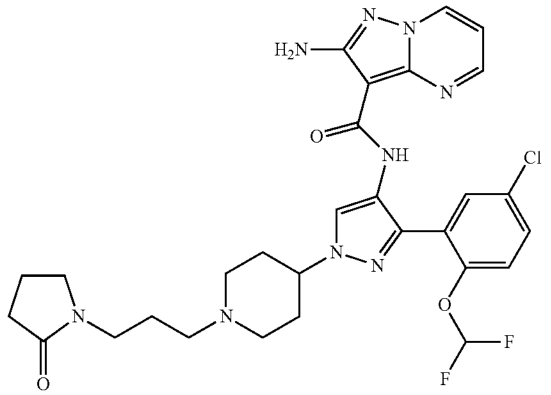 [SMILES: Nc1nn2cccnc2c1C(=O)Nc1cn(C2CCN(CCCN3CCCC3=O)CC2)nc1-c1cc(Cl)ccc1OC(F)F] | 2-amino-N-[3-[5-chloro-2-(difluoromethoxy)phenyl]-1-[1-[3-(2-oxopyrrolidin-1-yl)propyl]-4-piperidyl]pyrazol-4-yl]pyrazolo[1,5-a]pyrimidine-3-carboxamide |
| 147 | 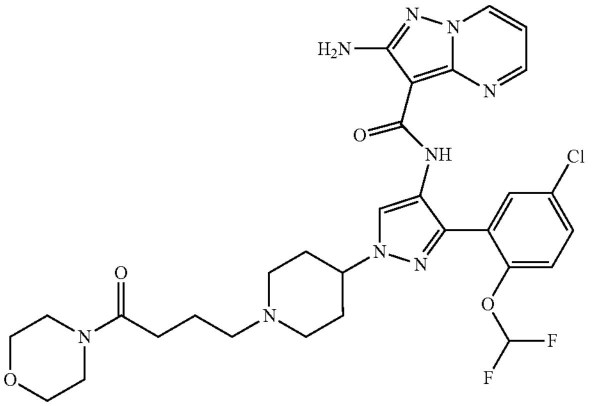 [SMILES: Nc1nn2cccnc2c1C(=O)Nc1cn(C2CCN(CCCC(=O)N3CCOCC3)CC2)nc1-c1cc(Cl)ccc1OC(F)F] | 2-amino-N-[3-[5-chloro-2-(difluoromethoxy)phenyl]-1-[1-(4-morpholino-4-oxo-butyl)-4-piperidyl]pyrazol-4-yl]pyrazolo[1,5-a]pyrimidine-3-carboxamide |

TABLE 1-continued

| Ex. | Structure | Name |
|---|---|---|
| Exemplary Compounds of the Present Invention | | |
| 148 | 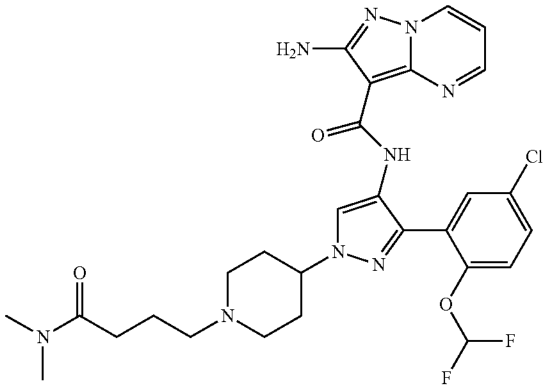 [SMILES: CN(C)C(=O)CCCN1CCC(n2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-[1-[4-(dimethylamino)-4-oxo-butyl]-4-piperidyl]pyrazol-4-yl]pyrazolo[1,5-a]pyrimidine-3-carboxamide |
| 149 | 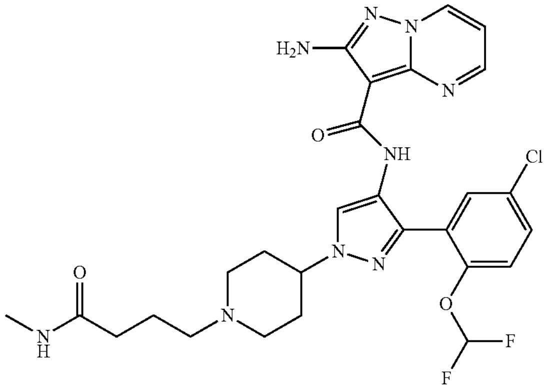 [SMILES: CNC(=O)CCCN1CCC(n2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-[1-[4-(methylamino)-4-oxo-butyl]-4-piperidyl]pyrazol-4-yl]pyrazolo[1,5-a]pyrimidine-3-carboxamide |
| 150 | 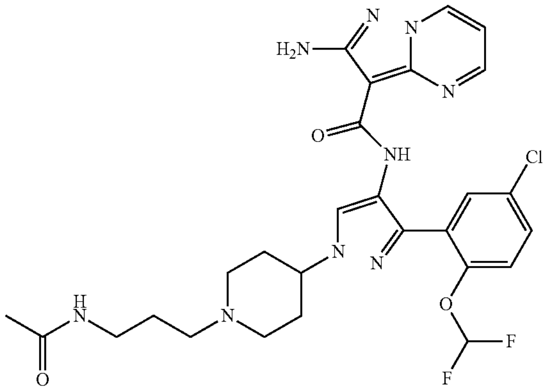 [SMILES: CC(=O)NCCCN1CCC(N/C=C(/NC(=O)/C(C(=N)N)=C2\N=CC=CN2)C(=N)c2cc(Cl)ccc2OC(F)F)CC1] | N-[1-[1-(3-acetamidopropyl)-4-piperidyl]-3-[5-chloro-2-(difluoromethoxy)phenyl] pyrazol-4-yl]-2-amino-pyrazolo[1,5-a]pyrimidine-3-carboxamide |
| 151 | 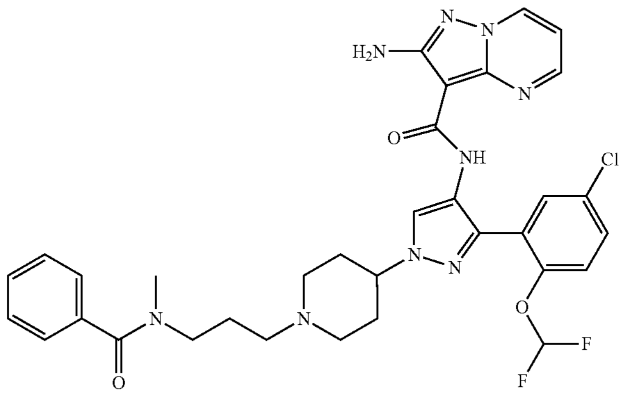 [SMILES: CN(CCCN1CCC(n2cc(NC(=O)c3c(N)nn4cccnc34)c(-c3cc(Cl)ccc3OC(F)F)n2)CC1)C(=O)c1ccccc1] | 2-amino-N-[1-[1-[3-[benzoyl(methyl)amino] propyl]-4-piperidyl]-3-[5-chloro-2-(difluoromethoxy)phenyl] pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 152 | 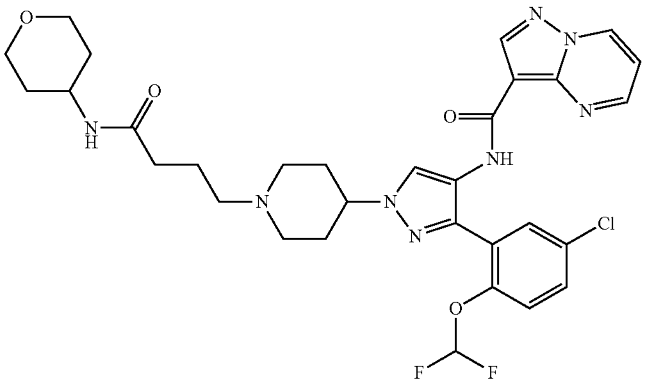 [SMILES: O=C(CCCN1CCC(n2cc(NC(=O)c3cnn4cccnc34)c(-c3cc(Cl)ccc3OC(F)F)n2)CC1)NC1CCOCC1] | N-[3-[5-chloro-2-(difluoromethoxy)phenyl]-1-[1-[4-oxo-4-(tetrahydropyran-4-ylamino)butyl]-4-piperidyl]pyrazol-4-yl]pyrazolo[1,5-a]pyrimidine-3-carboxamide |
| 153 | 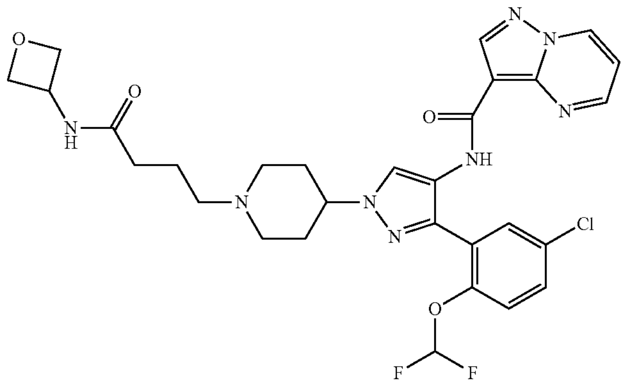 [SMILES: O=C(CCCN1CCC(n2cc(NC(=O)c3cnn4cccnc34)c(-c3cc(Cl)ccc3OC(F)F)n2)CC1)NC1COC1] | N-[3-[5-chloro-2-(difluoromethoxy)phenyl]-1-[1-[4-(oxetan-3-ylamino)-4-oxo-butyl]-4-piperidyl]pyrazol-4-yl]pyrazolo[1,5-a]pyrimidine-3-carboxamide |
| 154 | 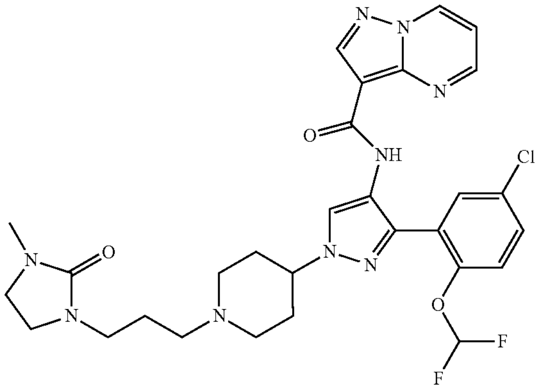 [SMILES: CN1CCN(CCCN2CCC(n3cc(NC(=O)c4cnn5cccnc45)c(-c4cc(Cl)ccc4OC(F)F)n3)CC2)C1=O] | N-[3-[5-chloro-2-(difluoromethoxy)phenyl]-1-[1-[3-(3-methyl-2-oxo-imidazolidin-1-yl)propyl]-4-piperidyl]pyrazol-4-yl]pyrazolo[1,5-a]pyrimidine-3-carboxamide |
| 155 | 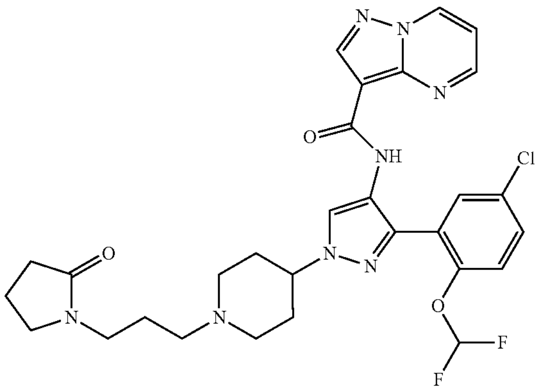 [SMILES: O=C(Nc1cn(C2CCN(CCCN3CCCC3=O)CC2)nc1-c1cc(Cl)ccc1OC(F)F)c1cnn2cccnc12] | N-[3-[5-chloro-2-(difluoromethoxy)phenyl]-1-[1-[3-(2-oxopyrrolidin-1-yl)propyl]-4-piperidyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 156 | 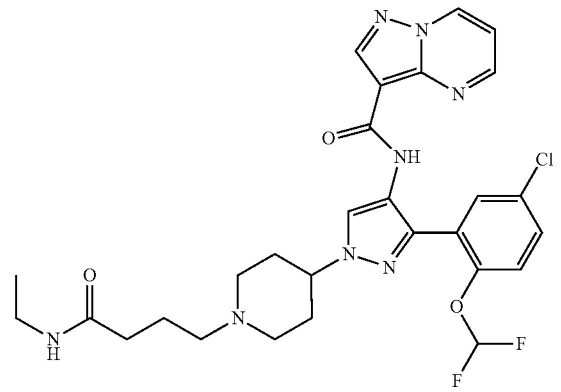 [SMILES: CCNC(=O)CCCN1CCC(n2cc(NC(=O)c3cnn4cccnc34)c(-c3cc(Cl)ccc3OC(F)F)n2)CC1] | N-[3-[5-chloro-2-(difluoromethoxy)phenyl]-1-[1-[4-(ethylamino)-4-oxo-butyl]-4-piperidyl]pyrazol-4-yl]pyrazolo[1,5-a]pyrimidine-3-carboxamide |
| 157 | 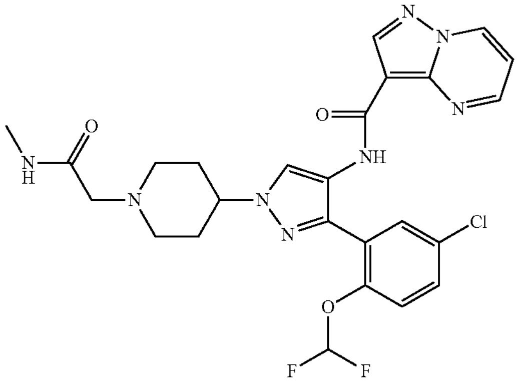 [SMILES: CNC(=O)CN1CCC(n2cc(NC(=O)c3cnn4cccnc34)c(-c3cc(Cl)ccc3OC(F)F)n2)CC1] | N-[3-[5-chloro-2-(difluoromethoxy)phenyl]-1-[1-[2-(methylamino)-2-oxo-ethyl]-4-piperidyl]pyrazol-4-yl]pyrazolo[1,5-a]pyrimidine-3-carboxamide |
| 158 | 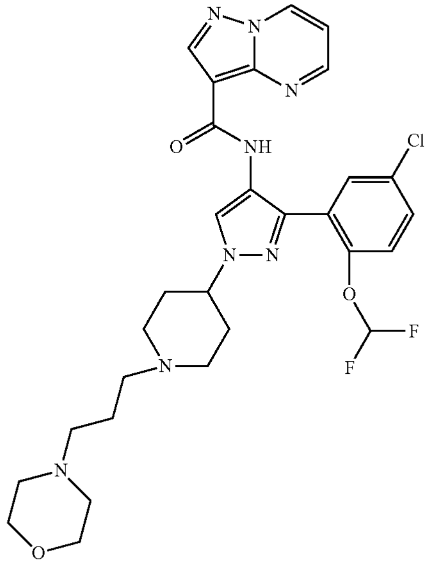 [SMILES: O=C(Nc1cn(C2CCN(CCCN3CCOCC3)CC2)nc1-c1cc(Cl)ccc1OC(F)F)c1cnn2cccnc12] | N-[3-[5-chloro-2-(difluoromethoxy)phenyl]-1-[1-(3-morpholinopropyl)-4-piperidyl]pyrazol-4-yl]pyrazolo[1,5-a]pyrimidine-3-carboxamide |

TABLE 1-continued

Exemplary Compounds of the Present Invention

| Ex. | Structure | Name |
|---|---|---|
| 159 | 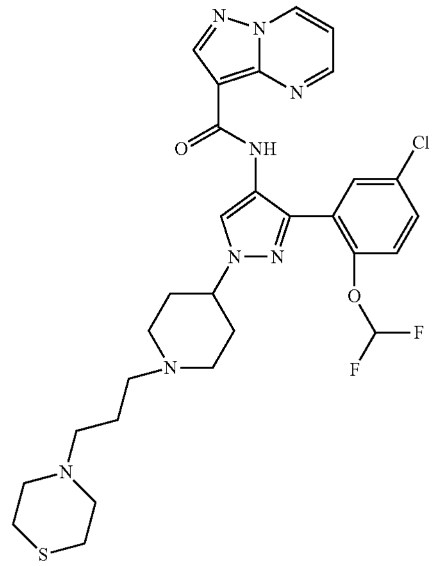 | N-[3-[5-chloro-2-(difluoromethoxy)phenyl]-1-[1-(3-thiomorpholinopropyl)-4-piperidyl]pyrazol-4-yl]pyrazolo[1,5-a]pyrimidine-3-carboxamide |
| 160 | 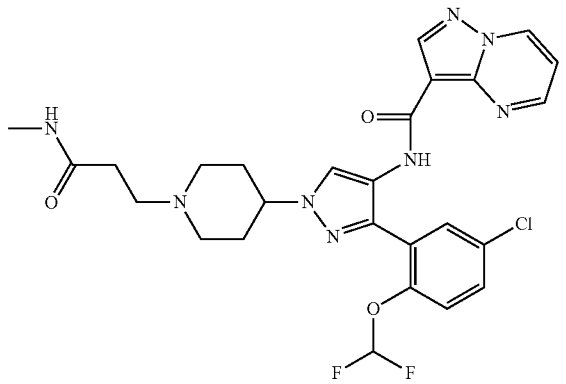 [SMILES: CNC(=O)CCN1CCC(n2cc(NC(=O)c3cnn4cccnc34)c(-c3cc(Cl)ccc3OC(F)F)n2)CC1] | N-[3-[5-chloro-2-(difluoromethoxy)phenyl]-1-[1-[3-(methylamino)-3-oxo-propyl]-4-piperidyl]pyrazol-4-yl]pyrazolo[1,5-a]pyrimidine-3-carboxamide |
| 161 | 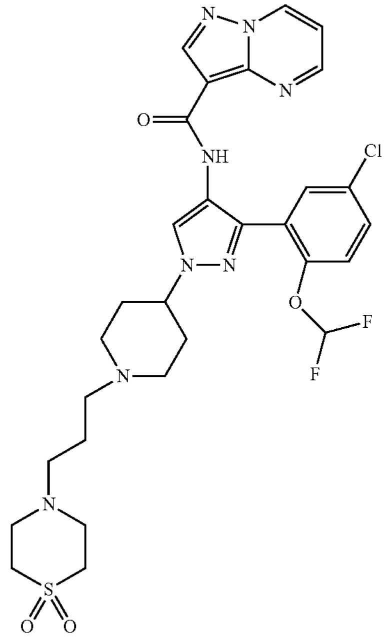 [SMILES: O=C(Nc1cn(C2CCN(CCCN3CCS(=O)(=O)CC3)CC2)nc1-c1cc(Cl)ccc1OC(F)F)c1cnn2cccnc12] | N-[3-[5-chloro-2-(difluoromethoxy)phenyl]-1-[1-[3-(1,1-dioxo-1,4-thiazinan-4-yl)propyl]-4-piperidyl]pyrazol-4-yl]pyrazolo[1,5-a]pyrimidine-3-carboxamide |

TABLE 1-continued
| Exemplary Compounds of the Present Invention | | |
|---|---|---|
| Ex. | Structure | Name |
| 162 | 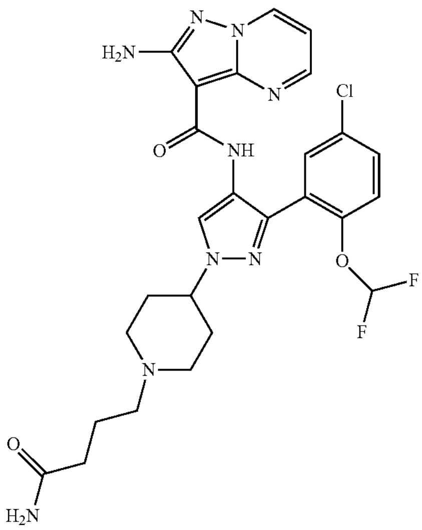 [SMILES: NC(=O)CCCN1CCC(n2cc(NC(=O)c3c(N)nn4cccnc34)c(-c3cc(Cl)ccc3OC(F)F)n2)CC1] | 2-amino-N-[1-[1-(4-amino-4-oxo-butyl)-4-piperidyl]-3-[5-chloro-2-(difluoromethoxy)phenyl] pyrazol-4-yl]pyrazolo[1,5-a]pyrimidine-3-carboxamide |
| 163 | 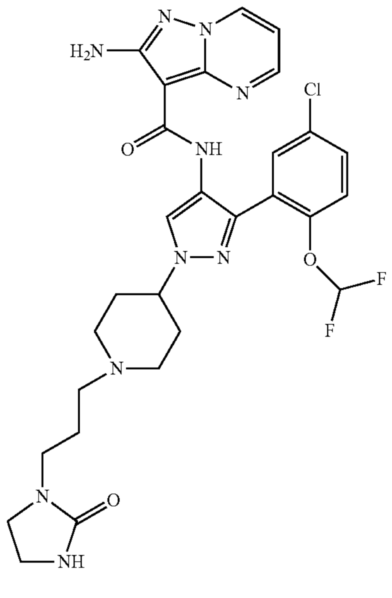 [SMILES: Nc1nn2cccnc2c1C(=O)Nc1cn(C2CCN(CCCN3CCNC3=O)CC2)nc1-c1cc(Cl)ccc1OC(F)F] | 2-amino-N-[3-[5-chloro-2-(difluoromethoxy)phenyl]-1-[1-[3-(2-oxoimidazolidin-1-yl)propyl]-4-piperidyl]pyrazol-4-yl]pyrazolo[1,5-a]pyrimidine-3-carboxamide |

TABLE 1-continued
| Exemplary Compounds of the Present Invention | | |
|---|---|---|
| Ex. | Structure | Name |
| 164 | 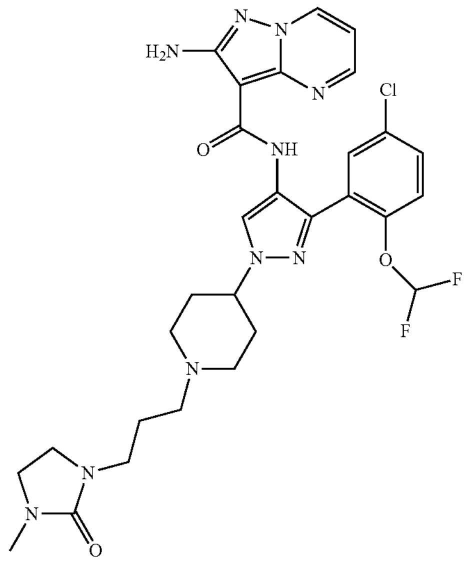 [SMILES: CN1CCN(CCCN2CCC(n3cc(NC(=O)c4c(N)nn5cccnc45)c(-c4cc(Cl)ccc4OC(F)F)n3)CC2)C1=O] | 2-amino-N-[3-[5-chloro-2-(difluoromethoxy)phenyl]-1-[1-[3-(3-methyl-2-oxo-imidazolidin-1-yl)propyl]-4-piperidyl]pyrazol-4-yl]pyrazolo[1,5-a]pyrimidine-3-carboxamide |
| 165 | 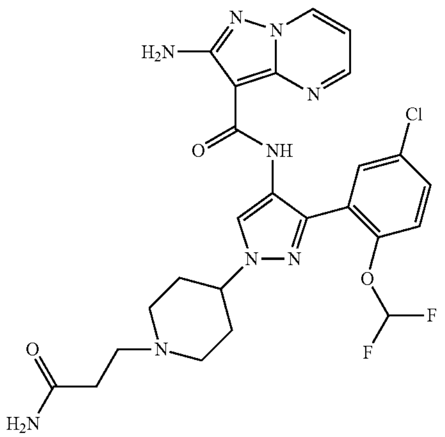 [SMILES: NC(=O)CCN1CCC(n2cc(NC(=O)c3c(N)nn4cccnc34)c(-c3cc(Cl)ccc3OC(F)F)n2)CC1] | 2-amino-N-[1-[1-(3-amino-3-oxo-propyl)-4-piperidyl]-3-[5-chloro-2-(difluoromethoxy)phenyl]pyrazol-4-yl]pyrazolo[1,5-a]pyrimidine-3-carboxamide |

TABLE 1-continued
| Exemplary Compounds of the Present Invention | | |
|---|---|---|
| Ex. | Structure | Name |
| 166 | 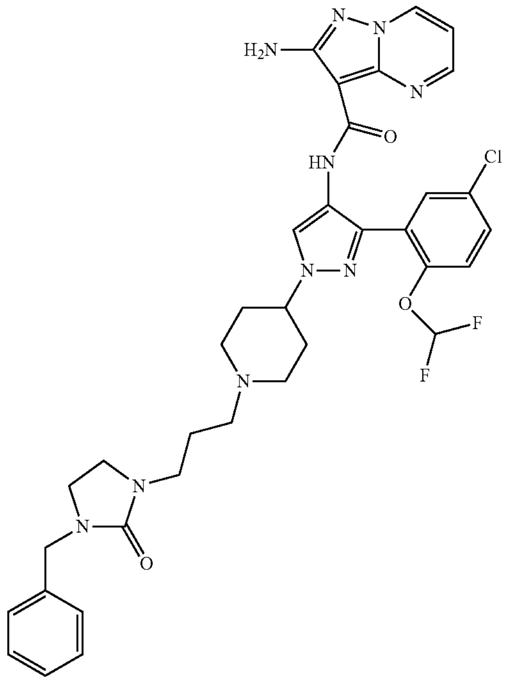 [SMILES: Nc1nn2cccnc2c1C(=O)Nc1cn(C2CCN(CCCN3CCN(Cc4ccccc4)C3=O)CC2)nc1-c1cc(Cl)ccc1OC(F)F] | 2-amino-N-[1-[1-[3-(3-benzyl-2-oxo-imidazolidin-1-yl)propyl]-4-piperidyl]-3-[5-chloro-2-(difluoromethoxy)phenyl]pyrazol-4-yl]pyrazolo[1,5-a]pyrimidine-3-carboxamide |
| 167 | 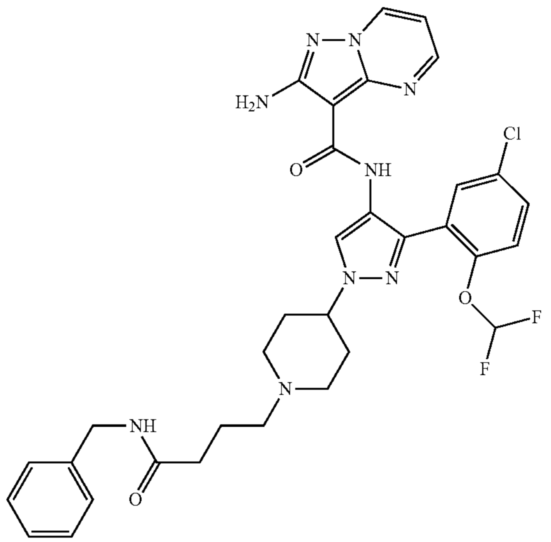 [SMILES: Nc1nn2cccnc2c1C(=O)Nc1cn(C2CCN(CCCC(=O)NCc3ccccc3)CC2)nc1-c1cc(Cl)ccc1OC(F)F] | 2-amino-N-[1-[1-[4-(benzylamino)-4-oxo-butyl]-4-piperidyl]-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 168 | 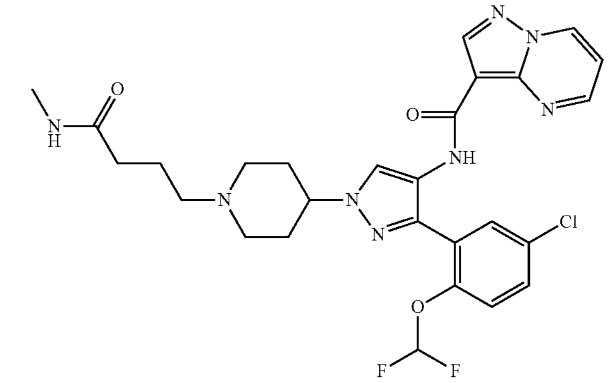 [SMILES: CNC(=O)CCCN1CCC(n2cc(NC(=O)c3cnn4cccnc34)c(-c3cc(Cl)ccc3OC(F)F)n2)CC1] | N-[3-[5-chloro-2-(difluoromethoxy)phenyl]-1-[1-[4-(methylamino)-4-oxo-butyl]-4-piperidyl]pyrazol-4-yl]pyrazolo[1,5-a]pyrimidine-3-carboxamide |
| 169 | 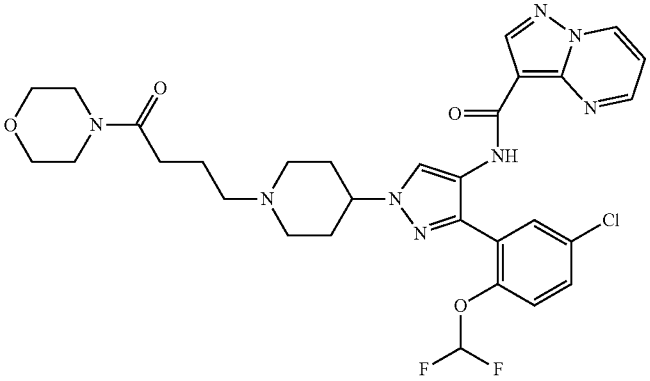 [SMILES: O=C(Nc1cn(C2CCN(CCCC(=O)N3CCOCC3)CC2)nc1-c1cc(Cl)ccc1OC(F)F)c1cnn2cccnc12] | N-[3-[5-chloro-2-(difluoromethoxy)phenyl]-1-[1-(4-morpholino-4-oxo-butyl)-4-piperidyl]pyrazol-4-yl]pyrazolo[1,5-a]pyrimidine-3-carboxamide |
| 170 | 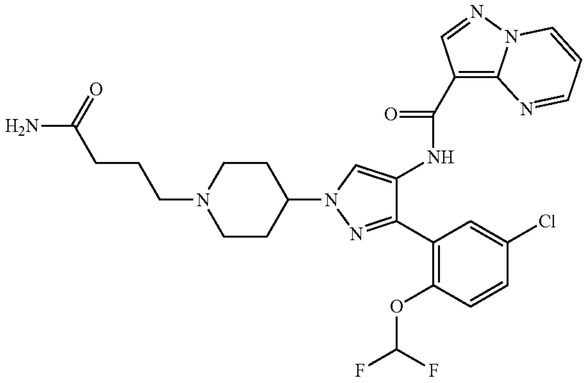 [SMILES: NC(=O)CCCN1CCC(n2cc(NC(=O)c3cnn4cccnc34)c(-c3cc(Cl)ccc3OC(F)F)n2)CC1] | N-[1-[1-(4-amino-4-oxo-butyl)-4-piperidyl]-3-[5-chloro-2-(difluoromethoxy)phenyl] pyrazol-4-yl]pyrazolo[1,5-a]pyrimidine-3-carboxamide |
| 171 | 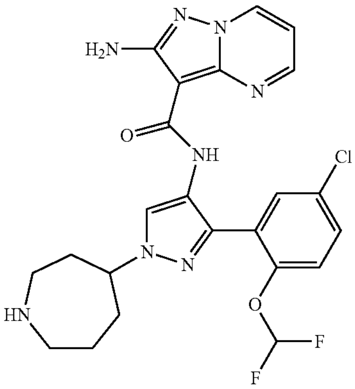 [SMILES: Nc1nn2cccnc2c1C(=O)Nc1cn(C2CCCNCC2)nc1-c1cc(Cl)ccc1OC(F)F] | 2-amino-N-[1-(azepan-4-yl)-3-[5-chloro-2-(difluoromethoxy)phenyl] pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 172 | 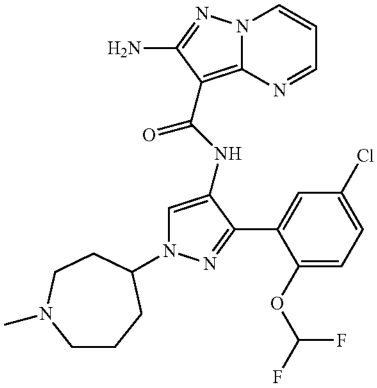 [SMILES: CN1CCCC(n2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-(1-methylazepan-4-yl)pyrazol-4-yl]pyrazolo[1,5-a]pyrimidine-3-carboxamide |
| 173 | 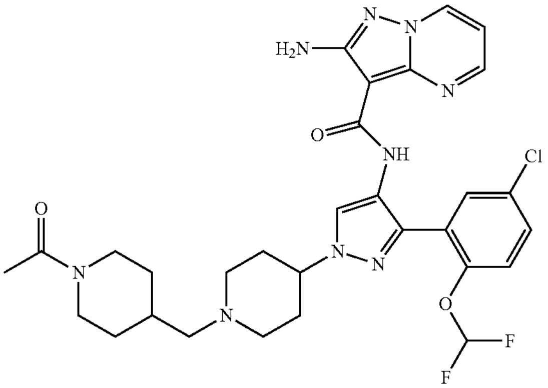 [SMILES: CC(=O)N1CCC(CN2CCC(n3cc(NC(=O)c4c(N)nn5cccnc45)c(-c4cc(Cl)ccc4OC(F)F)n3)CC2)CC1] | N-[1-[1-[(1-acetyl-4-piperidyl)methyl]-4-piperidyl]-3-[5-chloro-2-(difluoromethoxy)phenyl]pyrazol-4-yl]-2-amino-pyrazolo[1,5-a]pyrimidine-3-carboxamide |
| 174 | 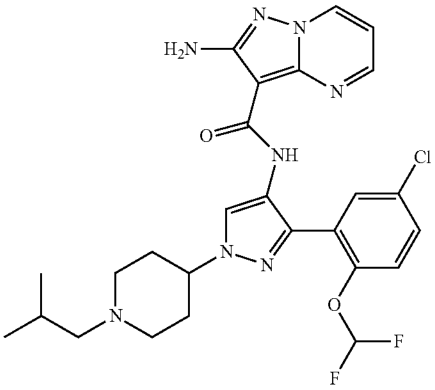 [SMILES: CC(C)CN1CCC(n2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-(1-isobutyl-4-piperidyl)pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 175 | 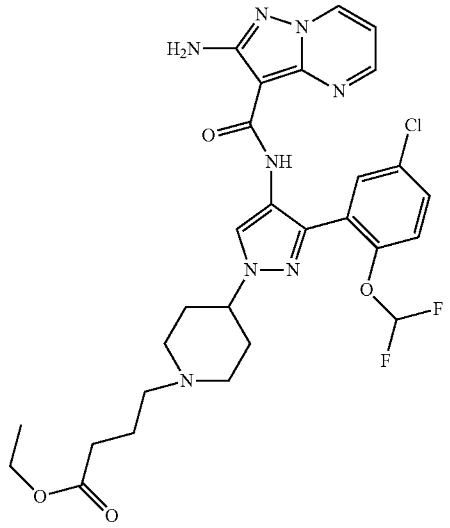 [SMILES: CCOC(=O)CCCN1CCC(n2cc(NC(=O)c3c(N)nn4cccnc34)c(-c3cc(Cl)ccc3OC(F)F)n2)CC1] | ethyl 4-[4-[4-[(2-aminopyrazolo[1,5-a]pyrimidine-3-carbonyl)amino]-3-[5-chloro-2-(difluoromethoxy)phenyl] pyrazol-1-yl]-1-piperidyl]butanoate |
| 176 | 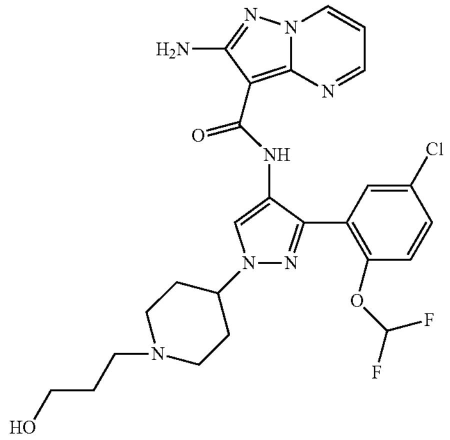 [SMILES: Nc1nn2cccnc2c1C(=O)Nc1cn(C2CCN(CCCO)CC2)nc1-c1cc(Cl)ccc1OC(F)F] | 2-amino-N-[3-[5-chloro-2-(difluoromethoxy)phenyl]-1-[1-(3-hydroxypropyl)-4-piperidyl]pyrazol-4-yl]pyrazolo[1,5-a]pyrimidine-3-carboxamide |
| 177 | 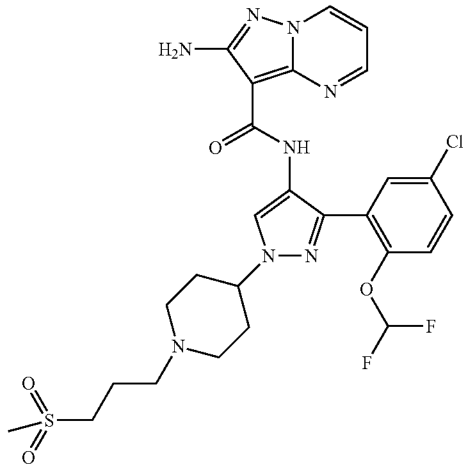 [SMILES: CS(=O)(=O)CCCN1CCC(n2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-[1-(3-methylsulfonylpropyl)-4-piperidyl]pyrazol-4-yl]pyrazolo[1,5-a]pyrimidine-3-carboxamide |

TABLE 1-continued
| Exemplary Compounds of the Present Invention | | |
|---|---|---|
| Ex. | Structure | Name |
| 178 | 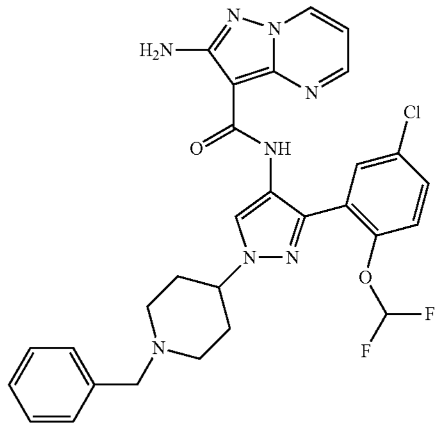 [SMILES: Nc1nn2cccnc2c1C(=O)Nc1cn(C2CCN(Cc3ccccc3)CC2)nc1-c1cc(Cl)ccc1OC(F)F] | 2-amino-N-[1-(1-benzyl-4-piperidyl)-3-[5-chloro-2-(difluoromethoxy)phenyl]pyrazol-4-yl]pyrazolo[1,5-a]pyrimidine-3-carboxamide |
| 179 | 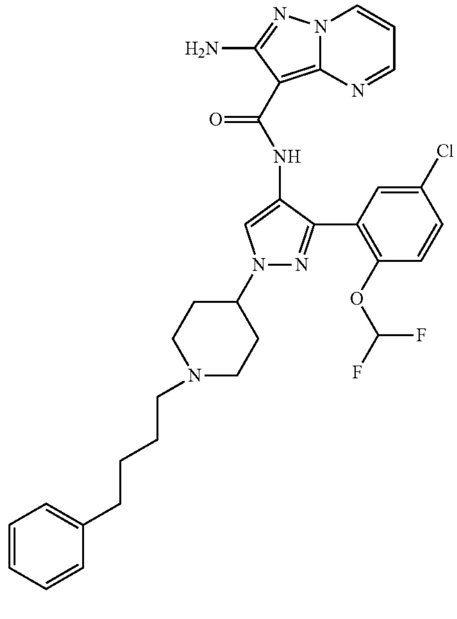 [SMILES: Nc1nn2cccnc2c1C(=O)Nc1cn(C2CCN(CCCCc3ccccc3)CC2)nc1-c1cc(Cl)ccc1OC(F)F] | 2-amino-N-[3-[5-chloro-2-(difluoromethoxy)phenyl]-1-[1-(4-phenylbutyl)-4-piperidyl]pyrazol-4-yl]pyrazolo[1,5-a]pyrimidine-3-carboxamide |

TABLE 1-continued
| Ex. | Structure | Name |
|---|---|---|
| | Exemplary Compounds of the Present Invention | |
| 180 | 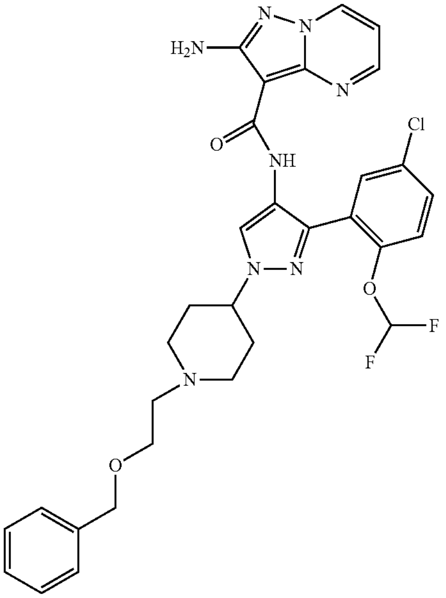 [SMILES: Nc1nn2cccnc2c1C(=O)Nc1cn(C2CCN(CCOCc3ccccc3)CC2)nc1-c1cc(Cl)ccc1OC(F)F] | 2-amino-N-[1-[1-(2-benzyloxyethyl)-4-piperidyl]-3-[5-chloro-2-(difluoromethoxy)phenyl]pyrazol-4-yl]pyrazolo[1,5-a]pyrimidine-3-carboxamide |
| 181 | 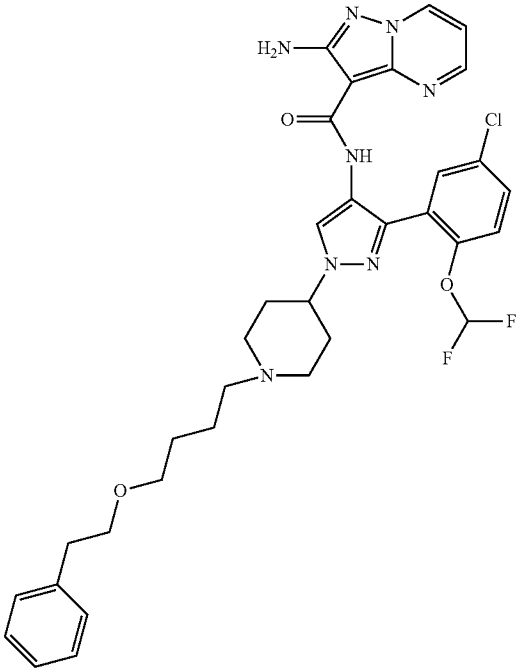 [SMILES: Nc1nn2cccnc2c1C(=O)Nc1cn(C2CCN(CCCCOCCc3ccccc3)CC2)nc1-c1cc(Cl)ccc1OC(F)F] | 2-amino-N-[3-[5-chloro-2-(difluoromethoxy)phenyl]-1-[1-[4-(2-phenylethoxy)butyl]-4-piperidyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 182 | 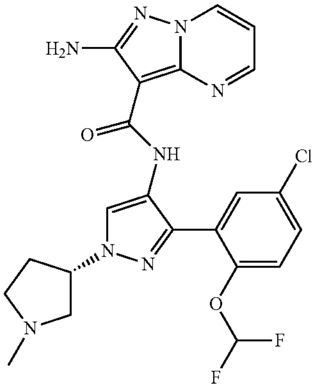 [SMILES: CN1CC[C@H](n2cc(NC(=O)c3c(N)nn4cccnc34)c(-c3cc(Cl)ccc3OC(F)F)n2)C1] | 2-amino-N-[3-[5-chloro-2-(difluoromethoxy)phenyl]-1-[(3S)-1-methylpyrrolidin-3-yl]pyrazol-4-yl]pyrazolo[1,5-a]pyrimidine-3-carboxamide |
| 183 | 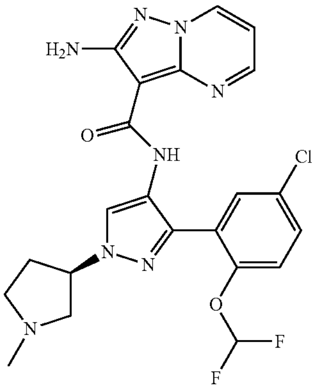 [SMILES: CN1CC[C@@H](n2cc(NC(=O)c3c(N)nn4cccnc34)c(-c3cc(Cl)ccc3OC(F)F)n2)C1] | 2-amino-N-[3-[5-chloro-2-(difluoromethoxy)phenyl]-1-[(3R)-1-methylpyrrolidin-3-yl]pyrazol-4-yl]pyrazolo[1,5-a]pyrimidine-3-carboxamide |
| 184 | 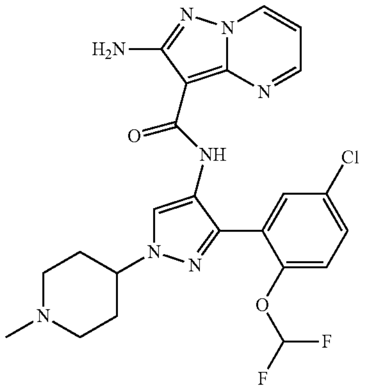 [SMILES: CN1CCC(n2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-(1-methyl-4-piperidyl)pyrazol-4-yl]pyrazolo[1,5-a]pyrimidine-3-carboxamide |
| 185 | 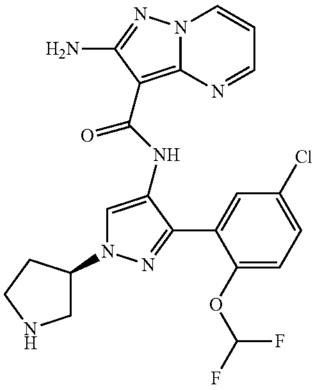 [SMILES: Nc1nn2cccnc2c1C(=O)Nc1cn([C@@H]2CCNC2)nc1-c1cc(Cl)ccc1OC(F)F] | 2-amino-N-[3-[5-chloro-2-(difluoromethoxy)phenyl]-1-[(3R)-pyrrolidin-3-yl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 186 | 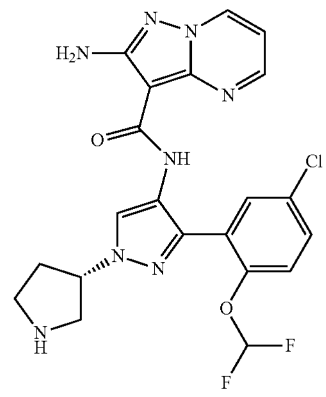 [SMILES: Nc1nn2cccnc2c1C(=O)Nc1cn([C@H]2CCNC2)nc1-c1cc(Cl)ccc1OC(F)F] | 2-amino-N-[3-[5-chloro-2-(difluoromethoxy)phenyl]-1-[(3S)-pyrrolidin-3-yl]pyrazol-4-yl]pyrazolo[1,5-a]pyrimidine-3-carboxamide |
| 187 | 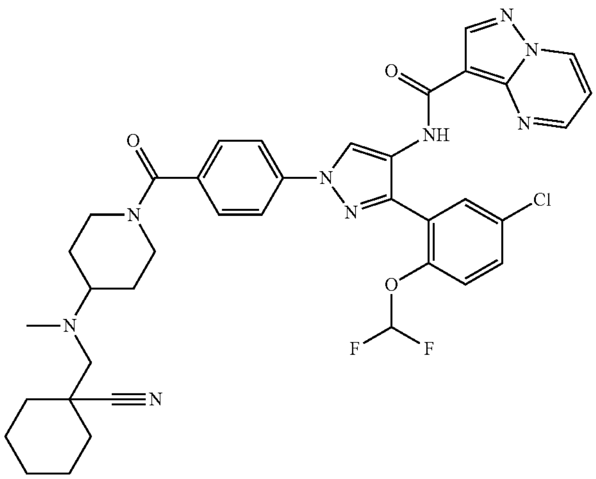 [SMILES: CN(CC1(C#N)CCCCC1)C1CCN(C(=O)c2ccc(-n3cc(NC(=O)c4cnn5cccnc45)c(-c4cc(Cl)ccc4OC(F)F)n3)cc2)CC1] | N-[3-[5-chloro-2-(difluoromethoxy)phenyl]-1-[4-[4-[(1-cyanocyclohexyl)methyl-methyl-amino]piperidine-1-carbonyl]phenyl]pyrazol-4-yl]pyrazolo[1,5-a]pyrimidine-3-carboxamide |
| 188 | 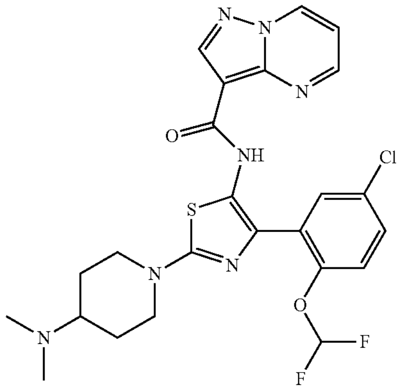 [SMILES: CN(C)C1CCN(c2nc(-c3cc(Cl)ccc3OC(F)F)c(NC(=O)c3cnn4cccnc34)s2)CC1] | N-[4-[5-chloro-2-(difluoromethoxy)phenyl]-2-[4-(dimethylamino)-1-piperidyl]thiazol-5-yl]pyrazolo[1,5-a]pyrimidine-3-carboxamide |

TABLE 1-continued

| Exemplary Compounds of the Present Invention | | |
|---|---|---|
| Ex. | Structure | Name |
| 189 | 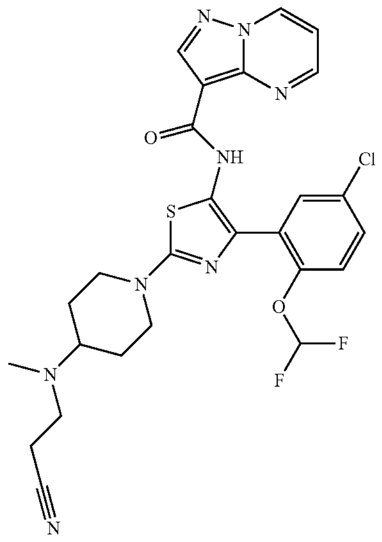 [SMILES: CN(CCC#N)C1CCN(c2nc(-c3cc(Cl)ccc3OC(F)F)c(NC(=O)c3cnn4cccnc34)s2)CC1] | N-[4-[5-chloro-2-(difluoromethoxy)phenyl]-2-[4-[2-cyanoethyl(methyl)amino]-1-piperidyl]thiazol-5-yl]pyrazolo[1,5-a]pyrimidine-3-carboxamide |
| 190 | 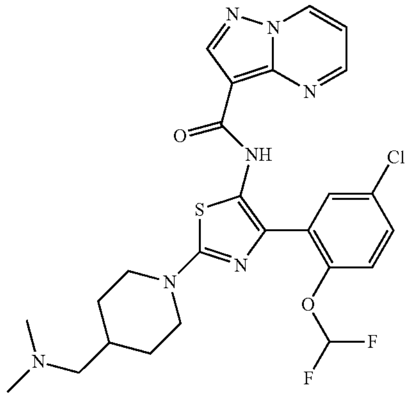 [SMILES: CN(C)CC1CCN(c2nc(-c3cc(Cl)ccc3OC(F)F)c(NC(=O)c3cnn4cccnc34)s2)CC1] | N-[4-[5-chloro-2-(difluoromethoxy)phenyl]-2-[4-[(dimethylamino)methyl]-1-piperidyl]thiazol-5-yl]pyrazolo[1,5-a]pyrimidine-3-carboxamide |
| 191 | 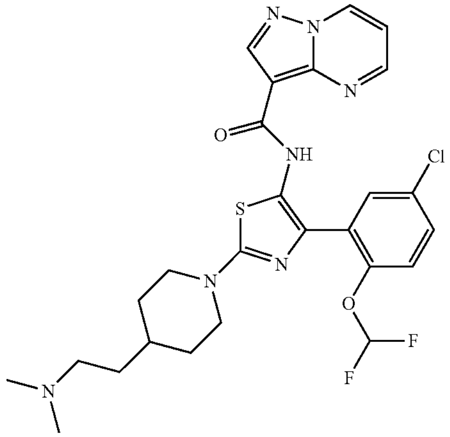 [SMILES: CN(C)CCC1CCN(c2nc(-c3cc(Cl)ccc3OC(F)F)c(NC(=O)c3cnn4cccnc34)s2)CC1] | N-[4-[5-chloro-2-(difluoromethoxy)phenyl]-2-[4-[2-(dimethylamino)ethyl]-1-piperidyl]thiazol-5-yl]pyrazolo[1,5-a]pyrimidine-3-carboxamide |

TABLE 1-continued

Exemplary Compounds of the Present Invention

| Ex. | Structure | Name |
| --- | --- | --- |
| 192 | 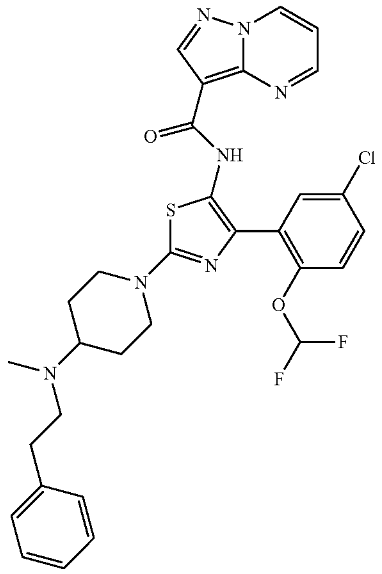 [SMILES: CN(CCc1ccccc1)C1CCN(c2nc(-c3cc(Cl)ccc3OC(F)F)c(NC(=O)c3cnn4cccnc34)s2)CC1] | N-[4-[5-chloro-2-(difluoromethoxy)phenyl]-2-[4-[methyl(2-phenylethyl)amino]-1-piperidyl]thiazol-5-yl]pyrazolo[1,5-a]pyrimidine-3-carboxamide |
| 193 | 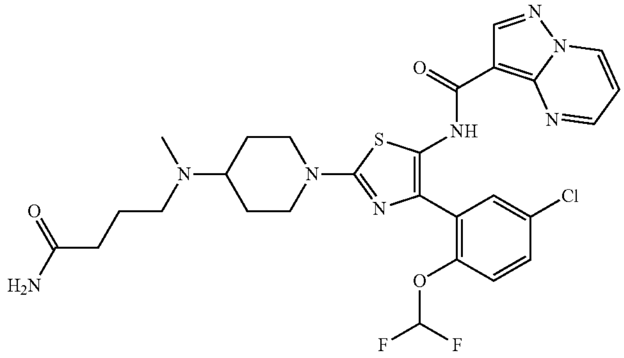 [SMILES: CN(CCCC(N)=O)C1CCN(c2nc(-c3cc(Cl)ccc3OC(F)F)c(NC(=O)c3cnn4cccnc34)s2)CC1] | N-[2-[4-[(4-amino-4-oxo-butyl)-methyl-amino]-1-piperidyl]-4-[5-chloro-2-(difluoromethoxy)phenyl]thiazol-5-yl]pyrazolo[1,5-a]pyrimidine-3-carboxamide |
| 194 | 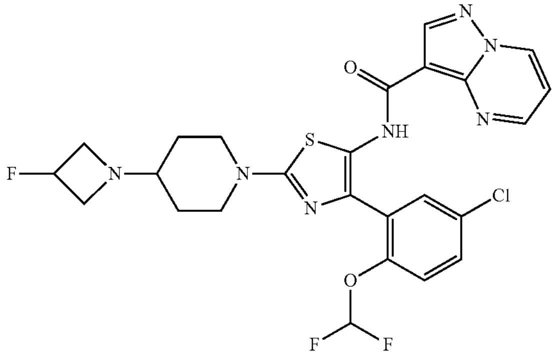 [SMILES: O=C(Nc1sc(N2CCC(N3CC(F)C3)CC2)nc1-c1cc(Cl)ccc1OC(F)F)c1cnn2cccnc12] | N-[4-[5-chloro-2-(difluoromethoxy)phenyl]-2-[4-(3-fluoroazetidin-1-yl)-1-piperidyl]thiazol-5-yl]pyrazolo[1,5-a]pyrimidine-3-carboxamide |

TABLE 1-continued

| Exemplary Compounds of the Present Invention | | |
|---|---|---|
| Ex. | Structure | Name |
| 195 | 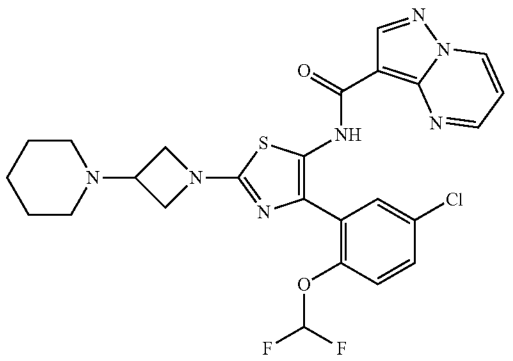 [SMILES: O=C(Nc1sc(N2CC(N3CCCCC3)C2)nc1-c1cc(Cl)ccc1OC(F)F)c1cnn2cccnc12] | N-[4-[5-chloro-2-(difluoromethoxy)phenyl]-2-[3-(1-piperidyl)azetidin-1-yl]thiazol-5-yl]pyrazolo[1,5-a]pyrimidine-3-carboxamide |
| 196 | 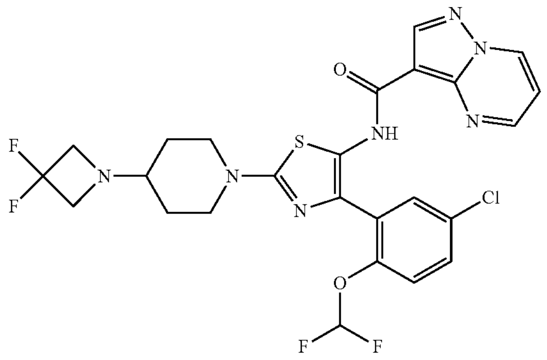 [SMILES: O=C(Nc1sc(N2CCC(N3CC(F)(F)C3)CC2)nc1-c1cc(Cl)ccc1OC(F)F)c1cnn2cccnc12] | N-[4-[5-chloro-2-(difluoromethoxy)phenyl]-2-[4-(3,3-difluoroazetidin-1-yl)-1-piperidyl]thiazol-5-yl]pyrazolo[1,5-a]pyrimidine-3-carboxamide |
| 197 | 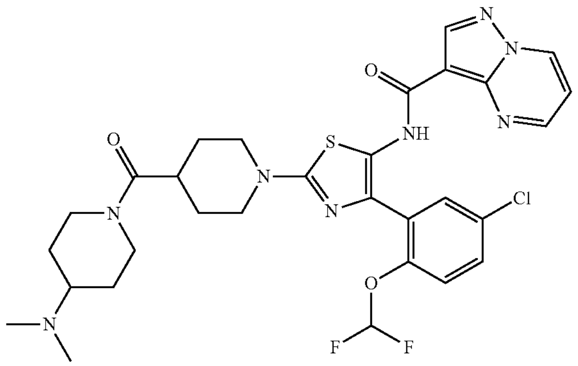 [SMILES: CN(C)C1CCN(C(=O)C2CCN(c3nc(-c4cc(Cl)ccc4OC(F)F)c(NC(=O)c4cnn5cccnc45)s3)CC2)CC1] | N-[4-[5-chloro-2-(difluoromethoxy)phenyl]-2-[4-[4-(dimethylamino)piperidine-1-carbonyl]-1-piperidyl]thiazol-5-yl]pyrazolo[1,5-a]pyrimidine-3-carboxamide |
| 198 | 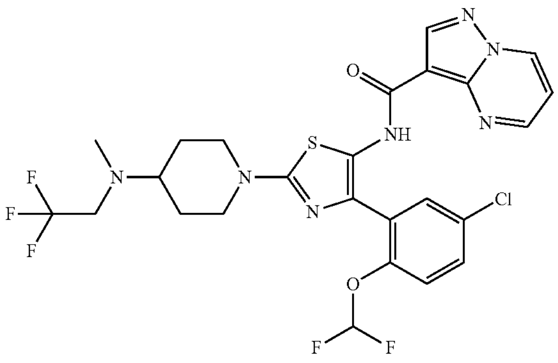 [SMILES: CN(CC(F)(F)F)C1CCN(c2nc(-c3cc(Cl)ccc3OC(F)F)c(NC(=O)c3cnn4cccnc34)s2)CC1] | N-[4-[5-chloro-2-(difluoromethoxy)phenyl]-2-[4-[methyl(2,2,2-trifluoroethyl)amino]-1-piperidyl]thiazol-5-yl]pyrazolo[1,5-a]pyrimidine-3-carboxamide |

TABLE 1-continued

| Exemplary Compounds of the Present Invention | | |
|---|---|---|
| Ex. | Structure | Name |
| 199 | 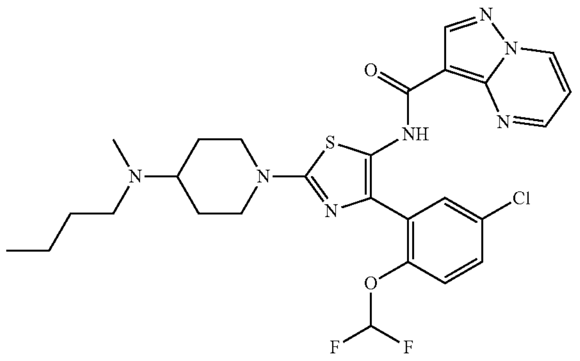 [SMILES: CCCCN(C)C1CCN(c2nc(-c3cc(Cl)ccc3OC(F)F)c(NC(=O)c3cnn4cccnc34)s2)CC1] | N-[2-[4-[butyl(methyl)amino]-1-piperidyl]-4-[5-chloro-2-(difluoromethoxy)phenyl]thiazol-5-yl]pyrazolo[1,5-a]pyrimidine-3-carboxamide |
| 200 | 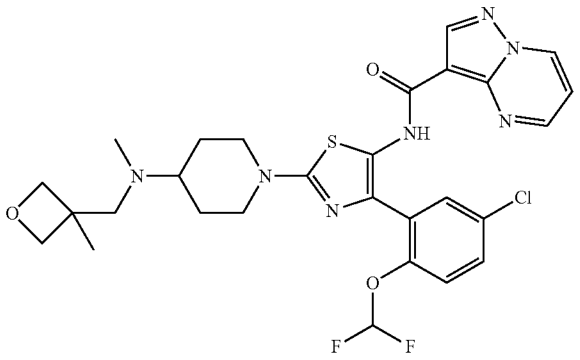 [SMILES: CN(CC1(C)COC1)C1CCN(c2nc(-c3cc(Cl)ccc3OC(F)F)c(NC(=O)c3cnn4cccnc34)s2)CC1] | N-[4-[5-chloro-2-(difluoromethoxy)phenyl]-2-[4-[methyl-[(3-methyloxetan-3-yl)methyl]amino]-1-piperidyl]thiazol-5-yl]pyrazolo[1,5-a]pyrimidine-3-carboxamide |
| 201 | 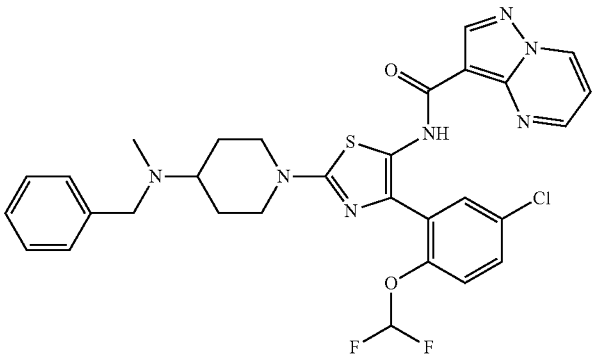 [SMILES: CN(Cc1ccccc1)C1CCN(c2nc(-c3cc(Cl)ccc3OC(F)F)c(NC(=O)c3cnn4cccnc34)s2)CC1] | N-[2-[4-[benzyl(methyl)amino]-1-piperidyl]-4-[5-chloro-2-(difluoromethoxy)phenyl]thiazol-5-yl]pyrazolo[1,5-a]pyrimidine-3-carboxamide |
| 202 | 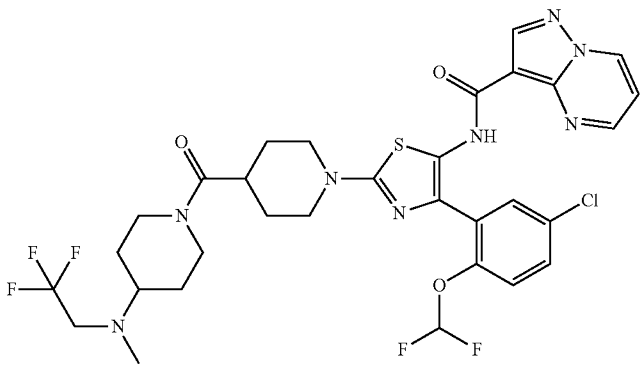 [SMILES: CN(CC(F)(F)F)C1CCN(C(=O)C2CCN(c3nc(-c4cc(Cl)ccc4OC(F)F)c(NC(=O)c4cnn5cccnc45)s3)CC2)CC1] | N-[4-[5-chloro-2-(difluoromethoxy)phenyl]-2-[4-[4-[methyl(2,2,2-trifluoroethyl)amino]piperidine-1-carbonyl]-1-piperidyl]thiazol-5-yl]pyrazolo[1,5-a]pyrimidine-3-carboxamide |

TABLE 1-continued

| Exemplary Compounds of the Present Invention | | |
|---|---|---|
| Ex. | Structure | Name |
| 203 | 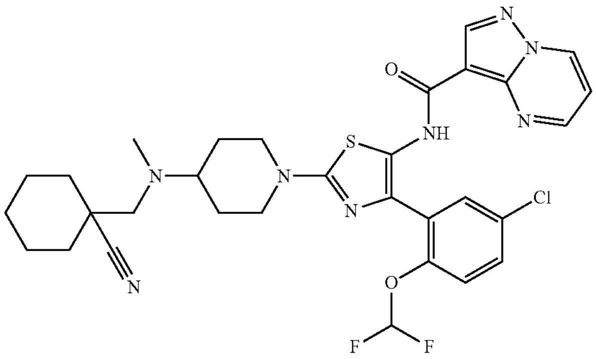 [SMILES: CN(CC1(C#N)CCCCC1)C1CCN(c2nc(-c3cc(Cl)ccc3OC(F)F)c(NC(=O)c3cnn4cccnc34)s2)CC1] | N-[4-[5-chloro-2-(difluoromethoxy)phenyl]-2-[4-[(1-cyanocyclohexyl)methyl-methyl-amino]-1-piperidyl]thiazol-5-yl]pyrazolo[1,5-a]pyrimidine-3-carboxamide |
| 204 | 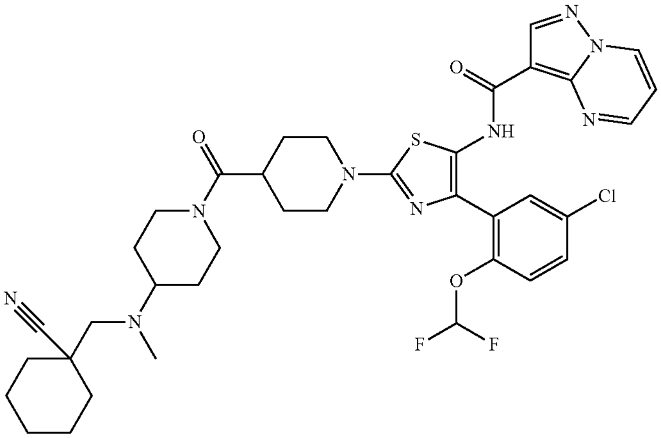 [SMILES: CN(CC1(C#N)CCCCC1)C1CCN(C(=O)C2CCN(c3nc(-c4cc(Cl)ccc4OC(F)F)c(NC(=O)c4cnn5cccnc45)s3)CC2)CC1] | N-[4-[5-chloro-2-(difluoromethoxy)phenyl]-2-[4-[4-[(1-cyanocyclohexyl)methyl-methyl-amino]piperidine-1-carbonyl]-1-piperidyl]thiazol-5-yl]pyrazolo[1,5-a]pyrimidine-3-carboxamide |
| 205 | 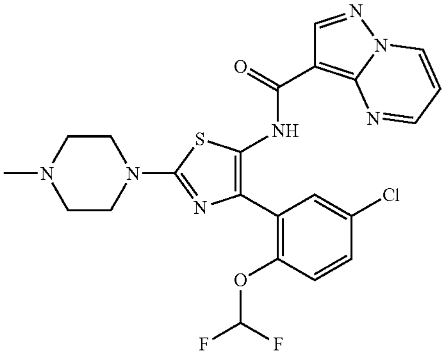 [SMILES: CN1CCN(c2nc(-c3cc(Cl)ccc3OC(F)F)c(NC(=O)c3cnn4cccnc34)s2)CC1] | N-[4-[5-chloro-2-(difluoromethoxy)phenyl]-2-(4-methylpiperazin-1-yl)thiazol-5-yl]pyrazolo[1,5-a]pyrimidine-3-carboxamide |
| 206 | 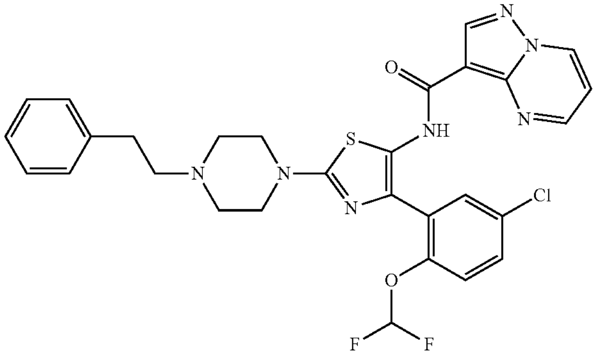 [SMILES: O=C(Nc1sc(N2CCN(CCc3ccccc3)CC2)nc1-c1cc(Cl)ccc1OC(F)F)c1cnn2cccnc12] | N-[4-[5-chloro-2-(difluoromethoxy)phenyl]-2-[4-(2-phenylethyl)piperazin-1-yl]thiazol-5-yl]pyrazolo[1,5-a]pyrimidine-3-carboxamide |

TABLE 1-continued

| Ex. | Structure | Name |
| --- | --- | --- |
| | Exemplary Compounds of the Present Invention | |
| 207 | 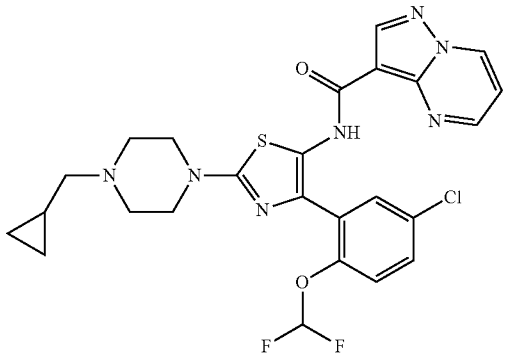 [SMILES: O=C(Nc1sc(N2CCN(CC3CC3)CC2)nc1-c1cc(Cl)ccc1OC(F)F)c1cnn2cccnc12] | N-[4-[5-chloro-2-(difluoromethoxy)phenyl]-2-[4-(cyclopropylmethyl) piperazin-1-yl]thiazol-5-yl]pyrazolo[1,5-a]pyrimidine-3-carboxamide |
| 208 | 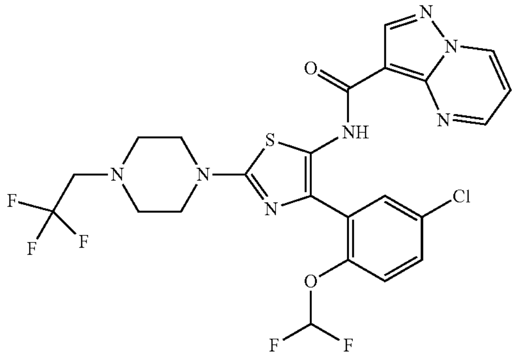 [SMILES: O=C(Nc1sc(N2CCN(CC(F)(F)F)CC2)nc1-c1cc(Cl)ccc1OC(F)F)c1cnn2cccnc12] | N-[4-[5-chloro-2-(difluoromethoxy)phenyl]-2-[4-(2,2,2-trifluoroethyl)piperazin-1-yl]thiazol-5-yl]pyrazolo[1,5-a]pyrimidine-3-carboxamide |
| 209 | 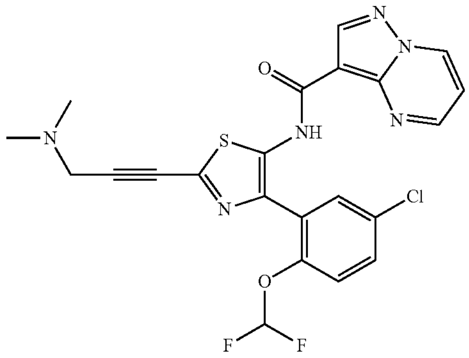 [SMILES: CN(C)CC#Cc1nc(-c2cc(Cl)ccc2OC(F)F)c(NC(=O)c2cnn3cccnc23)s1] | N-[4-[5-chloro-2-(difluoromethoxy)phenyl]-2-[3-(dimethylamino)prop-1-ynyl]thiazol-5-yl]pyrazolo[1,5-a]pyrimidine-3-carboxamide |
| 210 | 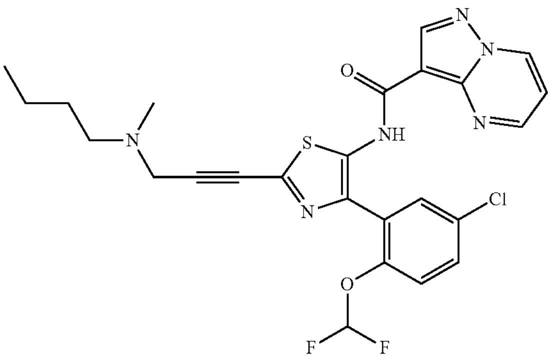 [SMILES: CCCCN(C)CC#Cc1nc(-c2cc(Cl)ccc2OC(F)F)c(NC(=O)c2cnn3cccnc23)s1] | N-[2-[3-[butyl(methyl)amino]prop-1-ynyl]-4-[5-chloro-2-(difluoromethoxy)phenyl] thiazol-5-yl]pyrazolo[1,5-a]pyrimidine-3-carboxamide |

TABLE 1-continued

| Exemplary Compounds of the Present Invention | | |
|---|---|---|
| Ex. | Structure | Name |
| 211 | 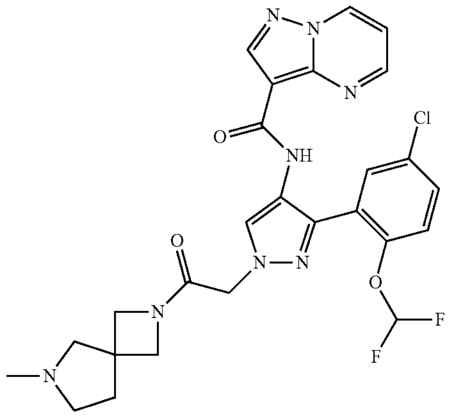 [SMILES: CN1CCC2(C1)CN(C(=O)Cn1cc(NC(=O)c3cnn4cccnc34)c(-c3cc(Cl)ccc3OC(F)F)n1)C2] | N-[3-[5-chloro-2-(difluoromethoxy)phenyl]-1-[2-(7-methyl-2,7-diazaspiro[3.4]octan-2-yl)-2-oxo-ethyl]pyrazol-4-yl]pyrazolo[1,5-a]pyrimidine-3-carboxamide |
| 212 | 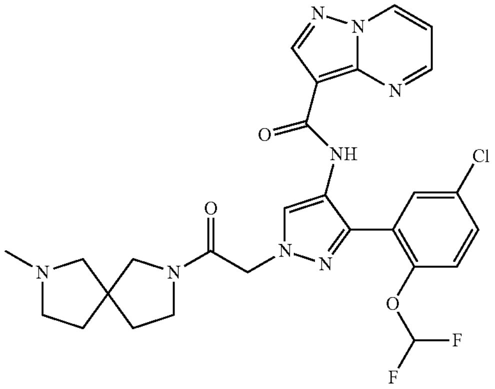 [SMILES: CN1CCC2(CCN(C(=O)Cn3cc(NC(=O)c4cnn5cccnc45)c(-c4cc(Cl)ccc4OC(F)F)n3)C2)C1] | N-[3-[5-chloro-2-(difluoromethoxy)phenyl]-1-[2-(7-methyl-2,7-diazaspiro[4.4]nonan-2-yl)-2-oxo-ethyl]pyrazol-4-yl]pyrazolo[1,5-a]pyrimidine-3-carboxamide |
| 213 | 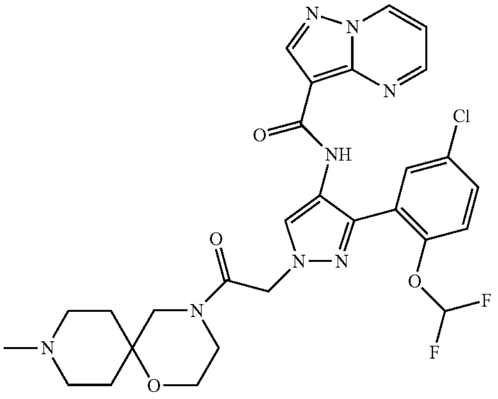 [SMILES: CN1CCC2(CC1)CN(C(=O)Cn1cc(NC(=O)c3cnn4cccnc34)c(-c3cc(Cl)ccc3OC(F)F)n1)CCO2] | N-[3-[5-chloro-2-(difluoromethoxy)phenyl]-1-[2-(9-methyl-1-oxa-4,9-diazaspiro[5.5]undecan-4-yl)-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 214 | 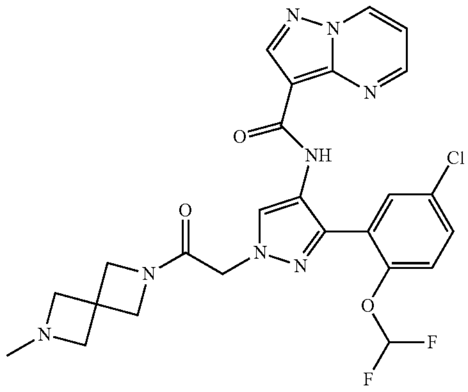 [SMILES: CN1CC2(C1)CN(C(=O)Cn1cc(NC(=O)c3cnn4cccnc34)c(-c3cc(Cl)ccc3OC(F)F)n1)C2] | N-[3-[5-chloro-2-(difluoromethoxy)phenyl]-1-[2-(6-methyl-2,6-diazaspiro[3.3]heptan-2-yl)-2-oxo-ethyl]pyrazol-4-yl]pyrazolo[1,5-a]pyrimidine-3-carboxamide |
| 215 | 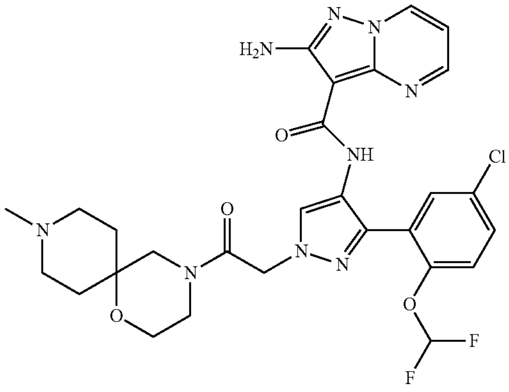 [SMILES: CN1CCC2(CC1)CN(C(=O)Cn1cc(NC(=O)c3c(N)nn4cccnc34)c(-c3cc(Cl)ccc3OC(F)F)n1)CCO2] | 2-amino-N-[3-[5-chloro-2-(difluoromethoxy)phenyl]-1-[2-(9-methyl-1-oxa-4,9-diazaspiro[5.5]undecan-4-yl)-2-oxo-ethyl]pyrazol-4-yl]pyrazolo[1,5-a]pyrimidine-3-carboxamide |
| 216 | 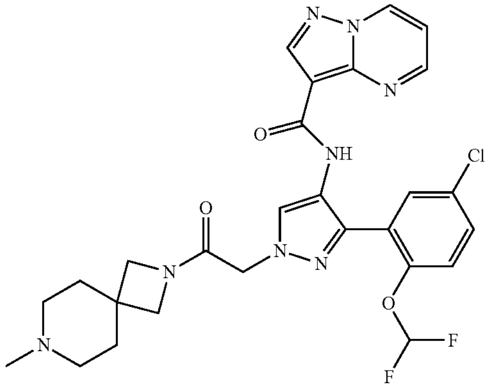 [SMILES: CN1CCC2(CC1)CN(C(=O)Cn1cc(NC(=O)c3cnn4cccnc34)c(-c3cc(Cl)ccc3OC(F)F)n1)C2] | N-[3-[5-chloro-2-(difluoromethoxy)phenyl]-1-[2-(7-methyl-2,7-diazaspiro[3.5]nonan-2-yl)-2-oxo-ethyl]pyrazol-4-yl]pyrazolo[1,5-a]pyrimidine-3-carboxamide |
| 217 | 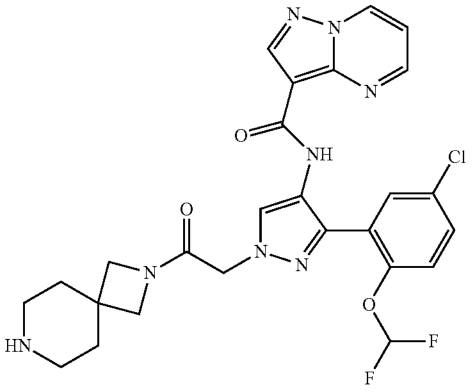 [SMILES: O=C(Nc1cn(CC(=O)N2CC3(CCNCC3)C2)nc1-c1cc(Cl)ccc1OC(F)F)c1cnn2cccnc12] | N-[3-[5-chloro-2-(difluoromethoxy)phenyl]-1-[2-(2,7-diazaspiro[3.5]nonan-2-yl)-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 218 | 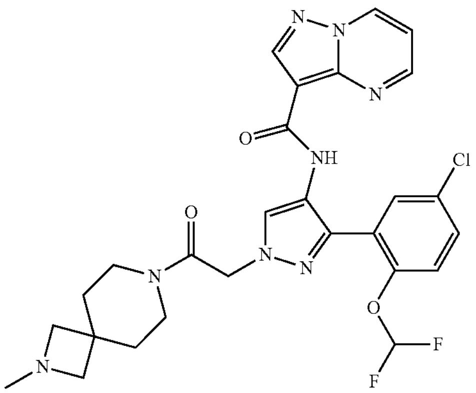 [SMILES: CN1CC2(CCN(C(=O)Cn3cc(NC(=O)c4cnn5cccnc45)c(-c4cc(Cl)ccc4OC(F)F)n3)CC2)C1] | N-[3-[5-chloro-2-(difluoromethoxy)phenyl]-1-[2-(2-methyl-2,7-diazaspiro[3.5]nonan-7-yl)-2-oxo-ethyl]pyrazol-4-yl]pyrazolo[1,5-a]pyrimidine-3-carboxamide |
| 219 | 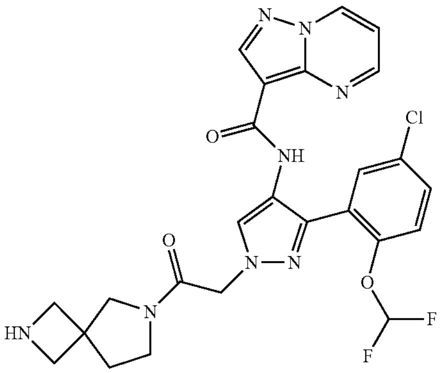 [SMILES: O=C(Nc1cn(CC(=O)N2CCC3(CNC3)C2)nc1-c1cc(Cl)ccc1OC(F)F)c1cnn2cccnc12] | N-[3-[5-chloro-2-(difluoromethoxy)phenyl]-1-[2-(2,6-diazaspiro[3.4]octan-6-yl)-2-oxo-ethyl]pyrazol-4-yl]pyrazolo[1,5-a]pyrimidine-3-carboxamide |
| 220 | 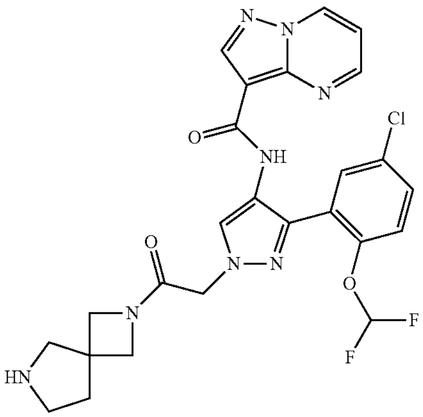 [SMILES: O=C(Nc1cn(CC(=O)N2CC3(CCNC3)C2)nc1-c1cc(Cl)ccc1OC(F)F)c1cnn2cccnc12] | N-[3-[5-chloro-2-(difluoromethoxy)phenyl]-1-[2-(2,7-diazaspiro[3.4]octan-2-yl)-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 221 | 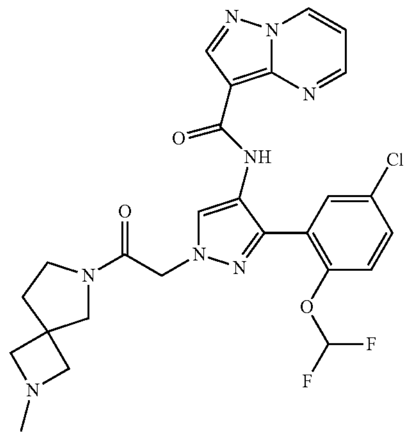 [SMILES: CN1CC2(CCN(C(=O)Cn3cc(NC(=O)c4cnn5cccnc45)c(-c4cc(Cl)ccc4OC(F)F)n3)C2)C1] | N-[3-[5-chloro-2-(difluoromethoxy)phenyl]-1-[2-(2-methyl-2,6-diazaspiro[3.4]octan-6-yl)-2-oxo-ethyl]pyrazol-4-yl]pyrazolo[1,5-a]pyrimidine-3-carboxamide |
| 222 | 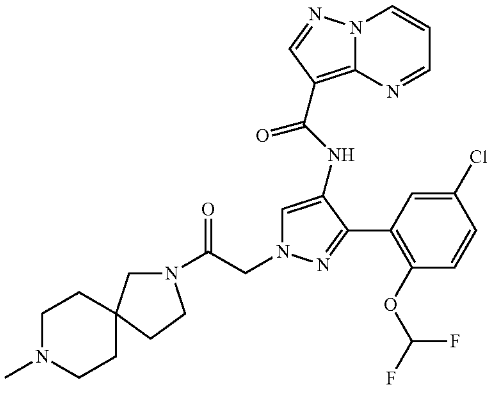 [SMILES: CN1CCC2(CC1)CCN(C(=O)Cn1cc(NC(=O)c3cnn4cccnc34)c(-c3cc(Cl)ccc3OC(F)F)n1)C2] | N-[3-[5-chloro-2-(difluoromethoxy)phenyl]-1-[2-(8-methyl-2,8-diazaspiro[4.5]decan-2-yl)-2-oxo-ethyl]pyrazol-4-yl]pyrazolo[1,5-a]pyrimidine-3-carboxamide |
| 223 | 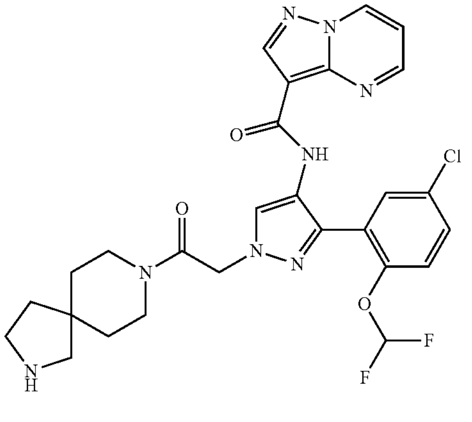 [SMILES: O=C(Nc1cn(CC(=O)N2CCC3(CCNC3)CC2)nc1-c1cc(Cl)ccc1OC(F)F)c1cnn2cccnc12] | N-[3-[5-chloro-2-(difluoromethoxy)phenyl]-1-[2-(2,8-diazaspiro[4.5]decan-8-yl)-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 224 | 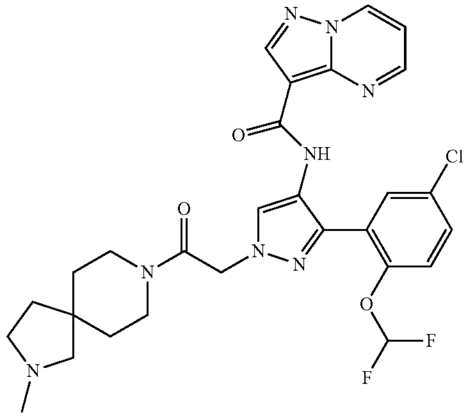 [SMILES: CN1CCC2(CCN(C(=O)Cn3cc(NC(=O)c4cnn5cccnc45)c(-c4cc(Cl)ccc4OC(F)F)n3)CC2)C1] | N-[3-[5-chloro-2-(difluoromethoxy)phenyl]-1-[2-(2-methyl-2,8-diazaspiro[4.5]decan-8-yl)-2-oxo-ethyl]pyrazol-4-yl]pyrazolo[1,5-a]pyrimidine-3-carboxamide |
| 225 | 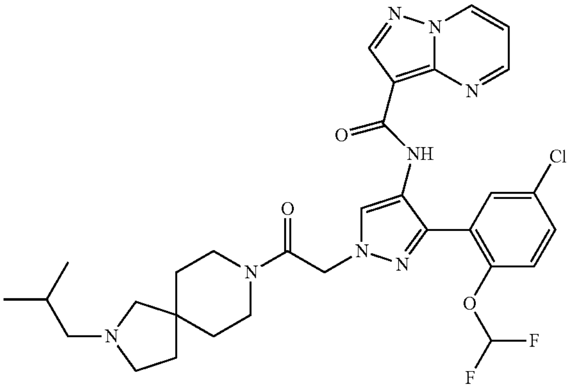 [SMILES: CC(C)CN1CCC2(CCN(C(=O)Cn3cc(NC(=O)c4cnn5cccnc45)c(-c4cc(Cl)ccc4OC(F)F)n3)CC2)C1] | N-[3-[5-chloro-2-(difluoromethoxy)phenyl]-1-[2-(2-isobutyl-2,8-diazaspiro[4.5]decan-8-yl)-2-oxo-ethyl]pyrazol-4-yl]pyrazolo[1,5-a]pyrimidine-3-carboxamide |
| 226 | 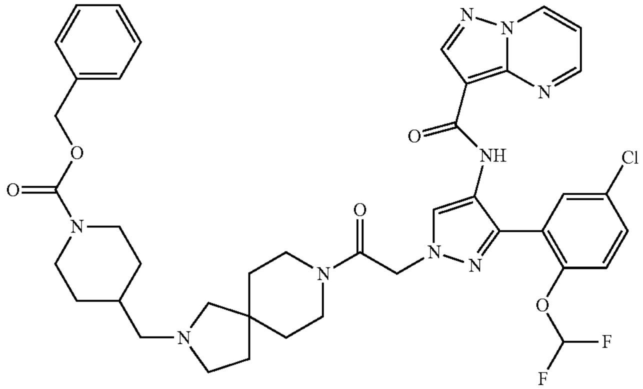 [SMILES: O=C(Nc1cn(CC(=O)N2CCC3(CCN(CC4CCN(C(=O)OCc5ccccc5)CC4)C3)CC2)nc1-c1cc(Cl)ccc1OC(F)F)c1cnn2cccnc12] | benzyl 4-[[8-[2-[3-[5-chloro-2-(difluoromethoxy)phenyl]-4-(pyrazolo[1,5-a]pyrimidine-3-carbonylamino)pyrazol-1-yl]acetyl]-2,8-diazaspiro[4.5]decan-2-yl]methyl]piperidine-1-carboxylate |
| 227 | 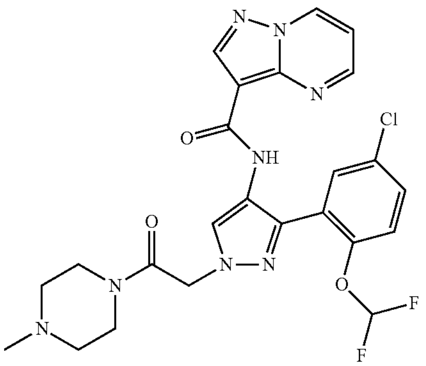 [SMILES: CN1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-(4-methylpiperazin-1-yl)-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 228 | 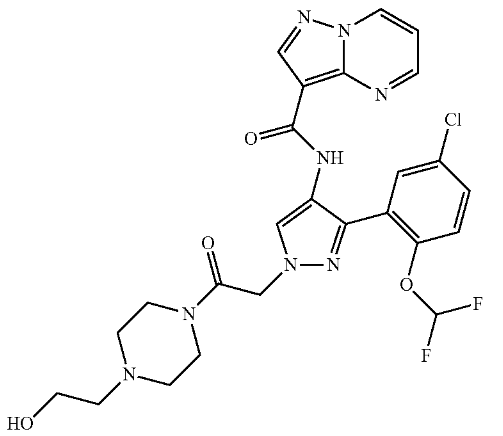 [SMILES: O=C(Nc1cn(CC(=O)N2CCN(CCO)CC2)nc1-c1cc(Cl)ccc1OC(F)F)c1cnn2cccnc12] | N-[3-[5-chloro-2-(difluoromethoxy)phenyl]-1-[2-[4-(2-hydroxyethyl)piperazin-1-yl]-2-oxo-ethyl]pyrazol-4-yl]pyrazolo[1,5-a]pyrimidine-3-carboxamide |
| 229 | 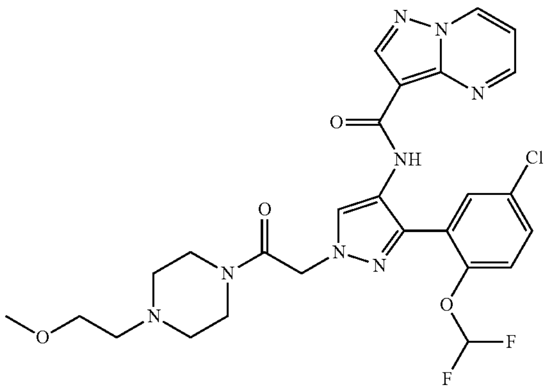 [SMILES: COCCN1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-(2-methoxyethyl)piperazin-1-yl]-2-oxo-ethyl]pyrazol-4-yl]pyrazolo[1,5-a]pyrimidine-3-carboxamide |
| 230 | 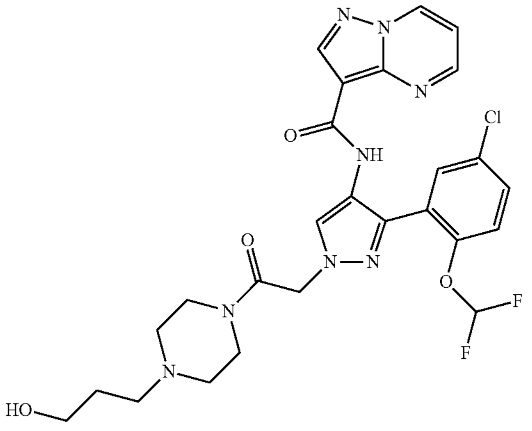 | N-[3-[5-chloro-2-(difluoromethoxy)phenyl]-1-[2-[4-(3-hydroxypropyl)piperazin-1-yl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 231 | 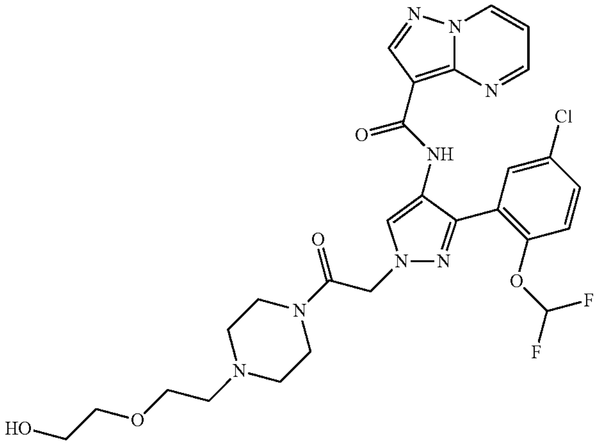 [SMILES: O=C(Nc1cn(CC(=O)N2CCN(CCOCCO)CC2)nc1-c1cc(Cl)ccc1OC(F)F)c1cnn2cccnc12] | N-[3-[5-chloro-2-(difluoromethoxy)phenyl]-1-[2-[4-[2-(2-hydroxyethoxy)ethyl]piperazin-1-yl]-2-oxo-ethyl]pyrazol-4-yl]pyrazolo[1,5-a]pyrimidine-3-carboxamide |
| 232 | 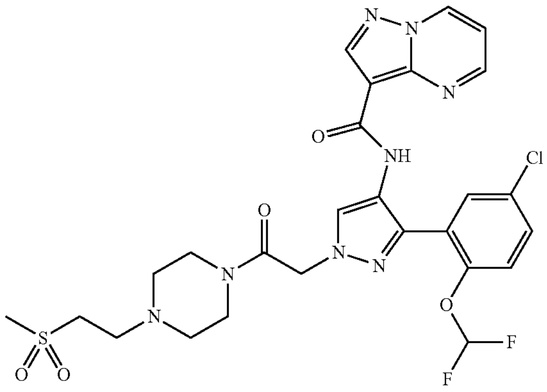 [SMILES: CS(=O)(=O)CCN1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-(2-methylsulfonylethyl)piperazin-1-yl]-2-oxo-ethyl]pyrazol-4-yl]pyrazolo[1,5-a]pyrimidine-3-carboxamide |
| 233 | 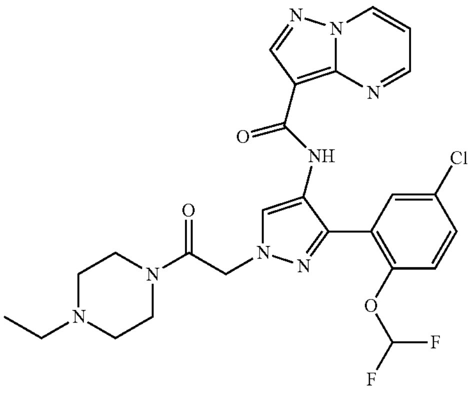 [SMILES: CCN1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-(4-ethylpiperazin-1-yl)-2-oxo-ethyl]pyrazol-4-yl]pyrazolo[1,5-a]pyrimidine-3-carboxamide |

TABLE 1-continued

| Ex. | Structure | Name |
|---|---|---|
| Exemplary Compounds of the Present Invention | | |
| 234 | 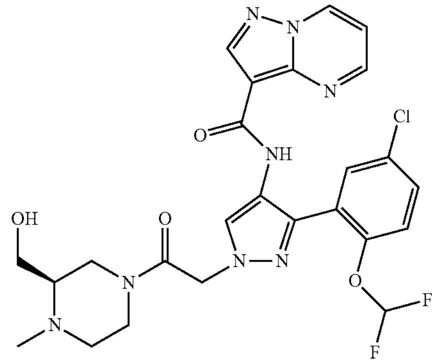 [SMILES: CN1CCN(C(=O)Cn2cc(NC(=O)c3cnn4cccnc34)c(-c3cc(Cl)ccc3OC(F)F)n2)C[C@@H]1CO] | N-[3-[5-chloro-2-(difluoromethoxy)phenyl]-1-[2-[(3R)-3-(hydroxymethyl)-4-methyl-piperazin-1-yl]-2-oxo-ethyl]pyrazol-4-yl]pyrazolo[1,5-a]pyrimidine-3-carboxamide |
| 235 | 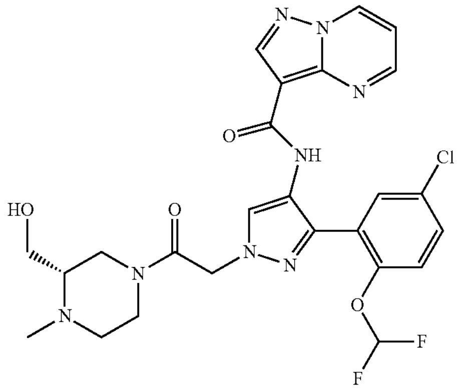 [SMILES: CN1CCN(C(=O)Cn2cc(NC(=O)c3cnn4cccnc34)c(-c3cc(Cl)ccc3OC(F)F)n2)C[C@H]1CO] | N-[3-[5-chloro-2-(difluoromethoxy)phenyl]-1-[2-[(3S)-3-(hydroxymethyl)-4-methyl-piperazin-1-yl]-2-oxo-ethyl]pyrazol-4-yl]pyrazolo[1,5-a]pyrimidine-3-carboxamide |
| 236 | 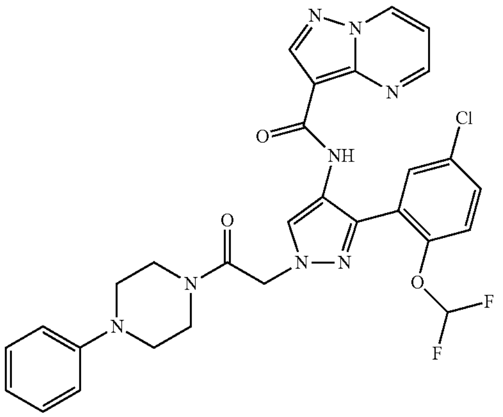 [SMILES: O=C(Nc1cn(CC(=O)N2CCN(c3ccccc3)CC2)nc1-c1cc(Cl)ccc1OC(F)F)c1cnn2cccnc12] | N-[3-[5-chloro-2-(difluoromethoxy)phenyl]-1-[2-oxo-2-(4-phenylpiperazin-1-yl)ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 237 | 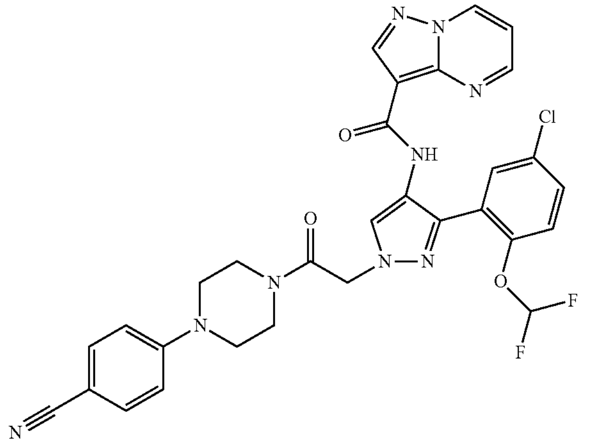 [SMILES: N#Cc1ccc(N2CCN(C(=O)Cn3cc(NC(=O)c4cnn5cccnc45)c(-c4cc(Cl)ccc4OC(F)F)n3)CC2)cc1] | N-[3-[5-chloro-2-(difluoromethoxy)phenyl]-1-[2-[4-(4-cyanophenyl)piperazin-1-yl]-2-oxo-ethyl]pyrazol-4-yl]pyrazolo[1,5-a]pyrimidine-3-carboxamide |
| 238 | 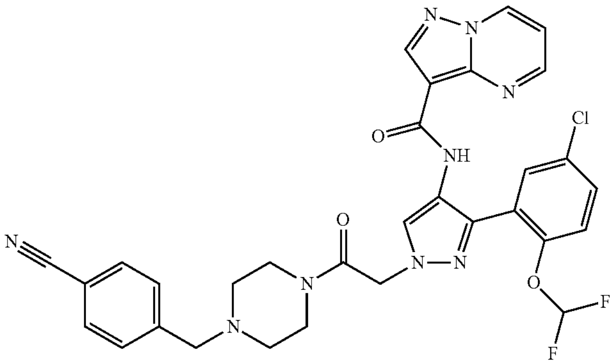 [SMILES: N#Cc1ccc(CN2CCN(C(=O)Cn3cc(NC(=O)c4cnn5cccnc45)c(-c4cc(Cl)ccc4OC(F)F)n3)CC2)cc1] | N-[3-[5-chloro-2-(difluoromethoxy)phenyl]-1-[2-[4-[(4-cyanophenyl)methyl]piperazin-1-yl]-2-oxo-ethyl]pyrazol-4-yl]pyrazolo[1,5-a]pyrimidine-3-carboxamide |
| 239 | 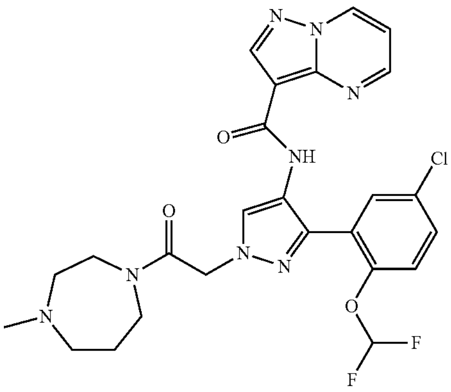 [SMILES: CN1CCCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-(4-methyl-1,4-diazepan-1-yl)-2-oxo-ethyl]pyrazol-4-yl]pyrazolo[1,5-a]pyrimidine-3-carboxamide |

TABLE 1-continued

| Ex. | Structure | Name |
|---|---|---|
| Exemplary Compounds of the Present Invention | | |
| 240 | 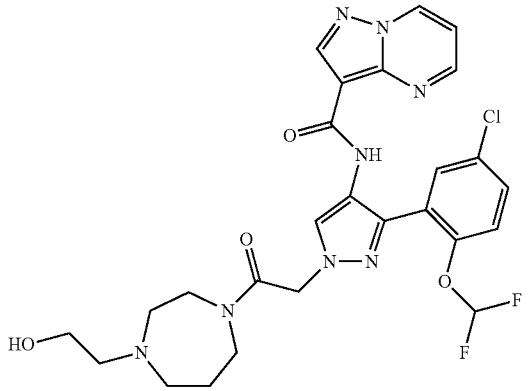 [SMILES: O=C(Nc1cn(CC(=O)N2CCCN(CCO)CC2)nc1-c1cc(Cl)ccc1OC(F)F)c1cnn2cccnc12] | N-[3-[5-chloro-2-(difluoromethoxy)phenyl]-1-[2-[4-(2-hydroxyethyl)-1,4-diazepan-1-yl]-2-oxo-ethyl]pyrazol-4-yl]pyrazolo[1,5-a]pyrimidine-3-carboxamide |
| 241 | 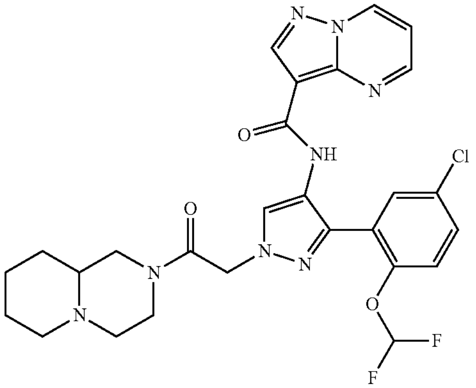 [SMILES: O=C(Nc1cn(CC(=O)N2CCN3CCCCC3C2)nc1-c1cc(Cl)ccc1OC(F)F)c1cnn2cccnc12] | N-[1-[2-(1,3,4,6,7,8,9,9a-octahydropyrido[1,2-a]pyrazin-2-yl)-2-oxo-ethyl]-3-[5-chloro-2-(difluoromethoxy)phenyl] pyrazol-4-yl]pyrazolo[1,5-a]pyrimidine-3-carboxamide |
| 242 | 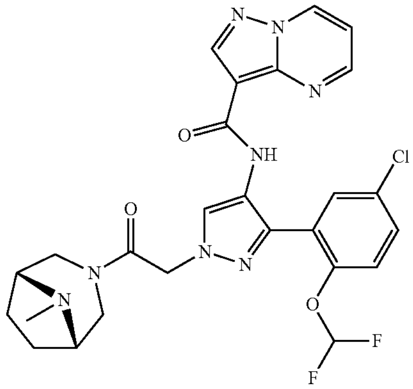 [SMILES: CN1[C@@H]2CC[C@H]1CN(C(=O)Cn1cc(NC(=O)c3cnn4cccnc34)c(-c3cc(Cl)ccc3OC(F)F)n1)C2] | N-[3-[5-chloro-2-(difluoromethoxy)phenyl]-1-[2-[(1S,5R)-8-methyl-3,8-diazabicyclo[3.2.1]octan-3-yl]-2-oxo-ethyl]pyrazol-4-yl]pyrazolo[1,5-a]pyrimidine-3-carboxamide |
| 243 | 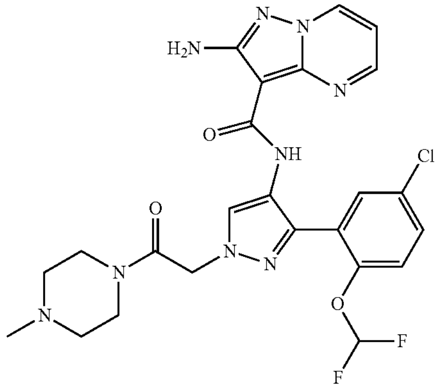 [SMILES: CN1CCN(C(=O)Cn2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-[2-(4-methylpiperazin-1-yl)-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 244 | 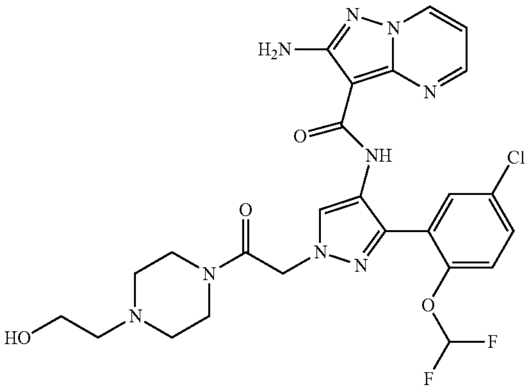 [SMILES: Nc1nn2cccnc2c1C(=O)Nc1cn(CC(=O)N2CCN(CCO)CC2)nc1-c1cc(Cl)ccc1OC(F)F] | 2-amino-N-[3-[5-chloro-2-(difluoromethoxy)phenyl]-1-[2-[4-(2-hydroxyethyl)piperazin-1-yl]-2-oxo-ethyl]pyrazol-4-yl]pyrazolo[1,5-a]pyrimidine-3-carboxamide |
| 245 | 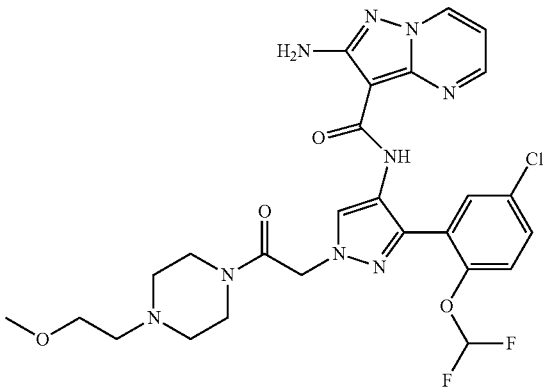 [SMILES: COCCN1CCN(C(=O)Cn2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-[2-[4-(2-methoxyethyl)piperazin-1-yl]-2-oxo-ethyl]pyrazol-4-yl]pyrazolo[1,5-a]pyrimidine-3-carboxamide |
| 246 | 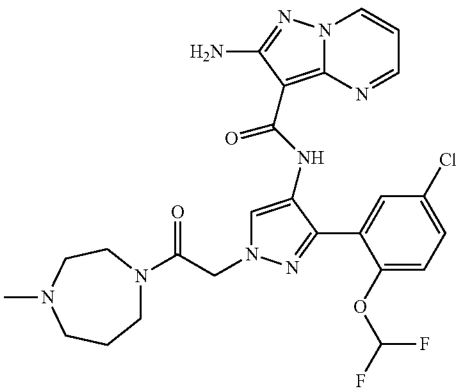 [SMILES: CN1CCCN(C(=O)Cn2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-[2-(4-methyl-1,4-diazepan-1-yl)-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 247 | 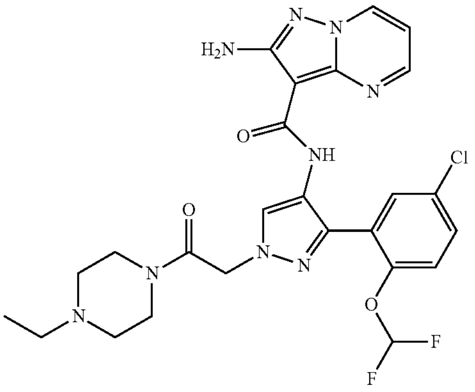 [SMILES: CCN1CCN(C(=O)Cn2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-[2-(4-ethylpiperazin-1-yl)-2-oxo-ethyl]pyrazol-4-yl]pyrazolo[1,5-a]pyrimidine-3-carboxamide |
| 248 | 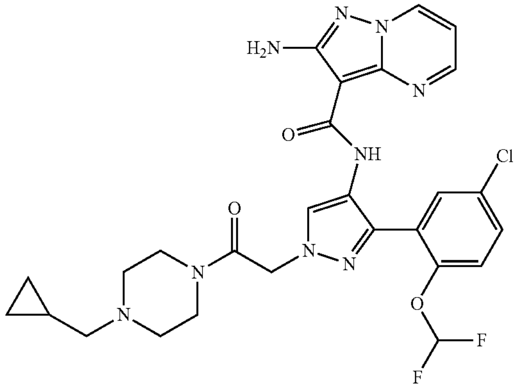 [SMILES: Nc1nn2cccnc2c1C(=O)Nc1cn(CC(=O)N2CCN(CC3CC3)CC2)nc1-c1cc(Cl)ccc1OC(F)F] | 2-amino-N-[3-[5-chloro-2-(difluoromethoxy)phenyl]-1-[2-[4-(cyclopropylmethyl) piperazin-1-yl]-2-oxo-ethyl]pyrazol-4-yl]pyrazolo[1,5-a]pyrimidine-3-carboxamide |
| 249 | 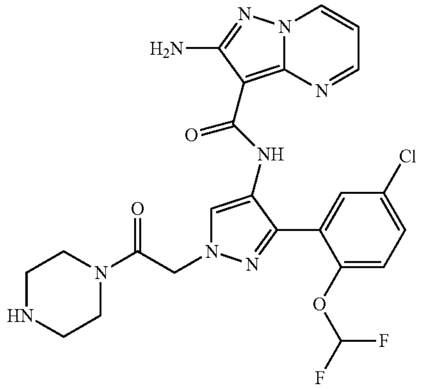 [SMILES: Nc1nn2cccnc2c1C(=O)Nc1cn(CC(=O)N2CCNCC2)nc1-c1cc(Cl)ccc1OC(F)F] | 2-amino-N-[3-[5-chloro-2-(difluoromethoxy)phenyl]-1-(2-oxo-2-piperazin-1-yl-ethyl)pyrazol-4-yl]pyrazolo[1,5-a]pyrimidine-3-carboxamide |
| 250 | 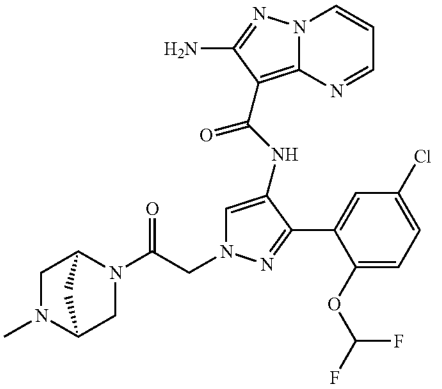 [SMILES: CN1C[C@@H]2C[C@H]1CN2C(=O)Cn1cc(NC(=O)c2c(N)nn3cccnc23)c(-c2cc(Cl)ccc2OC(F)F)n1] | 2-amino-N-[3-[5-chloro-2-(difluoromethoxy)phenyl]-1-[2-[(1S,4S)-5-methyl-2,5-diazabicyclo[2.2.1]heptan-2-yl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 251 | 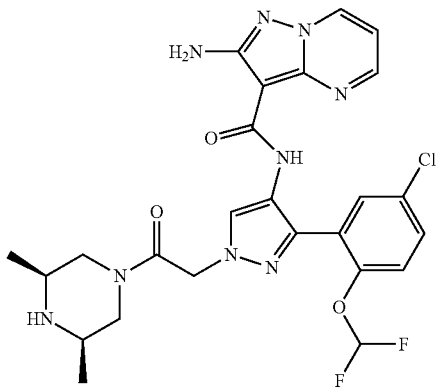 [SMILES: C[C@@H]1CN(C(=O)Cn2cc(NC(=O)c3c(N)nn4cccnc34)c(-c3cc(Cl)ccc3OC(F)F)n2)C[C@H](C)N1] | 2-amino-N-[3-[5-chloro-2-(difluoromethoxy)phenyl]-1-[2-[(3R,5S)-3,5-dimethylpiperazin-1-yl]-2-oxo-ethyl]pyrazol-4-yl]pyrazolo[1,5-a]pyrimidine-3-carboxamide |
| 252 | 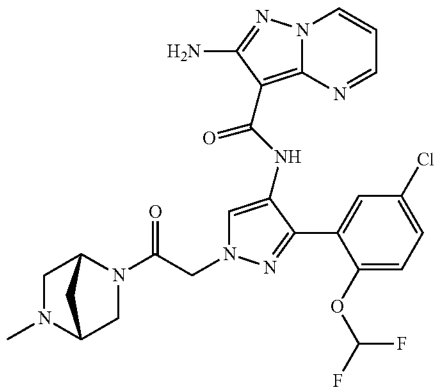 [SMILES: CN1C[C@H]2C[C@@H]1CN2C(=O)Cn1cc(NC(=O)c2c(N)nn3cccnc23)c(-c2cc(Cl)ccc2OC(F)F)n1] | 2-amino-N-[3-[5-chloro-2-(difluoromethoxy)phenyl]-1-[2-[(1R,4R)-5-methyl-2,5-diazabicyclo[2.2.1]heptan-2-yl]-2-oxo-ethyl]pyrazol-4-yl]pyrazolo[1,5-a]pyrimidine-3-carboxamide |
| 253 | 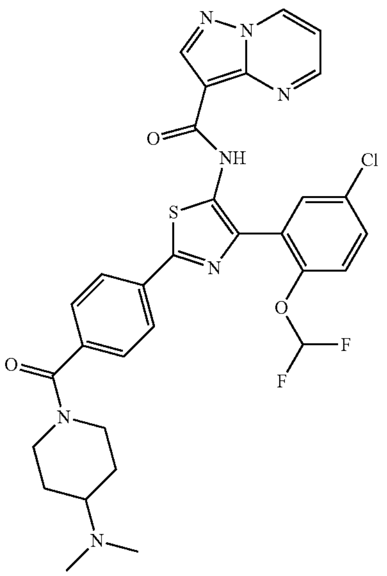 [SMILES: CN(C)C1CCN(C(=O)c2ccc(-c3nc(-c4cc(Cl)ccc4OC(F)F)c(NC(=O)c4cnn5cccnc45)s3)cc2)CC1] | N-[4-[5-chloro-2-(difluoromethoxy)phenyl]-2-[4-[4-(dimethylamino)piperidine-1-carbonyl]phenyl]thiazol-5-yl]pyrazolo[1,5-a]pyrimidine-3-carboxamide |

TABLE 1-continued

Exemplary Compounds of the Present Invention

| Ex. | Structure | Name |
|---|---|---|
| 254 | 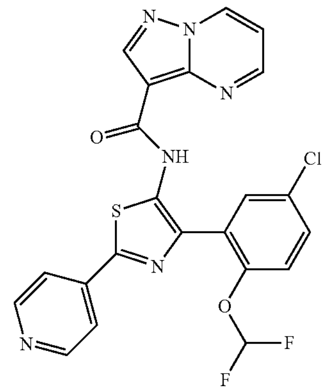 [SMILES: O=C(Nc1sc(-c2ccncc2)nc1-c1cc(Cl)ccc1OC(F)F)c1cnn2cccnc12] | N-[4-[5-chloro-2-(difluoromethoxy)phenyl]-2-(4-pyridyl)thiazol-5-yl]pyrazolo[1,5-a]pyrimidine-3-carboxamide |
| 255 | 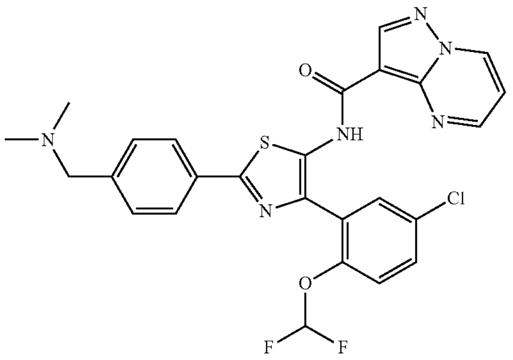 [SMILES: CN(C)Cc1ccc(-c2nc(-c3cc(Cl)ccc3OC(F)F)c(NC(=O)c3cnn4cccnc34)s2)cc1] | N-[4-[5-chloro-2-(difluoromethoxy)phenyl]-2-[4-[(dimethylamino)methyl]phenyl]thiazol-5-yl]pyrazolo[1,5-a]pyrimidine-3-carboxamide |
| 256 | 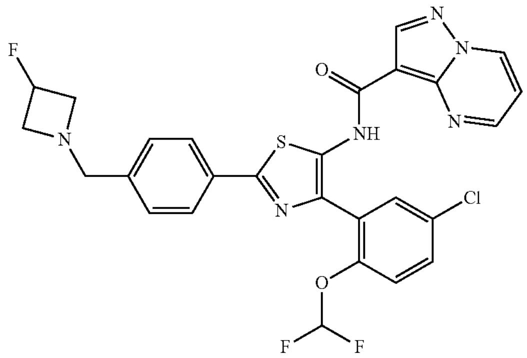 [SMILES: O=C(Nc1sc(-c2ccc(CN3CC(F)C3)cc2)nc1-c1cc(Cl)ccc1OC(F)F)c1cnn2cccnc12] | N-[4-[5-chloro-2-(difluoromethoxy)phenyl]-2-[4-[(3-fluoroazetidin-1-yl)methyl]phenyl]thiazol-5-yl]pyrazolo[1,5-a]pyrimidine-3-carboxamide |
| 257 | 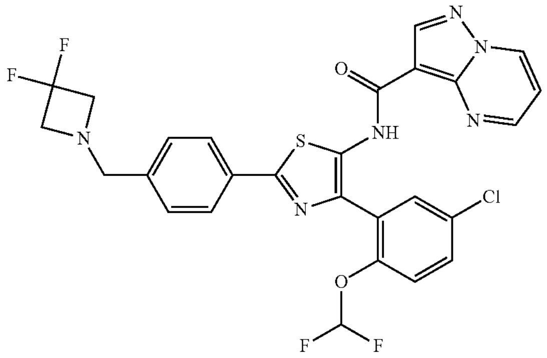 [SMILES: O=C(Nc1sc(-c2ccc(CN3CC(F)(F)C3)cc2)nc1-c1cc(Cl)ccc1OC(F)F)c1cnn2cccnc12] | N-[4-[5-chloro-2-(difluoromethoxy)phenyl]-2-[4-[(3,3-difluoroazetidin-1-yl)methyl]phenyl]thiazol-5-yl]pyrazolo[1,5-a]pyrimidine-3-carboxamide |

TABLE 1-continued

Exemplary Compounds of the Present Invention

| Ex. | Structure | Name |
| --- | --- | --- |
| 258 | 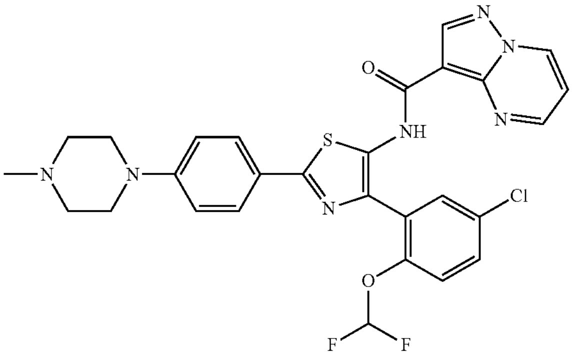 [SMILES: CN1CCN(c2ccc(-c3nc(-c4cc(Cl)ccc4OC(F)F)c(NC(=O)c4cnn5cccnc45)s3)cc2)CC1] | N-[4-[5-chloro-2-(difluoromethoxy)phenyl]-2-[4-(4-methylpiperazin-1-yl)phenyl]thiazol-5-yl]pyrazolo[1,5-a]pyrimidine-3-carboxamide |
| 259 | 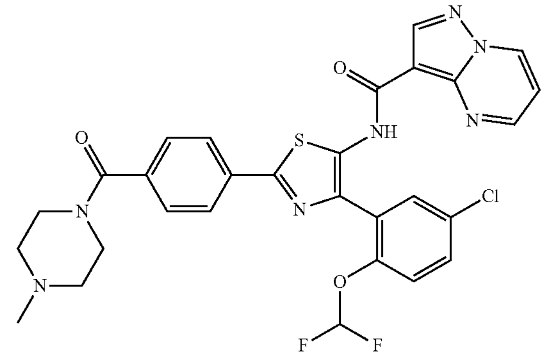 [SMILES: CN1CCN(C(=O)c2ccc(-c3nc(-c4cc(Cl)ccc4OC(F)F)c(NC(=O)c4cnn5cccnc45)s3)cc2)CC1] | N-[4-[5-chloro-2-(difluoromethoxy)phenyl]-2-[4-(4-methylpiperazine-1-carbonyl)phenyl]thiazol-5-yl]pyrazolo[1,5-a]pyrimidine-3-carboxamide |
| 260 | 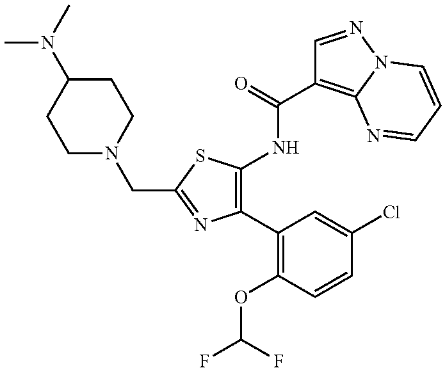 [SMILES: CN(C)C1CCN(Cc2nc(-c3cc(Cl)ccc3OC(F)F)c(NC(=O)c3cnn4cccnc34)s2)CC1] | N-[4-[5-chloro-2-(difluoromethoxy)phenyl]-2-[[4-(dimethylamino)-1-piperidyl]methyl]thiazol-5-yl]pyrazolo[1,5-a]pyrimidine-3-carboxamide |
| 261 | 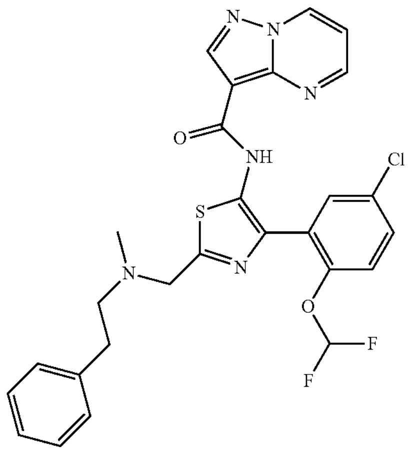 [SMILES: CN(CCc1ccccc1)Cc1nc(-c2cc(Cl)ccc2OC(F)F)c(NC(=O)c2cnn3cccnc23)s1] | N-[4-[5-chloro-2-(difluoromethoxy)phenyl]-2-[[methyl(2-phenylethyl)amino]methyl]thiazol-5-yl]pyrazolo[1,5-a]pyrimidine-3-carboxamide |

TABLE 1-continued

| Exemplary Compounds of the Present Invention | | |
|---|---|---|
| Ex. | Structure | Name |
| 262 | 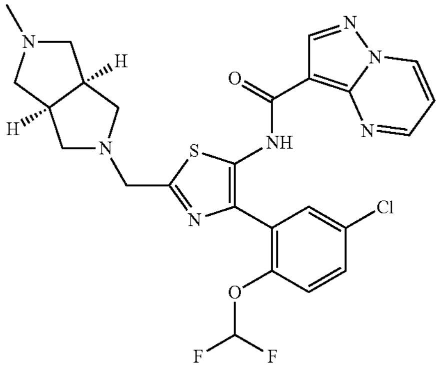 [SMILES: CN1C[C@@H]2CN(Cc3nc(-c4cc(Cl)ccc4OC(F)F)c(NC(=O)c4cnn5cccnc45)s3)C[C@@H]2C1] | N-[2-[[(3aR,6aS)-2-methyl-1,3,3a,4,6,6a-hexahydropyrrolo[3,4-c]pyrrol-5-yl]methyl]-4-[5-chloro-2-(difluoromethoxy)phenyl]thiazol-5-yl]pyrazolo[1,5-a]pyrimidine-3-carboxamide |
| 263 | 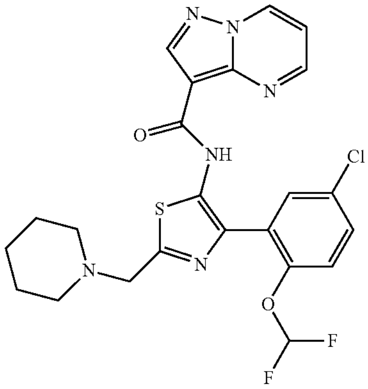 [SMILES: O=C(Nc1sc(CN2CCCCC2)nc1-c1cc(Cl)ccc1OC(F)F)c1cnn2cccnc12] | N-[4-[5-chloro-2-(difluoromethoxy)phenyl]-2-(1-piperidylmethyl)thiazol-5-yl]pyrazolo[1,5-a]pyrimidine-3-carboxamide |
| 264 | 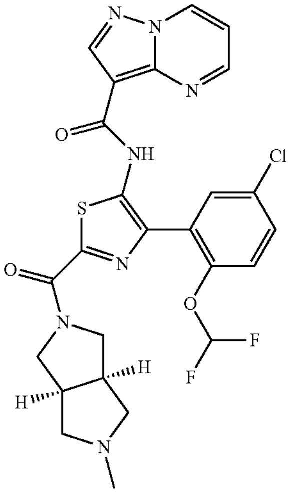 [SMILES: CN1C[C@@H]2CN(C(=O)c3nc(-c4cc(Cl)ccc4OC(F)F)c(NC(=O)c4cnn5cccnc45)s3)C[C@@H]2C1] | N-[2-[(3aR,6aS)-2-methyl-1,3,3a,4,6,6a-hexahydropyrrolo[3,4-c]pyrrole-5-carbonyl]-4-[5-chloro-2-(difluoromethoxy)phenyl]thiazol-5-yl]pyrazolo[1,5-a]pyrimidine-3-carboxamide |

TABLE 1-continued

| Exemplary Compounds of the Present Invention | | |
|---|---|---|
| Ex. | Structure | Name |
| 265 | 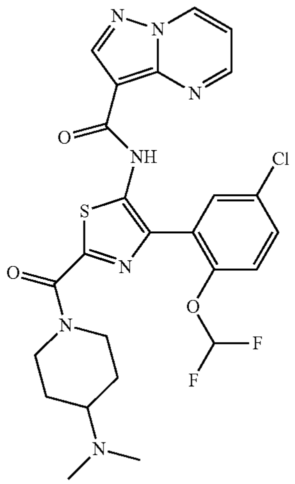 [SMILES: CN(C)C1CCN(C(=O)c2nc(-c3cc(Cl)ccc3OC(F)F)c(NC(=O)c3cnn4cccnc34)s2)CC1] | N-[4-[5-chloro-2-(difluoromethoxy)phenyl]-2-[4-(dimethylamino)piperidine-1-carbonyl]thiazol-5-yl]pyrazolo[1,5-a]pyrimidine-3-carboxamide |
| 266 | 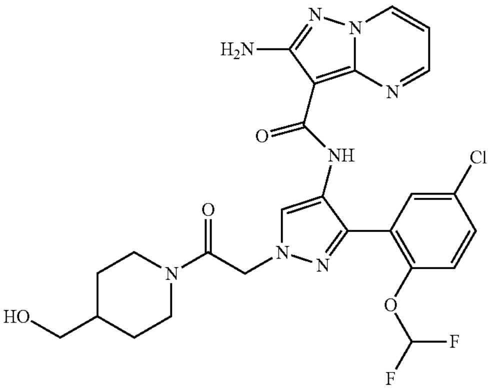 [SMILES: Nc1nn2cccnc2c1C(=O)Nc1cn(CC(=O)N2CCC(CO)CC2)nc1-c1cc(Cl)ccc1OC(F)F] | 2-amino-N-[3-[5-chloro-2-(difluoromethoxy)phenyl]-1-[2-[4-(hydroxymethyl)-1-piperidyl]-2-oxo-ethyl]pyrazol-4-yl]pyrazolo[1,5-a]pyrimidine-3-carboxamide |
| 267 | 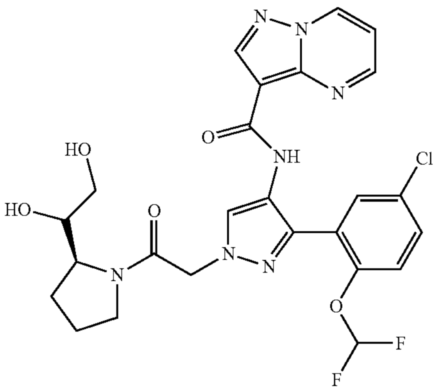 [SMILES: O=C(Nc1cn(CC(=O)N2CCC[C@H]2C(O)CO)nc1-c1cc(Cl)ccc1OC(F)F)c1cnn2cccnc12] | N-[3-[5-chloro-2-(difluoromethoxy)phenyl]-1-[2-[(2S)-2-(1,2-dihydroxyethyl)pyrrolidin-1-yl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 268 | 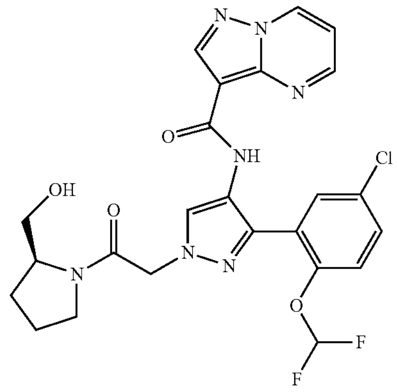 [SMILES: O=C(Nc1cn(CC(=O)N2CCC[C@H]2CO)nc1-c1cc(Cl)ccc1OC(F)F)c1cnn2cccnc12] | N-[3-[5-chloro-2-(difluoromethoxy)phenyl]-1-[2-[(2S)-2-(hydroxymethyl)pyrrolidin-1-yl]-2-oxo-ethyl]pyrazol-4-yl]pyrazolo[1,5-a]pyrimidine-3-carboxamide |
| 269 | 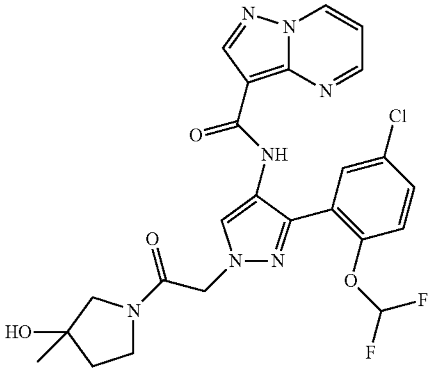 [SMILES: CC1(O)CCN(C(=O)Cn2cc(NC(=O)c3cnn4cccnc34)c(-c3cc(Cl)ccc3OC(F)F)n2)C1] | N-[3-[5-chloro-2-(difluoromethoxy)phenyl]-1-[2-(3-hydroxy-3-methyl-pyrrolidin-1-yl)-2-oxo-ethyl]pyrazol-4-yl]pyrazolo[1,5-a]pyrimidine-3-carboxamide |
| 270 | 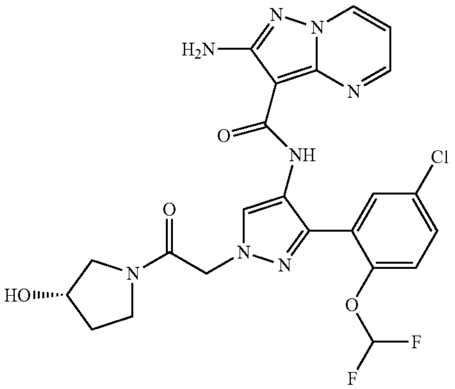 [SMILES: Nc1nn2cccnc2c1C(=O)Nc1cn(CC(=O)N2CC[C@H](O)C2)nc1-c1cc(Cl)ccc1OC(F)F] | 2-amino-N-[3-[5-chloro-2-(difluoromethoxy)phenyl]-1-[2-[(3S)-3-hydroxypyrrolidin-1-yl]-2-oxo-ethyl]pyrazol-4-yl]pyrazolo[1,5-a]pyrimidine-3-carboxamide |
| 271 | 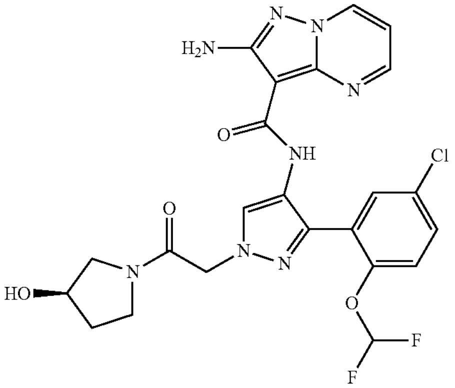 [SMILES: Nc1nn2cccnc2c1C(=O)Nc1cn(CC(=O)N2CC[C@@H](O)C2)nc1-c1cc(Cl)ccc1OC(F)F] | 2-amino-N-[3-[5-chloro-2-(difluoromethoxy)phenyl]-1-[2-[(3R)-3-hydroxypyrrolidin-1-yl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 272 | 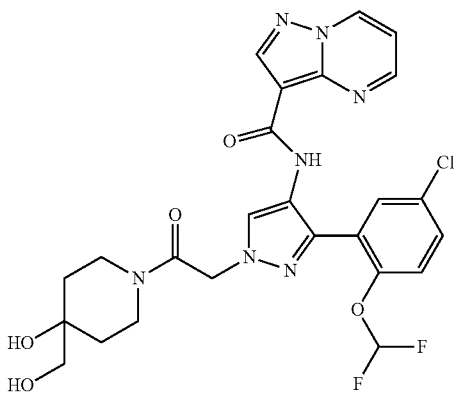 [SMILES: O=C(Nc1cn(CC(=O)N2CCC(O)(CO)CC2)nc1-c1cc(Cl)ccc1OC(F)F)c1cnn2cccnc12] | N-[3-[5-chloro-2-(difluoromethoxy)phenyl]-1-[2-[4-hydroxy-4-(hydroxymethyl)-1-piperidyl]-2-oxo-ethyl]pyrazol-4-yl]pyrazolo[1,5-a]pyrimidine-3-carboxamide |
| 273 | 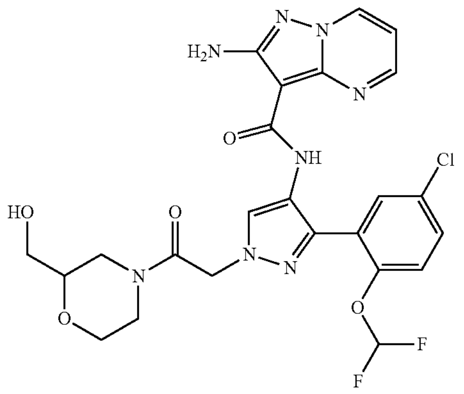 [SMILES: Nc1nn2cccnc2c1C(=O)Nc1cn(CC(=O)N2CCOC(CO)C2)nc1-c1cc(Cl)ccc1OC(F)F] | 2-amino-N-[3-[5-chloro-2-(difluoromethoxy)phenyl]-1-[2-[2-(hydroxymethyl)morpholin-4-yl]-2-oxo-ethyl]pyrazol-4-yl]pyrazolo[1,5-a]pyrimidine-3-carboxamide |
| 274 | 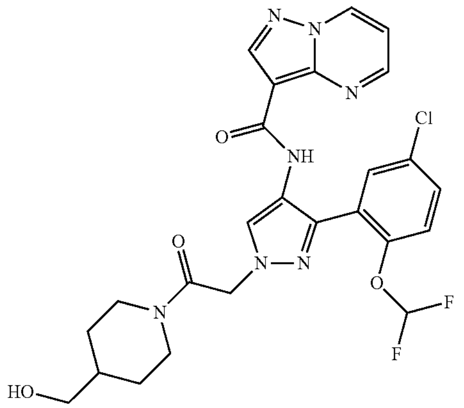 [SMILES: O=C(Nc1cn(CC(=O)N2CCC(CO)CC2)nc1-c1cc(Cl)ccc1OC(F)F)c1cnn2cccnc12] | N-[3-[5-chloro-2-(difluoromethoxy)phenyl]-1-[2-[4-(hydroxymethyl)-1-piperidyl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 275 | 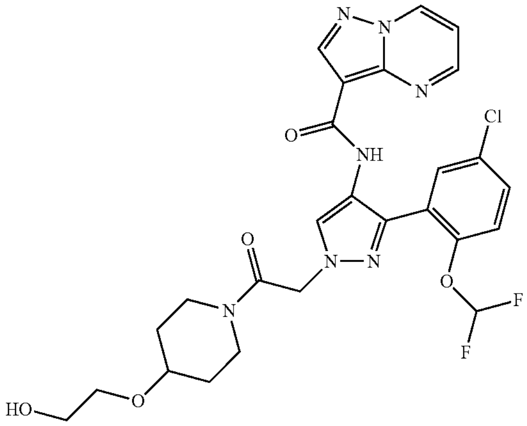 [SMILES: O=C(Nc1cn(CC(=O)N2CCC(OCCO)CC2)nc1-c1cc(Cl)ccc1OC(F)F)c1cnn2cccnc12] | N-[3-[5-chloro-2-(difluoromethoxy)phenyl]-1-[2-[4-(2-hydroxyethoxy)-1-piperidyl]-2-oxo-ethyl]pyrazol-4-yl]pyrazolo[1,5-a]pyrimidine-3-carboxamide |
| 276 | 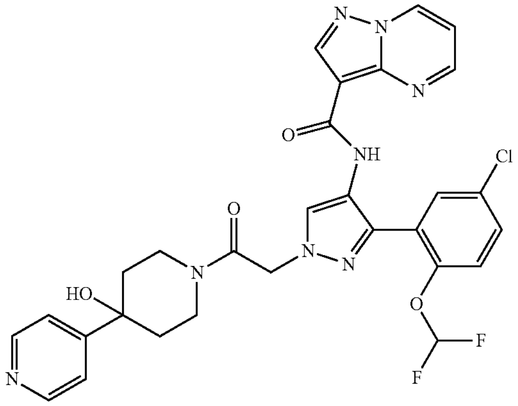 [SMILES: O=C(Nc1cn(CC(=O)N2CCC(O)(c3ccncc3)CC2)nc1-c1cc(Cl)ccc1OC(F)F)c1cnn2cccnc12] | N-[3-[5-chloro-2-(difluoromethoxy)phenyl]-1-[2-[4-hydroxy-4-(4-pyridyl)-1-piperidyl]-2-oxo-ethyl]pyrazol-4-yl]pyrazolo[1,5-a]pyrimidine-3-carboxamide |
| 277 | 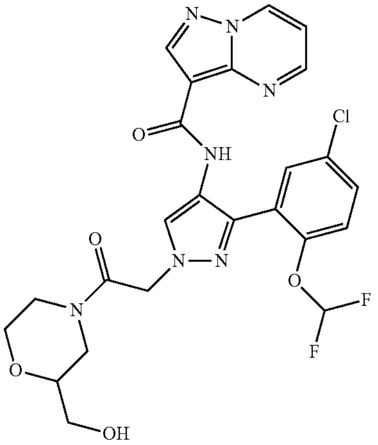 [SMILES: O=C(Nc1cn(CC(=O)N2CCOC(CO)C2)nc1-c1cc(Cl)ccc1OC(F)F)c1cnn2cccnc12] | N-[3-[5-chloro-2-(difluoromethoxy)phenyl]-1-[2-[2-(hydroxymethyl)morpholin-4-yl]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 278 | 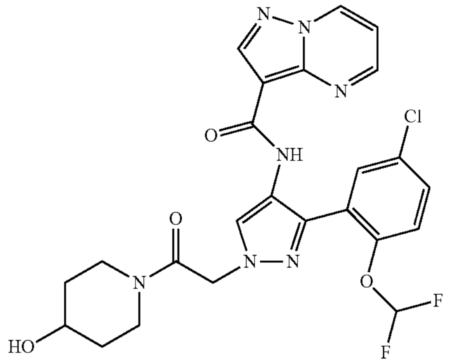 [SMILES: O=C(Nc1cn(CC(=O)N2CCC(O)CC2)nc1-c1cc(Cl)ccc1OC(F)F)c1cnn2cccnc12] | N-[3-[5-chloro-2-(difluoromethoxy)phenyl]-1-[2-(4-hydroxy-1-piperidyl)-2-oxo-ethyl]pyrazol-4-yl]pyrazolo[1,5-a]pyrimidine-3-carboxamide |
| 279 | 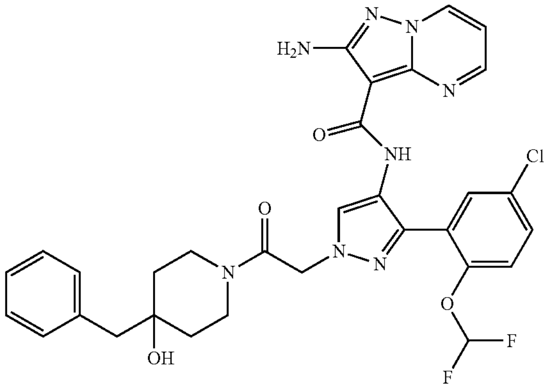 [SMILES: Nc1nn2cccnc2c1C(=O)Nc1cn(CC(=O)N2CCC(O)(Cc3ccccc3)CC2)nc1-c1cc(Cl)ccc1OC(F)F] | 2-amino-N-[1-[2-(4-benzyl-4-hydroxy-1-piperidyl)-2-oxo-ethyl]-3-[5-chloro-2-(difluoromethoxy)phenyl]pyrazol-4-yl]pyrazolo[1,5-a]pyrimidine-3-carboxamide |
| 280 | 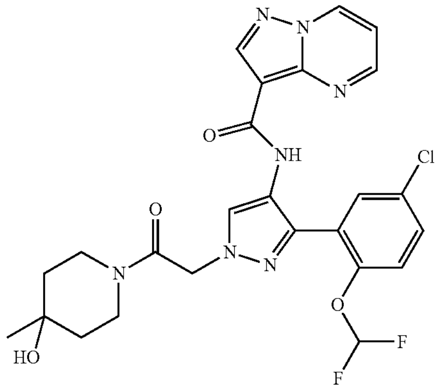 [SMILES: CC1(O)CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-(4-hydroxy-4-methyl-1-piperidyl)-2-oxo-ethyl]pyrazol-4-yl]pyrazolo[1,5-a]pyrimidine-3-carboxamide |
| 281 | 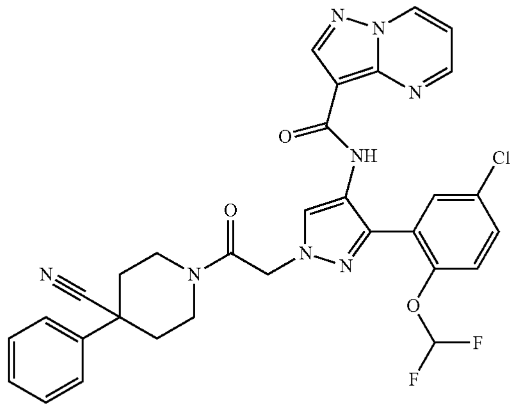 [SMILES: N#CC1(c2ccccc2)CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-(4-cyano-4-phenyl-1-piperidyl)-2-oxo-ethyl]pyrazol-4-yl]pyrazolo[1,5-a]pyrimidine-3-carboxamide |

TABLE 1-continued

| Ex. | Structure | Name |
| --- | --- | --- |
| Exemplary Compounds of the Present Invention | | |
| 282 | 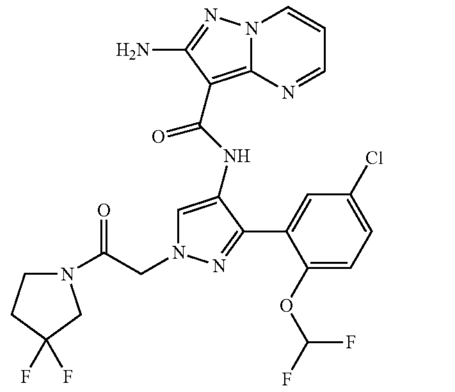 [SMILES: Nc1nn2cccnc2c1C(=O)Nc1cn(CC(=O)N2CCC(F)(F)C2)nc1-c1cc(Cl)ccc1OC(F)F] | 2-amino-N-[3-[5-chloro-2-(difluoromethoxy)phenyl]-1-[2-(3,3-difluoropyrrolidin-1-yl)-2-oxo-ethyl]pyrazol-4-yl]pyrazolo[1,5-a]pyrimidine-3-carboxamide |
| 283 | 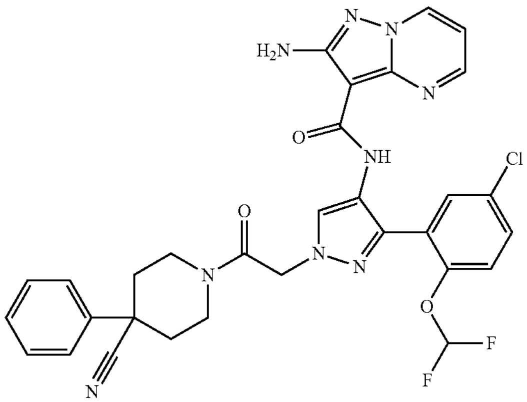 [SMILES: N#CC1(c2ccccc2)CCN(C(=O)Cn2cc(NC(=O)c3c(N)nn4cccnc34)c(-c3cc(Cl)ccc3OC(F)F)n2)CC1] | 2-amino-N-[3-[5-chloro-2-(difluoromethoxy)phenyl]-1-[2-(4-cyano-4-phenyl-1-piperidyl)-2-oxo-ethyl]pyrazol-4-yl]pyrazolo[1,5-a]pyrimidine-3-carboxamide |
| 284 | 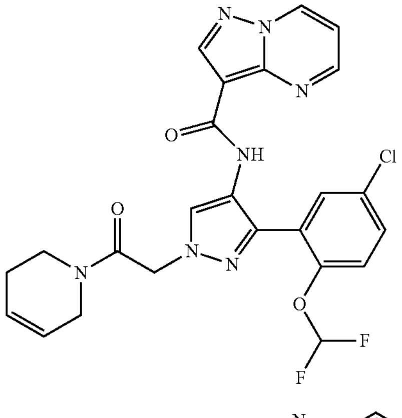 | N-[3-[5-chloro-2-(difluoromethoxy)phenyl]-1-[2-(3,6-dihydro-2H-pyridin-1-yl)-2-oxo-ethyl]pyrazol-4-yl]pyrazolo[1,5-a]pyrimidine-3-carboxamide |
| 285 | 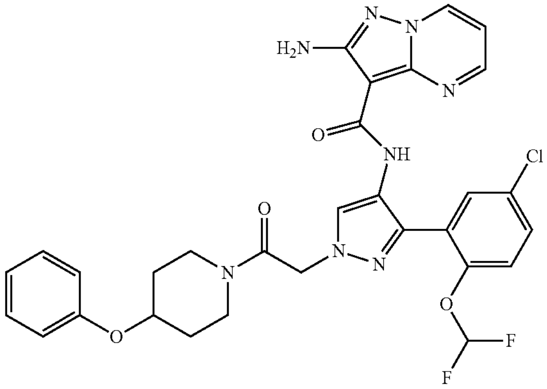 [SMILES: Nc1nn2cccnc2c1C(=O)Nc1cn(CC(=O)N2CCC(Oc3ccccc3)CC2)nc1-c1cc(Cl)ccc1OC(F)F] | 2-amino-N-[3-[5-chloro-2-(difluoromethoxy)phenyl]-1-[2-oxo-2-(4-phenoxy-1-piperidyl)ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 286 | 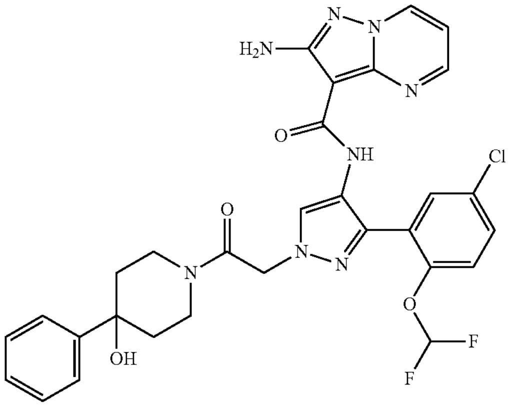 [SMILES: Nc1nn2cccnc2c1C(=O)Nc1cn(CC(=O)N2CCC(O)(c3ccccc3)CC2)nc1-c1cc(Cl)ccc1OC(F)F] | 2-amino-N-[3-[5-chloro-2-(difluoromethoxy)phenyl]-1-[2-(4-hydroxy-4-phenyl-1-piperidyl)-2-oxo-ethyl]pyrazol-4-yl]pyrazolo[1,5-a]pyrimidine-3-carboxamide |
| 287 | 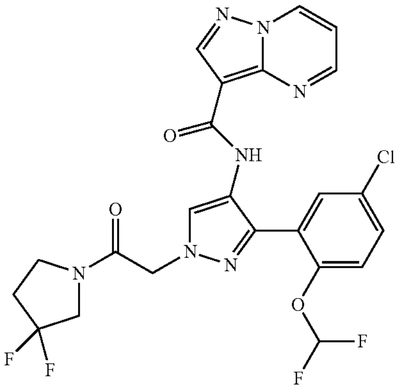 [SMILES: O=C(Nc1cn(CC(=O)N2CCC(F)(F)C2)nc1-c1cc(Cl)ccc1OC(F)F)c1cnn2cccnc12] | N-[3-[5-chloro-2-(difluoromethoxy)phenyl]-1-[2-(3,3-difluoropyrrolidin-1-yl)-2-oxo-ethyl]pyrazol-4-yl]pyrazolo[1,5-a]pyrimidine-3-carboxamide |
| 288 | 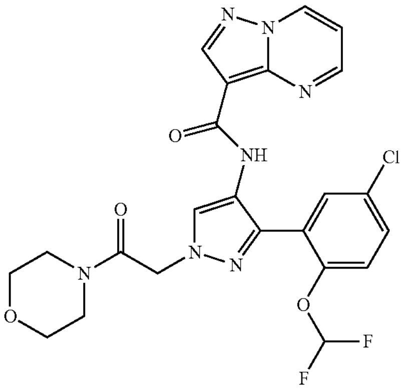 [SMILES: O=C(Nc1cn(CC(=O)N2CCOCC2)nc1-c1cc(Cl)ccc1OC(F)F)c1cnn2cccnc12] | N-[3-[5-chloro-2-(difluoromethoxy)phenyl]-1-(2-morpholino-2-oxo-ethyl)pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 289 | 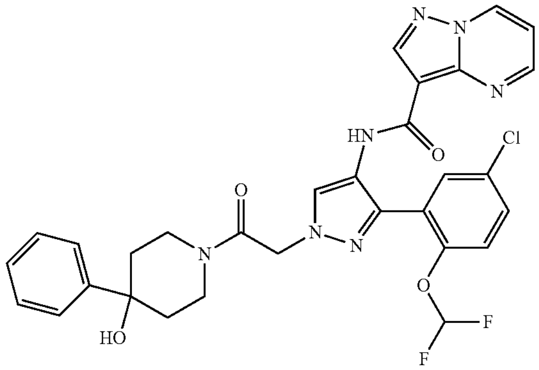 [SMILES: O=C(Nc1cn(CC(=O)N2CCC(O)(c3ccccc3)CC2)nc1-c1cc(Cl)ccc1OC(F)F)c1cnn2cccnc12] | N-[3-[5-chloro-2-(difluoromethoxy)phenyl]-1-[2-(4-hydroxy-4-phenyl-1-piperidyl)-2-oxo-ethyl]pyrazol-4-yl]pyrazolo[1,5-a]pyrimidine-3-carboxamide |
| 290 | 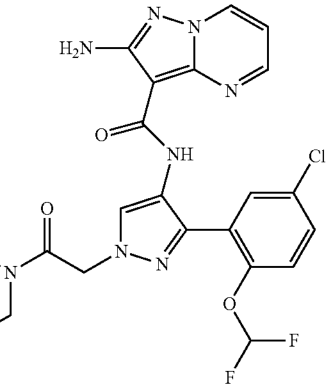 | 2-amino-N-[3-[5-chloro-2-(difluoromethoxy)phenyl]-1-(2-morpholino-2-oxo-ethyl)pyrazol-4-yl]pyrazolo[1,5-a]pyrimidine-3-carboxamide |
| 291 | 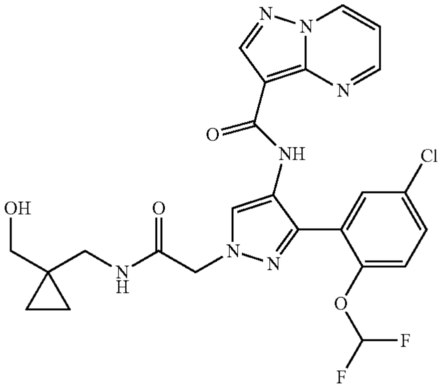 [SMILES: O=C(Cn1cc(NC(=O)c2cnn3cccnc23)c(-c2cc(Cl)ccc2OC(F)F)n1)NCC1(CO)CC1] | N-[3-[5-chloro-2-(difluoromethoxy)phenyl]-1-[2-[[1-(hydroxymethyl) cyclopropyl] methylamino]-2-oxo-ethyl]pyrazol-4-yl]pyrazolo[1,5-a]pyrimidine-3-carboxamide |
| 292 | 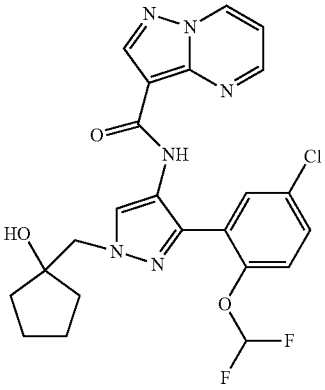 [SMILES: O=C(Nc1cn(CC2(O)CCCC2)nc1-c1cc(Cl)ccc1OC(F)F)c1cnn2cccnc12] | N-[3-[5-chloro-2-(difluoromethoxy)phenyl]-1-[(1-hydroxycyclopentyl) methyl]pyrazol-4-yl]pyrazolo[1,5-a]pyrimidine-3-carboxamide |

TABLE 1-continued

| Ex. | Structure | Name |
|---|---|---|
| 293 | 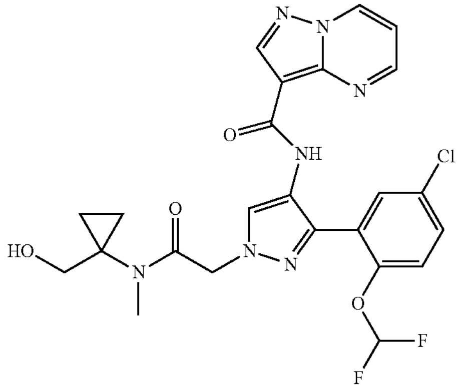 [SMILES: CN(C(=O)Cn1cc(NC(=O)c2cnn3cccnc23)c(-c2cc(Cl)ccc2OC(F)F)n1)C1(CO)CC1] | N-[3-[5-chloro-2-(difluoromethoxy)phenyl]-1-[2-[[1-(hydroxymethyl)cyclopropyl]-methyl-amino]-2-oxo-ethyl]pyrazol-4-yl]pyrazolo[1,5-a]pyrimidine-3-carboxamide |
| 294 | 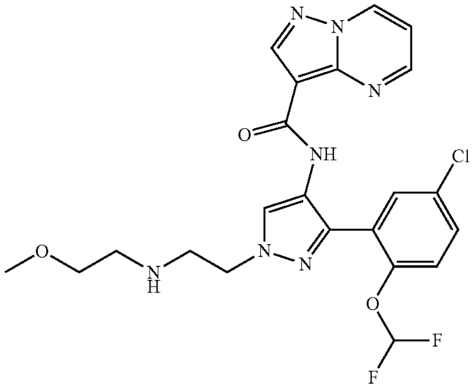 [SMILES: COCCNCCn1cc(NC(=O)c2cnn3cccnc23)c(-c2cc(Cl)ccc2OC(F)F)n1] | N-[3-[5-chloro-2-(difluoromethoxy)phenyl]-1-[2-(2-methoxyethylamino)ethyl]pyrazol-4-yl]pyrazolo[1,5-a]pyrimidine-3-carboxamide |
| 295 | 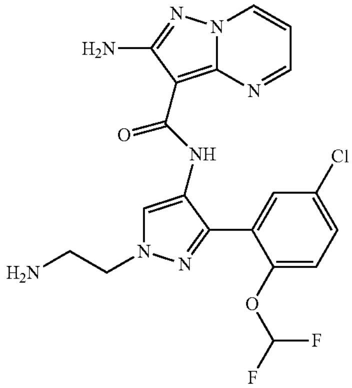 [SMILES: NCCn1cc(NC(=O)c2c(N)nn3cccnc23)c(-c2cc(Cl)ccc2OC(F)F)n1] | 2-amino-N-[1-(2-aminoethyl)-3-[5-chloro-2-(difluoromethoxy)phenyl]pyrazol-4-yl]pyrazolo[1,5-a]pyrimidine-3-carboxamide |
| 296 | 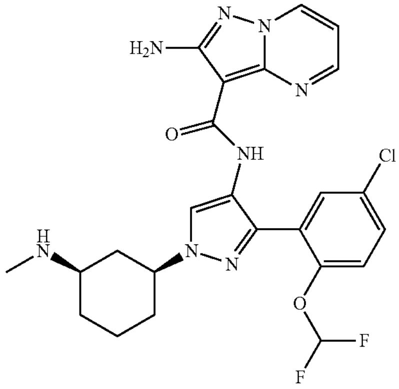 [SMILES: CN[C@@H]1CCC[C@H](n2cc(NC(=O)c3c(N)nn4cccnc34)c(-c3cc(Cl)ccc3OC(F)F)n2)C1] | 2-amino-N-[3-[5-chloro-2-(difluoromethoxy)phenyl]-1-[(1S,3R)-3-(methylamino)cyclohexyl]pyrazol-4-yl]pyrazolo[1,5-a]pyrimidine-3-carboxamide |

Exemplary Compounds of the Present Invention

TABLE 1-continued

| Exemplary Compounds of the Present Invention | | |
|---|---|---|
| Ex. | Structure | Name |
| 297 | 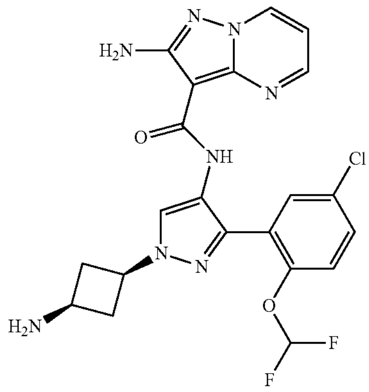 [SMILES: Nc1nn2cccnc2c1C(=O)Nc1cn([C@H]2C[C@@H](N)C2)nc1-c1cc(Cl)ccc1OC(F)F] | 2-amino-N-[1-(3-aminocyclobutyl)-3-[5-chloro-2-(difluoromethoxy)phenyl]pyrazol-4-yl]pyrazolo[1,5-a]pyrimidine-3-carboxamide |
| 298 | 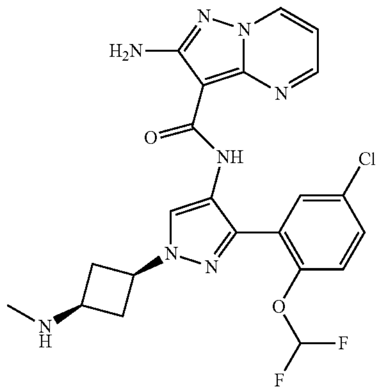 [SMILES: CN[C@H]1C[C@@H](n2cc(NC(=O)c3c(N)nn4cccnc34)c(-c3cc(Cl)ccc3OC(F)F)n2)C1] | 2-amino-N-[3-[5-chloro-2-(difluoromethoxy)phenyl]-1-[3-(methylamino)cyclobutyl]pyrazol-4-yl]pyrazolo[1,5-a]pyrimidine-3-carboxamide |
| 299 | 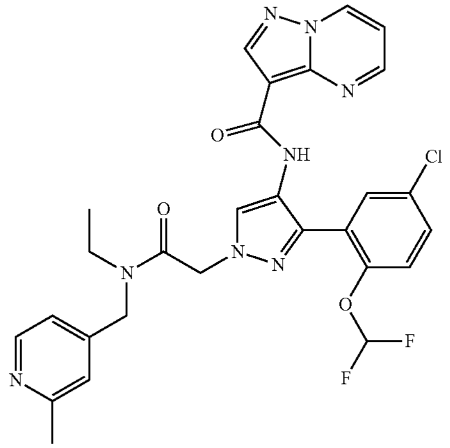 [SMILES: CCN(Cc1ccnc(C)c1)C(=O)Cn1cc(NC(=O)c2cnn3cccnc23)c(-c2cc(Cl)ccc2OC(F)F)n1] | N-[3-[5-chloro-2-(difluoromethoxy)phenyl]-1-[2-[ethyl-[(2-methyl-4-pyridyl)methyl]amino]-2-oxo-ethyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 300 | 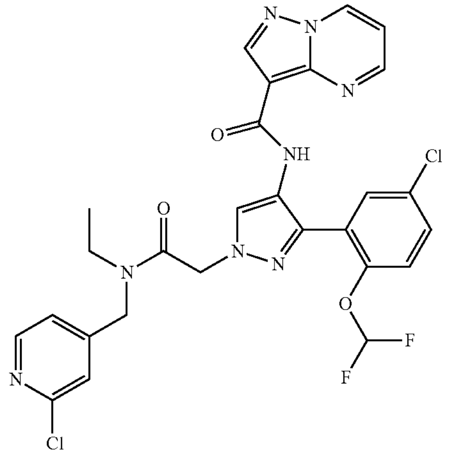 [SMILES: CCN(Cc1ccnc(Cl)c1)C(=O)Cn1cc(NC(=O)c2cnn3cccnc23)c(-c2cc(Cl)ccc2OC(F)F)n1] | N-[3-[5-chloro-2-(difluoromethoxy)phenyl]-1-[2-[(2-chloro-4-pyridyl)methyl-ethyl-amino]-2-oxo-ethyl]pyrazol-4-yl]pyrazolo[1,5-a]pyrimidine-3-carboxamide |
| 301 | 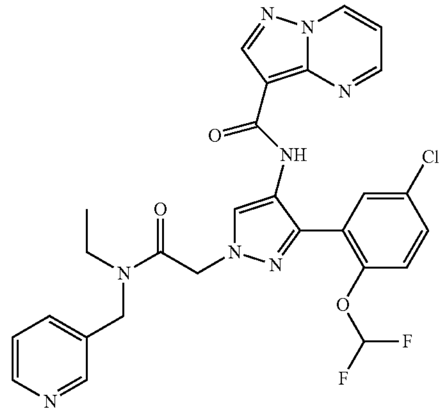 [SMILES: CCN(Cc1cccnc1)C(=O)Cn1cc(NC(=O)c2cnn3cccnc23)c(-c2cc(Cl)ccc2OC(F)F)n1] | N-[3-[5-chloro-2-(difluoromethoxy)phenyl]-1-[2-[ethyl(3-pyridylmethyl)amino]-2-oxo-ethyl]pyrazol-4-yl]pyrazolo[1,5-a]pyrimidine-3-carboxamide |
| 302 | 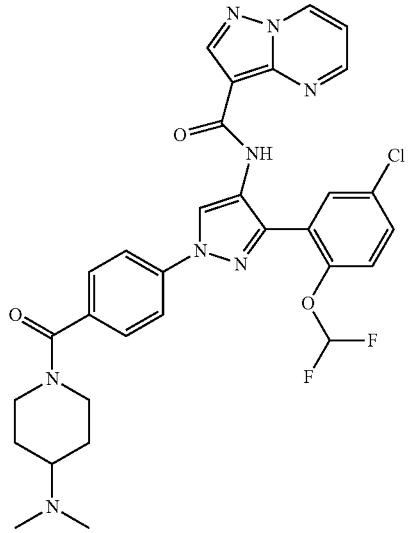 [SMILES: CN(C)C1CCN(C(=O)c2ccc(-n3cc(NC(=O)c4cnn5cccnc45)c(-c4cc(Cl)ccc4OC(F)F)n3)cc2)CC1] | N-[3-[5-chloro-2-(difluoromethoxy)phenyl]-1-[4-[4-(dimethylamino)piperidine-1-carbonyl]phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 303 | 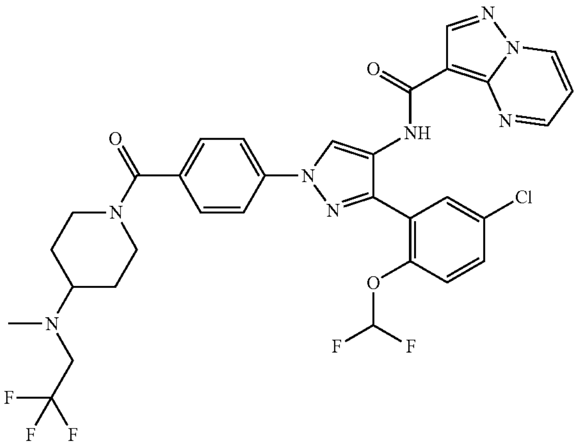 [SMILES: CN(CC(F)(F)F)C1CCN(C(=O)c2ccc(-n3cc(NC(=O)c4cnn5cccnc45)c(-c4cc(Cl)ccc4OC(F)F)n3)cc2)CC1] | N-[3-[5-chloro-2-(difluoromethoxy)phenyl]-1-[4-[4-[methyl(2,2,2-trifluoroethyl)amino]piperidine-1-carbonyl]phenyl]pyrazol-4-yl]pyrazolo[1,5-a]pyrimidine-3-carboxamide |
| 304 | 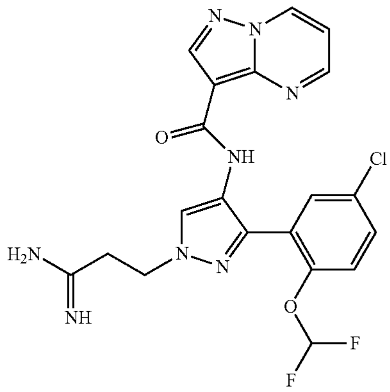 [SMILES: N=C(N)CCn1cc(NC(=O)c2cnn3cccnc23)c(-c2cc(Cl)ccc2OC(F)F)n1] | N-[1-(3-amino-3-imino-propyl)-3-[5-chloro-2-(difluoromethoxy)phenyl]pyrazol-4-yl]pyrazolo[1,5-a]pyrimidine-3-carboxamide |
| 305 | 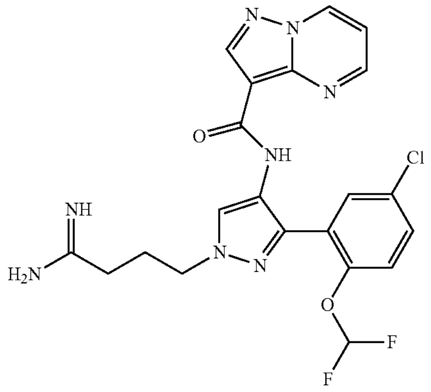 [SMILES: N=C(N)CCCn1cc(NC(=O)c2cnn3cccnc23)c(-c2cc(Cl)ccc2OC(F)F)n1] | N-[1-(4-amino-4-imino-butyl)-3-[5-chloro-2-(difluoromethoxy)phenyl]pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 306 | 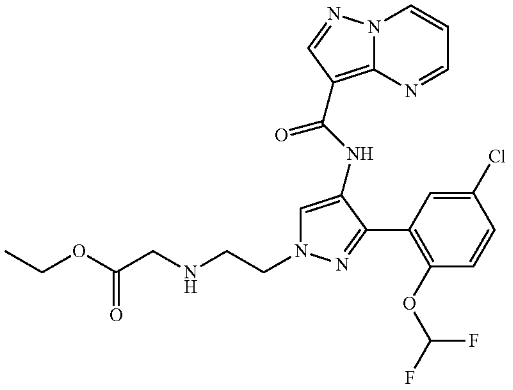 [SMILES: CCOC(=O)CNCCn1cc(NC(=O)c2cnn3cccnc23)c(-c2cc(Cl)ccc2OC(F)F)n1] | ethyl 2-[2-[3-[5-chloro-2-(difluoromethoxy)phenyl]-4-(pyrazolo[1,5-a]pyrimidine-3-carbonylamino)pyrazol-1-yl]ethylamino]acetate |
| 307 | 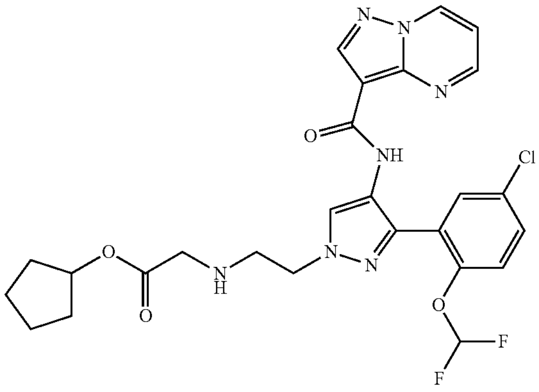 [SMILES: O=C(CNCCn1cc(NC(=O)c2cnn3cccnc23)c(-c2cc(Cl)ccc2OC(F)F)n1)OC1CCCC1] | cyclopentyl 2-[2-[3-[5-chloro-2-(difluoromethoxy)phenyl]-4-(pyrazolo[1,5-a]pyrimidine-3-carbonylamino)pyrazol-1-yl]ethylamino]acetate |
| 308 | 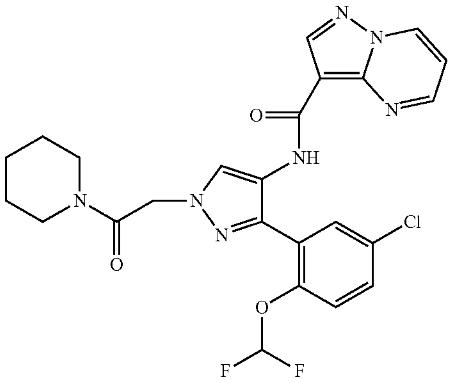 [SMILES: O=C(Nc1cn(CC(=O)N2CCCCC2)nc1-c1cc(Cl)ccc1OC(F)F)c1cnn2cccnc12] | N-[3-[5-chloro-2-(difluoromethoxy)phenyl]-1-[2-oxo-2-(1-piperidyl)ethyl]pyrazol-4-yl]pyrazolo[1,5-a]pyrimidine-3-carboxamide |
| 309 | 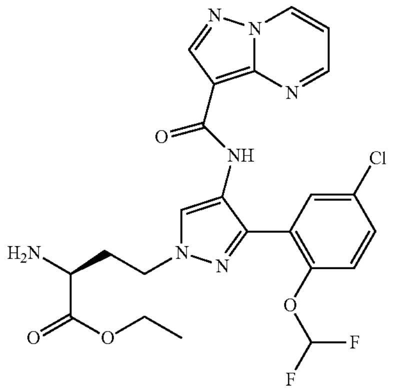 [SMILES: CCOC(=O)[C@@H](N)CCn1cc(NC(=O)c2cnn3cccnc23)c(-c2cc(Cl)ccc2OC(F)F)n1] | ethyl (2S)-2-amino-4-[3-[5-chloro-2-(difluoromethoxy)phenyl]-4-(pyrazolo[1,5-a]pyrimidine-3-carbonylamino)pyrazol-1-yl]butanoate |

TABLE 1-continued

Exemplary Compounds of the Present Invention

| Ex. | Structure | Name |
| --- | --- | --- |
| 310 | 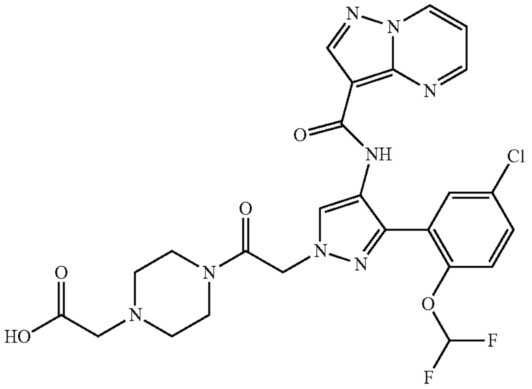 [SMILES: O=C(O)CN1CCN(C(=O)Cn2cc(NC(=O)c3cnn4cccnc34)c(-c3cc(Cl)ccc3OC(F)F)n2)CC1] | 2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]acetic acid |
| 311 | 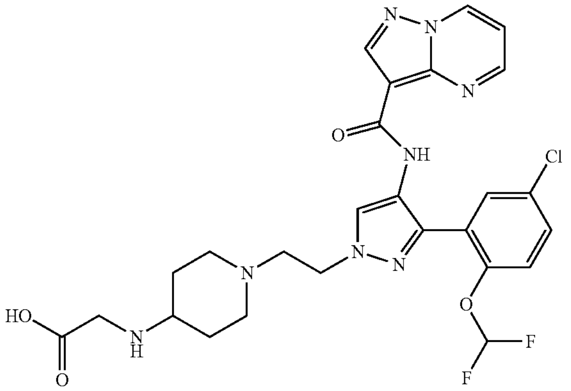 [SMILES: O=C(O)CNC1CCN(CCn2cc(NC(=O)c3cnn4cccnc34)c(-c3cc(Cl)ccc3OC(F)F)n2)CC1] | 2-[[1-(2-[3-[5-chloro-2-(difluoromethoxy)phenyl]-4-[pyrazolo[1,5-a]pyrimidine-3-amido]-1H-pyrazol-1-yl]ethyl)piperidin-4-yl]amino]acetic acid |
| 312 | 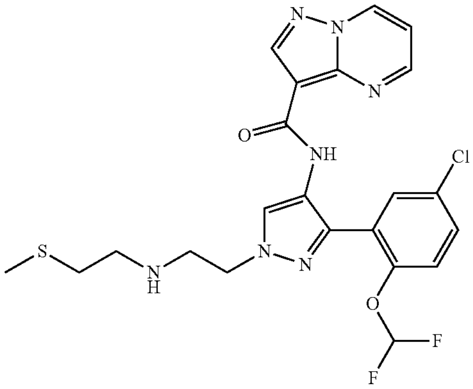 [SMILES: CSCCNCCn1cc(NC(=O)c2cnn3cccnc23)c(-c2cc(Cl)ccc2OC(F)F)n1] | N-[3-[5-chloro-2-(difluoromethoxy)phenyl]-1-(2-[[2-(methylsulfanyl)ethyl]amino]ethyl)-1H-pyrazol-4-yl]pyrazolo[1,5-a]pyrimidine-3-carboxamide |
| 313 | 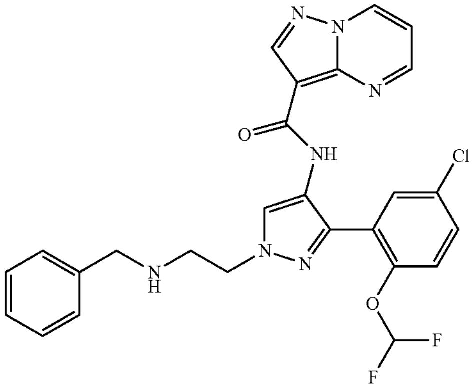 [SMILES: O=C(Nc1cn(CCNCc2ccccc2)nc1-c1cc(Cl)ccc1OC(F)F)c1cnn2cccnc12] | N-[1-[2-(benzylamino)ethyl]-3-[5-chloro-2-(difluoromethoxy)phenyl]-1H-pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 314 | 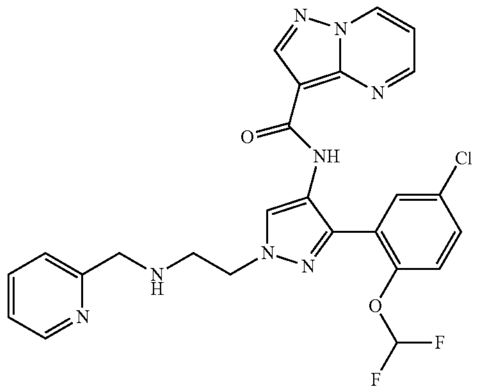 [SMILES: O=C(Nc1cn(CCNCc2ccccn2)nc1-c1cc(Cl)ccc1OC(F)F)c1cnn2cccnc12] | N-[3-[5-chloro-2-(difluoromethoxy)phenyl]-1-[2-[(pyridin-2-ylmethyl)amino]ethyl]-1H-pyrazol-4-yl]pyrazolo[1,5-a]pyrimidine-3-carboxamide |
| 315 | 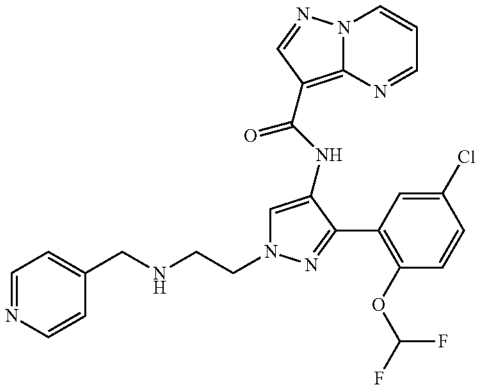 [SMILES: O=C(Nc1cn(CCNCc2ccncc2)nc1-c1cc(Cl)ccc1OC(F)F)c1cnn2cccnc12] | N-[3-[5-chloro-2-(difluoromethoxy)phenyl]-1-[2-[(pyridin-4-ylmethyl)amino]ethyl]-1H-pyrazol-4-yl]pyrazolo[1,5-a]pyrimidine-3-carboxamide |
| 316 | 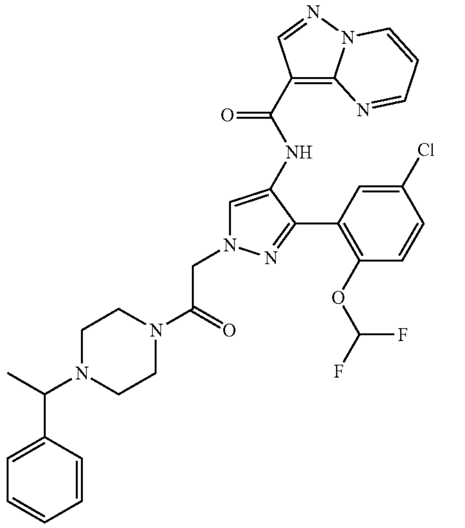 [SMILES: CC(c1ccccc1)N1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-oxo-2-[4-(1-phenylethyl)piperazin-1-yl]ethyl]-1H-pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 317 | 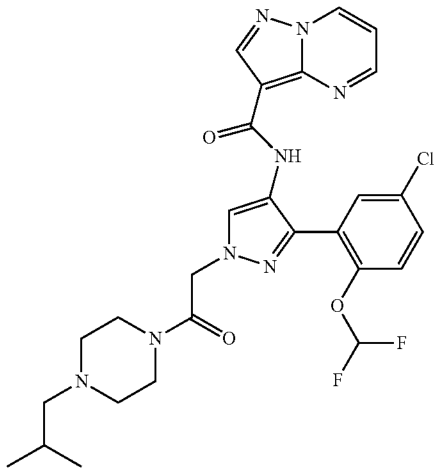 [SMILES: CC(C)CN1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-[4-(2-methylpropyl)piperazin-1-yl]-2-oxoethyl]-1H-pyrazol-4-yl]pyrazolo[1,5-a]pyrimidine-3-carboxamide |
| 318 | 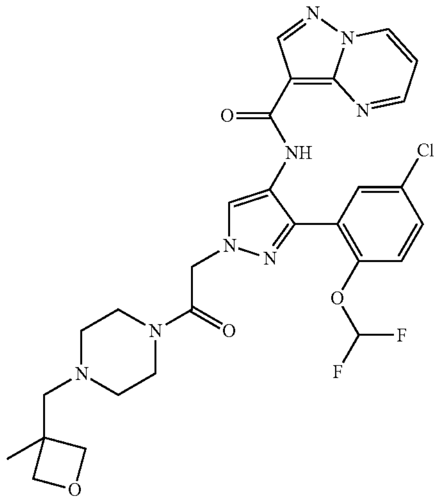 [SMILES: CC1(CN2CCN(C(=O)Cn3cc(NC(=O)c4cnn5cccnc45)c(-c4cc(Cl)ccc4OC(F)F)n3)CC2)COC1] | N-[3-[5-chloro-2-(difluoromethoxy)phenyl]-1-(2-[4-[(3-methyloxetan-3-yl)methyl]piperazin-1-yl]-2-oxoethyl)-1H-pyrazol-4-yl]pyrazolo[1,5-a]pyrimidine-3-carboxamide |
| 319 | 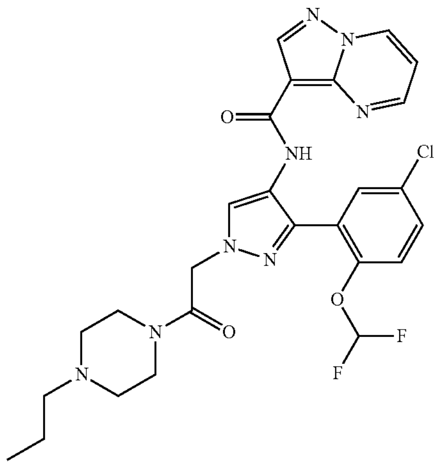 [SMILES: CCCN1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-oxo-2-(4-propylpiperazin-1-yl)ethyl]-1H-pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 320 | 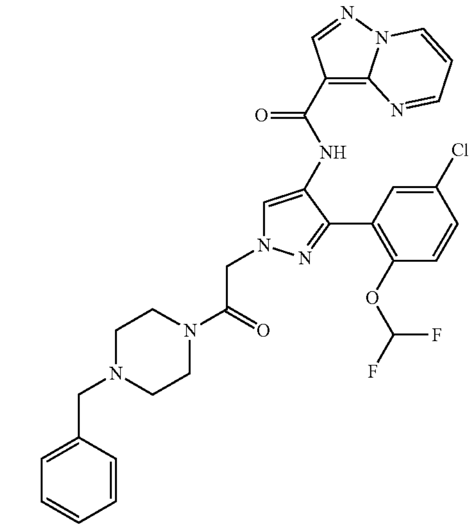 [SMILES: O=C(Nc1cn(CC(=O)N2CCN(Cc3ccccc3)CC2)nc1-c1cc(Cl)ccc1OC(F)F)c1cnn2cccnc12] | N-[1-[2-(4-benzylpiperazin-1-yl)-2-oxoethyl]-3-[5-chloro-2-(difluoromethoxy)phenyl]-1H-pyrazol-4-yl]pyrazolo[1,5-a]pyrimidine-3-carboxamide |
| 321 | 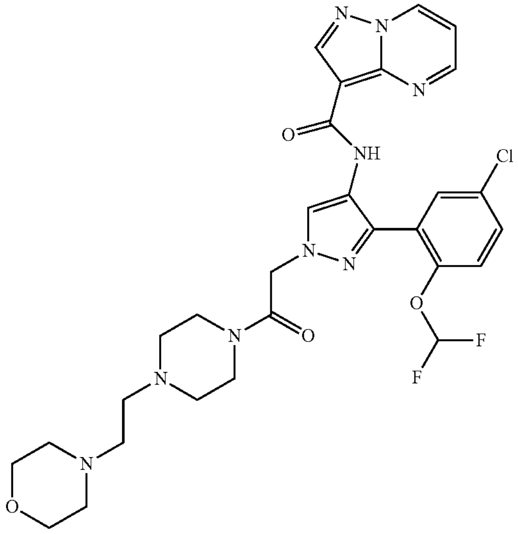 [SMILES: O=C(Nc1cn(CC(=O)N2CCN(CCN3CCOCC3)CC2)nc1-c1cc(Cl)ccc1OC(F)F)c1cnn2cccnc12] | N-[3-[5-chloro-2-(difluoromethoxy)phenyl]-1-(2-[4-[2-(morpholin-4-yl)ethyl]piperazin-1-yl]-2-oxoethyl)-1H-pyrazol-4-yl]pyrazolo[1,5-a]pyrimidine-3-carboxamide |
| 322 | 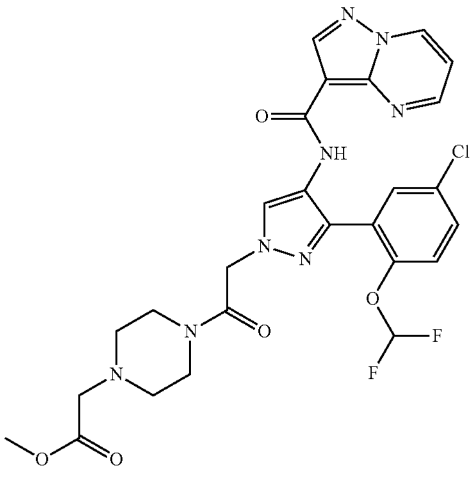 [SMILES: COC(=O)CN1CCN(C(=O)Cn2cc(NC(=O)c3cnn4cccnc34)c(-c3cc(Cl)ccc3OC(F)F)n2)CC1] | methyl 2-[4-(2-[3-[5-chloro-2-(difluoromethoxy) phenyl]-4-[pyrazolo[1,5-a]pyrimidine-3-amido]-1H-pyrazol-1-yl]acetyl)piperazin-1-yl]acetate |

TABLE 1-continued

| Exemplary Compounds of the Present Invention | | |
|---|---|---|
| Ex. | Structure | Name |
| 323 | 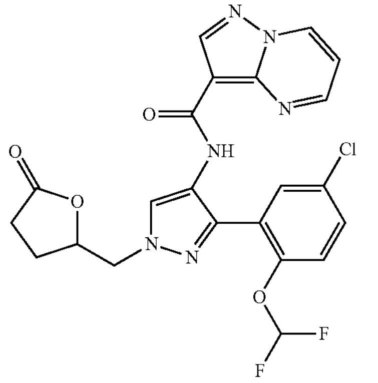 [SMILES: O=C1CCC(Cn2cc(NC(=O)c3cnn4cccnc34)c(-c3cc(Cl)ccc3OC(F)F)n2)O1] | N-[3-[5-chloro-2-(difluoromethoxy)pyridin-3-yl]-1-[(5-oxooxolan-2-yl)methyl]-1H-pyrazol-4-yl]pyrazolo[1,5-a]pyrimidine-3-carboxamide |
| 324 | 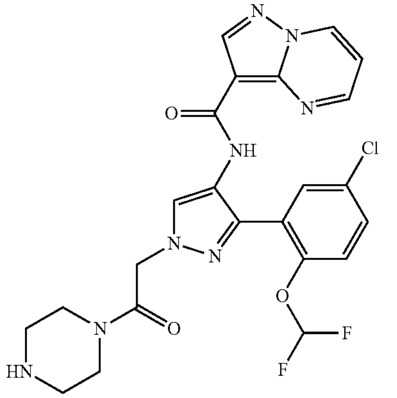 [SMILES: O=C(Nc1cn(CC(=O)N2CCNCC2)nc1-c1cc(Cl)ccc1OC(F)F)c1cnn2cccnc12] | N-[3-[5-chloro-2-(difluoromethoxy)phenyl]-1-[2-oxo-2-(piperazin-1-yl)ethyl]-1H-pyrazol-4-yl]pyrazolo[1,5-a]pyrimidine-3-carboxamide |
| 325 | 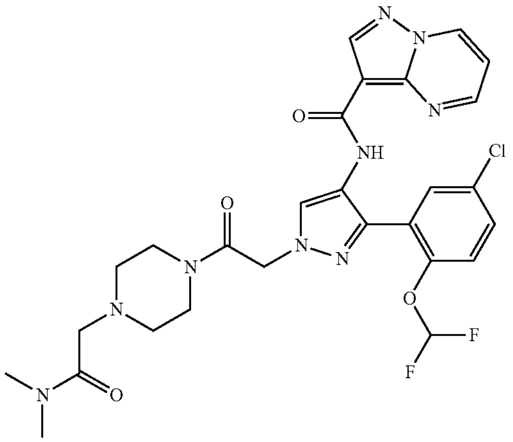 [SMILES: CN(C)C(=O)CN1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-(2-[4-[(dimethylcarbamoyl)methyl]piperazin-1-yl]-2-oxoethyl)-1H-pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 326 | 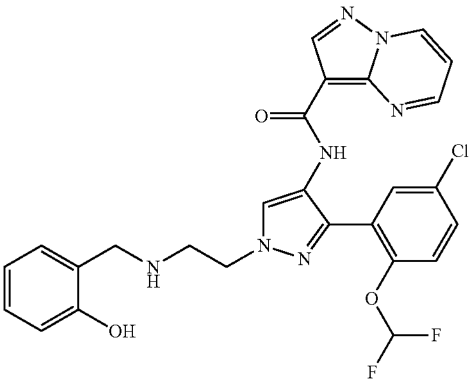 [SMILES: O=C(Nc1cn(CCNCc2ccccc2O)nc1-c1cc(Cl)ccc1OC(F)F)c1cnn2cccnc12] | N-[3-[5-chloro-2-(difluoromethoxy)phenyl]-1-(2-[[(2-hydroxyphenyl)methyl]amino]ethyl)-1H-pyrazol-4-yl]pyrazolo[1,5-a]pyrimidine-3-carboxamide |
| 327 | 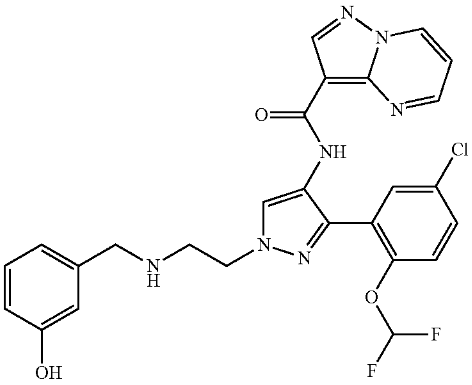 [SMILES: O=C(Nc1cn(CCNCc2cccc(O)c2)nc1-c1cc(Cl)ccc1OC(F)F)c1cnn2cccnc12] | N-[3-[5-chloro-2-(difluoromethoxy)phenyl]-1-(2-[[(3-hydroxyphenyl)methyl]amino]ethyl)-1H-pyrazol-4-yl]pyrazolo[1,5-a]pyrimidine-3-carboxamide |
| 328 | 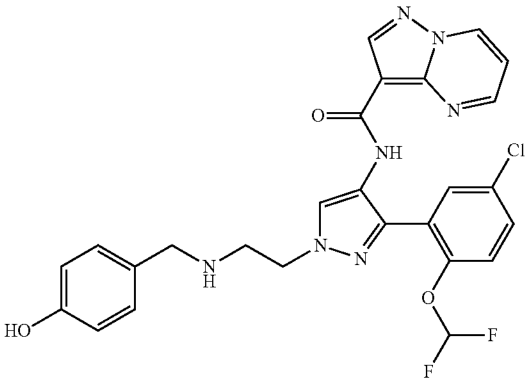 [SMILES: O=C(Nc1cn(CCNCc2ccc(O)cc2)nc1-c1cc(Cl)ccc1OC(F)F)c1cnn2cccnc12] | N-[3-[5-chloro-2-(difluoromethoxy)phenyl]-1-(2-[[(4-hydroxyphenyl)methyl]amino]ethyl)-1H-pyrazol-4-yl]pyrazolo[1,5-a]pyrimidine-3-carboxamide |
| 329 | 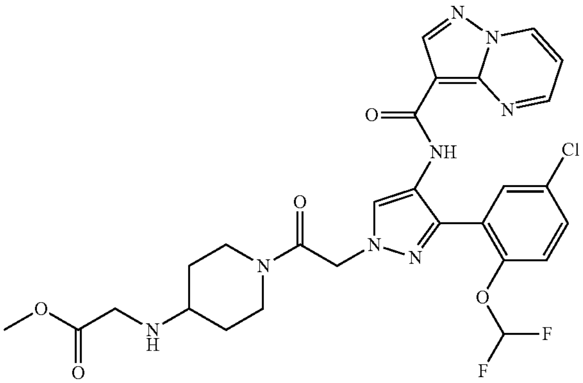 [SMILES: COC(=O)CNC1CCN(C(=O)Cn2cc(NC(=O)c3cnn4cccnc34)c(-c3cc(Cl)ccc3OC(F)F)n2)CC1] | methyl 2-[[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl]amino]acetate |

TABLE 1-continued

| Exemplary Compounds of the Present Invention | | |
|---|---|---|
| Ex. | Structure | Name |
| 330 | 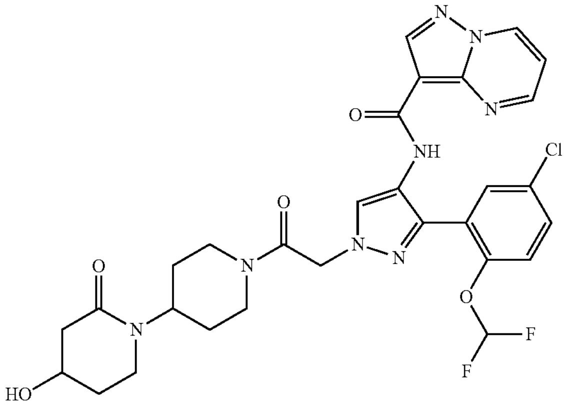 [SMILES: O=C(Nc1cn(CC(=O)N2CCC(N3CCC(O)CC3=O)CC2)nc1-c1cc(Cl)ccc1OC(F)F)c1cnn2cccnc12] | N-[3-[5-chloro-2-(difluoromethoxy)phenyl]-1-[2-[4-(5-hydroxy-2-oxopiperidin-1-yl)piperidin-1-yl]-2-oxoethyl]-1H-pyrazol-4-yl]pyrazolo[1,5-a]pyrimidine-3-carboxamide |
| 331 | 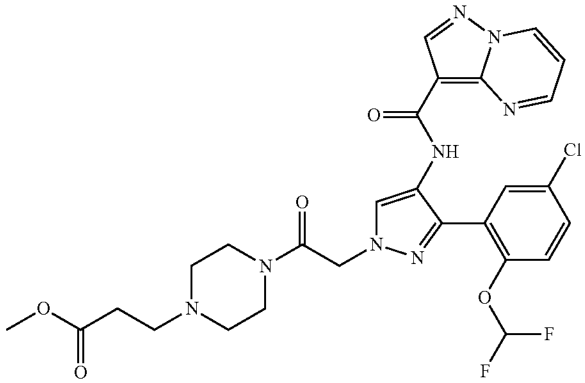 [SMILES: COC(=O)CCN1CCN(C(=O)Cn2cc(NC(=O)c3cnn4cccnc34)c(-c3cc(Cl)ccc3OC(F)F)n2)CC1] | methyl 3-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]propanoate |
| 332 | 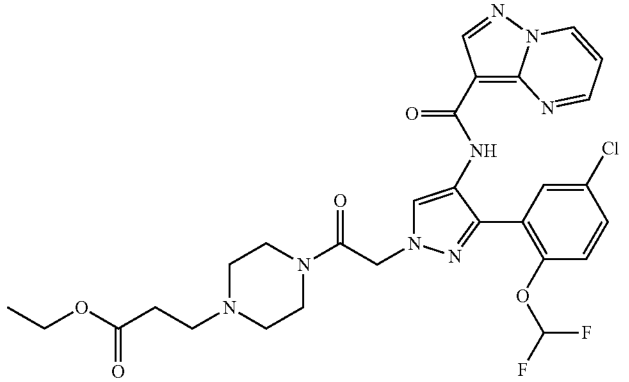 [SMILES: CCOC(=O)CCN1CCN(C(=O)Cn2cc(NC(=O)c3cnn4cccnc34)c(-c3cc(Cl)ccc3OC(F)F)n2)CC1] | 3-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]propanoate |

TABLE 1-continued

| Exemplary Compounds of the Present Invention | | |
|---|---|---|
| Ex. | Structure | Name |
| 333 | 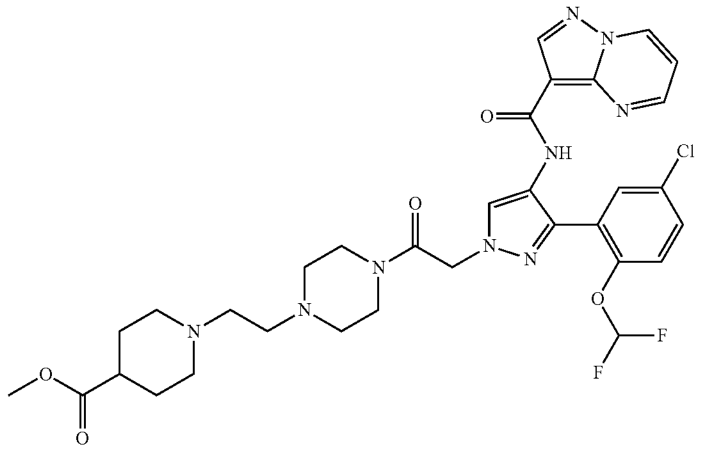 [SMILES: COC(=O)C1CCN(CCN2CCN(C(=O)Cn3cc(NC(=O)c4cnn5cccnc45)c(-c4cc(Cl)ccc4OC(F)F)n3)CC2)CC1] | methyl 1-[2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]ethyl]piperidine-4-carboxylate |
| 334 | 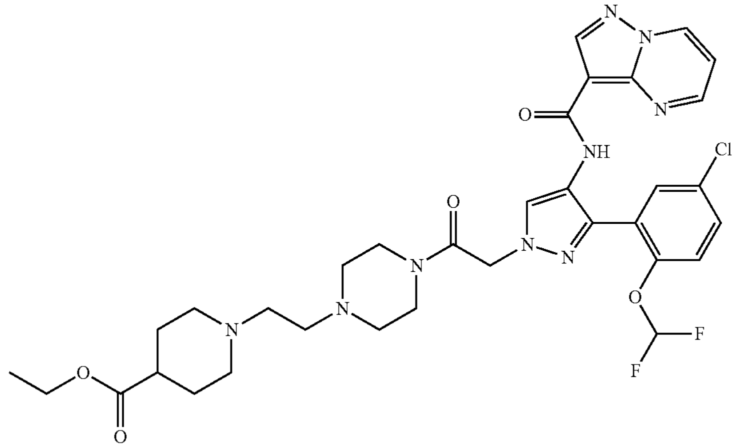 [SMILES: CCOC(=O)C1CCN(CCN2CCN(C(=O)Cn3cc(NC(=O)c4cnn5cccnc45)c(-c4cc(Cl)ccc4OC(F)F)n3)CC2)CC1] | ethyl 1-[2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]ethyl]piperidine-4-carboxylate |
| 335 | 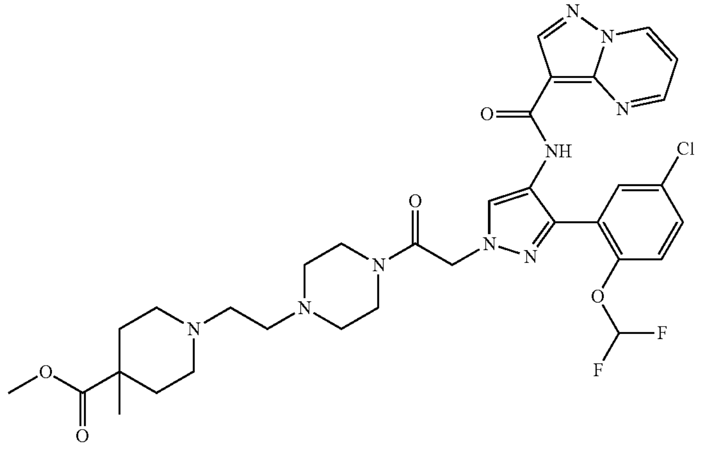 [SMILES: COC(=O)C1(C)CCN(CCN2CCN(C(=O)Cn3cc(NC(=O)c4cnn5cccnc45)c(-c4cc(Cl)ccc4OC(F)F)n3)CC2)CC1] | methyl 1-[2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]ethyl]-4-methylpiperidine-4-carboxylate |

TABLE 1-continued

Exemplary Compounds of the Present Invention

| Ex. | Structure | Name |
| --- | --- | --- |
| 336 | 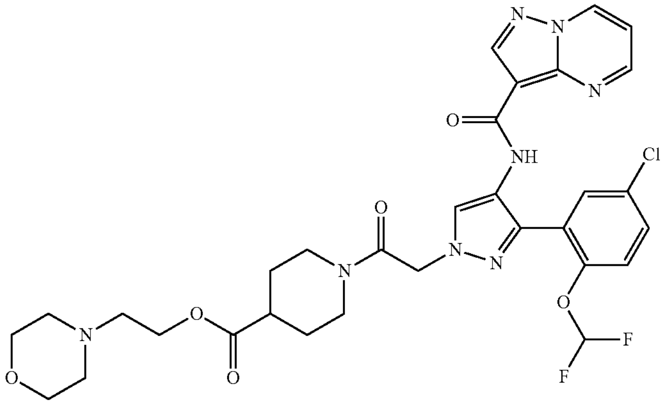 [SMILES: O=C(Nc1cn(CC(=O)N2CCC(C(=O)OCCN3CCOCC3)CC2)nc1-c1cc(Cl)ccc1OC(F)F)c1cnn2cccnc12] | 2-(morpholin-4-yl)ethyl 1-(2-[3-[5-chloro-2-(difluoromethoxy) phenyl]-4-[pyrazolo[1,5-a]pyrimidine-3-amido]-1H-pyrazol-1-yl]acetyl)piperidine-4-carboxylate |
| 337 | 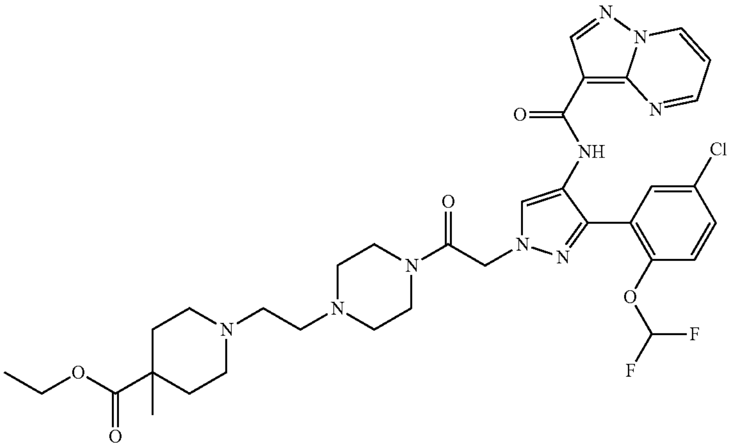 [SMILES: CCOC(=O)C1(C)CCN(CCN2CCN(C(=O)Cn3cc(NC(=O)c4cnn5cccnc45)c(-c4cc(Cl)ccc4OC(F)F)n3)CC2)CC1] | ethyl 1-[2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]ethyl]-4-methylpiperidine-4-carboxylate |
| 338 | 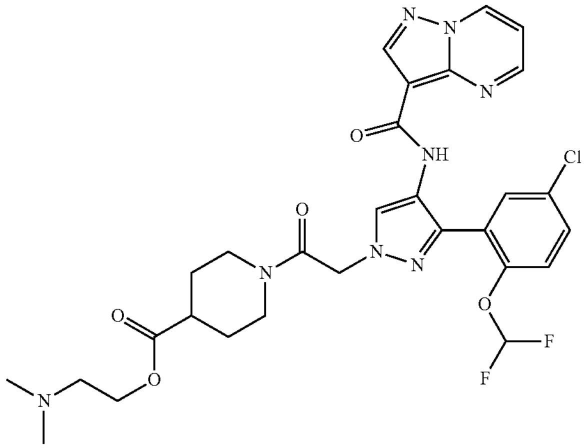 [SMILES: CN(C)CCOC(=O)C1CCN(C(=O)Cn2cc(NC(=O)c3cnn4cccnc34)c(-c3cc(Cl)ccc3OC(F)F)n2)CC1] | 2-(dimethylamino)ethyl 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylate |

TABLE 1-continued

Exemplary Compounds of the Present Invention

| Ex. | Structure | Name |
|---|---|---|
| 339 | 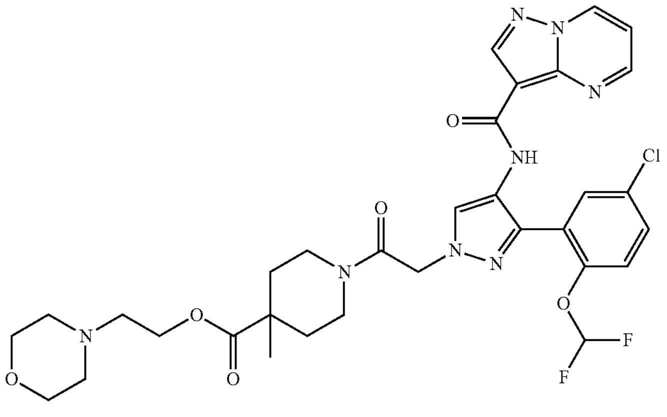 [SMILES: CC1(C(=O)OCCN2CCOCC2)CCN(C(=O)Cn2cc(NC(=O)c3cnn4cccnc34)c(-c3cc(Cl)ccc3OC(F)F)n2)CC1] | 2-(morpholin-4-yl)ethyl 1-(2-[3-[5-chloro-2-(difluoromethoxy)phenyl]-4-[pyrazolo[1,5-a]pyrimidine-3-amido]-1H-pyrazol-1-yl]acetyl)-4-methylpiperidine-4-carboxylate |
| 340 | 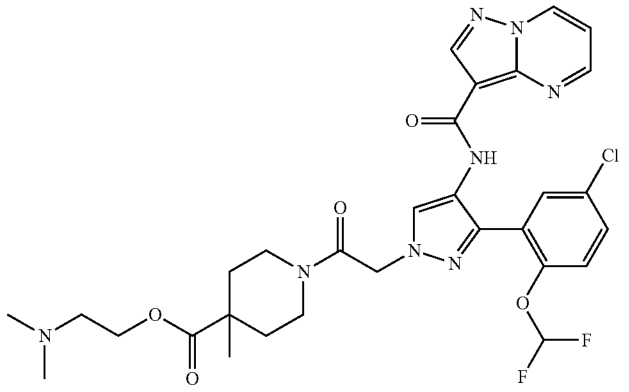 [SMILES: CN(C)CCOC(=O)C1(C)CCN(C(=O)Cn2cc(NC(=O)c3cnn4cccnc34)c(-c3cc(Cl)ccc3OC(F)F)n2)CC1] | 2-(dimethylamino)ethyl 1-(2-[3-[5-chloro-2-(difluoromethoxy) phenyl]-4-[pyrazolo[1,5-a]pyrimidine-3-amido]-1H-pyrazol-1-yl]acetyl)-4-methylpiperidine-4-carboxylate |
| 341 | 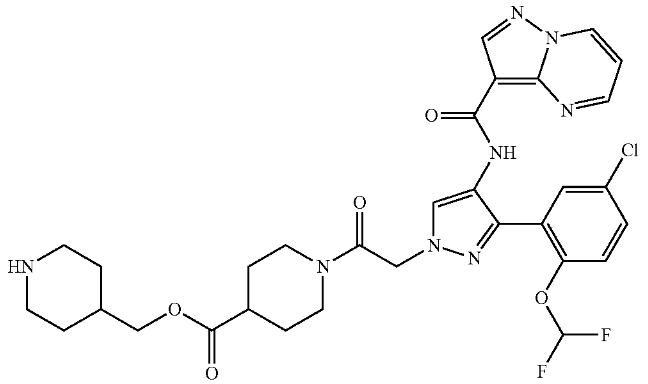 [SMILES: O=C(Nc1cn(CC(=O)N2CCC(C(=O)OCC3CCNCC3)CC2)nc1-c1cc(Cl)ccc1OC(F)F)c1cnn2cccnc12] | piperidin-4-ylmethyl 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylate |
| 342 | 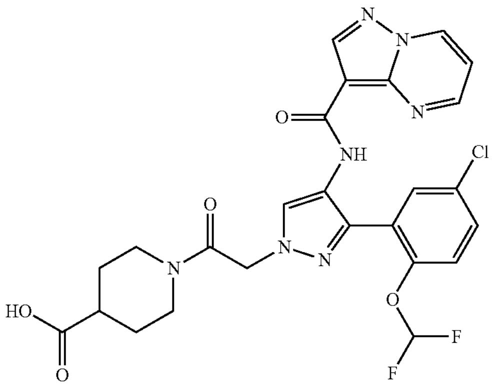 [SMILES: O=C(Nc1cn(CC(=O)N2CCC(C(=O)O)CC2)nc1-c1cc(Cl)ccc1OC(F)F)c1cnn2cccnc12] | 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylic acid |

TABLE 1-continued

| Exemplary Compounds of the Present Invention | | |
|---|---|---|
| Ex. | Structure | Name |
| 343 | 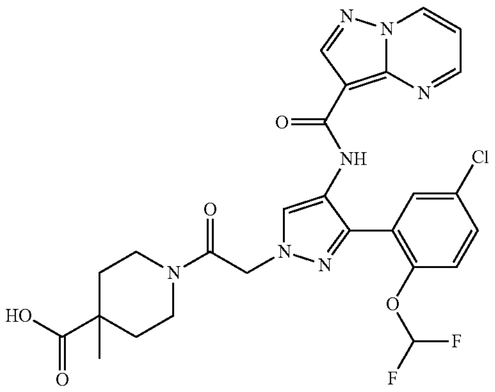 [SMILES: CC1(C(=O)O)CCN(C(=O)Cn2cc(NC(=O)c3cnn4cccnc34)c(-c3cc(Cl)ccc3OC(F)F)n2)CC1] | 1-(2-[3-[5-chloro-2-(difluoromethoxy)phenyl]-4-[pyrazolo[1,5-a]pyrimidine-3-amido]-1H-pyrazol-1-yl]acetyl)-4-methylpiperidine-4-carboxylic acid |
| 344 | 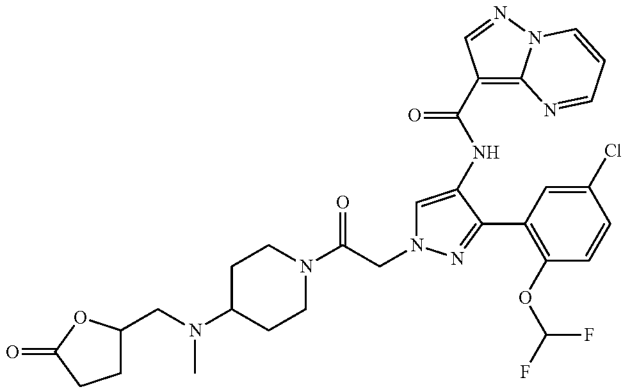 [SMILES: CN(CC1CCC(=O)O1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy) phenyl]-1-[2-(4-[methyl[(5-oxooxolan-2-yl)methyl]amino]piperidin-1-yl)-2-oxoethyl]-1H-pyrazol-4-yl]pyrazolo[1,5-a]pyrimidine-3-carboxamide |
| 345 | 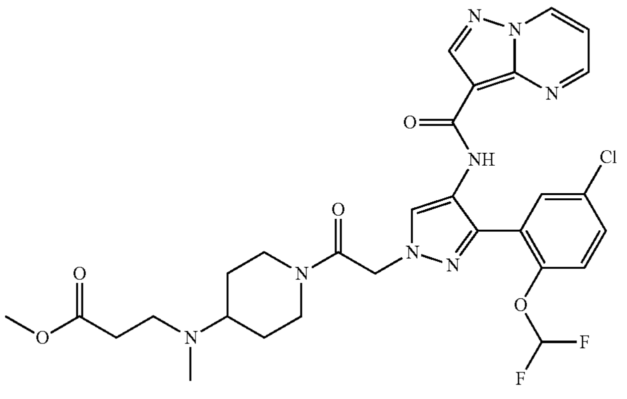 [SMILES: COC(=O)CCN(C)C1CCN(C(=O)Cn2cc(NC(=O)c3cnn4cccnc34)c(-c3cc(Cl)ccc3OC(F)F)n2)CC1] | methyl 3-[[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl](methyl)amino]propanoate |

TABLE 1-continued

| Exemplary Compounds of the Present Invention | | |
|---|---|---|
| Ex. | Structure | Name |
| 346 | 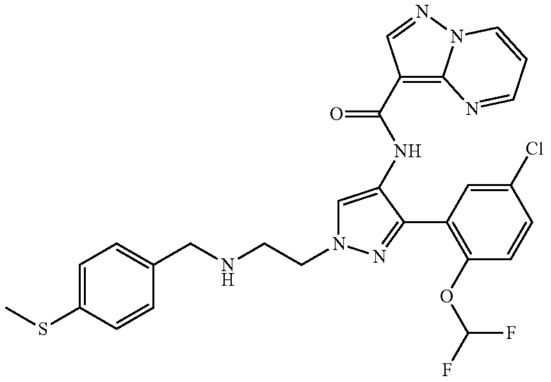 [SMILES: CSc1ccc(CNCCn2cc(NC(=O)c3cnn4cccnc34)c(-c3cc(Cl)ccc3OC(F)F)n2)cc1] | N-[3-[5-chloro-2-(difluoromethoxy)phenyl]-1-[2-([[4-(methylsulfanyl)phenyl]methyl]amino)ethyl]-1H-pyrazol-4-yl]pyrazolo[1,5-a]pyrimidine-3-carboxamide |
| 347 | 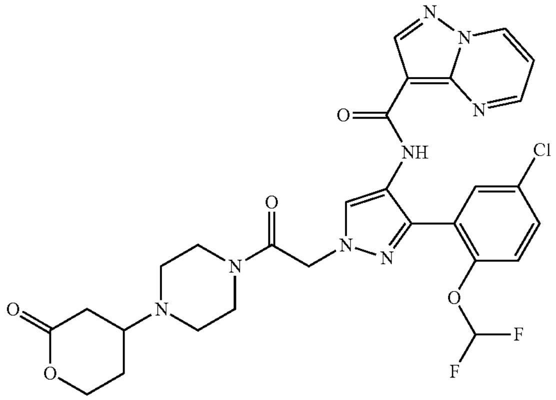 [SMILES: O=C1CC(N2CCN(C(=O)Cn3cc(NC(=O)c4cnn5cccnc45)c(-c4cc(Cl)ccc4OC(F)F)n3)CC2)CCO1] | N-[3-[5-chloro-2-(difluoromethoxy)phenyl]-1-[2-oxo-2-[4-(2-oxooxan-4-yl)piperazin-1-yl]ethyl]-1H-pyrazol-4-yl]pyrazolo[1,5-a]pyrimidine-3-carboxamide |
| 348 | 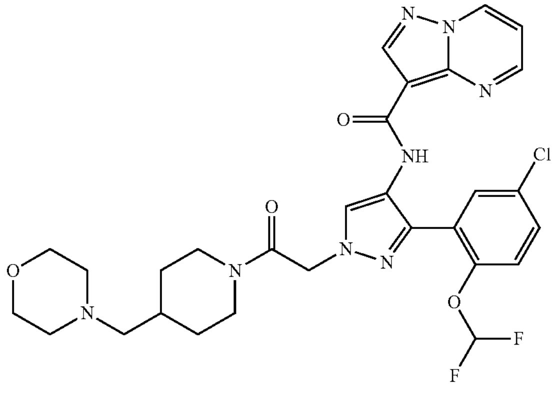 [SMILES: O=C(Nc1cn(CC(=O)N2CCC(CN3CCOCC3)CC2)nc1-c1cc(Cl)ccc1OC(F)F)c1cnn2cccnc12] | N-[3-[5-chloro-2-(difluoromethoxy)phenyl]-1-[2-[4-(morpholin-4-ylmethyl)piperidin-1-yl]-2-oxoethyl]-1H-pyrazol-4-yl]pyrazolo[1,5-a]pyrimidine-3-carboxamide |

TABLE 1-continued

Exemplary Compounds of the Present Invention

| Ex. | Structure | Name |
| --- | --- | --- |
| 349 | 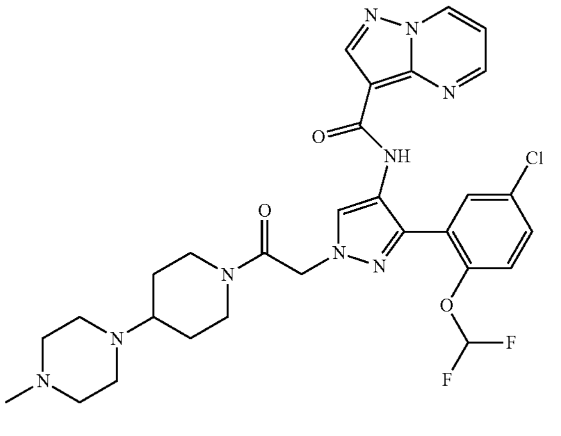 [SMILES: CN1CCN(C2CCN(C(=O)Cn3cc(NC(=O)c4cnn5cccnc45)c(-c4cc(Cl)ccc4OC(F)F)n3)CC2)CC1] | N-[3-[5-chloro-2-(difluoromethoxy)phenyl]-1-[2-[4-(4-methylpiperazin-1-yl)piperidin-1-yl]-2-oxoethyl]-1H-pyrazol-4-yl]pyrazolo[1,5-a]pyrimidine-3-carboxamide |
| 350 | 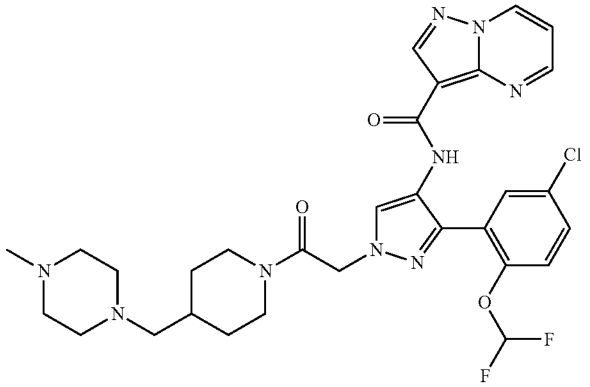 [SMILES: CN1CCN(CC2CCN(C(=O)Cn3cc(NC(=O)c4cnn5cccnc45)c(-c4cc(Cl)ccc4OC(F)F)n3)CC2)CC1] | N-[3-[5-chloro-2-(difluoromethoxy)phenyl]-1-(2-[4-[(4-methylpiperazin-1-yl)methyl]piperidin-1-yl]-2-oxoethyl)-1H-pyrazol-4-yl]pyrazolo[1,5-a]pyrimidine-3-carboxamide |
| 351 | 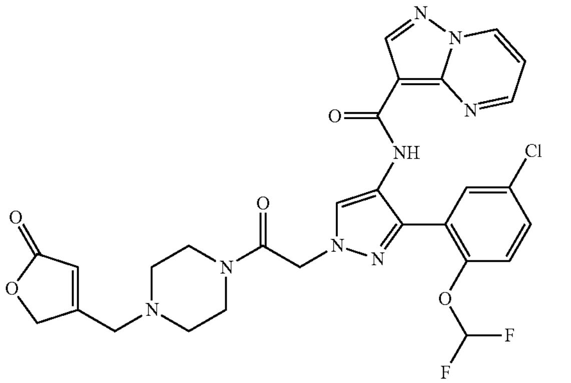 [SMILES: O=C1C=C(CN2CCN(C(=O)Cn3cc(NC(=O)c4cnn5cccnc45)c(-c4cc(Cl)ccc4OC(F)F)n3)CC2)CO1] | N-[3-[5-chloro-2-(difluoromethoxy)phenyl]-1-(2-oxo-2-[4-[(5-oxo-2,5-dihydrofuran-3-yl)methyl]piperazin-1-yl]ethyl)-1H-pyrazol-4-yl]pyrazolo[1,5-a]pyrimidine-3-carboxamide |

TABLE 1-continued

| Ex. | Structure | Name |
| --- | --- | --- |
| | Exemplary Compounds of the Present Invention | |
| 352 | 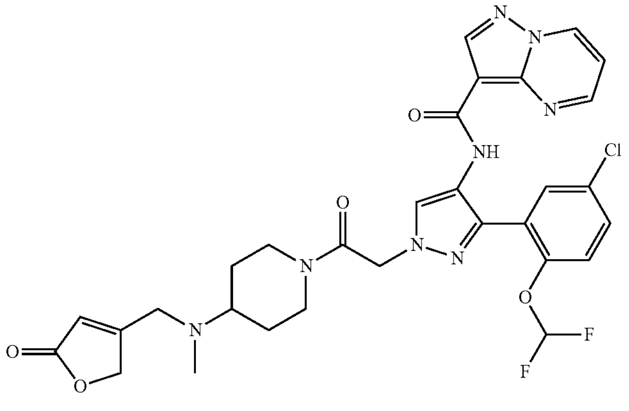 [SMILES: CN(CC1=CC(=O)OC1)C1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-(4-[methyl[(5-oxo-2,5-dihydrofuran-3-yl)methyl]amino]piperidin-1-yl)-2-oxoethyl]-1H-pyrazol-4-yl]pyrazolo[1,5-a]pyrimidine-3-carboxamide |
| 353 | 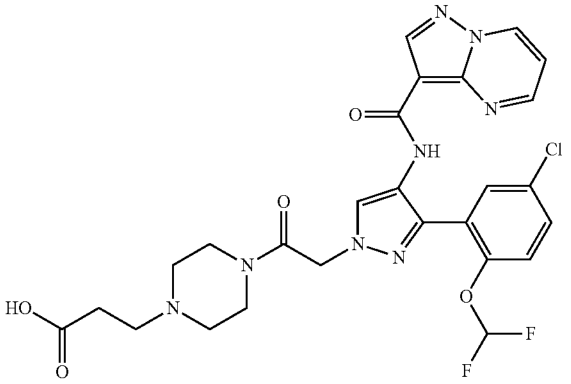 [SMILES: O=C(O)CCN1CCN(C(=O)Cn2cc(NC(=O)c3cnn4cccnc34)c(-c3cc(Cl)ccc3OC(F)F)n2)CC1] | 3-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]propanoic acid |
| 354 | 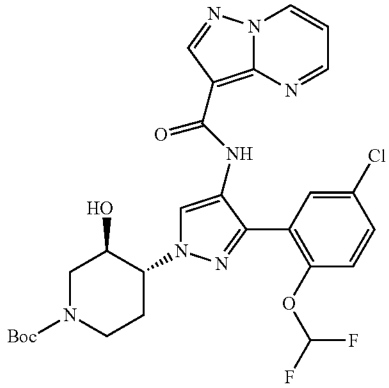 [SMILES: CC(C)(C)OC(=O)N1CC[C@@H](n2cc(NC(=O)c3cnn4cccnc34)c(-c3cc(Cl)ccc3OC(F)F)n2)[C@H](O)C1] Assumed | tert-butyl (3R,4R)-4-[3-[5-chloro-2-(difluoromethoxy)phenyl]-4-[pyrazolo[1,5-a]pyrimidine-3-amido]-1H-pyrazol-1-yl]-3-hydroxypiperidine-1-carboxylate |

TABLE 1-continued

Exemplary Compounds of the Present Invention

| Ex. | Structure | Name |
|---|---|---|
| 355 | 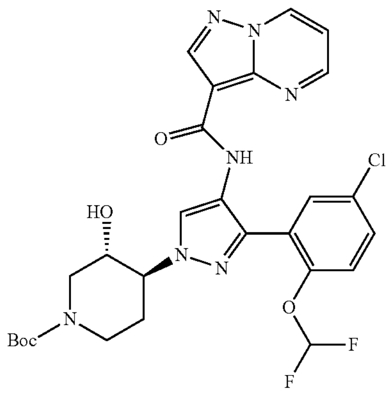 [SMILES: CC(C)(C)OC(=O)N1CC[C@H](n2cc(NC(=O)c3cnn4cccnc34)c(-c3cc(Cl)ccc3OC(F)F)n2)[C@@H](O)C1] assumed | (3S,4S)-4-[3-[5-chloro-2-(difluoromethoxy)phenyl]-4-[pyrazolo[1,5-a]pyrimidine-3-amido]-1H-pyrazol-1-yl]-3-hydroxypiperidine-1-carboxylate |
| 356 | 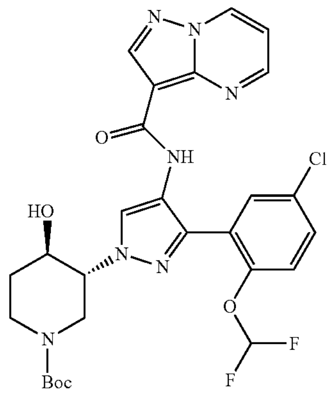 [SMILES: CC(C)(C)OC(=O)N1CC[C@@H](O)[C@H](n2cc(NC(=O)c3cnn4cccnc34)c(-c3cc(Cl)ccc3OC(F)F)n2)C1] assumed | (3R,4R)-3-[3-[5-chloro-2-(difluoromethoxy)phenyl]-4-[pyrazolo[1,5-a]pyrimidine-3-amido]-1H-pyrazol-1-yl]-4-hydroxypiperidine-1-carboxylate |
| 357 | 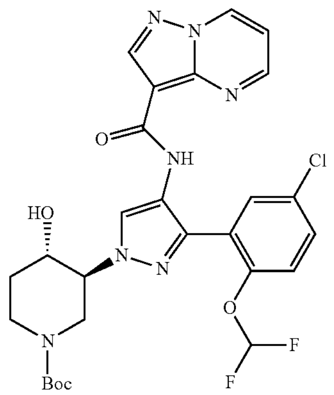 [SMILES: CC(C)(C)OC(=O)N1CC[C@H](O)[C@@H](n2cc(NC(=O)c3cnn4cccnc34)c(-c3cc(Cl)ccc3OC(F)F)n2)C1] assumed | tert-butyl (3S,4S)-3-[3-[5-chloro-2-(difluoromethoxy)phenyl]-4-[pyrazolo[1,5-a]pyrimidine-3-amido]-1H-pyrazol-1-yl]-4-hydroxypiperidine-1-carboxylate |

TABLE 1-continued

| Ex. | Structure | Name |
|---|---|---|
| Exemplary Compounds of the Present Invention | | |
| 358 | 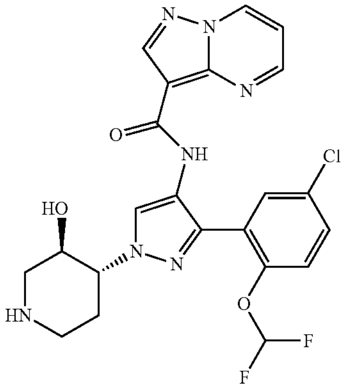 [SMILES: O=C(Nc1cn([C@@H]2CCNC[C@H]2O)nc1-c1cc(Cl)ccc1OC(F)F)c1cnn2cccnc12] | N-[3-[5-chloro-2-(difluoromethoxy)phenyl]-1-[(3R,4R)-3-hydroxypiperidin-4-yl]-1H-pyrazol-4-yl]pyrazolo[1,5-a]pyrimidine-3-carboxamide |
| 359 | 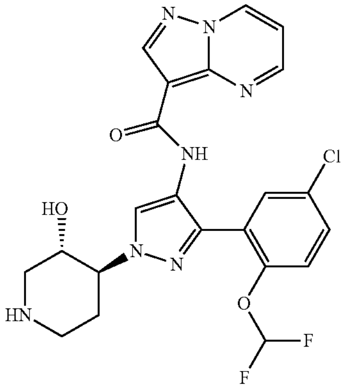 [SMILES: O=C(Nc1cn([C@H]2CCNC[C@@H]2O)nc1-c1cc(Cl)ccc1OC(F)F)c1cnn2cccnc12] | N-[3-[5-chloro-2-(difluoromethoxy) phenyl]-1-[(3S,4S)-3-hydroxypiperidin-4-yl]-1H-pyrazol-4-yl]pyrazolo[1,5-a]pyrimidine-3-carboxamide |
| 360 | 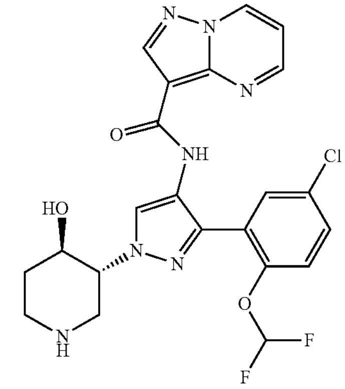 [SMILES: O=C(Nc1cn([C@@H]2CNCC[C@H]2O)nc1-c1cc(Cl)ccc1OC(F)F)c1cnn2cccnc12] | N-[3-[5-chloro-2-(difluoromethoxy)phenyl]-1-[(3R,4R)-4-hydroxypiperidin-3-yl]-1H-pyrazol-4-yl]pyrazolo[1,5-a]pyrimidine-3-carboxamide |
| 361 | 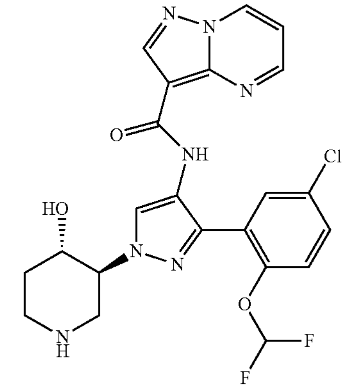 [SMILES: O=C(Nc1cn([C@H]2CNCC[C@@H]2O)nc1-c1cc(Cl)ccc1OC(F)F)c1cnn2cccnc12] | N-[3-[5-chloro-2-(difluoromethoxy)phenyl]-1-[(3S,4S)-4-hydroxypiperidin-3-yl]-1H-pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 362 | 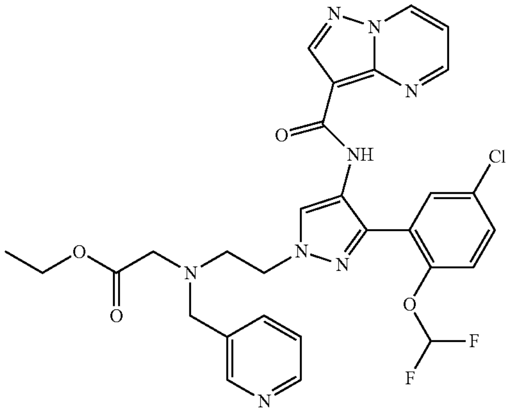 [SMILES: CCOC(=O)CN(CCn1cc(NC(=O)c2cnn3cccnc23)c(-c2cc(Cl)ccc2OC(F)F)n1)Cc1cccnc1] | ethyl 2-[(2-[3-[5-chloro-2-(difluoromethoxy)phenyl]-4-[pyrazolo[1,5-a]pyrimidine-3-amido]-1H-pyrazol-1-yl]ethyl)(pyridin-3-ylmethyl)amino]acetate |
| 363 | 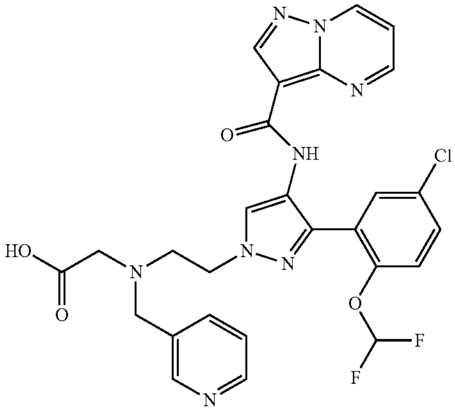 [SMILES: O=C(O)CN(CCn1cc(NC(=O)c2cnn3cccnc23)c(-c2cc(Cl)ccc2OC(F)F)n1)Cc1cccnc1] | 2-[(2-[3-[5-chloro-2-(difluoromethoxy)phenyl]-4-[pyrazolo[1,5-a]pyrimidine-3-amido]-1H-pyrazol-1-yl]ethyl)(pyridin-3-ylmethyl)amino]acetic |
| 364 | 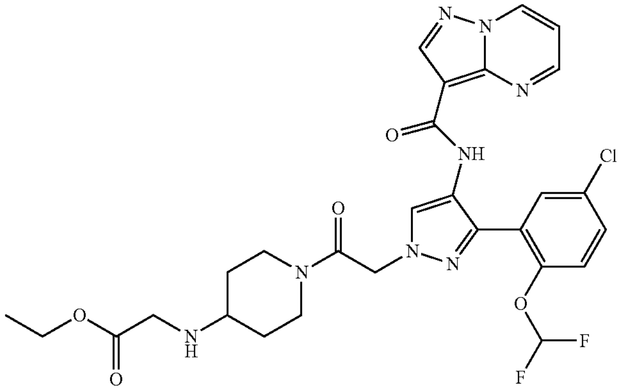 [SMILES: CCOC(=O)CNC1CCN(C(=O)Cn2cc(NC(=O)c3cnn4cccnc34)c(-c3cc(Cl)ccc3OC(F)F)n2)CC1] | ethyl 2-[[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl]amino]acetate |

TABLE 1-continued

| Exemplary Compounds of the Present Invention | | |
|---|---|---|
| Ex. | Structure | Name |
| 365 | 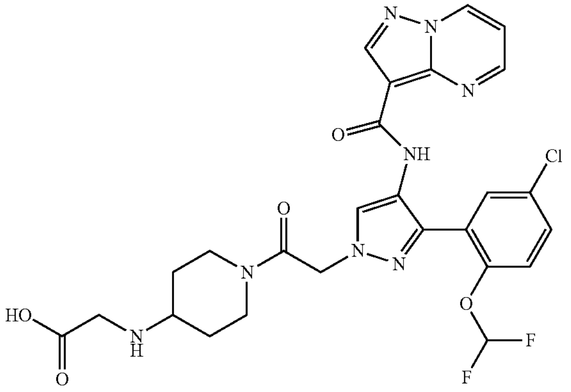 [SMILES: O=C(O)CNC1CCN(C(=O)Cn2cc(NC(=O)c3cnn4cccnc34)c(-c3cc(Cl)ccc3OC(F)F)n2)CC1] | 2-[[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl]amino]acetic acid |
| 366 | 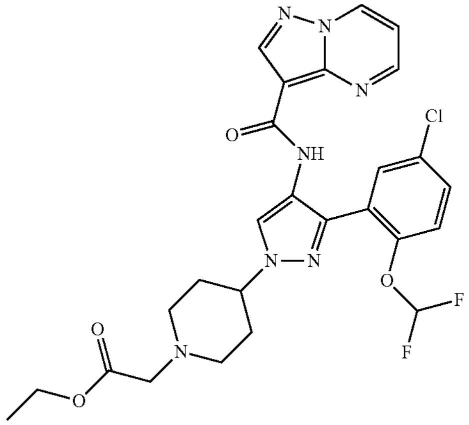 [SMILES: CCOC(=O)CN1CCC(n2cc(NC(=O)c3cnn4cccnc34)c(-c3cc(Cl)ccc3OC(F)F)n2)CC1] | ethyl 2-(4-[3-[5-chloro-2-(difluoromethoxy)phenyl]-4-[pyrazolo[1,5-a]pyrimidine-3-amido]-1H-pyrazol-1-yl]piperidin-1-yl)acetate |
| 367 | 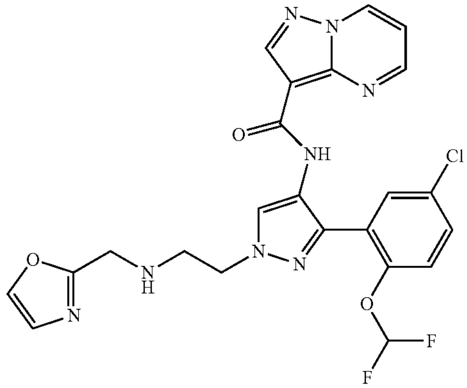 [SMILES: O=C(Nc1cn(CCNCc2ncco2)nc1-c1cc(Cl)ccc1OC(F)F)c1cnn2cccnc12] | N-[3-[5-chloro-2-(difluoromethoxy)phenyl]-1-[2-[(1,3-oxazol-2-ylmethyl)amino]ethyl]-1H-pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 368 | 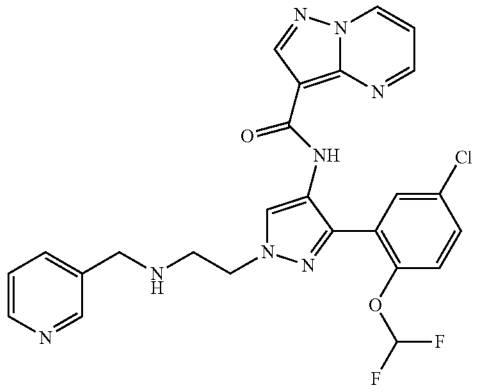 [SMILES: O=C(Nc1cn(CCNCc2cccnc2)nc1-c1cc(Cl)ccc1OC(F)F)c1cnn2cccnc12] | N-[3-[5-chloro-2-(difluoromethoxy)phenyl]-1-[2-[(pyridin-3-ylmethyl)amino]ethyl]-1H-pyrazol-4-yl]pyrazolo[1,5-a]pyrimidine-3-carboxamide |
| 369 | 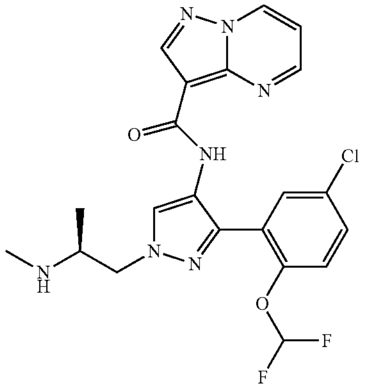 [SMILES: CN[C@@H](C)Cn1cc(NC(=O)c2cnn3cccnc23)c(-c2cc(Cl)ccc2OC(F)F)n1] | N-[3-[5-chloro-2-(difluoromethoxy)phenyl]-1-[(2S)-2-(methylamino)propyl]-1H-pyrazol-4-yl]pyrazolo[1,5-a]pyrimidine-3-carboxamide |
| 370 | 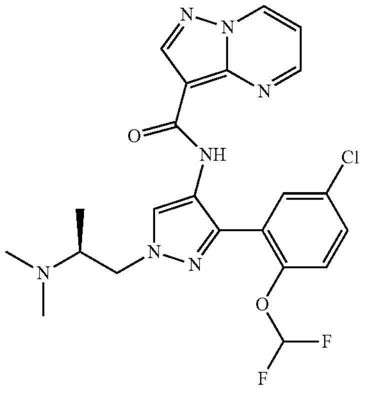 [SMILES: C[C@@H](Cn1cc(NC(=O)c2cnn3cccnc23)c(-c2cc(Cl)ccc2OC(F)F)n1)N(C)C] | N-[3-[5-chloro-2-(difluoromethoxy)phenyl]-1-[(2S)-2-(dimethylamino)propyl]-1H-pyrazol-4-yl]pyrazolo[1,5-a]pyrimidine-3-carboxamide |
| 371 | 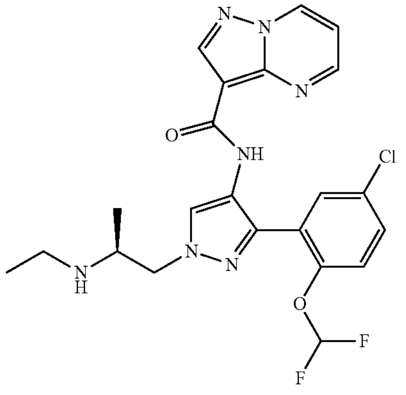 [SMILES: CCN[C@@H](C)Cn1cc(NC(=O)c2cnn3cccnc23)c(-c2cc(Cl)ccc2OC(F)F)n1] | N-[3-[5-chloro-2-(difluoromethoxy)phenyl]-1-[(2S)-2-(ethylamino)propyl]-1H-pyrazol-4-yl]pyrazolo[1,5-a]pyrimidine-3-carboxamide |

TABLE 1-continued

| Ex. | Structure | Name |
|---|---|---|
| | Exemplary Compounds of the Present Invention | |
| 372 | 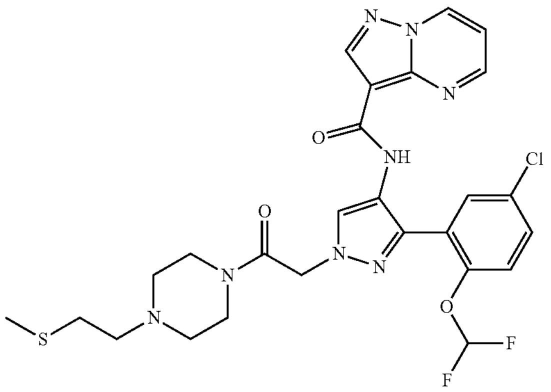 [SMILES: CSCCN1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-(2-[4-[2-(methylsulfanyl)ethyl]piperazin-1-yl]-2-oxoethyl)-1H-pyrazol-4-yl]pyrazolo[1,5-a]pyrimidine-3-carboxamide |
| 373 | 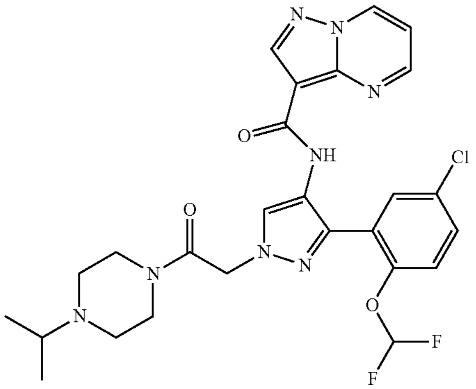 [SMILES: CC(C)N1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-[2-oxo-2-[4-(propan-2-yl)piperazin-1-yl]ethyl]-1H-pyrazol-4-yl]pyrazolo[1,5-a]pyrimidine-3-carboxamide |
| 374 | 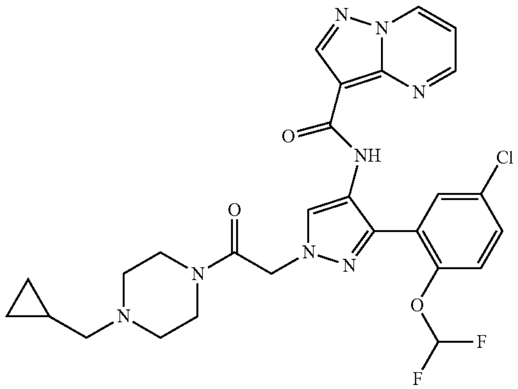 [SMILES: O=C(Nc1cn(CC(=O)N2CCN(CC3CC3)CC2)nc1-c1cc(Cl)ccc1OC(F)F)c1cnn2cccnc12] | N-[3-[5-chloro-2-(difluoromethoxy)phenyl]-1-[2-[4-(cyclopropylmethyl)piperazin-1-yl]-2-oxoethyl]-1H-pyrazol-4-yl]pyrazolo[1,5-a]pyrimidine-3-carboxamide |
| 375 | 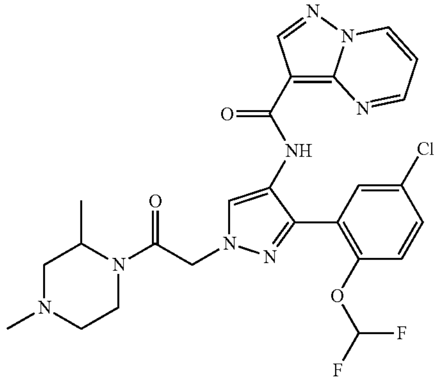 [SMILES: CC1CN(C)CCN1C(=O)Cn1cc(NC(=O)c2cnn3cccnc23)c(-c2cc(Cl)ccc2OC(F)F)n1] | N-[3-[5-chloro-2-(difluoromethoxy)phenyl]-1-[2-(2,4-dimethylpiperazin-1-yl)-2-oxoethyl]-1H-pyrazol-4-yl]pyrazolo[1,5-a]pyrimidine-3-carboxamide |

TABLE 1-continued

| Ex. | Structure | Name |
| --- | --- | --- |
| | Exemplary Compounds of the Present Invention | |
| 376 | 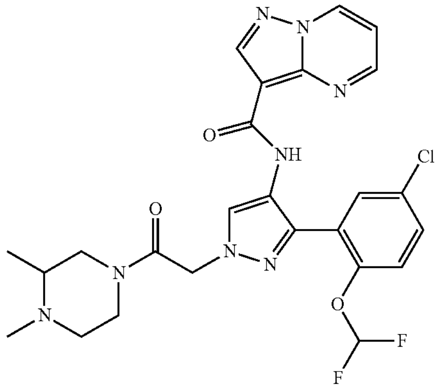 [SMILES: CC1CN(C(=O)Cn2cc(NC(=O)c3cnn4cccnc34)c(-c3cc(Cl)ccc3OC(F)F)n2)CCN1C] | N-[3-[5-chloro-2-(difluoromethoxy)phenyl]-1-[2-(3,4-dimethylpiperazin-1-yl)-2-oxoethyl]-1H-pyrazol-4-yl]pyrazolo[1,5-a]pyrimidine-3-carboxamide |
| 377 | 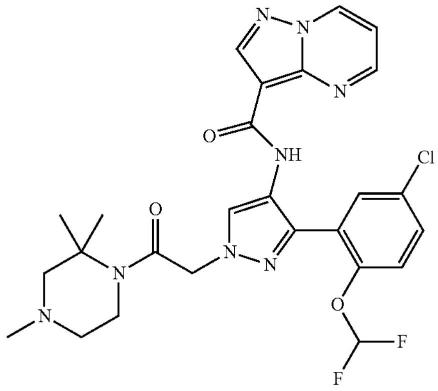 [SMILES: CN1CCN(C(=O)Cn2cc(NC(=O)c3cnn4cccnc34)c(-c3cc(Cl)ccc3OC(F)F)n2)C(C)(C)C1] | N-[3-[5-chloro-2-(difluoromethoxy)phenyl]-1-[2-oxo-2-(2,2,4-trimethylpiperazin-1-yl)ethyl]-1H-pyrazol-4-yl]pyrazolo[1,5-a]pyrimidine-3-carboxamide |
| 378 | 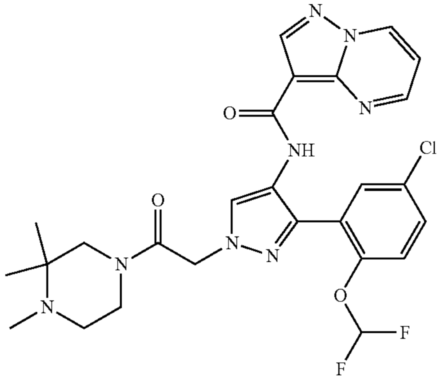 [SMILES: CN1CCN(C(=O)Cn2cc(NC(=O)c3cnn4cccnc34)c(-c3cc(Cl)ccc3OC(F)F)n2)CC1(C)C] | N-[3-[5-chloro-2-(difluoromethoxy)phenyl]-1-[2-oxo-2-(3,3,4-trimethylpiperazin-1-yl)ethyl]-1H-pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 379 | 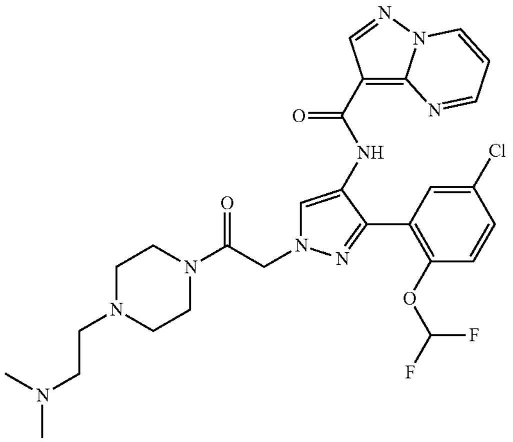 [SMILES: CN(C)CCN1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-(2-[4-[2-(dimethylamino)ethyl] piperazin-1-yl]-2-oxoethyl)-1H-pyrazol-4-yl]pyrazolo[1,5-a]pyrimidine-3-carboxamide |
| 380 | 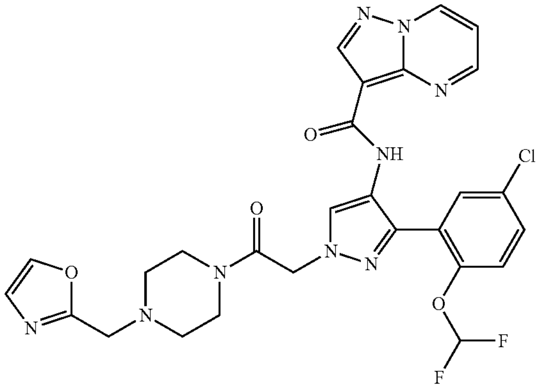 [SMILES: O=C(Nc1cn(CC(=O)N2CCN(Cc3ncco3)CC2)nc1-c1cc(Cl)ccc1OC(F)F)c1cnn2cccnc12] | N-[3-[5-chloro-2-(difluoromethoxy)phenyl]-1-[2-[4-(1,3-oxazol-2-ylmethyl)piperazin-1-yl]-2-oxoethyl]-1H-pyrazol-4-yl]pyrazolo[1,5-a]pyrimidine-3-carboxamide |
| 381 | 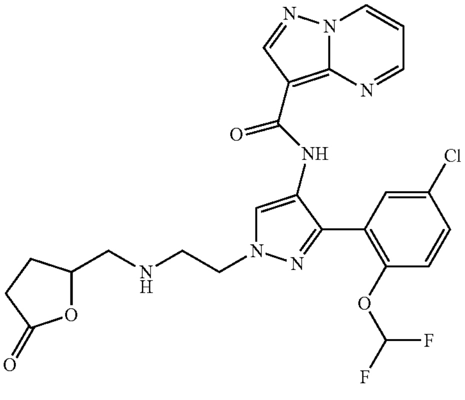 [SMILES: O=C1CCC(CNCCn2cc(NC(=O)c3cnn4cccnc34)c(-c3cc(Cl)ccc3OC(F)F)n2)O1] | N-[3-[5-chloro-2-(difluoromethoxy)phenyl]-1-(2-[[(5-oxooxolan-2-yl)methyl]amino]ethyl)-1H-pyrazol-4-yl]pyrazolo[1,5-a]pyrimidine-3-carboxamide |

TABLE 1-continued

| Exemplary Compounds of the Present Invention | | |
|---|---|---|
| Ex. | Structure | Name |
| 382 | 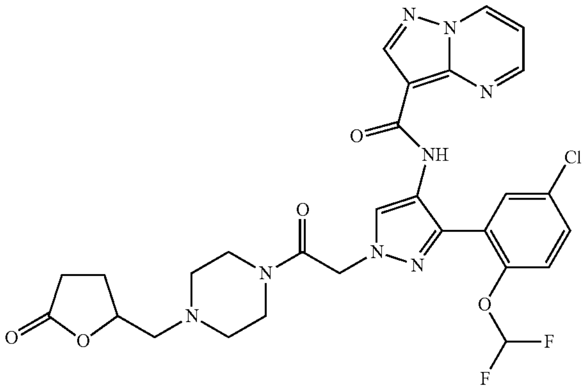 [SMILES: O=C1CCC(CN2CCN(C(=O)Cn3cc(NC(=O)c4cnn5cccnc45)c(-c4cc(Cl)ccc4OC(F)F)n3)CC2)O1] | N-[3-[5-chloro-2-(difluoromethoxy)phenyl]-1-(2-oxo-2-[4-[(5-oxooxolan-2-yl)methyl]piperazin-1-yl]ethyl)-1H-pyrazol-4-yl]pyrazolo[1,5-a]pyrimidine-3-carboxamide |
| 383 | 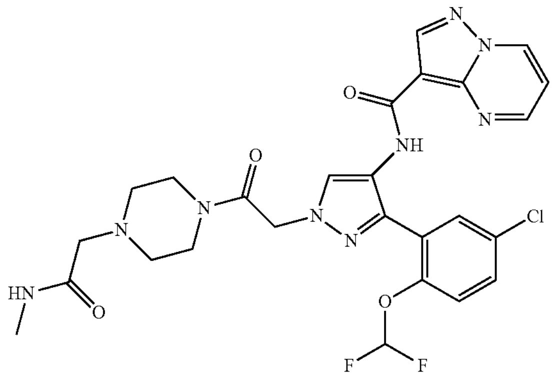 [SMILES: CNC(=O)CN1CCN(C(=O)Cn2cc(NC(=O)c3cnn4cccnc34)c(-c3cc(Cl)ccc3OC(F)F)n2)CC1] | N-[3-[5-chloro-2-(difluoromethoxy)phenyl]-1-(2-[4-[(methylcarbamoyl) methyl]piperazin-1-yl]-2-oxoethyl)-1H-pyrazol-4-yl]pyrazolo[1,5-a]pyrimidine-3-carboxamide |
| 384 | 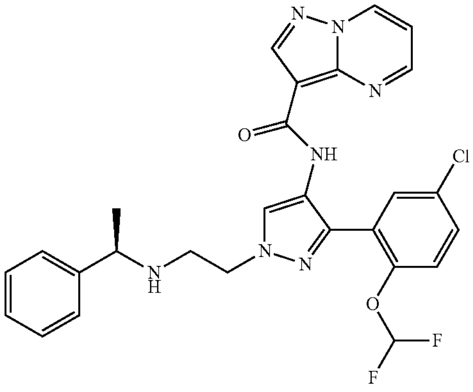 [SMILES: C[C@@H](NCCn1cc(NC(=O)c2cnn3cccnc23)c(-c2cc(Cl)ccc2OC(F)F)n1)c1ccccc1] | N-[3-[5-chloro-2-(difluoromethoxy)phenyl]-1-(2-[[(1R)-1-phenylethyl]amino]ethyl)-1H-pyrazol-4-yl]pyrazolo[1,5-a]pyrimidine-3-carboxamide |
| 385 | 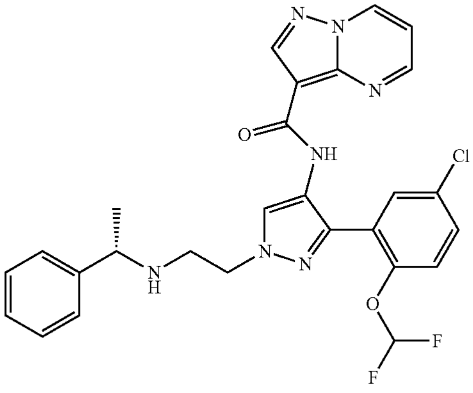 [SMILES: C[C@H](NCCn1cc(NC(=O)c2cnn3cccnc23)c(-c2cc(Cl)ccc2OC(F)F)n1)c1ccccc1] | N-[3-[5-chloro-2-(difluoromethoxy)phenyl]-1-(2-[[(1S)-1-phenylethyl]amino]ethyl)-1H-pyrazol-4-yl]pyrazolo[1,5-a]pyrimidine-3-carboxamide |

TABLE 1-continued

| Ex. | Structure | Name |
|---|---|---|
| | Exemplary Compounds of the Present Invention | |
| 386 | 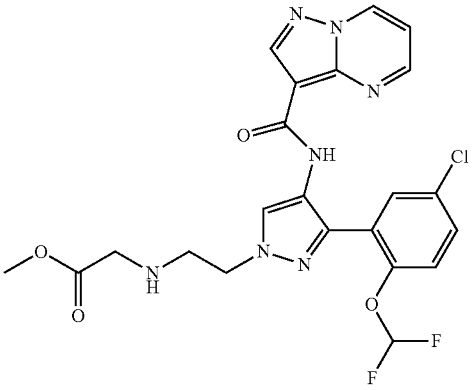 [SMILES: COC(=O)CNCCn1cc(NC(=O)c2cnn3cccnc23)c(-c2cc(Cl)ccc2OC(F)F)n1] | methyl 2-[(2-[3-[5-chloro-2-(difluoromethoxy)phenyl]-4-[pyrazolo[1,5-a]pyrimidine-3-amido]-1H-pyrazol-1-yl]ethyl)amino]acetate |
| 387 | 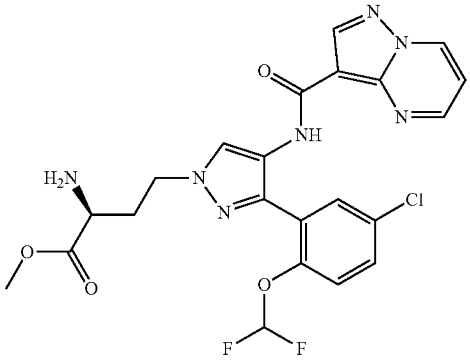 [SMILES: COC(=O)[C@@H](N)CCn1cc(NC(=O)c2cnn3cccnc23)c(-c2cc(Cl)ccc2OC(F)F)n1] | methyl (2S)-2-amino-4-[3-[5-chloro-2-(difluoromethoxy)phenyl]-4-[pyrazolo[1,5-a]pyrimidine-3-amido]-1H-pyrazol-1-yl]butanoate |
| 388 | 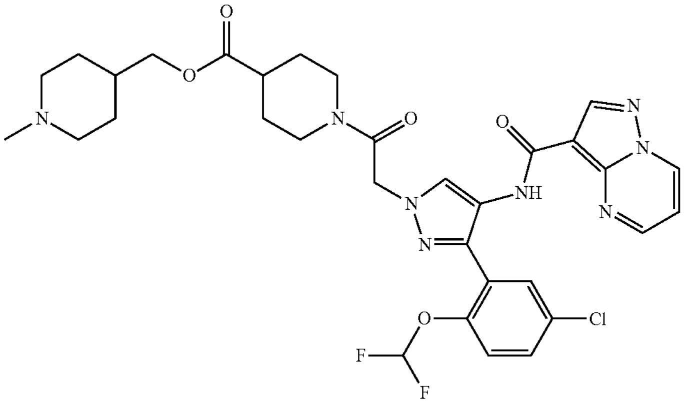 [SMILES: CN1CCC(COC(=O)C2CCN(C(=O)Cn3cc(NC(=O)c4cnn5cccnc45)c(-c4cc(Cl)ccc4OC(F)F)n3)CC2)CC1] | (1-methylpiperidin-4-yl)methyl 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylate |
| 389 | 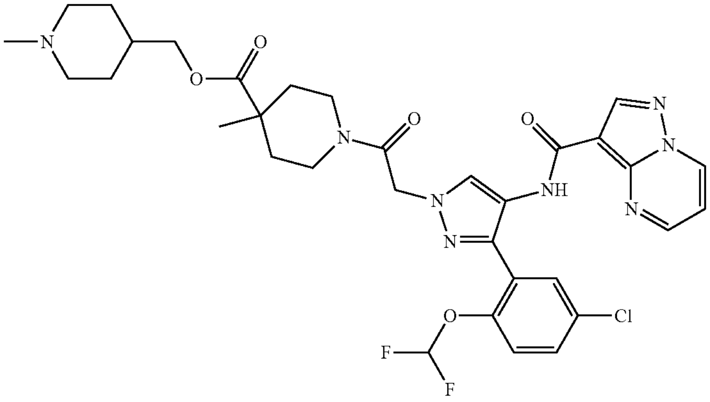 [SMILES: CN1CCC(COC(=O)C2(C)CCN(C(=O)Cn3cc(NC(=O)c4cnn5cccnc45)c(-c4cc(Cl)ccc4OC(F)F)n3)CC2)CC1] | (1-methylpiperidin-4-yl)methyl 1-(2-[3-[5-chloro-2-(difluoromethoxy)phenyl]-4-[pyrazolo[1,5-a]pyrimidine-3-amido]-1H-pyrazol-1-yl]acetyl)-4-methylpiperidine-4-carboxylate |

TABLE 1-continued

| Exemplary Compounds of the Present Invention | | |
|---|---|---|
| Ex. | Structure | Name |
| 390 | 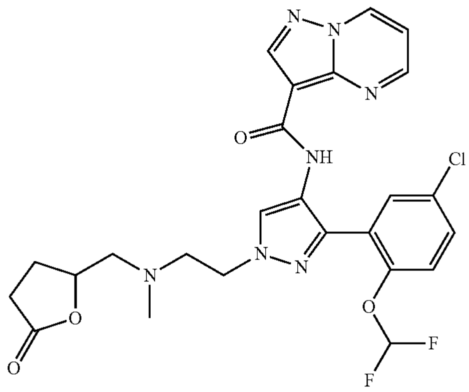 [SMILES: CN(CCn1cc(NC(=O)c2cnn3cccnc23)c(-c2cc(Cl)ccc2OC(F)F)n1)CC1CCC(=O)O1] | N-[3-[5-chloro-2-(difluoromethoxy)phenyl]-1-(2-[methyl[(5-oxooxolan-2-yl)methyl]amino]ethyl)-1H-pyrazol-4-yl]pyrazolo[1,5-a]pyrimidine-3-carboxamide |
| 391 | 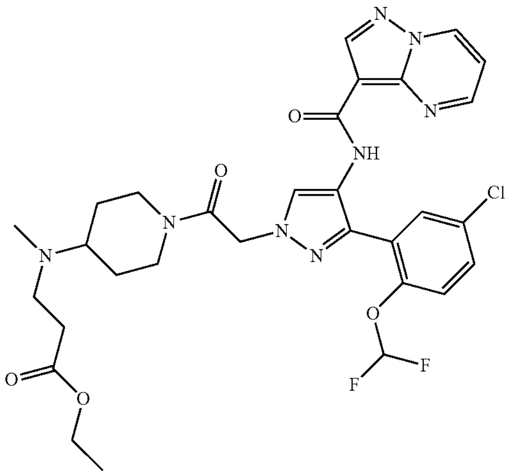 [SMILES: CCOC(=O)CCN(C)C1CCN(C(=O)Cn2cc(NC(=O)c3cnn4cccnc34)c(-c3cc(Cl)ccc3OC(F)F)n2)CC1] | ethyl 3-[[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl](methyl)amino]propanoate |
| 392 | 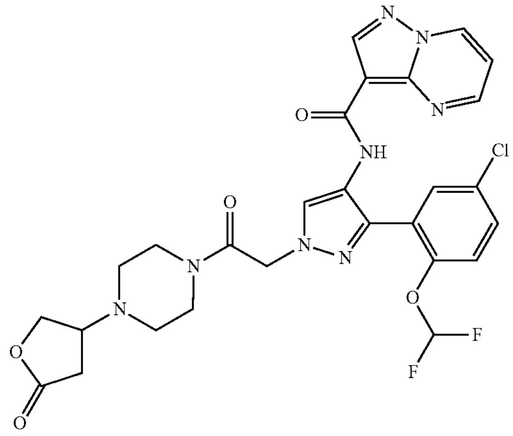 [SMILES: O=C1CC(N2CCN(C(=O)Cn3cc(NC(=O)c4cnn5cccnc45)c(-c4cc(Cl)ccc4OC(F)F)n3)CC2)CO1] | N-[3-[5-chloro-2-(difluoromethoxy)phenyl]-1-[2-oxo-2-[4-(5-oxooxolan-3-yl)piperazin-1-yl]ethyl]-1H-pyrazol-4-yl]pyrazolo[1,5-a]pyrimidine-3-carboxamide |

TABLE 1-continued

| Ex. | Structure | Name |
|---|---|---|
| Exemplary Compounds of the Present Invention | | |
| 393 | 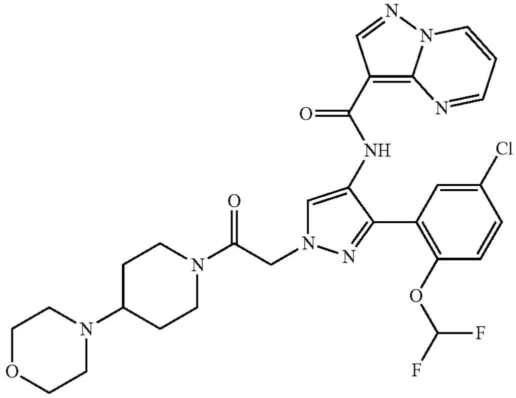 [SMILES: O=C(Nc1cn(CC(=O)N2CCC(N3CCOCC3)CC2)nc1-c1cc(Cl)ccc1OC(F)F)c1cnn2cccnc12] | N-[3-[5-chloro-2-(difluoromethoxy)phenyl]-1-[2-[4-(morpholin-4-yl)piperidin-1-yl]-2-oxoethyl]-1H-pyrazol-4-yl]pyrazolo[1,5-a]pyrimidine-3-carboxamide |
| 394 | 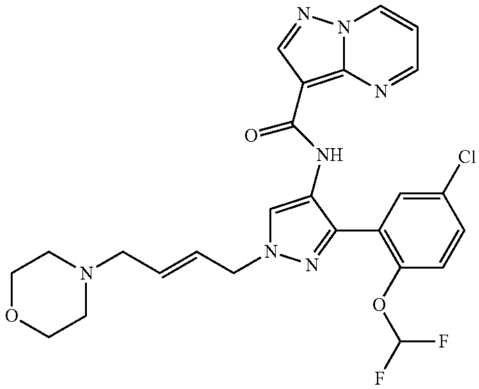 [SMILES: O=C(Nc1cn(C/C=C/CN2CCOCC2)nc1-c1cc(Cl)ccc1OC(F)F)c1cnn2cccnc12] | N-[3-[5-chloro-2-(difluoromethoxy)phenyl]-1-[(2E)-4-(morpholin-4-yl)but-2-en-1-yl]-1H-pyrazol-4-yl]pyrazolo[1,5-a]pyrimidine-3-carboxamide |
| 395 | 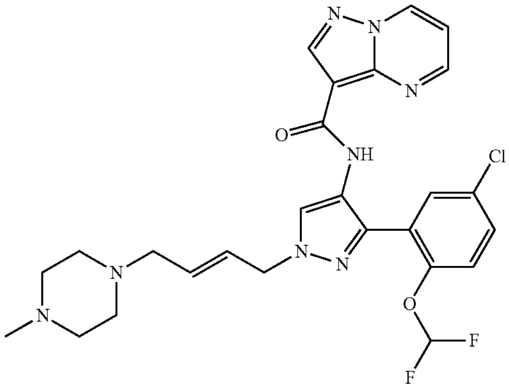 [SMILES: CN1CCN(C/C=C/Cn2cc(NC(=O)c3cnn4cccnc34)c(-c3cc(Cl)ccc3OC(F)F)n2)CC1] | N-[3-[5-chloro-2-(difluoromethoxy)phenyl]-1-[(2E)-4-(4-methylpiperazin-1-yl)but-2-en-1-yl]-1H-pyrazol-4-yl]pyrazolo[1,5-a]pyrimidine-3-carboxamide |
| 396 | 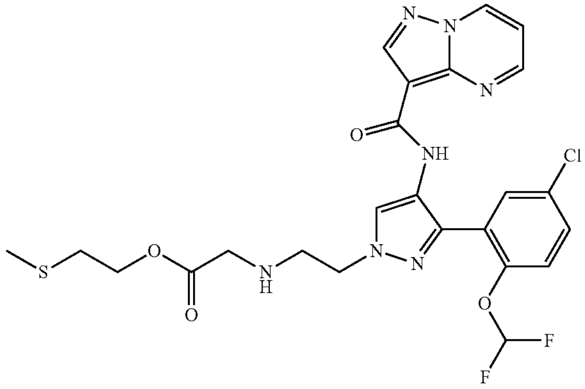 [SMILES: CSCCOC(=O)CNCCn1cc(NC(=O)c2cnn3cccnc23)c(-c2cc(Cl)ccc2OC(F)F)n1] | 2-(methylthio)ethyl 2-(2-(3-(5-chloro-2-(difluoromethoxy)phenyl)-4-(pyrazolo[1,5-a]pyrimidine-3-carboxamido)-1H-pyrazol-1-yl)ethylamino)acetate |

TABLE 1-continued

Exemplary Compounds of the Present Invention

| Ex. | Structure | Name |
| --- | --- | --- |
| 397 | 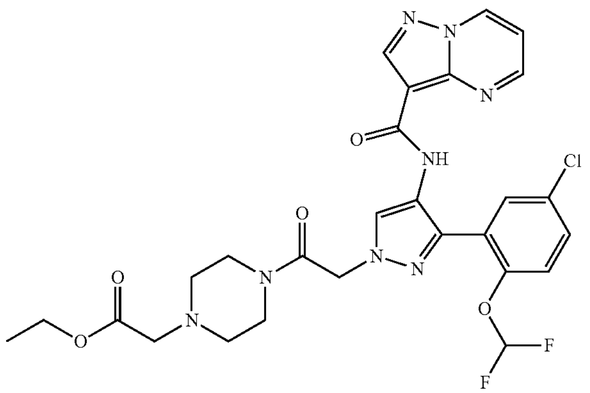 [SMILES: CCOC(=O)CN1CCN(C(=O)Cn2cc(NC(=O)c3cnn4cccnc34)c(-c3cc(Cl)ccc3OC(F)F)n2)CC1] | ethyl 2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]acetate |
| 398 | 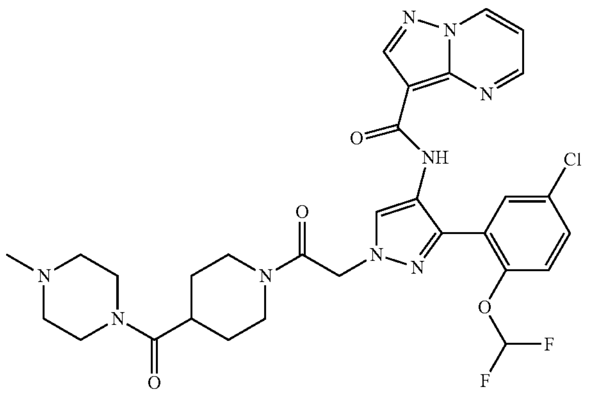 [SMILES: CN1CCN(C(=O)C2CCN(C(=O)Cn3cc(NC(=O)c4cnn5cccnc45)c(-c4cc(Cl)ccc4OC(F)F)n3)CC2)CC1] | N-(3-(5-chloro-2-(difluoromethoxy)phenyl)-1-(2-(4-(4-methylpiperazine-1-carbonyl)piperidin-1-yl)-2-oxoethyl)-1H-pyrazol-4-yl)pyrazolo[1,5-a]pyrimidine-3-carboxamide |
| 399 | 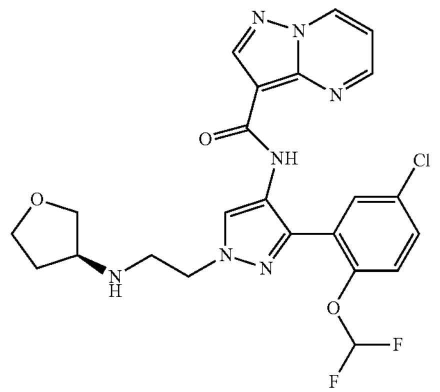 [SMILES: O=C(Nc1cn(CCN[C@H]2CCOC2)nc1-c1cc(Cl)ccc1OC(F)F)c1cnn2cccnc12] | N-(3-(5-chloro-2-(difluoromethoxy)phenyl)-1-(2-((S)-tetrahydrofuran-3-ylamino)ethyl)-1H-pyrazol-4-yl)pyrazolo[1,5-a]pyrimidine-3-carboxamide |

TABLE 1-continued

| Exemplary Compounds of the Present Invention | | |
|---|---|---|
| Ex. | Structure | Name |
| 400 | 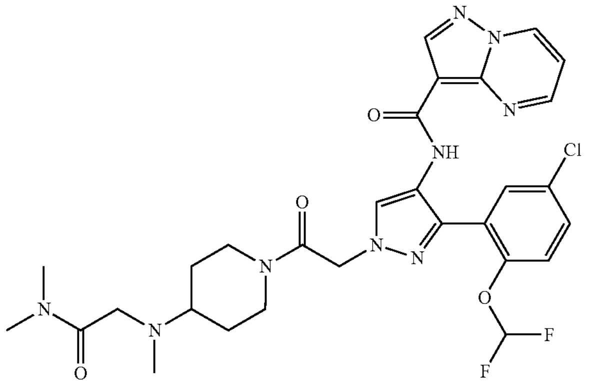 [SMILES: CN(C)C(=O)CN(C)C1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-((2-(dimethylamino)-2-oxoethyl)(methyl)amino)piperidin-1-yl)-2-oxoethyl)-1H-pyrazol-4-yl)pyrazolo[1,5-a]pyrimidine-3-carboxamide |
| 401 | 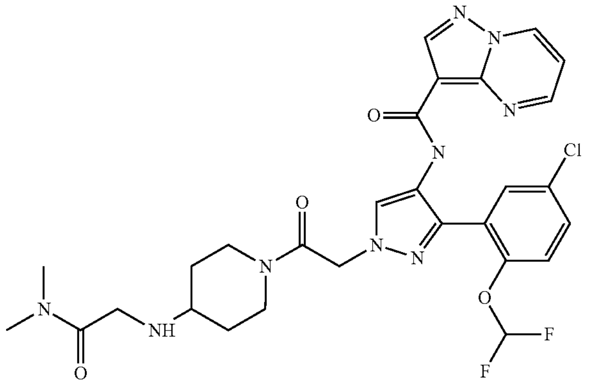 [SMILES: CN(C)C(=O)CNC1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-(2-(dimethylamino)-2-oxoethylamino)piperidin-1-yl)-2-oxoethyl)-1H-pyrazol-4-yl)pyrazolo[1,5-a]pyrimidine-3-carboxamide |
| 402 | 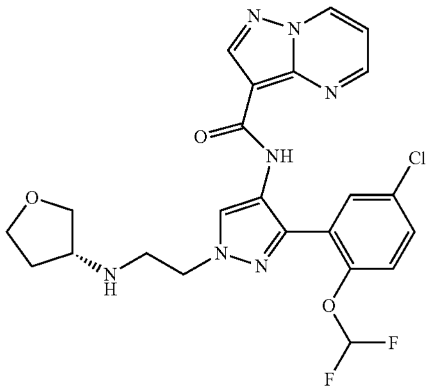 [SMILES: O=C(Nc1cn(CCN[C@@H]2CCOC2)nc1-c1cc(Cl)ccc1OC(F)F)c1cnn2cccnc12] | N-(3-(5-chloro-2-(difluoromethoxy)phenyl)-1-(2-((R)-tetrahydrofuran-3-ylamino)ethyl)-1H-pyrazol-4-yl)pyrazolo[1,5-a]pyrimidine-3-carboxamide |
| 403 | 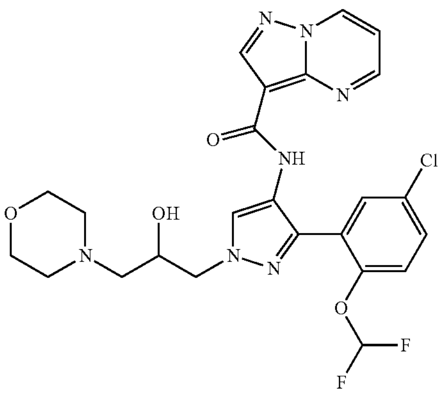 [SMILES: O=C(Nc1cn(CC(O)CN2CCOCC2)nc1-c1cc(Cl)ccc1OC(F)F)c1cnn2cccnc12] | N-(3-(5-chloro-2-(difluoromethoxy)phenyl)-1-(2-hydroxy-3-morpholinopropyl)-1H-pyrazol-4-yl)pyrazolo[1,5-a]pyrimidine-3-carboxamide |

TABLE 1-continued

| Ex. | Structure | Name |
|---|---|---|
| Exemplary Compounds of the Present Invention | | |
| 404 | 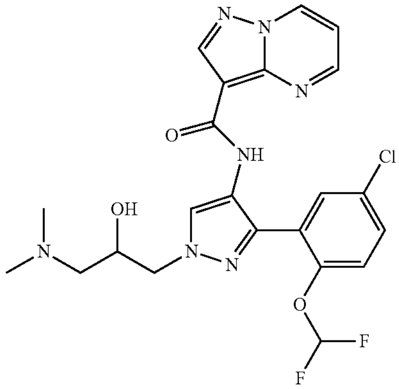 [SMILES: CN(C)CC(O)Cn1cc(NC(=O)c2cnn3cccnc23)c(-c2cc(Cl)ccc2OC(F)F)n1] | N-(3-(5-chloro-2-(difluoromethoxy)phenyl)-1-(3-(dimethylamino)-2-hydroxypropyl)-1H-pyrazol-4-yl)pyrazolo[1,5-a]pyrimidine-3-carboxamide |
| 405 | 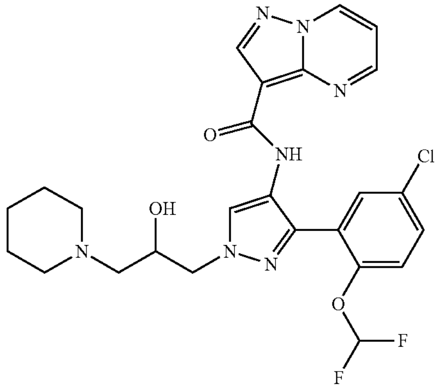 [SMILES: O=C(Nc1cn(CC(O)CN2CCCCC2)nc1-c1cc(Cl)ccc1OC(F)F)c1cnn2cccnc12] | N-(3-(5-chloro-2-(difluoromethoxy)phenyl)-1-(2-hydroxy-3-(piperidin-1-yl)propyl)-1H-pyrazol-4-yl)pyrazolo[1,5-a]pyrimidine-3-carboxamide |
| 406 | 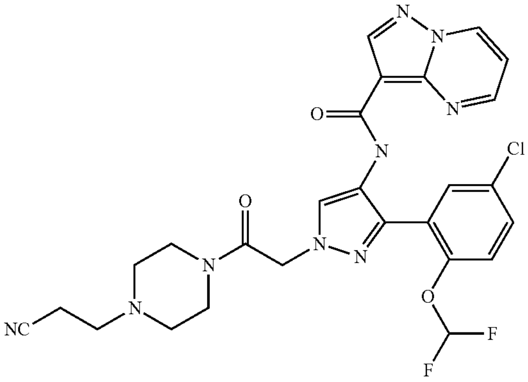 [SMILES: N#CCCN1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-(2-cyanoethyl)piperazin-1-yl)-2-oxoethyl)-1H-pyrazol-4-yl)pyrazolo[1,5-a]pyrimidine-3-carboxamide |
| 407 | 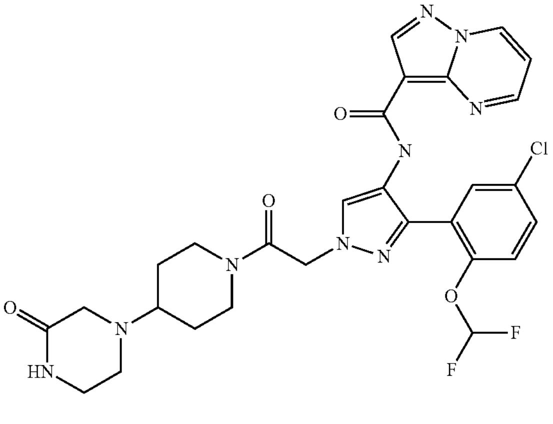 [SMILES: O=C1CN(C2CCN(C(=O)Cn3cc(NC(=O)c4cnn5cccnc45)c(-c4cc(Cl)ccc4OC(F)F)n3)CC2)CCN1] | N-(3-(5-chloro-2-(difluoromethoxy)phenyl)-1-(2-oxo-2-(4-(3-oxopiperazin-1-yl)piperidin-1-yl)ethyl)-1H-pyrazol-4-yl)pyrazolo[1,5-a]pyrimidine-3-carboxamide |

TABLE 1-continued

| Ex. | Structure | Name |
|---|---|---|
| Exemplary Compounds of the Present Invention | | |
| 408 | 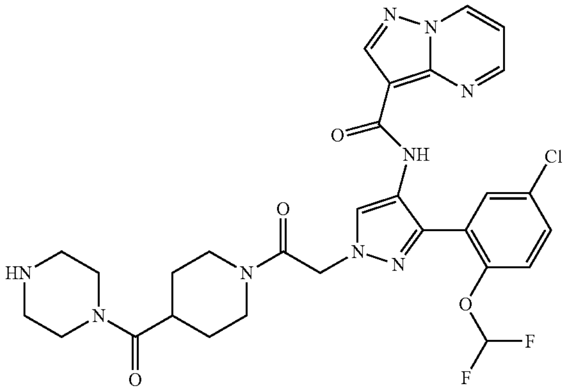 [SMILES: O=C(Nc1cn(CC(=O)N2CCC(C(=O)N3CCNCC3)CC2)nc1-c1cc(Cl)ccc1OC(F)F)c1cnn2cccnc12] | N-(3-(5-chloro-2-(difluoromethoxy)phenyl)-1-(2-oxo-2-(4-(piperazine-1-carbonyl)piperidin-1-yl)ethyl)-1H-pyrazol-4-yl)pyrazolo[1,5-a]pyrimidine-3-carboxamide |
| 409 | 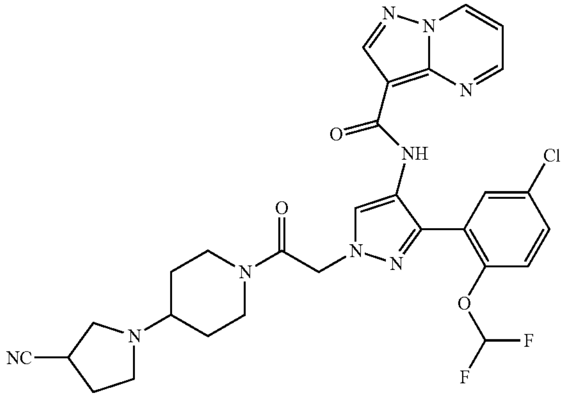 [SMILES: N#CC1CCN(C2CCN(C(=O)Cn3cc(NC(=O)c4cnn5cccnc45)c(-c4cc(Cl)ccc4OC(F)F)n3)CC2)C1] | N-(3-(5-chloro-2-(difluoromethoxy)phenyl)-1-(2-(4-(3-cyanopyrrolidin-1-yl)piperidin-1-yl)-2-oxoethyl)-1H-pyrazol-4-yl)pyrazolo[1,5-a]pyrimidine-3-carboxamide |
| 410 | 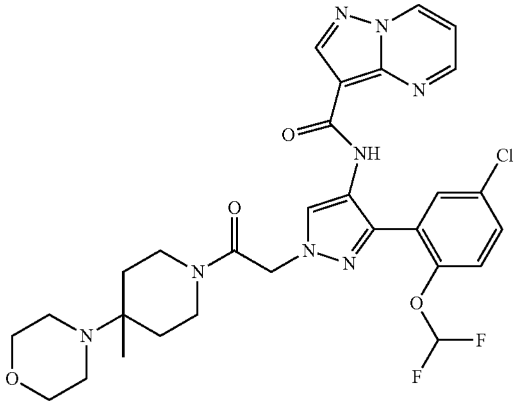 [SMILES: CC1(N2CCOCC2)CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-methyl-4-morpholinopiperidin-1-yl)-2-oxoethyl)-1H-pyrazol-4-yl)pyrazolo[1,5-a]pyrimidine-3-carboxamide |

TABLE 1-continued

| Exemplary Compounds of the Present Invention | | |
|---|---|---|
| Ex. | Structure | Name |
| 411 | 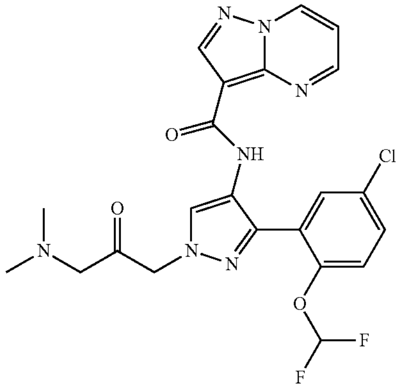 [SMILES: CN(C)CC(=O)Cn1cc(NC(=O)c2cnn3cccnc23)c(-c2cc(Cl)ccc2OC(F)F)n1] | N-(3-(5-chloro-2-(difluoromethoxy)phenyl)-1-(3-(dimethylamino)-2-oxopropyl)-1H-pyrazol-4-yl)pyrazolo[1,5-a]pyrimidine-3-carboxamide |
| 412 | 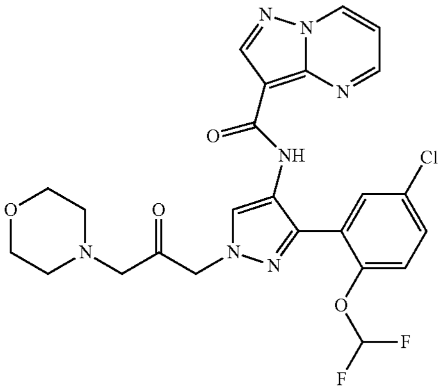 [SMILES: O=C(CN1CCOCC1)Cn1cc(NC(=O)c2cnn3cccnc23)c(-c2cc(Cl)ccc2OC(F)F)n1] | N-(3-(5-chloro-2-(difluoromethoxy)phenyl)-1-(3-morpholino-2-oxopropyl)-1H-pyrazol-4-yl)pyrazolo[1,5-a]pyrimidine-3-carboxamide |
| 413 | 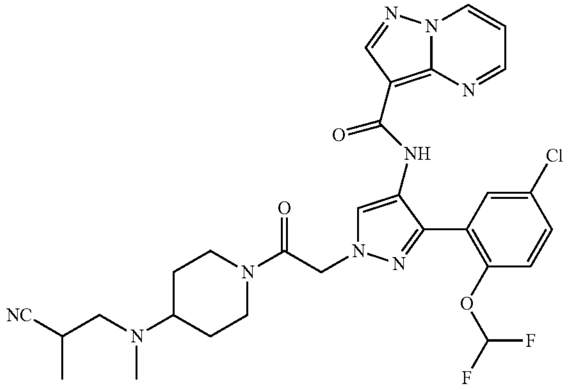 [SMILES: CC(C#N)CN(C)C1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-((2-cyanopropyl)(methyl)amino)piperidin-1-yl)-2-oxoethyl)-1H-pyrazol-4-yl)pyrazolo[1,5-a]pyrimidine-3-carboxamide |

TABLE 1-continued

| Ex. | Structure | Name |
|---|---|---|
| Exemplary Compounds of the Present Invention | | |
| 414 | 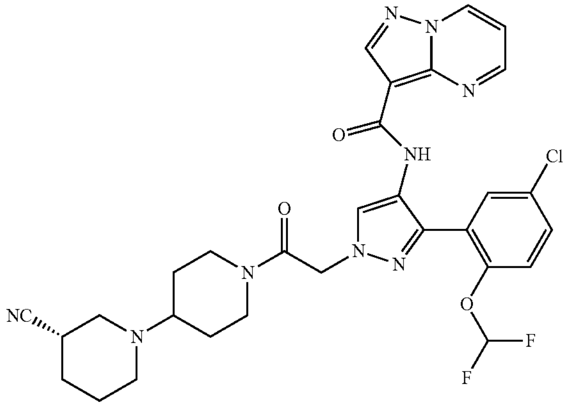 [SMILES: N#C[C@H]1CCCN(C2CCN(C(=O)Cn3cc(NC(=O)c4cnn5cccnc45)c(-c4cc(Cl)ccc4OC(F)F)n3)CC2)C1] | N-(3-(5-chloro-2-(difluoromethoxy)phenyl)-1-(2-((S)-3-cyano-1,4'-bipiperidin-1'-yl)-2-oxoethyl)-1H-pyrazol-4-yl)pyrazolo[1,5-a]pyrimidine-3-carboxamide |
| 415 | 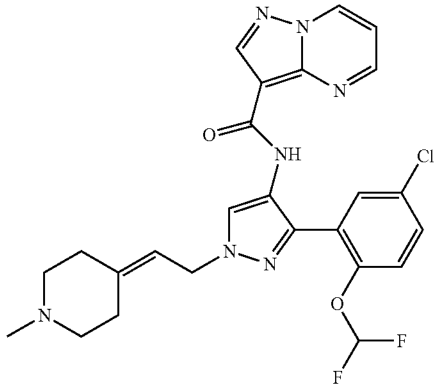 [SMILES: CN1CCC(=CCn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(1-methylpiperidin-4-ylidene)ethyl)-1H-pyrazol-4-yl)pyrazolo[1,5-a]pyrimidine-3-carboxamide |
| 416 | 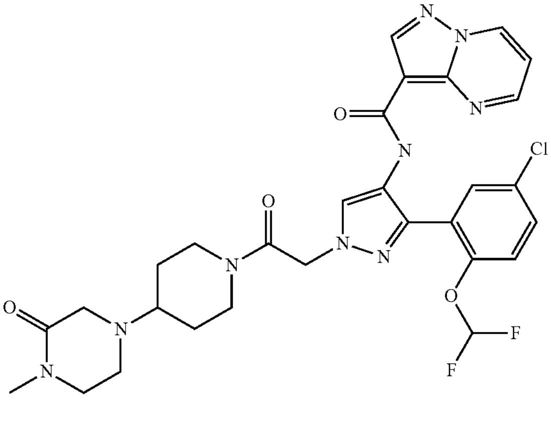 [SMILES: CN1CCN(C2CCN(C(=O)Cn3cc(NC(=O)c4cnn5cccnc45)c(-c4cc(Cl)ccc4OC(F)F)n3)CC2)CC1=O] | N-(3-(5-chloro-2-(difluoromethoxy)phenyl)-1-(2-(4-(4-methyl-3-oxopiperazin-1-yl)piperidin-1-yl)-2-oxoethyl)-1H-pyrazol-4-yl)pyrazolo[1,5-a]pyrimidine-3-carboxamide |

TABLE 1-continued

| Exemplary Compounds of the Present Invention | | |
|---|---|---|
| Ex. | Structure | Name |
| 417 | 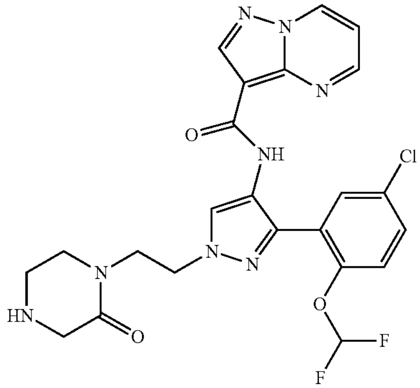 [SMILES: O=C(Nc1cn(CCN2CCNCC2=O)nc1-c1cc(Cl)ccc1OC(F)F)c1cnn2cccnc12] | N-(3-(5-chloro-2-(difluoromethoxy)phenyl)-1-(2-(2-oxopiperazin-1-yl)ethyl)-1H-pyrazol-4-yl)pyrazolo[1,5-a]pyrimidine-3-carboxamide |
| 418 | 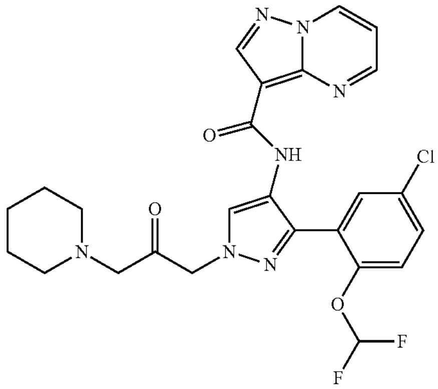 [SMILES: O=C(CN1CCCCC1)Cn1cc(NC(=O)c2cnn3cccnc23)c(-c2cc(Cl)ccc2OC(F)F)n1] | N-(3-(5-chloro-2-(difluoromethoxy)phenyl)-1-(2-oxo-3-(piperidin-1-yl)propyl)-1H-pyrazol-4-yl)pyrazolo[1,5-a]pyrimidine-3-carboxamide |
| 419 | 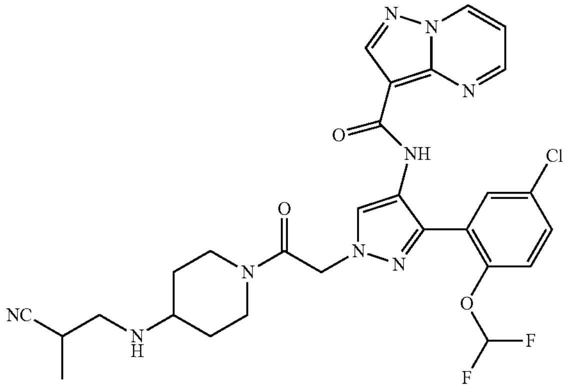 [SMILES: CC(C#N)CNC1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-(2-cyanopropylamino) piperidin-1-yl)-2-oxoethyl)-1H-pyrazol-4-yl)pyrazolo[1,5-a]pyrimidine-3-carboxamide |
| 420 | 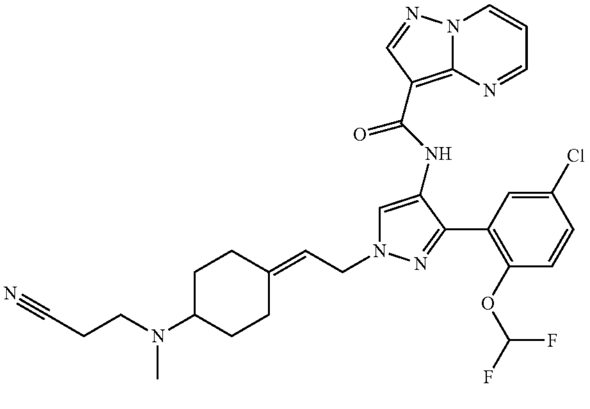 [SMILES: CN(CCC#N)C1CCC(=CCn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-((2-cyanoethyl)(methyl)amino) cyclohexylidene)ethyl)-1H-pyrazol-4-yl)pyrazolo[1,5-a]pyrimidine-3-carboxamide |

TABLE 1-continued

| Ex. | Structure | Name |
|---|---|---|
| 421 | 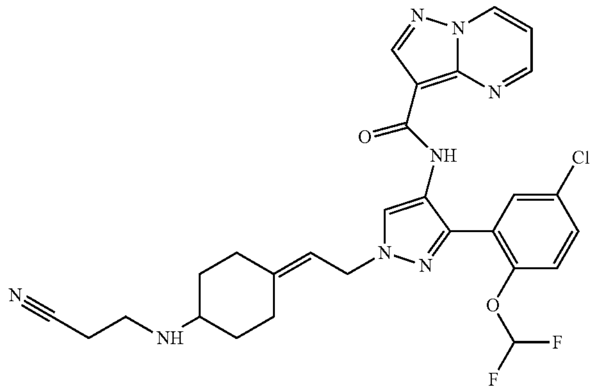 [SMILES: N#CCCNC1CCC(=CCn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-(2-cyanoethylamino)cyclohexylidene)ethyl)-1H-pyrazol-4-yl)pyrazolo[1,5-a]pyrimidine-3-carboxamide |
| 422 | 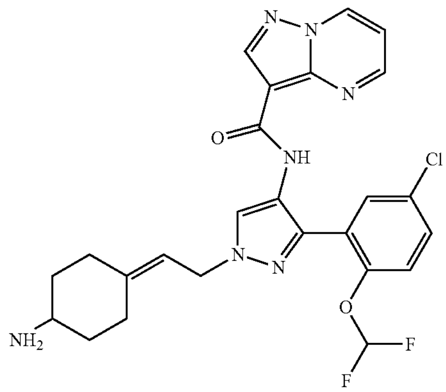 [SMILES: NC1CCC(=CCn2cc(NC(=O)c3cnn4cccnc34)c(-c3cc(Cl)ccc3OC(F)F)n2)CC1] | N-(1-(2-(4-aminocyclohexylidene)ethyl)-3-(5-chloro-2-(difluoromethoxy)phenyl)-1H-pyrazol-4-yl)pyrazolo[1,5-a]pyrimidine-3-carboxamide |
| 423 | 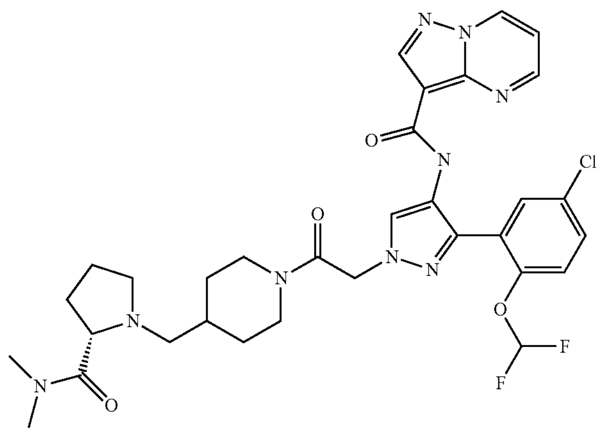 [SMILES: CN(C)C(=O)[C@@H]1CCCN1CC1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-(((S)-2-(dimethylcarbamoyl)pyrrolidin-1-yl)methyl)piperidin-1-yl)-2-oxoethyl)-1H-pyrazol-4-yl)pyrazolo[1,5-a]pyrimidine-3-carboxamide |

Exemplary Compounds of the Present Invention

TABLE 1-continued

| Exemplary Compounds of the Present Invention | | |
|---|---|---|
| Ex. | Structure | Name |
| 424 | 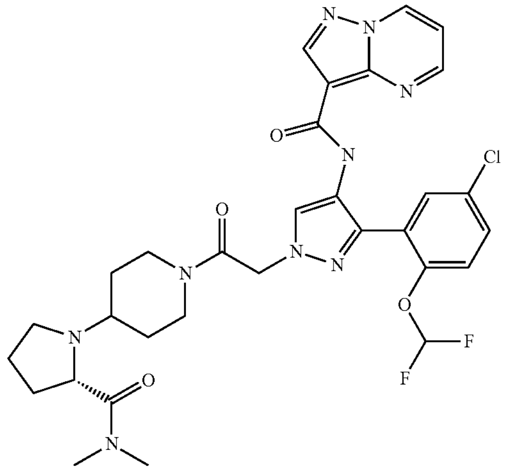 [SMILES: CN(C)C(=O)[C@@H]1CCCN1C1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-((S)-2-(dimethylcarbamoyl)pyrrolidin-1-yl)piperidin-1-yl)-2-oxoethyl)-1H-pyrazol-4-yl)pyrazolo[1,5-a]pyrimidine-3-carboxamide |
| 425 | 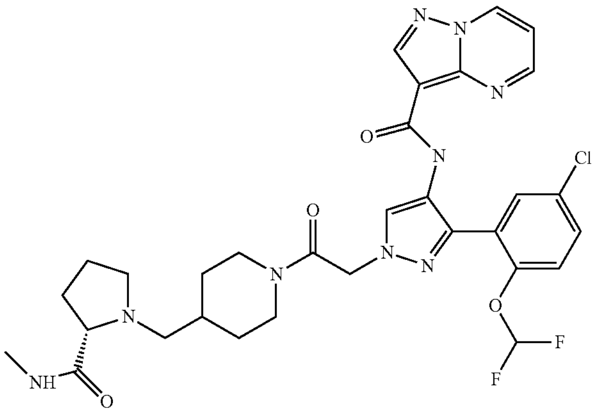 [SMILES: CNC(=O)[C@@H]1CCCN1CC1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-(((S)-2-(methylcarbamoyl)pyrrolidin-1-yl)methyl)piperidin-1-yl)-2-oxoethyl)-1H-pyrazol-4-yl)pyrazolo[1,5-a]pyrimidine-3-carboxamide |
| 426 | 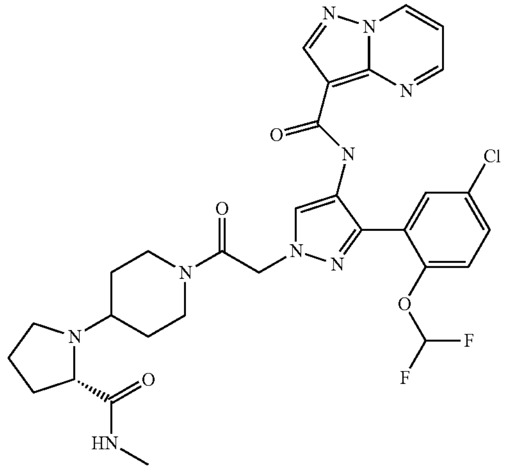 [SMILES: CNC(=O)[C@@H]1CCCN1C1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-((S)-2-(methylcarbamoyl)pyrrolidin-1-yl)piperidin-1-yl)-2-oxoethyl)-1H-pyrazol-4-yl)pyrazolo[1,5-a]pyrimidine-3-carboxamide |

TABLE 1-continued

| Exemplary Compounds of the Present Invention | | |
|---|---|---|
| Ex. | Structure | Name |
| 427 | 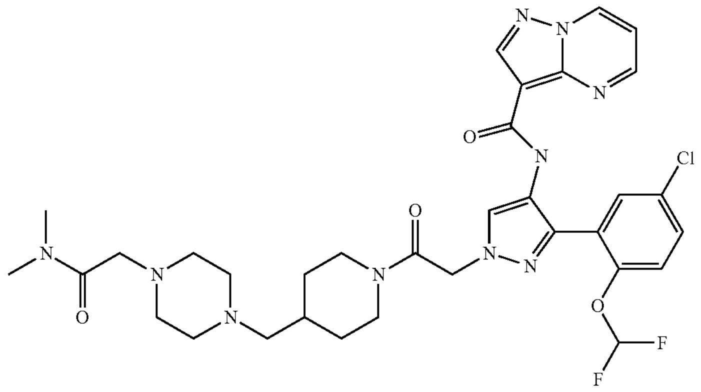 [SMILES: CN(C)C(=O)CN1CCN(CC2CCN(C(=O)Cn3cc(NC(=O)c4cnn5cccnc45)c(-c4cc(Cl)ccc4OC(F)F)n3)CC2)CC1] | N-(3-(5-chloro-2-(difluoromethoxy)phenyl)-1-(2-(4-((4-(2-(dimethylamino)-2-oxoethyl)piperazin-1-yl)methyl)piperidin-1-yl)-2-oxoethyl)-1H-pyrazol-4-yl)pyrazolo[1,5-a]pyrimidine-3-carboxamide |
| 428 | 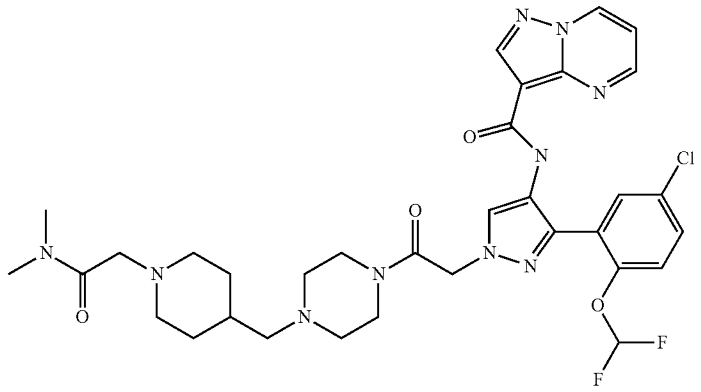 [SMILES: CN(C)C(=O)CN1CCC(CN2CCN(C(=O)Cn3cc(NC(=O)c4cnn5cccnc45)c(-c4cc(Cl)ccc4OC(F)F)n3)CC2)CC1] | N-(3-(5-chloro-2-(difluoromethoxy)phenyl)-1-(2-(4-((1-(2-(dimethylamino)-2-oxoethyl)piperidin-4-yl)methyl)piperazin-1-yl)-2-oxoethyl)-1H-pyrazol-4-yl)pyrazolo[1,5-a]pyrimidine-3-carboxamide |
| 429 | 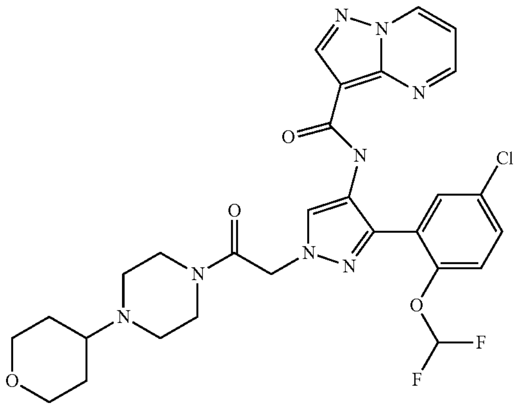 [SMILES: O=C(Nc1cn(CC(=O)N2CCN(C3CCOCC3)CC2)nc1-c1cc(Cl)ccc1OC(F)F)c1cnn2cccnc12] | N-(3-(5-chloro-2-(difluoromethoxy)phenyl)-1-(2-oxo-2-(4-(tetrahydro-2H-pyran-4-yl)piperazin-1-yl)ethyl)-1H-pyrazol-4-yl)pyrazolo[1,5-a]pyrimidine-3-carboxamide |

TABLE 1-continued

| Ex. | Structure | Name |
| --- | --- | --- |
| | Exemplary Compounds of the Present Invention | |
| 430 | 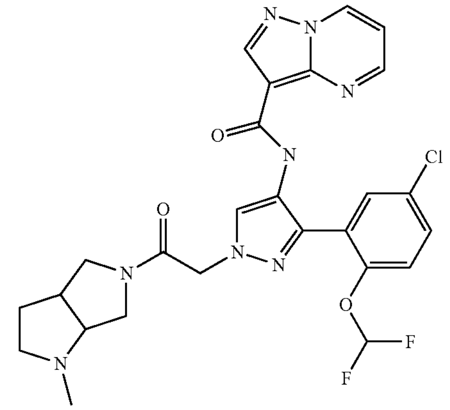 [SMILES: CN1CCC2CN(C(=O)Cn3cc(NC(=O)c4cnn5cccnc45)c(-c4cc(Cl)ccc4OC(F)F)n3)CC21] | N-(3-(5-chloro-2-(difluoromethoxy)phenyl)-1-(2-(1-methyl-hexahydropyrrolo[3,4-b]pyrrol-5(1H)-yl)-2-oxoethyl)-1H-pyrazol-4-yl)pyrazolo[1,5-a]pyrimidine-3-carboxamide |
| 431 | 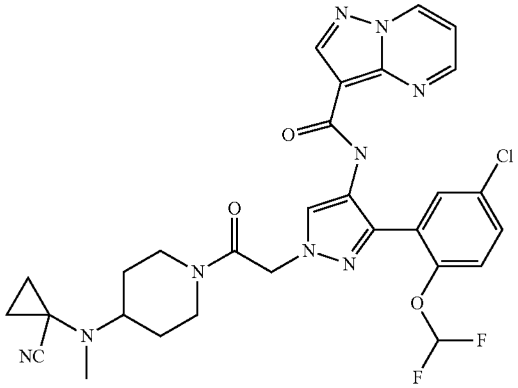 [SMILES: CN(C1CCN(C(=O)Cn2cc(NC(=O)c3cnn4cccnc34)c(-c3cc(Cl)ccc3OC(F)F)n2)CC1)C1(C#N)CC1] | N-(3-(5-chloro-2-(difluoromethoxy)phenyl)-1-(2-(4-((1-cyanocyclopropyl)(methyl)amino)piperidin-1-yl)-2-oxoethyl)-1H-pyrazol-4-yl)pyrazolo[1,5-a]pyrimidine-3-carboxamide |
| 432 | 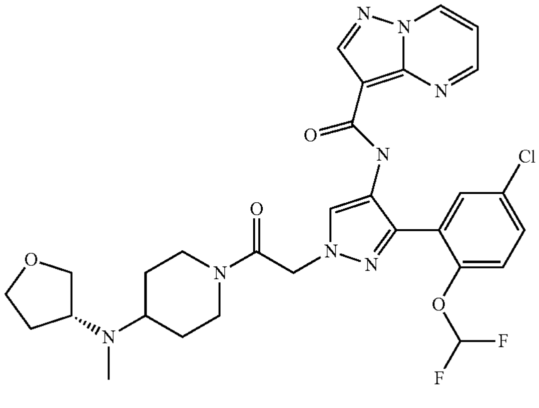 [SMILES: CN(C1CCN(C(=O)Cn2cc(NC(=O)c3cnn4cccnc34)c(-c3cc(Cl)ccc3OC(F)F)n2)CC1)[C@@H]1CCOC1] | N-(3-(5-chloro-2-(difluoromethoxy)phenyl)-1-(2-(4-(methyl((R)-tetrahydrofuran-3-yl)amino)piperidin-1-yl)-2-oxoethyl)-1H-pyrazol-4-yl)pyrazolo[1,5-a]pyrimidine-3-carboxamide |

TABLE 1-continued

| Exemplary Compounds of the Present Invention | | |
|---|---|---|
| Ex. | Structure | Name |
| 433 | 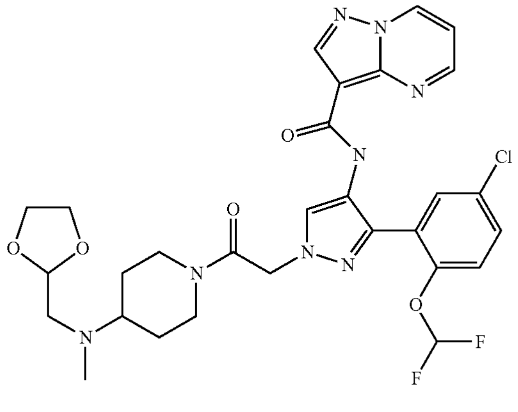 [SMILES: CN(CC1OCCO1)C1CCN(C(=O)Cn2cc(NC(=O)c3cnn4cccnc34)c(-c3cc(Cl)ccc3OC(F)F)n2)CC1] | N-(1-(2-(4-(((1,3-dioxolan-2-yl)methyl)(methyl)amino) piperidin-1-yl)-2-oxoethyl)-3-(5-chloro-2-(difluoromethoxy)phenyl)-1H-pyrazol-4-yl)pyrazolo[1,5-a]pyrimidine-3-carboxamide |
| 434 | 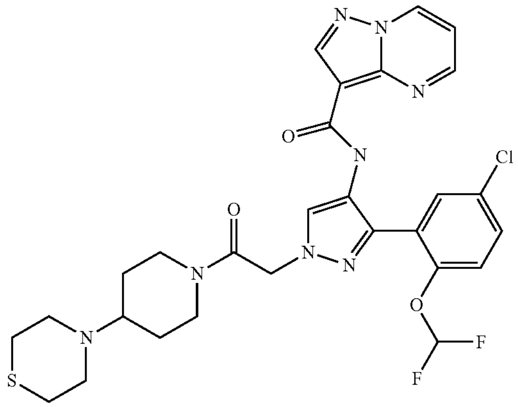 [SMILES: O=C(Nc1cn(CC(=O)N2CCC(N3CCSCC3)CC2)nc1-c1cc(Cl)ccc1OC(F)F)c1cnn2cccnc12] | N-(3-(5-chloro-2-(difluoromethoxy)phenyl)-1-(2-oxo-2-(4-thiomorpholinopiperidin-1-yl)ethyl)-1H-pyrazol-4-yl)pyrazolo[1,5-a]pyrimidine-3-carboxamide |
| 435 | 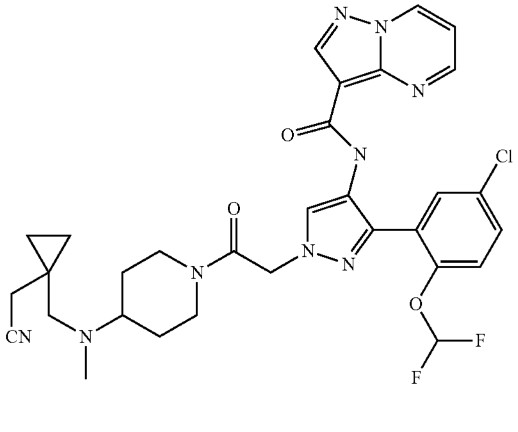 [SMILES: CN(CC1(CC#N)CC1)C1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-(((1-(cyanomethyl)cyclopropyl) methyl)(methyl)amino) piperidin-1-yl)-2-oxoethyl)-1H-pyrazol-4-yl)pyrazolo[1,5-a]pyrimidine-3-carboxamide |

TABLE 1-continued

| Ex. | Structure | Name |
| --- | --- | --- |
| Exemplary Compounds of the Present Invention | | |
| 436 | 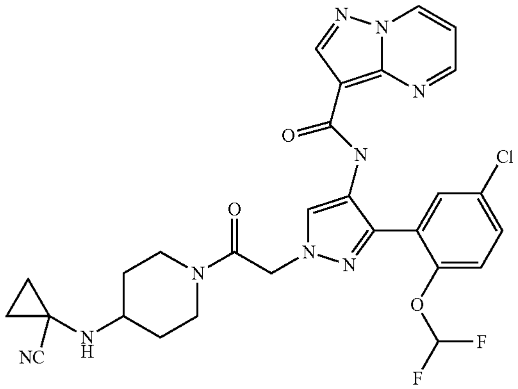 [SMILES: N#CC1(NC2CCN(C(=O)Cn3cc(NC(=O)c4cnn5cccnc45)c(-c4cc(Cl)ccc4OC(F)F)n3)CC2)CC1] | N-(3-(5-chloro-2-(difluoromethoxy)phenyl)-1-(2-(4-(1-cyanocyclopropylamino)piperidin-1-yl)-2-oxoethyl)-1H-pyrazol-4-yl)pyrazolo[1,5-a]pyrimidine-3-carboxamide |
| 437 | 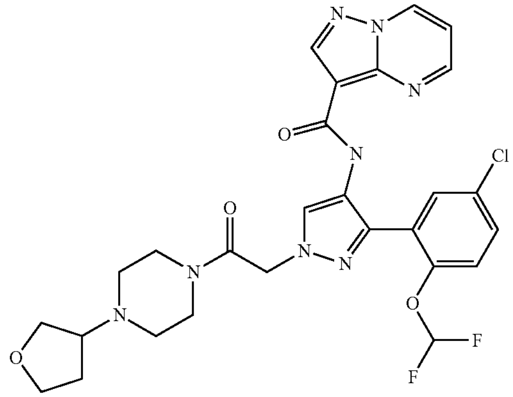 [SMILES: O=C(Nc1cn(CC(=O)N2CCN(C3CCOC3)CC2)nc1-c1cc(Cl)ccc1OC(F)F)c1cnn2cccnc12] | N-(3-(5-chloro-2-(difluoromethoxy)phenyl)-1-(2-oxo-2-(4-(tetrahydrofuran-3-yl)piperazin-1-yl)ethyl)-1H-pyrazol-4-yl)pyrazolo[1,5-a]pyrimidine-3-carboxamide |
| 438 | 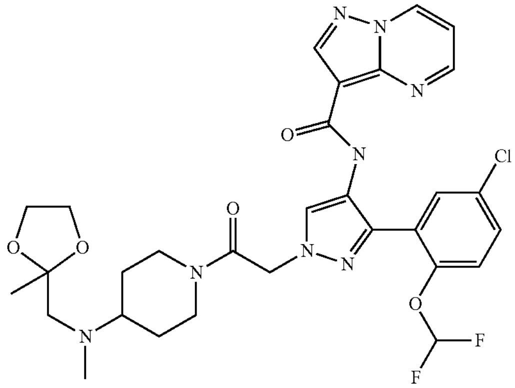 [SMILES: CN(CC1(C)OCCO1)C1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-(methyl((2-methyl-1,3-dioxolan-2-yl)methyl)amino)piperidin-1-yl)-2-oxoethyl)-1H-pyrazol-4-yl)pyrazolo[1,5-a]pyrimidine-3-carboxamide |
| 439 | 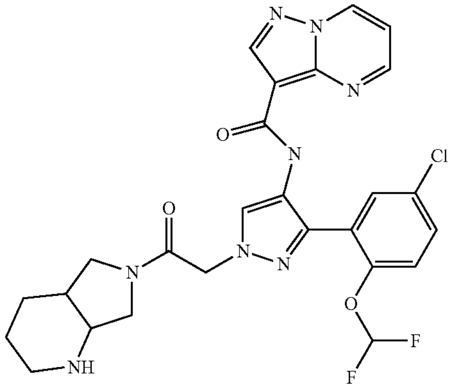 [SMILES: O=C(Nc1cn(CC(=O)N2CC3CCCNC3C2)nc1-c1cc(Cl)ccc1OC(F)F)c1cnn2cccnc12] | N-(3-(5-chloro-2-(difluoromethoxy)phenyl)-1-(2-(octahydropyrrolo[3,4-b]pyridin-6-yl)-2-oxoethyl)-1H-pyrazol-4-yl)pyrazolo[1,5-a]pyrimidine-3-carboxamide |

TABLE 1-continued

| Exemplary Compounds of the Present Invention | | |
|---|---|---|
| Ex. | Structure | Name |
| 440 | 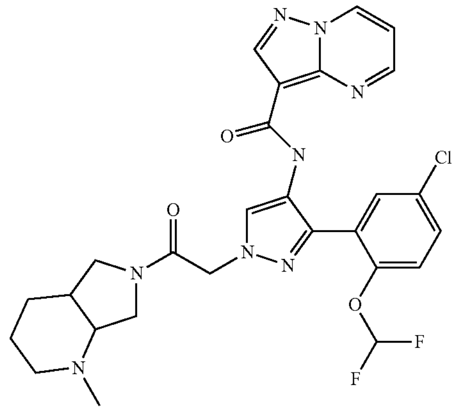 [SMILES: CN1CCCC2CN(C(=O)Cn3cc(NC(=O)c4cnn5cccnc45)c(-c4cc(Cl)ccc4OC(F)F)n3)CC21] | N-(3-(5-chloro-2-(difluoromethoxy)phenyl)-1-(2-(1-methyl-octahydropyrrolo[3,4-b]pyridin-6-yl)-2-oxoethyl)-1H-pyrazol-4-yl)pyrazolo[1,5-a]pyrimidine-3-carboxamide |
| 441 | 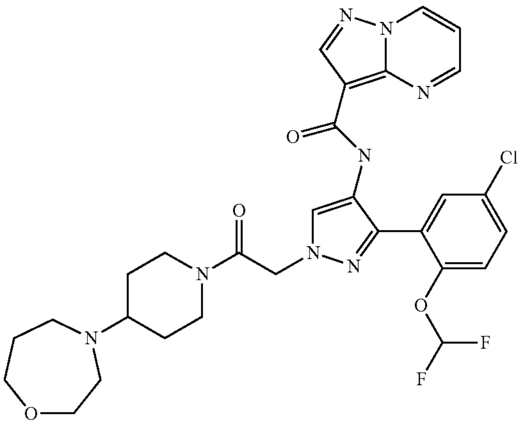 [SMILES: O=C(Nc1cn(CC(=O)N2CCC(N3CCCOCC3)CC2)nc1-c1cc(Cl)ccc1OC(F)F)c1cnn2cccnc12] | N-(1-(2-(4-(1,4-oxazepan-4-yl)piperidin-1-yl)-2-oxoethyl)-3-(5-chloro-2-(difluoromethoxy)phenyl)-1H-pyrazol-4-yl)pyrazolo[1,5-a]pyrimidine-3-carboxamide |
| 442 | 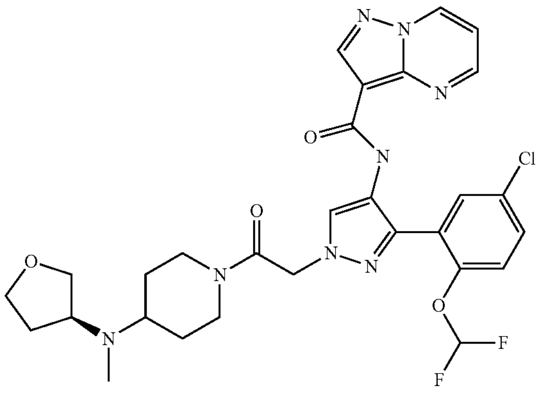 [SMILES: CN(C1CCN(C(=O)Cn2cc(NC(=O)c3cnn4cccnc34)c(-c3cc(Cl)ccc3OC(F)F)n2)CC1)[C@H]1CCOC1] | N-(3-(5-chloro-2-(difluoromethoxy)phenyl)-1-(2-(4-(methyl((S)-tetrahydrofuran-3-yl)amino)piperidin-1-yl)-2-oxoethyl)-1H-pyrazol-4-yl)pyrazolo[1,5-a]pyrimidine-3-carboxamide |

TABLE 1-continued

| Ex. | Structure | Name |
|---|---|---|
| | Exemplary Compounds of the Present Invention | |
| 443 | 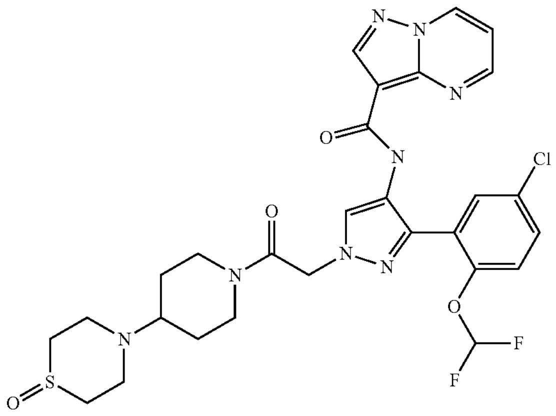 [SMILES: O=C(Nc1cn(CC(=O)N2CCC(N3CCS(=O)CC3)CC2)nc1-c1cc(Cl)ccc1OC(F)F)c1cnn2cccnc12] | N-(3-(5-chloro-2-(difluoromethoxy)phenyl)-1-(2-oxo-2-(4-thiomorpholinopiperidin-1-yl)ethyl)-1H-pyrazol-4-yl)pyrazolo[1,5-a]pyrimidine-3-carboxamide oxide |
| 444 | 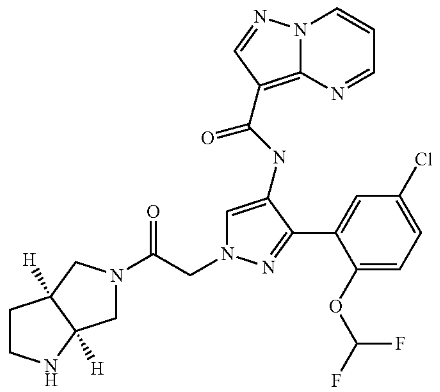 [SMILES: O=C(Nc1cn(CC(=O)N2C[C@@H]3CCN[C@@H]3C2)nc1-c1cc(Cl)ccc1OC(F)F)c1cnn2cccnc12] | N-(3-(5-chloro-2-(difluoromethoxy)phenyl)-1-(2-((3aS,6aS)-hexahydropyrrolo[3,4-b]pyrrol-5(1H)-yl)-2-oxoethyl)-1H-pyrazol-4-yl)pyrazolo[1,5-a]pyrimidine-3-carboxamide |
| 445 | 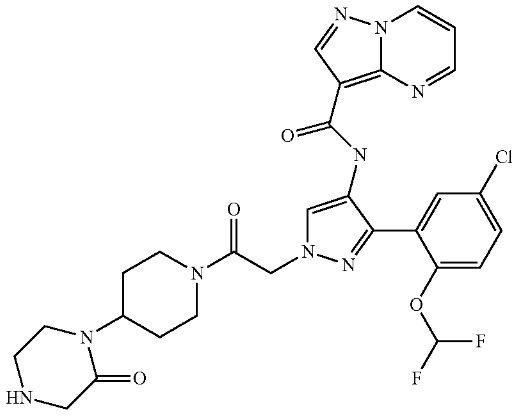 [SMILES: O=C(Nc1cn(CC(=O)N2CCC(N3CCNCC3=O)CC2)nc1-c1cc(Cl)ccc1OC(F)F)c1cnn2cccnc12] | N-(3-(5-chloro-2-(difluoromethoxy)phenyl)-1-(2-oxo-2-(4-(2-oxopiperazin-1-yl)piperidin-1-yl)ethyl)-1H-pyrazol-4-yl)pyrazolo[1,5-a]pyrimidine-3-carboxamide |

TABLE 1-continued

| Ex. | Structure | Name |
| --- | --- | --- |
| | Exemplary Compounds of the Present Invention | |
| 446 | 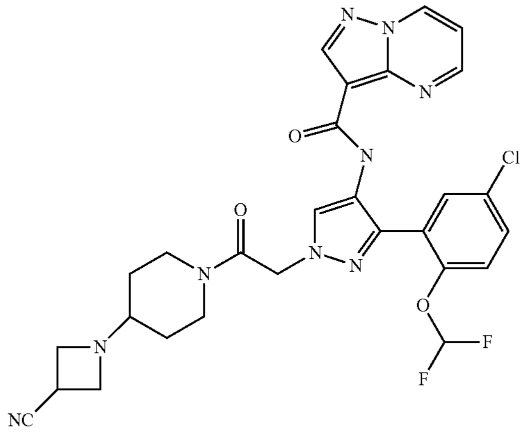 [SMILES: N#CC1CN(C2CCN(C(=O)Cn3cc(NC(=O)c4cnn5cccnc45)c(-c4cc(Cl)ccc4OC(F)F)n3)CC2)C1] | N-(3-(5-chloro-2-(difluoromethoxy)phenyl)-1-(2-(4-(3-cyanoazetidin-1-yl)piperidin-1-yl)-2-oxoethyl)-1H-pyrazol-4-yl)pyrazolo[1,5-a]pyrimidine-3-carboxamide |
| 447 | 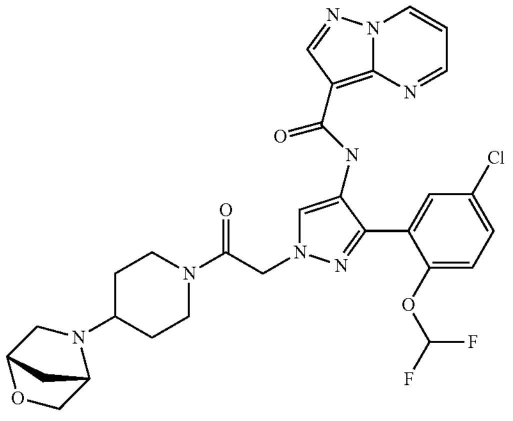 [SMILES: O=C(Nc1cn(CC(=O)N2CCC(N3C[C@@H]4C[C@H]3CO4)CC2)nc1-c1cc(Cl)ccc1OC(F)F)c1cnn2cccnc12] | N-(1-(2-(4-((1S,4S)-5-oxa-2-aza-bicyclo[2.2.1]heptan-2-yl)piperidin-1-yl)-2-oxoethyl)-3-(5-chloro-2-(difluoromethoxy)phenyl)-1H-pyrazol-4-yl)pyrazolo[1,5-a]pyrimidine-3-carboxamide |
| 448 | 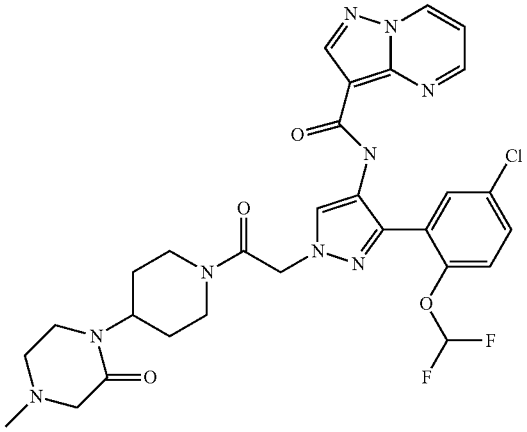 [SMILES: CN1CCN(C2CCN(C(=O)Cn3cc(NC(=O)c4cnn5cccnc45)c(-c4cc(Cl)ccc4OC(F)F)n3)CC2)C(=O)C1] | N-(3-(5-chloro-2-(difluoromethoxy)phenyl)-1-(2-(4-(4-methyl-2-oxopiperazin-1-yl)piperidin-1-yl)-2-oxoethyl)-1H-pyrazol-4-yl)pyrazolo[1,5-a]pyrimidine-3-carboxamide |

TABLE 1-continued

| Exemplary Compounds of the Present Invention | | |
|---|---|---|
| Ex. | Structure | Name |
| 449 | 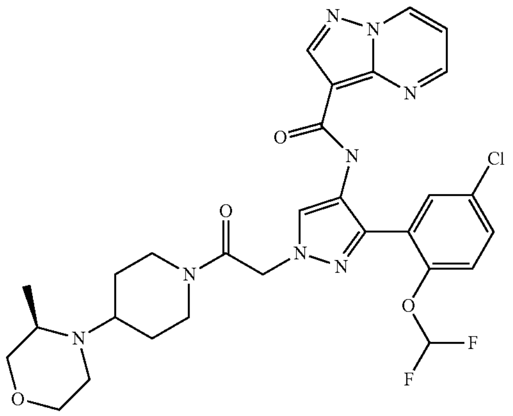 [SMILES: C[C@@H]1COCCN1C1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-((R)-3-methylmorpholino)piperidin-1-yl)-2-oxoethyl)-1H-pyrazol-4-yl)pyrazolo[1,5-a]pyrimidine-3-carboxamide |
| 450 | 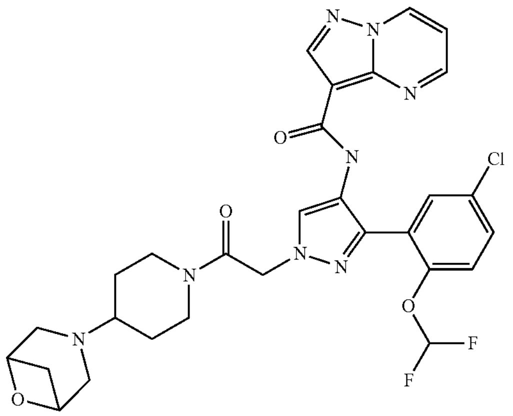 [SMILES: O=C(Nc1cn(CC(=O)N2CCC(N3CC4CC(C3)O4)CC2)nc1-c1cc(Cl)ccc1OC(F)F)c1cnn2cccnc12] | N-(1-(2-(4-(6-oxa-3-aza-bicyclo[3.1.1]heptan-3-yl)piperidin-1-yl)-2-oxoethyl)-3-(5-chloro-2-(difluoromethoxy)phenyl)-1H-pyrazol-4-yl)pyrazolo[1,5-a]pyrimidine-3-carboxamide |
| 451 | 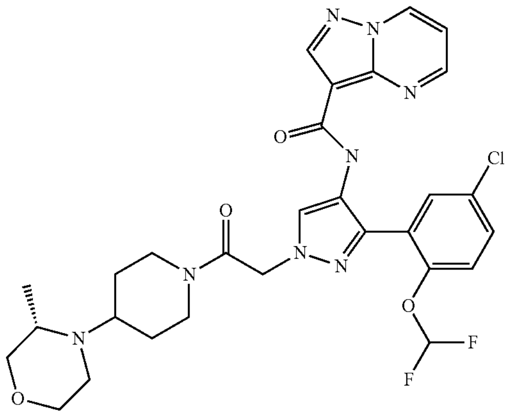 [SMILES: C[C@H]1COCCN1C1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-((S)-3-methylmorpholino)piperidin-1-yl)-2-oxoethyl)-1H-pyrazol-4-yl)pyrazolo[1,5-a]pyrimidine-3-carboxamide |

TABLE 1-continued

| Ex. | Structure | Name |
|---|---|---|
| Exemplary Compounds of the Present Invention | | |
| 452 | 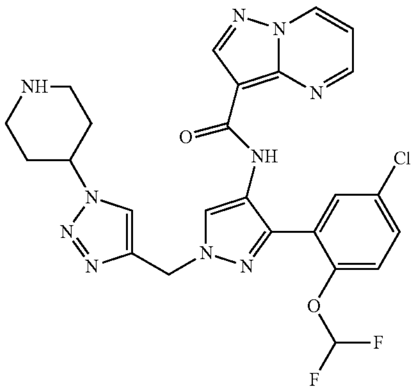 [SMILES: O=C(Nc1cn(Cc2cn(C3CCNCC3)nn2)nc1-c1cc(Cl)ccc1OC(F)F)c1cnn2cccnc12] | N-(3-(5-chloro-2-(difluoromethoxy)phenyl)-1-((1-(piperidin-4-yl)-1H-1,2,3-triazol-4-yl)methyl)-1H-pyrazol-4-yl)pyrazolo[1,5-a]pyrimidine-3-carboxamide |
| 453 | 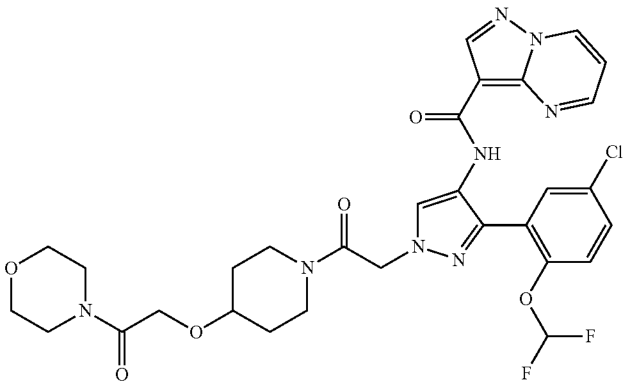 [SMILES: O=C(Nc1cn(CC(=O)N2CCC(OCC(=O)N3CCOCC3)CC2)nc1-c1cc(Cl)ccc1OC(F)F)c1cnn2cccnc12] | N-(3-(5-chloro-2-(difluoromethoxy)phenyl)-1-(2-(4-(2-morpholino-2-oxoethoxy)piperidin-1-yl)-2-oxoethyl)-1H-pyrazol-4-yl)pyrazolo[1,5-a]pyrimidine-3-carboxamide |
| 454 | 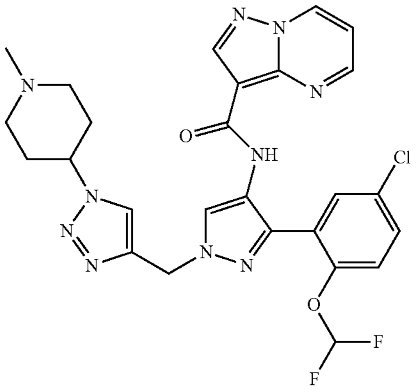 [SMILES: CN1CCC(n2cc(Cn3cc(NC(=O)c4cnn5cccnc45)c(-c4cc(Cl)ccc4OC(F)F)n3)nn2)CC1] | N-(3-(5-chloro-2-(difluoromethoxy)phenyl)-1-((1-(1-methylpiperidin-4-yl)-1H-1,2,3-triazol-4-yl)methyl)-1H-pyrazol-4-yl)pyrazolo[1,5-a]pyrimidine-3-carboxamide |

TABLE 1-continued

| Exemplary Compounds of the Present Invention | | |
|---|---|---|
| Ex. | Structure | Name |
| 455 | 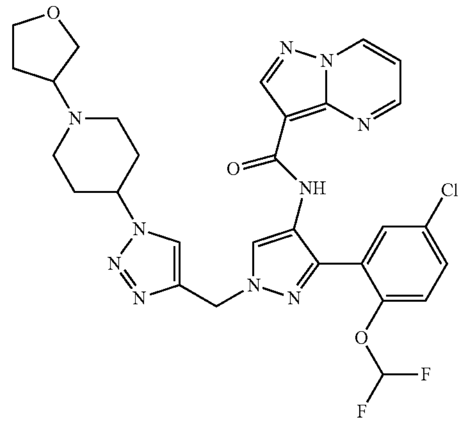 [SMILES: O=C(Nc1cn(Cc2cn(C3CCN(C4CCOC4)CC3)nn2)nc1-c1cc(Cl)ccc1OC(F)F)c1cnn2cccnc12] | N-(3-(5-chloro-2-(difluoromethoxy)phenyl)-1-((1-(1-(tetrahydrofuran-3-yl)piperidin-4-yl)-1H-1,2,3-triazol-4-yl)methyl)-1H-pyrazol-4-yl)pyrazolo[1,5-a]pyrimidine-3-carboxamide |
| 456 | 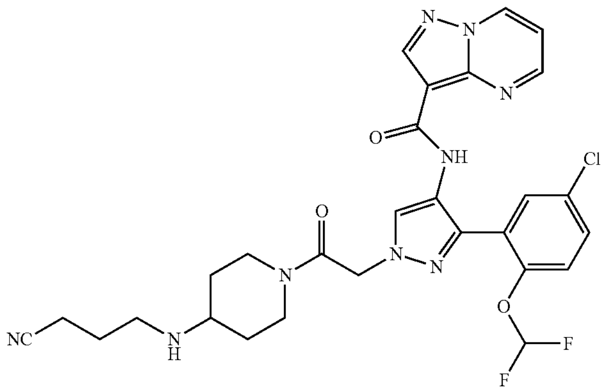 [SMILES: N#CCCCNC1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-(3-cyanopropylamino)piperidin-1-yl)-2-oxoethyl)-1H-pyrazol-4-yl)pyrazolo[1,5-a]pyrimidine-3-carboxamide |
| 457 | 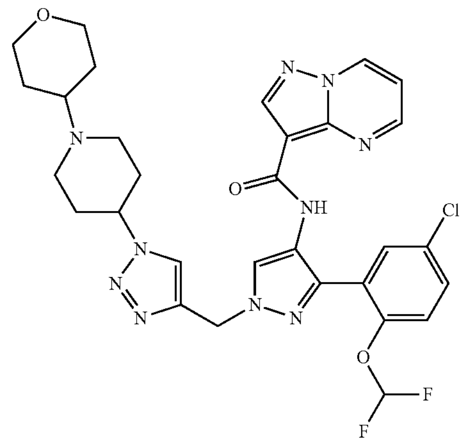 [SMILES: O=C(Nc1cn(Cc2cn(C3CCN(C4CCOCC4)CC3)nn2)nc1-c1cc(Cl)ccc1OC(F)F)c1cnn2cccnc12] | N-(3-(5-chloro-2-(difluoromethoxy)phenyl)-1-((1-(1-(tetrahydro-2H-pyran-4-yl)piperidin-4-yl)-1H-1,2,3-triazol-4-yl)methyl)-1H-pyrazol-4-yl)pyrazolo[1,5-a]pyrimidine-3-carboxamide |

TABLE 1-continued

| Ex. | Structure | Name |
|---|---|---|
| Exemplary Compounds of the Present Invention | | |
| 458 | 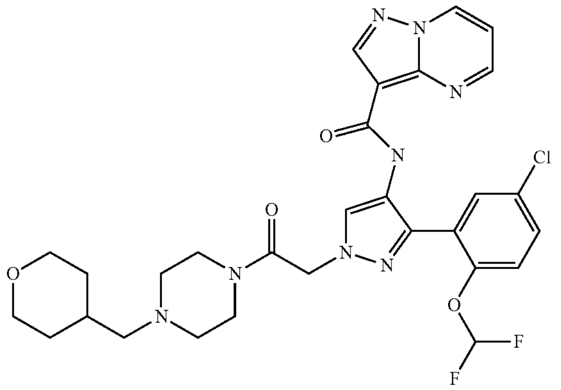 [SMILES: O=C(Nc1cn(CC(=O)N2CCN(CC3CCOCC3)CC2)nc1-c1cc(Cl)ccc1OC(F)F)c1cnn2cccnc12] | N-(3-(5-chloro-2-(difluoromethoxy)phenyl)-1-(2-oxo-2-(4-((tetrahydro-2H-pyran-4-yl)methyl)piperazin-1-yl)ethyl)-1H-pyrazol-4-yl)pyrazolo[1,5-a]pyrimidine-3-carboxamide |
| 459 | 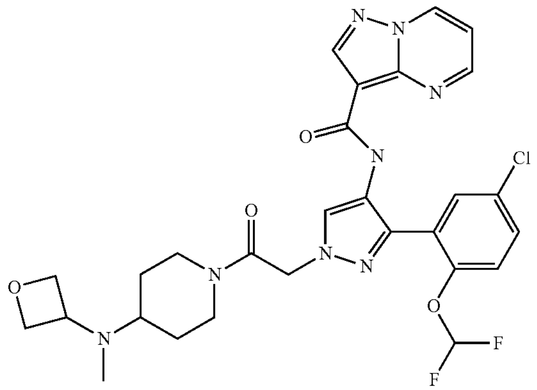 [SMILES: CN(C1CCN(C(=O)Cn2cc(NC(=O)c3cnn4cccnc34)c(-c3cc(Cl)ccc3OC(F)F)n2)CC1)C1COC1] | N-(3-(5-chloro-2-(difluoromethoxy)phenyl)-1-(2-(4-(methyl(oxetan-3-yl)amino)piperidin-1-yl)-2-oxoethyl)-1H-pyrazol-4-yl)pyrazolo[1,5-a]pyrimidine-3-carboxamide |
| 460 | 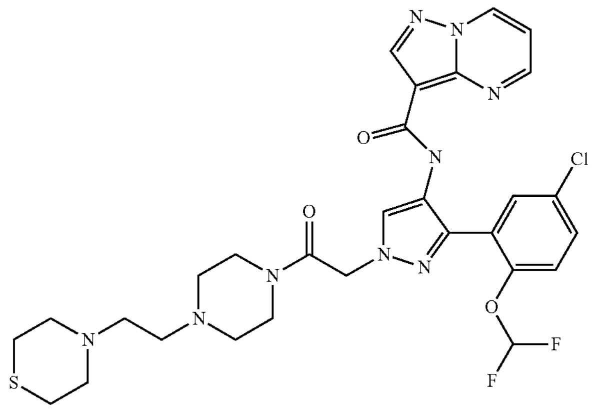 [SMILES: O=C(Nc1cn(CC(=O)N2CCN(CCN3CCSCC3)CC2)nc1-c1cc(Cl)ccc1OC(F)F)c1cnn2cccnc12] | N-(3-(5-chloro-2-(difluoromethoxy)phenyl)-1-(2-oxo-2-(4-(2-thiomorpholinoethyl) piperazin-1-yl)ethyl)-1H-pyrazol-4-yl)pyrazolo[1,5-a]pyrimidine-3-carboxamide |
| 461 | 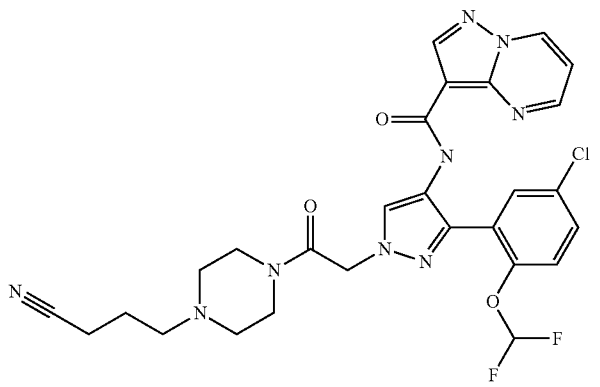 [SMILES: N#CCCCN1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-(3-cyanopropyl)piperazin-1-yl)-2-oxoethyl)-1H-pyrazol-4-yl)pyrazolo[1,5-a]pyrimidine-3-carboxamide |

TABLE 1-continued

| Exemplary Compounds of the Present Invention | | |
|---|---|---|
| Ex. | Structure | Name |
| 462 | 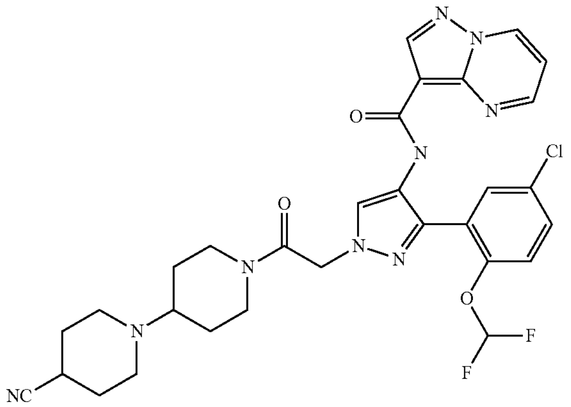 [SMILES: N#CC1CCN(C2CCN(C(=O)Cn3cc(NC(=O)c4cnn5cccnc45)c(-c4cc(Cl)ccc4OC(F)F)n3)CC2)CC1] | N-(3-(5-chloro-2-(difluoromethoxy)phenyl)-1-(2-(4-cyano-1,4'-bipiperidin-1'-yl)-2-oxoethyl)-1H-pyrazol-4-yl)pyrazolo[1,5-a]pyrimidine-3-carboxamide |
| 463 | 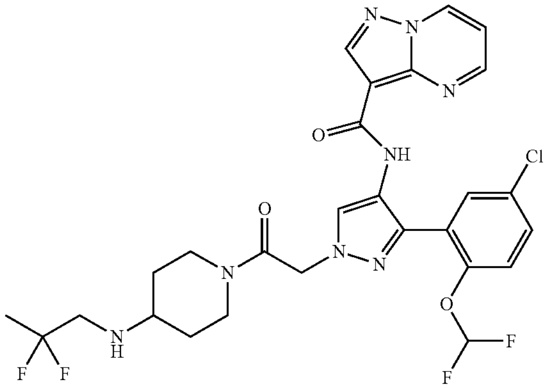 [SMILES: CC(F)(F)CNC1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-(2,2-difluoropropylamino)piperidin-1-yl)-2-oxoethyl)-1H-pyrazol-4-yl)pyrazolo[1,5-a]pyrimidine-3-carboxamide |
| 464 | 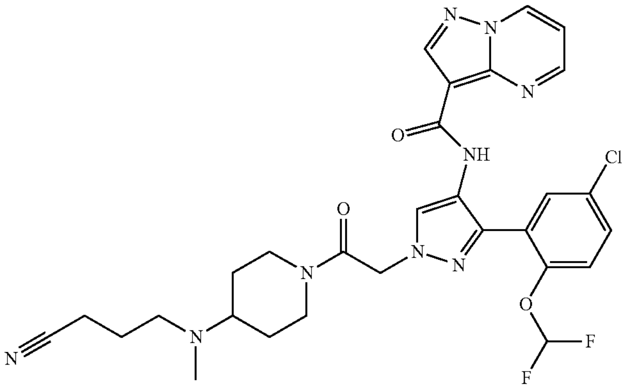 [SMILES: CN(CCCC#N)C1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-((3-cyanopropyl)(methyl)amino)piperidin-1-yl)-2-oxoethyl)-1H-pyrazol-4-yl)pyrazolo[1,5-a]pyrimidine-3-carboxamide |

TABLE 1-continued

| Ex. | Structure | Name |
| --- | --- | --- |
| | Exemplary Compounds of the Present Invention | |
| 465 | 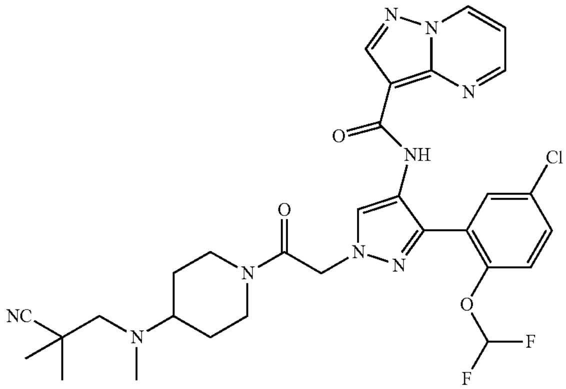 [SMILES: CN(CC(C)(C)C#N)C1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-((2-cyano-2-methylpropyl)(methyl)amino)piperidin-1-yl)-2-oxoethyl)-1H-pyrazol-4-yl)pyrazolo[1,5-a]pyrimidine-3-carboxamide |
| 466 | 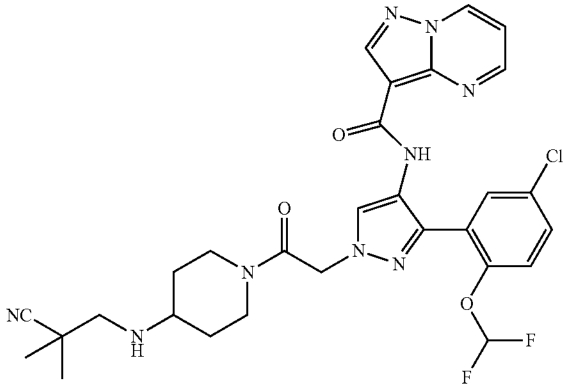 [SMILES: CC(C)(C#N)CNC1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-(2-cyano-2-methylpropylamino)piperidin-1-yl)-2-oxoethyl)-1H-pyrazol-4-yl)pyrazolo[1,5-a]pyrimidine-3-carboxamide |
| 467 | 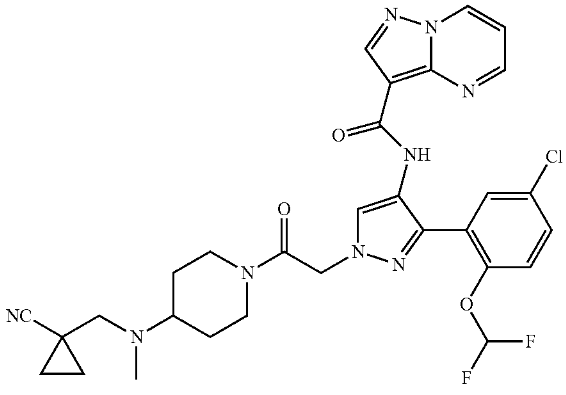 [SMILES: CN(CC1(C#N)CC1)C1CCN(C(=O)Cn2cc(NC(=O)c3cnn4cccnc34)c(-c3cc(Cl)ccc3OC(F)F)n2)CC1] | N-(3-(5-chloro-2-(difluoromethoxy)phenyl)-1-(2-(4-(((1-cyanocyclopropyl)methyl)(methyl)amino)piperidin-1-yl)-2-oxoethyl)-1H-pyrazol-4-yl)pyrazolo[1,5-a]pyrimidine-3-carboxamide |

TABLE 1-continued

| Exemplary Compounds of the Present Invention | | |
|---|---|---|
| Ex. | Structure | Name |
| 468 | 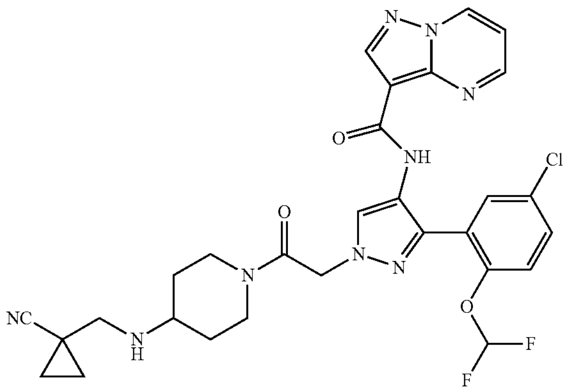 [SMILES: N#CC1(CNC2CCN(C(=O)Cn3cc(NC(=O)c4cnn5cccnc45)c(-c4cc(Cl)ccc4OC(F)F)n3)CC2)CC1] | N-(3-(5-chloro-2-(difluoromethoxy)phenyl)-1-(2-(4-(((1-cyanocyclopropyl)methyl)amino)piperidin-1-yl)-2-oxoethyl)-1H-pyrazol-4-yl)pyrazolo[1,5-a]pyrimidine-3-carboxamide |

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

Another aspect includes prodrugs of the compounds of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, including known amino-protecting and carboxy-protecting groups which are released, for example hydrolyzed, to yield the compound of the present invention under physiologic conditions.

The term "prodrug" refers to a precursor or derivative form of a pharmaceutically active substance that is less efficacious to the patient compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, and 5-fluorocytosine and 5-fluorouridine prodrugs.

A particular class of prodrugs are compounds in which a nitrogen atom in an amino, amidino, aminoalkyleneamino, iminoalkyleneamino or guanidino group is substituted with a hydroxy group, an alkylcarbonyl (—CO—R) group, an alkoxycarbonyl (—CO—OR), or an acyloxyalkyl-alkoxycarbonyl (—CO—O—R—O—CO—R) group where R is a monovalent or divalent group, for example alkyl, alkylene or aryl, or a group having the Formula —C(O)—O—CP1P2-haloalkyl, where P1 and P2 are the same or different and are hydrogen, alkyl, alkoxy, cyano, halogen, alkyl or aryl. In a particular embodiment, the nitrogen atom is one of the nitrogen atoms of the amidino group of the compounds of Formula (00A), (0A) or (A) or a subformula thereof. Prodrugs may be prepared by reacting a compound of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, with an activated group, such as acyl groups, to bond, for example, a nitrogen atom in the compound to the exemplary carbonyl of the activated acyl group. Examples of activated carbonyl compounds are those containing a leaving group bonded to the carbonyl group, and include, for example, acyl halides, acyl amines, acyl pyridinium salts, acyl alkoxides, acyl phenoxides such as p-nitrophenoxy acyl, dinitrophenoxy acyl, fluorophenoxy acyl, and difluorophenoxy acyl. The reactions are generally carried out in inert solvents at reduced temperatures such as −78 to about 50° C. The reactions may also be carried out in the presence of an inorganic base, for example potassium carbonate or sodium bicarbonate, or an organic base such as an amine, including pyridine, trimethylamine, triethylamine, triethanolamine, or the like.

Additional types of prodrugs are also encompassed. For instance, a free carboxyl group of a compound of the invention, such as a compound of Formula (00A), (0A), (A), (Ia), (Ib), (II), (III), (IV), (V), (VI), (VII), (VIII), (IX), or (X), or suitable free carboxyl-containing compound of Table 1 or of Examples 1-468, can be derivatized as an amide or alkyl ester. As another example, compounds of the present invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, alpha-amino($C_1$-$C_4$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_1$-$C_6)alkyl)_2$ or glycosyl (the radical resulting from the removal of a hydroxyl group of the hemiacetal form of a carbohydrate).

"Leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

Synthesis of Janus Kinase Inhibitor Compounds

Compounds of the present invention may be synthesized by synthetic routes described herein. In certain embodiments, processes well-known in the chemical arts can be used, in addition to, or in light of, the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, N.Y. (1967-1999 ed.), Beilsteins Handbuch der organischen Chemie, 4, Aufl. ed. Springer-Verlag, Berlin, including supplements (also available via the Beilstein online database)), or Comprehensive Heterocyclic Chemistry, Editors Katrizky and Rees, Pergamon Press, 1984.

Compounds may be prepared singly or as compound libraries comprising at least 2, for example 5 to 1,000 compounds, or 10 to 100 compounds. Libraries of compounds may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of the present invention, such as a compound of Formula (00A), (0A), (A), (Ia), (Ib), (II), (III), (IV), (V), (VI), (VII), (VIII), (IX), or (X), or a compound of Table 1 or of Examples 1-468.

For illustrative purposes, reaction Schemes 1-26 depicted below provide routes for synthesizing the compounds of the present invention as well as key intermediates. For a more detailed description of the individual reaction steps, see the Examples section below. Those skilled in the art will appreciate that other synthetic routes may be used. Although some specific starting materials and reagents are depicted in the Schemes and discussed below, other starting materials and reagents can be substituted to provide a variety of derivatives or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, benzyl, phenylsulfonyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Other conversions commonly used in the synthesis of compounds of the present invention, and which can be carried out using a variety of reagents and conditions, include the following:

(1) Reaction of a carboxylic acid with an amine to form an amide. Such a transformation can be achieved using various reagents known to those skilled in the art but a comprehensive review can be found in *Tetrahedron,* 2005, 61, 10827-10852.

(2) Reaction of a primary or secondary amine with an aryl halide or pseudo halide, e.g., a triflate, commonly known as a "Buchwald-Hartwig cross-coupling," can be achieved using a variety of catalysts, ligands and bases. A review of these methods is provided in *Comprehensive Organic Name Reactions and Reagents,* 2010, 575-581.

(3) A palladium cross-coupling reaction between an aryl halide and a vinyl boronic acid or boronate ester. This transformation is a type of "Suzuki-Miyaura cross-coupling," a class of reaction that has been thoroughly reviewed in *Chemical Reviews,* 1995, 95(7), 2457-2483.

(4) The hydrolysis of an ester to give the corresponding carboxylic acid is well known to those skilled in the art and conditions include: for methyl and ethyl esters, the use of a strong aqueous base such as lithium, sodium or potassium hydroxide or a strong aqueous mineral acid such as HCl; for a tert-butyl ester, hydrolysis would be carried out using acid, for example, HCl in dioxane or trifluoroacetic acid (TFA) in dichloromethane (DCM).

Other exemplary transformations are discussed following the Schemes below.

Reaction Scheme 1

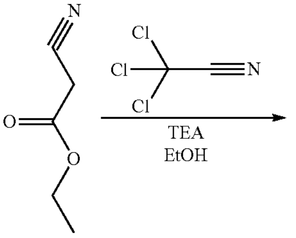

-continued

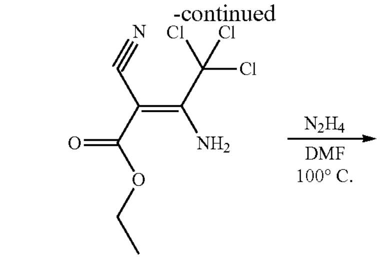

1

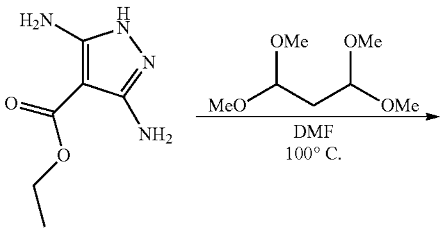

2

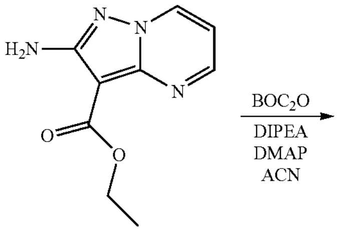

3

-continued

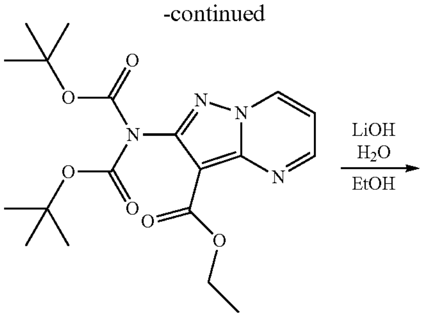

4

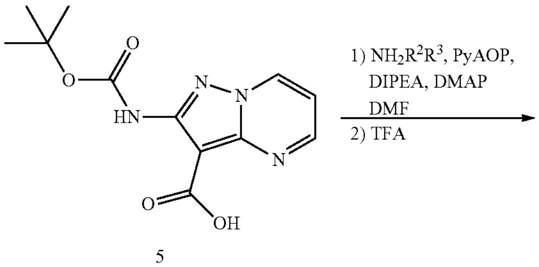

5

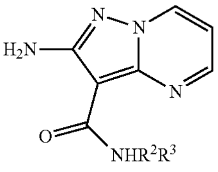

6

Compounds of formula 6 can be synthesized as shown in reaction Scheme 1. Trichloroacetonitrile can be reacted with cyanoacetic acid ethyl ester to give compound 34. Compound 1 can be condensed with hydrazine to give compound 2, which can then be condensed with 1,1,3,3-tetramethoxypropane to give compound 3. Amine 3 can be doubly Boc-protected to give compound 4, which can then be hydrolyzed with lithium hydroxide to give carboxylic acid 5. Carboxylic acid 5 can then be coupled to various amines in the presence of PyAOP, DIEA, and DMAP to give compounds of formula 6.

Reaction Scheme 2

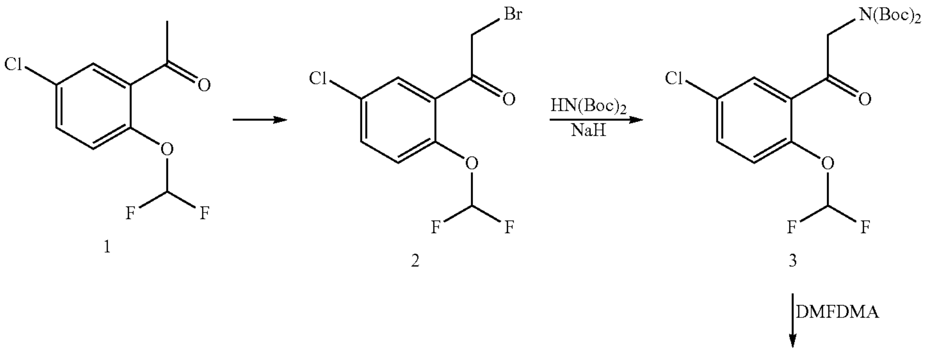

1 2 3

-continued

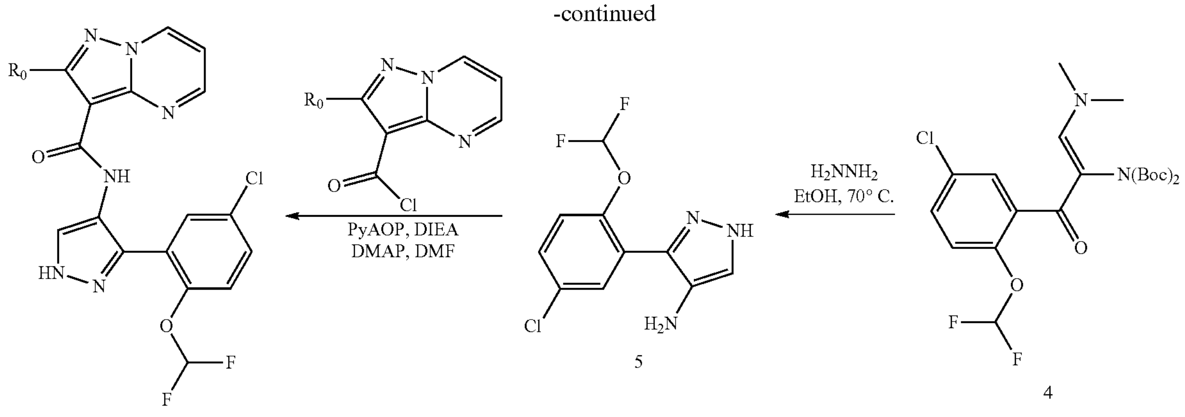

6 5 4

A method for the synthesis of compounds of Formula 5 is illustrated in Reaction Scheme 2. α-Bromoketones can be generated from compound 1 with a reagent such as bromine. Alkylation of di-tert-butyl iminodicarbonate with sodium hydride and various α-bromoketones 2 generates compound 3. Compound 3 can be heated with DMFDMA to give compound 4. Cyclization of compound 4 with hydrazine in ethanol provides pyrazole compound 5. Coupling of compound 5 with pyrazolo[1,5-a]pyrimidine-3-carboxylic acid in the presence of PyAOP, DIEA, and DMAP provides compounds of Formula 6.

Reaction Scheme 3

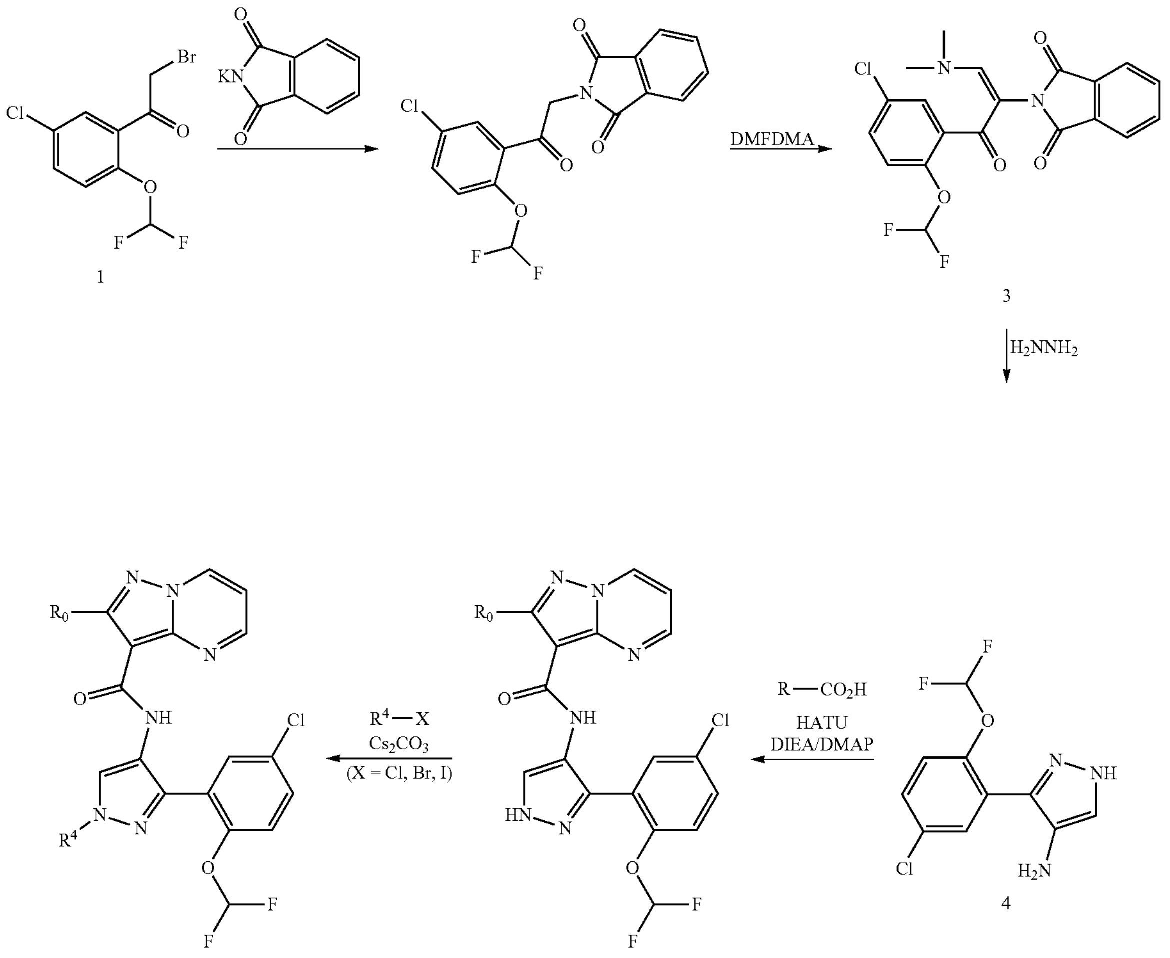

1 3 6 5 4

An alternative method for the synthesis of compounds of Formula 6 is described in Reaction Scheme 3. Alkylation of potassium phthalimide with α-bromoketones 1 generates compound 2. Condensation with DMFDMA yields compounds 3. Compound 3 may be cyclized with hydrazine to yield compound 4, which may then be coupled with pyrazolo[1,5-a]pyrimidine-3-carboxylic acid under amide formation conditions using HATU to provide compounds of Formula 5. Alkylation of compound 5 with alkyl halides in the presence of cesium carbonate gives compounds of Formula 6.

Reaction Scheme 4

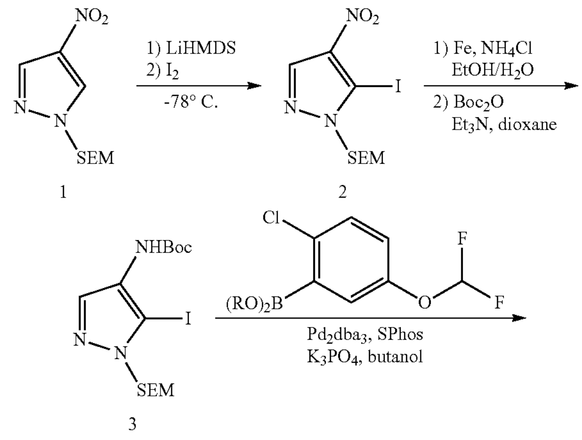

-continued

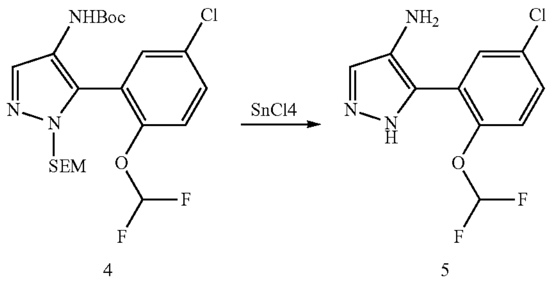

Reaction Scheme 4 illustrates an alternate synthesis for compounds of formula 5. Nitro-SEM pyrazole compound 1, prepared as in Reaction Scheme 5, may be regioselectively deprotonated with lithium hexamethyldisilazide at low temperature and quenched with iodine to yield 2. The nitro group of compound 2 can be reduced in the presence of iron and ammonium chloride, followed by Boc protection to generate compound 3. Compound 3 may be coupled under Suzuki conditions with aryl boronic acids or aryl boronates to yield compounds 4. After cleavage of the Boc group with tin tetrachloride, compounds of formula 5 are obtained.

Reaction Scheme 5

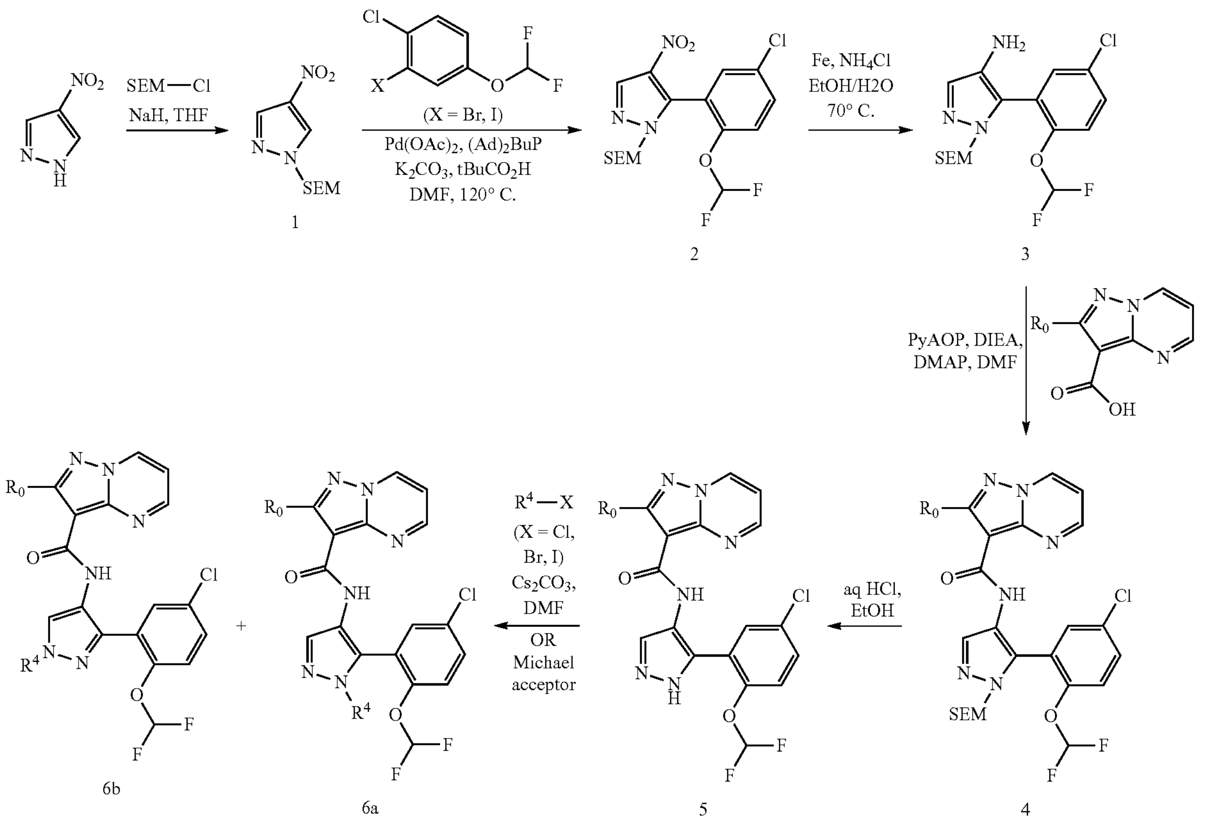

An alternate method for the synthesis of compounds of Formula 6a and 6b is shown in Reaction Scheme 5. Commercially available 4-nitro-1H-pyrazole may be protected with a [β-(trimethylsilyl)ethoxy]methyl (SEM) group by treatment with sodium hydride and (2-(chloromethoxy) ethyl)trimethylsilane. The resulting compound 1 can be arylated with aryl bromides or iodides under palladium catalyzed conditions to generated 4-nitro-5-aryl-pyrazoles of formula 2. The nitro group of compounds 2 can be reduced in the presence of iron and ammonium chloride to generate amino pyrazoles 3. Amide bond coupling with commercially available pyrazolo[1,5-a]pyrimidine-3-carboxylic acid in the presence of PyAOP, DIEA, and DMAP provides compounds 4. Removal of the SEM protecting group by aqueous HCl in ethanol generates compounds 5, which may be alkylated with alkyl halides in the presence of a suitable base such as cesium carbonate or with Michael acceptors to provide compounds of Formula 6a and 6b.

Reaction Scheme 6

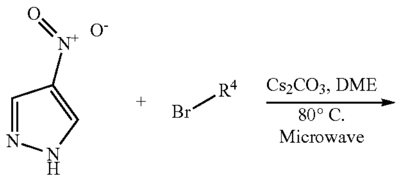

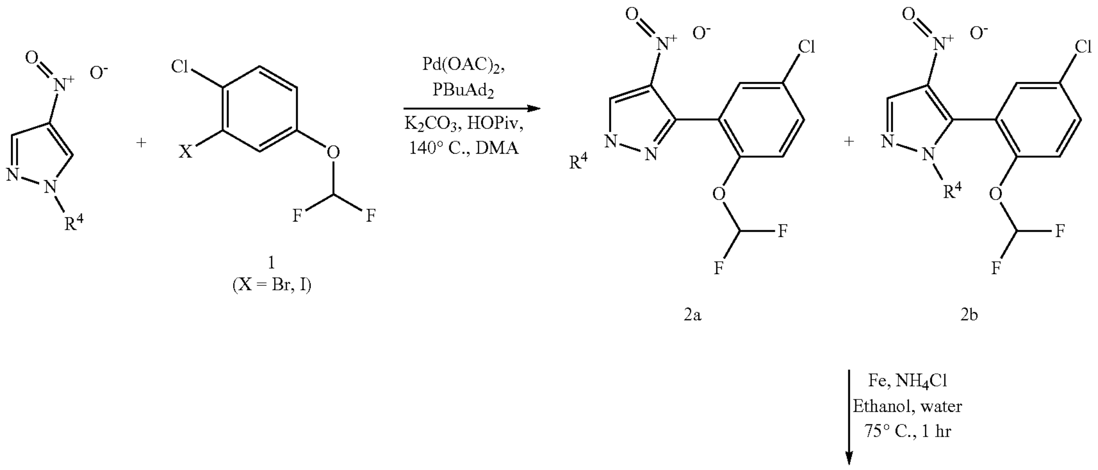

1
(X = Br, I)

2a

2b

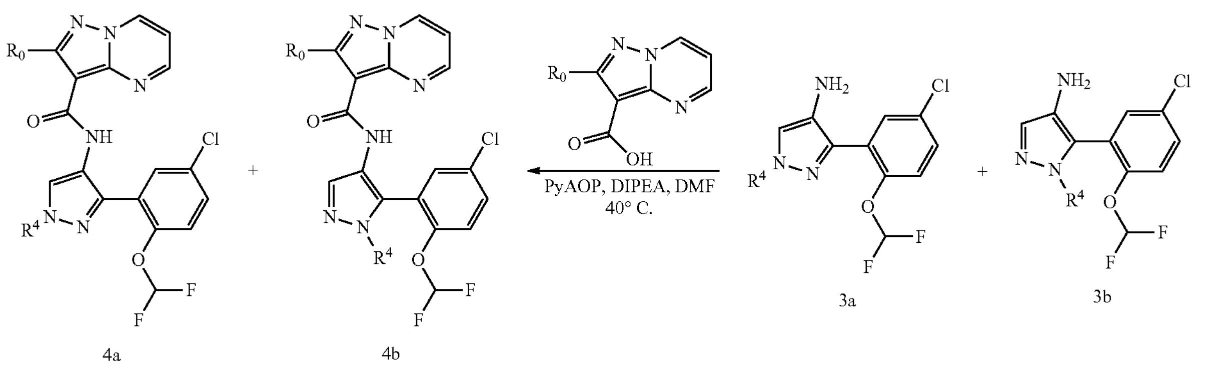

4a

4b

3a

3b

An alternate method for the synthesis of compounds of Formula 4a and 4b is shown in Reaction Scheme 6. Commercially available 4-Nitro-1H-pyrazole can be reacted with alkyl bromides in the presence of cesium carbonate at 55° C. for 12 hours to give compound 1. Compound 1 can be reacted with aryl bromides in N,N-Dimethylacetamide in the presence of Palladium (II) acetate, Di(1-adamntyl)-n-butylphosphine, potassium carbonate and trimethylacetic acid to give compounds 2a and 2b. The ratio of products 2a:2b varies depending on the substituent R1, but the reaction generally favors formation of product 2b. Compounds 32a and 32b can be reduced to compounds 3a and 3b in the presence of iron and ammonium chloride in ethanol and water. Coupling of compounds 3a and 3b with pyrazolo[1,5-a]pyrimidine-3-carboxylic acid in the presence of PyAOP, DIEA, and DMAP can provide compounds of Formula 4a and 4b.

Reaction Scheme 7

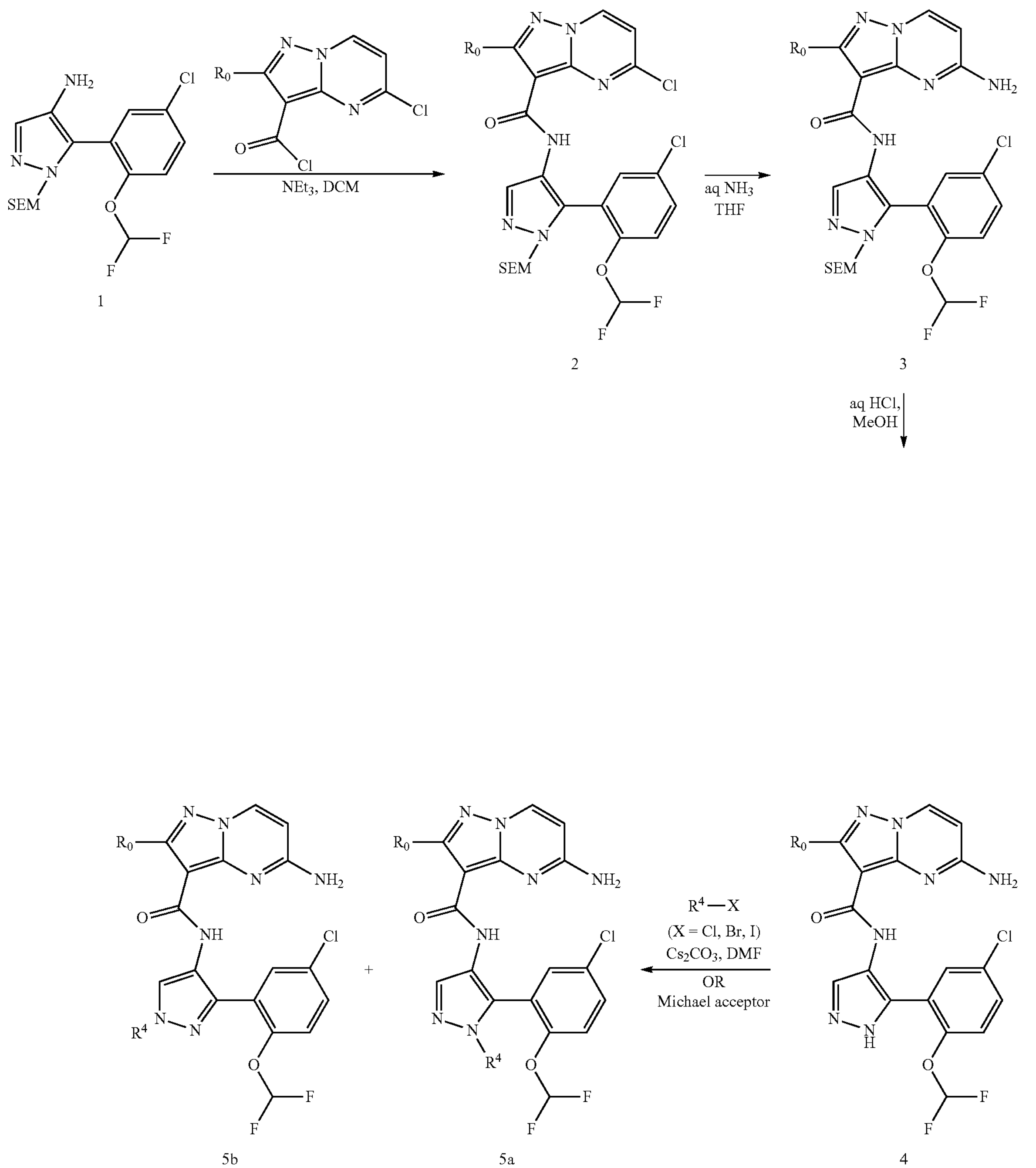

1, 2, 3, 5b, 5a, 4

Amide bond coupling of 1 with 5-chloro-pyrazolo[1,5-α] pyrimidine-3-carbonyl chloride (prepared according to the procedure in Journal of Medicinal Chemistry, 55(22), 10090-10107; 2012) in the presence of triethylamine provides compounds of formula 2. Treatment of 2 with aqueous ammonia generates compounds of formula 3. Removal of the SEM protecting group by aqueous HCl in methanol generates compounds of formula 4, which may be alkylated with alkyl halides in the presence of a suitable base such as cesium carbonate or with Michael acceptors to provide compounds of Formula 5a and 5b.

Reaction Scheme 8

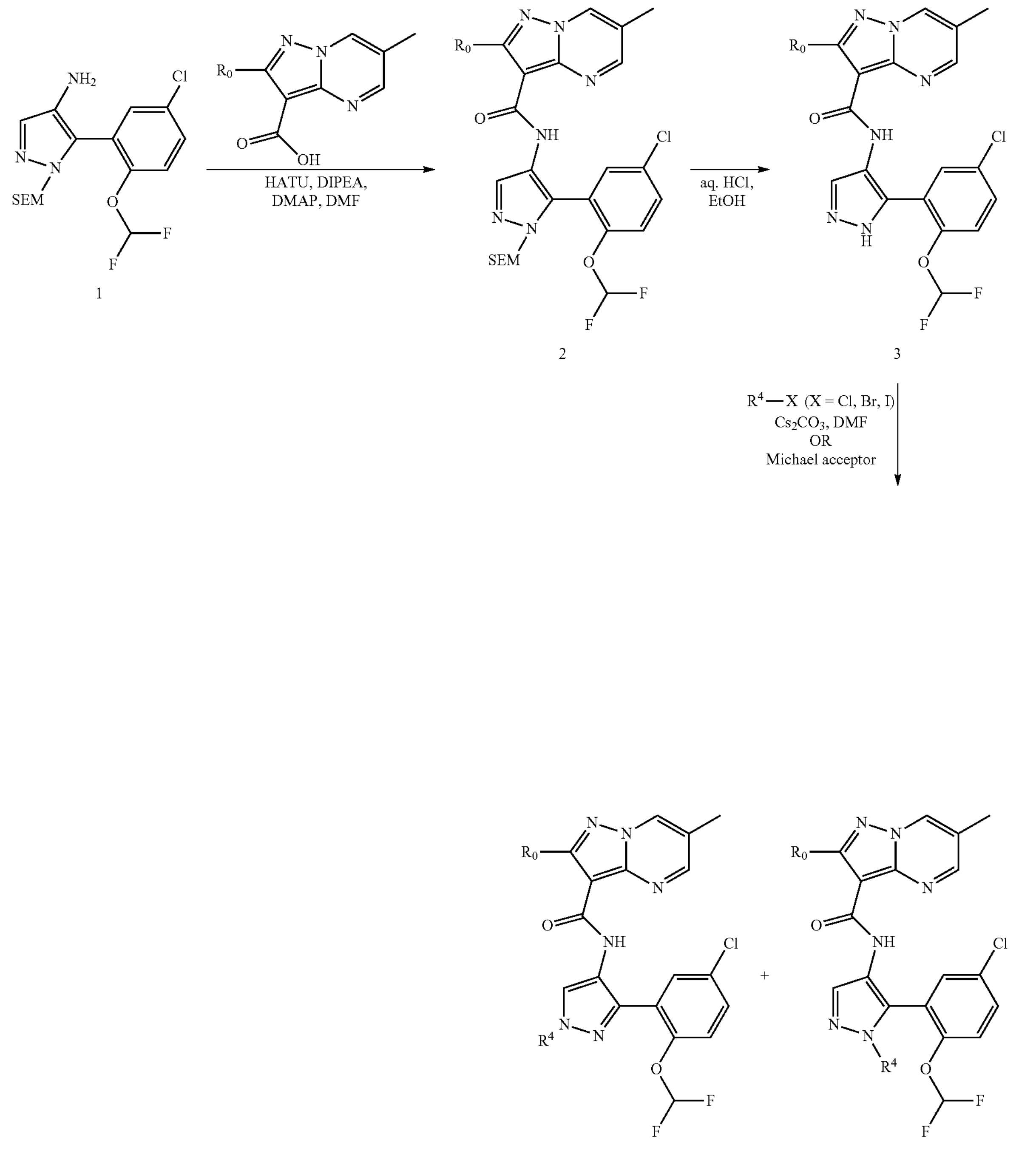

1

2

3

4b

4a

A method for the synthesis of compounds of Formula 4a and 4b is shown in Reaction Scheme 8. An amide bond coupling of compound 1 with commercially available 6-methyl-pyrazolo[1,5-a]pyrimidine-3-carboxylic acid in the presence of HATU and DIPEA provides compound 2. Removal of the SEM protecting group by aqueous HCl in ethanol generates compounds 3, which may be alkylated with alkyl halides in the presence of a suitable base such as cesium carbonate or with Michael acceptors to provide compounds of Formula 4a and 4b.

Reaction Scheme 9

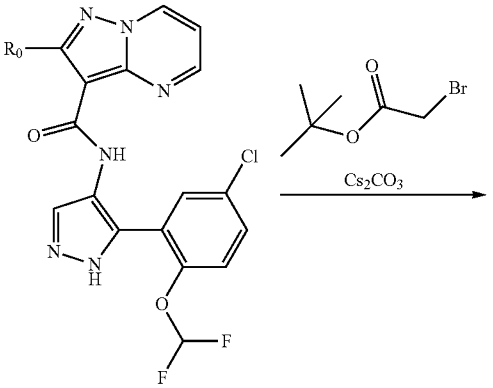

1

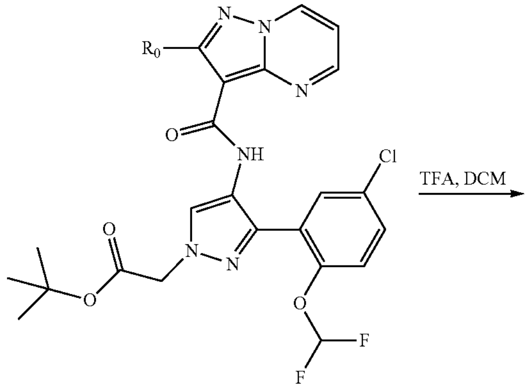

2

-continued

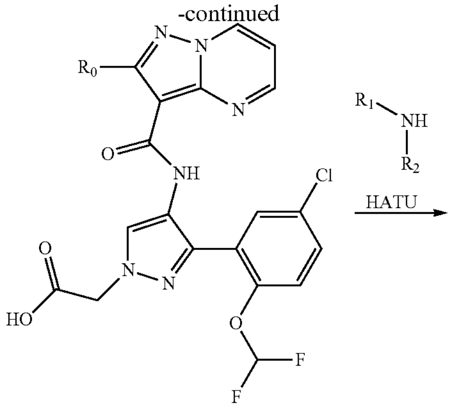

3

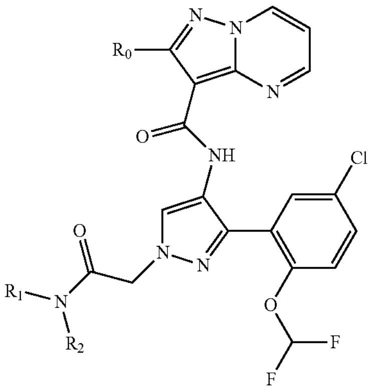

4

Compounds of formula 4 can be synthesized as shown in reaction Scheme 9. Pyrazole compound 1 (prepared as described herein) may be alkylated with t-butyl-bromoacetate in the presence of cesium carbonate to give intermediate 2. 2 may be treated with trifluoroacetic acid to give acids 3, which may then be reacted with primary or secondary amines in the presence of a coupling reagent such as N,N,N',N'-tetramethyl-O-(7-azabenzotriazol-1-yl)uronium hexafluorophosphate (HATU) to give compounds of formula 4.

Reaction Scheme 10

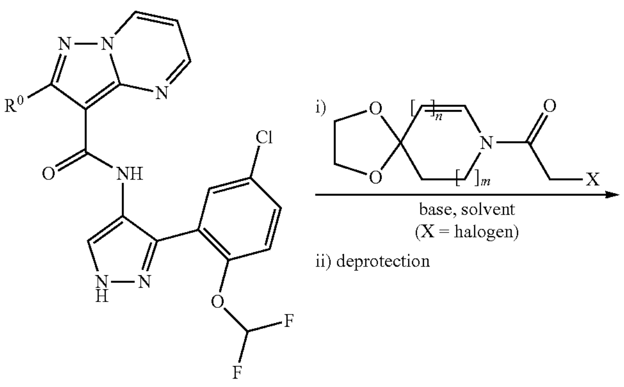

(1)

-continued
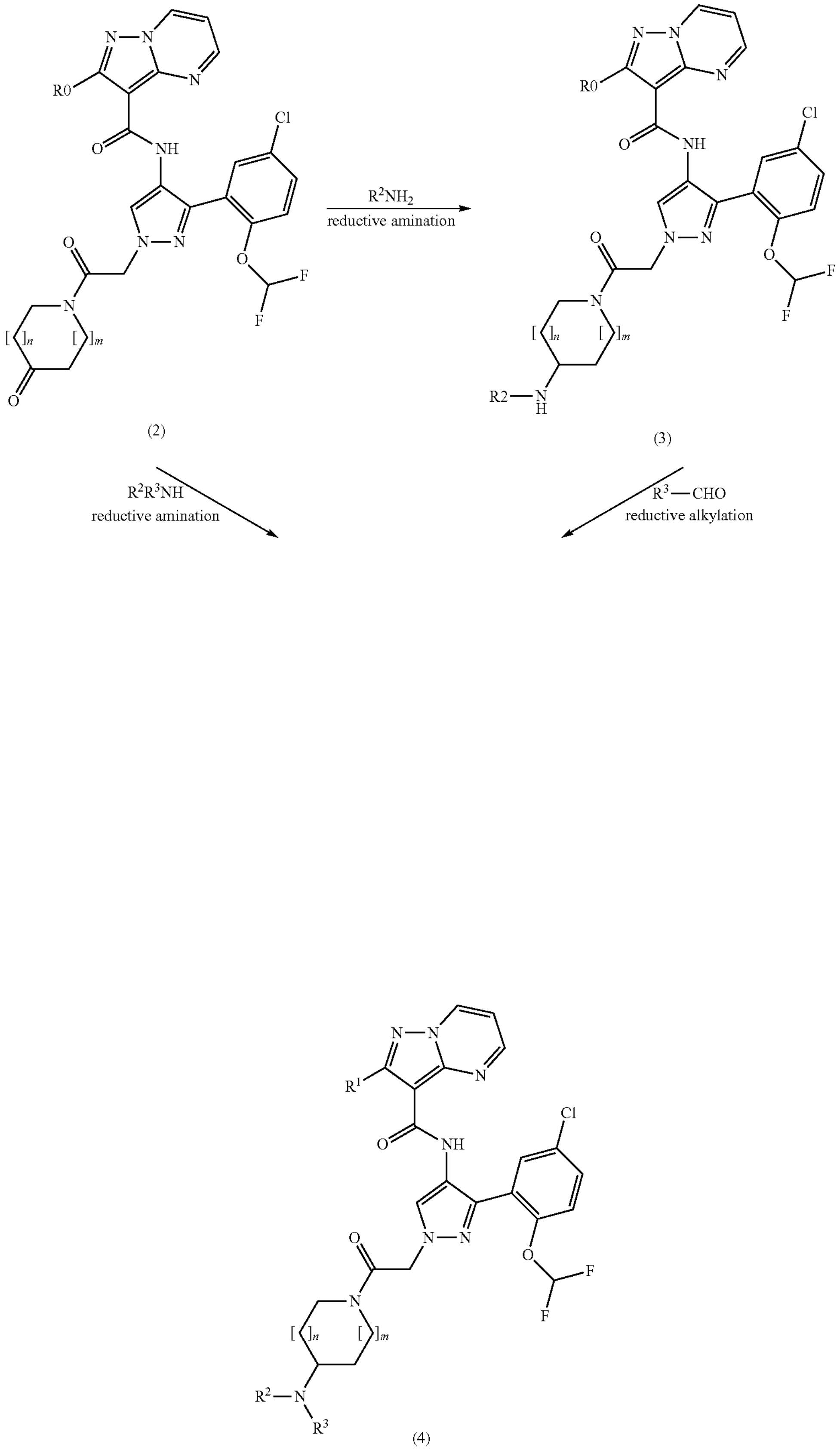

According to Scheme 10, compound 1 can be reacted with an α-haloamide in the presence of a base such as cesium carbonate and subsequently deprotected under aqueous acidic conditions to give compounds of type 2. Compounds of type 2 can be reacted with either primary or secondary amines under reductive conditions to give compounds of type 4 and 3 respectively, using a reducing agent for example sodium triacetoxyborohydride. Intermediate 3 can be further elaborated by reaction with aldehydes in the presence of an appropriate reducing agent such as sodium triacetoxyborohydride to give compounds 4.

Reaction Scheme 11

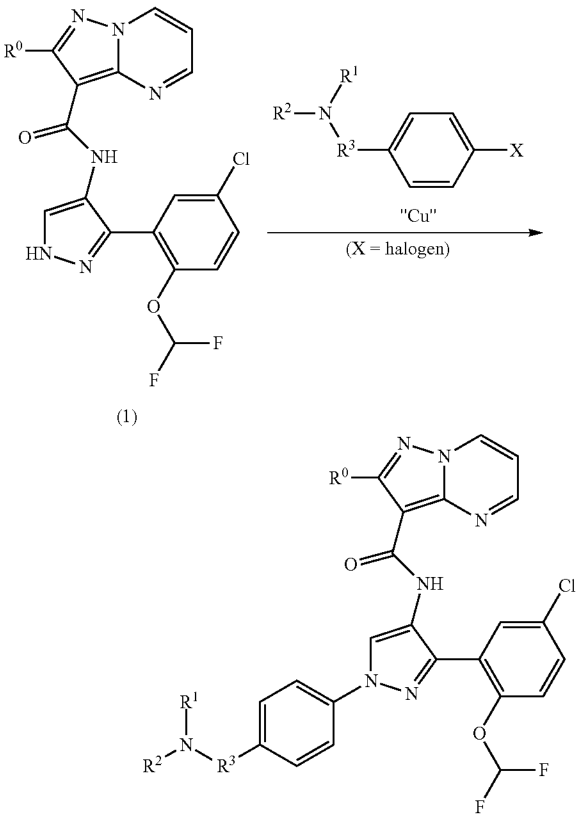

(1)

(2)

Pyrazole compounds of the formula 1 may be elaborated via a copper catalyzed coupling with for example a phenyl iodide containing a secondary or tertiary amine sidechain to afford compound 2.

Reaction Scheme 12

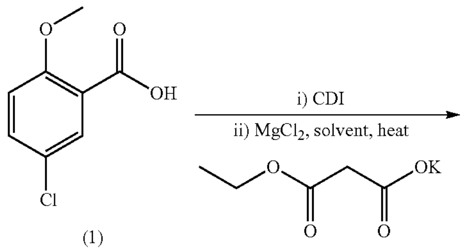

(1)

-continued

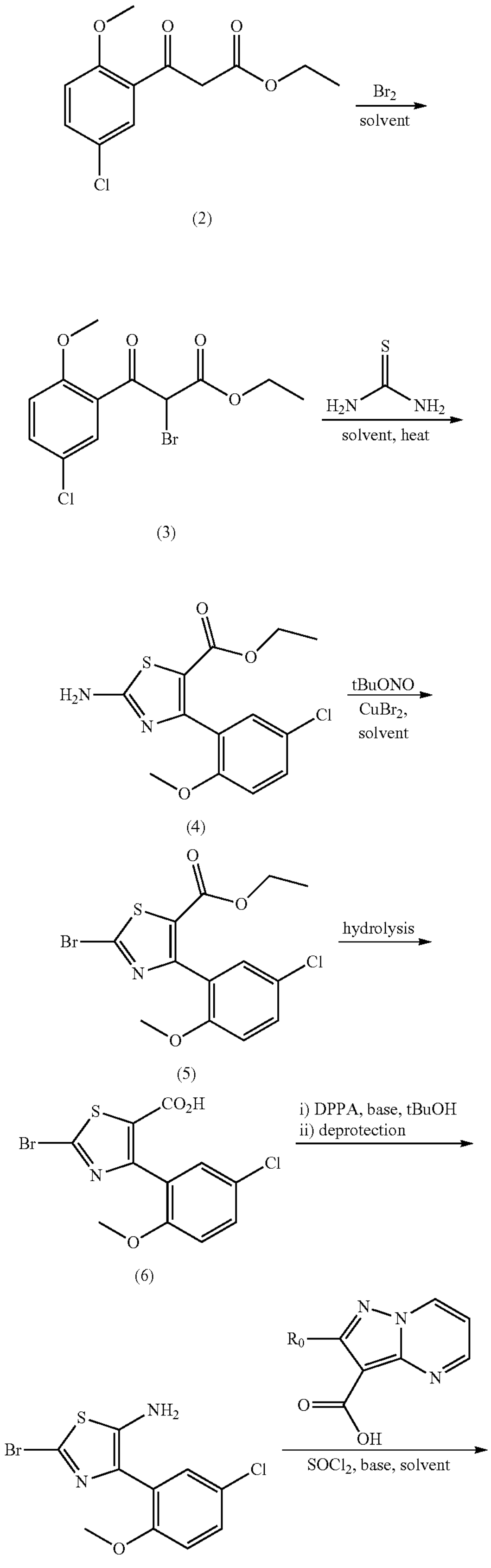

(2)

(3)

(4)

(5)

(6)

(7)

-continued

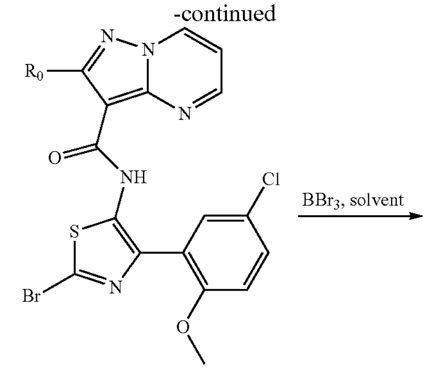

(8)

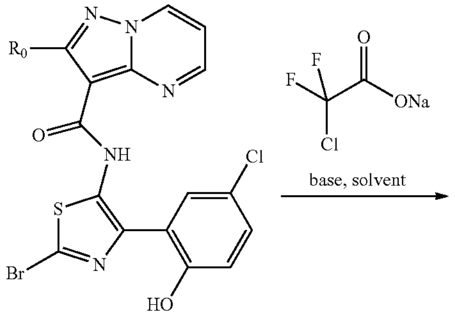

(9)

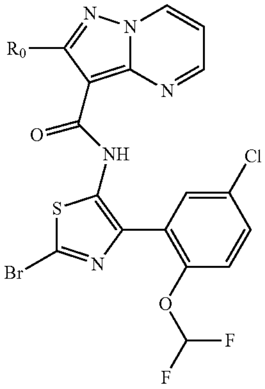

(10)

Treatment of compound 3 with thiourea in an appropriate solvent such as ethanol with heating provides thiazole compound 4. Aminothiazole 4 can be converted to the bromide 5 by treatment with tBuONO, $CuBr_2$ in a suitable solvent, for example acetonitrile. Subsequent hydrolysis of compound 5 using an aqueous base such as potassium hydroxide in a compatible solvent like ethanol will afford acid (6). Compound 7 can be prepared by treatment of compound 6 with diphenylphosphoryl azide (DPPA) in tert-butanol followed by deprotection under acidic conditions. Activation of pyrazolo[1,5-a]pyrimidine-3-carboxylic acid with thionyl chloride in a solvent such as THF in the presence of a base like DIPEA and subsequent reaction with 7 to give compound 8. Demethylation of aryl methylether 8 with for example $BBr_3$ in DCM followed by alkylation with sodium chlorodifluoroacetate and an appropriate base and solvent combination such as cesium carbonate in DMF will give compound 10.

Reaction Scheme 13

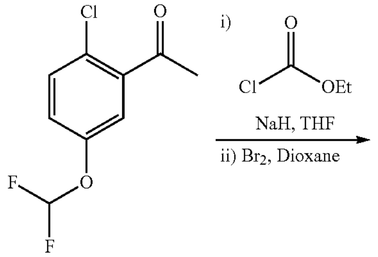

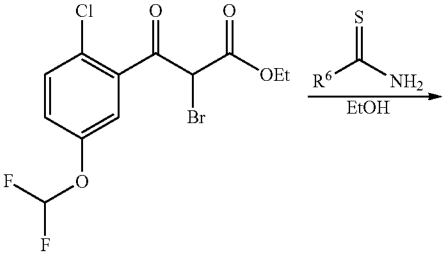

1

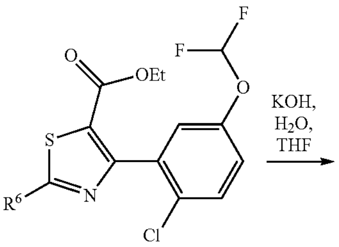

2

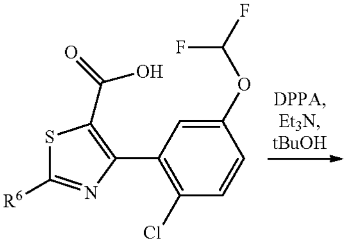

3

-continued

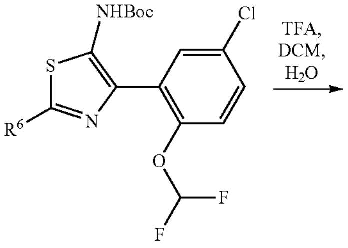

4

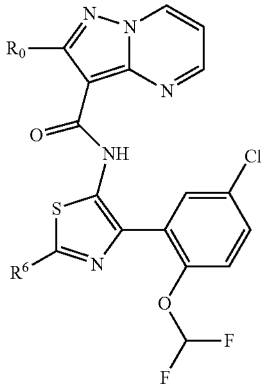

6

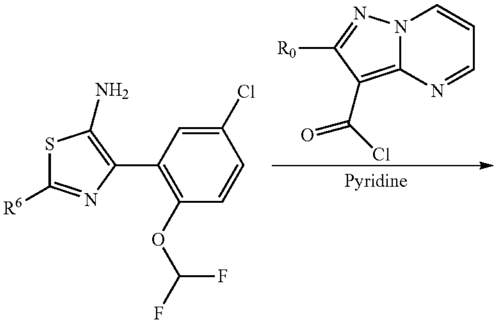

5

Alternatively compounds of Formula 6 can be synthesized as shown in Reaction Scheme 13. For example, compounds 1 can be prepared by treatment of commercially available substituted acetophenones with diethyl carbonate and subsequent bromination using for example bromine in dioxane. Treatment of compounds 1 with a suitably substituted thioamide or thiourea provides thiazole compounds 2. Compounds 2 can be hydrolysed using an aqueous base such as potassium hydroxide in a compatible solvent such as THF to afford acid compounds 35. Compounds 4 can be prepared by treatment of compounds 3 with diphenylphosphoryl azide (DPPA) in tert-butanol. Deprotection of compounds 4 under acidic conditions provides amino compounds 5. Compounds of formula 6 can prepared by treatment of compounds 5 with pyrazolo[1,5-a]pyrimidine-3-carbonyl chloride in pyridine.

Reaction Scheme 14

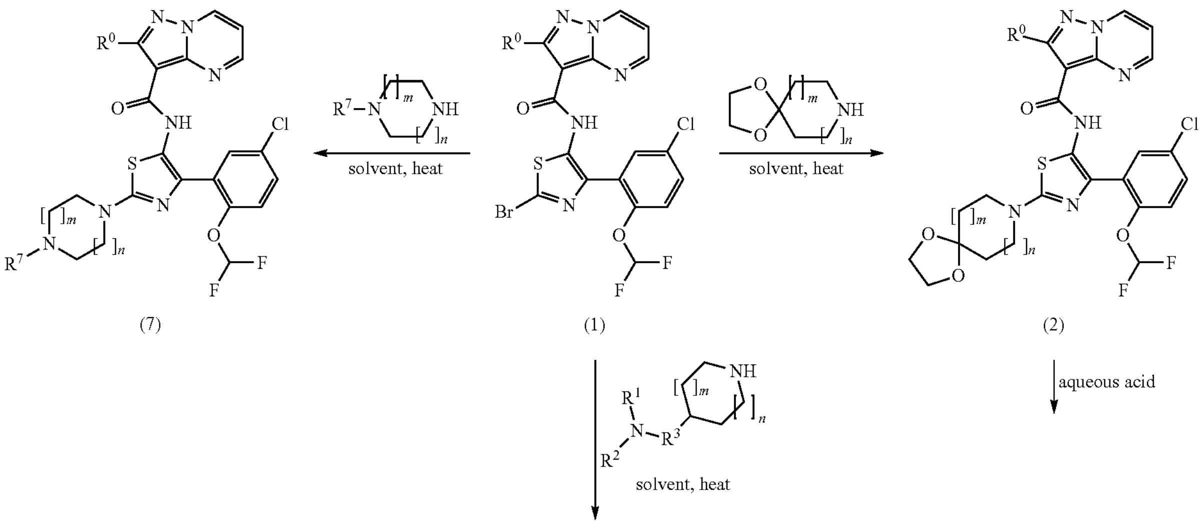

(7) (1) (2)

-continued
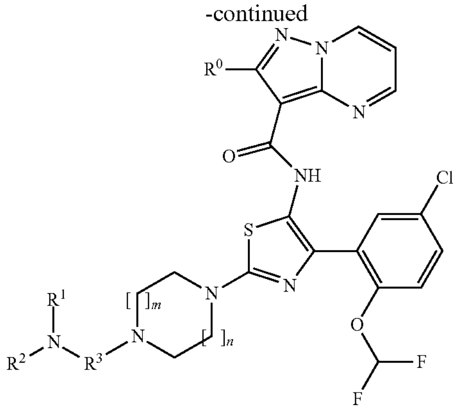
(6)
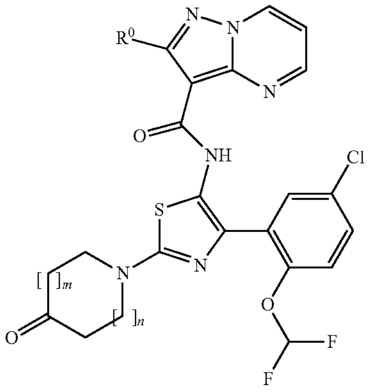
(3)
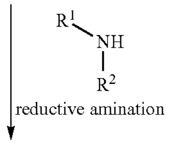
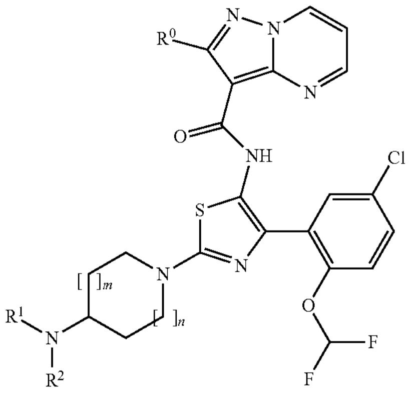
(4)
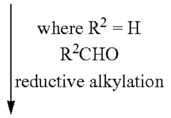
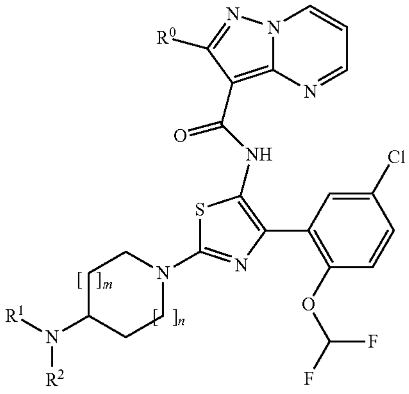
(5)

Compounds of type 1 can be reacted with suitable nucleophiles such as appropriately mono-substituted cyclic diamines, acetal containing cyclic amines and cyclic amines containing a substituted second amino group can be achieved with heating in a solvent such as DMA to give compounds 7, 2 and 6 respectively. Compounds of type 2 can be deprotected under aqueous acidic conditions to provide structures of type 3. Compounds 3 can be reductively aminated with mono or di-substituted amines, with regards to the mono substituted amino products they can be further elaborated via a reductively alkylated with a suitable aldehyde in the presence of a reducing agent such as sodium cyanoborohydride giving compounds of type 5.

Reaction Scheme 15

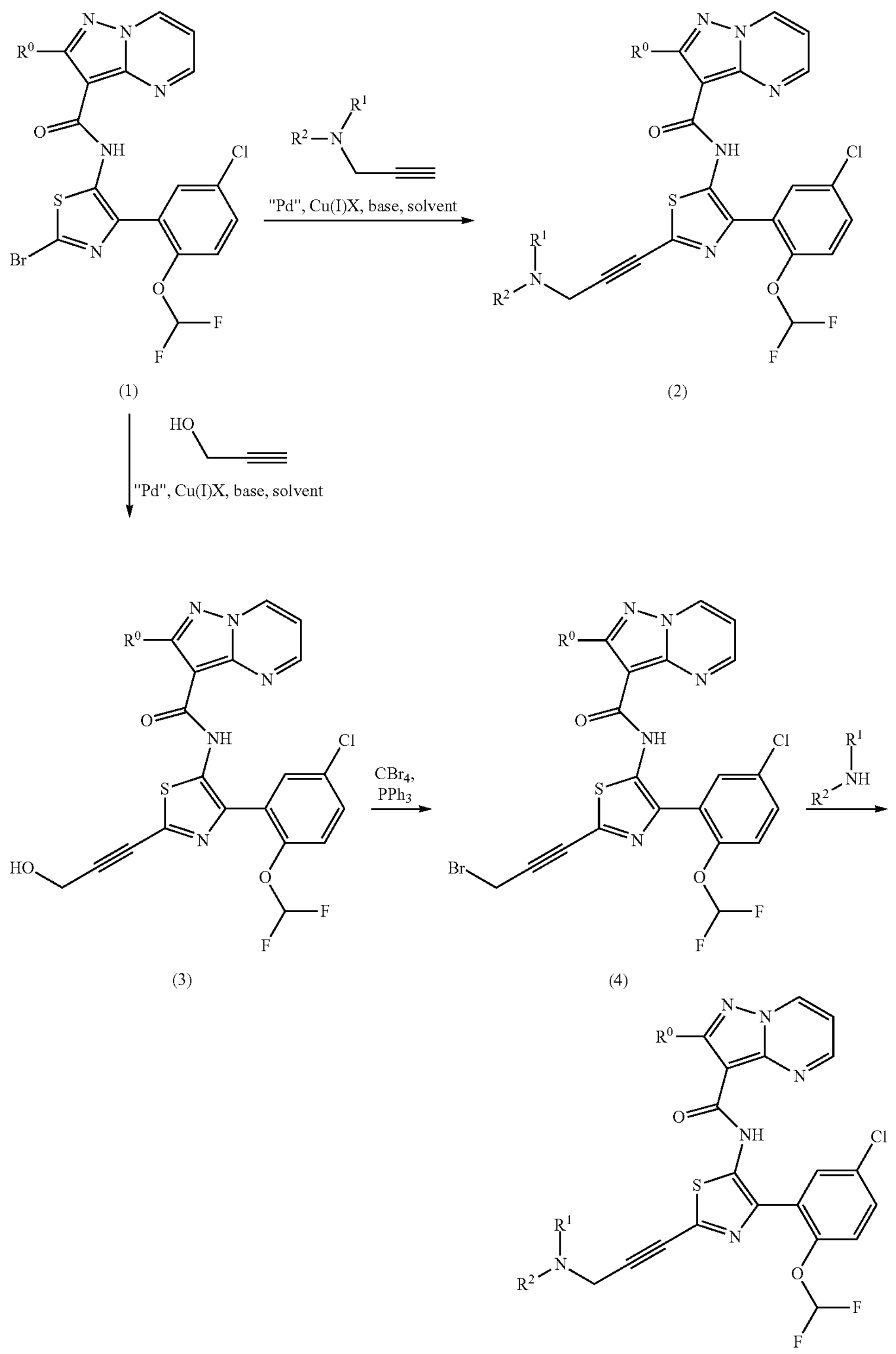

(1) (2) (3) (4) (5)

Compound 1 can undergo a Sonogashria reaction with an N-substituted propargyl amine or propargyl alcohol to give compounds 2 and 3 respectively in the presence of a palladium source, a copper (i) halide and base in an appropriate solvent with heating. For example, this could be a combination of $Pd(PPh_3)_2Cl_2$, Cu(I)I, $Et_3N$ in THF. Alcohol 3 can be converted to the bromide 4 with $CBr_4$, $PPh_3$ in a suitable solvent such as DCM. The bromide can be then displaced with primary and secondary amines giving structures of type 5.

Reaction Scheme 16

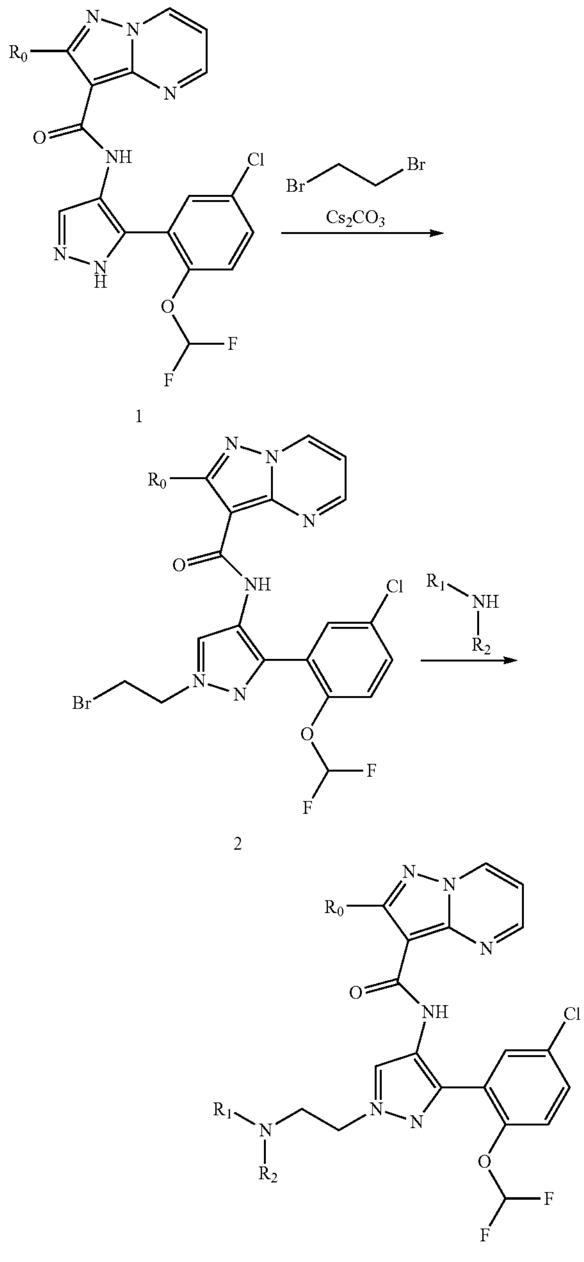

1

2

4

As shown in Scheme 16, compounds of type 1 can be reacted with 1,2-dibromo ethane to give alkyl bromides 2. Reaction of 2 with amine nucleophiles can produce structures of type 4.

Reaction Scheme 17

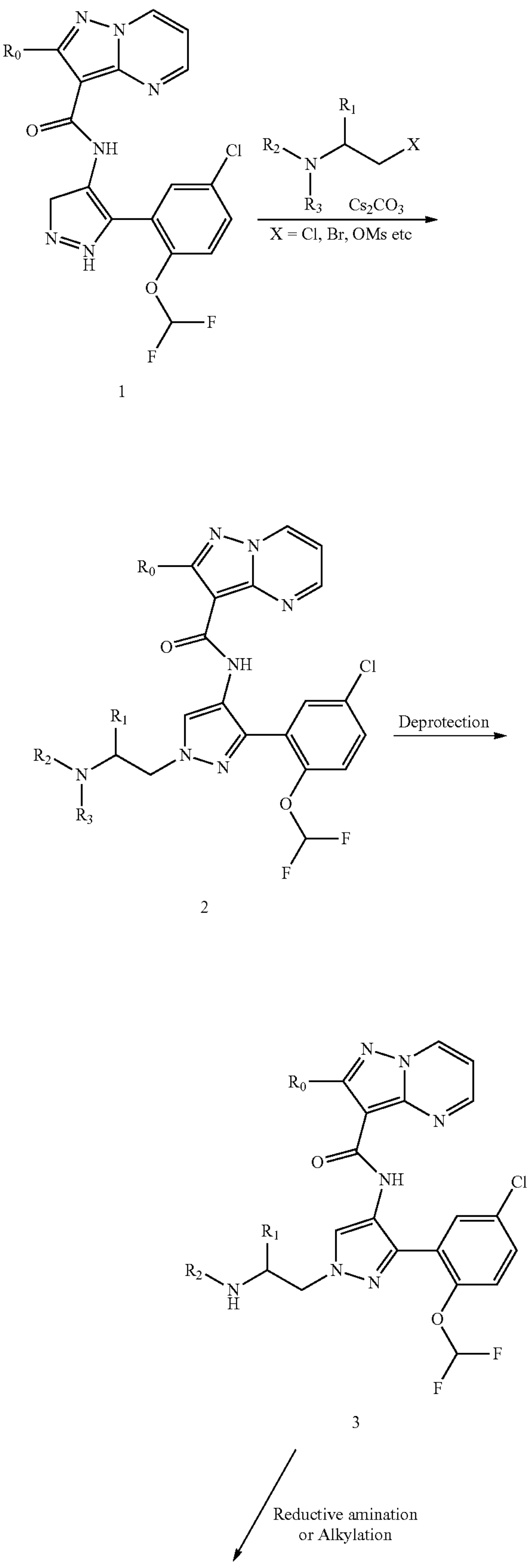

1

2

3

-continued

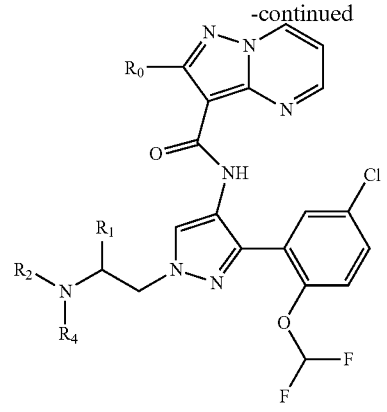

4

As shown in Scheme 17, compounds of type 1 can be alkylated with amine containing electrophiles to produce compounds 2. Manipulation of functional groups on the pendant amine can produce structures of type 3 and 4.

Reaction Scheme 18

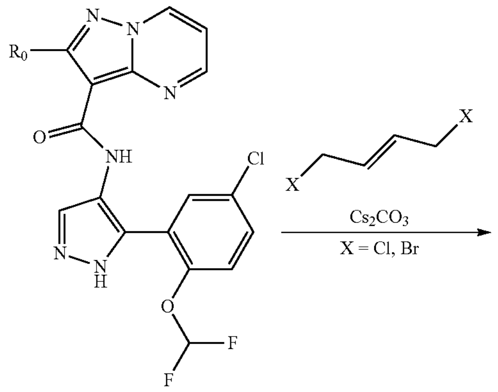

1

-continued

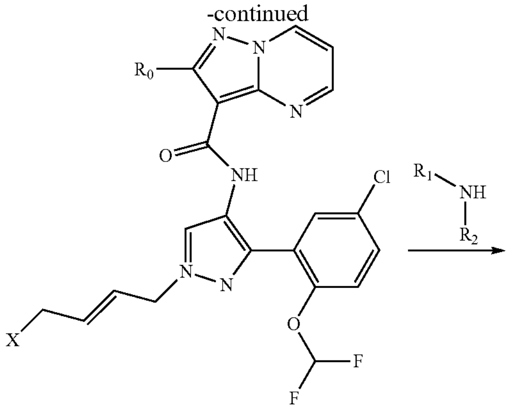

2

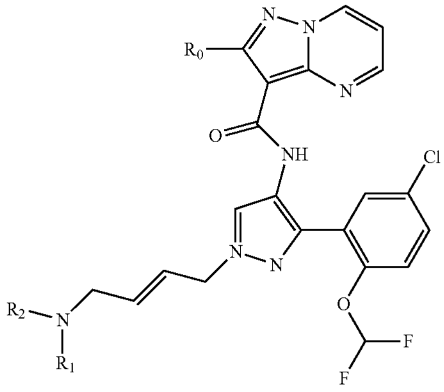

4

As shown in Scheme 18, compounds of type 1 can be reacted with allylic dihalides to produce compounds 2. Further reaction of the pendant allylic halide with amine nucleophiles can produce structures of type 4.

Reaction Scheme 19

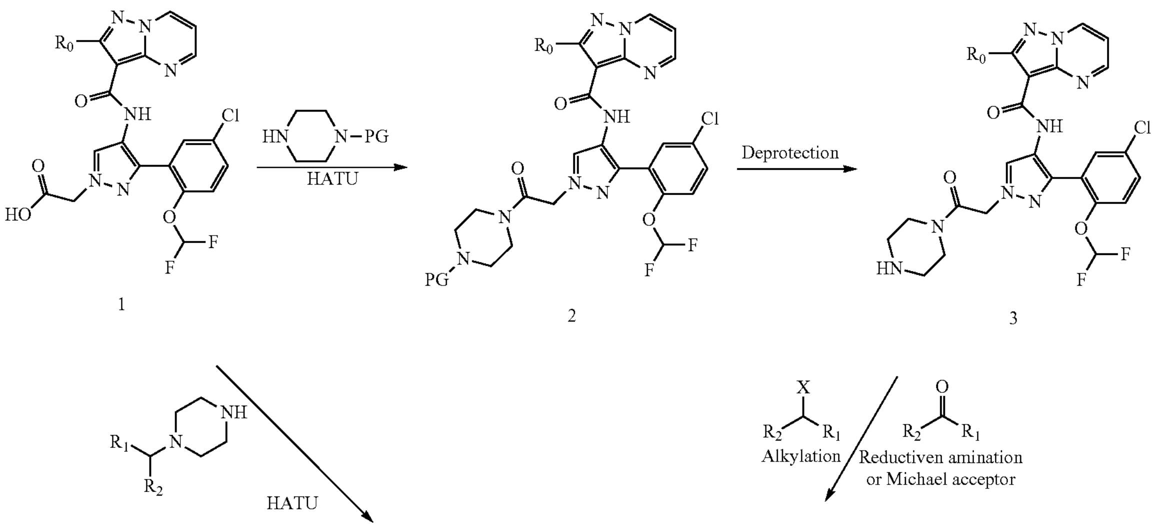

1 2 3

-continued

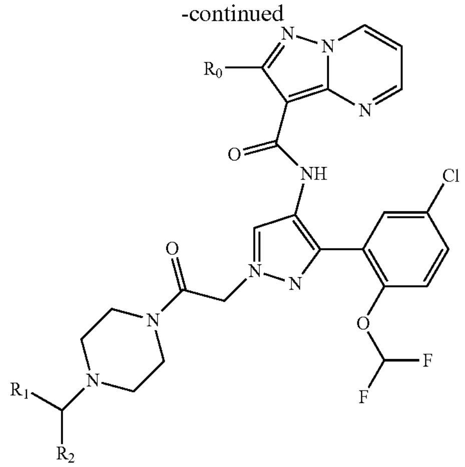

4

As shown in Scheme 19, compounds of type 1 can be reacted with substituted piperazines and an appropriate dehydrating agent (such as HATU) to produce structures of type 4. Alternatively, compounds of type 1 can be coupled with appropriately mono-protected piperazines to produce compounds 2. Compounds 2 can then be deprotected and further reacted with appropriate electrophiles to produce structures of type 4.

Reaction Scheme 20

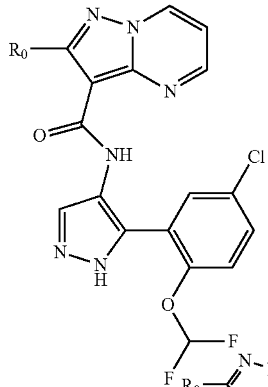

1

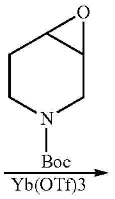

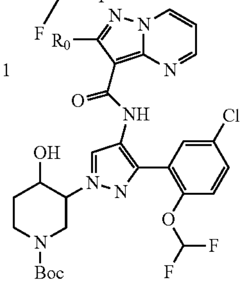

2

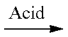

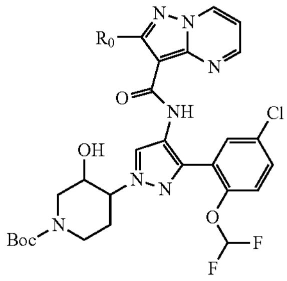

3

-continued

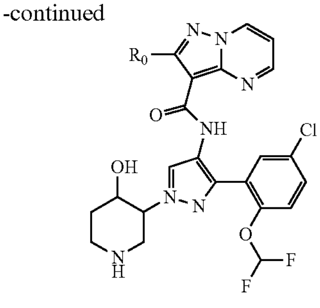

4

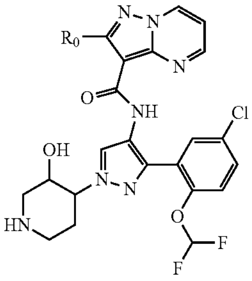

5

As shown in Scheme 20, compounds of type 1 can be reacted with epoxides in the presence of a Lewis acid such as $Yb(OTf)_3$ to produce structures such as 2 and 3. Deprotection can then produce structures of type 4 and 5.

Reaction Scheme 21

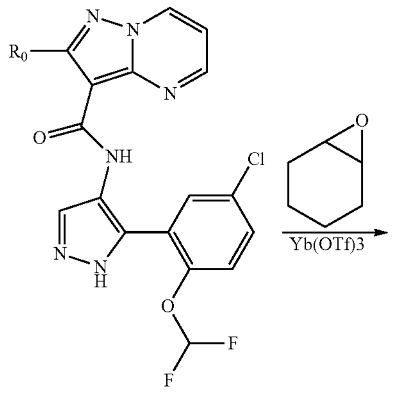

1

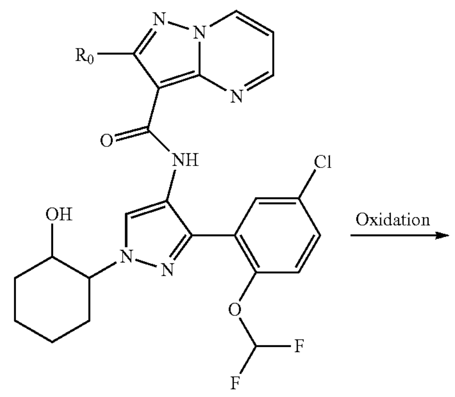

2

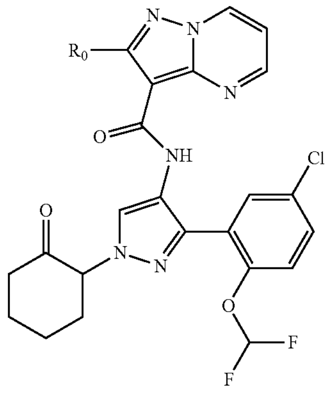

3

Reaction Scheme 22

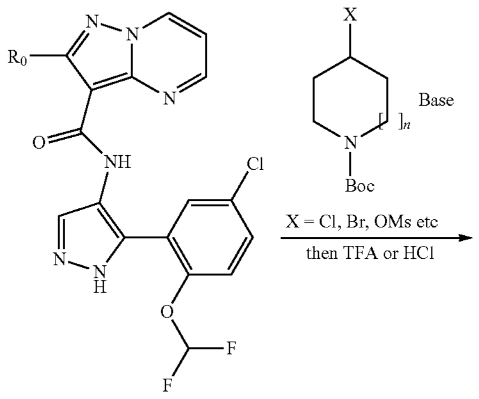

1

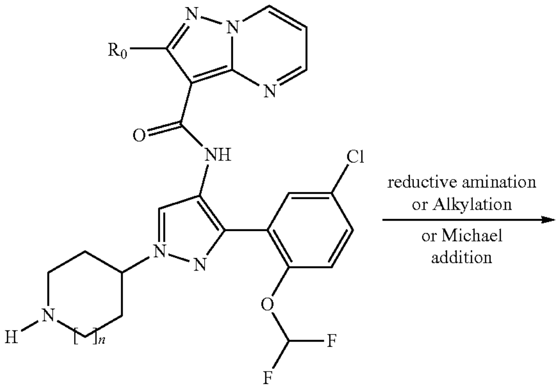

2

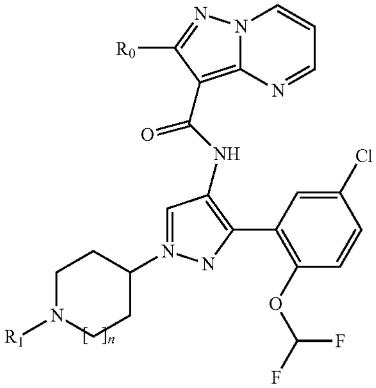

3

As shown in Scheme 21, compounds of type 1 can be reacted with epoxides in the presence of a Lewis acid such as $Yb(OTf)_3$ to produce structures such as 2. The resulting alcohol can then be oxidized to produce structures of type 3.

As shown in Scheme 22, reaction of compounds of type 1 with appropriate electrophiles in the presence of base, followed by deprotection can produce structures such as 2. Further manipulation of the reactive amine can then produce structures of type 3.

Reaction Scheme 23

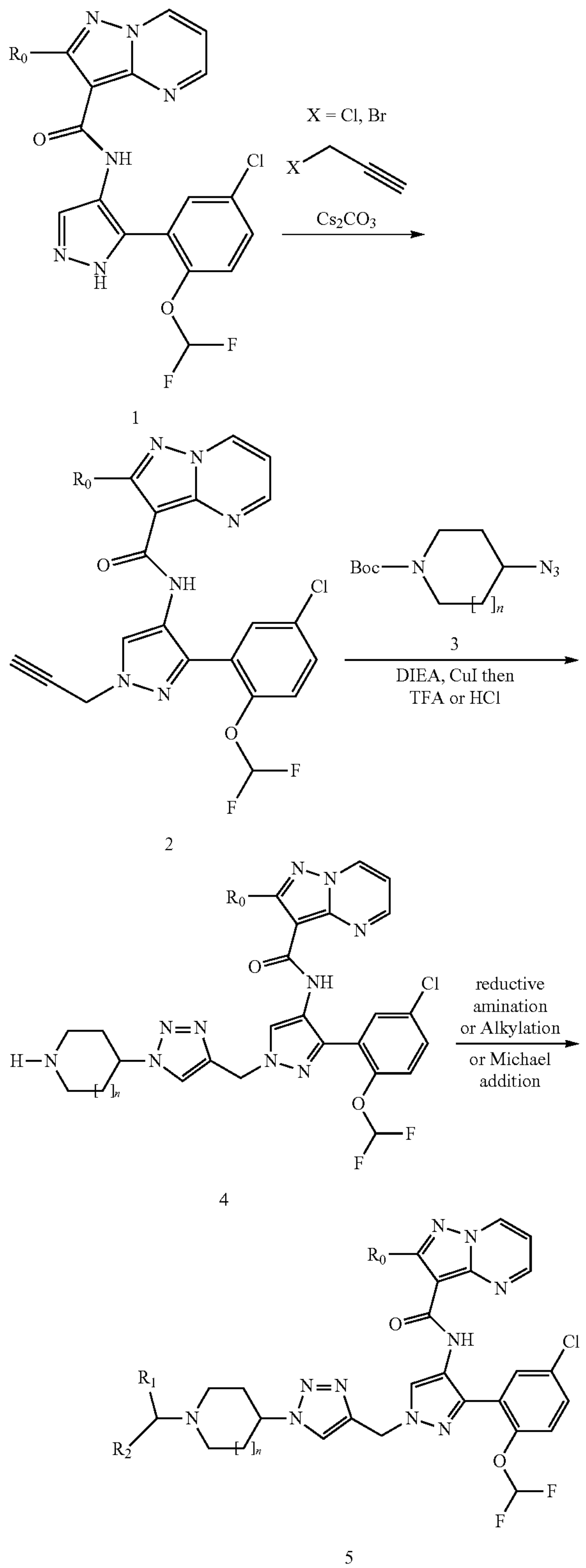

As shown in Scheme 23, reaction of compounds of type 1 with propargyl bromide or chloride in the presence of a base can produce compounds of type 2. Reaction of 2 with azide compounds such as 3 in the presence of a copper halide and organic base, followed by deprotection can lead to triazole compounds of type 4. Further manipulation of the reactive amine can then produce structures of type 5.

Reaction Scheme 24

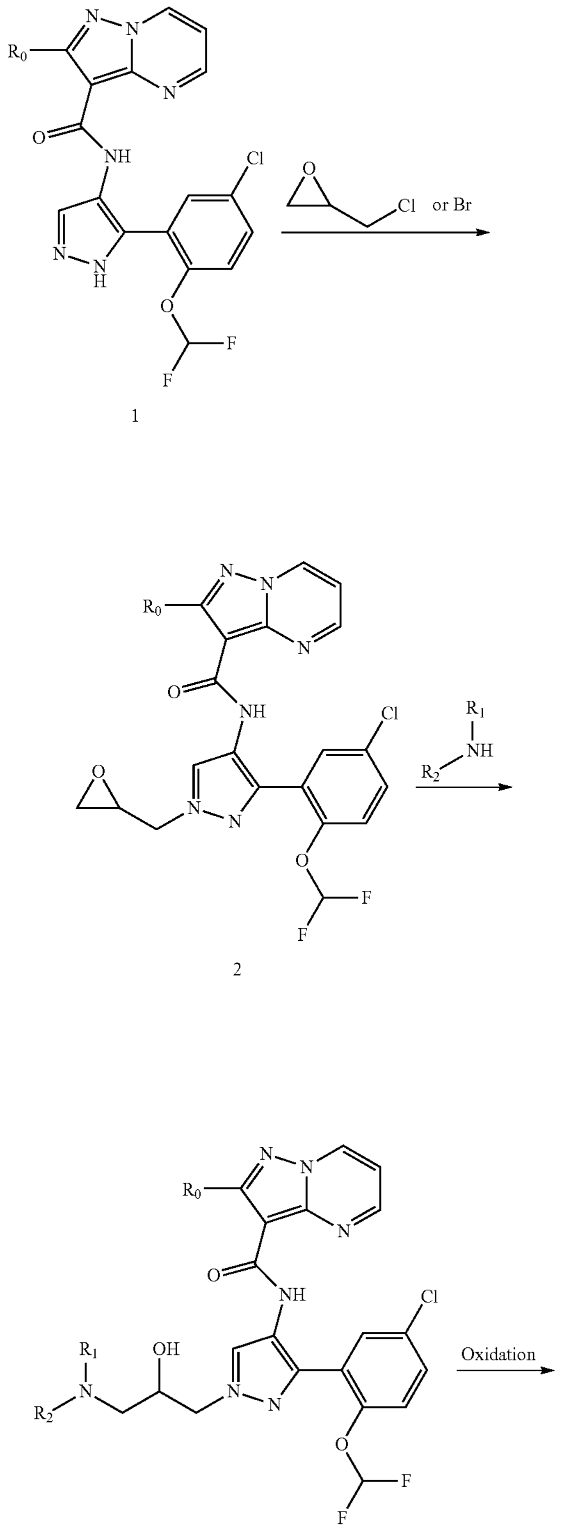

3

-continued

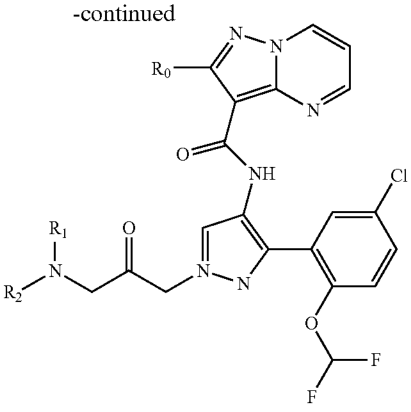

4

As shown in Scheme 24, reaction of compounds of type 1 with a 2-(halomethyl)oxirane can produce compounds of type 2. Reaction of compounds of type 2 with nucleophilic amines can lead to compounds of type 3. Oxidation of 3 leads to compounds of type 4.

Reaction Scheme 25

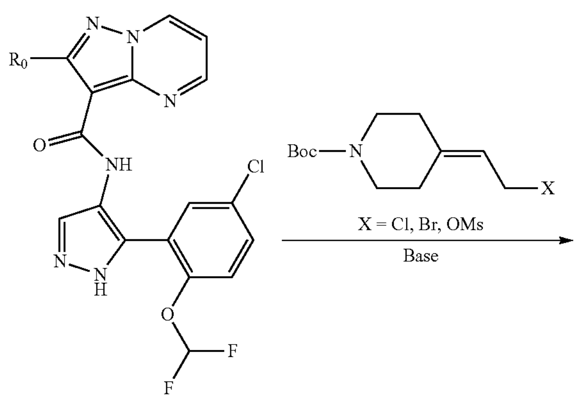

1

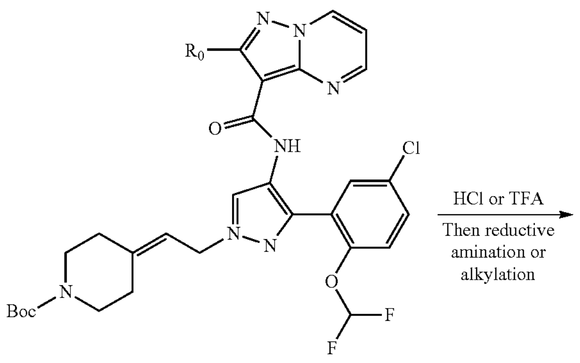

2

-continued

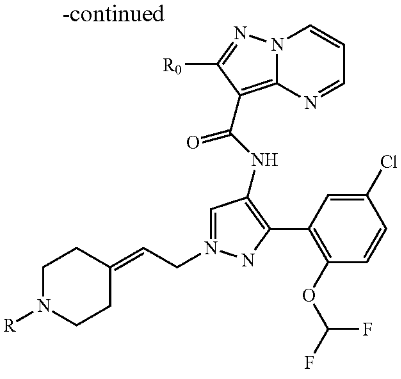

3

As shown in Scheme 25, reaction of compounds of type 1 with appropriate allylic alkylating reagents in the presence of base leads to compounds of type 2. Deprotection of the amino protecting group under acidic conditions, followed by reductive amination or alkylation of the reactive amine leads to compounds of type 3.

Reaction Scheme 26

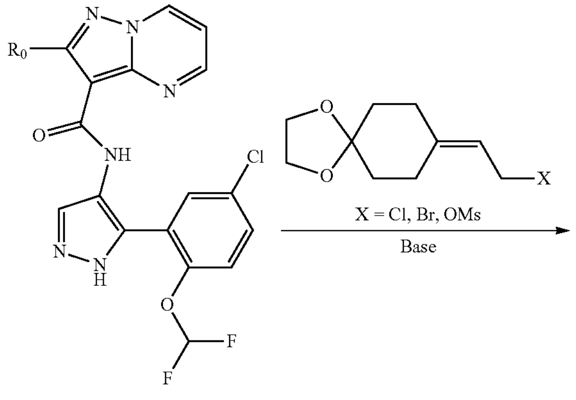

1

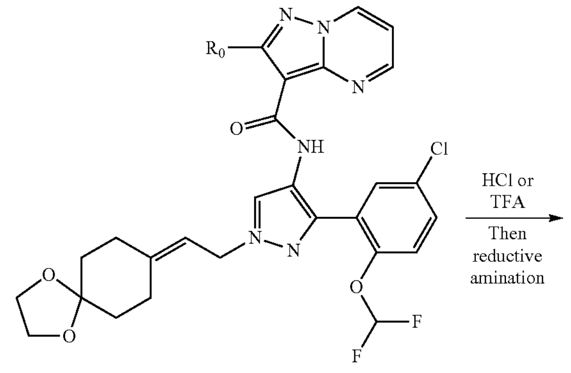

2

-continued

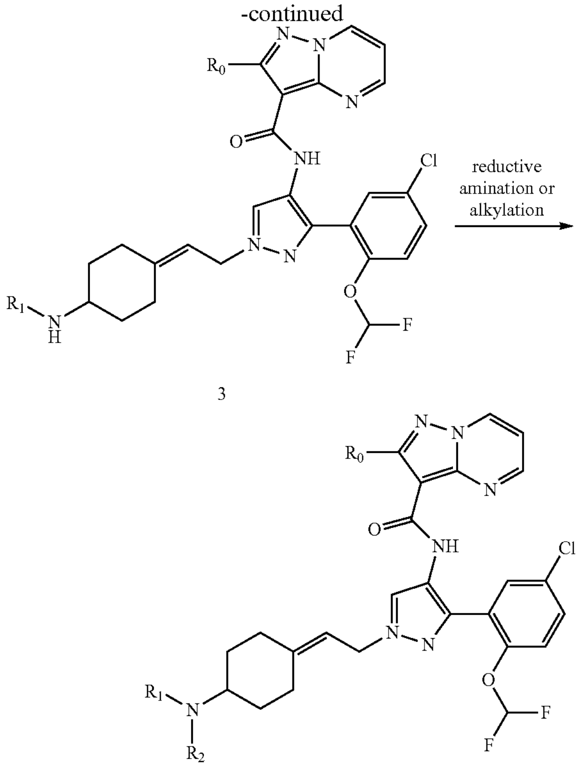

3

3

As shown in Scheme 26, reaction of compounds of type 1 with appropriate allylic alkylating reagents leads to compounds of type 2. Removal of the ketal protecting group under acidic conditions, followed by reaction of the liberated ketone with an amine under reductive amination conditions leads to compounds of type 3. A subsequent reductive amination or alkylation step produces structures of type 3.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

In a further example, primary amine or secondary amine groups may be converted into amide groups (—NHCOR' or —NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such HATU (O-(7-azabenzotriazol-1-yl)-N,N,N',N'-tetramethyluronium hexafluorophosphate) in a suitable solvent such as dichloromethane. Similarly, amine groups may be converted into sulphonamide groups (—$NHSO_2R'$ or —$NR''SO_2R'$) groups by reaction with an appropriate sulphonyl chloride in the presence of a suitable base, such as triethylamine, in a suitable solvent such as dichloromethane. Primary or secondary amine groups can be converted into urea groups (—NHCONR'R" or —NRCONR'R") by reaction with an appropriate isocyanate in the presence of a suitable base such as triethylamine, in a suitable solvent, such as dichloromethane.

An amine (—$NH_2$) may be obtained by reduction of a nitro (—$NO_2$) group, for example by catalytic hydrogenation, using for example hydrogen in the presence of a metal catalyst, for example palladium on a support such as carbon in a solvent such as ethyl acetate or an alcohol e.g. methanol. Alternatively, the transformation may be carried out by chemical reduction using for example a metal, e.g. tin or iron, in the presence of an acid such as hydrochloric acid.

In a further example, amine (—$CH_2NH_2$) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g. a cyclic ether such as tetrahydrofuran, at an appropriate temperature, for example from about −78° C. to the reflux temperature of the solvent.

In a further example, amine (—$NH_2$) groups may be obtained from carboxylic acid groups (—$CO_2H$) by conversion to the corresponding acyl azide (—$CON_3$), Curtius rearrangement and hydrolysis of the resultant isocyanate (—N═C═O).

Aldehyde groups (—CHO) may be converted to amine groups (—$CH_2NR'R''$)) by reductive amination employing an amine and a borohydride, for example sodium triacetoxyborohydride or sodium cyanoborohydride, in a solvent such as a halogenated hydrocarbon, for example dichloromethane, or an alcohol such as ethanol, where necessary in the presence of an acid such as acetic acid at around ambient temperature.

In a further example, aldehyde groups may be converted into alkenyl groups (—CH═CHR') by the use of a Wittig or Wadsworth-Emmons reaction using an appropriate phosphorane or phosphonate under standard conditions known to those skilled in the art.

Aldehyde groups may be obtained by reduction of ester groups (such as —$CO_2Et$) or nitriles (—CN) using diisobutylaluminium hydride in a suitable solvent such as toluene. Alternatively, aldehyde groups may be obtained by the oxidation of alcohol groups using any suitable oxidising agent known to those skilled in the art.

Ester groups (—$CO_2R'$) may be converted into the corresponding acid group (—$CO_2H$) by acid- or base-catalysed hydrolysis, depending on the nature of R. If R is t-butyl, acid-catalysed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—$CO_2H$) may be converted into amides (CONHR' or —CONR'R") by reaction with an appropriate amine in the presence of a suitable coupling agent, such as HATU, in a suitable solvent such as dichloromethane.

In a further example, carboxylic acids may be homologated by one carbon (i.e—$CO_2H$ to —$CH_2CO_2H$) by conversion to the corresponding acid chloride (—COCl) followed by Arndt-Eistert synthesis.

In a further example, —OH groups may be generated from the corresponding ester (e.g. —$CO_2R'$), or aldehyde (—CHO) by reduction, using for example a complex metal hydride such as lithium aluminium hydride in diethyl ether or tetrahydrofuran, or sodium borohydride in a solvent such as methanol. Alternatively, an alcohol may be prepared by reduction of the corresponding acid (—$CO_2H$), using for example lithium aluminium hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g. trifluoromethylsulfonyloxy or arylsulfonyloxy, e.g. p-toluenesulfonyloxy group using conditions known to those skilled in the art. For example, an alcohol may be reacted with thioyl chloride in a halogenated hydrocarbon (e.g. dichloromethane) to yield the corresponding chloride. A base (e.g. triethylamine) may also be used in the reaction.

In another example, alcohol, phenol or amide groups may be alkylated by coupling a phenol or amide with an alcohol in a solvent such as tetrahydrofuran in the presence of a phosphine, e.g. triphenylphosphine and an activator such as diethyl-, diisopropyl, or dimethylazodicarboxylate. Alternatively alkylation may be achieved by deprotonation using a suitable base e.g. sodium hydride followed by subsequent addition of an alkylating agent, such as an alkyl halide.

Aromatic halogen substituents in the compounds may be subjected to halogen-metal exchange by treatment with a base, for example a lithium base such as n-butyl or t-butyl lithium, optionally at a low temperature, e.g. around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g. palladium or copper) catalysed reactions, to introduce, for example, acid, ester, cyano, amide, aryl, heteraryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

Methods of Separation

In each of the exemplary Schemes it may be advantageous to separate reaction products from one another or from starting materials. The desired products of each step or series of steps is separated or purified (hereinafter separated) to the desired degree of homogeneity by the techniques common in the art. Typically such separations involve multiphase extraction, crystallization or trituration from a solvent or solvent mixture, distillation, sublimation, or chromatography. Chromatography can involve any number of methods including, for example: reverse-phase and normal phase; size exclusion; ion exchange; supercritical fluid; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. Example separation methods include boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereoisomers on the basis of their physical chemical differences by methods well known to those skilled in the art, such as by chromatography or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column or supercritical fluid chromatography.

A single stereoisomer, e.g., an enantiomer, substantially free of its stereoisomer may be obtained by resolution of the racemic mixture using a method such as formation of diastereomers using optically active resolving agents (Eliel, E. and Wilen, S., Stereochemistry of Organic Compounds, John Wiley & Sons, Inc., New York, 1994; Lochmuller, C. H., J. Chromatogr., 113(3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Drug Stereochemistry, Analytical Methods and Pharmacology, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., Stereochemistry of Organic Compounds, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob, J. Org. Chem. 47:4165 (1982)), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111, incorporated herein by reference). By method (3), a racemic mixture of two enantiomers can be separated by chromatography using a chiral stationary phase (Chiral Liquid Chromatography W. J. Lough, Ed., Chapman and Hall, New York, (1989); Okamoto, J. of Chromatogr. 513:375-378 (1990)). Enriched or purified enantiomers can be distinguished by methods used to distinguish other chiral molecules with asymmetric carbon atoms, such as optical rotation and circular dichroism. The absolute stereochemistry of chiral centers and enantiomers can be determined by x-ray crystallography.

Positional isomers, for example E and Z forms, of compounds of Formula (00A), (0A), (A), (Ia), (Ib), (II), (III), (IV), (V), (VI), (VII), (VIII), (IX), or (X), and intermediates for their synthesis, may be observed by characterization methods such as NMR and analytical HPLC. For certain compounds where the energy barrier for interconversion is sufficiently high, the E and Z isomers may be separated, for example by preparatory HPLC.

Pharmaceutical Compositions and Administration

The compounds with which the invention is concerned are JAK kinase inhibitors, such as JAK1 inhibitors, and are useful in the treatment of several diseases, for example, inflammatory diseases, such as asthma.

Accordingly, another embodiment provides pharmaceutical compositions or medicaments containing a compound of the invention, such as a compound of Formula (00A), (0A), (A), (Ia), (Ib), (II), (III), (IV), (V), (VI), (VII), (VIII), (IX), or (X), or a compound of Table 1 or of Examples 1-468, and a pharmaceutically acceptable carrier, diluent or excipient, as well as methods of using the compounds of the invention to prepare such compositions and medicaments.

In one example, a compound of Formula (00A), (0A), (A), (Ia), (Ib), (II), (III), (IV), (V), (VI), (VII), (VIII), (IX), or (X), or a compound of Table 1 or of Examples 1-468, may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but typically ranges anywhere from about 3 to about 8. In one example, a compound of Formula (00A), (0A), (A), (Ia), (Ib), (II), (III), (IV), (V), (VI), (VII), (VIII), (IX), or (X), or a compound of Table 1 or of Examples 1-468, is formulated in an acetate buffer, at pH 5. In another embodiment, the compounds of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, as is required in the pharmaceutical art. In general, the daily dose range for oral administration will lie within the range of from about 0.001 mg to about 100 mg per kg body weight of a human, often 0.01 mg to about 50 mg per kg, for example 0.1 to 10 mg per kg, in single or divided doses. In general, the daily dose range for inhaled administration will lie within the range of from about 0.1 μg to about 1 mg per kg body weight of a human, preferably 0.1 μg to 50 μg per kg, in single or divided doses. On the other hand, it may be necessary to use dosages outside these limits in some cases.

The compounds of the invention, such as a compound of Formula (00A), (0A), (A), (Ia), (Ib), (II), (III), (IV), (V), (VI), (VII), (VIII), (IX), or (X), or a compound of Table 1 or of Examples 1-468, may be administered by any suitable means, including oral, topical (including buccal and sublingual), rectal, vaginal, transdermal, parenteral, subcutaneous, intraperitoneal, intrapulmonary, intradermal, intrathecal, inhaled and epidural and intranasal, and, if desired for local treatment, intralesional administration. Parenteral infusions include intramuscular, intravenous, intraarterial, intraperitoneal, or subcutaneous administration. In some embodiments, inhaled administration is employed.

The compounds of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, may be administered in any convenient administrative form, e.g., tablets, powders, capsules, lozenges, granules, solutions, dispersions, suspensions, syrups, sprays, vapors, suppositories, gels, emulsions, patches, etc. Such compositions may contain components conventional in pharmaceutical preparations, e.g., diluents (e.g., glucose, lactose or mannitol), carriers, pH modifiers, buffers, sweeteners, bulking agents, stabilizing agents, surfactants, wetting agents, lubricating agents, emulsifiers, suspending agents, preservatives, antioxidants, opaquing agents, glidants, processing aids, colorants, perfuming agents, flavoring agents, other known additives as well as further active agents.

Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. For example, carriers include solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated. Exemplary excipients include dicalcium phosphate, mannitol, lactose, starch, magnesium stearate, sodium saccharine, cellulose, magnesium carbonate or combinations thereof. A pharmaceutical composition may comprise different types of carriers or excipients depending on whether it is to be administered in solid, liquid or aerosol form, and whether it need to be sterile for such routes of administration.

For example, tablets and capsules for oral administration may be in unit dose presentation form, and may contain conventional excipients such as binding agents, for example syrup, acacia, gelatin, sorbitol, tragacanth, or polyvinylpyrrolidone; fillers, for example, lactose, sugar, maize-starch, calcium phosphate, sorbitol or glycine; tabletting lubricant, for example, magnesium stearate, talc, polyethylene glycol or silica; disintegrants, for example, potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example, sorbitol, syrup, methyl cellulose, glucose syrup, gelatin hydrogenated edible fats; emulsifying agents, for example, lecithin, sorbitan monooleate, or acacia; non-aqueous vehicles (which may include edible oils), for example, almond oil, fractionated coconut oil, oily esters such as glycerine, propylene glycol, or ethyl alcohol; preservatives, for example, methyl or propyl p-hydroxybenzoate or sorbic acid, and if desired conventional flavoring or coloring agents.

For topical application to the skin, a compound may be made up into a cream, lotion or ointment. Cream or ointment formulations which may be used for the drug are conventional formulations well known in the art, for example as described in standard textbooks of pharmaceutics such as the British Pharmacopoeia.

Compounds of the invention, such as a compound of Formula (00A), (0A), (A), (Ia), (Ib), (II), (III), (IV), (V), (VI), (VII), (VIII), (IX), or (X), or a compound of Table 1 or of Examples 1-468, may also be formulated for inhalation, for example, as a nasal spray, or dry powder or aerosol inhalers. For delivery by inhalation, the compound is typically in the form of microparticles, which can be prepared by a variety of techniques, including spray-drying, freeze-drying and micronisation. Aerosol generation can be carried out using, for example, pressure-driven jet atomizers or ultrasonic atomizers, such as by using propellant-driven metered aerosols or propellant-free administration of micronized compounds from, for example, inhalation capsules or other "dry powder" delivery systems.

By way of example, a composition of the invention may be prepared as a suspension for delivery from a nebulizer or as an aerosol in a liquid propellant, for example, for use in a pressurized metered dose inhaler (PMDI). Propellants suitable for use in a PMDI are known to the skilled person, and include CFC-12, HFA-134a, HFA-227, HCFC-22 ($CCl_2F_2$) and HFA-152 ($CH_4F_2$ and isobutane).

In some embodiments, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of, for example, greater than 90 μm.

In the case of an aerosol-based formulation, an example is:

| | | |
|---|---|---|
| Compound of the invention* | 24 | mg/canister |
| Lecithin, NF Liq. Conc. | 1.2 | mg/canister |
| Trichlorofluoromethane, NF | 4.025 | g/canister |
| Dichlorodifluoromethane, NF | 12.15 | g/canister. |

*Such as a compound of Formula (00A), (0A), (A), (Ia), (Ib), (II), (III), (IV), (V), (VI), (VII), (VIII), (IX), or (X), or a compound of Table 1 or of Examples 1-468.

A compound, such as a compound of Formula (00A), (0A), (A), (Ia), (Ib), (II), (III), (IV), (V), (VI), (VII), (VIII), (IX), or (X), or a compound of Table 1 or of Examples 1-468, may be dosed as described depending on the inhaler system used. In addition to the compound, the administration forms may additionally contain excipients as described above, or, for example, propellants (e.g., Frigen in the case of metered aerosols), surface-active substances, emulsifiers, stabilizers, preservatives, flavorings, fillers (e.g., lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g., Nebulator®, Volumatic®), and automatic devices emitting a puffer spray (Autohaler®), for metered aerosols, in the case of powder inhalers in particular, a number of technical solutions are available (e.g., Diskhaler®, Rotadisk®, Turbohaler® or the inhalers, for example, as described in U.S. Pat. No. 5,263,475, incorporated herein by reference). Additionally, compounds of the invention, such as a compound of Formula (00A), (0A), (A), (Ia), (Ib), (II), (III), (IV), (V), (VI), (VII), (VIII), (IX), or (X), or a compound of Table 1 or of Examples 1-468, may be delivered in multi-chamber devices thus allowing for delivery of combination agents.

The compound, such as a compound of Formula (00A), (0A), (A), (Ia), (Ib), (II), (III), (IV), (V), (VI), (VII), (VIII), (IX), or (X), or a compound of Table 1 or of Examples 1-468, may also be administered parenterally in a sterile medium. Depending on the vehicle and concentration used, the compound can either be suspended or dissolved in the vehicle. Advantageously, adjuvants such as a local anaesthetic, preservative or buffering agents can be dissolved in the vehicle.

Targeted Inhaled Drug Delivery

Optimisation of drugs for delivery to the lung by topical (inhaled) administration has been recently reviewed (Cooper, A. E. et al. Curr. Drug Metab. 2012, 13, 457-473). Due to limitations in the delivery device, the dose of an inhaled drug is likely to be low (approximately <1 mg/day) in humans which necessitates highly potent molecules. For compounds destined to be delivered via dry powder inhalation there is also a requirement to be able to generate crystalline forms of the compound that can be micronized to 1-5 μm in size. Additionally, the compound needs to maintain a sufficient concentration in the lung over a given time period so as to be able to exert a pharmacological effect of the desired duration, and for pharmacological targets where systemic inhibition of said target is undesired, to have a low systemic exposure. The lung has an inherently high permeability to both large molecules (proteins, peptides) as well as small molecules with concomitant short lung half-lives, thus it is necessary to attenuate the lung absorption rate through modification of one or more features of the compounds:

minimizing membrane permeability, reducing dissolution rate, or introducing a degree of basicity into the compound to enhance binding to the phospholipid-rich lung tissue or through trapping in acidic sub-cellular compartments such as lysosomes (pH 5). Accordingly, in some embodiments, compounds of the present invention exhibit one or more of these features.

Matched Pair Analysis

FIG. 1 depicts a matched pair analysis of certain compounds of the present invention containing either an OMe (i) or $OCHF_2$ (ii) group at the indicated position. Any two dots joined by a line represent two compounds with identical $R_1$ and $R_2$ groups, and differing only by an OMe or $OCHF_2$ substitution at the indicated position. FIG. 1 demonstrates that $OCHF_2$ substituted analogs (ii) are consistently more potent in the JAK1 biochemical assay (described below) than the corresponding OMe analogs (i).

Methods of Treatment with and Uses of Janus Kinase Inhibitors

The compounds of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, inhibit the activity of a Janus kinase, such as JAK1 kinase. For example, a compound of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, inhibits the phosphorylation of signal transducers and activators of transcription (STATs) by JAK1 kinase as well as STAT mediated cytokine production. Compounds of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, are useful for inhibiting JAK1 kinase activity in cells through cytokine pathways, such as IL-6, IL-15, IL-7, IL-2, IL-4, IL-9, IL-10, IL-13, IL-21, G-CSF, IFNalpha, IFNbeta or IFNgamma pathways. Accordingly, in one embodiment is provided a method of contacting a cell with a compound of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, to inhibit a Janus kinase activity in the cell (e.g., JAK1 activity).

The compounds of the present invention, such as compounds of Formula (00A), (0A), (A), (Ia), (Ib), (II), (III), (IV), (V), (VI), (VII), (VIII), (IX), or (X), or a compound of Table 1 or of Examples 1-468, can be used for the treatment of immunological disorders driven by aberrant IL-6, IL-15, IL-7, IL-2, IL-4, IL9, IL-10, IL-13, IL-21, G-CSF, IFNalpha, IFNbeta or IFNgamma cytokine signaling.

Accordingly, one embodiment includes compounds of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, for use in therapy.

In some embodiments, there is provided use a compound of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, in the treatment of an inflammatory disease. Further provided is use of a compound of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, for the preparation of a medicament for the treatment of an inflammatory disease, such as asthma. Also provided is a compound of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, for use in the treatment of an inflammatory disease, such as asthma.

Another embodiment includes a method of preventing, treating or lessening the severity of a disease or condition, such as asthma, responsive to the inhibition of a Janus kinase activity, such as JAK1 kinase activity, in a patient. The method can include the step of administering to a patient a therapeutically effective amount of a compound of the present invention, such as a compound of Formula (00A), (0A), (A), (Ia), (Ib), (II), (III), (IV), (V), (VI), (VII), (VIII), (IX), or (X), or a compound of Table 1 or of Examples 1-468. In one embodiment, the disease or condition responsive to the inhibition of a Janus kinase, such as JAK1 kinase, is asthma.

In one embodiment, the disease or condition is cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation (e.g., transplant rejection), immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In one embodiment, the inflammatory disease is rheumatoid arthritis, psoriasis, asthma, inflammatory bowel disease, contact dermatitis or delayed hypersensitivity reactions. In one embodiment, the autoimmune disease is rheumatoid arthritis, lupus or multiple sclerosis.

In one embodiment, the cancer is breast, ovary, cervix, prostate, testis, penile, genitourinary tract, seminoma, esophagus, larynx, gastric, stomach, gastrointestinal, skin, keratoacanthoma, follicular carcinoma, melanoma, lung, small cell lung carcinoma, non-small cell lung carcinoma (NSCLC), lung adenocarcinoma, squamous carcinoma of the lung, colon, pancreas, thyroid, papillary, bladder, liver, biliary passage, kidney, bone, myeloid disorders, lymphoid disorders, hairy cells, buccal cavity and pharynx (oral), lip, tongue, mouth, salivary gland, pharynx, small intestine, colon, rectum, anal, renal, prostate, vulval, thyroid, large intestine, endometrial, uterine, brain, central nervous system, cancer of the peritoneum, hepatocellular cancer, head cancer, neck cancer, Hodgkin's or leukemia.

In one embodiment, the disease is a myeloproliferative disorder. In one embodiment, the myeloproliferative disorder is polycythemia vera, essential thrombocytosis, myelofibrosis or chronic myelogenous leukemia (CML).

Another embodiment includes the use of a compound of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, for the manufacture of a medicament for the treatment of a disease described herein (e.g., an inflammatory disorder, an immunological disorder or cancer). In one embodiment, the invention provides a method of treating a disease or condition as described herein e.g., an inflammatory disorder, an immunological disorder or cancer) by targeting inhibition of a JAK kinase, such as JAK1.

Combination Therapy

The compounds of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, may be employed alone or in combination with other agents for treatment. The second compound of a pharmaceutical composition or dosing regimen typically has complementary activities to the compound of this invention such that they do not adversely affect each other. Such agents are suitably present in combination in amounts that are effective for the purpose intended. The compounds may be administered together in a unitary pharmaceutical composition or separately and, when administered separately this may occur simultaneously or sequentially. Such sequential administration may be close or remote in time.

For example, other compounds may be combined with compounds with which the invention is concerned for the prevention or treatment of inflammatory diseases, such as asthma. Thus the present invention is also concerned with pharmaceutical compositions comprising a therapeutically effective amount of a compound of the invention and one or more other therapeutic agents. Suitable therapeutic agents for a combination therapy with compounds of the invention include, but are not limited to: an adenosine A2A receptor antagonist; an anti-infective; a non-steroidal Glucocorticoid Receptor (GR Receptor) agonist; an antioxidant; a β2 adrenoceptor agonist; a CCR1 antagonist; a chemokine antagonist (not CCR1); a corticosteroid; a CRTh2 antagonist; a DP1 antagonist; a formyl peptide receptor antagonist; a histone deacetylase activator; a chloride channel hCLCA1 blocker; an epithelial sodium channel blocker (ENAC blocker; an inter-cellular adhesion molecule 1 blocker (ICAM blocker); an IKK2 inhibitor; a JNK inhibitor; a cyclooxygenase inhibitor (COX inhibitor); a lipoxygenase inhibitor; a leukotriene receptor antagonist; a dual β2 adrenoceptor agonist/M3 receptor antagonist (MABA compound); a MEK-1 inhibitor; a myeloperoxidase inhibitor (MPO inhibitor); a muscarinic antagonist; a p38 MAPK inhibitor; a phosphodiesterase PDE4 inhibitor; a phosphatidylinositol 3-kinase δ inhibitor (PI3-kinase δ inhibitor); a phosphatidylinositol 3-kinase γ inhibitor (PI3-kinase γ inhibitor); a peroxisome proliferator activated receptor agonist (PPARγ agonist); a protease inhibitor; a retinoic acid receptor modulator (RAR γ modulator); a statin; a thromboxane antagonist; a TLR7 receptor agonist; or a vasodilator.

In addition, compounds of the invention, such as a compound of Formula (00A), (0A), (A), (Ia), (Ib), (II), (III), (IV), (V), (VI), (VII), (VIII), (IX), or (X), or a compound of Table 1 or of Examples 1-468, may be combined with: (1) corticosteroids, such as alclometasone dipropionate, amelometasone, beclomethasone dipropionate, budesonide, butixocort propionate, biclesonide, blobetasol propionate, desisobutyrylciclesonide, dexamethasone, dtiprednol dicloacetate, fluocinolone acetonide, fluticasone furoate, fluticasone propionate, loteprednol etabonate (topical) or mometasone furoate; (2) β2-adrenoreceptor agonists such as salbutamol, albuterol, terbutaline, fenoterol, bitolterol, carbuterol, clenbuterol, pirbuterol, rimoterol, terbutaline, tretoquinol, tulobuterol and long acting β2-adrenoreceptor agonists such as metaproterenol, isoproterenol, isoprenaline, salmeterol, indacaterol, formoterol (including formoterol fumarate), arformoterol, carmoterol, abediterol, vilanterol trifenate, olodaterol; (3) corticosteroid/long acting β2 agonist combination products such as salmeterol/fluticasone propionate (Advair®, also sold as Seretide®), formoterol/budesonide (Symbicort®), formoterol/fluticasone propionate (Flutiform®), formoterol/ciclesonide, formoterol/mometasone furoate, indacaterol/mometasone furoate, vilanterol trifenate/fluticasone furoate, or arformoterol/ciclesonide; (4) anticholinergic agents, for example, muscarinic-3 (M3) receptor antagonists such as ipratropium bromide, tiotropium bromide, aclidinium (LAS-34273), glycopyrronium bromide, umeclidinium bromide; (5) M3-anticholinergic/β2-adrenoreceptor agonist combination products such as vilanterol/umeclidinium (Anoro® Ellipta®), olodaterol/tiotropium bromide, glycopyrronium bromide/indacaterol (Ultibro®, also sold as Xoterna®), fenoterol hydrobromide/ipratropium bromide (Berodual®), albuterol sulfate/ipratropium bromide (Combivent®), formoterol fumarate/glycopyrrolate, or aclidinium bromide/formoterol (6) dual pharmacology M3-anticholinergic/β2-adrenoreceptor agonists such as batefenterol succinate, AZD-2115 or LAS-190792; (7) leukotriene modulators, for example, leukotriene antagonists such as montelukast, zafirulast or pranlukast or leukotriene biosynthesis inhibitors such as zileuton, or LTB4 antagonists such as amelubant, or FLAP inhibitors such as fiboflapon, GSK-2190915; (8) phosphodiesterase-IV (PDE-IV) inhibitors (oral or inhaled), such as roflumilast, cilomilast, oglemilast, rolipram, tetomilast, AVE-8112, revamilast, CHF 6001; (9) antihistamines, for example, selective histamine-1 (H1) receptor antagonists such as fexofenadine, citirizine, loratidine or astemizole or dual H1/H3 receptor antagonists such as GSK 835726, or GSK 1004723; (10) antitussive agents, such as codeine or dextramorphan; (11) a mucolytic, for example, N-acetyl cysteine or fudostein; (12) a expectorant/mucokinetic modulator, for example, ambroxol, hypertonic solutions (e.g., saline or mannitol) or surfactant; (13) a peptide mucolytic, for example, recombinant human deoxyribonoclease I (dornase-alpha and rhDNase) or helicidin; (14) antibiotics, for example azithromycin, tobramycin or aztreonam; (15) non-selective COX-1/COX-2 inhibitors, such as ibuprofen or ketoprofen; (16) COX-2 inhibitors, such as celecoxib and rofecoxib; (17) VLA-4 antagonists, such as those described in WO97/03094 and WO97/02289, each incorporated herein by reference; (18) TACE inhibitors and TNF-α inhibitors, for example anti-TNF monoclonal antibodies, such as Remicade® and CDP-870 and TNF receptor immunoglobulin molecules, such as Enbrel®; (19) inhibitors of matrix metalloprotease, for example MMP-12; (20) human neutrophil elastase inhibitors, such as BAY-85-8501 or those described in WO2005/026124, WO2003/053930 and WO06/082412, each incorporated herein by reference; (21) A2b antagonists such as those described in WO2002/42298, incorporated herein by reference; (22) modulators of chemokine receptor function, for example antagonists of CCR3 and CCR8; (23) compounds which modulate the action of other prostanoid receptors, for example, a thromboxane $A_2$ antagonist; DP1 antagonists such as laropiprant or asapiprant CRTH2 antagonists such as OC000459, fevipiprant, ADC 3680 or ARRY 502; (24) PPAR agonists including PPAR alpha agonists (such as fenofibrate), PPAR delta agonists, PPAR gamma agonists such as pioglitazone, rosiglitazone and balaglitazone; (25) methylxanthines such as theophylline or aminophylline and methylxanthine/corticosteroid combinations such as theophylline/budesonide, theophylline/fluticasone propionate, theophylline/ciclesonide, theophylline/mometasone furoate and theophylline/beclometasone dipropionate; (26) A2a agonists such as those described in EP1052264 and EP1241176; (27) CXCR2 or IL-8 antagonists such as AZD-5069, AZD-4721, danirixin; (28) IL-R signalling modulators such as kineret and ACZ 885; (29) MCP-1 antagonists such as ABN-912; (30) a p38 MAPK inhibitor such as BCT197, JNJ49095397, losmapimod or PH-797804; (31) TLR7 receptor agonists such as AZD 8848; (32) PI3-kinase inhibitors such as RV1729 or GSK2269557.

In some embodiments, the compounds of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, can be used in combination with one or more additional drugs, for example anti-hyperproliferative, anti-cancer, cytostatic, cytotoxic, anti-inflammatory or chemotherapeutic agents, such as those agents disclosed in U.S. Publ. Appl. No. 2010/0048557, incorporated herein by reference. A compound of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, can be also used in combination with radiation therapy or surgery, as is known in the art.

Articles of Manufacture

Another embodiment includes an article of manufacture (e.g., a kit) for treating a disease or disorder responsive to the inhibition of a Janus kinase, such as a JAK1 kinase. The kit can comprise:

(a) a first pharmaceutical composition comprising a compound of the present invention, such as a compound of Formula (00A), (0A), (A), (Ia), (Ib), (II), (III), (IV), (V), (VI), (VII), (VIII), (IX), or (X), or a compound of Table 1 or of Examples 1-468; and (b) instructions for use.

In another embodiment, the kit further comprises:

(c) a second pharmaceutical composition, such as a pharmaceutical composition comprising an agent for treatment as described above, such as an agent for treatment of an inflammatory disorder, or a chemotherapeutic agent.

In one embodiment, the instructions describe the simultaneous, sequential or separate administration of said first and second pharmaceutical compositions to a patient in need thereof.

In one embodiment, the first and second compositions are contained in separate containers. In another embodiment, the first and second compositions are contained in the same container.

Containers for use include, for example, bottles, vials, syringes, blister pack, etc. The containers may be formed from a variety of materials such as glass or plastic. The container includes a compound of the present invention, such as a compound of Formula (00A), (0A), (A), (Ia), (Ib), (II), (III), (IV), (V), (VI), (VII), (VIII), (IX), or (X), or a compound of Table 1 or of Examples 1-468, or composition thereof, which is effective for treating the condition and may have a sterile access port (for example the container may be an intravenous solution bag or a vial having a stopper pierceable by a hypodermic injection needle). The label or package insert indicates that the compound or composition is used for treating the condition of choice, such as asthma or cancer. In one embodiment, the label or package inserts indicates that the compound or composition can be used to treat a disorder. In addition, the label or package insert may indicate that the patient to be treated is one having a disorder characterized by overactive or irregular Janus kinase activity, such as overactive or irregular JAK1 activity. The label or package insert may also indicate that the compound or composition can be used to treat other disorders.

Alternatively, or additionally, the kit may further comprise a second (or third) container comprising a pharmaceutically acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare other compounds of the present invention, and alternative methods for preparing the compounds are within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

EXAMPLES

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

General Experimental Details:

All solvents and commercial reagents were used as received unless otherwise stated. Where products were purified by chromatography on silica this was carried out using either a glass column manually packed with silica gel (Kieselgel 60, 220-440 mesh, 35-75 μm) or an Isolute® SPE Si II cartridge. 'Isolute SPE Si cartridge' refers to a pre-packed polypropylene column containing unbonded activated silica with irregular particles with average size of 50 μm and nominal 60 Å porosity. Where an Isolute® SCX-2 cartridge was used, 'Isolute® SCX-2 cartridge' refers to a pre-packed polypropylene column containing a non-end-capped propylsulphonic acid functionalised silica strong cation exchange sorbent.

Preparative HPLC Conditions

HPLC System 1: C18-reverse-phase column (250×21.2 mm Gemini column with 5 μm particle size), eluting with a gradient of A: water+0.1% formic acid; B: acetonitrile+0.1% formic acid with a flow rate typically 20 mL/min and a gradient increasing in B. UV detection at 254 nm. Compounds were obtained as the formate salt where stated.

HPLC System 2: Phenylhexyl reverse-phase column (250×21.2 mm Gemini column with 5 μm particle size), eluting with a gradient of A: water+0.1% formic acid; B: acetonitrile+0.1% formic acid with a flow rate typically 20 mL/min and gradient of 1%/min increasing in B. UV detection at 254 nm. Compounds were obtained as the formate salt where stated.

HPLC System 3: C18-reverse-phase end-capped column (250×21.2 mm Gemini column with 5 μm particle size), eluting with a gradient of A: water+0.1% ammonia; B: acetonitrile+0.1% ammonia with a flow rate typically 20 mL/min and a gradient increasing in B. UV detection at 254 nm. Compounds were obtained as the free base.

NMR Analytical Methods $^{1}H$ NMR spectra were recorded at ambient temperature using one of the following:

i. Varian Unity Inova (400 MHz) spectrometer with a 400 4NUC 5 mm probe.

ii. Bruker Avance DRX400 (400 MHz) spectrometer with a PABBO 5 mm probe.

iii. Varian Unity Inova (400 MHz) spectrometer with a 5 mm inverse detection triple resonance probe.

iv. Bruker Avance DRX (400 MHz) spectrometer with a 5 mm inverse detection triple resonance TXI probe.

Chemical shifts are expressed in ppm relative to tetramethylsilane.

LC-MS Analytical Methods

LC-MS information is provided in Table 2.

LC-MS Method 1: Waters Platform LC with a C18-reverse-phase column (30×4.6 mm Phenomenex Luna 3 μm particle size), elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection - MS, ELS, UV (100 μl split to MS with in-line UV detector)
MS ionisation method - Electrospray (positive and negative ion)

LC-MS Method 2: Waters Micromass ZMD with a C18-reverse-phase column (30×4.6 mm Phenomenex Luna 3 μm particle size), elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection - MS, ELS, UV (100 μl split to MS with in-line UV detector)
MS ionisation method - Electrospray (positive and negative ion)

LC-MS Method 3: VG Platform II quadrupole spectrometer with a C18-reverse-phase column (30×4.6 mm Phenomenex Luna 3 μm particle size), elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection - MS, ELS, UV (200 μl/min split to the ESI source with inline HP1050 DAD detection)
MS ionisation method - Electrospray (positive and negative ion)

LC-MS Method 4: Finnigan AQA with a C18-reverse-phase column (30×4.6 mm Phenomenex Luna 3 μm particle size), elution with A: water+0.1% formic acid; B: acetonitrile+0.1% formic acid. Gradient:

| Gradient - Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection - MS, ELS, UV
MS ionisation method - Electrospray (positive ion)

LC-MS Method 5: Waters Micromass ZQ2000 quadrupole mass spectrometer with a C18-reverse-phase column (100×2.1 mm Acquity BEH C18 1.7μ, Acquity BEH Shield RP18 1.7μ, or Acquity HSST3 1.8μ) maintained at 40° C., elution with A: water+0.1% formic acid; B: acetonitrile+0.1% formic acid. Gradient:

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection - MS, UV PDA
MS ionisation method - Electrospray (positive ion)

LC-MS Method 6: Waters Acquity UPLC with a C18-reverse-phase column (100×2.1 mm Acquity BEH C18, 1.7 μm particle size), elution with solvent A: water+0.1% formic acid; solvent B: acetonitrile+0.1% formic acid at 40° C. Gradient:

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 8.00 | 0.4 | 95 | 5 |

Detection - UV (220 nm)
MS ionisation method - $ESI^+$

LC-MS Method 7: SHIMADZU 20A HPLC with a C18-reverse-phase column (30×2.1 mm Xtimate TM-C18, 3 μm particle size), elution with solvent A: water+0.038% trifluoroacetic acid; solvent B: acetonitrile+0.02% trifluoroacetic acid. Gradient:

| Gradient - Time | flow mL/min | % A | % B |
|---|---|---|---|
| 0.00 | 1.2 | 90 | 10 |
| 0.90 | 1.2 | 20 | 80 |
| 1.5 | 1.2 | 20 | 80 |
| 2.0 | 1.2 | 90 | 10 |

Detection - UV (220 nm)
MS ionisation method - $ESI^+$

LC-MS Method 8: SHIMADZU 20A HPLC with a C18-reverse-phase column (30×2.1 mm Xtimate TM-C18, 3 μm particle size), elution with solvent A: water+0.038% trifluoroacetic acid; solvent B: acetonitrile+0.02% trifluoroacetic acid. Gradient:

| Gradient - Time | flow mL/min | % A | % B |
|---|---|---|---|
| 0.00 | 1.2 | 90 | 10 |
| 1.35 | 1.2 | 20 | 80 |
| 2.25 | 1.2 | 20 | 80 |
| 2.75 | 1.2 | 90 | 10 |

Detection - UV (220 nm)
MS ionisation method - $ESI^+$

LC-MS Method 9: SHIMADZU 20A HPLC with a C18-reverse-phase column (30×2.1 mm Xtimate TM-C18, 3 μm particle size), elution with solvent A: water+0.038% trifluoroacetic acid; solvent B: acetonitrile+0.02% trifluoroacetic acid. Gradient:

| Gradient - Time | flow mL/min | % A | % B |
|---|---|---|---|
| 0.00 | 1.2 | 100 | 0 |
| 0.90 | 1.2 | 40 | 60 |
| 1.5 | 1.2 | 40 | 60 |
| 2.0 | 1.2 | 100 | 0 |

Detection - UV (220 nm)
MS ionisation method - $ESI^+$

LC-MS Method 10: SHIMADZU 20A HPLC with a C18-reverse-phase column (30×2.1 mm Xtimate TM-C18, 3 μm particle size), elution with solvent A: water+0.038% trifluoroacetic acid; solvent B: acetonitrile+0.02% trifluoroacetic acid. Gradient:

| Gradient - Time | flow mL/min | % A | % B |
|---|---|---|---|
| 0.00 | 0.8 | 100 | 0 |
| 6.0 | 0.8 | 40 | 60 |
| 6.5 | 0.8 | 40 | 60 |
| 7.0 | 0.8 | 100 | 0 |

Detection - UV (220 nm)
MS ionisation method - $ESI^+$

LC-MS Method 11: Agilent 1200 HPLC with an Xtimate C18 column (3 um, 30×2.1 mm), elution with A: water+0.038% trifluoroacetic acid; B: acetonitrile+0.02% trifluoroacetic acid.

| Gradient - Time | flow mL/min | % A | % B |
|---|---|---|---|
| 0.00 | 1.2 | 90 | 10 |
| 0.90 | 1.2 | 20 | 80 |
| 1.50 | 1.2 | 90 | 10 |
| 2.00 | 1.2 | 90 | 10 |

Detection - MS, UV (PDA detector)
MS ionisation method - Electrospray (positive ion)

LC-MS Method 12: Agilent 1200 HPLC with an Xtimate C18 column (3 um, 30×2.1 mm), elution with A: water+0.038% trifluoroacetic acid; B: acetonitrile+0.02% trifluoroacetic acid.

| Gradient - Time | flow mL/min | % A | % B |
|---|---|---|---|
| 0.00 | 1.2 | 100 | 0 |
| 0.90 | 1.2 | 40 | 60 |
| 1.50 | 1.2 | 100 | 0 |
| 2.00 | 1.2 | 100 | 0 |

Detection - MS, UV (PDA detector)
MS ionisation method - Electrospray (positive ion)

LC-MS Method 13: Agilent 1200 HPLC with an Xtimate C18 column (3 um, 30×2.1 mm), elution with A: water+0.038% trifluoroacetic acid; B: acetonitrile+0.02% trifluoroacetic acid.

| Gradient - Time | flow mL/min | % A | % B |
|---|---|---|---|
| 0.00 | 0.8 | 100 | 0 |
| 1.35 | 0.8 | 40 | 60 |
| 2.25 | 0.8 | 100 | 0 |
| 3.00 | 0.8 | 100 | 0 |

Detection - MS, UV (PDA detector)
MS ionisation method - Electrospray (positive ion)

LC-MS Method 14: SHIMADZU 20A HPLC with a C18-reverse-phase column (50×2.0 mm Shim-pack XR-ODS, 1.6 μm particle size), elution with solvent A: water+0.05% trifluoroacetic acid; solvent B: acetonitrile+0.05% trifluoroacetic acid. Gradient:

| Gradient - Time | flow mL/min | % A | % B |
|---|---|---|---|
| 0.01 | 0.7 | 90 | 10 |
| 2.20 | 0.7 | 0 | 100 |
| 3.20 | 0.7 | 0 | 100 |
| 3.30 | 0.7 | 90 | 10 |

Detection - UV (254 nm)
MS ionisation method - $ESI^+$

LC-MS Method 15: SHIMADZU 20A HPLC with a C18-reverse-phase column (50×3.0 mm Shim-pack XR-ODS, 1.6 μm particle size), elution with solvent A: water+0.05% trifluoroacetic acid; solvent B: acetonitrile+0.05% trifluoroacetic acid. Gradient:

| Gradient - Time | flow mL/min | % A | % B |
|---|---|---|---|
| 0.01 | 1.0 | 95 | 5 |
| 3.00 | 1.0 | 20 | 80 |
| 3.80 | 1.0 | 20 | 80 |
| 3.90 | 1.0 | 95 | 5 |

Detection - UV (254 nm)
MS ionisation method - $ESI^+$

LC-MS Method 16: SHIMADZU 20A HPLC with a C18-reverse-phase column (50×3.0 mm Shim-pack XR-ODS, 2.2 μm particle size), elution with solvent A: water+0.05% trifluoroacetic acid; solvent B: acetonitrile+0.05% trifluoroacetic acid. Gradient:

| Gradient - Time | flow mL/min | % A | % B |
|---|---|---|---|
| 0.01 | 1.0 | 95 | 5 |
| 4.20 | 1.0 | 25 | 75 |
| 5.20 | 1.0 | 25 | 75 |
| 5.30 | 1.0 | 95 | 5 |

Detection - UV (254 nm)
MS ionisation method - $ESI^+$

LC-MS Method 17: SHIMADZU 20A HPLC with a C18-reverse-phase column (50×3.0 mm Shim-pack XR-ODS, 2.2 μm particle size), elution with solvent A: water+0.05% trifluoroacetic acid; solvent B: acetonitrile+0.05% trifluoroacetic acid. Gradient:

| Gradient - Time | flow mL/min | % A | % B |
|---|---|---|---|
| 0.01 | 1.0 | 95 | 5 |
| 2.20 | 1.0 | 0 | 100 |
| 3.20 | 1.0 | 0 | 100 |
| 3.30 | 1.0 | 95 | 5 |

Detection - UV (254 nm)
MS ionisation method - $ESI^+$

LC-MS Method 18: SHIMADZU LCMS-2020 HPLC column (150×4.6 mm Venusil XBP Silica, 5.0 μm particle size), elution with solvent A: Hexane; solvent B: Ethanol.

| Gradient - Time | flow mL/min | % A | % B |
|---|---|---|---|
| 0.01 | 1.0 | 80 | 20 |
| 6.00 | 1.0 | 0 | 100 |
| 12.0 | 1.0 | 0 | 100 |

Detection - UV (254 nm)
MS ionisation method - $ESI^+$

LC-MS Method 19: SHIMADZU 20A HPLC with a C18-reverse-phase column (50×3 mm Xtimate TM-C18, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
|---|---|---|---|
| 0.00 | 1.0 | 95 | 5 |
| 2.00 | 1.0 | 0 | 100 |
| 3.10 | 1.0 | 0 | 100 |
| 3.30 | 1.0 | 95 | 5 |

Detection - UV (220 and 254 nm)
MS ionization method - Electrospray (positive ion)

LC-MS Methods 20: SHIMADZU 20A HPLC with a C18-reverse-phase column (50×3 mm Xtimate TM-C18, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
|---|---|---|---|
| 0.00 | 1.0 | 95 | 5 |
| 2.00 | 1.0 | 0 | 100 |
| 3.20 | 1.0 | 0 | 100 |
| 3.30 | 1.0 | 95 | 5 |

Detection - UV (220 and 254 nm)
MS ionization method - Electrospray (positive ion)

LC-MS Method 21: SHIMADZU 20A HPLC with a C18-reverse-phase column (50×3 mm Xtimate TM-C18, 2.2 μm particle size), elution with solvent A: water+0.05% trifluoroacetic acid; solvent B: acetonitrile+0.05% trifluoroacetic acid. Gradient:

| Gradient - Time | flow ml/min | % A | % B |
|---|---|---|---|
| 0.00 | 1.0 | 95 | 5 |
| 2.00 | 1.0 | 0 | 100 |
| 3.20 | 1.0 | 0 | 100 |
| 3.30 | 1.0 | 95 | 5 |

Detection - UV (220 and 254 nm)
MS ionization method - Electrospray (positive ion)

LC-MS Method 22: SHIMADZU 20A HPLC with a C18-reverse-phase column (50×3 mm Xtimate TM-C18, 2.2 μm particle size), elution with solvent A: water+0.05% formic acid; solvent B: acetonitrile+0.05% formic acid. Gradient:

| Gradient - Time | flow ml/min | % A | % B |
|---|---|---|---|
| 0.00 | 1.0 | 95 | 5 |
| 1.20 | 1.0 | 0 | 100 |
| 2.20 | 1.0 | 0 | 100 |
| 2.30 | 1.0 | 95 | 5 |

Detection - UV (220 and 254 nm)
MS ionization method - Electrospray (positive ion)

LC-MS Method 23: SHIMADZU 20A HPLC with a C18-reverse-phase column (50×3 mm Xtimate TM-C18, 2.2 μm particle size), elution with solvent A: water+0.1% formic acid; solvent B: acetonitrile+0.05% formic acid. Gradient:

| Gradient - Time | flow ml/min | % A | % B |
|---|---|---|---|
| 0.00 | 1.0 | 95 | 5 |
| 2.00 | 1.0 | 0 | 100 |
| 3.10 | 1.0 | 0 | 100 |
| 3.20 | 1.0 | 95 | 5 |

Detection - UV (220 and 254 nm)
MS ionization method - Electrospray (positive ion)

LC-MS Method 24: SHIMADZU 20A HPLC with a C18-reverse-phase column (50×3 mm Xtimate TM-C18, 2.2 μm particle size), elution with solvent A: water+0.04% ammonium hydroxide; solvent B: acetonitrile. Gradient:

| Gradient - Time | flow ml/min | % A | % B |
|---|---|---|---|
| 0.00 | 1.2 | 95 | 5 |
| 1.20 | 1.2 | 0 | 100 |
| 2.20 | 1.2 | 0 | 100 |
| 2.30 | 1.2 | 95 | 5 |

Detection - UV (220 and 254 nm)
MS ionization method - Electrospray (positive ion)

LC-MS Method 25: SHIMADZU 20A HPLC with a C18-reverse-phase column (30×2.1 mm Xtimate TM-C18, 3 μm particle size), elution with solvent A: water+0.05% trifluoroacetic acid; solvent B: acetonitrile+0.05% trifluoroacetic acid. Gradient:

| Gradient - Time | flow ml/min | % A | % B |
|---|---|---|---|
| 0.00 | 1.0 | 95 | 5 |
| 1.10 | 1.0 | 0 | 100 |
| 1.60 | 1.0 | 0 | 100 |
| 1.70 | 1.0 | 95 | 5 |

Detection - UV (220 and 254 nm)
MS ionization method - Electrospray (positive ion)

LC-MS Method 26: SHIMADZU 20A HPLC with a C18-reverse-phase column (50×3.0 mm Xtimate TM-C18, 2.6 μm particle size), elution with solvent A: Water/0.1% formic acid; solvent B: Acetonitrile/0.1% formic acid. Gradient:

| Gradient - Time | flow ml/min | % A | % B |
|---|---|---|---|
| 0.00 | 1.5 | 90 | 10 |
| 2.00 | 1.5 | 0 | 100 |

-continued

| Gradient - Time | flow ml/min | % A | % B |
|---|---|---|---|
| 2.70 | 1.5 | 0 | 100 |
| 2.8 | 1.5 | 90 | 10 |

Detection - UV (220 and 254 nm)
MS ionization method - Electrospray (positive ion)

LC-MS Method 27: SHIMADZU 20A HPLC with a C18-reverse-phase column (50×2.1 mm Xtimate TM-C18, 2.7 μm particle size), elution with solvent A: Water/0.05% formic acid; solvent B: Acetonitrile/0.1% formic acid:

| Gradient - Time | flow ml/min | % A | % B |
|---|---|---|---|
| 0.00 | 1.0 | 95 | 5 |
| 2.00 | 1.0 | 5 | 95 |
| 2.70 | 1.0 | 5 | 95 |
| 2.8 | 1.0 | 95 | 5 |

Detection - UV (220 and 254 nm)
MS ionization method - Electrospray (positive ion)

LC-MS Method 28: SHIMADZU 20A HPLC with a C18-reverse-phase column (50×3.0 mm Xtimate TM-C18, 2.5 μm particle size), elution with solvent A: Water/5 mM $NH_4HCO_3$; solvent B: Acetonitrile:

| Gradient - Time | flow ml/min | % A | % B |
|---|---|---|---|
| 0.00 | 1.5 | 90 | 10 |
| 2.10 | 1.5 | 5 | 95 |
| 2.70 | 1.5 | 5 | 95 |
| 3.0 | 1.5 | 95 | 5 |

Detection - UV (220 and 254 nm)
MS ionization method - Electrospray (positive ion)

LC-MS Methods 29: SHIMADZU LCMS-2020 C18 reverse-phase column (50×3.0 mm, Shim-pack XR-ODS, 2.5 μm particle size), elution with solvent A: Water/0.05% $TFA_3$; solvent B: Acetonitrile/0.05% TFA:

| Gradient - Time | flow ml/min | % A | % B |
|---|---|---|---|
| 0.00 | 1.0 | 95 | 5 |
| 2.20 | 1.0 | 5 | 95 |
| 3.20 | 1.0 | 5 | 95 |
| 3.30 | 1.0 | 95 | 5 |

Detection - UV (220 and 254 nm)
MS ionization method - Electrospray (positive ion)

LC-MS Methods 30: SHIMADZU LCMS-2020 C18 reverse-phase column (50×2.1 mm, Shiseido CAPCELL CORE C18, 2.7 μm particle size), elution with solvent A: Water/0.05% $TFA_3$; solvent B: Acetonitrile/0.05% TFA:

| Gradient - Time | flow ml/min | % A | % B |
|---|---|---|---|
| 0.00 | 1.0 | 95 | 5 |
| 2.0 | 1.0 | 5 | 95 |
| 2.75 | 1.0 | 5 | 95 |
| 2.80 | 1.0 | 95 | 5 |

Detection - UV (220 and 254 nm)
MS ionization method - Electrospray (positive ion)

LC-MS Methods 31: SHIMADZU LCMS-2020 C18 reverse-phase column (50×2.1 mm, Waters BEH C18, 1.7 μm particle size), elution with solvent A: Water/0.1% $TFA_3$; solvent B: Acetonitrile/0.1% TFA:

| Gradient - Time | flow ml/min | % A | % B |
|---|---|---|---|
| 0.00 | 0.7 | 90 | 10 |
| 3.50 | 0.7 | 5 | 95 |
| 4.60 | 0.7 | 5 | 95 |
| 4.70 | 0.7 | 90 | 10 |

Detection - UV (220 and 254 nm)
MS ionization method - Electrospray (positive ion)

LC-MS Methods 32: SHIMADZU LCMS-2020 C18 reverse-phase column (50×3.0 mm, Gemini-NX 3μ C18 110A, 3.0 μm particle size), elution with solvent A: Water/6.5 mM $NH_4HCO_3$ pH10; solvent B: Acetonitrile

| Gradient - Time | flow ml/min | % A | % B |
|---|---|---|---|
| 0.00 | 1.2 | 95 | 5 |
| 0.50 | 1.2 | 95 | 5 |
| 2.20 | 1.2 | 5 | 95 |
| 3.00 | 1.2 | 5 | 95 |
| 3.20 | 1.2 | 90 | 10 |

Detection - UV (220 and 254 nm)
MS ionization method - Electrospray (positive ion)

LC-MS Methods 33: SHIMADZU LCMS-2020 C18 reverse-phase column (50×2.1 mm, Waters BEH C18, 1.7 μm particle size), elution with solvent A: Water/0.05% $TFA_3$; solvent B: Acetonitrile/0.05% TFA:

| Gradient - Time | flow ml/min | % A | % B |
|---|---|---|---|
| 0.00 | 0.7 | 95 | 5 |
| 2.00 | 0.7 | 5 | 95 |
| 2.60 | 0.7 | 5 | 95 |
| 2.70 | 0.7 | 95 | 5 |

Detection - UV (220 and 254 nm)
MS ionization method - Electrospray (positive ion)

LC-MS Methods 34: SHIMADZU LCMS-2020 C18 reverse-phase column (50×2.1 mm, Waters BEH C18, 1.7 μm particle size), elution with solvent A: Water/0.05% $TFA_3$; solvent B: Acetonitrile/0.05% TFA:

| Gradient - Time | flow ml/min | % A | % B |
|---|---|---|---|
| 0.00 | 0.7 | 95 | 5 |
| 4.00 | 0.7 | 20 | 80 |
| 5.00 | 0.7 | 20 | 80 |
| 5.20 | 0.7 | 95 | 5 |

Detection - UV (220 and 254 nm)
MS ionization method - Electrospray (positive ion)

LC-MS Methods 35: SHIMADZU LCMS-2020 C18 reverse-phase column (50×3.0 mm, Shim-pack XR-ODS, 2.2 μm particle size), elution with solvent A: Water/0.05% $TFA_3$; solvent B: Acetonitrile/0.05% TFA:

| Gradient - Time | flow ml/min | % A | % B |
|---|---|---|---|
| 0.00 | 1.0 | 95 | 5 |
| 3.20 | 1.0 | 40 | 60 |
| 3.80 | 1.0 | 0 | 100 |
| 4.70 | 1.0 | 0 | 100 |
| 4.80 | 1.0 | 95 | 5 |

Detection - UV (220 and 254 nm)
MS ionization method - Electrospray (positive ion)

LC-MS Methods 36: SHIMADZU 20A HPLC with a C18-reverse-phase column (50×3.0 mm, Gemini-NX 3μ C18

110A, 3.0 μm particle size), elution with solvent A: Water/5 mM $NH_4HCO_3$; solvent B: Acetonitrile:

| Gradient - Time | flow ml/min | % A | % B |
|---|---|---|---|
| 0.00 | 1.2 | 90 | 10 |
| 4.00 | 1.2 | 40 | 60 |
| 5.20 | 1.2 | 40 | 60 |
| 5.30 | 1.2 | 90 | 10 |

Detection - UV (220 and 254 nm)
MS ionization method - Electrospray (positive ion)

LC/MS Methods 37: Agilent 10-min LCMS method:
Experiments performed on an Agilent 1100 HPLC coupled with Agilent MSD mass spectrometer using ESI as ionization source. The LC separation was using a Phenomenex XB-C18, 1.7 um, 50×2.1 mm column with a 0.4 ml/minute flow rate. Solvent A is water with 0.1% FA and solvent B is acetonitrile with 0.1% FA. The gradient consisted with 2-98% solvent B over 7 min and hold 97% B for 1.5 min following equilibration for 1.5 min. LC column temperature is 40° C. UV absorbance was collected at 220 nm and 254 nm and mass spec full scan was applied to all experiments.
LC/MS Methods 38: Waters 10-min LCMS method:
Experiments performed on a Waters Acquity UPLC with Waters LCT Premier XE mass spectrometer using ESI as ionization source. The LC separation was using an Acquity UPLC BEH C18, 1.7 um, 2.1×50 mm column and a 0.6 ml/minute flow rate. Solvent A is water with 0.0500 TFA and solvent B is acetonitrile with 0.05% TFA The gradient consisted of 2-980% solvent B over 7 min and hold 98% B for 1.5 min following equilibration for 1.5 min. LC column temperature is 40° C. UV absorbance was collected at 220 nm and 254 nm and mass spec full scan was applied to all experiments.
LC/MS Methods 39: Shimadzu 5-min LCMS method:
Experiments performed on a Shimadzu LC with LC-30AD solvent pump, SPD-M30A UV detector and 2020 MS using both ESI and APCI as ionization source. The LC separation was using a Waters UPLC BEH C18, 1.7 mm, 2.1×50 mm column and a 0.7 ml/minute flow rate. Solvent A is water with 0.1% FA and solvent B is acetonitrile with 0.1% FA. The gradient consisted of 2-98% solvent B over 4.5 min and hold 98% B for 0.5 min following equilibration for 0.5 min. LC column temperature is 40° C. UV absorbance was collected at 254 nm and mass spec full scan was applied to all experiments.
Preparative Mass Directed Automated Purification Conditions
MDAP Method 1: Agilent 1260 infinity purification system. Agilent 6100 series single Quadrupole LC/MS. XSEELECT CSH Prep C18 5 μm OBD, 30×150 mm, RT. Elution with solvent A: 0.1% aqueous formic acid; solvent B: 0.1% formic acid in acetonitrile 60 ml/min. 10%-95%, 22 min, centred around a specific focused gradient. Injection of a 20-60 mg/ml solution in DMSO (+ optional formic acid and water)
MDAP Method 2: Agilent 1260 infinity purification system. Agilent 6100 series single Quadrupole LC/MS. XBridge Prep C18 5 μm OBD, 30×150 mm, RT. Elution with solvent A: 0.1% aqueous ammonia; solvent B: 0.1% ammonia in acetonitrile 60 ml/min. 10%-95%, 22 min, centred around a specific focused gradient. Injection of a 20-60 mg/ml solution in DMSO (+ optional formic acid and water)

ABBREVIATIONS $CH_3OD$ Deuterated Methanol
$CDCl_3$ Deuterated Chloroform
DCM Dichloromethane
DIPEA Diisopropylethylamine
DMAP 4-Dimethylaminopyridine
DMF Dimethylformamide
DMSO Dimethylsulfoxide
DMSO-d6 Deuterated dimethylsulfoxide
EtOAc Ethyl acetate
EtOH Ethanol
HOAc Acetic acid
g Gram
HATU (O-(7-azabenzotriazol-1-yl)-N,N,N',N'-tetramethyluronium hexafluorophosphate)
HCl Hydrochloric acid
IMS Industrial methylated spirits
L Liter
MDAP Mass directed automated purification
MeOH Methanol
mg Milligram
mL Milliliter
SCX-2 Strong cation exchange
THF Tetrahydrofuran
TFA Trifluoroacetic acid Example A

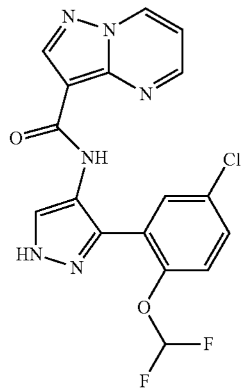 [SMILES: O=C(Nc1c[nH]nc1-c1cc(Cl)ccc1OC(F)F)c1cnn2cccnc12]

Pyrazolo[1,5-a]pyrimidine-3-carboxylic acid [3-(5-chloro-2-difluoromethoxyphenyl)-1H-pyrazol-4-yl] amide To a solution of 2-bromo-4-chlorophenol (4.98 g, 24.0 mmol) in DMF (25 mL) was added sodium chlorodifluoroacetate (8.42 g, 55.2 mmol), cesium carbonate (10.97 g, 33.67 mmol) and water (2.5 mL). The reaction was stirred at 100° C. for 16 hours. The reaction mixture was partitioned between ethyl acetate and water, the organic portion washed with brine, dried ($MgSO_4$), and evaporated. The crude product was purified by flash chromatography on silica eluting with 0-20% EtOAc in heptanes to yield 2-bromo-4-chloro-1-(difluoromethoxy)benzene as a clear, colorless oil (2.98 g, 48%). LCMS (ESI) no m/z signal; $^1$H NMR (400 MHz, DMSO-$d_6$) δ: (ppm) 7.90 (d, 1H), 7.54 (dd, 1H), 7.38 (d, 1H), 7.28 (t, 1H).

To a solution of 4-nitro-1-(2-trimethylsilanylethoxymethyl)-1H-pyrazole (preparation described in WO2011003065) (46.5 g, 191 mmol) in DMA (350 mL) was added 2-bromo-4-chloro-1-difluoromethoxybenzene (64.0 g, 248 mmol), palladium (II) acetate (2.15 g, 9.6 mmol), di-(adamantyl)-n-butylphosphine (5.0 g, 13.4 mmol), potassium carbonate (79.2 g, 573 mmol) and trimethylacetic acid (5.27 g, 51.6 mmol). The mixture was degassed with nitrogen for 10 minutes then heated at 130° C. for 8 hours. The reaction mixture was allowed to cool to room temperature, diluted with ethyl acetate and washed with water and brine, dried ($MgSO_4$), filtered and evaporated. The resultant crude material was purified by flash chromatography on silica eluting with 0-10% EtOAc in cyclohexane to afford 5-(5-chloro-2-difluoromethoxyphenyl)-4-nitro-1-(2-trimethylsilanylethoxymethyl)-1H-pyrazole (62.4 g, 78%). $^1$H NMR (400 MHz, $CDCl_3$) δ: (ppm) 8.24 (s, 1H), 7.52-7.53 (m, 2H), 6.39 (t, 1H), 5.29-5.30 (m, 2H), 3.63-3.64 (m, 2H), 0.90 (s, 9H).

To a solution of 5-(5-chloro-2-difluoromethoxyphenyl)-4-nitro-1-(2-trimethylsilanylethoxymethyl)-1H-pyrazole (62 g, 148 mmol) in ethanol (600 mL) was added water (200 mL), ammonium chloride (32 g, 590 mmol) and iron powder (41 g, 740 mmol). The mixture was heated at 80° C. for 2 hours then allowed to cool to room temperature. The residual solid was removed by filtration through Celite®. The filtrate was evaporated under reduced pressure, diluted with water and extracted twice with DCM. The combined organic extracts were washed with water and brine, dried ($MgSO_4$) and evaporated to afford a dark oil. The oil was purified by flash chromatography on silica eluting with 0-25% EtOAc in DCM. Appropriate fractions were collected and the solvent removed in-vacuo to afford 5-(5-chloro-2-difluoromethoxyphenyl)-1-(2-trimethylsilanyl-ethoxymethyl)-1H-pyrazol-4-ylamine as a brown oil (30.8 g, 54%). $^1$H NMR (400 MHz, $CDCl_3$) δ: (ppm) 7.56 (d, 1H), 7.44 (dd, 1H), 7.34 (s, 1H), 7.30-7.25 (m, 1H), 6.37 (t, 1H), 5.29 (s, 2H), 3.56 (t, 2H), 0.88 (dd, 2H), 0.00 (s, 9H).

A solution of 5-(5-chloro-2-difluoromethoxyphenyl)-1-(2-trimethylsilanyl-ethoxymethyl)-1H-pyrazol-4-ylamine (60.0 g, 154 mmol) in THF (100 mL) was added dropwise over 30 minutes to an ice/water cooled mixture of pyrazolo [1,5-a]pyrimidine-3-carbonyl chloride (27.8 g, 153 mmol), and DIPEA (49.5 g, 383 mmol) in THF (300 mL). On complete addition the mixture was left to stir at room temperature for 1 hour. The solvent was evaporated and the residue diluted with 0.5 N aqueous HCl and extracted with ethyl acetate. The combined organic extract was passed through Celite® to remove the residual solid and the filtrate washed with 1M aqueous $K_2CO_3$, water and brine, dried ($Na_2SO_4$) and evaporated to give a red solid. The solid was triturated with 10% diethyl ether in cyclohexane. The solid was collected by filtration, washed with 1:1 diethyl ether in cyclohexane and left to air dry to afford pyrazolo[1,5-a] pyrimidine-3-carboxylic acid [5-(5-chloro-2-difluoromethoxyphenyl)-1-(2-trimethylsilanylethoxymethyl)-1H-pyrazol-4-yl]amide as an off-white solid (59.2 g, 73%). $^1$H NMR (300 MHz, $CDCl_3$): δ (ppm) 9.61 (s, 1H), 8.77-8.78 (m, 1H), 8.51 (dd, 1H), 8.36 (s, 1H), 7.65 (d, 1H), 7.52 (dd, 1H), 7.36 (d, 1H), 7.29 (s, 1H), 7.01 (dd, 1H), 6.42 (t, 1H), 5.39-5.41 (m, 2H), 3.60-3.64 (m, 2H), 0.87-0.89 (m, 2H), 0.09 (s, 9H).

A suspension of pyrazolo[1,5-a]pyrimidine-3-carboxylic acid [5-(5-chloro-2-difluoromethoxyphenyl)-1-(2-trimethylsilanylethoxymethyl)-1H-pyrazol-4-yl]amide (59.0 g, 110 mmol) in methanol (420 mL) was treated with 6N HCl (80 mL) and the mixture heated at 60° C. for 4 hours. The solvent was evaporated and the residue triturated with water. The solid was collected by filtration, washed with water and left to air dry. The solid was triturated with a minimum volume of acetonitrile, collected by filtration, washed with diethyl ether and dried at 60° C. under high vacuum to afford the title compound as a yellow solid (42.9 g, 96%). $^1$H NMR (400 MHz, DMSO-$d_6$) δ: (ppm) 9.71 (s, 1H), 9.34 (dd, 1H), 8.68-8.69 (m, 1H), 8.66 (s, 1H), 8.25 (s, 1H), 7.62 (dd, 2H), 7.43-7.46 (m, 1H), 7.29 (dd, 1H), 7.23 (d, 1H).

Example B

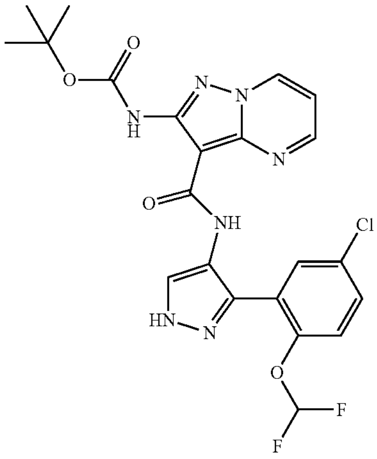 [SMILES: CC(C)(C)OC(=O)Nc1nn2cccnc2c1C(=O)Nc1c[nH]nc1-c1cc(Cl)ccc1OC(F)F]

tert-Butyl (3-((3-(5-chloro-2-(difluoromethoxy)phenyl)-1H-pyrazol-4-yl)carbamoyl)pyrazolo[1,5-a] pyrimidin-2-yl)carbamate To a solution of compound 2-tert-butoxycarbonylamino-pyrazolo[1,5-a]pyrimidine-3-carboxylic acid (2.78 g, 0.01 mol) in DMF (40 mL) was added DIPEA (3.9 g, 0.03 mol), HATU (3.8 g, 0.01 mol) and 5-(5-chloro-2-difluoromethoxyphenyl)-1H-pyrazol-4-ylamine (2.6 g, 0.01 mmol), and the reaction mixture was stirred at room temperature overnight. The reaction mixture was poured into water and the precipitate was collected to give the target compound as a solid (4 g, 77%). LCMS (Method 7) $[M+Na]^+$=541.9, $R_T$=1.20 min. $^1$H NMR (400 MHz, DMSO-$d_6$) δ: (ppm) 13.13 (s, 1H), 9.58 (s, 2H), 9.2 (dd, 1H, J=7.2, 1.6 Hz), 8.58 (d, 1H, J=2), 8.27 (s, 1H), 7.60 (m, 2H), 7.23-7.04 (m, 3H), 1.48 (s, 9H).

Example C

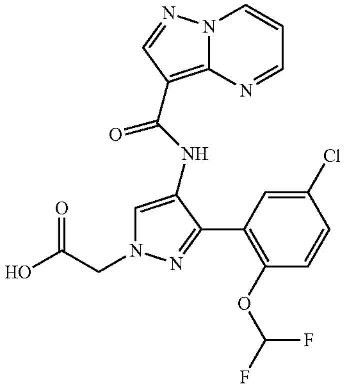 [SMILES: O=C(O)Cn1cc(NC(=O)c2cnn3cccnc23)c(-c2cc(Cl)ccc2OC(F)F)n1]

{3-(5-Chloro-2-difluoromethoxyphenyl)-4-[(pyrazolo[1,5-a]pyrimidine-3-carbonyl)amino]pyrazol-1-yl}acetic acid A solution of pyrazolo[1,5-a]pyrimidine-3-carboxylic acid [3-(5-chloro-2-difluoromethoxyphenyl)-1H-pyrazol-4-yl]amide (42.0 g, 104 mmol) in DMF (400 mL) was treated with cesium carbonate (37.2 g, 114 mmol) and tert-butyl-bromoacetate (22.3 g, 114 mmol) and was left to stir at room temperature for 18 hours. The reaction mixture was diluted with water and extracted twice with ethyl acetate. The combined organic extract was washed with water and brine, dried ($Na_2SO_4$), filtered and evaporated to afford an orange solid. The resultant solid was triturated with diethyl ether then recrystallised from acetone to afford a white solid (33.2 g, 62%). The mother liquors were combined and evaporated to afford an orange oil. The residual oil was purified by flash chromatography on silica eluting with 0-50% EtOAc in DCM. Appropriate fractions were combined and evaporated to afford a white solid (12.3 g, 23%). Combined yield of {3-(5-chloro-2-difluoromethoxyphenyl)-4-[(pyrazolo[1,5-a]pyrimidine-3-carbonyl)amino]pyrazol-1-yl}acetic acid tert-butyl ester (45.2 g, 85%). LCMS (Method 3) $[M+H]^+$=519.1, $R_T$=3.72 min. $^1H$ NMR (400 MHz, $CDCl_3$) δ: (ppm) 9.86 (s, 1H), 8.75-8.76 (m, 2H), 8.56 (dd, 1H), 8.40 (s, 1H), 7.70 (d, 1H), 7.42 (dd, 1H), 6.99 (dd, 1H), 6.47 (t, 1H), 4.86 (s, 2H), 1.49 (s, 9H).

To a solution of {3-(5-chloro-2-difluoromethoxyphenyl)-4-[(pyrazolo[1,5-a]pyrimidine-3-carbonyl)amino]pyrazol-1-yl}acetic acid tert-butyl ester (45.0 g, 86.7 mmol) in dichloromethane (350 mL) was added TFA (100 mL) and the mixture left to stir at room temperature for 18 hours. The solvent was evaporated and the resultant residue triturated with diethyl ether. The resultant solid was collected by filtration, washed with diethyl ether and left to air dry to afford the title compound as a white solid (40.0 g, 99%). LCMS (Method 3) $[M+H]^+$=463.1, $R_T$=2.89 min. $^1H$ NMR (400 MHz, $CDCl_3$) δ: (ppm) 9.86 (s, 1H), 8.78 (dd, 1H), 8.71 (s, 1H), 8.56 (dd, 1H), 8.40 (s, 1H), 7.70 (d, 1H), 7.42 (dd, 1H), 7.30 (s, 1H), 6.99 (dd, 1H), 6.47 (t, 1H), 4.86 (s, 2H), 1.49 (s, 9H).

Example D

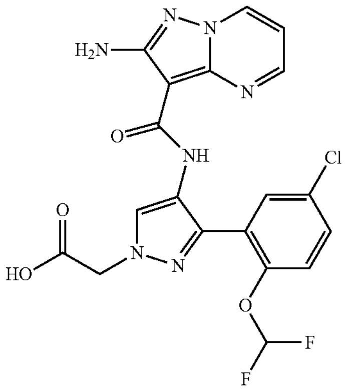 [SMILES: Nc1nn2cccnc2c1C(=O)Nc1cn(CC(=O)O)nc1-c1cc(Cl)ccc1OC(F)F]

[4-[(2-Amino-pyrazolo[1,5-a]pyrimidine-3-carbonyl)-amino]-3-(5-chloro-2-difluoromethoxy-phenyl)-pyrazol-1-yl]-acetic acid A solution of tert-butyl (3-((3-(5-chloro-2-(difluoromethoxy)phenyl)-1H-pyrazol-4-yl)carbamoyl)pyrazolo[1,5-a]pyrimidin-2-yl)carbamate (1.0 g, 1.92 mmol) in DMF (10 mL) was treated with cesium carbonate (0.69 g, 2.12 mmol) and tert-butyl-bromoacetate (0.43 g, 2.12 mmol) and was left to stir at room temperature for 2.5 hours. The reaction mixture was diluted with water and the resultant precipitate was collected by filtration. The resultant solid was purified by flash chromatography on silica eluting with 0-70% EtOAc in cyclohexane. Appropriate fractions were combined and evaporated to afford [4-[(2-tert-butoxycarbonylamino-pyrazolo[1,5-a]pyrimidine-3-carbonyl)-amino]-3-(5-chloro-2-difluoromethoxy-phenyl)-pyrazol-1-yl]-acetic acid tert-butyl ester as a white solid (0.91 g, 74%). LCMS (Method 3) $[M+H]^+$=633.9, $R_T$=4.46 min. $^1H$ NMR (400 MHz, $CDCl_3$) δ: (ppm) 9.78 (s, 1H), 9.70 (s, 1H), 8.76 (dd, 1H, J=1.8, 6.8 Hz), 8.47 (dd, 1H, J=1.8, 4.3 Hz), 8.34 (s, 1H), 7.69 (d, 1H, J=2.5 Hz), 7.41 (dd, 1H, J=2.7, 8.7 Hz), 7.28 (d, 1H, J=8.8 Hz), 6.92 (dd, 1H, J=4.4, 6.9 Hz), 6.47 (t, 1H, J=74.0 Hz), 4.85 (s, 2H), 1.56 (s, 9H), 1.49 (s, 9H).

To a solution of [4-[(2-tert-butoxycarbonylamino-pyrazolo[1,5-a]pyrimidine-3-carbonyl)-amino]-3-(5-chloro-2-difluoromethoxy-phenyl)-pyrazol-1-yl]-acetic acid tert-butyl ester (0.91 g, 1.43 mmol) in dichloromethane (7 mL) was added TFA (15 mL) and the mixture left to stir at room temperature for 6 hours. The solvent was evaporated and the resultant residue azeotroped with dichlromethane/methanol to afford the title compound as a pale yellow solid (0.66 g, 97%). LCMS (Method 3) $[M+H]^+$=477.8, $R_T$=2.95 min. $^1H$ NMR (400 MHz, DMSO-$d_6$) δ: (ppm) 13.15 (br s, 1H), 9.56 (s, 1H), 8.93 (dd, 1H, J=1.5, 6.8 Hz), 8.37-8.34 (m, 1H), 8.35 (s, 1H), 7.63 (dd, 1H, J=2.8, 8.8 Hz), 7.56 (d, 1H, J=2.8 Hz), 7.46 (d, 1H, J=8.9 Hz), 7.26 (t, 1H, J=73.4 Hz), 7.00 (dd, 1H, J=4.5, 6.8 Hz), 6.58 (br s, 2H), 5.05 (s, 2H).

Example E

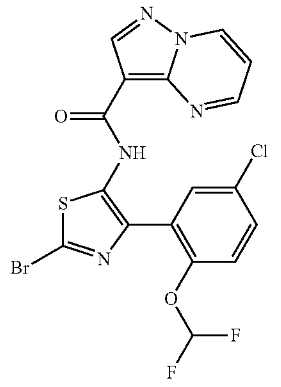 [SMILES: O=C(Nc1sc(Br)nc1-c1cc(Cl)ccc1OC(F)F)c1cnn2cccnc12]

Pyrazolo[1,5-a]pyrimidine-3-carboxylic acid [2-bromo-4-(5-chloro-2-difluoromethoxy-phenyl)-thiazol-5-yl]-amide Sodium hydride (60% dispersion in mineral oil, 2.17 g, 54.2 mmol) was added portionwise to a stirred solution of 1-(5-chloro-2-methoxy-phenyl)-ethanone (10.0 g, 54.2 mmol) in THF (100 mL) at 0° C. The mixture was then stirred for 10 minutes before addition of diethyl carbonate (7.68 g, 65.0 mmol) and then for an additional 1 hour. The mixture was warmed to room temperature for 2 hours and then heated to 65° C. for 2 hours. Diethyl ether was added, the organics washed with water and brine, then evaporated to dryness. The resultant residue was purified by flash chromatography on silica gel (50 to 100% dichloromethane in cyclohexane) to yield 3.41 g of ethyl 3-(5-chloro-2-methoxyphenyl)-3-oxopropanoate. LCMS (method 1) $[M+H]^+$=257.2, $R_T$=3.55 min. $^1$H NMR (400 MHz, $CDCl_3$): δ (ppm) 7.59 (d, 1H), 7.38 (dd, 1H), 6.89 (d, 1H), 4.18 (q, 2H), 3.95 (s, 2H), 3.88 (s, 3H), 1.24 (t, 3H).

Bromine (0.70 mL, 13.6 mmol) was added to a solution of ethyl 3-(5-chloro-2-methoxyphenyl)-3-oxopropanoate (3.39 g, 13.2 mmol) in dioxane (25 mL) and stirred for 1 hour. The reaction was poured onto ice water, extracted with ethyl acetate, the organics washed with water and brine and evaporated to dryness to give ethyl 2-bromo-3-(5-chloro-2-methoxyphenyl)-3-oxopropanoate. LCMS (method 1) $[M+H]^+$=337.2, $R_T$=3.84 min.

A mixture of ethyl 2-bromo-3-(5-chloro-2-methoxyphenyl)-3-oxopropanoate (assumed to be 13.2 mmol) and thiourea (1.01 g, 13.3 mmol) in ethanol (25 mL) were heated to reflux for 3 hours, then cooled to room temperature for 18 hours. The resultant solid was removed by filtration and the filtrate evaporated under vacuum. DCM was added to the residue, the organics washed with sodium hydrogen carbonate (sat. aq.), water and brine, and evaporated to dryness. The residue was triturated (DCM) to give ethyl 2-amino-4-(5-chloro-2-methoxyphenyl)thiazole-5-carboxylate (1.30 g, 31%) as a yellow solid. LCMS (method 1) $[M+H]^+$=313.2, $R_T$=3.15 min. $^1$H NMR (400 MHz, DMSO-$d_6$): δ (ppm) 7.77 (s, br, 2H), 7.39 (dd, 1H), 7.22 (d, 1H), 7.05 (d, 1H), 4.00 (q, 2H), 3.70 (s, 3H), 1.04 (t, 3H).

Copper bromide (1.07 g, 4.79 mmol) in acetonitrile (20 mL) was degassed with nitrogen and cooled to 0° C. before addition of tert-butyl nitrite (0.80 mL, 6.00 mmol), then a suspension of ethyl 2-amino-4-(5-chloro-2-methoxyphenyl) thiazole-5-carboxylate (1.25 g, 3.99 mmol) in acetonitrile (20 mL) was added and stirred at room temperature for 18 hours. The reaction was concentrated under vacuum, ethyl acetate added, the organics washed with sodium hydrogen carbonate (sat. aq.) and brine, then evaporated to dryness to give ethyl 2-bromo-4-(5-chloro-2-methoxyphenyl)thiazole-5-carboxylate (1.40 g, 93%). LCMS (method 1) $[M+H]^+$=378.1, $R_T$=4.26 min. $^1$H NMR (400 MHz, DMSO-$d_6$): δ (ppm) 7.50 (dd, 1H), 7.42 (d, 1H), 7.14 (d, 1H), 4.16 (q, 2H), 3.73 (s, 3H), 1.12 (t, 3H).

A mixture of ethyl 2-bromo-4-(5-chloro-2-methoxyphenyl)thiazole-5-carboxylate (1.40 g, 3.72 mmol), potassium hydroxide (278 mg) in THF (40 mL) and water (10 mL) was stirred for 20 hours at ambient temperature. The mixture was treated with 1M HCl aq. (ca. 8 mL, 2 eq.), DCM was added, and the organics separated and evaporated to dryness to give 2-bromo-4-(5-chloro-2-methoxyphenyl)thiazole-5-carboxylic acid (1.23 g, 95%) as a yellow solid. LCMS (method 2) $[M+H]^+$=350.1, $R_T$=3.28 min. $^1$H NMR (400 MHz, DMSO-$d_6$): δ (ppm) 7.47 (dd, 1H), 7.39 (d, 1H), 7.13 (d, 1H), 3.73 (s, 3H).

2-bromo-4-(5-chloro-2-methoxyphenyl)thiazole-5-carboxylic acid (1.22 g, 3.50 mmol), diphenylphosphoryl azide (963 mg, 3.50 mmol) and triethylamine (354 mg, 3.50 mmol) in tert-butanol (30 mL) were stirred at 85° C. for 4 hours. After cooling, the reaction was partitioned between ethyl acetate and water, the organics separated then washed with brine, and evaporated to dryness. The resulting residues were purified by flash chromatography on silica gel (50 to 100% dichloromethane in cyclohexane) to yield tert-butyl 2-bromo-4-(5-chloro-2-methoxyphenyl)thiazol-5-ylcarbamate (970 mg, 66%). LCMS (method 1) $[M+H-^tBu]^+$=364.8, $R_T$=4.61 min. $^1$H NMR (400 MHz, DMSO-$d_6$): δ (ppm) 7.43 (dd, 1H), 7.30 (d, 1H), 7.11 (d, 1H), 3.77 (s, 3H), 1.45 (s, 9H).

TFA (4.0 mL) was added to a solution of tert-butyl 2-bromo-4-(5-chloro-2-methoxyphenyl)thiazol-5-ylcarbamate (360 mg, 0.86 mmol) in DCM (10 mL) and water (3 drops). The reaction mixture was stirred for 1.5 hours at room temperature and then evaporated to dryness. The residue was taken up into DCM and washed with sodium hydrogen carbonate (sat. aq.), water and brine, and concentrated under vacuum to give 2-bromo-4-(5-chloro-2-methoxyphenyl)thiazol-5-amine as an orange residue. LCMS (method 1) $[M+H]^+$=321.3, $R_T$=3.63 min. $^1$H NMR (400 MHz, DMSO-$d_6$): δ (ppm) 7.36 (d, 1H), 7.34-7.32 (m, 1H), 7.10 (d, 1H), 3.83 (s, 3H).

Using 2-bromo-4-(5-chloro-2-methoxyphenyl)thiazol-5-amine and pyrazolo[1,5-a]pyrimidine-3-carbonyl chloride the title compound was prepared following the synthetic procedures described for pyrazolo[1,5-a]pyrimidine-3-carboxylic acid [3-(5-chloro-2-difluoromethoxyphenyl)-1H-pyrazol-4-yl]amide with further purification by flash chromatography on silica gel (0 to 40% ethyl acetate in DCM) to give N-(2-bromo-4-(5-chloro-2-methoxyphenyl)thiazol-5-yl)pyrazzolo[1,5-a]pyrimidine-3-carboxamide. LCMS (method 1) $[M+H]^+$=465.8, $R_T$=4.01 min. $^1$H NMR (400 MHz, DMSO-$d_6$): δ 10.68 (s, br, 1H), 9.41 (dd, 1H), 8.78 (s, 1H), 8.76 (dd, 1H), 7.57 (dd, 1H), 7.50 (d, 1H), 7.37-7.34 (m, 2H), 3.81 (s, 3H).

To a solution of pyrazolo[1,5-a]pyrimidine-3-carboxylic acid [2-bromo-4-(5-chloro-2-methoxy-phenyl)-thiazol-5-yl]-amide (4.3 g, 9.3 mmol) in DCM (90 mL) at −78° C. under an atmosphere of $N_2$ was added boron tribromide (1M in DCM, 45 mL, 45 mmol) dropwise. The mixture was stirred at −78° C. for 1 hour and then allowed slowly to room temperature and stirred for a further 16 hours. The mixture was poured cautiously onto an aqueous solution of sodium hydrogen carbonate, stirred for 15 mins, filtered and the solid collected and dried to afford pyrazolo[1,5-a]pyrimidine-3-carboxylic acid [2-bromo-4-(5-chloro-2-hydroxy-phenyl)-thiazol-5-yl]-amide as a beige solid (6 g, >100%). LCMS (Method 3) $[M+H]^+$=450.1, $R_T$=3.71 min. $^1$H NMR (400 MHz, DMSO-$d_6$) δ: 15.96 (s, 1H), 9.18 (dd, 1H, J=1.6, 6.9 Hz), 8.70 (dd, 1H, J=1.8, 4.0 Hz), 8.59 (s, 1H), 7.80 (d, 1H, J=2.8 Hz), 7.15 (dd, 1H, J=4.0, 7.1 Hz), 7.05 (dd, 1H, J=2.8, 8.6 Hz), 6.77 (d, 1H, J=8.6 Hz).

To a solution of pyrazolo[1,5-a]pyrimidine-3-carboxylic acid [2-bromo-4-(5-chloro-2-hydroxy-phenyl)-thiazol-5-yl]-amide (1.1 g, 2.4 mmol) in DMF (20 mL) and water (2 mL) was added cesium carbonate (1.1 g, 3.4 mmol) and then sodium chlorodifluoroacetate (839 mg, 5.5 mmol). The mixture was stirred at 100° C. for 16 hours before further cesium carbonate (2.2 g, 6.8 mmol) and sodium chlorodifluoroacetate (1.7 g, 11 mmol) was added and stirring continued at 100° C. for 6 hours. The mixture was allowed to cool to room temperature and partitioned between ethyl acetate and water and the phases separated. The organic layer was washed with brine. The combined aqueous layer was extracted with ethyl acetate once and the combined organic layer dried ($Na_2SO_4$), filtered and evaporated. The resultant residue was purified by flash chromatography on silica eluting with 50% ethyl acetate in cyclohexane to give the title compound as a yellow solid (710 mg, 59%). LCMS (Method 3) $[M+H]^+$=500.1, $R_T$=3.97 min. $^1$H NMR (400 MHz, DMSO-$d_6$) δ: 10.84 (s, 1H), 9.42 (dd, 1H, J=1.6, 6.9 Hz), 8.79 (s, 1H), 8.66 (dd, 1H, J=1.6, 4.3 Hz), 7.76 (d, 1H, J=2.8 Hz), 7.51 (d, 1H, J=8.8 Hz), 7.36 (dd, 1H, J=4.2, 7.0 Hz), 7.22 (t, 1H, J=73.1 Hz).

Example 1

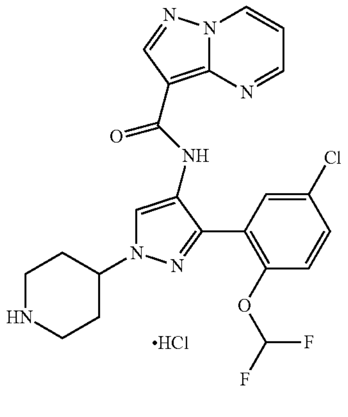 [SMILES: O=C(Nc1cn(C2CCNCC2)nc1-c1cc(Cl)ccc1OC(F)F)c1cnn2cccnc12 ; Cl]

Pyrazolo[1,5-a]pyrimidine-3-carboxylic acid [3-(5-chloro-2-difluoromethoxyphenyl)-1-piperidin-4-yl-1H-pyrazol-4-yl]amide hydrochloride Pyrazolo[1,5-a]pyrimidine-3-carboxylic acid [3-(5-chloro-2-difluoromethoxyphenyl)-1H-pyrazol-4-yl]amide (200 mg, 0.49 mmol) was dissolved in DMF (5 mL), 4-(toluene-4-sulfonyloxy)piperidine-1-carboxylic acid tert-butyl ester (263 mg, 0.74 mmol) and cesium carbonate (240 mg, 0.74 mmol) were added and the mixture heated at 90° C. for 2 hours. The mixture was allowed to cool to room temperature, diluted with water and extracted with DCM (×3). The combined organic extract was washed with brine, dried ($Na_2SO_4$), filtered and evaporated. The resultant yellow oil was purified by flash chromatography on silica eluting with 0-2% MeOH in DCM. The appropriate fractions were collected and evaporated to afford 4-{3-(5-chloro-2-difluoromethoxyphenyl)-4-[(pyrazolo[1,5-a]pyrimidine-3-carbonyl)amino]pyrazol-1-yl}piperidine-1-carboxylic acid tert-butyl ester a yellow oil. The crude product was taken onto the next step without further purification. LCMS (Method 4) $[M+Na]^+$=610.0; $R_T$=4.30 min.

4-{3-(5-Chloro-2-difluoromethoxyphenyl)-4-[(pyrazolo[1,5-a]pyrimidine-3-carbonyl)amino]pyrazol-1-yl}piperidine-1-carboxylic acid tert-butyl ester (600 mg, 0.97 mmol) was dissolved in DCM (3 mL) and TFA (3 mL) was added. The mixture was allowed to stir at room temperature for 30 minutes. The solvent was evaporated and the residue was dissolved in MeOH and loaded onto an SCX-2 cartridge which had been conditioned with MeOH. After flushing with MeOH, the product was eluted with 2M ammonia in MeOH. Evaporation gave a glass which was purified by HPLC (Method 3). Appropriate fractions were combined and evaporated to afford an off-white solid. The solid was dissolved in MeOH and 1.25M methanolic HCl (1 mL) was added. The solvent was evaporated, azeotroped three times with methanol and triturated with ethyl acetate to afford the title compound as an off-white solid (144 mg, 28%). LCMS (Method 5) $[M+H]^+$=488.0, $R_T$=2.93 min. $^1$H NMR (400 MHz, DMSO-$d_6$) δ: (ppm) 9.76 (s, 1H), 9.35 (dd, 1H, J=1.6, 7.0 Hz), 8.98 (d, 1H, J=9.9 Hz), 8.69 (dd, 1H, J=1.7, 4.3 Hz), 8.67 (s, 1H), 8.38 (s, 1H), 7.65-7.62 (m, 2H), 7.30 (dd, 1H, J=4.2, 7.2 Hz), 7.26 (t, 1H, J=73.6 Hz), 4.66-4.57 (m, 1H), 3.47-3.42 (m, 2H), 3.17-3.03 (m, 2H), 2.32-2.18 (m, 4H).

Example 2

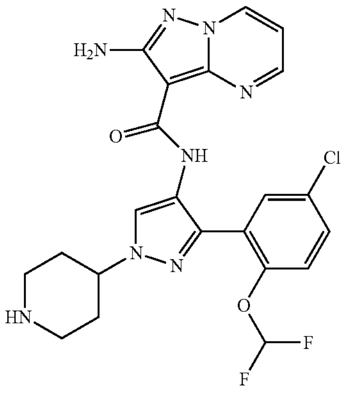 [SMILES: Nc1nn2cccnc2c1C(=O)Nc1cn(C2CCNCC2)nc1-c1cc(Cl)ccc1OC(F)F]

2-Amino-pyrazolo[1,5-a]pyrimidine-3-carboxylic acid [3-(5-chloro-2-difluoromethoxy-phenyl)-1-piperidin-4-yl-1H-pyrazol-4-yl]-amide The title compound was prepared from tert-butyl (3-((3-(5-chloro-2-(difluoromethoxy)phenyl)-1H-pyrazol-4-yl)carbamoyl)pyrazolo[1,5-a]pyrimidin-2-yl) carbamate following the procedure outlined in Example 1 to afford an amber solid. LCMS (Method 3) $[M+H]^+$=503.3, $R_T$=2.32 min. $^1$H NMR (400 MHz, DMSO-$d_6$) δ: (ppm) 9.55 (s, 1H), 8.93 (dd, 1H, J=1.5, 6.8 Hz), 8.37 (dd, 1H, J=1.5, 4.5 Hz), 8.29 (s, 1H), 7.64-7.58 (m, 2H), 7.44 (d, 1H, J=8.7 Hz), 7.25 (t, 1H, J=73.5 Hz), 7.00 (dd, 1H, J=4.5, 6.7 Hz), 6.57 (s, 2H), 4.33-4.22 (m, 1H), 3.07 (d, 2H, J=12.6 Hz), 2.66-2.57 (m, 2H), 2.06-1.96 (m, 2H), 1.89-1.75 (m, 2H).

Example 3

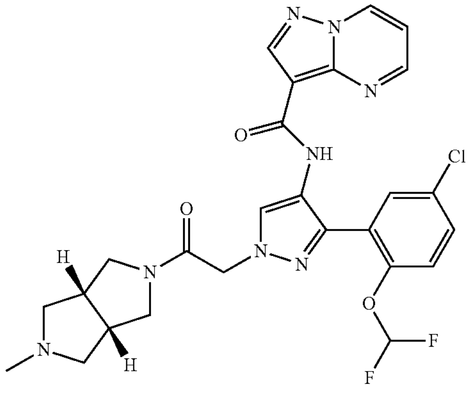 [SMILES: CN1C[C@@H]2CN(C(=O)Cn3cc(NC(=O)c4cnn5cccnc45)c(-c4cc(Cl)ccc4OC(F)F)n3)C[C@@H]2C1]

Cis-pyrazolo[1,5-a]pyrimidine-3-carboxylic acid {3-(5-chloro-2-difluoromethoxyphenyl)1-[2-(5-methylhexahydropyrrolo[3,4-c]pyrrol-2-yl)-2-oxo-ethyl]-1H-pyrazol-4-yl}amide A solution of {3-(5-chloro-2-difluoromethoxyphenyl)-4-[(pyrazolo[1,5-a]pyrimidine-3-carbonyl)amino]pyrazol-1-yl}acetic acid (20.0 g, 43.2 mmol) in DMF (150 mL) was treated with DIPEA (6.7 g, 5.2 mmol), cis-2-methyloctahydropyrrolo[3,4-c]pyrrole (6.27 g, 49.7 mmol) and HATU (18.9 g, 49.7 mmol) and the mixture left to stir at room temperature for 1 hour. The reaction mixture was diluted with 0.5M aqueous $K_2CO_3$ solution and extracted with ethyl acetate (×2). The combined organic extract was washed with water (×2) and brine, dried ($Na_2SO_4$) and evaporated to afford a solid. The resultant solid was purified by flash chromatography on silica eluting with 0-10% 2M $NH_3$/MeOH in DCM. Collecting appropriate fractions, followed by evaporation gave the title compound as a cream solid (17.1 g, 69%). LCMS (Method 5) $[M+H]^+$=570.9, $R_T$=2.82. $^1H$ NMR (400 MHz, DMSO-$d_6$) δ: (ppm) 9.70 (s, 1H), 9.30 (dd, 1H, J=7.0, 1.6 Hz), 8.62-8.63 (m, 2H), 8.27 (s, 1H), 7.59 (dd, 1H, J=8.8, 2.7 Hz), 7.52 (d, 1H, J=2.7 Hz), 7.42 (d, 1H, J=8.8 Hz), 7.25 (dd, 1H, J=7.0, 4.2 Hz), 7.11 (t, 1H, J=73.3 Hz), 5.07 (d, 2H, J=5.9 Hz), 3.69 (dd, 1H, J=10.8, 8.6 Hz), 3.56 (dd, 1H, J=12.2, 8.8 Hz), 3.36 (dd, 1H, J=10.8, 4.4 Hz), 3.22 (dd, 1H, J=12.3, 4.5 Hz), 2.45-2.46 (m, 3H), 2.37-2.39 (m, 3H), 2.17 (s, 3H).

Example 4

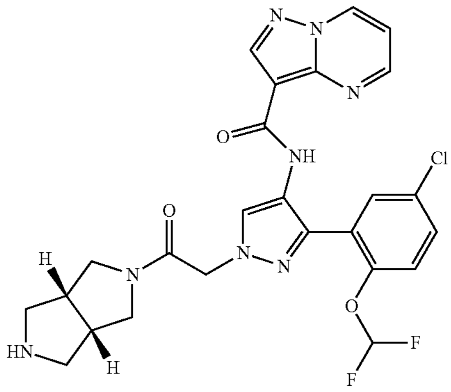 [SMILES: O=C(Nc1cn(CC(=O)N2C[C@H]3CNC[C@H]3C2)nc1-c1cc(Cl)ccc1OC(F)F)c1cnn2cccnc12]

Cis-pyrazolo[1,5-a]pyrimidine-3-carboxylic acid {3-(5-chloro-2-difluoromethoxyphenyl)-1-[2-(hexahydropyrrolo[3,4-c]pyrrol-2-yl)-2-oxoethyl]-1H-pyrazol-4-yl}amide {3-(5-Chloro-2-difluoromethoxyphenyl)-4-[(pyrazolo[1,5-a]pyrimidine-3-carbonyl)amino]pyrazol-1-yl}acetic acid (3.35 g, 7.25 mmol) was dissolved in DMF (30 mL) and HATU (2.85 g, 9.42 mmol) was added. cis-hexahydropyrrolo[3,4-c]pyrrole-2-carboxylic acid tert-butyl ester (2.0 g, 9.42 mmol) and DIPEA (1.63 mL, 9.42 mmol) were added and the mixture was stirred at room temperature for 17 hours. The volatiles were evaporated and the resultant residue azeotroped with toluene. The solid was partitioned between water and DCM and the organic layer was separated, dried ($Na_2SO_4$) and evaporated. The residue was dissolved in DCM (10 mL) and TFA (10 mL) was added. The solution was stirred at room temperature for 4 hours and then evaporated. The residue was dissolved in MeOH and loaded onto an SCX-2 cartridge which had been conditioned with MeOH. After flushing with MeOH, the product was eluted with 2M ammonia in MeOH. The solvent was evaporated and the product was crystallised from MeOH/$Et_2O$. The desired product was obtained as an off-white solid (3.7 g, 90%). LCMS (Method 5) $[M+H]^+$=556.9, $R_T$=2.83 min. $^1H$ NMR (400 MHz, DMSO-$d_6$) δ: (ppm) 9.76 (s, 1H), 9.35 (dd, 1H, J=1.6, 7.0 Hz), 9.38-9.22 (m, 2H), 8.69 (dd, 2H, J=1.7, 4.2 Hz), 8.67 (s, 1H), 8.31 (s, 1H), 7.64 (dd, 1H, J=2.7, 8.8 Hz), 7.56 (d, 1H, J=2.6 Hz), 7.47 (d, 1H, J=8.8 Hz), 7.30 (dd, 2H, J=4.3, 7.0 Hz), 7.27 (t, 1H, J=73.4 Hz), 5.15 (s, 2H), 3.80-3.67 (m, 2H), 3.65-3.53 (m, 2H), 3.49-3.32 (m, 3H), 3.16-2.94 (m, 4H).

Example 5

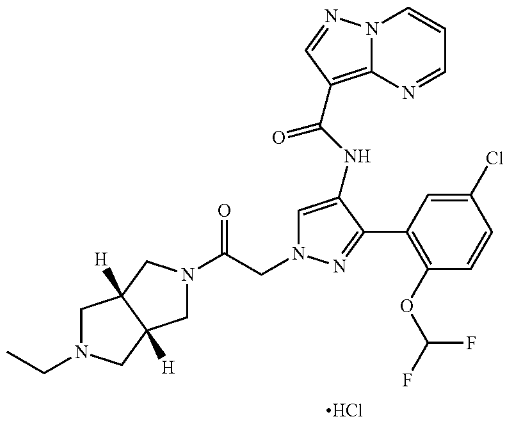 [SMILES: CCN1C[C@@H]2CN(C(=O)Cn3cc(NC(=O)c4cnn5cccnc45)c(-c4cc(Cl)ccc4OC(F)F)n3)C[C@@H]2C1 ; Cl]

Cis pyrazolo[1,5-a]pyrimidine-3-carboxylic acid {3-(5-chloro-2-difluoromethoxyphenyl)-1-[2-(5 ethyl-hexahydro-pyrrolo[3,4-c]pyrrol-2-yl)-2-oxo-ethyl]-1H-pyrazol-4-yl}amide hydrochloride To a solution of cis-pyrazolo[1,5-a]pyrimidine-3-carboxylic acid {3-(5-chloro-2-difluoromethoxyphenyl)-1-[2-(hexahydropyrrolo[3,4-c]pyrrol-2-yl)-2-oxoethyl]-1H-pyrazol-4-yl}amide (100 mg, 0.18 mmol) in acetonitrile (4 mL) was added potassium carbonate (37 mg, 0.27 mmol) and bromoethane (20 μL, 0.27 mmol). The reaction was heated at 50° C. for 2 hours and then allowed to cool to room temperature. The mixture was applied directly to an SCX-2 cartridge. Elution with 2M ammonia in MeOH gave the desired product. The product was purified by HPLC (Method 1) and the pure fractions were combined as passed through an SCX-2 cartridge. Elution with 2M ammonia in MeOH gave the free base on evaporation of the solvent. The solid was dissolved in 1.25M methanolic HCl and then the volatiles were evaporated. The HCl salt was crystallised from MeOH/$Et_2O$ and obtained as a white solid (32 mg, 40%). LCMS (Method 5) $[M+H]^+$=585.0, $R_T$=2.88 min. $^1H$ NMR (400 MHz, DMSO-$d_6$) δ: (ppm) 10.44 (d, 1H, J=35.0 Hz), 9.79-9.74 (m, 1H), 9.35 (dd, 1H, J=1.3, 7.0 Hz), 8.69 (dd, 1H, J=1.5, 4.2 Hz), 8.67 (s, 1H), 8.31 (d, 1H, J=3.8 Hz), 7.64 (dd, 1H, J=2.5, 8.8 Hz), 7.57 (d, 1H, J=2.6 Hz), 7.47 (d, 1H, J=8.9 Hz), 7.30 (dd, 1H, J=4.3, 7.0 Hz), 7.27 (t, 1H, J=73.6 Hz), 5.22-5.10 (m, 2H), 3.43 (s, 12H), 3.84-2.77 (m, 12H), 1.29-1.19 (m, 3H).

Example 6

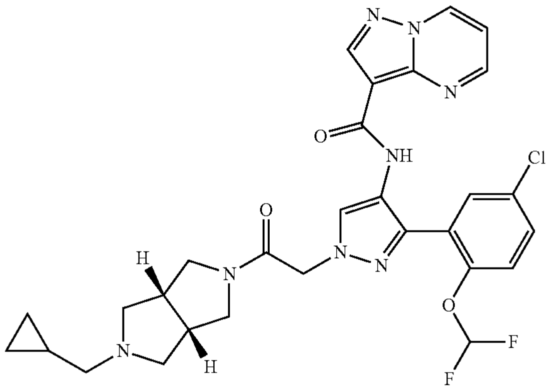 [SMILES: O=C(Nc1cn(CC(=O)N2C[C@H]3CN(CC4CC4)C[C@H]3C2)nc1-c1cc(Cl)ccc1OC(F)F)c1cnn2cccnc12]

Cis-pyrazolo[1,5-a]pyrimidine-3-carboxylic acid {3-(5-chloro-2-difluoromethoxyphenyl)-1-[2-(5-cyclopropylmethylhexahydropyrrolo[3,4-c]pyrrol-2-yl)-2-oxoethyl]-1H-pyrazol-4-yl}amide To a solution of cis-pyrazolo[1,5-a]pyrimidine-3-carboxylic acid {3-(5-chloro-2-difluoromethoxyphenyl)-1-[2-(hexahydropyrrolo[3,4-c]pyrrol-2-yl)-2-oxoethyl]-1H-pyrazol-4-yl}amide (100 mg, 0.18 mmol) in 2,2,2-trifluoroethanol (3 mL) was added cyclopropanecarbaldehyde (67 μL, 0.90 mmol). After stirring at room temperature for 15 minutes, sodium borohydride (21 mg, 0.54 mmol) was added and the reaction was heated at 90° C. for 2 hours. MeOH was added to quench the reaction and the mixture was loaded onto an SCX-2 cartridge which had been conditioned with MeOH. After flushing with MeOH, the product was eluted with 2M ammonia in MeOH. Evaporation gave a crude product which was purified by HPLC (Method 1). The pure fractions loaded onto an SCX-2 cartridge which had been conditioned with MeOH. After flushing with MeOH, the product was eluted with 2M ammonia in MeOH. Evaporation gave the title compound as a free base which was crystallised from MeOH/$Et_2O$ and obtained as a yellow solid (55 mg, 50%). LCMS (Method 5) $[M+H]^+$=611.1, $R_T$=3.02 min. $^1H$ NMR (400 MHz, DMSO-$d_6$) δ: (ppm) 10.94-10.88 (m, 1H), 9.57-9.55 (m, 1H), 8.95-8.92 (m, 1H), 8.38-8.35 (m, 1H), 8.29-8.28 (m, 1H), 7.65-7.61 (m, 1H), 7.56-7.54 (m, 1H), 7.47 (d, 1H, J=8.9 Hz), 7.45-7.07 (m, 1H), 7.08 (d, 1H, J=1.9 Hz), 7.02-6.99 (m, 1H), 5.24-5.07 (m, 2H), 3.86-3.52 (m, 5H), 3.52-3.22 (m, 2H), 3.17-3.11 (m, 1H), 3.07-3.00 (m, 2H), 3.00-2.79 (m, 1H), 1.27-1.01 (m, 1H), 0.63-0.56 (m, 2H), 0.42-0.34 (m, 2H).

Atropisomers Present

Example 7

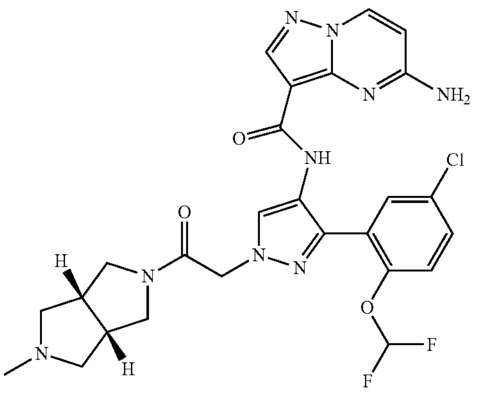 [SMILES: CN1C[C@@H]2CN(C(=O)Cn3cc(NC(=O)c4cnn5ccc(N)nc45)c(-c4cc(Cl)ccc4OC(F)F)n3)C[C@@H]2C1]

5-Amino-pyrazolo[1,5-a]pyrimidine-3-carboxylic acid {3-(5-chloro-2-difluoromethoxy-phenyl)-1-[2-((3 aR,6aS)-5-methyl-hexahydro-pyrrolo[3,4-c]pyrrol-2-yl)-2-oxo-ethyl]-1H-pyrazol-4-yl}-amide hydrochloride A mixture of 5-chloro-pyrazolo[1,5-a]pyrimidine-3-carbonyl chloride (500 mg, 2.3 mmol) (prepared according to the procedure in Journal of Medicinal Chemistry, 55(22), 10090-10107; 2012) and 5-(5-chloro-2-difluoromethoxy-phenyl)-1-(2-trimethylsilanyl-ethoxymethyl)-1H-pyrazol-4-ylamine (868 mg, 2.3 mmol) were suspended in triethylamine (0.35 mL, 2.5 mmol) and DCM (10 mL) and the mixture was left to stir at room temperature for 2 hours. The reaction mixture was diluted with dichloromethane and the resultant organic layer was washed with saturated aqueous sodium hydrogen carbonate solution, and brine, dried ($Na_2SO_4$) and evaporated to afford an oil. The resultant oil was purified by flash chromatography on silica eluting with 0-2% MeOH in DCM. Collecting appropriate fractions, followed by evaporation gave 5-chloro-pyrazolo[1,5-a]pyrimidine-3-carboxylic acid [5-(5-chloro-2-difluoromethoxy-phenyl)-1-(2-trimethylsilanyl-ethoxymethyl)-1H-pyrazol-4-yl]-amide as a brown oil (1.19 g, 91%). $^1H$ NMR (400 MHz, DMSO-$d_6$) δ: (ppm) 9.07 (s, 1H), 8.72 (s, 1H), 8.67 (d, 1H, J=7.3 Hz), 8.38 (s, 1H), 7.60 (d, 1H, J=2.3 Hz), 7.51 (dd, 1H, J=2.6, 8.8 Hz), 7.38 (d, 1H, J=8.9 Hz), 6.95 (d, 1H, J=7.2 Hz), 6.43 (t, 1H, J=72.8 Hz), 5.41 (d, 1H, J=10.9 Hz), 5.31 (d, 1H, J=11.0 Hz), 3.76-3.49 (m, 2H), 1.27 (s, 1H), 0.94-0.84 (m, 2H), 0.00 (s, 9H).

5-chloro-pyrazolo[1,5-a]pyrimidine-3-carboxylic acid [5-(5-chloro-2-difluoromethoxy-phenyl)-1-(2-trimethylsilanyl-ethoxymethyl)-1H-pyrazol-4-yl]-amide (756 mg, 1.32 mmol) was dissolved in THF (10 mL) and concentrated aqueous ammonia (10 mL) added. The mixture was heated at 50° C. for 3 hours then allowed to cool to ambient temperature. The solvent was evaporated and the residue azeotroped with methanol (×2) to afford 5-amino-pyrazolo[1,5-a]pyrimidine-3-carboxylic acid [5-(5-chloro-2-difluoromethoxy-phenyl)-1-(2-trimethyl silanyl-ethoxymethyl)-1H-pyrazol-4-yl]-amide as a white solid (724 mg, 99%). LCMS (Method 4) $[M+H]^+$=549.9, $R_T$=4.11 min.

A suspension of 5-amino-pyrazolo[1,5-a]pyrimidine-3-carboxylic acid [5-(5-chloro-2-difluoromethoxy-phenyl)-1-(2-trimethylsilanyl-ethoxymethyl)-1H-pyrazol-4-yl]-amide (720 mg, 1.31 mmol) in methanol (20 mL) was treated with concentrated aqueous HCl (3 mL) and the mixture heated at 80° C. for 1 hour. The solvent was evaporated and the residue azeotroped with methanol (×3). The resultant solid was triturated with ethyl acetate, collected by filtration, washed with ethyl acetate and diethyl ether and left to air dry. The residual solid was purified by flash chromatography on silica eluting with 0-12% 2M $NH_3$/MeOH in DCM. Collecting appropriate fractions, followed by evaporation gave 5-amino-pyrazolo[1,5-a]pyrimidine-3-carboxylic acid [3-(5-chloro-2-difluoromethoxy-phenyl)-1H-pyrazol-4-yl]-amide as a brown solid (378 mg, 69%). LCMS (Method 4) $[M+H]^+$=419.9, $R_T$=2.93

5-Amino-pyrazolo[1,5-a]pyrimidine-3-carboxylic acid [3-(5-chloro-2-difluoromethoxy-phenyl)-1H-pyrazol-4-yl]-amide was converted to the title compound following the procedures outlined in Example C and Example 1 to afford a white solid. LCMS (Method 5) $[M+H]^+$=586.0, $R_T$=2.58 min. $^1H$ NMR (400 MHz, DMSO-$d_6$) δ: (ppm) 9.76 (s, 1H), 9.35 (dd, 1H, J=1.6, 7.1 Hz), 9.38-9.21 (m, 2H), 8.69 (dd, 1H, J=1.7, 4.3 Hz), 8.67 (s, 1H), 8.31 (s, 1H), 7.64 (dd, 1H, J=2.7, 8.8 Hz), 7.56 (d, 1H, J=2.6 Hz), 7.48 (d, 1H, J=8.6

Hz), 7.30 (dd, 1H, J=4.3, 6.9 Hz), 7.27 (t, 1H, J=73.3 Hz), 5.15 (s, 2H), 3.93-3.67 (m, 3H), 3.65-3.32 (m, 6H), 3.19-2.94 (m, 4H).

Example 8

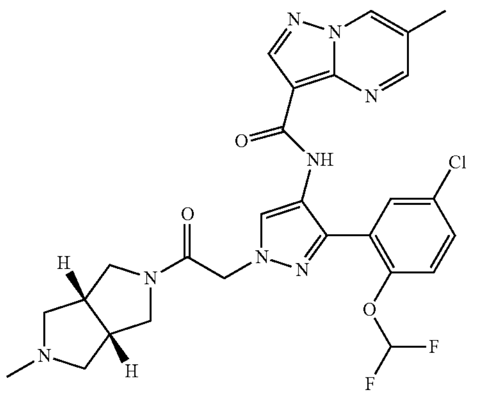 [SMILES: Cc1cnc2c(C(=O)Nc3cn(CC(=O)N4C[C@H]5CN(C)C[C@H]5C4)nc3-c3cc(Cl)ccc3OC(F)F)cnn2c1]

6-Methyl-pyrazolo[1,5-a]pyrimidine-3-carboxylic acid {3-(5-chloro-2-difluoromethoxy-phenyl)-1-[2-((3aR,6aS)-5-methyl-hexahydro-pyrrolo[3,4-c]pyrrol-2-yl)-2-oxo-ethyl]-1H-pyrazol-4-yl}-amide hydrochloride The title compound was prepared from commercially available 6-methyl-pyrazolo[1,5-a]pyrimidine-3-carboxylic acid following the procedure outlined above for Example B and Example 1 to afford a white solid. LCMS (Method 5) $[M+H]^+$=585.0, $R_T$=3.03 min. $^1H$ NMR (400 MHz, DMSO-$d_6$) δ: (ppm) 10.74-10.49 (m, 1H), 9.70 (s, 1H), 9.21 (dd, 1H, J=1.1, 2.0 Hz), 8.60 (d, 1H, J=2.0 Hz), 8.58 (s, 1H), 8.31 (s, 1H), 7.65 (dd, 1H, J=2.7, 8.8 Hz), 7.55 (d, 1H, J=2.7 Hz), 7.49 (d, 1H, J=8.8 Hz), 7.28 (t, 1H, J=73.3 Hz), 5.19 (d, 1H, J=16.8 Hz), 5.13 (d, 1H, J=16.8 Hz), 3.94-2.88 (m, 10H), 2.82 (s, 3H), 2.39 (s, 3H).

Example 63

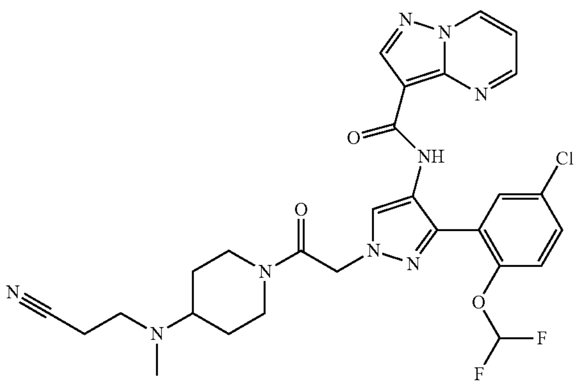 [SMILES: CN(CCC#N)C1CCN(C(=O)Cn2cc(NC(=O)c3cnn4cccnc34)c(-c3cc(Cl)ccc3OC(F)F)n2)CC1]

Pyrazolo[1,5-a]pyrimidine-3-carboxylic acid [3-(5-chloro-2-difluoromethoxy-phenyl)-1-(2-{4-[(2-cyano-ethyl)-methyl-amino]-piperidin-1-yl}-2-oxo-ethyl)-1H-pyrazol-4-yl]-amide A solution of pyrazolo[1,5-a]pyrimidine-3-carboxylic acid [3-(5-chloro-2-difluoromethoxy-phenyl)-1H-pyrazol-4-yl]-amide (32.0 g, 79.1 mmol) in DMF (400 mL) was treated with 2-chloro-1-(1,4-dioxa-8-aza-spiro[4.5]dec-8-yl)-ethanone (20.8 g, 94.9 mmol) and $Cs_2CO_3$ (51.5 g, 158.1 mmol) and the mixture was stirred at room temperature for 19 hours. The reaction was diluted with water (~1.6 L) and the resultant precipitate was collected by filtration. The solid was washed with water dried under reduced pressure to afford pyrazolo[1,5-a]pyrimidine-3-carboxylic acid {3-(5-chloro-2-difluoromethoxy-phenyl)-1-[2-(1,4-dioxa-8-aza-spiro[4.5]dec-8-yl)-2-oxo-ethyl]-1H-pyrazol-4-yl}-amide as a beige solid (33.3 g, 72%). LCMS (Method 3) $[M+H]^+$=588.2, $R_T$=3.02 min. $^1H$ NMR (400 MHz, $CDCl_3$) δ: (ppm) 9.85 (s, 1H), 8.78 (dd, 1H, J=1.6, 6.9 Hz), 8.71 (s, 1H), 8.56 (dd, 1H, J=1.8, 4.0 Hz), 8.42 (s, 1H), 7.69 (d, 1H, J=2.5 Hz), 7.41 (dd, 1H, J=2.7, 8.7 Hz), 7.30-7.26 (m, 1H), 7.00 (dd, 1H, J=4.2, 6.9 Hz), 6.48 (t, 1H, J=74.0 Hz), 5.06 (s, 2H), 4.00-3.95 (m, 4H), 3.74 (dd, 2H, J=5.8, 5.8 Hz), 3.61 (dd, 2H, J=5.8, 5.8 Hz), 1.74-1.64 (m, 4H).

A suspension of pyrazolo[1,5-a]pyrimidine-3-carboxylic acid {3-(5-chloro-2-difluoromethoxy-phenyl)-1-[2-(1,4-dioxa-8-aza-spiro[4.5]dec-8-yl)-2-oxo-ethyl]-1H-pyrazol-4-yl}-amide (46.7 g, 79.5 mmol) in dioxane (280 mL) was cooled in an ice bath before being treated with concentrated hydrochloric acid (210 mL) at a rate which maintained an internal temperature below 22° C. On complete addition, the reaction was allowed to warm to room temperature and stirred for 4 hours. The reaction was cooled in an ice bath, diluted with ethyl acetate and water and the pH of the aqueous phase adjusted to ~8 by the portionwise addition of solid $Na_2CO_3$. The mixture was extracted with ethyl acetate (×4) and the combined organic extract was dried ($Na_2CO_3$) and evaporated to afford pyrazolo[1,5-a]pyrimidine-3-carboxylic acid {3-(5-chloro-2-difluoromethoxy-phenyl)-1-[2-oxo-2-(4-oxo-piperidin-1-yl)-ethyl]-1H-pyrazol-4-yl}-amide.dioxane as a beige solid (48.8 g, 97%). LCMS (Method 3) $[M+H]^+$=544.2, $R_T$=2.85 min. $^1H$ NMR (400 MHz, $CDCl_3$) δ: (ppm) 9.87 (s, 1H), 8.79 (dd, 1H, J=1.8, 7.0 Hz), 8.70 (s, 1H), 8.57 (dd, 1H, J=1.8, 4.0 Hz), 8.47 (s, 1H), 7.67 (d, 1H, J=2.8 Hz), 7.43 (dd, 1H, J=2.7, 8.7 Hz), 7.29 (d, 1H, J=8.8 Hz), 7.01 (dd, 1H, J=4.3, 7.0 Hz), 6.48 (t, 1H, J=74.0 Hz), 5.14 (s, 2H), 3.93 (t, 2H, J=6.2 Hz), 3.85 (t, 2H, J=6.2 Hz), 3.70 (s, 8H), 2.50 (t, 2H, J=6.2 Hz), 2.42 (t, 2H, J=6.1 Hz).

A solution of pyrazolo[1,5-a]pyrimidine-3-carboxylic acid {3-(5-chloro-2-difluoromethoxy-phenyl)-1-[2-oxo-2-(4-oxo-piperidin-1-yl)-ethyl]-1H-pyrazol-4-yl}-amide.dioxane (36 g, 57.0 mmol) in DCM (500 mL) was treated with 3-amino-propionitrile (5.0 mL, 68.4 mmol) and acetic acid (50 mL). The mixture was cooled in an ice bath before the addition of sodium triacetoxyborohydride (18.1 g, 85.4 mmol) portionwise. The reaction was allowed to warm to room temperature and stirred for 1.5 hours. The mixture was diluted with methanol and loaded onto a pad of Isolute® SCX-2 which had been conditioned with MeOH. After flushing with MeOH, the product was eluted with 2M ammonia in MeOH. The basic fractions were combined and evaporated to afford pyrazolo[1,5-a]pyrimidine-3-carboxylic acid (3-(5-chloro-2-difluoromethoxy-phenyl)-1-{2-[4-(2-cyano-ethylamino)-piperidin-1-yl]-2-oxo-ethyl)}-1H-pyrazol-4-yl)-amide as a pale brown solid (31.1 g, 91%). LCMS (Method 3) $[M+H]^+$=598.2, $R_T$=2.25 min. $^1H$ NMR (400 MHz, $CDCl_3$) δ: (ppm) 9.84 (s, 1H), 8.78 (dd, 1H, J=1.6, 6.9 Hz), 8.69 (s, 1H), 8.58-8.55 (m, 1H), 8.40 (s, 1H), 7.68 (d, 1H, J=2.5 Hz), 7.41 (dd, 1H, J=2.7, 8.7 Hz), 7.28 (d, 1H, J=8.7 Hz), 7.28 (s, 1H), 7.00 (dd, 1H, J=4.2, 6.9 Hz), 6.50 (t, 1H, J=74.1 Hz), 5.08 (d, 1H, J=15.4 Hz), 5.02 (d, 1H, J=15.5 Hz), 4.37 (d, 1H, J=13.4 Hz), 3.88 (d, 1H, J=13.4

Hz), 3.22-3.12 (m, 1H), 3.02 (t, 1H, J=6.4 Hz), 2.98-2.86 (m, 2H), 2.82-2.72 (m, 1H), 2.52-2.46 (m, 2H), 1.96-1.83 (m, 2H), 1.36-1.20 (m, 2H).

A solution of pyrazolo[1,5-a]pyrimidine-3-carboxylic acid (3-(5-chloro-2-difluoromethoxy-phenyl)-1-{2-[4-(2-cyano-ethylamino)-piperidin-1-yl]-2-oxo-ethyl})-1H-pyrazol-4-yl)-amide (31.1 g, 52.0 mmol) in DCM (500 mL) was treated with 37% aqueous formaldehyde solution (21.3 mL, 286.2 mmol). On complete addition the reaction was cooled in an ice bath before the addition of sodium triacetoxyborohydride (44.1 g, 208.2 mmol) portionwise. The reaction mixture was warmed to room temperature and stirred for 1.5 hours, after which, the reaction was filtered and the filtrate diluted with methanol. The mixture was diluted with methanol and loaded onto a pad of Isolute® SCX-2 which had been conditioned with MeOH. After flushing with MeOH, the product was eluted with 2M ammonia in MeOH. The basic fractions were combined and evaporated. The resultant residue was purified by flash column chromatography on silica eluting with 0-10% 2M $NH_3$/MeOH in DCM. Appropriate fractions were combined and evaporated. The resultant residue was recrystallized from ethyl acetate to afford the title compound as a pale brown solid (30.7 g, 96%). LCMS (Method 5) $[M+H]^+$=612.2, $R_T$=2.84 min. $^1H$ NMR (400 MHz, DMSO-$d_6$) δ: (ppm) 9.75 (s, 1H), 9.34 (dd, 1H, J=7.0, 1.6 Hz), 8.70-8.67 (m, 1H), 8.68 (s, 1H), 8.32 (s, 1H), 7.63 (dd, 1H, J=8.8, 2.7 Hz), 7.56 (d, 1H, J=2.7 Hz), 7.47 (d, 1H, J=8.8 Hz), 7.29 (dd, 1H, J=7.0, 4.2 Hz), 7.26 (t, 1H, J=73.4 Hz), 5.22-5.24 (m, 2H), 4.38 (d, 1H, J=12.9 Hz), 3.96 (d, 1H, J=13.5 Hz), 3.06 (t, 1H, J=12.7 Hz), 2.62-2.65 (m, 6H), 2.22 (s, 3H), 1.72 (d, 2H, J=11.9 Hz), 1.34-1.40 (m, 2H).

Example 142

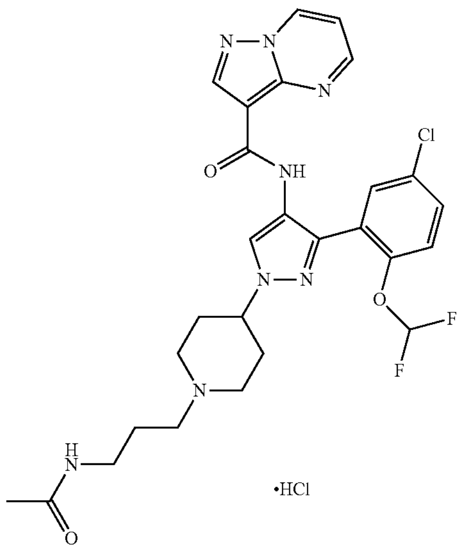 [SMILES: CC(=O)NCCCN1CCC(n2cc(NC(=O)c3cnn4cccnc34)c(-c3cc(Cl)ccc3OC(F)F)n2)CC1 ; Cl]

Pyrazolo[1,5-a]pyrimidine-3-carboxylic acid [1-[1-(3-acetylaminopropyl)piperidin-4-yl]-3-(5-chloro-2-difluoromethoxyphenyl)-1H-pyrazol-4-yl]amide hydrochloride A mixture of pyrazolo[1,5-a]pyrimidine-3-carboxylic acid [3-(5-chloro-2-difluoromethoxyphenyl)-1-piperidin-4-yl-1H-pyrazol-4-yl]amide (100 mg, 0.20 mmol), (3-bromopropyl)-carbamic acid tert-butyl ester (71 mg, 0.3 mmol) and potassium carbonate (45 mg, 0.32 mmol) in DMF (2 mL) was heated at 60° C. for 1.5 hours. The reaction mixture was allowed to cool to ambient temperature, diluted with water and extracted with dichloromethane. The organic layer was separated, washed with brine, dried ($Na_2SO_4$) and evaporated. The resultant residue was chromatographed on silica eluting with dichloromethane on a gradient of 2M ammonia in methanol (0-6%) to give [3-(4-{3-(5-chloro-2-difluoromethoxyphenyl)-4-[(pyrazolo[1,5-a]pyrimidine-3-carbonyl)amino]pyrazol-1-yl}piperidin-1-yl)propyl]carbamic acid tert-butyl ester as a yellow oil (131 mg, 100%). LCMS (Method 4) $[M+H]^+$=675.0, $R_T$=2.86 min.

[3-(4-{3-(5-Chloro-2-difluoromethoxyphenyl)-4-[(pyrazolo[1,5-a]pyrimidine-3-carbonyl)amino]pyrazol-1-yl}piperidin-1-yl)propyl]carbamic acid tert-butyl ester (129 mg, 0.20 mmol) was dissolved in DCM (2 mL) and TFA (2 mL) was added. The reaction was stirred at room temperature for 1 hour and then evaporated to dryness. The residue was dissolved in MeOH and loaded onto an SCX-2 cartridge which had been conditioned with MeOH. After flushing with MeOH, the product was eluted with 2M ammonia in MeOH. Evaporation of the basic fractions gave a residue which was dissolved in pyridine (2 mL). Acetyl chloride (21 μL, 0.30 mmol) was added and the solution was allowed to stand at room temperature for 5 days. The volatiles were evaporated and azeotroped with toluene. The residue was dissolved in MeOH and loaded onto an SCX-2 cartridge which had been conditioned with MeOH. After flushing with MeOH, the product was eluted with 2M ammonia in MeOH. Evaporation gave a glassy solid which was purified by HPLC (Method 3). The pure amine was dissolved in MeOH and 1.25M methanolic HCl was added. The volatiles were evaporated and the solid product was triturated with EtOAc/$Et_2O$ to give the title compound as a white solid (40 mg, 32%). LCMS (Method 5) $[M+H]^+$=587.0, $R_T$=2.91 min. $^1H$ NMR (400 MHz, DMSO-$d_6$) δ: (ppm) 9.89 (s, 1H), 9.76 (s, 1H), 9.35 (dd, 1H, J=1.5, 7.0 Hz), 8.69 (dd, 1H, J=1.6, 4.2 Hz), 8.67 (s, 1H), 8.39 (s, 1H), 8.04 (t, 1H, J=5.8 Hz), 7.67-7.61 (m, 2H), 7.46 (d, 2H, J=8.4 Hz), 7.31 (dd, 1H, J=4.2, 6.9 Hz), 7.26 (t, 1H, J=73.4 Hz), 4.64-4.54 (m, 1H), 3.64 (d, 2H, J=12.2 Hz), 3.21-3.01 (m, 6H), 2.40-2.29 (m, 4H), 1.84 (m, 5H).

Example 302

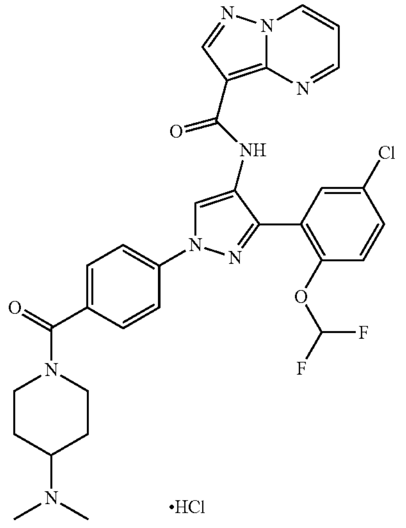 [SMILES: CN(C)C1CCN(C(=O)c2ccc(-n3cc(NC(=O)c4cnn5cccnc45)c(-c4cc(Cl)ccc4OC(F)F)n3)cc2)CC1 ; Cl]

Pyrazolo[1,5-a]pyrimidine-3-carboxylic acid {3-(5-chloro-2-difluoromethoxy-phenyl)-1-[4-(4-dimethyl-amino-piperidine-1-carbonyl)-phenyl]-1H-pyrazol-4-yl}-amide hydrochloride A solution of 4-iodo-benzoyl chloride (4.72 g, 17.71 mmol) in DCM (70 mL) at 0° C. was treated with dimethyl-piperidin-4-yl-amine (2.27 g, 17.71 mmol). The resultant suspension was warmed to room temperature and stirred for 2.5 hours. The reaction mixture was diluted with 1M aqueous $Na_2CO_3$ solution and the phases separated. The aqueous phase was extracted twice with DCM and the combined organic phase was dried ($Na_2SO_4$) and evaporated to afford (4-dimethylamino-piperidin-1-yl)-(4-iodo-phenyl)-methanone as a white solid (6.2 g, 98%). LCMS (Method 3) $[M+H]^+$=359.2, $R_T$=1.82 min.

A microwave vial was charged with pyrazolo[1,5-a]pyrimidine-3-carboxylic acid [3-(5-chloro-2-difluoromethoxy-phenyl)-1H-pyrazol-4-yl]-amide (100 mg, 0.25 mmol), (4-dimethylamino-piperidin-1-yl)-(4-iodo-phenyl)-methanone (107 mg, 0.30 mmol), copper (I) iodide (15 mg, 0.08 mmol), potassium carbonate (73 mg, 0.53 mmol), trans-N,N'-dimethyl-1,2-cyclohexane diamine (24 μL, 0.15 mmol). The vessel was sealed and purged with argon before the addition of toluene (1.0 mL). The reaction mixture was stirred at 110° C. for 18 hours. The reaction was cooled to room temperature, diluted with water and the resultant precipitate was collected by filtration, washed with ethyl acetate and dried under reduced pressure. The resultanat solid was purified by MDAP (Method 1), the solid was taken up into a mixture of MeOH/DCM and loaded onto an Isolute®SCX-2 cartridge which had been conditioned with MeOH. The cartridge was washed with MeOH then eluted with 2M $NH_3$/MeOH. The basic fractions were combined, evaporated and the resultant solid suspended in MeOH before being treated with 1.25M HCl in MeOH. The suspension was allowed to evaporate and the solid was triturated with ethyl acetate, dried under reduced pressure giving the title compound as a yellow solid (67 mg, 40%). LCMS (Method 5) $[M+H]^+$=635.2, $R_T$=3.27 min. $^1$H NMR (400 MHz, DMSO-$d_6$) δ: (ppm) 9.88 (s, 1H), 9.38 (dd, 1H, J=7.1, 1.8 Hz), 9.04 (s, 1H), 8.71 (s, 1H), 8.70 (dd, 1H, J=4.3, 1.7 Hz), 8.04-7.99 (m, 2H), 7.79 (d, 1H, J=2.7 Hz), 7.72 (dd, 1H, J=8.8, 2.6 Hz), 7.63-7.57 (m, 2H), 7.53 (d, 1H, J=8.8 Hz), 7.33 (dd, 1H, J=7.0, 4.3 Hz), 7.31 (t, 1H, J=73.1 Hz), 4.65 (brs, 1H), 2.98 (s, 2H), 2.67 (s, 6H), 2.14-1.82 (m, 2H), 1.69-1.54 (m, 2H).

Example 188

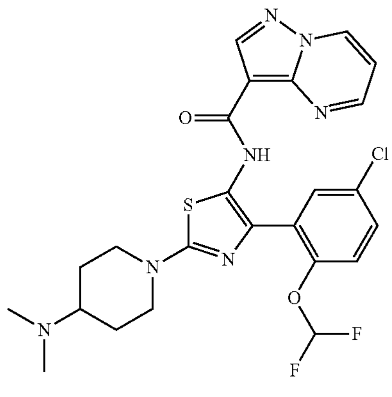 [SMILES: CN(C)C1CCN(c2nc(-c3cc(Cl)ccc3OC(F)F)c(NC(=O)c3cnn4cccnc34)s2)CC1]

Pyrazolo[1,5-a]pyrimidine-3-carboxylic acid [4-(5-chloro-2-difluoromethoxy-phenyl)-2-(4-dimethyl-amino-piperidin-1-yl)-thiazol-5-yl]-amide Pyrazolo[1,5-a]pyrimidine-3-carboxylic acid [2-bromo-4-(5-chloro-2-difluoromethoxy-phenyl)-thiazol-5-yl]-amide (100 mg, 0.2 mmol) and 4-dimethylaminopiperidine (128 mg, 1 mmol) were dissolved in DMA (1 ml) and heated in a microwave at 160° C. for 1 hour. The residue was dissolved in MeOH and loaded onto an SCX-2 cartridge which had been conditioned with MeOH. After flushing with MeOH, the product was eluted with 2M ammonia in MeOH. The resulting yellow glass was purified by MDAP (Method 1). Appropriate fractions were combined and evaporated to afford a yellow solid. The residue was dissolved in MeOH and loaded onto an SCX-2 cartridge which had been conditioned with MeOH. After flushing with MeOH, the product was eluted with 2M ammonia in MeOH to give the title compound as a yellow-orange solid (43 mg, 39%). LCMS (Method 5) $[M+H]^+$=548.1, $R_T$=3.20 min. $^1$H NMR (400 MHz, DMSO-$d_6$) δ: (ppm) 10.23 (s, 1H), 9.36 (dd, 1H, J=1.6, 7.0 Hz), 8.68 (s, 1H), 8.63 (dd, 1H, J=1.6, 4.2 Hz), 7.66 (d, 1H, J=2.7 Hz), 7.59 (dd, 1H, J=2.6, 8.8 Hz), 7.41 (d, 1H, J=9.0 Hz), 7.31 (dd, 1H, J=4.2, 6.7 Hz), 7.18 (t, 1H, J=73.5 Hz), 3.93 (d, 2H, J=12.7 Hz), 3.02 (dd, 2H, J=10.3, 12.3 Hz), 3.05-2.95 (m, 1H), 2.40-2.26 (m, 6H), 1.92-1.89 (m, 2H), 1.58-1.47 (m, 2H).

Example 189

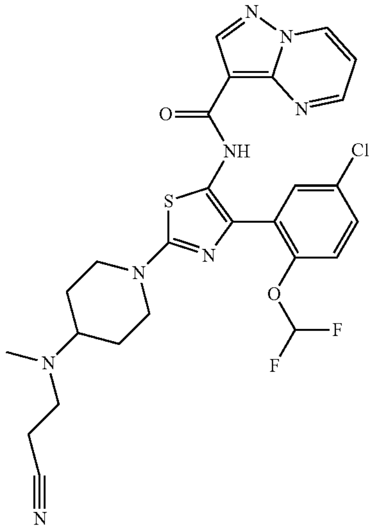 [SMILES: CN(CCC#N)C1CCN(c2nc(-c3cc(Cl)ccc3OC(F)F)c(NC(=O)c3cnn4cccnc34)s2)CC1]

Pyrazolo[1,5-a]pyrimidine-3-carboxylic acid (4-(5-chloro-2-difluoromethoxy-phenyl)-2-{4-[(2-cyano-ethyl)-methyl-amino]-piperidin-1-yl}-thiazol-5-yl)-amide Pyrazolo[1,5-a]pyrimidine-3-carboxylic acid [2-bromo-4-(5-chloro-2-difluoromethoxy-phenyl)-thiazol-5-yl]-amide (820 mg, 1.64 mmol) and 1,4 dioxa-8-azaspiro[4.5]decane (1.05 ml, 8.2 mmol) were dissolved in DMA (10 ml) and heated in a microwave at 165° C. for 1 hour. The reaction mixture partitioned between ethyl acetate and water and the phases separated. The organic layer was washed with brine.

The combined aqueous layers were extracted with ethyl acetate once and the organic layers combined, dried ($Na_2SO_4$), filtered and the solvent removed. The crude product was chromatographed on silica eluting with 50-60% ethyl acetate in cyclohexane. Appropriate fractions were combined and evaporated to afford pyrazolo[1,5-a]pyrimidine-3-carboxylic acid [4-(5-chloro-2-difluoromethoxy-phenyl)-2-(1,4-dioxa-8-aza-spiro[4.5]dec-8-yl)-thiazol-5-yl]-amide as a yellow solid (541 mg, 59%). LCMS (Method 3) $[M+H]^+$=563.3, $R_T$=3.68 min. $^1H$ NMR (400 MHz, DMSO-$d_6$) δ: (ppm) 10.26 (s, 1H), 9.37 (dd, 1H, J=1.6, 6.9 Hz), 8.69 (s, 1H), 8.64 (dd, 1H, J=1.5, 4.4 Hz), 7.68 (d, 1H, J=2.5 Hz), 7.59 (dd, 1H, J=2.7, 8.7 Hz), 7.42 (d, 1H, J=8.5 Hz), 7.31 (dd, 1H, J=4.3, 7.0 Hz), 7.18 (t, 1H, J=73.8 Hz), 3.94 (s, 4H), 3.52 (dd, 4H, J=5.7, 5.7 Hz), 1.75 (dd, 4H, J=5.7, 5.7 Hz).

[4-(5-chloro-2-difluoromethoxy-phenyl)-2-(1,4-dioxa-8-aza-spiro[4.5]dec-8-yl)-thiazol-5-yl]-amide (536 mg, 0.95 mmol) was dissolved in dioxane (10 ml) and conc. hydrochloric acid (10 ml) and stirred at room temperature for 3 hours. The mixture was cooled to 0° C. and basified to ca. pH 13 with 50% aqueous sodium hydroxide and then partitioned between ethyl acetate and water and the phases separated. The organic layer was washed with brine. The combined aqueous layers were extracted with ethyl acetate once and the organic layers combined, dried ($Na_2SO_4$), filtered and the solvent removed to yield pyrazolo[1,5-a]pyrimidine-3-carboxylic acid [4-(5-chloro-2-difluoromethoxy-phenyl)-2-(4-oxo-piperidin-1-yl)-thiazol-5-yl]-amide as a yellow-orange solid (465 mg, 94%). LCMS (Method 3) $[M+H]^+$=519.3, $R_T$=3.39 min. $^1H$ NMR (400 MHz, DMSO-$d_6$) δ: (ppm) 10.30 (s, 1H), 9.38 (dd, 1H, J=1.5, 7.1 Hz), 8.70 (s, 1H), 8.65 (dd, 1H, J=1.4, 4.3 Hz), 7.70 (d, 1H, J=2.5 Hz), 7.61 (dd, 1H, J=2.8, 8.8 Hz), 7.43 (d, 1H, J=9.2 Hz), 7.32 (dd, 1H, J=4.2, 7.1 Hz), 7.20 (t, 1H, J=74.0 Hz), 3.81 (dd, 4H, J=6.2, 6.2 Hz), 2.54 (d, 4H, J=6.1 Hz).

Pyrazolo[1,5-a]pyrimidine-3-carboxylic acid [4-(5-chloro-2-difluoromethoxy-phenyl)-2-(4-oxo-piperidin-1-yl)-thiazol-5-yl]-amide (90 mg, 0.17 mmol) was dissolved in DCM (2 ml) and N-methyl-β-alaninenitrile (20 μl, 0.21 mmol), acetic acid (200 μl) and macroporous polymer supported cyanoborohydride (166 mg, 0.36 mmol) were successively added and stirred at room temperature for 16 hours. The mixture was diluted with MeOH and loaded onto an SCX-2 cartridge which had been conditioned with MeOH. After flushing with MeOH, the product was eluted with 2M ammonia in MeOH. The resulting yellow glass was purified by MDAP (Method 1). Appropriate fractions were combined and evaporated to afford a yellow glass. The residue was dissolved in MeOH and loaded onto an SCX-2 cartridge which had been conditioned with MeOH. After flushing with MeOH, the product was eluted with 2M ammonia in MeOH to give the title compound as a yellow solid (46 mg, 46%). LCMS (Method 5) $[M+H]^+$=587.2, $R_T$=3.19 min. $^1H$ NMR (400 MHz, DMSO-$d_6$) δ: (ppm) 10.23 (s, 1H), 9.36 (dd, 1H, J=1.6, 7.0 Hz), 8.68 (s, 1H), 8.64 (dd, 1H, J=1.6, 4.3 Hz), 7.67 (d, 1H, J=2.6 Hz), 7.59 (dd, 1H, J=2.7, 8.9 Hz), 7.41 (d, 1H, J=8.6 Hz), 7.31 (dd, 1H, J=4.3, 7.1 Hz), 7.18 (t, 1H, J=73.9 Hz), 3.94 (d, 2H, J=12.8 Hz), 3.04-2.96 (m, 2H), 2.72-2.60 (m, 5H), 2.24 (s, 3H), 1.79 (d, 2H, J=10.9 Hz), 1.59-1.47 (m, 2H).

Example 205

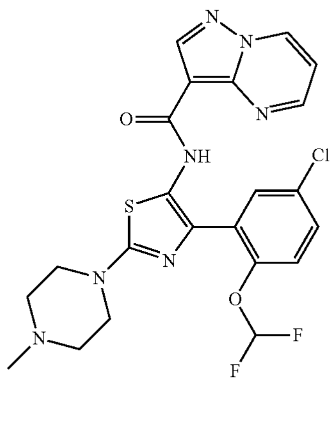 [SMILES: CN1CCN(c2nc(-c3cc(Cl)ccc3OC(F)F)c(NC(=O)c3cnn4cccnc34)s2)CC1]

Pyrazolo[1,5-a]pyrimidine-3-carboxylic acid [4-(5-chloro-2-difluoromethoxy-phenyl)-2-(4-methyl-piperazin-1-yl)-thiazol-5-yl]-amide The title compound was prepared in an analogous manner to pyrazolo[1,5-a]pyrimidine-3-carboxylic acid [4-(5-chloro-2-difluoromethoxy-phenyl)-2-(4-dimethylamino-piperidin-1-yl)-thiazol-5-yl]-amide to afford the title compound as a yellow-orange solid. LCMS (Method 5) $[M+H]^+$=520.2, $R_T$=3.02 min. $^1H$ NMR (400 MHz, DMSO-$d_6$) δ: (ppm) 10.25 (s, 1H), 9.37 (dd, 1H, J=1.6, 7.0 Hz), 8.69 (s, 1H), 8.64 (dd, 1H, J=1.6, 4.3 Hz), 7.67 (d, 1H, J=2.6 Hz), 7.59 (dd, 1H, J=2.7, 8.8 Hz), 7.42 (d, 1H, J=9.2 Hz), 7.31 (dd, 1H, J=4.2, 7.3 Hz), 7.18 (t, 1H, J=73.7 Hz), 3.41 (dd, 4H, J=4.9, 4.9 Hz), 2.48-2.42 (m, 4H), 2.24 (s, 3H).

Example 209

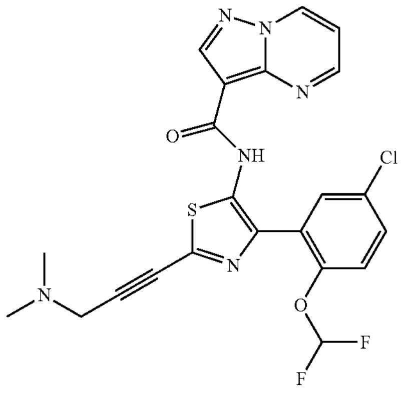 [SMILES: CN(C)CC#Cc1nc(-c2cc(Cl)ccc2OC(F)F)c(NC(=O)c2cnn3cccnc23)s1]

Pyrazolo[1,5-a]pyrimidine-3-carboxylic acid [4-(5-chloro-2-difluoromethoxy-phenyl)-2-(3-dimethyl-amino-prop-1-ynyl)-thiazol-5-yl]-amide To a solution of pyrazolo[1,5-a]pyrimidine-3-carboxylic acid [2-bromo-4-(5-chloro-2-difluoromethoxy-phenyl)-thiazol-5-yl]-amide (150 mg, 0.3 mmol), bis(triphenylphosphine)palladium(II) dichloride (11 mg, 0.015 mmol), copper (I)iodide (5 mg, 0.024 mmol) in THF (1 mL) was added propargyl alcohol (35 μL, 0.6 mmol) then triethylamine (1 mL) under an atmosphere of nitrogen. The resultant mixture was stirred at 50° C. for 3 hours before being cooled to room temperature. The mixture was partitioned between ethyl acetate and water. The phases were separated and the organic phase washed with brine, dried ($Na_2SO_4$) and evaporated. The resultant residue was purified by flash column chromatography on silica eluting with 80% ethyl acetate in cyclohexane to afford pyrazolo[1,5-a]pyrimidine-3-carboxylic acid [4-(5-chloro-2-difluoromethoxy-phenyl)-2-(3-hydroxy-prop-1-ynyl)-thiazol-5-yl]-amide as a yellow solid (112 mg, 78%). LCMS (Method 3) $[M+H]^+$=476.2, $R_T$=3.19 min.

To a suspension of pyrazolo[1,5-a]pyrimidine-3-carboxylic acid [4-(5-chloro-2-difluoromethoxy-phenyl)-2-(3-hydroxy-prop-1-ynyl)-thiazol-5-yl]-amide (110 mg, 0.23 mmol) and triphenylphosphine (105 mg, 0.4 mmol) in DCM (3 mL) was added carbon tetrabromide (132 mg, 0.4 mmol) portionwise. The reaction was stirred at room temperature before the addition of 2M methylamine in THF (1 mL). The resultant mixture was stirred at room temperature for 3 hours. The mixture was evaporated and the residue taken up into MeOH and loaded onto an Isolute® SCX-2 cartridge which had been conditioned with MeOH. The cartridge was washed with MeOH before being eluted with 2M $NH_3$ in MeOH. The basic fractions were combined and evaporated. The residue was purified by MDAP (Method 1), after evaporation the material was taken up into MeCN and loaded onto an Isolute® SCX-2 cartridge which had been conditioned with MeCN. The cartridge was washed with MeCN before being eluted with 2M $NH_3$ in MeOH. The basic fractions were combined and evaporated, giving the title compound as an orange solid (18 mg, 15%). LCMS (Method 5) $[M+H]^+$=503.0, $R_T$=3.16 min. $^1H$ NMR (400 MHz, DMSO-$d_6$) δ: (ppm) 10.85 (s, 1H), 9.41 (dd, 1H, J=7.1, 1.3 Hz), 8.79 (s, 1H), 8.63 (dd, 1H, J=4.4, 1.5 Hz), 7.76 (d, 1H, J=2.6 Hz), 7.72 (dd, 1H, J=8.8, 2.6 Hz), 7.52 (d, 1H, J=8.8 Hz), 7.36 (dd, 1H, J=7.0, 4.3 Hz), 7.19 (t, 1H, J=73.2 Hz), 3.61 (s, 2H), 2.29 (s, 6H).

Example 211

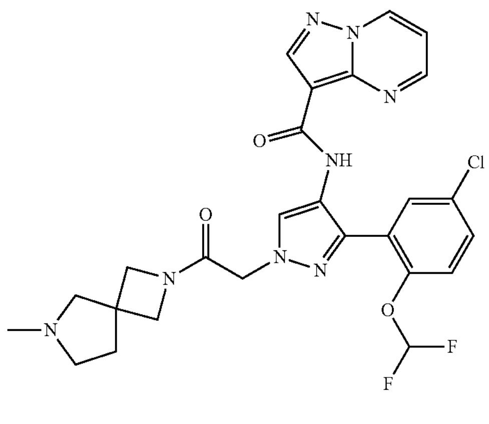 [SMILES: CN1CCC2(C1)CN(C(=O)Cn1cc(NC(=O)c3cnn4cccnc34)c(-c3cc(Cl)ccc3OC(F)F)n1)C2]

Pyrazolo[1,5-a]pyrimidine-3-carboxylic acid {3-(5-chloro-2-difluoromethoxyphenyl)-1-[2-(6-methyl-2,6-diazaspiro[3.4]oct-2-yl)-2-oxoethyl]-1H-pyrazol-4-yl}amide Pyrazolo[1,5-a]pyrimidine-3-carboxylic acid {3-(5-chloro-2-difluoromethoxy-phenyl)-1-[2-(2,6-diazaspiro[3.4]oct-2-yl)-2-oxoethyl]-1H-pyrazol-4-yl}amide was prepared using a method similar to that used in the synthesis of pyrazolo[1,5-a]pyrimidine-3-carboxylic acid {3-(5-chloro-2-difluoromethoxy-phenyl)-1-[2-(hexahydro-pyrrolo[3,4-c]pyrrol-2-yl)-2-oxoethyl]-1H-pyrazol-4-yl}amide. LCMS (Method 5) $[M+H]^+$=556.9, $R_T$=2.84 min.

Pyrazolo[1,5-a]pyrimidine-3-carboxylic acid {3-(5-chloro-2-difluoromethoxy-phenyl)-1-[2-(2,6-diaza-spiro[3.4]oct-2-yl)-2-oxoethyl]-1H-pyrazol-4-yl}amide (70 mg, 0.13 mmol) and paraformaldehyde (19 mg, 0.63 mmol) were stirred in 2,2,2-trifluoroethanol for 15 minutes. Sodium borohydride (14 mg, 0.38 mmol) was added and the reaction mixture was heated at 90° C. for 2 hours. The reaction mixture was allowed to cool to room temperature and was quenched with MeOH. The mixture was loaded onto an SCX-2 cartridge which had been conditioned with MeOH. After flushing with MeOH, the product was eluted with 2M ammonia in MeOH. Evaporation gave a crude product which was purified by HPLC (Method 1). The pure fractions were loaded onto an SCX-2 cartridge which had been conditioned with MeOH. After flushing with MeOH, the product was eluted with 2M ammonia in MeOH. Evaporation gave the free base which was crystallised from MeOH/$Et_2O$. The title compound was obtained as a white solid (28 mg, 39%). LCMS (Method 5) $[M+H]^+$=570.9, $R_T$=2.86 min. $^1H$ NMR (400 MHz, DMSO-$d_6$) δ: (ppm) 9.75 (s, 1H), 9.34 (dd, 1H, J=1.5, 7.0 Hz), 8.69-8.66 (m, 2H), 8.34 (s, 1H), 8.15 (s, 1H), 7.64 (dd, 1H, J=2.7, 8.9 Hz), 7.57 (d, 1H, J=2.7 Hz), 7.47 (d, 1H, J=8.8 Hz), 7.29 (dd, 2H, J=4.3, 7.1 Hz), 7.25 (t, 1H, J=73.5 Hz), 4.94 (s, 2H), 4.04 (q, 2H, J=8.8 Hz), 3.90-3.81 (m, 2H), 2.69 (s, 2H), 2.27 (s, 3H), 2.03 (dd, 2H, J=6.8, 6.8 Hz).

Example 227

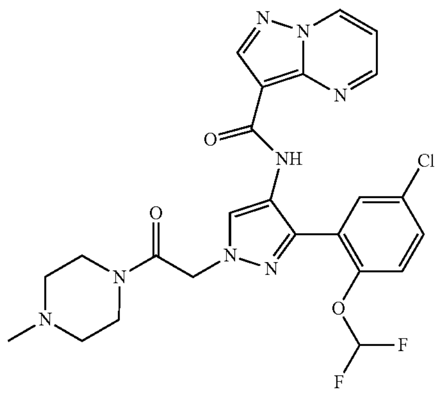 [SMILES: CN1CCN(C(=O)Cn2cc(NC(=O)c3cnn4cccnc34)c(-c3cc(Cl)ccc3OC(F)F)n2)CC1]

Pyrazolo[1,5-a]pyrimidine-3-carboxylic acid {3-(5-chloro-2-difluoromethoxyphenyl)-1-[2-(4-methyl-piperazin-1-yl)-2-oxoethyl]-1H-pyrazol-4-yl}amide The title compound was prepared in an analogous manner to cis-pyrazolo[1,5-a]pyrimidine-3-carboxylic acid {3-(5-chloro-2-difluoromethoxyphenyl) 1-[2-(5-methylhexahydropyrrolo[3,4-c]pyrrol-2-yl)-2-oxoethyl]-1H-pyrazol-4-yl}amide using {3-(5-chloro-2-difluoromethoxy-phenyl)-4-[(pyrazolo[1,5-a]pyrimidine-3-carbonyl)amino]pyrazol-1-yl}acetic acid and methyl piperazine to afford the title compound as a pale yellow solid. LCMS (Method 5) $[M+H]^+$=545.1, $R_T$=2.89 min. $^1H$ NMR (400 MHz, $CDCl_3$)

δ: (ppm) 9.85 (s, 1H), 8.78 (dd, 1H, J=1.6, 7.0 Hz), 8.71 (s, 1H), 8.56 (dd, 1H, J=1.7, 4.1 Hz), 8.41 (s, 1H), 7.69 (d, 1H, J=2.6 Hz), 7.41 (dd, 1H, J=2.6, 8.7 Hz), 7.28 (d, 1H, J=9.1 Hz), 7.00 (dd, 1H, J=4.2, 7.0 Hz), 6.47 (t, 1H, J=74.1 Hz), 5.04 (s, 2H), 3.72-3.65 (m, 2H), 3.57 (dd, 2H, J=4.8, 4.8 Hz), 2.47-2.39 (m, 4H), 2.31 (s, 3H).

Example 233

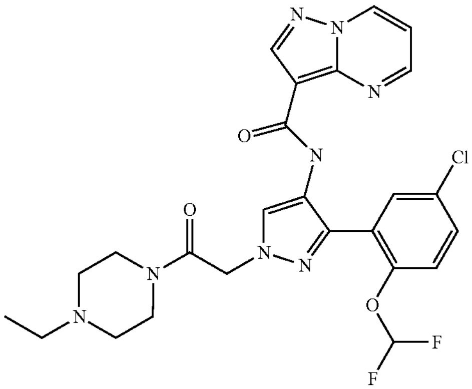 [SMILES: CCN1CCN(C(=O)Cn2cc(NC(=O)c3cnn4cccnc34)c(-c3cc(Cl)ccc3OC(F)F)n2)CC1]

Pyrazolo[1,5-a]pyrimidine-3-carboxylic acid {3-(5-chloro-2-difluoromethoxy-phenyl)-1-[2-(4-ethyl-piperazin-1-yl)-2-oxo-ethyl]-1H-pyrazol-4-yl}-amide The title compound was prepared in an analogous manner to cis-pyrazolo[1,5-a]pyrimidine-3-carboxylic acid {3-(5-chloro-2-difluoromethoxyphenyl) 1-[2-(5-methylhexahydropyrrolo[3,4-c]pyrrol-2-yl)-2-oxoethyl]-1H-pyrazol-4-yl}amide using {3-(5-chloro-2-difluoromethoxy-phenyl)-4-[(pyrazolo[1,5-a]pyrimidine-3-carbonyl)amino]pyrazol-1-yl}acetic acid and ethyl piperazine to afford the title compound as a white solid. LCMS (Method 5) $[M+H]^+$=559.1, $R_T$=2.89 min. $^1H$ NMR (400 MHz, DMSO-$d_6$) δ: (ppm) 9.75 (s, 1H), 9.34 (dd, 1H, J=1.6, 7.0 Hz), 8.69-8.67 (m, 2H), 8.31 (s, 1H), 7.63 (dd, 1H, J=2.7, 8.8 Hz), 7.56 (d, 1H, J=2.6 Hz), 7.46 (d, 1H, J=9.0 Hz), 7.29 (dd, 1H, J=4.2, 7.1 Hz), 7.25 (t, 1H, J=73.5 Hz), 5.23 (s, 2H), 3.50-3.49 (m, 4H), 2.41-2.32 (m, 6H), 1.02 (t, 3H, J=7.1 Hz).

Example 253

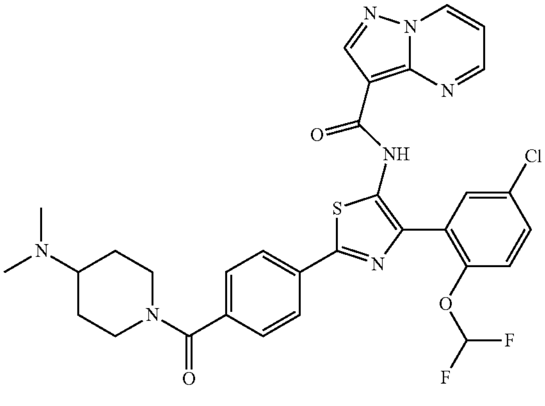 [SMILES: CN(C)C1CCN(C(=O)c2ccc(-c3nc(-c4cc(Cl)ccc4OC(F)F)c(NC(=O)c4cnn5cccnc45)s3)cc2)CC1]

Pyrazolo[1,5-a]pyrimidine-3-carboxylic acid {4-(5-chloro-2-difluoromethoxy-phenyl)-2-[4-(4-dimethylamino-piperidine-1-carbonyl)-phenyl]-thiazol-5-yl}-amide hydrochloride Pyrazolo[1,5-a]pyrimidine-3-carboxylic acid [2-bromo-4-(5-chloro-2-difluoromethoxy-phenyl)-thiazol-5-yl]-amide (100 mg, 0.2 mmol), 4-carboxybenzeneboronic acid (40 mg, 0.24 mmol), [1,1'-bis(diphenylphosphino)ferrocene]dichloropalladium dichloromethane complex (16 mg, 0.02 mmol) and potassium carbonate (110 mg, 0.8 mmol) were dissolved in dioxane (3.2 ml) and water (0.8 ml) under an atmosphere of $N_2$ and heated in a microwave at 120° C. for 30 mins. The mixture was partitioned between ethyl acetate and water and the phases separated. The aqueous layer was acidified with 1M HCl and the resulting precipitate was filtered and the solid collected and dried.

The resultant residue was dissolved in DMF (2 ml) and DIPEA (52 μl, 0.3 mmol) and HATU (91 mg, 0.24 mmol) were added and stirred at room temperature for 5 mins before the addition of 4-dimethylaminopiperidine (31 mg, 0.24 mmol). The resulting mixture was stirred at room temperature for a further 16 hours. The mixture was diluted with MeOH and loaded onto an SCX-2 cartridge which had been conditioned with MeOH. After flushing with MeOH, the product was eluted with 2M ammonia in MeOH. The resulting yellow glass was purified by HPLC (MDAP, Method 1). Appropriate fractions were combined and evaporated to afford an off-white solid. The residue was dissolved in MeOH and loaded onto an SCX-2 cartridge which had been conditioned with MeOH. After flushing with MeOH, the product was eluted with 2M ammonia in MeOH to give the title compound as an off-white solid (27 mg, 21%). LCMS (Method 5) $[M+H]^+$=652.3, $R_T$=3.35 min. $^1H$ NMR (400 MHz, DMSO-$d_6$) δ: (ppm) 10.82 (1H, s), 9.42 (1H, dd, J=1.4, 6.9 Hz), 8.80 (1H, s), 8.65 (1H, dd, J=1.4, 4.3 Hz), 8.03 (2H, d, J=8.2 Hz), 7.85 (1H, d, J=2.6 Hz), 7.73 (1H, dd, J=2.7, 8.8 Hz), 7.56-7.51 (3H, m), 7.37 (1H, dd, J=4.3, 6.9 Hz), 7.25 (1H, t, J=73.5 Hz), 4.71-4.39 (m, 1H), 3.73-3.65 (1H, m), 3.52-3.41 (1H, m), 3.13-3.11 (1H, m), 2.89-2.88 (1H, m), 2.51 (s, 6H), 2.06-1.74 (2H, m), 1.49 (2H, dd, J=7.6, 14.7 Hz).

Example 260

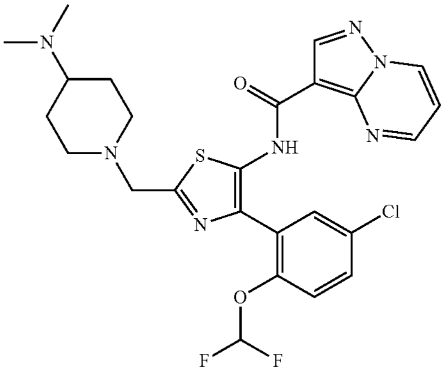 [SMILES: CN(C)C1CCN(Cc2nc(-c3cc(Cl)ccc3OC(F)F)c(NC(=O)c3cnn4cccnc34)s2)CC1]

Pyrazolo[1,5-a]pyrimidine-3-carboxylic acid [4-(5-chloro-2-difluoromethoxy-phenyl)-2-(4-dimethyl amino-piperidin-1-ylmethyl)-thiazol-5-yl]-amide Pyrazolo[1,5-a]pyrimidine-3-carboxylic acid [2-bromo-4-(5-chloro-2-difluoromethoxy-phenyl)-thiazol-5-yl]-amide (600 mg, 1.2 mmol), potassium vinyltrifluoroborate (177 mg, 1.32 mmol), [1,1'-bis(diphenylphosphino)ferrocene]dichloropalladium dichloromethane complex (48 mg, 0.06 mmol) and DIPEA (627 μl, 3.6 mmol) were dissolved in 2-propanol (9 ml) and water (4.5 ml) under an atmosphere on $N_2$ and heated in a microwave at 100° C. for 40 mins. The mixture was partitioned between ethyl acetate and water and the phases separated. The organic layer was washed with brine, dried ($Na_2SO_4$), filtered and the solvent removed.

The resulting residue was suspended in acetone (12 ml) and water (1.2 ml), then potassium osmate dihydrate (25 mg, 0.06 mmol) and N-methylmorpholine N-oxide (280 mg, 2.4 mmol) were added and the mixture stirred vigorously at room temperature for 16 hours. The reaction was quenched by the addition of solid sodium metabisulfite (2 g), and then partitioned between ethyl acetate and water and the phases separated. The organic layer was washed with brine. The combined aqueous layers were extracted with ethyl acetate once and the organic layers combined, dried ($Na_2SO_4$), filtered and the solvent removed.

The resulting residue was dissolved in THF (15 ml) and water (15 ml) and sodium periodate (514 mg, 2.4 mmol) was added and the mixture was stirred vigorously at room temperature for 1.5 hours. The reaction mixture partitioned between ethyl acetate and water and the phases separated. The organic layer was washed with brine. The combined aqueous layer was extracted with ethyl acetate once and the organic layer combined, dried ($Na_2SO_4$), filtered and the solvent removed to yield the title compound as an orange solid (509 mg, 94%).

A portion of the resultant solid (100 mg, 0.22 mmol) was dissolved in DCM (2 ml) and 4-dimethylaminopiperidine (33 mg, 0.26 mmol), acetic acid (200 μl) and macroporous polymer supported cyanoborohydride (216 mg, 0.44 mmol) were successively added and stirred at room temperature for 16 hours. The mixture was diluted with MeOH and loaded onto an SCX-2 cartridge which had been conditioned with MeOH. After flushing with MeOH, the product was eluted with 2M ammonia in MeOH. The resulting yellow glass was purified by HPLC (MDAP, Method 1). Appropriate fractions were combined and evaporated to afford a yellow glass. The residue was dissolved in MeOH and loaded onto an SCX-2 cartridge which had been conditioned with MeOH. After flushing with MeOH, the product was eluted with 2M ammonia in MeOH to give the title compound as a pale yellow solid (52 mg, 42%). LCMS (Method 5) $[M+H]^+$ =562.1, $R_T$=2.56 min. $^1H$ NMR (400 MHz, DMSO-$d_6$) δ: (ppm) 10.59 (s, 1H), 9.39 (dd, 1H, J=1.6, 7.0 Hz), 8.75 (s, 1H), 8.62 (dd, 1H, J=1.6, 4.3 Hz), 7.48 (d, 1H, J=8.8 Hz), 7.34 (dd, 1H, J=4.2, 7.0 Hz), 7.17 (t, 1H, J=73.4 Hz), 3.78 (s, 2H), 2.98 (d, 2H, J=11.5 Hz), 2.19 (s, 6H), 2.17-2.08 (m, 3H), 1.79-1.72 (m, 2H), 1.50-1.38 (m, 2H).

Example 264

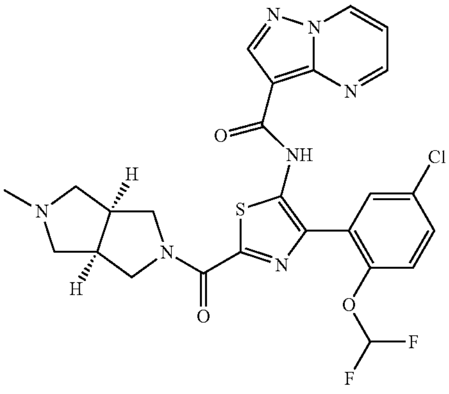 [SMILES: CN1C[C@@H]2CN(C(=O)c3nc(-c4cc(Cl)ccc4OC(F)F)c(NC(=O)c4cnn5cccnc45)s3)C[C@@H]2C1]

Pyrazolo[1,5-a]pyrimidine-3-carboxylic acid [4-(5-chloro-2-difluoromethoxy-phenyl)-2-(5-methyl-hexahydro-pyrrolo[3,4-c]pyrrole-2-carbonyl)-thiazol-5-yl]-amide Pyrazolo[1,5-a]pyrimidine-3-carboxylic acid [2-bromo-4-(5-chloro-2-difluoromethoxy-phenyl)-thiazol-5-yl]-amide (200 mg, 0.4 mmol), 2-methyl-octahydro-pyrrolo[3,4-c]pyrrole (70 mg, 0.56 mmol), Herrmann's catalyst (4.5 mg, 0.0048 mmol), tri-tert-butyl phosphine hydrofluoroborate (3.5 mg, 0.011 mmol), molybdenum hexacarbonyl (53 mg, 0.2 mmol) and DBU (40 μl, 0.27 mmol) were dissolved in THF (2 ml) and heated in a microwave at 125° C. for 15 mins. The residue was dissolved in MeOH and loaded onto an SCX-2 cartridge which had been conditioned with MeOH. After flushing with MeOH, the product was eluted with 2M ammonia in MeOH. The resulting yellow glass was purified by HPLC (MDAP, Method 1). Appropriate fractions were combined and evaporated to afford a yellow solid. The residue was dissolved in MeOH and loaded onto an SCX-2 cartridge which had been conditioned with MeOH. After flushing with MeOH, the product was eluted with 2M ammonia in MeOH to give the title compound as a pale yellow solid (18 mg, 8%). LCMS (Method 5) $[M+H]^+$= 574.1, $R_T$=3.06 min. $^1H$ NMR (400 MHz, DMSO-$d_6$) δ: (ppm) 10.88 (s, 1H), 9.42 (dd, 1H, J=1.6, 7.0 Hz), 8.81 (s, 1H), 8.61 (dd, 1H, J=1.5, 4.3 Hz), 7.84 (d, 1H, J=2.6 Hz), 7.73 (dd, 1H, J=2.6, 8.8 Hz), 7.54 (d, 1H, J=8.8 Hz), 7.36 (dd, 1H, J=4.3, 7.0 Hz), 7.22 (t, 1H, J=73.1 Hz), 4.24 (dd, 1H, J=8.6, 12.3 Hz), 4.09 (dd, 1H, J=3.9, 12.3 Hz), 3.80 (dd, 1H, J=8.9, 12.6 Hz), 3.59-3.47 (m, 1H), 3.02-2.92 (m, 1H), 2.88-2.80 (m, 1H), 2.65-2.48 (m, 4H), 2.29 (s, 3H).

Example 297

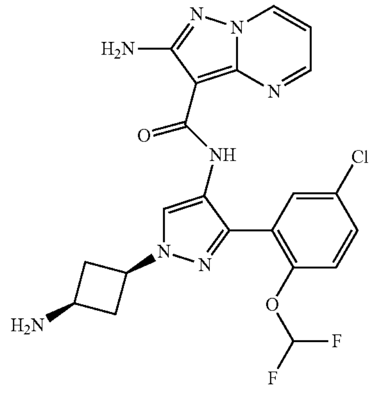 [SMILES: Nc1nn2cccnc2c1C(=O)Nc1cn([C@H]2C[C@@H](N)C2)nc1-c1cc(Cl)ccc1OC(F)F]

2-Amino-pyrazolo[1,5-a]pyrimidine-3-carboxylic acid [1-(3-amino-cyclobutyl)-3-(5-chloro-2-difluoromethoxy-phenyl)-1H-pyrazol-4-yl]-amide The title compound was prepared in an analogous manner to 2-amino-pyrazolo[1,5-a]pyrimidine-3-carboxylic acid [3-(5-chloro-2-difluoromethoxy-phenyl)-1-piperidin-4-yl-1H-pyrazol-4-yl]-amide using tert-butyl (3-((3-(5-chloro-2-(difluoromethoxy)phenyl)-1H-pyrazol-4-yl)carbamoyl) pyrazolo[1,5-a]pyrimidin-2-yl) carbamate and trans-toluene-4-sulfonic acid 3-tert-butoxycarbonylamino-cyclobutyl ester to afford the title compound as a white solid.

LCMS (Method 5) $[M+H]^+$=489.1, $R_T$=2.87 min. $^1H$ NMR (400 MHz, DMSO-$d_6$) δ: (ppm) 9.53 (s, 1H), 8.93 (dd, 1H, J=1.6, 6.8 Hz), 8.37-8.34 (m, 2H), 7.63-7.60 (m, 2H), 7.45 (d, 1H, J=7.2 Hz), 7.25 (t, 1H, J=72.6 Hz), 7.00 (dd, 1H, J=4.5, 6.5 Hz), 6.56 (s, 2H), 4.51-4.41 (m, 1H), 3.18-3.07 (m, 1H), 2.75-2.67 (m, 2H), 2.24-2.14 (m, 2H).

Example 304

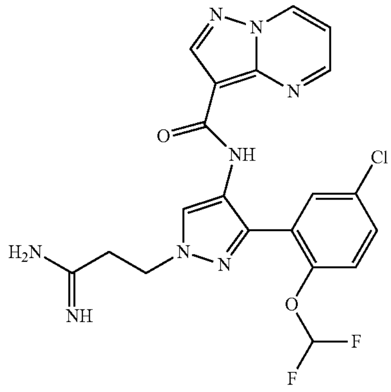 [SMILES: N=C(N)CCn1cc(NC(=O)c2cnn3cccnc23)c(-c2cc(Cl)ccc2OC(F)F)n1]

N-[1-(2-carbamimidoylethyl)-3-[5-chloro-2-(difluoromethoxy)phenyl]-1H-pyrazol-4-yl]pyrazolo[1,5-a]pyrimidine-3-carboxamide A mixture of N-[3-[5-chloro-2-(difluoromethoxy)phenyl]-1H-pyrazol-4-yl]pyrazolo[1,5-a]pyrimidine-3-carboxamide (500 mg, 1.24 mmol), 3-bromopropanenitrile (412 mg, 3.08 mmol), $Cs_2CO_3$ (1.21 g, 3.70 mol) in N,N-dimethylformamide (15 mL) was purged with a gentle flow of nitrogen gas. The resulting mixture was stirred in a sealed tube at 65° C. for 16 then poured into water (200 mL). The crude product was collected by filtration and then purified by flash chromatography on silica eluting with ethyl acetate/petroleum ether (1:2). Appropriate fractions were collected and evaporated to afford N-[3-[5-chloro-2-(difluoromethoxy)phenyl]-1-(2-cyanoethyl)-1H-pyrazol-4-yl]pyrazolo[1,5-a]pyrimidine-3-carboxamide as a light yellow solid (320 mg, 57%). LCMS (Method 17) $[M+H]^+$=458.1, $R_T$=1.67 min.

To a solution of N-[3-[5-chloro-2-(difluoromethoxy)phenyl]-1-(2-cyanoethyl)-1H-pyrazol-4-yl]pyrazolo[1,5-a]pyrimidine-3-carboxamide (200 mg, 0.44 mmol) and methanol (280 mg, 8.74 mmol) in toluene (10 mL) was added acetyl chloride (341 mg, 4.34 mmol) dropwise with stirring at 0° C. The resulting solution was stirred for 2 hours at room temperature. To this was added a solution of concentrated ammonium hydroxide (459 mg) in methanol (3 mL) dropwise with stirring at 0° C. The resulting solution was stirred overnight at room temperature and concentrated under reduced pressure. The residue was purified by flash chromatography on silica eluting with dichloromethane/methanol (5/1). Appropriate fractions were collected and concentrated to afford a white solid (130 mg), which was further purified by high pH Prep-HPLC to afford N-[1-(2-carbamimidoylethyl)-3-[5-chloro-2-(difluoromethoxy)-phenyl]-1H-pyrazol-4-yl]pyrazolo[1,5-a]pyrimidine-3-carboxamide as a white solid (36.8 mg). LCMS (Method 17) $[M+H]^+$=475.1 (Note: under method 17, decomposition products observed), LCMS (method 18) $R_T$=6.52 min. $^1H$ NMR (300 MHz, DMSO-$d_6$) δ: (ppm) 9.72 (s, 1H), 9.36 (dd, J=1.8, 7.2 Hz, 1H), 8.68-8.66 (m, 2H), 8.35 (s, 1H), 7.64-7.60 (m, 2H), 7.48-7.24 (m, 3H), 6.39 (s, 2H), 4.44 (t, J=7.2 Hz, 2H), 2.67 (t, J=7.2 Hz, 2H).

Example 306

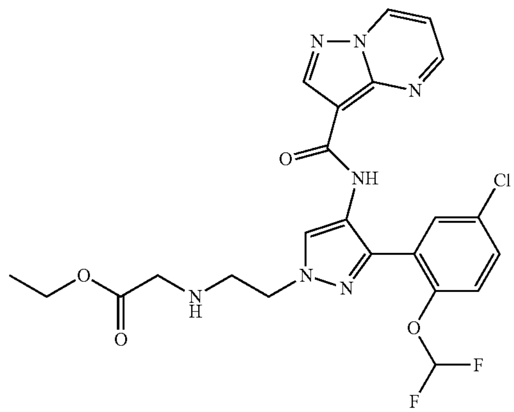 [SMILES: CCOC(=O)CNCCn1cc(NC(=O)c2cnn3cccnc23)c(-c2cc(Cl)ccc2OC(F)F)n1]

Ethyl 2-[(2-[3-[5-chloro-2-(difluoromethoxy)phenyl]-4-[pyrazolo[1,5-a]pyrimidine-3-amido]-1H-pyrazol-1-yl]ethyl)amino]acetate A mixture of N-[3-[5-chloro-2-(difluoromethoxy)phenyl]-1H-pyrazol-4-yl]pyrazolo[1,5-a]pyrimidine-3-carboxamide (3.00 g, 7.41 mmol), $Cs_2CO_3$ (9.90 g, 30.38 mmol), tetrahydrofuran (90 mL), 1,2-dibromoethane (7.00 g, 37.26 mmol) was stirred at 70° C. for 3 hours in an oil bath. The mixture was allowed to cool to ambient temperature then concentrated under reduced pressure. The residue was purified by flash chromatography on silica eluting with ethyl acetate/petroleum ether (1:1) to afford N-[1-(2-bromoethyl)-3-[5-chloro-2-(difluoromethoxy)phenyl]-1H-pyrazol-4-yl]pyrazolo[1,5-a]-pyrimidine-3-carboxamide as a off-white solid (2.2 g, 58%). TLC: $R_f$=0.6; ethyl acetate/petroleum ether=1:1; LCMS (Method 14) $[M+H]^+$=513.2, $R_T$=1.03 min.

A mixture of N-[1-(2-bromoethyl)-3-[5-chloro-2-(difluoromethoxy)-phenyl]-1H-pyrazol-4-yl]pyrazolo[1,5-a]pyrimidine-3-carboxamide (200 mg, 0.39 mmol), triethylamine (394 mg, 3.89 mmol), ethyl 2-aminoacetate hydrochloride (271 mg, 1.94 mmol) in ethanol (20 mL) was stirred at 80° C. for 24 hours then concentrated under reduced pressure. The crude product was purified by high pH Prep-HPLC to afford the title compound as an off-white solid (31.9 mg, 15%). LCMS (Method 14) $[M+H]^+$=534.2, $R_T$=1.13 min. $^1H$ NMR (300 MHz, $CD_3OD$-$d_4$) δ: (ppm) 9.11 (dd, J=1.5, 7.0 Hz, 1H), 8.66-6.65 (m, 2H), 8.36 (s, 1H), 7.68 (d, J=2.4 Hz, 1H), 7.58 (dd, J=2.7, 8.7 Hz, 1H), 7.42 (d, J=8.7 Hz, 1H), 7.39 (dd, J=4.5, 7.2 Hz, 1H), 6.55 (t, J=73.5 Hz, 1H), 4.35 (t, J=5.7 Hz, 2H), 4.17 (q, J=7.2 Hz, 2H), 3.41 (s, 2H), 3.15 (t, J=6.0 Hz, 2H), 1.25 (t, J=7.2 Hz, 3H).

Example 310

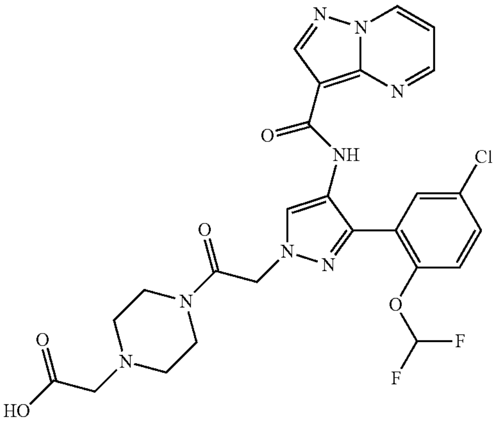 [SMILES: O=C(O)CN1CCN(C(=O)Cn2cc(NC(=O)c3cnn4cccnc34)c(-c3cc(Cl)ccc3OC(F)F)n2)CC1]

2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]acetic acid Potassium hydroxide (200 mg, 3.56 mmol) in water (2 mL) was added to a solution of ethyl 2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]acetate (200 mg, 0.32 mmol) in ethanol (20 mL), The resulting solution was stirred at room temperature for 2 h and neutralized with 1 M HCl aqueous solution until pH-7. The resultant solution was concentrated under vacuum. The crude product was purified by Prep-HPLC with the following conditions (Prep-HPLC-005): Column, XBridge Prep C18 OBD Column, 5 um, 19*150 mm; mobile phase, water with 10 mmol NH4HCO3 and MeCN (30.0% up to 60.0% in 10 min, up to 95.0% in 1 min, hold 95.0% in 1 min, down to 30.0% in 2 min); Detector, UV 254/220 nm. This resulted in 20.6 mg (11%) of 2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]acetic acid as a white solid. LCMS (Method 26) $[M+H]^+$=589.2, $R_T$=0.82 min. $^1H$ NMR (400 MHz, $CD_3OD-d_4$) δ: (ppm) 9.10 (dd, 1H, J=1.6, 7.2 Hz), 8.66 (s, 1H), 8.65 (d, 1H, J=2.8 Hz), 8.38 (s, 1H), 7.69 (d, 1H, J=2.4 Hz), 7.57 (dd, 1H, J=2.4, 8.8 Hz), 7.42 (d, 1H, J=8.8 Hz), 7.21 (J=4.0, 6.8 Hz), 6.63 (t, 1H, J=73.6 Hz), 5.30 (s, 2H), 3.93-3.86 (m, 4H), 3.50 (s, 2H), 3.32-3.13 (m, 4H).

Example 311

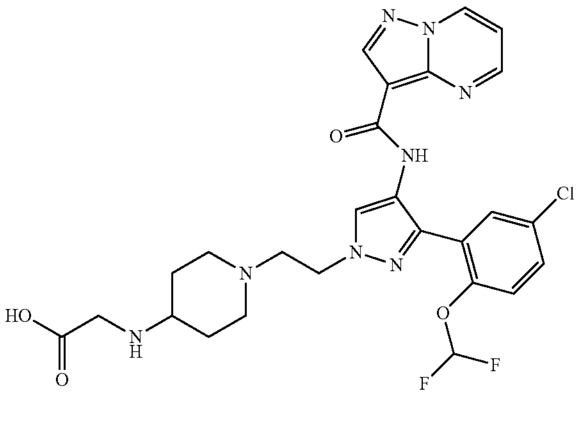 [SMILES: O=C(O)CNC1CCN(CCn2cc(NC(=O)c3cnn4cccnc34)c(-c3cc(Cl)ccc3OC(F)F)n2)CC1]

2-[[1-(2-[3-[5-chloro-2-(difluoromethoxy)phenyl]-4-[pyrazolo[1,5-a]pyrimidine-3-amido]-1H-pyrazol-1-yl]ethyl)piperidin-4-yl]amino]acetic acid A mixture of t-butyl N-(piperidin-4-yl)carbamate (627 mg, 3.13 mmol) and N-[1-(2-bromoethyl)-3-[5-chloro-2-(difluoromethoxy)phenyl]-1H-pyrazol-4-yl]pyrazolo[1,5-a]-pyrimidine-3-carboxamide (400 mg, 0.78 mmol) in DMF (5 mL) was stirred at 100° C. for 5 h and cooled to room temperature. Water (50 mL) was added. The precipitates were collected by filtration and dried. This resulted in 400 mg (81%) of tert-butyl N-[1-(2-[3-[5-chloro-2-(difluoromethoxy)phenyl]-4-[pyrazolo[1,5-a]pyrimidine-3-amido]-1H-pyrazol-1-yl]ethyl)piperidin-4-yl]carbamate as a yellow solid. LCMS (Method 21) $[M+H]^+$=631.1, $R_T$=1.21 min.

Saturated HCl dioxane solution (15 mL) was added to tert-butyl N-[1-(2-[3-[5-chloro-2-(difluoromethoxy)phenyl]-4-[pyrazolo[1,5-a]pyrimidine-3-amido]-1H-pyrazol-1-yl]ethyl)piperidin-4-yl]carbamate (400 mg, 0.63 mmol). The resulting solution was stirred at room temperature overnight and concentrated under vacuum. The pH value of the remaining solution was adjusted to 8-9 with saturated aqueous $Na_2CO_3$. The resulting mixture was concentrated under vacuum. The residue was purified by flash chromatography on silica eluting with MeOH/DCM (1:1) to afford 330 mg (98%) of N-[1-[2-(4-aminopiperidin-1-yl)ethyl]-3-[5-chloro-2-(difluoromethoxy)phenyl]-1H-pyrazol-4-yl]pyrazolo[1,5-a]pyrimidine-3-carboxamide as a yellow solid. LCMS (Method 28) $[M+H]^+$=531.1, $R_T$=0.49 min.

Potassium carbonate (98 mg, 0.71 mmol) was added to a solution of N-[1-[2-(4-aminopiperidin-1-yl)ethyl]-3-[5-chloro-2-(difluoromethoxy)phenyl]-1H-pyrazol-4-yl]pyrazolo[1,5-a]pyrimidine-3-carboxamide (290 mg, 0.55 mmol) and tert-butyl 2-bromoacetate (96 mg, 0.49 mmol) in DMF (5 mL). The resulting mixture was stirred at 50° C. overnight. The resulting mixture was concentrated under vacuum. The residue was purified by flash chromatography on silica eluting with 15% MeOH in DCM to afford 150 mg (43%) of tert-butyl 2-[[1-(2-[3-[5-chloro-2-(difluoromethoxy)phenyl]-4-[pyrazolo[1,5-a]pyrimidine-3-amido]-1H-pyrazol-1-yl]ethyl)piperidin-4-yl]amino]-acetate as a yellow solid. LCMS (Method 24) $[M+H]^+$=645.2, $R_T$=1.39 min.

A solution of tert-butyl ester from previous step (150 mg, 0.23 mmol) in DCM (2 mL) and TFA (2 mL) was stirred at room temperature overnight. The resulting mixture was concentrated under vacuum. The crude product was purified by Prep-HPLC with the following conditions (Prep-HPLC-005): Column, XBridge Prep C18 OBD Column, 5 um, 19*150 mm; mobile phase, water with 0.05% FA and MeCN (20.0% up to 27.0% in 10 min, up to 95.0% in 1 min, hold 95.0% in 1 min, down to 20.0% in 2 min); Detector, UV 254/220 nm. This resulted in 63.5 mg (43%) of the formic acid salt of 2-[[1-(2-[3-[5-chloro-2-(difluoromethoxy)phenyl]-4-[pyrazolo[1,5-a]pyrimidine-3-amido]-1H-pyrazol-1-yl]ethyl)piperidin-4-yl]amino]acetic acid as an off-white solid. LCMS (Method 25) $[M+H]^+$=589.1, $R_T$=0.85 min. $^1H$ NMR (400 MHz, DMSO-$d_6$) δ: (ppm) 9.73 (s, 1H), 9.34 (d, 1H, J=8.0 Hz), 8.79-8.65 (m, 2H), 8.46-8.35 (m, 1H), 7.64-6.98 (m, 5H), 4.30 (s, 2H), 3.10-2.82 (m, 5H), 2.54-2.53 (m, 2H), 2.17-1.93 (m, 4H), 1.58-1.45 (m, 2H).

Example 312

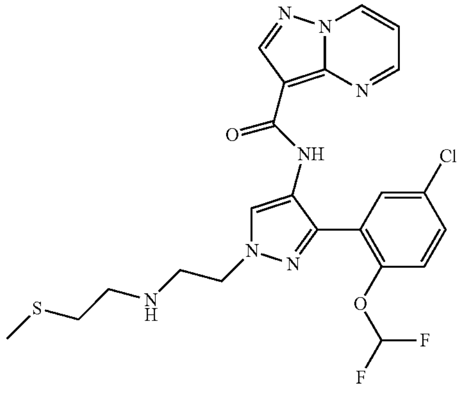 [SMILES: CSCCNCCn1cc(NC(=O)c2cnn3cccnc23)c(-c2cc(Cl)ccc2OC(F)F)n1]

N-[3-[5-chloro-2-(difluoromethoxy)phenyl]-1-(2-[[2-(methylsulfanyl)ethyl]amino]ethyl)-1H-pyrazol-4-yl]pyrazolo[1,5-a]pyrimidine-3-carboxamide 2-(Methylsulfanyl)ethan-1-amine (0.5 mL, 5.34 mmol) was added to a solution of N-[1-(2-bromoethyl)-3-[5-chloro-2-(difluoromethoxy)phenyl]-1H-pyrazol-4-yl]pyrazolo[1,5-a]pyrimidine-3-carboxamide (120 mg, 0.23 mmol) in $CH_3CN$ (3 mL). The resulting solution was stirred at 80° C. for 2 h and concentrated under vacuum. The crude product was purified by Prep-HPLC with the following conditions (Prep-HPLC-005): Column, XBridge Prep C18 OBD Column, 5 um, 19*150 mm; mobile phase, water with 10 mmol $NH_4HCO_3$ and MeCN (40.0% up to 57.0% in 10 min, up to 95.0% in 1 min, hold 95.0% in 1 min, down to 40.0% in 2 min); Detector, UV 254/220 nm. This resulted in 58.2 mg (48%) of N-[3-[5-chloro-2-(difluoromethoxy)phenyl]-1-(2-[[2-(methylsulfanyl)ethyl]-amino]ethyl)-1H-pyrazol-4-yl]pyrazolo[1,5-a]pyrimidine-3-carboxamide as a yellow solid. LCMS (Method 20) $[M+H]^+$=522.2, $R_T$=2.50 min. $^1H$ NMR (400 MHz, DMSO-$d_6$) δ: (ppm) 9.73 (s, 1H), 9.34 (dd, 1H, J=1.6, 6.8 Hz), 8.67 (dd, 1H, J=1.6, 4.4 Hz), 8.67 (s, 1H), 8.36 (s, 1H), 7.68-7.61 (m, 2H), 7.46-7.44 (m, 1H), 7.28 (dd, 1H, J=4.4, 7.2 Hz), 7.06 (t, 1H, J=73.2 Hz), 4.23 (t, 2H, J=6.4 Hz), 2.98 (t, 2H, J=6.0 Hz), 2.71 (t, 2H, J=6.8 Hz), 2.53 (t, 2H, J=6.8 Hz), 2.03 (s, 3H).

Example 313

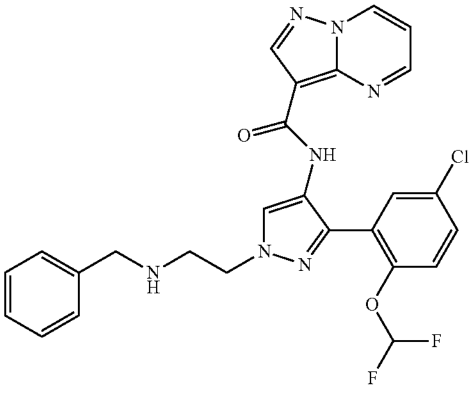 [SMILES: O=C(Nc1cn(CCNCc2ccccc2)nc1-c1cc(Cl)ccc1OC(F)F)c1cnn2cccnc12]

N-[1-[2-(benzylamino)ethyl]-3-[5-chloro-2-(difluoromethoxy)phenyl]-1H-pyrazol-4-yl]pyrazolo[1,5-a]pyrimidine-3-carboxamide Using synthetic method analogous to that of N-[3-[5-chloro-2-(difluoromethoxy)phenyl]-1-(2-[[2-(methylsulfanyl)ethyl]amino]ethyl)-1H-pyrazol-4-yl]pyrazolo[1,5-a]pyrimidine-3-carboxamide, the title compound was prepared from N-[1-(2-bromoethyl)-3-[5-chloro-2-(difluoromethoxy)phenyl]-1H-pyrazol-4-yl]pyrazolo[1,5-a]pyrimidine-3-carboxamide and phenylmethanamine. LCMS (Method 20) $[M+H]^+$=538.2, $R_T$=2.70 min. $^1H$ NMR (400 MHz, DMSO-$d_6$) δ: (ppm) 9.84 (s, 1H), 9.34 (dd, 1H, J=1.6, 6.8 Hz), 8.67 (dd, 1H, J=1.6, 4.4 Hz), 8.67 (s, 1H), 8.37 (s, 1H), 7.64-7.59 (m, 2H), 7.46-7.42 (m, 1H), 7.32-7.19 (m, 6H), 7.06 (t, 1H, J=73.2 Hz), 4.25 (t, 2H, J=6.4 Hz), 3.73 (s, 2H), 2.93 (t, 2H, J=6.4 Hz).

Example 314

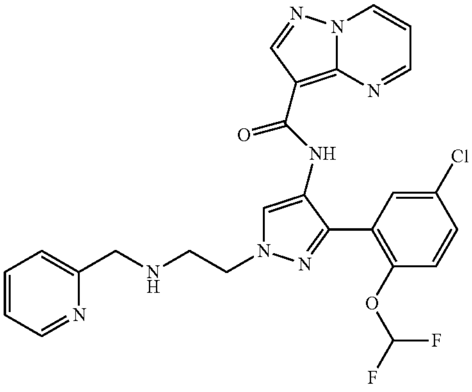 [SMILES: O=C(Nc1cn(CCNCc2ccccn2)nc1-c1cc(Cl)ccc1OC(F)F)c1cnn2cccnc12]

N-[3-[5-chloro-2-(difluoromethoxy)phenyl]-1-[2-[(pyridin-2-ylmethyl)amino]ethyl]-1H-pyrazol-4-yl]pyrazolo[1,5-a]pyrimidine-3-carboxamide Using synthetic method analogous to that of N-[3-[5-chloro-2-(difluoromethoxy)phenyl]-1-(2-[[2-(methylsulfanyl)ethyl]amino]ethyl)-1H-pyrazol-4-yl]pyrazolo[1,5-a]pyrimidine-3-carboxamide, the title compound was prepared from N-[1-(2-bromoethyl)-3-[5-chloro-2-(difluoromethoxy)phenyl]-1H-pyrazol-4-yl]pyrazolo[1,5-a]pyrimidine-3-carboxamide and pyridin-2-ylmethanamine. LCMS (Method 20) $[M+H]^+$=539.2, $R_T$=2.53 min. $^1H$ NMR (400 MHz, DMSO-$d_6$) δ: (ppm) 9.75 (s, 1H), 9.34 (dd, 1H, J=1.6, 6.8 Hz), 8.68 (dd, 1H, J=1.6, 4.0 Hz), 8.67 (s, 1H), 8.49 (d, 1H, J=4.0 Hz), 8.37 (s, 1H), 7.72 (dd, 1H, J=1.6, 7.6 Hz), 7.70-7.61 (m, 2H), 7.46-7.06 (m, 5H), 4.27 (t, 2H, J=6.0 Hz), 3.83 (s, 2H), 2.98 (t, 2H, J=6.0 Hz).

Example 315

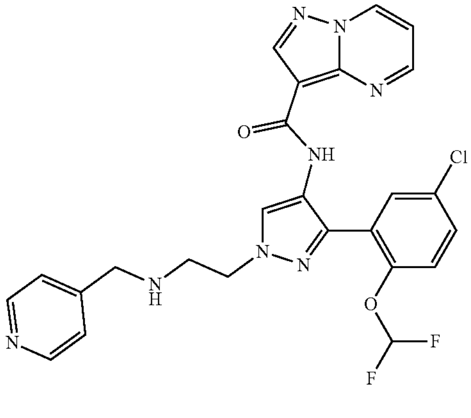 [SMILES: O=C(Nc1cn(CCNCc2ccncc2)nc1-c1cc(Cl)ccc1OC(F)F)c1cnn2cccnc12]

N-[3-[5-chloro-2-(difluoromethoxy)phenyl]-1-[2-[(pyridin-4-ylmethyl)amino]ethyl]-1H-pyrazol-4-yl]pyrazolo[1,5-a]pyrimidine-3-carboxamide Using synthetic method analogous to that of N-[3-[5-chloro-2-(difluoromethoxy)phenyl]-1-(2-[[2-(methylsulfanyl)ethyl]amino]ethyl)-1H-pyrazol-4-yl]pyrazolo[1,5-a]pyrimidine-3-carboxamide, the title compound was prepared from N-[1-(2-bromoethyl)-3-[5-chloro-2-(difluoromethoxy)phenyl]-1H-pyrazol-4-yl]pyrazolo[1,5-a]pyrimidine-3-carboxamide and pyridin-4-ylmethanamine. LCMS (Method 25) $[M+H]^+$=539.1, $R_T$=1.45 min. $^1H$ NMR (400 MHz, DMSO-$d_6$) δ: (ppm) 9.74 (s, 1H), 9.34 (dd, 1H, J=1.6, 6.8 Hz), 8.68 (dd, 1H, J=1.6, 4.4 Hz), 8.45 (d, 2H, J=6.0 Hz), 8.38 (s, 1H), 7.64-7.59 (m, 2H), 7.44 (d, 1H, J=8.8 Hz), 7.32-7.28 (m, 3H), 7.07 (t, 1H, J=73.2 Hz), 4.26 (t, 2H, J=6.0 Hz), 3.76 (s, 2H), 2.93 (t, 2H, J=6.0 Hz).

Example 316

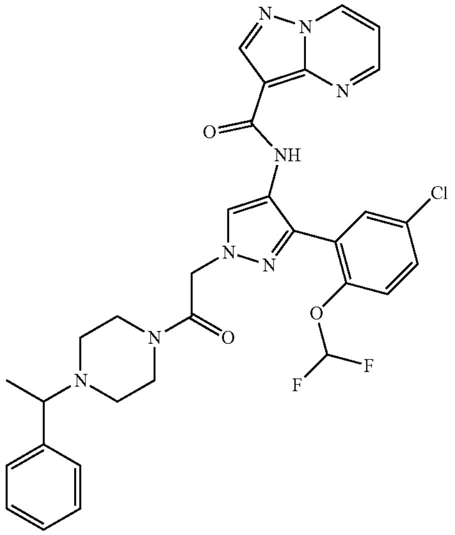 [SMILES: CC(c1ccccc1)N1CCN(C(=O)Cn2cc(NC(=O)c3cnn4cccnc34)c(-c3cc(Cl)ccc3OC(F)F)n2)CC1]

N-[3-[5-chloro-2-(difluoromethoxy)phenyl]-1-[2-oxo-2-[4-(1-phenylethyl)piperazin-1-yl]ethyl]-1H-pyrazol-4-yl]pyrazolo[1,5-a]pyrimidine-3-carboxamide To a solution of tert-butyl piperazine-1-carboxylate (1.00 g, 5.37 mmol) and 1-phenylethan-1-one (774 mg, 6.44 mmol) in methanol (30 mL) was added $NaBH_3CN$ (511 mg, 8.13 mmol). The resulting solution was stirred at 50° C. overnight. Water (50 mL) was added. Methanol was stripped off under vacuum. The remaining solution was extracted with ethyl acetate (×2). The organic layers were combined, washed with brine, dried over anhydrous sodium sulfate and concentrated under vacuum. The residue was purified by flash chromatography on silica gel column eluting with ethyl acetate/petroleum ether (1:1). This resulted in 750 mg (48%) of tert-butyl 4-(1-phenylethyl)piperazine-1-carboxylate as yellow oil. LCMS (Method 20) $[M+H]^+$=291.1, $R_T$=1.14 min.

A solution of tert-butyl 4-(1-phenylethyl)piperazine-1-carboxylate (750 mg, 2.58 mmol) and saturated HCl dioxane solution (20 mL) was stirred at room temperature for 3 h. The solids were collected by filtration and dried. This resulted in 320 mg (55%) of 1-(1-phenylethyl)piperazine hydrochloride as a white solid.

To a solution of {3-(5-Chloro-2-difluoromethoxyphenyl)-4-[(pyrazolo[1,5-a]pyrimidine-3-carbonyl)amino]pyrazol-1-yl}acetic acid (100 mg) in DMF (4 mL) was added 1-(1-phenylethyl)piperazine hydrochloride (47 mg, 0.21 mmol), DIEA (67 mg, 0.52 mmol), HATU (79.2 mg, 0.21 mmol). The resulting mixture was stirred at room temperature overnight and concentrated under vacuum. The crude product was purified by Prep-HPLC with the following conditions (Prep-HPLC-005): Column, XBridge Prep C18 OBD Column, 5 um, 19*150 mm; mobile phase, water with 10 mmol NH4HCO3 and MeCN (40.0% up to 65.0% in 10 min, up to 95.0% in 1 min, hold 95.0% in 1 min, down to 40.0% in 2 min); Detector, UV 254/220 nm. This resulted in 31.3 mg (28%) of N-[3-[5-chloro-2-(difluoromethoxy)phenyl]-1-[2-oxo-2-[4-(1-phenylethyl)piperazin-1-yl]ethyl]-1H-pyrazol-4-yl]pyrazolo[1,5-a]pyrimidine-3-carboxamide as an off-white solid. LCMS (Method 21) $[M+H]^+$=635.0, $R_T$=1.56 min. $^1H$ NMR (400 MHz, DMSO-$d_6$) δ: (ppm) 9.74 (s, 1H), 9.34 (dd, 1H, J=1.6, 7.2 Hz), 8.67 (d, 1H, J=4.8 Hz), 8.28 (s, 1H), 7.62 (dd, 1H, J=2.8, 8.8 Hz), 7.53 (d, 1H, J=2.8 Hz), 7.45 (d, 1H, J=8.8 Hz), 7.35-7.26 (m, 6H), 7.07 (t, 1H, J=73.2 Hz), 5.19 (s, 2H), 3.49-3.46 (m, 5H), 2.49-2.33 (m, 4H), 1.31 (d, 3H, J=6.4 Hz).

Example 317

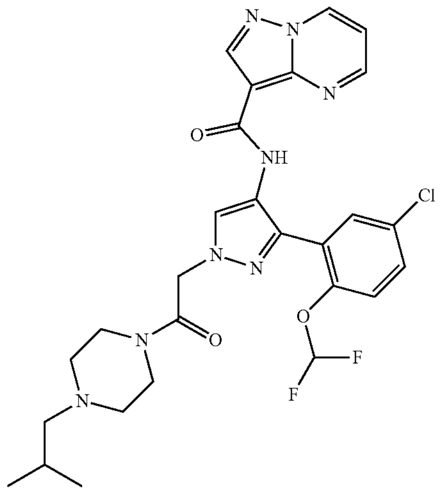 [SMILES: CC(C)CN1CCN(C(=O)Cn2cc(NC(=O)c3cnn4cccnc34)c(-c3cc(Cl)ccc3OC(F)F)n2)CC1]

N-[3-[5-chloro-2-(difluoromethoxy)phenyl]-1-[2-[4-(2-methylpropyl)piperazin-1-yl]-2-oxoethyl]-1H-pyrazol-4-yl]pyrazolo[1,5-a]pyrimidine-3-carboxamide Using synthetic method analoguous to that of N-[3-[5-chloro-2-(difluoromethoxy)phenyl]-1-[2-oxo-2-[4-(1-phenylethyl)piperazin-1-yl]ethyl]-1H-pyrazol-4-yl]pyrazolo[1,5-a]pyrimidine-3-carboxamide, the title compound was prepared from {3-(5-Chloro-2-difluoromethoxyphenyl)-4-[(pyrazolo[1,5-a]pyrimidine-3-carbonyl)amino]pyrazol-1-yl}acetic acid and 1-(2-methylpropyl)piperazine. LCMS (Method 25) $[M+H]^+$=587.1, $R_T$=1.80 min. $^1H$ NMR (300 MHz, DMSO-$d_6$) δ: (ppm) 9.75 (s, 1H), 9.33 (dd, 1H, J=1.8, 6.9 Hz), 8.68 (dd, 1H, J=1.5, 3.9 Hz), 8.67 (s, 1H), 8.31 (s, 1H), 7.62 (dd, 1H, J=3.0, 8.7 Hz), 7.55 (d, 1H, J=2.7 Hz), 7.45 (d, 1H, J=9.0 Hz), 7.28 (dd, 1H, J=4.2, 7.2 Hz), 7.02 (t, 1H, J=73.2 Hz), 5.23 (s, 2H), 3.57-3.42 (m, 4H), 2.40-2.21 (m, 4H), 2.05 (d, 2H, J=7.2 Hz), 1.81-1.76 (m, 1H), 0.86 (d, 6H, J=6.3 Hz).

Example 318

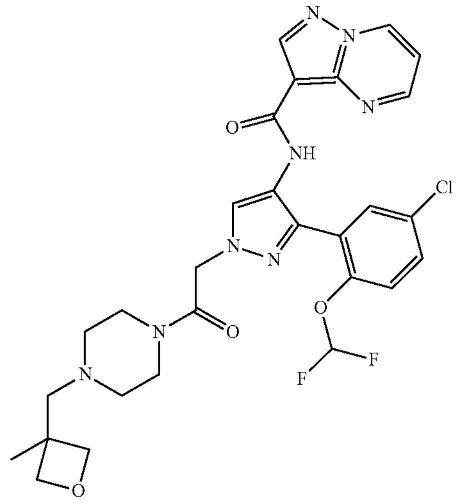

N-[3-[5-chloro-2-(difluoromethoxy)phenyl]-1-(2-[4-[(3-methyloxetan-3-yl)methyl]piperazin-1-yl]-2-oxoethyl)-1H-pyrazol-4-yl]pyrazolo[1,5-a]pyrimidine-3-carboxamide To a solution of 3-methyloxetane-3-carbaldehyde (17.2 mg, 0.17 mmol) and N-[3-[5-chloro-2-(difluoromethoxy)phenyl]-1-[2-oxo-2-(piperazin-1-yl)ethyl]-1H-pyrazol-4-yl]pyrazolo[1,5-a]pyrimidine-3-carboxamide (70 mg, 0.13 mmol) in methanol (5 mL) was added $NaBH_3CN$ (12.5 mg, 0.20 mmol). The resulting solution was stirred at room temperature overnight. The reaction was then quenched by the addition of 5 mL of water. The resulting mixture was concentrated under vacuum. The residue was dissolved in ethyl acetate (30 mL), washed with brine, dried and concentrated. The crude product was purified by Prep-HPLC with the following conditions (Prep-HPLC-005): Column, XBridge Prep C18 OBD Column, 5 um, 19*150 mm; mobile phase, water with 10 mmol $NH_4HCO_3$ and MeCN (55.0% up to 65.0% in 10 min, up to 95.0% in 1 min, hold 95.0% in 1 min, down to 55.0% in 2 min); Detector, UV 254/220 nm. This resulted in 39.8 mg (49%) of N-[3-[5-chloro-2-(difluoromethoxy)phenyl]-1-(2-[4-[(3-methyloxetan-3-yl)methyl]piperazin-1-yl]-2-oxoethyl)-1H-pyrazol-4-yl]pyrazolo[1,5-a]pyrimidine-3-carboxamide. LCMS (Method 25) $[M+H]^+$=615.2, $R_T$=0.93 min. $^1H$ NMR (400 MHz, DMSO-$d_6$) δ: (ppm) 9.92 (s, 1H), 9.36-9.27 (m, 1H), 8.91-8.68 (m, 2H), 8.31 (s, 1H), 7.73-7.46 (m, 3H), 7.37-7.06 (m, 2H), 5.23 (s, 2H), 4.52-4.20 (m, 4H), 3.60-3.11 (m, 6H), 2.43-2.20 (m, 4H), 1.46 (s, 3H).

Example 319

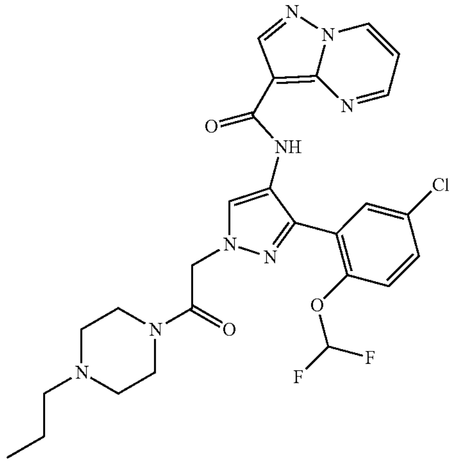 [SMILES: CCCN1CCN(C(=O)Cn2cc(NC(=O)c3cnn4cccnc34)c(-c3cc(Cl)ccc3OC(F)F)n2)CC1]

N-[3-[5-chloro-2-(difluoromethoxy)phenyl]-1-[2-oxo-2-(4-propylpiperazin-1-yl)ethyl]-1H-pyrazol-4-yl]pyrazolo[1,5-a]pyrimidine-3-carboxamide To a solution of 1-propylpiperazine dihydrobromide (60.4 mg, 0.21 mmol) and {3-(5-Chloro-2-difluoromethoxyphenyl)-4-[(pyrazolo[1,5-a]pyrimidine-3-carbonyl)amino]pyrazol-1-yl}acetic acid (100 mg) in DMF (2 mL) was added DIEA (112 mg, 0.866 mmol), HATU (79.2 mg, 0.21 mmol). The resulting solution was stirred at room temperature overnight and concentrated under vacuum. The crude product was purified by Prep-HPLC with the following conditions (Prep-HPLC-005): Column, XBridge Prep C18 OBD Column, 5 um, 19*150 mm; mobile phase, water with 10 mmol NH4HCO3 and MeCN (50.0% up to 61.0% in 10 min, up to 95.0% in 1 min, hold 95.0% in 1 min, down to 50.0% in 2 min); Detector, UV 254/220 nm. This resulted in 69.1 mg (70%) of N-[3-[5-chloro-2-(difluoromethoxy)phenyl]-1-[2-oxo-2-(4-propylpiperazin-1-yl)ethyl]-1H-pyrazol-4-yl]pyrazolo[1,5-a]pyrimidine-3-carboxamide as a white solid. LCMS (Method 20) $[M+H]^+$=573.2, $R_T$=2.86 min. $^1H$ NMR (400 MHz, DMSO-$d_6$) δ: (ppm) 9.76 (s, 1H), 9.34 (dd, 1H, J=1.6, 6.8 Hz), 8.68 (dd, 1H, J=1.6, 7.6 Hz), 8.67 (s, 1H), 8.31 (s, 1H), 7.62 (dd, 1H, J=2.4, 8.8 Hz), 7.55 (d, 1H, J=2.4 Hz), 7.45 (d, 1H, J=8.8 Hz), 7.28 (dd, 1H, J=4.4, 6.8 Hz), 7.08 (t, 1H, J=73.6 Hz), 5.23 (s, 2H), 3.48 (t, 4H, J=6.0 Hz), 2.40-2.34 (m, 4H), 2.24 (t, 2H, J=7.2 Hz), 1.48-1.41 (m, 2H), 0.85 (t, 3H, J=7.2 Hz).

Example 320

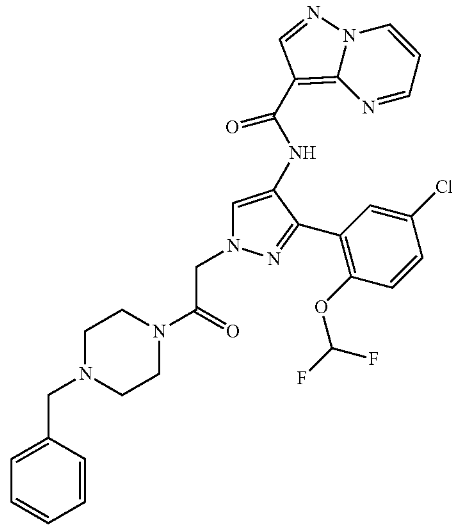 [SMILES: O=C(Nc1cn(CC(=O)N2CCN(Cc3ccccc3)CC2)nc1-c1cc(Cl)ccc1OC(F)F)c1cnn2cccnc12]

N-[1-[2-(4-benzylpiperazin-1-yl)-2-oxoethyl]-3-[5-chloro-2-(difluoromethoxy)phenyl]-1H-pyrazol-4-yl]pyrazolo[1,5-a]pyrimidine-3-carboxamide To a solution of 2-[3-[5-chloro-2-(difluoromethoxy)phenyl]-4-[pyrazolo[1,5-a]pyrimidine-3-amido]-1H-pyrazol-1-yl]acetic acid (100 mg, 0.17 mmol) in DMF (4 mL) and 1-benzylpiperazine (33.6 mg, 0.19 mmol) was added DIEA (44.8 mg, 0.35 mmol), HATU (79.2 mg, 0.21 mmol). The resulting solution was stirred at room temperature overnight. The resulting mixture was concentrated under vacuum. The crude product was purified by Prep-HPLC with the following conditions (Prep-HPLC-005): Column, XBridge Prep C18 OBD Column, 5 um, 19*150 mm; mobile phase, water with 10 mmol $NH_4HCO_3$ and MeCN (37.0% MeCN up to 50.0% in 10 min, up to 95.0% in 1 min, hold 95.0% in 1 min, down to 37.0% in 2 min); Detector, UV 254/220 nm. This resulted in 53.8 mg (50%) of N-[1-[2-(4-benzylpiperazin-1-yl)-2-oxoethyl]-3-[5-chloro-2-(difluoromethoxy)phenyl]-1H-pyrazol-4-yl]pyrazolo[1,5-a]pyrimidine-3-carboxamide as an off-white solid. LCMS (Method 21) $[M+H]^+$=621.0, $R_T$=1.53 min. $^1H$ NMR (400 MHz, DMSO-$d_6$) δ: (ppm) 9.75 (s, 1H), 9.34 (dd, 1H, J=1.6, 7.2 Hz), 8.69-8.68 (m, 2H), 8.30 (s, 1H), 7.62 (dd, 1H, J=2.8, 8.8 Hz), 7.55 (d, 1H, J=2.8 Hz), 7.45 (d, 1H, J=8.8 Hz), 7.65-7.24 (m, 6H), 7.08 (t, 1H, J=73.2 Hz), 5.23 (m, 2H), 3.52-3.46 (m, 6H), 2.49-2.33 (m, 4H).

Example 321

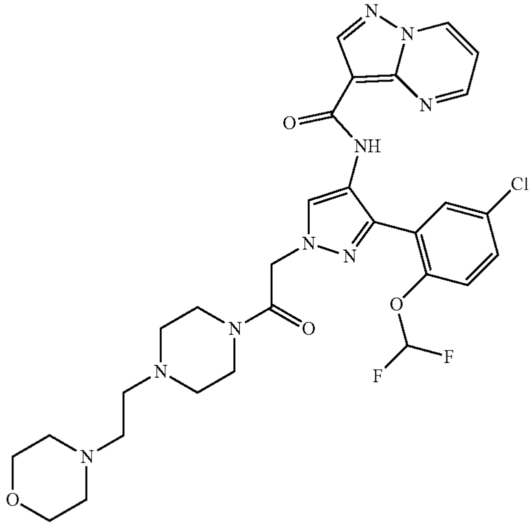 [SMILES: O=C(Nc1cn(CC(=O)N2CCN(CCN3CCOCC3)CC2)nc1-c1cc(Cl)ccc1OC(F)F)c1cnn2cccnc12]

N-[3-[5-chloro-2-(difluoromethoxy)phenyl]-1-(2-[4-[2-(morpholin-4-yl)ethyl]piperazin-1-yl]-2-oxoethyl)-1H-pyrazol-4-yl]pyrazolo[1,5-a]pyrimidine-3-carboxamide To a solution of {3-(5-Chloro-2-difluoromethoxyphenyl)-4-[(pyrazolo[1,5-a]pyrimidine-3-carbonyl)amino]pyrazol-1-yl}acetic acid (100 mg) and 4-[2-(piperazin-1-yl)ethyl]morpholine (41 mg, 0.21 mmol) in DMF (5 mL) was added DIEA (45 mg, 0.35 mmol), HATU (79 mg, 0.21 mmol). The resulting solution was stirred at room temperature for 3 h. The resulting mixture was concentrated under vacuum. The crude product was purified by Prep-HPLC with the following conditions (Prep-HPLC-005): Column, XBridge Prep C18 OBD Column, 5 um, 19*150 mm; mobile phase, water with 10 mmol $NH_4HCO_3$ and MeCN (37.0% MeCN up to 52.0% in 10 min, up to 95.0% in 1 min, hold 95.0% in 1 min, down to 37.0% in 2 min); Detector, UV 254/220 nm. This resulted in 62.0 mg (56%) of N-[3-[5-chloro-2-(difluoromethoxy)phenyl]-1-(2-[4-[2-(morpholin-4-yl)ethyl]piperazin-1-yl]-2-oxoethyl)-1H-pyrazol-4-yl]pyrazolo[1,5-a]pyrimidine-3-carboxamide as a white solid. LCMS (Method 20) $[M+H]^+$=644.2, $R_T$=2.34 min. $^1H$ NMR (400 MHz, DMSO-$d_6$) δ: (ppm) 9.76 (s, 1H), 9.34 (dd, 1H, J=1.6, 7.2 Hz), 8.68-8.67 (m, 2H), 8.31 (s, 1H), 7.63 (dd, 1H, J=2.8, 8.8 Hz), 7.55 (d, 1H, J=2.8 Hz), 7.46 (d, 1H, J=8.8 Hz), 7.28 (dd, 1H, J=4.4, 6.8 Hz), 7.09 (t, 1H, J=73.6 Hz), 5.23 (s, 2H), 3.54 (t, 4H, J=4.4 Hz), 3.50-3.46 (m, 4H), 2.49-2.39 (m, 12H).

Example 322

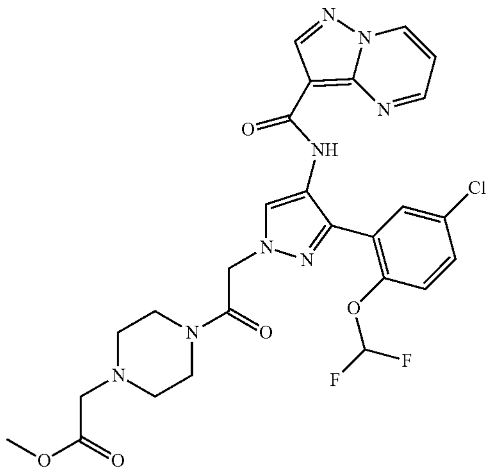 [SMILES: COC(=O)CN1CCN(C(=O)Cn2cc(NC(=O)c3cnn4cccnc34)c(-c3cc(Cl)ccc3OC(F)F)n2)CC1]

methyl 2-[4-(2-[3-[5-chloro-2-(difluoromethoxy) phenyl]-4-[pyrazolo[1,5-a]pyrimidine-3-amido]-1H-pyrazol-1-yl]acetyl)piperazin-1-yl]acetate To a solution of tert-butyl piperazine-1-carboxylate (5 g, 26.85 mmol) in DMF (50 mL) was added and $Cs_2CO_3$ (11 g, 33.76 mmol) and methyl 2-bromoacetate (3.4 g, 22.2 mmol). The resulting mixture was stirred at room temperature for 6 h. Water (50 mL) and DCM (100 mL) was added. Phases were separated. The aqueous phase was extracted with DCM (100 mL). The combined organic phases were washed with brine, dried over anhydrous sodium sulfate and concentrated under vacuum. This resulted in 7.1 g (crude) of tert-butyl 4-(2-methoxy-2-oxoethyl)piperazine-1-carboxylate as yellow oil. LCMS (Method 27) $[M+H]^+=259.2$, $R_T=1.08$ min.

A solution of tert-butyl 4-(2-methoxy-2-oxoethyl)piperazine-1-carboxylate (1.50 g, 5.81 mmol) and saturated HCl dioxane solution (20 mL) was stirred at room temperature for 3 h. The solids were collected by filtration and dried. This resulted in 950 mg (84%) of methyl 2-(piperazin-1-yl) acetate hydrochloride as a white solid.

To a solution of {3-(5-Chloro-2-difluoromethoxyphenyl)-4-[(pyrazolo[1,5-a]pyrimidine-3-carbonyl)amino]pyrazol-1-yl}acetic acid (100 mg) in DMF (2 mL) was added methyl 2-(piperazin-1-yl)acetate hydrochloride (41 mg, 0.21 mmol), DIEA (67.2 mg, 0.52 mmol), HATU (79.2 mg, 0.21 mmol). The resulting solution was stirred at room temperature for 2 h and concentrated under vacuum. The residue was passed through a short pad of silica gel eluting with 10% MeOH in DCM. The crude product was purified by Prep-HPLC with the following conditions (Prep-HPLC-005): Column, XBridge Prep C18 OBD Column, 5 um, 19*150 mm; mobile phase, water with 10 mmol $NH_4HCO_3$ and MeCN (40.0% up to 59.0% in 10 min, up to 95.0% in 1 min, hold 95.0% in 1 min, down to 40.0% in 2 min); Detector, UV 254/220 nm. This resulted in 49.2 mg (47%) of methyl 2-[4-(2-[3-[5-chloro-2-(difluoromethoxy)phenyl]-4-[pyrazolo[1,5-a]pyrimidine-3-amido]-1H-pyrazol-1-yl]acetyl) piperazin-1-yl]acetate as a white solid. LCMS (Method 20) $[M+H]^+=603.2$, $R_T=2.83$ min. $^1$H NMR (400 MHz, DMSO-$d_6$) δ: (ppm) 9.76 (s, 1H), 9.34 (dd, 1H, J=1.6, 7.2 Hz), 8.69-8.67 (m, 2H), 8.31 (s, 1H), 7.62 (dd, 1H, J=2.8, 8.8 Hz), 7.56 (d, 1H, J=2.4 Hz), 7.45 (d, 1H, J=8.8 Hz), 7.28 (dd, 1H, J=4.4, 7.2 Hz), 7.08 (t, 1H, J=73.2 Hz), 5.24 (s, 2H), 3.63 (s, 3H), 3.52-3.48 (m, 4H), 3.30 (s, 2H), 2.67-2.51 (m, 4H).

Example 323

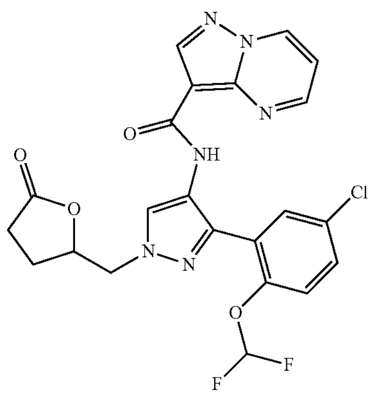 [SMILES: O=C1CCC(Cn2cc(NC(=O)c3cnn4cccnc34)c(-c3cc(Cl)ccc3OC(F)F)n2)O1]

N-[3-[5-chloro-2-(difluoromethoxy)pyridin-3-yl]-1-[(5-oxooxolan-2-yl)methyl]-1H-pyrazol-4-yl]pyrazolo[1,5-a]pyrimidine-3-carboxamide A 8-mL microwave tube was charged with N-[3-[5-chloro-2-(difluoromethoxy)phenyl]-1H-pyrazol-4-yl]pyrazolo[1,5-a]pyrimidine-3-carboxamide (150 mg, 0.37 mmol), 5-(chloromethyl)oxolan-2-one (74.6 mg, 0.55 mmol), $Cs_2CO_3$ (242 mg, 0.74 mmol) in DMF (2 mL). The vessel was evacuated under vacuum and refilled with nitrogen 3 times. The final reaction mixture was irradiated with microwave radiation at 120° C. for 30 min. The resulting mixture was concentrated under vacuum. The residue was passed through a short pad of silica gel eluting with ethyl acetate. The crude product was purified by Prep-HPLC with the following conditions (Prep-HPLC-005): Column, XBridge Prep C18 OBD Column, 5 um, 19*150 mm; mobile phase, water with 0.05% FA and MeCN (39.0% up to 53.0% in 10 min, up to 95.0% in 1 min, hold 95.0% in 1 min, down to 39.0% in 2 min); Detector, UV 254/220 nm. This resulted in 35.8 mg (19%) of N-[3-[5-chloro-2-(difluoromethoxy)pyridin-3-yl]-1-[(5-oxooxolan-2-yl)methyl]-1H-pyrazol-4-yl] pyrazolo[1,5-a]pyrimidine-3-carboxamide as a white solid. LCMS (Method 20) $[M+H]^+=503.1$, $R_T=1.65$ min. $^1$H NMR (300 MHz, DMSO-$d_6$) δ: (ppm) 9.76 (s, 1H), 9.34 (dd, 1H, J=1.5, 6.9 Hz), 8.68-8.66 (m, 2H), 8.38 (s, 1H), 7.63 (dd, 1H, J=2.7, 8.7 Hz), 7.61 (d, 1H, J=2.7 Hz), 7.45 (d, 1H, J=8.7 Hz), 7.28 (dd, 1H, J=4.2, 6.9 Hz), 7.00 (t, 1H, J=73.2 Hz), 4.98-4.94 (m, 1H), 4.48 (d, 2H, J=5.1 Hz), 2.46-2.23 (m, 3H), 2.07-1.98 (m, 1H).

Example 324

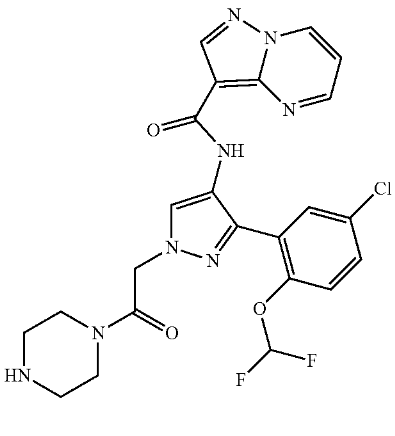 [SMILES: O=C(Nc1cn(CC(=O)N2CCNCC2)nc1-c1cc(Cl)ccc1OC(F)F)c1cnn2cccnc12]

N-[3-[5-chloro-2-(difluoromethoxy)phenyl]-1-[2-oxo-2-(piperazin-1-yl)ethyl]-1H-pyrazol-4-yl]pyrazolo[1,5-a]pyrimidine-3-carboxamide To a solution of {3-(5-Chloro-2-difluoromethoxyphenyl)-4-[(pyrazolo[1,5-a]pyrimidine-3-carbonyl)amino]pyrazol-1-yl}acetic acid (200 mg) in DMF (5 mL) was added tert-butyl piperazine-1-carboxylate (77.5 mg, 0.42 mmol), DIEA (89.6 mg, 0.69 mmol), HATU (158.3 mg, 0.42 mmol). The resulting solution was stirred at room temperature for 3 h and concentrated under vacuum. The residue was purified by flash chromatography on silica gel eluting with 3% MeOH in DCM to afford 279 mg of tert-butyl 4-(2-[3-[5-chloro-2-(difluoromethoxy)phenyl]-4-[pyrazolo[1,5-a]pyrimidine-3-amido]-1H-pyrazol-1-yl]acetyl)piperazine-1-carboxylate as a yellow solid. LCMS (Method 22) $[M+H]^+$=631.4, $R_T$=1.49 min.

A solution of tert-butyl 4-(2-[3-[5-chloro-2-(difluoromethoxy)phenyl]-4-[pyrazolo[1,5-a]pyrimidine-3-amido]-1H-pyrazol-1-yl]acetyl)piperazine-1-carboxylate (279 mg, 0.44 mmol) and saturated HCl dioxane solution (10 mL) was stirred at room temperature overnight. The reaction mixture was concentrated under vacuum. The residue was redissolved in methanol and neutralized with DIEA. The neutralized solution was concentrated under vacuum. The crude product was purified by Prep-HPLC with the following conditions (Prep-HPLC-005): Column, XBridge Prep C18 OBD Column, 5 um, 19*150 mm; mobile phase, water with 10 mmol $NH_4HCO_3$ and MeCN (35.0% MeCN up to 48.0% in 10 min, up to 95.0% in 1 min, hold 95.0% in 1 min, down to 35.0% in 2 min); Detector, UV 254/220 nm. This resulted in 95.6 mg (41%) of N-[3-[5-chloro-2-(difluoromethoxy)phenyl]-1-[2-oxo-2-(piperazin-1-yl)ethyl]-1H-pyrazol-4-yl]pyrazolo[1,5-a]pyrimidine-3-carboxamide as a white solid. LCMS (Method 20) $[M+H]^+$=531.2, $R_T$=2.67 min. $^1$H NMR (400 MHz, DMSO-$d_6$) δ: (ppm) 9.76 (s, 1H), 9.34 (dd, 1H, J=1.6, 6.8 Hz), 8.69-8.67 (m, 2H), 8.30 (s, 1H), 7.62 (dd, 1H, J=2.8, 8.8 Hz), 7.55 (d, 1H, J=2.8 Hz), 7.45 (d, 1H, J=8.8 Hz), 7.28 (dd, 1H, J=4.4, 6.8 Hz), 7.08 (t, 1H, J=73.2 Hz), 5.22 (s, 2H), 3.47-3.41 (m, 4H), 2.73-2.67 (m, 4H).

Example 325

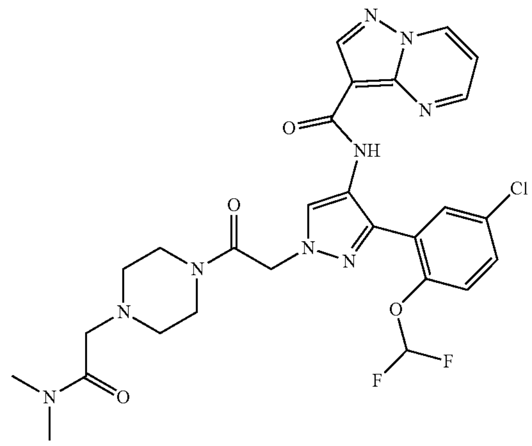 [SMILES: CN(C)C(=O)CN1CCN(C(=O)Cn2cc(NC(=O)c3cnn4cccnc34)c(-c3cc(Cl)ccc3OC(F)F)n2)CC1]

N-[3-[5-chloro-2-(difluoromethoxy)phenyl]-1-(2-[4-[(dimethylcarbamoyl)methyl]piperazin-1-yl]-2-oxoethyl)-1H-pyrazol-4-yl]pyrazolo[1,5-a]pyrimidine-3-carboxamide To a solution of tert-butyl piperazine-1-carboxylate (1 g, 5.37 mmol) in DMF (15 mL) was added $Cs_2CO_3$ (3.5 g, 10.74 mmol), 2-bromo-N,N-dimethylacetamide (1.80 g, 10.84 mmol). The resulting mixture was stirred at room temperature overnight. Water (40 mL) and EtOAc (100 mL) was added. Phases were separated. The aqueous phase was extracted with EtOAc. The combined organic layers were washed with brine, dried over anhydrous sodium sulfate and concentrated under vacuum. The residue was purified by flash chromatography on silica gel eluting with 3% MeOH in DCM. This resulted in 880 mg (60%) of tert-butyl 4-[(dimethylcarbamoyl)methyl]piperazine-1-carboxylate as yellow oil. TLC: $R_f$=0.3; dichloromethane/methanol=1/10.

A solution of tert-butyl 4-[(dimethylcarbamoyl)methyl]piperazine-1-carboxylate (880 mg, 3.24 mmol) and saturated HCl dioxane solution (20 mL) was stirred at room temperature overnight. The solids were collected by filtration. This resulted in 450 mg (67%) of N,N-dimethyl-2-(piperazin-1-yl)acetamide hydrochloride as a white solid.

To a solution of {3-(5-Chloro-2-difluoromethoxyphenyl)-4-[(pyrazolo[1,5-a]pyrimidine-3-carbonyl)amino]pyrazol-1-yl}acetic acid (100 mg) in DMF (4 mL) was added N,N-dimethyl-2-(piperazin-1-yl)acetamide hydrochloride (72 mg, 0.35 mmol), DIEA (67.2 mg, 0.52 mmol), HATU (79.2 mg, 0.21 mmol). The resulting solution was stirred at room temperature overnight and concentrated under vacuum. The crude product was purified by Prep-HPLC with the following conditions (Prep-HPLC-005): Column, XBridge Prep C18 OBD Column, 5 um, 19*150 mm; mobile phase, water with 0.05% FA and MeCN (27.0% up to 36.0% in 10 min, up to 95.0% in 1 min, hold 95.0% in 1 min, down to 27.0% in 2 min); Detector, UV 254/220 nm. This resulted in 73.4 mg (64%) of the formic acid salt of N-[3-[5-chloro-2-(difluoromethoxy)phenyl]-1-(2-[4-[(dimethylcarbamoyl)methyl]piperazin-1-yl]-2-oxoethyl)-1H-pyrazol-4-yl]pyrazolo[1,5-a]pyrimidine-3-carboxamide as a light yellow solid. LCMS (Method 20) $[M+H]^+$=616.3, $R_T$=2.41 min. $^1$H NMR (400 MHz, $CD_3OD$-$d_4$) δ: (ppm) 9.09 (dd, 1H, J=1.6, 7.2 Hz), 8.66-8.64 (m, 2H), 8.37 (s, 1H), 8.11 (s, 1H), 7.68

(d, 1H, J=2.8 Hz), 7.57 (dd, 1H, J=2.8, 8.8 Hz), 7.42 (d, 1H, J=8.8 Hz), 7.21 (dd, 1H, J=4.4, 7.2 Hz), 6.63 (t, 1H, J=73.6 Hz), 5.29 (s, 2H), 3.84-3.77 (m, 4H), 3.75 (s, 2H), 3.08 (s, 3H), 3.06-2.96 (m, 7H).

Example 326

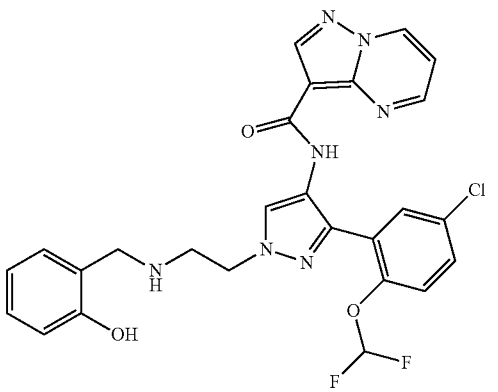 [SMILES: O=C(Nc1cn(CCNCc2ccccc2O)nc1-c1cc(Cl)ccc1OC(F)F)c1cnn2cccnc12]

N-[3-[5-chloro-2-(difluoromethoxy)phenyl]-1-(2-[[(2-hydroxyphenyl)methyl]amino]ethyl)-1H-pyrazol-4-yl]pyrazolo[1,5-a]pyrimidine-3-carboxamide $NaBH_3CN$ (112 mg, 1.78 mmol) was added portionwise to a solution of 2-hydroxybenzaldehyde (55 mg, 0.45 mmol) and N-[1-(2-aminoethyl)-3-[5-chloro-2-(difluoromethoxy)phenyl]-1H-pyrazol-4-yl]pyrazolo[1,5-a]pyrimidine-3-carboxamide (200 mg, 0.45 mmol) in methanol (10 mL). The resulting solution was stirred at room temperature overnight. The reaction was then quenched by the addition of 0.5 mL of water. The resulting mixture was concentrated under vacuum. The residue was passed through a short pad of silica gel eluting with 3% MEOH in DCM. The crude product was purified by Prep-HPLC with the following conditions (Prep-HPLC-005): Column, XBridge Prep $C_{18}$ OBD Column, 5 um, 19*150 mm; mobile phase, water with 10 mmol $NH_4HCO_3$ and MeCN (38.0% up to 45.0% in 10 min, up to 95.0% in 1 min, hold 95.0% in 1 min, down to 38.0% in 2 min); Detector, UV 254/220 nm. This resulted in 28.8 mg (12%) of N-[3-[5-chloro-2-(difluoromethoxy)phenyl]-1-(2-[[(2-hydroxyphenyl) methyl]amino]ethyl)-1H-pyrazol-4-yl]pyrazolo[1,5-a]pyrimidine-3-carboxamide as a white solid. LCMS (Method 20) $[M+H]^+$=554.2, $R_T$=2.79 min. $^1H$ NMR (400 MHz, DMSO-$d_6$) δ: (ppm) 9.74 (s, 1H), 9.34 (dd, 1H, J=1.6, 7.2 Hz), 8.69-8.67 (m, 2H), 8.37 (s, 1H), 7.63 (dd, 1H, J=2.4, 8.0 Hz), 7.61 (d, 1H, J=2.8 Hz), 7.44 (d, 1H, J=8.8 Hz), 7.28 (dd, 1H, J=4.4, 7.2 Hz), 7.09-7.04 (m, 2H), 7.06 (t, 1H, J=73.6 Hz), 6.73-6.69 (m, 2H), 4.29 (t, 2H, J=6.0 Hz), 3.82 (s, 2H), 2.98 (t, 2H, J=6.0 Hz).

Example 327

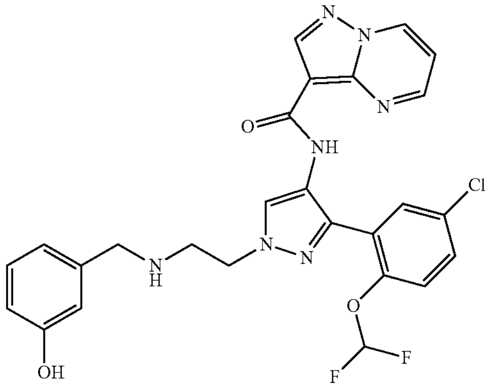 [SMILES: O=C(Nc1cn(CCNCc2cccc(O)c2)nc1-c1cc(Cl)ccc1OC(F)F)c1cnn2cccnc12]

N-[3-[5-chloro-2-(difluoromethoxy)phenyl]-1-(2-[[(3-hydroxyphenyl)methyl]amino]ethyl)-1H-pyrazol-4-yl]pyrazolo[1,5-a]pyrimidine-3-carboxamide $NaBH_3CN$ (28 mg, 0.45 mmol) was added to a solution of N-[1-(2-aminoethyl)-3-[5-chloro-2-(difluoromethoxy)phenyl]-1H-pyrazol-4-yl]pyrazolo[1,5-a]pyrimidine-3-carboxamide (100 mg, 0.22 mmol) in MeOH (10 mL) and 3-hydroxybenzaldehyde (55 mg, 0.45 mmol). The resulting solution was stirred for at room temperature overnight. The reaction was then quenched by the addition of 0.2 mL of water. The resulting mixture was concentrated under vacuum. The residue was passed through a short pad of silica gel eluting with 2.5% MeOH in DCM. The crude product was purified by Prep-HPLC with the following conditions (Prep-HPLC-005): Column, XBridge Prep C18 OBD Column, 5 um, 19*150 mm; mobile phase, water with 0.05% FA and MeCN (32.0% up to 36.0% in 10 min, up to 95.0% in 1 min, hold 95.0% in 1 min, down to 32.0% in 2 min); Detector, UV 254/220 nm. This resulted in 25.7 mg (19%) of the formic acid salt of N-[3-[5-chloro-2-(difluoromethoxy)phenyl]-1-(2-[[(3-hydroxyphenyl)-methyl] amino]ethyl)-1H-pyrazol-4-yl]pyrazolo[1,5-a]pyrimidine-3-carboxamide formate as a white solid. LCMS (Method 20) $[M+H]^+$=554.2, $R_T$=1.58 min. $^1H$ NMR (400 MHz, DMSO-$d_6$) δ: (ppm) 9.37 (s, 1H), 9.34 (dd, 1H, J=1.6, 7.2 Hz), 8.68-8.67 (m, 2H), 8.37 (s, 1H), 7.61 (dd, 1H, J=2.4, 8.8 Hz), 7.60 (d, 1H, J=2.4 Hz), 7.44 (d, 1H, J=8.4 Hz), 7.28 (dd, 1H, J=4.4, 7.2 Hz), 7.05 (t, 1H, J=73.2 Hz), 7.10-7.06 (m, 1H), 6.74-6.72 (m, 2H), 6.60 (d, 1H, J=7.2 Hz), 4.25 (t, 2H, J=6.0 Hz), 3.66 (s, 2H), 2.94 (t, 2H, J=6.0 Hz).

Example 328

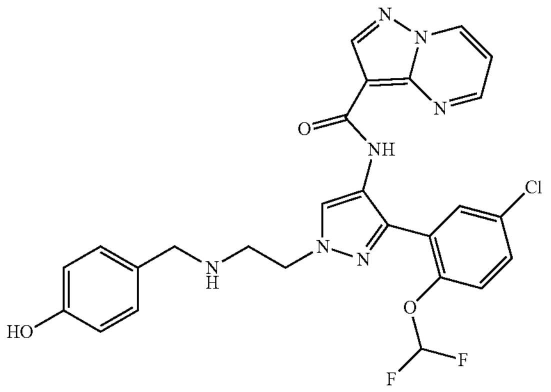 [SMILES: O=C(Nc1cn(CCNCc2ccc(O)cc2)nc1-c1cc(Cl)ccc1OC(F)F)c1cnn2cccnc12]

N-[3-[5-chloro-2-(difluoromethoxy)phenyl]-1-(2-[[(4-hydroxyphenyl)methyl]amino]ethyl)-1H-pyrazol-4-yl]pyrazolo[1,5-a]pyrimidine-3-carboxamide A solution of 4-hydroxybenzaldehyde (55 mg, 0.45 mmol) and N-[1-(2-aminoethyl)-3-[5-chloro-2-(difluoromethoxy)phenyl]-1H-pyrazol-4-yl]pyrazolo[1,5-a]pyrimidine-3-carboxamide (100 mg, 0.22 mmol) in THF (10 mL) was stirred at room temperature for 2 h and then $NaBH_3CN$ (28 mg, 0.45 mmol) was added. The resulting solution was stirred at room temperature overnight. The reaction was then quenched by the addition of 0.1 mL of water. The resulting mixture was concentrated under vacuum. The residue was passed through a short pad of silica gel eluting with 3% MeOH in DCM. The crude product was purified by Prep-HPLC with the following conditions (Prep-HPLC-005): Column, XBridge Prep C18 OBD Column, 5 um, 19*150 mm; mobile phase, water with 0.05% FA and MeCN (34.0% MeCN up to 38.0% in 10 min, up to 95.0% in 1 min, hold 95.0% in 1 min, down to 34.0% in 2 min); Detector, UV 254/220 nm. This resulted in 31.4 mg (23%) of the formic acid salt of N-[3-[5-chloro-2-(difluoromethoxy)phenyl]-1-(2-[[(4-hydroxyphenyl)methyl]amino]ethyl)-1H-pyrazol-4-yl]pyrazolo[1,5-a]pyrimidine-3-carboxamide as an off-white solid. LCMS (Method 20) $[M+H]^+$=554.2, $R_T$=1.58 min. $^1H$ NMR (400 MHz, DMSO-$d_6$) δ: (ppm) 9.74 (s, 1H), 9.34 (dd, 1H, J=1.6, 7.2 Hz), 8.69-8.67 (m, 2H), 8.37 (s, 1H), 7.62 (dd, 1H, J=2.8, 8.8 Hz), 7.60 (d, 1H, J=2.4 Hz), 7.44 (d, 1H, J=8.4 Hz), 7.28 (dd, 1H, J=4.4, 7.2 Hz), 7.10 (d, 2H, J=8.4 Hz), 7.06 (t, 1H, J=73.2 Hz), 6.68 (d, 2H, J=8.4 Hz), 4.25 (t, 2H, J=6.4 Hz), 3.63 (s, 2H), 2.95 (t, 2H, J=6.0 Hz).

Example 329

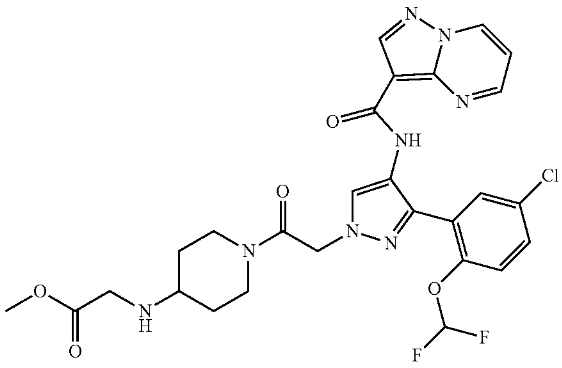 [SMILES: COC(=O)CNC1CCN(C(=O)Cn2cc(NC(=O)c3cnn4cccnc34)c(-c3cc(Cl)ccc3OC(F)F)n2)CC1]

methyl 2-[[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl]amino]acetate formate To a solution of {3-(5-Chloro-2-difluoromethoxyphenyl)-4-[(pyrazolo[1,5-a]pyrimidine-3-carbonyl)amino]pyrazol-1-yl}acetic acid (500 mg) in DMF (10 mL) was added tert-butyl N-(piperidin-4-yl)carbamate (208 mg, 1.04 mmol), DIEA (224 mg, 1.73 mmol), HATU (395.9 mg, 1.04 mmol). The resulting solution was stirred at room temperature overnight. Water (50 mL) was added. The precipitates were collected by filtration and dried. This resulted in 600 mg of tert-butyl N-[1-(2-[3-[5-chloro-2-(difluoromethoxy)phenyl]-4-[pyrazolo[1,5-a]pyrimidine-3-amido]-1H-pyrazol-1-yl]acetyl) piperidin-4-yl]carbamate as a yellow crude solid. LCMS (Method 25) $[M+H]^+$=645.1, $R_T$=1.02 min.

A solution of the crude product from previous step (600 mg) and saturated HCl dioxane solution (15 mL) was stirred at room temperature overnight. The resulting solution was diluted with 100 mL of methanol and neutralized with saturated aqueous. $Na_2CO_3$ and concentrated under vacuum. The residue was passed through a short pad of silica gel eluting with 30% MeOH in DCM. Collection of appropriate fractions and evaporation of solvent afforded N-[1-[2-(4-aminopiperidin-1-yl)-2-oxoethyl]-3-[5-chloro-2-(difluoromethoxy)phenyl]-1H-pyrazol-4-yl]pyrazolo[1,5-a]pyrimidine-3-carboxamide (520 mg) as a yellow solid. LCMS (Method 25) $[M+H]^+$=545.1, $R_T$=0.62 min.

Methyl 2-bromoacetate (30.74 mg, 0.20 mmol) was added to a mixture of N-[1-[2-(4-aminopiperidin-1-yl)-2-oxoethyl]-3-[5-chloro-2-(difluoromethoxy)phenyl]-1H-pyrazol-4-yl]pyrazolo[1,5-a]pyrimidine-3-carboxamide (100 mg, 0.18 mmol) in DMF (5 mL) and potassium carbonate (38.1 mg, 0.28 mmol). The resulting mixture was stirred at room temperature overnight. Additional amount of methyl 2-bromoacetate (30.74 mg, 0.20 mmol) was added and the resulting solution was stirred at 60° C. for 2 h. The resulting mixture was concentrated under vacuum. The crude product was purified by Prep-HPLC with the following conditions (Prep-HPLC-005): Column, XBridge Prep C18 OBD Column, 5 um, 19*150 mm; mobile phase, water with 0.05% FA and MeCN (25.0% MeCN up to 32.0% in 10 min, up to 95.0% in 1 min, hold 95.0% in 1 min, down to 25.0% in 2 min); Detector, UV 254/220 nm. This resulted in 68.9 mg (57%) of the formic acid salt of methyl 2-[[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl]amino]-acetate as an off-white solid. LCMS (Method 24) $[M+H]^+$=617.2, $R_T$=1.53 min. $^1H$ NMR (400 MHz, DMSO-$d_6$) δ: (ppm) 9.75 (s, 1H), 9.34 dd, 1H, J=1.6, 7.2 Hz), 8.69-8.67 (m, 2H), 8.30 (s, 1H), 7.62 (dd, 1H, J=2.4, 8.8 Hz), 7.55 (d, 1H, J=2.8 Hz), 7.45 (d, 1H, J=8.8 Hz), 7.28 (dd, 1H, J=4.0, 6.8 Hz), 7.08 (t, 1H, J=73.2 Hz), 5.23-5.20 (m, 2H), 4.11-4.07 (m, 1H), 3.83-3.80 (m, 1H), 3.63 (s, 3H), 3.39-3.31 (m, 2H), 3.15-3.12 (m, 1H), 2.87-2.83 (m, 1H), 2.71-2.67 (m, 1H), 1.83-1.77 (m, 2H), 1.29-1.14 (m, 2H).

Example 330

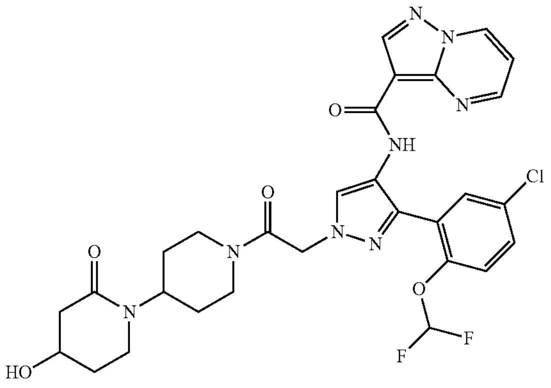 [SMILES: O=C(Nc1cn(CC(=O)N2CCC(N3CCC(O)CC3=O)CC2)nc1-c1cc(Cl)ccc1OC(F)F)c1cnn2cccnc12]

N-[3-[5-chloro-2-(difluoromethoxy)phenyl]-1-[2-[4-(5-hydroxy-2-oxopiperidin-1-yl)piperidin-1-yl]-2-oxoethyl]-1H-pyrazol-4-yl]pyrazolo[1,5-a]pyrimidine-3-carboxamide formate DIEA (71 mg, 0.55 mmol) was added to a solution of N-[1-[2-(4-aminopiperidin-1-yl)-2-oxoethyl]-3-[5-chloro-2-(difluoromethoxy)phenyl]-1H-pyrazol-4-yl]pyrazolo[1,5-a]pyrimidine-3-carboxamide (100 mg, 0.18 mmol) and (5-oxooxolan-2-yl)methyl trifluoromethanesulfonate (69 mg, 0.28 mmol) in $CH_3CN$ (30 mL). The resulting solution was stirred overnight at room temperature. The resulting mixture was concentrated under vacuum. The crude product was purified by Prep-HPLC with the following conditions (Prep-HPLC-005): Column, XBridge Prep $C_{18}$ OBD Column, 5 um, 19*150 mm; mobile phase, water with 0.05% FA and MeCN (38.0% up to 46.0% in 10 min, up to 95.0% in 1 min, hold 95.0% in 1 min, down to 38.0% in 2 min); Detector, UV 254/220 nm. This resulted in 41.6 mg (33%) of N-[3-[5-chloro-2-(difluoromethoxy)phenyl]-1-[2-[4-(5-hydroxy-2-oxopiperidin-1-yl)piperidin-1-yl]-2-oxoethyl]-1H-pyrazol-4-yl]pyrazolo[1,5-a]pyrimidine-3-carboxamide as an off-white solid. LCMS (Method 25) $[M+H]^+$=643.2, $R_T$=1.49 min. $^1H$ NMR (400 MHz, DMSO-$d_6$) δ: (ppm) 9.75 (s, 1H), 9.35 (dd, 1H, J=1.6, 6.8 Hz), 8.69-8.68 (m, 2H), 8.32 (s, 1H), 7.63 (dd, 1H, J=2.8, 8.8 Hz), 7.56 (d, 1H, J=2.8 Hz), 7.46 (d, 1H, J=8.8 Hz), 7.29 (dd, 1H, J=4.4, 7.2 Hz), 7.09 (t, 1H, J=73.2 Hz), 5.26-5.24 (m, 2H), 4.89 (br, 1H), 4.59-4.45 (m, 2H), 4.08-3.90 (m, 2H), 3.25-2.97 (m, 3H), 2.68-2.58 (m, 1H), 2.46-2.21 (m, 2H), 1.86-1.65 (m, 3H), 1.57-1.50 (m, 3H).

Example 331

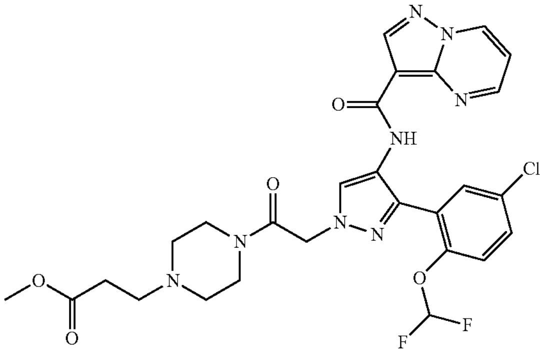 [SMILES: COC(=O)CCN1CCN(C(=O)Cn2cc(NC(=O)c3cnn4cccnc34)c(-c3cc(Cl)ccc3OC(F)F)n2)CC1]

methyl 3-[4-(2-[3-[5-chloro-2-(difluoromethoxy) phenyl]-4-[pyrazolo[1,5-a]pyrimidine-3-amido]-1H-pyrazol-1-yl]acetyl)piperazin-1-yl]propanoate To a solution of tert-butyl piperazine-1-carboxylate (1 g, 5.37 mmol) in DMF (20 mL) was added $Cs_2CO_3$ (589 mg, 1.81 mmol) and methyl 3-bromopropanoate (744 mg, 4.46 mmol). The resulting mixture was stirred at room temperature overnight. Water (50 m) and EtOAc (50 mL) was added. Phases were separated. The aqueous phase was extracted with EtOAc (50 mL). The organic layers were combined, washed with brine, dried over anhydrous sodium sulfate and concentrated under vacuum. The residue was purified by flash chromatography on silica gel eluting with 3.5% MeOH in DCM. Collection of appropriate fractions and evaporation of solvent afforded tert-butyl 4-(3-methoxy-3-oxopropyl) piperazine-1-carboxylate (895 mg, 74%) as yellow oil. TLC: $R_f$=0.3; ethyl acetate/petroleum ether=1/2.

A solution of tert-butyl 4-(3-methoxy-3-oxopropyl)piperazine-1-carboxylate (895 mg, 3.29 mmol) and saturated HCl dioxane solution (15 mL) was stirred at room temperature overnight. The solids were collected by filtration. This resulted in 710 mg of methyl 3-(piperazin-1-yl)propanoate hydrochloride as a white crude solid.

To a solution of {3-(5-Chloro-2-difluoromethoxyphenyl)-4-[(pyrazolo[1,5-a]pyrimidine-3-carbonyl)amino]pyrazol-1-yl}acetic acid (100 mg) in DMF (5 mL) was added methyl 3-(piperazin-1-yl)propanoate hydrochloride (44 mg, 0.21 mmol), DIEA (90 mg, 0.70 mmol), HATU (79.2 mg, 0.21 mmol). The resulting solution was stirred at room temperature for 4 h and concentrated under vacuum. The crude product was purified by Prep-HPLC with the following conditions (Prep-HPLC-005): Column, XBridge Prep $C_{18}$ OBD Column, 5 um, 19*150 mm; mobile phase, water with 0.05% FA and MeCN (40.0% up to 51.0% in 10 min, up to 95.0% in 1 min, hold 95.0% in 1 min, down to 40.0% in 2 min); Detector, UV 254/220 nm. This resulted in 56.1 mg (49%) of the formic acid salt of methyl 3-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]propanoate as a light yellow solid. LCMS (Method 25) $[M+H]^+$=617.1, $R_T$=1.51 min. $^1H$ NMR (400 MHz, DMSO-$d_6$) δ: (ppm) 9.76 (s, 1H), 9.34 (dd, 1H, J=1.6, 7.2 Hz), 8.68-8.67 (m, 2H), 8.31 (s, 1H), 7.62 (dd, 1H, J=2.8, 8.8 Hz), 7.55 (d, 1H, J=2.8 Hz), 7.45 (d, 1H, J=8.8 Hz), 7.28 (dd, 1H, J=4.4, 6.8 Hz), 7.08 (t, 1H, J=73.2 Hz), 5.23 (s, 2H), 3.60 (s, 3H), 3.49-3.41 (m, 4H), 2.59 (t, 2H, J=6.4 Hz), 2.51 (t, 2H, J=6.4 Hz), 2.39-2.33 (m, 4H).

Example 332

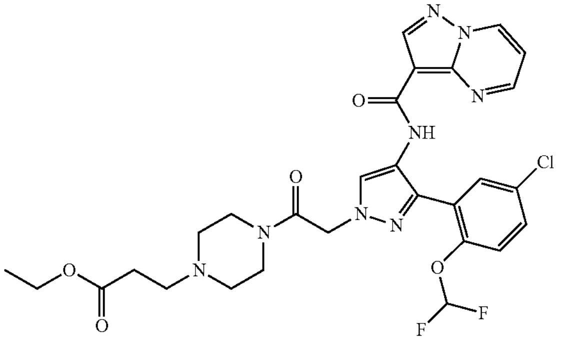 [SMILES: CCOC(=O)CCN1CCN(C(=O)Cn2cc(NC(=O)c3cnn4cccnc34)c(-c3cc(Cl)ccc3OC(F)F)n2)CC1]

3-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]propanoate Using synthetic methods analoguous to that of methyl 3-[4-(2-[3-[5-chloro-2-(difluoromethoxy)phenyl]-4-[pyrazolo[1,5-a]pyrimidine-3-amido]-1H-pyrazol-1-yl]acetyl) piperazin-1-yl]propanoate, the title compound was prepared from ethyl 3-bromopropanoate. LCMS (Method 28) $[M+H]^+$=631.2, $R_T$=0.89 min. $^1H$ NMR (300 MHz, DMSO-$d_6$) δ: (ppm) 9.76 (s, 1H), 9.34 (d, 1H, J=6.9 Hz), 8.69-8.67 (m, 2H), 8.30 (s, 1H), 7.62 (dd, 1H, J=2.7, 8.7 Hz), 7.55 (d, 1H, J=2.4 Hz), 7.45 (d, 1H, J=9.0 Hz), 7.28 (dd, 1H, J=4.2, 6.9 Hz), 7.07 (t, 1H, J=72.9 Hz), 5.23 (s, 2H), 4.03 (q, 2H, J=7.2 Hz), 3.59-3.47 (m, 4H), 2.61-2.59 (m, 2H), 2.50-2.33 (m, 6H), 1.16 (t, 3H, J=7.2 Hz).

Example 333

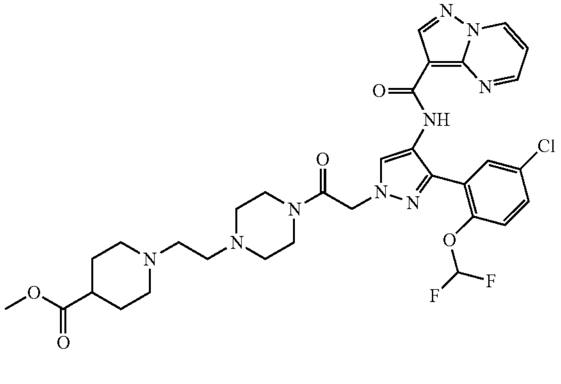 [SMILES: COC(=O)C1CCN(CCN2CCN(C(=O)Cn3cc(NC(=O)c4cnn5cccnc45)c(-c4cc(Cl)ccc4OC(F)F)n3)CC2)CC1]

methyl 1-[2-[4-(2-[3-[5-chloro-2-(difluoromethoxy)phenyl]-4-[pyrazzolo[1,5-a]pyrimidine-3-amido]-1H-pyrazol-1-yl]acetyl)piperazin-1-yl]ethyl]piperidine-4-carboxylate To a stirring solution of tert-butyl 4-(2-hydroxyethyl)piperazine-1-carboxylate (1.5 g, 6.51 mmol) and DIEA (2.5 g, 19.34 mmol) in DCM (50 mL) was added MsCl (817 mg, 7.13 mmol) dropwise g at 0° C. The resulting solution was stirred for 1 h at room temperature. Water (100 mL) was added. Phases were separated. The aqueous phase was extracted with dichloromethane and the organic layers combined. The organic phases were washed with brine, dried over anhydrous sodium sulfate and concentrated under vacuum. This resulted in 1.8 g (crude) of tert-butyl 4-[2-(methanesulfonyloxy)ethyl]piperazine-1-carboxylate as light yellow oil.

To a solution of tert-butyl 4-[2-(methanesulfonyloxy)ethyl]piperazine-1-carboxylate (431 mg, 1.39 mmol) in DMF (5 mL) was added methyl piperidine-4-carboxylate (300 mg, 2.095 mmol) and DIEA (361 mg, 2.79 mmol). The resulting solution was stirred at room temperature overnight. The resulting mixture was concentrated under vacuum. The residue was purified by flash chromatography on silica gel eluting with 3% MeOH in DCM. This resulted in 285 mg (57%) of tert-butyl 4-[2-[4-(methoxycarbonyl)piperidin-1-yl]ethyl]piperazine-1-carboxylate as yellow oil. LCMS (Method 20) $[M+H]^+$=356.2, $R_T$=0.99 min.

A solution of tert-butyl 4-[2-[4-(methoxycarbonyl)piperidin-1-yl]ethyl]piperazine-1-carboxylate (285 mg, 0.80 mmol) and saturated HCl dioxane solution (15 mL) was stirred at room temperature overnight. The resulting mixture was concentrated under vacuum. This resulted in 205 mg (88%) of methyl 1-[2-(piperazin-1-yl)ethyl]piperidine-4-carboxylate hydrochloride as a yellow solid. LCMS (Method 20) $[M+H]^+$=256.2, $R_T$=0.44 min.

To a solution of {3-(5-Chloro-2-difluoromethoxyphenyl)-4-[(pyrazolo[1,5-a]pyrimidine-3-carbonyl)amino]pyrazol-1-yl}acetic acid (150 mg, 0.32 mmol) in DMF (10 mL) was added methyl 1-[2-(piperazin-1-yl)ethyl]piperidine-4-carboxylate hydrochloride (190 mg, 0.65 mmol), DIEA (126 mg, 0.97 mmol), HATU (148 mg, 0.39 mmol). The resulting solution was stirred at room temperature overnight and concentrated under vacuum. The residue was passed through a short pad of silica gel eluting with 4% MeOH in DCM. The crude product was purified by Prep-HPLC with the following conditions (Prep-HPLC-005): Column, XBridge Prep $C_{18}$ OBD Column, 5 um, 19*150 mm; mobile phase, water with 0.05% FA and MeCN (22.0% up to 31.0% in 10 min, up to 95.0% in 1 min, hold 95.0% in 1 min, down to 22.0% in 2 min); Detector, UV 254/220 nm. This resulted in 96.5 mg (40%) of the formic acid salt of methyl 1-[2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]ethyl]piperidine-4-carboxylate as a light yellow solid. LCMS (Method 24) $[M+H]^+$=700.2, $R_T$=2.21 min. $^1$H NMR (400 MHz, DMSO-$d_6$) δ: (ppm) 9.75 (s, 1H), 9.34 (dd, 1H, J=1.6, 6.8 Hz), 8.69-8.68 (m, 2H), 8.30 (s, 1H), 7.62 (dd, 1H, J=2.8, 8.8 Hz), 7.55 (d, 1H, J=2.4 Hz), 7.46 (d, 1H, J=8.8 Hz), 7.28 (dd, 1H, J=4.4, 6.8 Hz), 7.08 (t, 1H, J=73.2 Hz), 5.23 (s, 2H), 3.59 (s, 3H), 3.49-3.46 (m, 4H), 2.84-2.81 (m, 2H), 2.54-2.52 (m, 6H), 2.50-2.40 (m, 2H), 2.33-2.27 (m, 1H), 2.04-1.99 (m, 2H), 1.88-1.70 (m, 2H), 1.55-1.50 (m, 2H).

Example 334

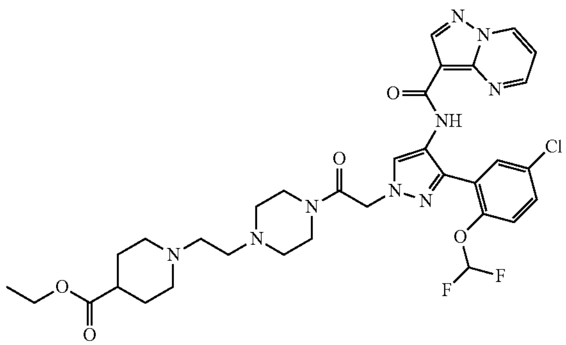 [SMILES: CCOC(=O)C1CCN(CCN2CCN(C(=O)Cn3cc(NC(=O)c4cnn5cccnc45)c(-c4cc(Cl)ccc4OC(F)F)n3)CC2)CC1]

ethyl 1-[2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]ethyl]piperidine-4-carboxylate To a solution of tert-butyl 4-[2-(methanesulfonyloxy)ethyl]piperazine-1-carboxylate (392 mg, 1.27 mmol) in DMF (5 mL) was added DIEA (329 mg, 2.55 mmol) and ethyl piperidine-4-carboxylate (300 mg, 1.91 mmol). The resulting solution was stirred at room temperature overnight and concentrated under vacuum. The residue was purified by flash chromatography on silica gel eluting with 5% MeOH in DCM. This resulted in 310 mg (66%) of tert-butyl 4-[2-[4-(ethoxycarbonyl)piperidin-1-yl]ethyl]piperazine-1-carboxylate as a yellow solid. LCMS (Method 28) $[M+H]^+$=370.3, $R_T$=0.50 min.

A mixture of tert-butyl 4-[2-[4-(ethoxycarbonyl)piperidin-1-yl]ethyl]piperazine-1-carboxylate (310 mg, 0.84 mmol) and saturated HCl dioxane solution (15 mL) was stirred at room temperature overnight. The resulting mixture was concentrated under vacuum. This resulted in 220 mg (86%) of ethyl 1-[2-(piperazin-1-yl)ethyl]piperidine-4-carboxylate hydrochloride as a light yellow solid. LCMS (Method 28) $[M+H]^+$=270.3, $R_T$=0.89 min.

To a solution of 2-[3-[5-chloro-2-(difluoromethoxy)phenyl]-4-[pyrazolo[1,5-a]pyrimidine-3-amido]-1H-pyrazol-1-yl]acetic acid (150 mg, 0.32 mmol) in DMF (10 mL) was added ethyl 1-[2-(piperazin-1-yl)ethyl]piperidine-4-carboxylate hydrochloride (199 mg, 0.65 mmol), DIEA (126 mg, 0.97 mmol), HATU (148 mg, 0.39 mmol). The resulting solution was stirred at room temperature overnight and concentrated under vacuum. The residue was passed through a short pad of silica gel eluting with 3% MeOH in DCM. The crude product was purified by Prep-HPLC with the following conditions (Prep-HPLC-005): Column, XBridge Prep C18 OBD Column, 5 um, 19*150 mm; mobile phase, water with 0.05% FA and MeCN (18.0% MeCN up to 27.0% in 10 min, up to 95.0% in 1 min, hold 95.0% in 1 min, down to 18.0% in 2 min); Detector, UV 254/220 nm. This resulted in 66.1 mg (27%) of the formic acid salt of ethyl 1-[2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]ethyl]piperidine-4-carboxylate. LCMS (Method 24) $[M+H]^+$=714.2, $R_T$=2.42 min. $^1H$ NMR (400 MHz, DMSO-$d_6$) δ: (ppm) 9.76 (s, 1H), 9.34 (dd, 1H, J=1.6, 6.8 Hz), 8.69-8.68 (m, 2H), 8.31 (s, 1H), 7.62 (dd, 1H, J=2.8, 8.8 Hz), 7.56 (d, 1H, J=2.4 Hz), 7.46 (d, 1H, J=8.8 Hz), 7.29 (dd, 1H, J=4.4, 6.8 Hz), 7.08 (t, 1H, J=73.2 Hz), 5.23 (m, 2H), 4.03 (q, 2H, J=6.8 Hz), 3.50-3.47 (m, 4H), 2.88-2.85 (m, 2H), 2.52-2.51 (m, 6H), 2.47-2.26 (m, 3H), 2.12-2.07 (m, 2H), 1.80-1.78 (m, 2H), 1.60-1.55 (m, 2H), 1.16 (t, 3H, J=7.2 Hz). □

Example 335

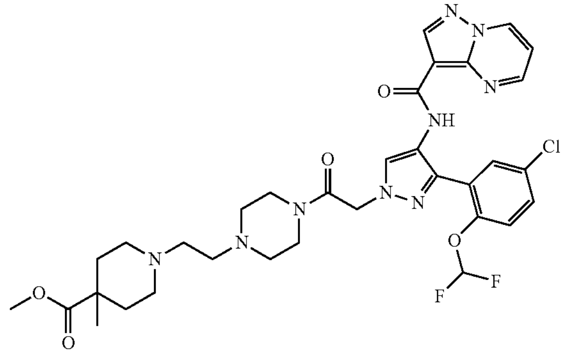 [SMILES: COC(=O)C1(C)CCN(CCN2CCN(C(=O)Cn3cc(NC(=O)c4cnn5cccnc45)c(-c4cc(Cl)ccc4OC(F)F)n3)CC2)CC1]

methyl 1-[2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]ethyl]-4-methylpiperidine-4-carboxylate formate Using synthetic method analoguous to that of ethyl 1-[2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]ethyl]piperidine-4-carboxylate, the title compound was prepared from methyl 4-methylpiperidine-4-carboxylate hydrochloride.

LCMS (Method 24) $[M+H]^+$=714.2, $R_T$=1.94 min. $^1H$ NMR (400 MHz, DMSO-$d_6$) δ: (ppm) 9.75 (s, 1H), 9.34 (dd, 1H, J=1.6, 6.8 Hz), 8.69-8.68 (m, 2H), 8.30 (s, 1H), 7.65-7.62 (dd, 1H, J=2.8, 8.8 Hz), 7.55 (d, 1H, J=2.8 Hz), 7.45 (d, 1H, J=8.8 Hz), 7.28 (dd, 1H, J=4.4, 6.8 Hz), 7.08 (t, 1H, J=73.6 Hz), 5.22 (s, 2H), 3.62 (s, 3H), 3.48-3.45 (m, 4H), 2.57-2.51 (m, 2H), 2.49-2.39 (m, 8H), 2.01-1.93 (m, 4H), 1.41-1.35 (m, 2H), 1.10 (s, 3H). □

Example 336

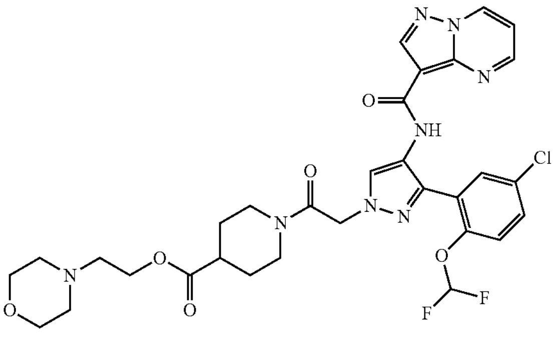 [SMILES: O=C(Nc1cn(CC(=O)N2CCC(C(=O)OCCN3CCOCC3)CC2)nc1-c1cc(Cl)ccc1OC(F)F)c1cnn2cccnc12]

2-(morpholin-4-yl)ethyl 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylate To a solution of 1-[(tert-butoxy)carbonyl]piperidine-4-carboxylic acid (1.00 g, 4.36 mmol) in DCM (15 mL) was added 2-(morpholin-4-yl)ethan-1-ol (858 mg, 6.54 mmol), EDC.HCl (1.00 g, 5.22 mmol), 4-dimethylaminopyridine (53.3 mg, 0.44 mmol). The resulting solution was stirred at room temperature overnight. Water (30 mL) and DCM (50 mL) was added. Phases were separated. The aqueous phase was extracted with DCM and the organic layers combined. The combined organic layers were washed with brine, dried over anhydrous sodium sulfate and concentrated under vacuum. The residue was purified by flash chromatography on silica gel eluting with dichloromethane/ethyl acetate (2:3). This resulted in 1.4 g (crude) of 1-tert-butyl 4-[2-(morpholin-4-yl)ethyl]piperidine-1,4-dicarboxylate as yellow oil. TLC: $R_f$=0.3; ethyl acetate.

A mixture of 1-tert-butyl 4-[2-(morpholin-4-yl)ethyl]piperidine-1,4-dicarboxylate (1.4 g, 4.09 mmol) and saturated HCl dioxane solution (20 mL) was stirred at room temperature overnight. The resulting mixture was concentrated under vacuum. This resulted in 1.2 g (crude) of 2-(morpholin-4-yl)ethyl piperidine-4-carboxylate hydrochloride as yellow oil.

To a solution of {3-(5-Chloro-2-difluoromethoxyphenyl)-4-[(pyrazolo[1,5-a]pyrimidine-3-carbonyl)amino]pyrazol-1-yl}acetic acid (150 mg, 0.26 mmol) in DMF (2 mL) was added 2-(morpholin-4-yl)ethyl piperidine-4-carboxylate hydrochloride (140 mg, 0.50 mmol), DIEA (101 mg, 0.78 mmol), HATU (119 mg, 0.31 mmol). The resulting solution was stirred at room temperature overnight and concentrated under vacuum. The residue was passed through a short pad of silica gel eluting with 10% MeOH in DCM. The crude product was purified by Prep-HPLC with the following conditions (Prep-HPLC-005): Column, XBridge Prep C18 OBD Column, 5 um, 19*150 mm; mobile phase, water with 0.05% FA and MeCN (31.0% MeCN up to 38.0% in 10 min, up to 95.0% in 1 min, hold 95.0% in 1 min, down to 31.0% in 2 min); Detector, UV 254/220 nm. This resulted in 35.6 mg (20%) of the formic acid salt of 2-(morpholin-4-yl)ethyl 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylate as a off-white solid. LCMS (Method 28) $[M+H]^+$=687.2, $R_T$=0.86 min. $^1H$ NMR (400 MHz, DMSO-$d_6$) δ: (ppm) 9.76 (s, 1H), 9.34 (dd, 1H, J=1.6, 7.2 Hz), 8.69-8.68 (m, 2H), 8.32 (s, 1H), 7.63 (dd, 1H, J=2.4, 8.8 Hz), 7.55 (d, 1H, J=2.8 Hz), 7.46 (d, 1H, J=8.8 Hz), 7.29 (dd, 1H, J=4.4, 6.8 Hz), 7.08 (t, 1H, J=73.2 Hz), 5.27-5.22 (m, 2H), 4.20-4.15 (m, 3H), 3.89-3.82 (m, 1H), 3.58-3.55 (m, 4H), 3.26-3.17 (m, 1H), 2.89-2.78 (m, 1H), 2.69-2.59 (m, 1H), 2.53-2.51 (m, 2H), 2.40-2.32 (m, 4H), 1.91-1.80 (m, 2H), 1.69-1.41 (m, 2H).

Example 337

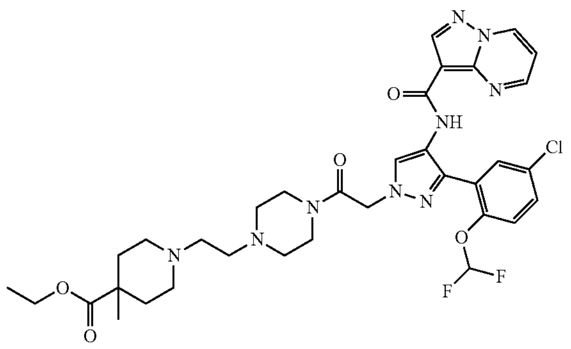 [SMILES: CCOC(=O)C1(C)CCN(CCN2CCN(C(=O)Cn3cc(NC(=O)c4cnn5cccnc45)c(-c4cc(Cl)ccc4OC(F)F)n3)CC2)CC1]

ethyl 1-[2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]ethyl]-4-methylpiperidine-4-carboxylate formate Using synthetic method analoguous to that of ethyl 1-[2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]ethyl]piperidine-4-carboxylate, the title compound was prepared from ethyl 4-methylpiperidine-4-carboxylate hydrochloride. LCMS (Method 24) $[M+H]^+$=728.2, $R_T$=1.87 min. $^1$H NMR (400 MHz, DMSO-$d_6$) δ: (ppm) 9.75 (s, 1H), 9.34 (dd, 1H, J=1.2, 6.8 Hz), 8.69-8.68 (m, 2H), 8.30 (s, 1H), 7.62 (dd, 1H, J=2.8, 8.8 Hz), 7.55 (d, 1H, J=2.8 Hz), 7.46 (d, 1H, J=8.8 Hz), 7.28 (dd, 1H, J=4.4, 6.8 Hz), 7.08 (t, 1H, J=73.2 Hz), 5.22 (s, 2H), 4.06 (q, 2H, J=7.2 Hz), 2.67-2.60 (m, 2H), 2.44-2.38 (m, 8H), 2.09-2.04 (m, 2H), 1.97-1.93 (m, 2H), 1.42-1.41 (m, 2H), 1.16 (t, 3H, J=7.2 Hz), 1.10 (s, 3H).

Example 338

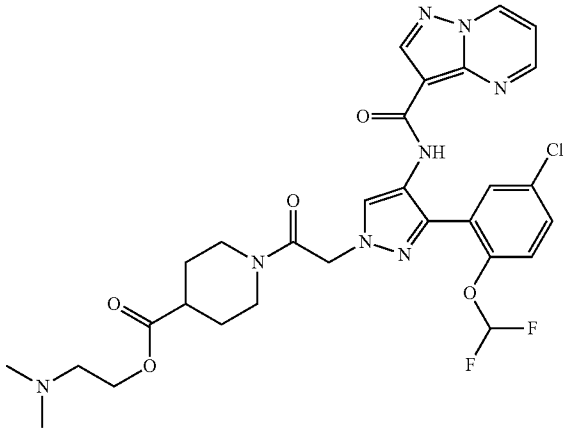 [SMILES: CN(C)CCOC(=O)C1CCN(C(=O)Cn2cc(NC(=O)c3cnn4cccnc34)c(-c3cc(Cl)ccc3OC(F)F)n2)CC1]

2-(dimethylamino)ethyl 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylate Using synthetic method analoguous to that of 2-(morpholin-4-yl)ethyl 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylate, the title compound was prepared from 2-(dimethylamino)ethan-1-ol. LCMS (Method 24) $[M+H]^+$=645.2, $R_T$=2.97 min. $^1$H NMR (400 MHz, DMSO-$d_6$) δ: (ppm) 9.76 (s, 1H), 9.34 (dd, 1H, J=1.6, 6.8 Hz), 8.68-8.67 (m, 2H), 8.31 (s, 1H), 7.62 (dd, 1H, J=2.4, 8.8 Hz), 7.55 (d, 1H, J=2.4 Hz), 7.45 (d, 1H, J=8.8 Hz), 7.28 (dd, 1H, J=4.4, 7.2 Hz), 7.21 (t, J=73.1 Hz, 1H) 5.30-5.14 (m, 2H), 4.21-4.10 (m, 3H), 3.89-3.78 (m, 1H), 3.24-3.14 (m, 1H), 2.89-2.60 (m, 2H), 2.49-2.45 (m, 2H), 2.16 (s, 6H), 1.89-1.81 (m, 2H), 1.68-1.37 (m, 2H).

Example 339

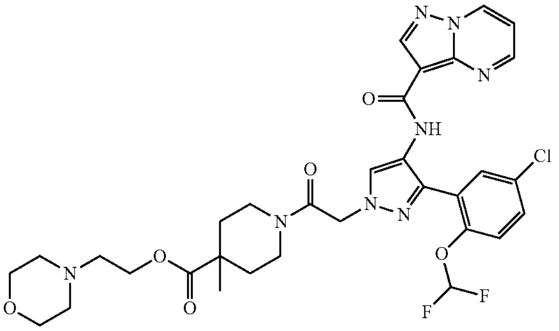 [SMILES: CC1(C(=O)OCCN2CCOCC2)CCN(C(=O)Cn2cc(NC(=O)c3cnn4cccnc34)c(-c3cc(Cl)ccc3OC(F)F)n2)CC1]

2-(morpholin-4-yl)ethyl 1-(2-[3-[5-chloro-2-(difluoromethoxy)phenyl]-4-[pyrazolo[1,5-a]pyrimidine-3-amido]-1H-pyrazol-1-yl]acetyl)-4-methylpiperidine-4-carboxylate To a solution of 1-[(tert-butoxy)carbonyl]-4-methylpiperidine-4-carboxylic acid (1.00 g, 4.11 mmol) in DCM (10 mL) was added 2-(morpholin-4-yl)ethan-1-ol (1.08 g, 8.23 mmol), HOBt (667 mg, 4.94 mmol). The mixture was stirred at room temperature for 2 hr, then EDC.HCl (943 mg, 4.92 mmol) was added. The resulting solution was stirred at room temperature overnight and diluted with 30 mL of DCM. The resulting mixture was washed with water, brine, dried over anhydrous sodium sulfate and concentrated under vacuum. The residue was purified by flash chromatography on silica gel eluting with 4% MeOH in DCM. This resulted in 800 mg (55%) of 1-tert-butyl 4-[2-(morpholin-4-yl)ethyl]4-methylpiperidine-1,4-dicarboxylate as yellow oil. LCMS (Method 28) $[M+H]^+$=357.2, $R_T$=0.64 min.

A solution of 1-tert-butyl 4-[2-(morpholin-4-yl)ethyl]4-methylpiperidine-1,4-dicarboxylate (800 mg, 2.24 mmol) and saturated HCl dioxane solution (30 mL) was stirred at room temperature overnight. The resulting mixture was concentrated under vacuum. This resulted in 600 mg (crude) of 2-(morpholin-4-yl)ethyl 4-methylpiperidine-4-carboxylate hydrochloride as a white crude solid. LCMS (Method 28) $[M+H]^+$=257.0, $R_T$=0.86 min.

To a solution of {3-(5-Chloro-2-difluoromethoxyphenyl)-4-[(pyrazolo[1,5-a]pyrimidine-3-carbonyl)amino]pyrazol- 1-yl}acetic acid (100 mg) in DMF (3 mL) was added 2-(morpholin-4-yl)ethyl 4-methylpiperidine-4-carboxylate hydrochloride (76.2 mg, 0.26 mmol), DIEA (67.2 mg, 0.52 mmol), HATU (79.2 mg, 0.21 mmol). The resulting solution was stirred at room temperature overnight and concentrated under vacuum. The crude product was purified by Prep-HPLC with the following conditions (Prep-HPLC-005): Column, XBridge Prep $C_{18}$ OBD Column, 5 um, 19*150 mm; mobile phase, water with 0.05% FA and MeCN (34.0% up to 38.0% in 10 min, up to 95.0% in 1 min, hold 95.0% in 1 min, down to 34.0% in 2 min); Detector, UV 254/220 nm. This resulted in 43.0 mg (33%) of the formic acid salt of 2-(morpholin-4-yl)ethyl 1-(2-[3-[5-chloro-2-(difluoromethoxy)phenyl]-4-[pyrazolo[1,5-a]pyrimidine-3-amido]-1H-pyrazol-1-yl]-acetyl)-4-methyl piperidine-4-carboxylate. LCMS (Method 20) $[M+H]^+$=701.2, $R_T$=0.92 min. 1H NMR (400 MHz, DMSO-d6) δ: (ppm) 9.75 (s, 1H), 9.35 (dd, 1H, J=1.6, 7.2 Hz), 8.69-8.68 (m, 2H), 8.31 (s, 1H), 7.63 (dd, 1H, J=2.4, 8.8 Hz), 7.55 (d, 1H, J=2.8 Hz), 7.46 (d, 1H, J=9.6 Hz), 7.29 (dd, 1H, J=4.4, 6.8 Hz), 7.09 (t, 1H, J=73.2 Hz), 5.23 (s, 2H), 4.21 (t, 2H, J=5.6 Hz), 4.02-3.98 (m, 1H), 3.77-3.74 (m, 1H), 3.53-3.51 (m, 4H), 3.27-3.22 (m, 1H), 3.00-2.94 (m, 1H), 2.55-2.52 (m, 2H), 2.49-2.39 (m, 4H), 2.04-1.97 (m, 2H), 1.18 (s, 3H).

Example 340

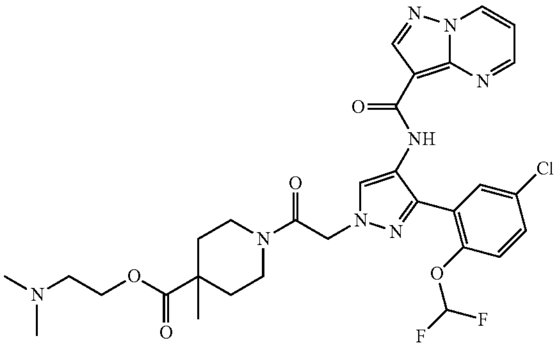 [SMILES: CN(C)CCOC(=O)C1(C)CCN(C(=O)Cn2cc(NC(=O)c3cnn4cccnc34)c(-c3cc(Cl)ccc3OC(F)F)n2)CC1]

2-(dimethylamino)ethyl 1-(2-[3-[5-chloro-2-(difluoromethoxy)phenyl]-4-[pyrazolo[1,5-a]pyrimidine-3-amido]-1H-pyrazol-1-yl]acetyl)-4-methylpiperidine-4-carboxylate To a solution of 1-[(tert-butoxy)carbonyl]-4-methylpiperidine-4-carboxylic acid (1 g, 4.11 mmol) in DCM (10 mL) was added 2-(dimethylamino)ethan-1-ol (733 mg, 8.22 mmol), HOBt (667 mg, 4.94 mmol). The mixture was stirred at room temperature for 2 h, then EDC.HCl (943 mg, 4.92 mmol) was added. The resulting solution was stirred at room temperature overnight and water (30 mL) was added. The resulting solution was extracted with DCM (×2) and the organic layers combined. The organic phase was washed with brine, dried over anhydrous sodium sulfate and concentrated under vacuum. The residue was purified by flash chromatography on silica gel eluting with 4% MeOH in DCM. This resulted in 800 mg (62%) of 1-tert-butyl 4-[2-(dimethylamino)ethyl]4-methylpiperidine-1,4-dicarboxylate as yellow oil. TLC: $R_f$=0.3; dichloromethane/methanol=10/1.

A mixture of 1-tert-butyl 4-[2-(dimethylamino)ethyl]4-methylpiperidine-1,4-dicarboxylate (800 mg, 2.54 mmol) and saturated HCl dioxane solution (20 mL) was stirred at room temperature overnight. The resulting mixture was concentrated under vacuum. This resulted in 340 mg (53%) of 2-(dimethylamino)ethyl 4-methylpiperidine-4-carboxylate hydrochloride as a white solid.

To a solution of {3-(5-Chloro-2-difluoromethoxyphenyl)-4-[(pyrazolo[1,5-a]pyrimidine-3-carbonyl)amino]pyrazol-1-yl}acetic acid (100 mg) in DMF (3 mL) was added 2-(dimethylamino)ethyl 4-methylpiperidine-4-carboxylate hydrochloride (87 mg, 0.35 mmol), DIEA (67.2 mg, 0.52 mmol), HATU (79.2 mg, 0.21 mmol). The resulting solution was stirred at room temperature overnight and concentrated under vacuum. The crude product was purified by Prep-HPLC with the following conditions (Prep-HPLC-005): Column, XBridge Prep $C_{18}$ OBD Column, 5 um, 19*150 mm; mobile phase, water with 0.05% FA and MeCN (38.0% MeCN up to 42.0% in 10 min, up to 95.0% in 1 min, hold 95.0% in 1 min, down to 38.0% in 2 min); Detector, UV 254/220 nm. This resulted in 49.7 mg (41%) of the formic acid salt of 2-(dimethylamino)ethyl 1-(2-[3-[5-chloro-2-(difluoromethoxy)phenyl]-4-[pyrazolo[1,5-a]pyrimidine-3-amido]-1H-pyrazol-1-yl]acetyl)-4-methylpiperidine-4-carboxylate. LCMS (Method 28) $[M+H]^+$=659.2, $R_T$=1.23 min. $^1$H NMR (400 MHz, DMSO-$d_6$) δ: (ppm) 9.76 (s, 1H), 9.35 (dd, 1H, J=1.2, 7.2 Hz), 8.68-8.64 (m, 2H), 8.31 (s, 1H), 7.63 (dd, 1H, J=2.8, 8.8 Hz), 7.55 (d, 1H, J=2.8 Hz), 7.46 (d, 1H, J=9.2 Hz), 7.29 (dd, 1H, J=4.4, 6.8 Hz), 7.09 (t, 1H, J=73.2 Hz), 5.23 (s, 2H), 4.16 (t, 2H, J=5.6 Hz), 3.97-3.93 (m, 1H), 3.75-3.71 (m, 1H), 3.25-3.20 (m, 1H), 3.00-2.94 (m, 1H), 2.48-2.47 (m, 2H), 2.33 (s, 6H), 2.16-1.95 (m, 2H), 1.49-1.44 (m, 2H), 1.18 (s, 3H).

Example 341

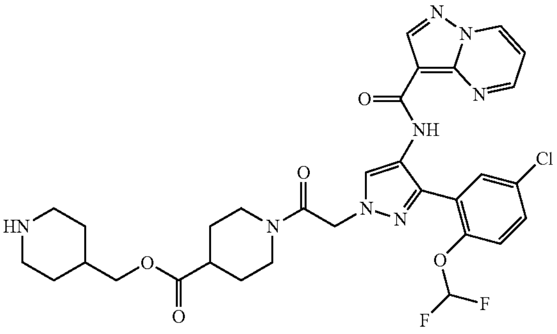 [SMILES: O=C(Nc1cn(CC(=O)N2CCC(C(=O)OCC3CCNCC3)CC2)nc1-c1cc(Cl)ccc1OC(F)F)c1cnn2cccnc12]

piperidin-4-ylmethyl 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylate To a solution of 1-(2-[3-[5-chloro-2-(difluoromethoxy) phenyl]-4-[pyrazolo[1,5-a]pyrimidine-3-amido]-1H-pyrazol-1-yl]acetyl)piperidine-4-carboxylic acid (150 mg, 0.26 mmol) in DMF (5 mL) was added tert-butyl 4-(hydroxymethyl)piperidine-1-carboxylate (281 mg, 1.31 mmol), 4-dimethylaminopyridine (10 mg, 0.08 mmol), HATU (120 mg, 0.32 mmol). The resulting solution was stirred at room temperature overnight. Then DIEA (68 mg, 0.53 mmol) was added. The resulting solution was stirred for an additional 3 h at room temperature and concentrated under vacuum. The residue was purified by flash chromatography on silica gel eluting with 3% MeOH in DCM. This resulted in 150 mg (74%) of [1-[(tert-butoxy)carbonyl]piperidin-4-yl]methyl 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylate as yellow oil. LCMS (Method 28) $[M+H]^+$=771.2, $R_T$=1.10 min.

A solution of [1-[(tert-butoxy)carbonyl]piperidin-4-yl]methyl 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylate (150 mg, 0.19 mmol) and saturated HCl dioxane solution (10 mL) was stirred at room temperature overnight. The resulting mixture was concentrated under vacuum. The resulting solution was diluted with 10 mL of methanol. The resulting mixture was concentrated under vacuum. The crude product was purified by Prep-HPLC with the following conditions (Prep-HPLC-005): Column, XBridge Prep C18 OBD Column, 5 um, 19*150 mm; mobile phase, water with 0.05% FA and MeCN (30.0% up to 33.0% in 10 min, up to 95.0% in 1 min, hold 95.0% in 1 min, down to 30.0% in 2 min); Detector, UV 254/220 nm. This resulted in 82.3 mg (59%) of the formic acid salt of piperidin-4-ylmethyl 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylate as a light yellow solid. LCMS (Method 20) $[M+H]^+$=671.3, $R_T$=1.58 min. $^1$H NMR (300 MHz, DMSO-$d_6$) δ: (ppm) 9.76 (s, 1H), 9.33 (dd, 1H, J=1.2, 6.9 Hz), 8.68-8.67 (m, 2H), 8.31 (s, 1H), 7.62 (dd, 1H, J=2.7, 8.7 Hz), 7.55 (d, 1H, J=2.7 Hz), 7.45 (d, 1H, J=8.7 Hz), 7.28 (dd, 1H, J=4.5, 7.2 Hz), 7.01 (t, 1H, J=73.5), 5.25-5.23 (m, 2H), 4.24-4.19 (m, 1H), 3.93-3.85 (m, 3H), 2.83-2.80 (m, 1H), 2.72-2.64 (m, 3H), 1.92-1.87 (m, 3H), 1.71-1.67 (m, 3H), 1.59-1.48 (m, 1H), 1.44-1.23 (m, 2H).

Example 342

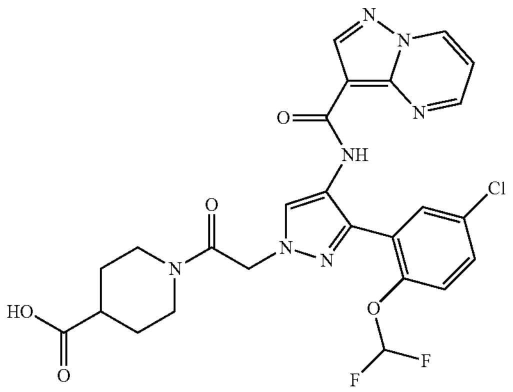 [SMILES: O=C(Nc1cn(CC(=O)N2CCC(C(=O)O)CC2)nc1-c1cc(Cl)ccc1OC(F)F)c1cnn2cccnc12]

1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylic acid To a solution of {3-(5-Chloro-2-difluoromethoxyphenyl)-4-[(pyrazolo[1,5-a]pyrimidine-3-carbonyl)amino]pyrazol-1-yl}acetic acid (500 mg, 1.08 mmol) in DMF (5 mL) was added methyl piperidine-4-carboxylate (232.1 mg, 1.62 mmol), DIEA (279.2 mg, 2.16 mmol), HATU (493.5 mg, 1.30 mmol). The resulting solution was stirred at room temperature overnight. The resulting mixture was concentrated under vacuum. The residue was purified by flash chromatography on silica gel eluting with 3% MeOH in DCM. This resulted in 500 mg (79%) of methyl 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylate as yellow oil. LCMS (Method 25) $[M+H]^+$=588.1, $R_T$=0.87 min.

$K_2CO_3$ (500 mg, 3.59 mmol) in $H_2O$ (5 mL) was added to methyl 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylate (500 mg, 0.85 mmol) in methanol (10 mL). The resulting solution was stirred at 50° C. overnight and acidified with 1 N HCl to pH 2. The solids were collected by filtration. The crude product was purified by Prep-HPLC with the following conditions (Prep-HPLC-005): Column, XBridge Prep C18 OBD Column, 5 um, 19*150 mm; mobile phase, water with 0.05% FA and MeCN (30.0% MeCN up to 34.0% in 10 min, up to 95.0% in 1 min, hold 95.0% in 1 min, down to 30.0% in 2 min); Detector, UV 254/220 nm. This resulted in 390 mg (80%) of 1-(2-[3-[5-chloro-2-(difluoromethoxy)phenyl]-4-[pyrazolo[1,5-a]pyrimidine-3-amido]-1H-pyrazol-1-yl]-acetyl)piperidine-4-carboxylic acid as a light yellow solid. LCMS (Method 28) $[M+H]^+$=574.1, $R_T$=1.11 min. $^1$H NMR (400 MHz, DMSO-$d_6$) δ: (ppm) 12.34 (s, 1H), 9.76 (s, 1H), 9.34 (dd, 1H, J=1.6, 7.2 Hz), 8.69-8.67 (m, 2H), 8.31 (s, 1H), 7.62 (dd, 1H, J=2.8, 8.8 Hz), 7.55 (d, 1H, J=2.4 Hz), 7.46 (d, 1H, J=8.8 Hz), 7.28 (dd, 1H, J=4.4, 6.8 Hz), 7.08 (t, 1H, J=73.2 Hz), 5.29-5.19 (m, 2H), 4.28-4.18 (m, 1H), 3.87-3.84 (m, 1H), 3.19-3.13 (m, 1H), 2.83-2.77 (m, 1H), 1.86-1.85 (m, 2H), 1.60-1.57 (m, 1H), 1.43-1.41 (m, 2H).

Example 343

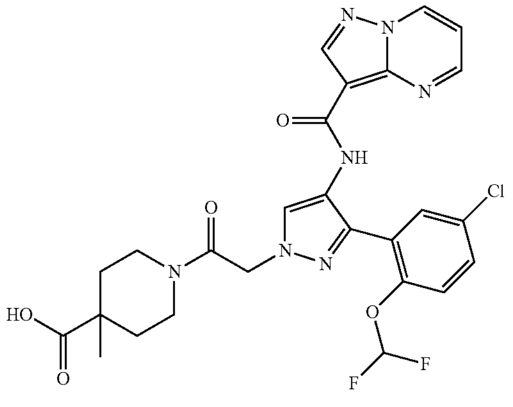 [SMILES: CC1(C(=O)O)CCN(C(=O)Cn2cc(NC(=O)c3cnn4cccnc34)c(-c3cc(Cl)ccc3OC(F)F)n2)CC1]

1-(2-[3-[5-chloro-2-(difluoromethoxy)phenyl]-4-[pyrazolo[1,5-a]pyrimidine-3-amido]-1H-pyrazol-1-yl]acetyl)-4-methylpiperidine-4-carboxylic acid To a solution of 2-[3-[5-chloro-2-(difluoromethoxy)phenyl]-4-[pyrazolo[1,5-a]pyrimidine-3-amido]-1H-pyrazol-1-yl]acetic acid (500 mg, 1.08 mmol) in DMF (4 mL) was added methyl 4-methylpiperidine-4-carboxylate (275 mg, 1.75 mmol), DIEA (419 mg, 3.24 mmol), HATU (494 mg, 1.30 mmol). The resulting solution was stirred for 4 h at room temperature. The resulting mixture was concentrated under vacuum. The residue was purified by flash chromatography on silica gel eluting with 3% MEOH in DCM. This resulted in 500 mg (77%) of methyl 1-(2-[3-[5-chloro-2-(difluoromethoxy)phenyl]-4-[pyrazolo[1,5-a]pyrimidine-3-amido]-1H-pyrazol-1-yl]acetyl)-4-methylpiperidine-4-carboxylate as yellow oil. LCMS (Method 25) $[M+H]^+$=602.1, $R_T$=0.92 min.

To a solution of methyl 1-(2-[3-[5-chloro-2-(difluoromethoxy)phenyl]-4-[pyrazolo[1,5-a]pyrimidine-3-amido]-1H-pyrazol-1-yl]acetyl)-4-methylpiperidine-4-carboxylate (500 mg, 0.83 mmol) in methanol (10 mL) was added a solution of potassium carbonate (700 mg, 5.06 mmol) in water (5 mL). The resulting solution was stirred at 60° C. overnight and acidified with 1 N HCl to pH 2. The solids were collected by filtration. The crude product was purified by Prep-HPLC with the following conditions (Prep-HPLC-005): Column, XBridge Prep C18 OBD Column, 5 um, 19*150 mm; mobile phase, water with 0.05% FA and MeCN (30.0% MeCN up to 35.0% in 10 min, up to 95.0% in 1 min, hold 95.0% in 1 min, down to 30.0% in 2 min); Detector, UV 254/220 nm. This resulted in 26.6 mg of 1-(2-[3-[5-chloro-2-(difluoromethoxy)phenyl]-4-[pyrazolo[1,5-a]pyrimidine-3-amido]-1H-pyrazol-1-yl]acetyl)-4-methylpiperidine-4-carboxylic acid as a white solid. LCMS (Method 20) $[M+H]^+$=588.2, $R_T$=2.79 min. $^1H$ NMR (400 MHz, DMSO-$d_6$) δ: (ppm) 12.5 (br, 1H), 9.76 (s, 1H), 9.34 (d, 1H, J=6.8 Hz), 8.69-8.68 (m, 2H), 8.32 (s, 1H), 7.63 (dd, 1H, J=2.8, 8.8 Hz), 7.56 (d, 1H, J=2.8 Hz), 7.46 (d, 1H, J=8.8 Hz), 7.29 (dd, 1H, J=4.4, 7.2 Hz), 7.08 (t, 1H, J=73.2 Hz), 5.28-5.18 (m, 2H), 3.96-3.93 (m, 1H), 3.74-3.70 (m, 1H), 3.26-3.23 (m, 1H), 3.01-2.95 (m, 1H), 1.98-1.93 (m, 2H), 1.46-1.30 (m, 2H), 1.18 (s, 3H).

Example 344

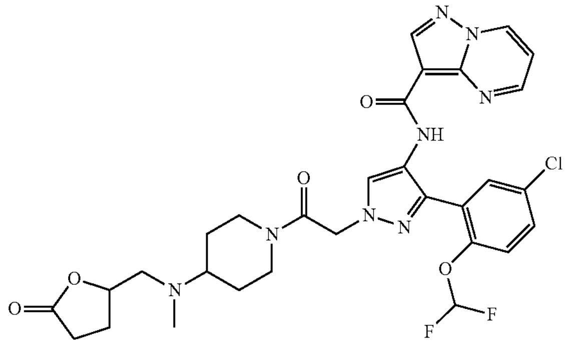 [SMILES: CN(CC1CCC(=O)O1)C1CCN(C(=O)Cn2cc(NC(=O)c3cnn4cccnc34)c(-c3cc(Cl)ccc3OC(F)F)n2)CC1]

N-[3-[5-chloro-2-(difluoromethoxy)phenyl]-1-[2-(4-[methyl[(5-oxooxolan-2-yl)methyl]amino]piperidin-1-yl)-2-oxoethyl]-1H-pyrazol-4-yl]pyrazolo[1,5-a]pyrimidine-3-carboxamide To a cold solution of 5-(hydroxymethyl)oxolan-2-one (100 mg, 0.86 mmol), DIEA (340 mg, 2.63 mmol) in DCM (5 mL) was added $Tf_2O$ (247 mg, 0.88 mmol) at 0° C. The resulting solution was stirred at room temperature for 3 h and quenched with saturated $Na_2CO_3$ solution. The resulting solution was extracted with dichloromethane (×3) and the organic layers combined. The combined organic layers were washed with brine., dried over anhydrous sodium sulfate and concentrated under vacuum. This resulted in 180 mg (84%) of (5-oxooxolan-2-yl)methyl trifluoromethanesulfonate as yellow oil.

To a solution of N-[3-[5-chloro-2-(difluoromethoxy)phenyl]-1-[2-[4-(methylamino)piperidin-1-yl]-2-oxoethyl]-1H-pyrazol-4-yl]pyrazolo[1,5-a]pyrimidine-3-carboxamide (100 mg, 0.18 mmol) in $CH_3CN$ (5 mL) was added DIEA (70 mg, 0.54 mmol) and (5-oxooxolan-2-yl)methyl trifluoromethanesulfonate (66.5 mg, 0.27 mmol). The resulting solution was stirred overnight at room temperature. The crude product was purified by Prep-HPLC with the following conditions (Prep-HPLC-005): Column, XBridge Prep C18 OBD Column, 5 um, 19*150 mm; mobile phase, water with 0.05% FA and MeCN (30.0% up to 36.0% in 10 min, up to 95.0% in 1 min, hold 95.0% in 1 min, down to 30.0% in 2 min); Detector, UV 254/220 nm. This resulted in 37 mg (31%) of N-[3-[5-chloro-2-(difluoromethoxy)phenyl]-1-[2-(4-[methyl[(5-oxooxolan-2-yl)methyl]amino]piperidin-1-yl)-2-oxoethyl]-1H-pyrazol-4-yl]pyrazolo[1,5-a]pyrimidine-3-carboxamide as a yellow solid. LCMS (Method 24) $[M+H]^+$=657.2, $R_T$=1.68 min. $^1H$ NMR (400 MHz, DMSO-$d_6$) δ: (ppm) 9.75 (s, 1H), 9.34 (dd, 1H, J=1.2, 7.2 Hz), 8.69-8.68 (m, 2H), 8.31 (s, 1H), 7.62 (dd, 1H, J=2.4, 8.8 Hz), 7.55 (d, 1H, J=2.8 Hz), 7.46 (d, 1H, J=8.8 Hz), 7.29 (dd, 1H, J=4.0, 6.8 Hz), 7.09 (t, 1H, J=73.2 Hz), 5.24-5.17 (m, 2H), 4.58-4.54 (m, 1H), 4.41-4.38 (m, 1H), 3.98-3.95 (m, 1H), 3.16-3.03 (m, 1H), 2.69-2.55 (m, 4H), 2.46-2.44 (m, 2H), 2.26 (s, 3H), 2.24-2.16 (m, 1H), 1.88-1.83 (m, 1H), 1.79-1.71 (m, 2H), 1.48-1.44 (m, 1H), 1.29-1.21 (m, 1H).

Example 345

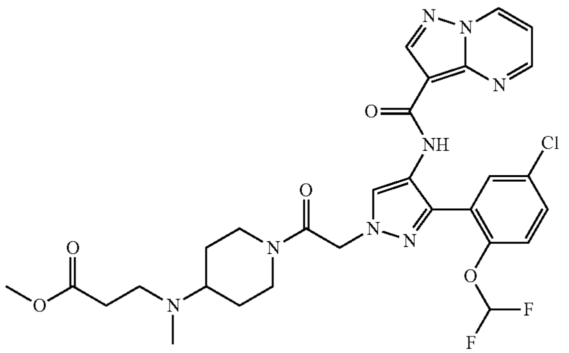 [SMILES: COC(=O)CCN(C)C1CCN(C(=O)Cn2cc(NC(=O)c3cnn4cccnc34)c(-c3cc(Cl)ccc3OC(F)F)n2)CC1]

methyl 3-[[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl](methyl)amino]propanoate To a solution of tert-butyl 4-aminopiperidine-1-carboxylate (1.00 g, 4.99 mmol) in $CH_3CN$ (20 mL) was added potassium carbonate (1.38 g, 9.99 mmol) and methyl 3-bromopropanoate (3.34 g, 20.00 mmol). The resulting solution was heated to reflux for 20 h and cooled to room temperature. Water (100 mL) and DCM (100 mL) was added. Phases were separated. The aqueous phase was extracted with DCM. The combined organic layers were washed with brine, dried over anhydrous sodium sulfate and concentrated under vacuum. The residue was purified by flash chromatography on silica gel eluting with 4% MeOH in DCM. This resulted in 300 mg (21%) of tert-butyl 4-[(3-methoxy-3-oxopropyl)amino]piperidine-1-carboxylate as yellow oil. LCMS (Method 20) $[M+H]^+$=287.0, $R_T$=1.06 min.

To a solution of tert-butyl 4-[(3-methoxy-3-oxopropyl)amino]piperidine-1-carboxylate (300 mg, 1.05 mmol) in methanol (10 mL) was added polyformaldehyde (HCHO)n (90 mg, 3.00 mmol). The reaction mixture was stirred at room temperature for 6 hr, then $NaBH_3CN$ (130 mg, 2.07 mmol) was added. The resulting solution was stirred at room temperature overnight and quenched with water (0.5 mL). The resulting mixture was concentrated under vacuum. The residue was purified by flash chromatography on silica gel eluting with 4% MeOH in DCM. This resulted in 300 mg (crude) of tert-butyl 4-[(3-methoxy-3-oxopropyl)(methyl)amino]piperidine-1-carboxylate as yellow oil. LCMS (Method 20) $[M+H]^+$=301.0, $R_T$=1.08 min.

A solution of tert-butyl 4-[(3-methoxy-3-oxopropyl)(methyl)amino]piperidine-1-carboxylate (300 mg, 1.00 mmol) and saturated HCl dioxane solution (10 mL) was stirred at room temperature overnight. The resulting mixture was concentrated under vacuum. This resulted in 300 mg (crude) of methyl 3-[methyl(piperidin-4-yl)amino]propanoate hydrochloride as a white solid. LCMS (Method 20) $[M+H]^+$=201.0, $R_T$=0.31 min.

To a solution of {3-(5-Chloro-2-difluoromethoxyphenyl)-4-[(pyrazolo[1,5-a]pyrimidine-3-carbonyl)amino]pyrazol-1-yl}acetic acid trifluoroacetate (100 mg, 0.17 mmol) in DMF (3 mL) was added methyl 3-[methyl(piperidin-4-yl)amino]propanoate hydrochloride (62 mg, 0.26 mmol), DIEA (67.2 mg, 0.52 mmol), HATU (79.2 mg, 0.21 mmol). The resulting solution was stirred at room temperature overnight and concentrated under vacuum. The residue was passed through a short pad of silica gel eluting with ethyl acetate/petroleum ether (10:1). The crude product was purified by Prep-HPLC with the following conditions (Prep-HPLC-005): Column, XBridge Prep $C_{18}$ OBD Column, 5 um, 19*150 mm; mobile phase, water with 0.05% FA and MeCN (37.0% up to 43.0% in 10 min, up to 95.0% in 1 min, hold 95.0% in 1 min, down to 37.0% in 2 min); Detector, UV 254/220 nm. This resulted in 45.2 mg (38%) of the formic acid salt of methyl 3-[[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl](methyl)amino]propanoate as an off-white solid. LCMS (Method 24) $[M+H]^+$=645.2, $R_T$=1.64 min. $^1H$ NMR (300 MHz, DMSO-$d_6$) δ: (ppm) 9.75 (s, 1H), 9.35 (dd, 1H, J=1.5, 6.9 Hz), 8.69-8.68 (m, 2H), 8.31 (s, 1H), 7.63 (dd, 1H, J=2.7, 8.7 Hz), 7.55 (d, 1H, J=2.7 Hz), 7.46 (d, 1H, J=8.7 Hz), 7.29 (dd, 1H, J=4.5, 7.2 Hz), 7.04 (t, 1H, J=73.2 Hz), 5.33-5.27 (m, 2H), 4.52-4.48 (m, 1H), 4.10-4.06 (m, 1H), 3.66 (s, 3H), 3.51-3.34 (m, 2H), 3.16-3.08 (m, 2H), 2.86-2.51 (m, 6H), 2.28-1.99 (m, 2H), 1.73-1.70 (m, 1H), 1.55-1.45 (m, 1H).

Example 346

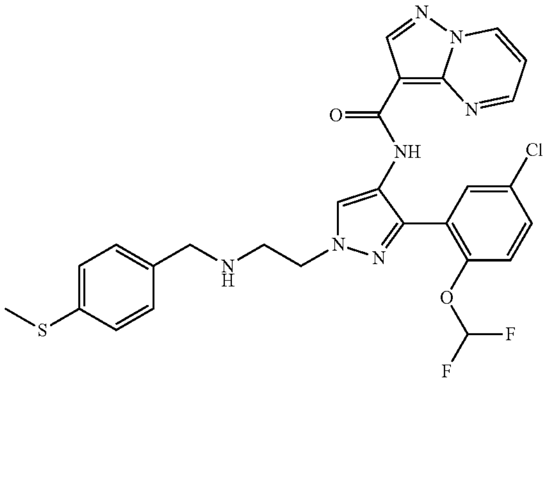 [SMILES: CSc1ccc(CNCCn2cc(NC(=O)c3cnn4cccnc34)c(-c3cc(Cl)ccc3OC(F)F)n2)cc1]

N-[3-[5-chloro-2-(difluoromethoxy)phenyl]-1-[2-([[4-(methylsulfanyl)phenyl]methyl]amino)ethyl]-1H-pyrazol-4-yl]pyrazolo[1,5-a]pyrimidine-3-carboxamide formate To a solution of N-[1-(2-aminoethyl)-3-[5-chloro-2-(difluoromethoxy)phenyl]-1H-pyrazol-4-yl]pyrazolo[1,5-a]pyrimidine-3-carboxamide (130 mg, 0.29 mmol) in methanol (5 mL) was added 4-(methylsulfanyl)benzaldehyde (66.3 mg, 0.44 mmol). The mixture was stirred for 2 hr, then $NaBH_3CN$ (27.5 mg, 0.44 mmol) was added. The resulting solution was stirred at room temperature overnight and quenched with water (1 mL). The resulting mixture was concentrated under vacuum. The crude product was purified by Prep-HPLC with the following conditions (Prep-HPLC-005): Column, XBridge Prep C18 OBD Column, 5 um, 19*150 mm; mobile phase, water with 0.05% FA and MeCN (30.0% up to 37.0% in 10 min, up to 95.0% in 1 min, hold 95.0% in 1 min, down to 30.0% in 2 min); Detector, UV 254/220 nm. This resulted in 39.6 mg (23%) of the formic acid salt of N-[3-[5-chloro-2-(difluoromethoxy)phenyl]-1-[2-([[4-(methylsulfanyl)phenyl]methyl]amino)-ethyl]-1H-pyrazol-4-yl]pyrazolo[1,5-a]pyrimidine-3-carboxamide as a light yellow solid. LCMS (Method 20) $[M+H]^+$=584.2, $R_T$=2.23 min. $^1H$ NMR (400 MHz, DMSO-$d_6$) δ: (ppm) 9.74 (s, 1H), 9.34 (dd, 1H, J=1.6, 7.2 Hz), 8.69-8.67 (m, 2H), 8.37 (s, 1H), 7.61 (dd, 1H, J=2.8, 8.8 Hz), 7.59 (d, 1H, J=2.8 Hz), 7.44 (d, 1H, J=8.8 Hz), 7.31-7.27 (m, 3H), 7.18 (d, 2H, J=8.0 Hz), 7.07 (t, 1H, J=73.6 Hz), 4.25 (t, 2H, J=5.2 Hz), 3.70 (s, 2H), 2.95-2.92 (m, 2H), 2.50 (s, 3H).

Example 347

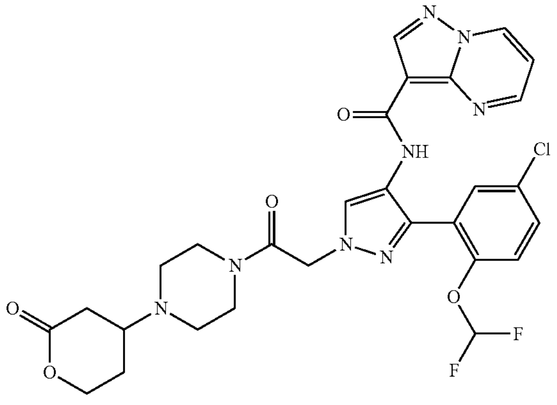 [SMILES: O=C1CC(N2CCN(C(=O)Cn3cc(NC(=O)c4cnn5cccnc45)c(-c4cc(Cl)ccc4OC(F)F)n3)CC2)CCO1]

N-[3-[5-chloro-2-(difluoromethoxy)phenyl]-1-[2-oxo-2-[4-(2-oxooxan-4-yl)piperazin-1-yl]ethyl]-1H-pyrazol-4-yl]pyrazolo[1,5-a]pyrimidine-3-carboxamide To a solution of tert-butyl piperazine-1-carboxylate (500 mg, 2.68 mmol) in MeOH (20 mL) was added 5,6-dihydro-2H-pyran-2-one (530 mg, 5.40 mmol). The resulting solution was stirred at room temperature for 20 h. The resulting mixture was concentrated under vacuum. The residue was purified by flash chromatography on silica gel eluting with 3% MeOH in DCM. This resulted in 550 mg (72%) of tert-butyl 4-(2-oxooxan-4-yl)piperazine-1-carboxylate as yellow oil. LCMS (Method 28) $[M+H]^+$=285.0, $R_T$=0.53 min.

A mixture of tert-butyl 4-(2-oxooxan-4-yl)piperazine-1-carboxylate (550 mg, 1.93 mmol) and saturated HCl dioxane solution (10 mL) was stirred overnight at room temperature. The solids were collected by filtration. This resulted in 335 mg (78%) of 4-(piperazin-1-yl)oxan-2-one hydrochloride as a white solid.

To a solution of {3-(5-Chloro-2-difluoromethoxyphenyl)-4-[(pyrazolo[1,5-a]pyrimidine-3-carbonyl)amino]pyrazol-1-yl}acetic acid trifluoroacetate (100 mg, 0.17 mmol) in DMF (3 mL) was added 4-(piperazin-1-yl)oxan-2-one hydrochloride (76 mg, 0.34 mmol), DIEA (67.2 mg, 0.52 mmol), HATU (79.2 mg, 0.21 mmol). The resulting solution was stirred at room temperature overnight and concentrated under vacuum. The crude product was purified by Prep-HPLC with the following conditions (Prep-HPLC-005): Column, XBridge Prep $C_{18}$ OBD Column, 5 um, 19*150 mm; mobile phase, water with 0.05% FA and MeCN (35.0% up to 39.0% in 10 min, up to 95.0% in 1 min, hold 95.0% in 1 min, down to 35.0% in 2 min); Detector, UV 254/220 nm. This resulted in 14.5 mg (13%) of N-[3-[5-chloro-2-(difluoromethoxy)phenyl]-1-[2-oxo-2-[4-(2-oxooxan-4-yl)piperazin-1-yl]ethyl]-1H-pyrazol-4-yl]pyrazolo[1,5-a]pyrimidine-3-carboxamide as a white solid. LCMS (Method 28) $[M+H]^+$=629.1, $R_T$=1.44 min. $^1H$ NMR (400 MHz, DMSO-$d_6$) δ: (ppm) 9.76 (s, 1H), 9.34 (dd, 1H, J=2.0, 7.2 Hz), 8.69-8.68 (m, 2H), 8.31 (s, 1H), 7.62 (dd, 1H, J=2.8, 8.8 Hz), 7.55 (d, 1H, J=2.8 Hz), 7.45 (d, 1H, J=8.8 Hz), 7.28 (dd, 1H, J=4.4, 7.2 Hz), 7.08 (t, 1H, J=73.2 Hz), 5.24 (s, 2H), 4.35-4.29 (m, 1H), 4.19-4.16 (m, 1H), 3.50-3.32 (m, 6H), 3.02-2.99 (m, 1H), 2.69-2.51 (m, 4H), 2.08-1.98 (m, 1H), 1.77-1.75 (m, 1H).

Example 348

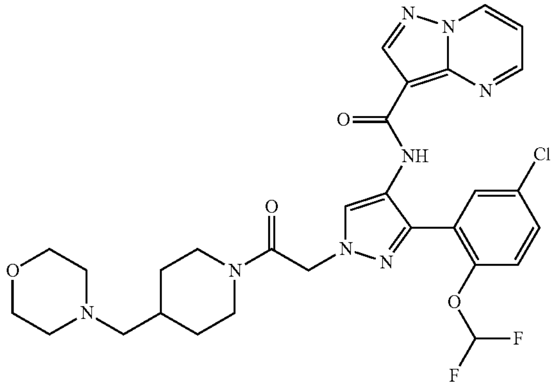 [SMILES: O=C(Nc1cn(CC(=O)N2CCC(CN3CCOCC3)CC2)nc1-c1cc(Cl)ccc1OC(F)F)c1cnn2cccnc12]

N-[3-[5-chloro-2-(difluoromethoxy)phenyl]-1-[2-[4-(morpholin-4-ylmethyl)piperidin-1-yl]-2-oxoethyl]-1H-pyrazol-4-yl]pyrazolo[1,5-a]pyrimidine-3-carboxamide To a solution of tert-butyl 4-formylpiperidine-1-carboxylate (1.00 g, 4.69 mmol) in MeOH (10 mL) was added morpholine (613 mg, 7.04 mmol). The resulting mixture was stirred for 6 hr, then $NaBH_3CN$ (444 mg, 7.07 mmol) was added. The resulting solution was stirred at room temperature overnight and quenched with $H_2O$ (1 mL). The resulting mixture was concentrated under vacuum. The residue was purified by flash chromatography on silica gel eluting with 3% MeOH in DCM. This resulted in 1.0 g (75%) of tert-butyl 4-(morpholin-4-ylmethyl) piperidine-1-carboxylate as yellow oil. LCMS (Method 25) $[M+H]^+$=285.0, $R_T$=0.59 min.

A solution of tert-butyl 4-(morpholin-4-ylmethyl)piperidine-1-carboxylate (1.0 g, 3.52 mmol) and saturated HCl dioxane solution (20 mL) was stirred at room temperature overnight. This resulted in 660 mg (85%) of 4-(piperidin-4-ylmethyl)morpholine hydrochloride as a white solid. LCMS (Method 20) $[M+H]^+$=185.0, $R_T$=0.30 min.

To a solution of {3-(5-Chloro-2-difluoromethoxyphenyl)-4-[(pyrazolo[1,5-a]pyrimidine-3-carbonyl)amino]pyrazol-1-yl}acetic acid (150 mg, 0.26 mmol) in DMF (2 mL) was added 4-(piperidin-4-ylmethyl)morpholine hydrochloride (69 mg, 0.31 mmol), DIEA (101.2 mg, 0.78 mmol), HATU (119.2 mg, 0.31 mmol). The resulting solution was stirred at room temperature overnight. The resulting mixture was concentrated under vacuum. The crude product was purified by Prep-HPLC with the following conditions (Prep-HPLC-005): Column, XBridge Prep C18 OBD Column, 5 um, 19*150 mm; mobile phase, water with 10 mmol $NH_4HCO_3$ and MeCN (25.0% MeCN up to 36.0% in 10 min, up to 95.0% in 1 min, hold 95.0% in 1 min, down to 25.0% in 2 min); Detector, UV 254/220 nm. This resulted in 61 mg (37%) of N-[3-[5-chloro-2-(difluoromethoxy)phenyl]-1-[2-[4-(morpholin-4-ylmethyl)piperidin-1-yl]-2-oxoethyl]-1H-pyrazol-4-yl]pyrazolo[1,5-a]pyrimidine-3-carboxamide as a solid. LCMS (Method 20) $[M+H]^+$=629.2, $R_T$=1.55 min. $^1H$ NMR (400 MHz, DMSO-$d_6$) δ: (ppm) 9.75 (s, 1H), 9.34 (dd, 1H, J=1.6, 7.2 Hz), 8.69-8.68 (m, 2H), 8.30 (s, 1H), 7.62 (dd, 1H, J=2.8, 8.8 Hz), 7.55 (d, 1H, J=2.4), 7.45 (d, 1H, J=8.8 Hz), 7.28 (dd, 1H, J=4.0, 6.8 Hz), 7.08 (t, 1H, J=73.2 Hz), 5.27-5.16 (m, 2H), 4.34-4.30 (m, 1H), 3.92-3.89 (m, 1H), 3.56 (t, 4H, J=4.2 Hz), 3.17-3.06 (m, 1H), 2.67-2.59 (m, 1H), 2.39-2.25 (m, 4H), 2.13-2.12 (m, 2H), 1.90-1.71 (m, 3H), 1.20-1.08 (m, 1H), 0.97-0.95 (m, 1H).

Example 349

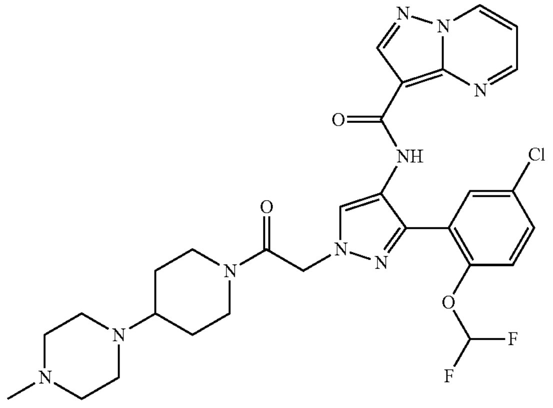 [SMILES: CN1CCN(C2CCN(C(=O)Cn3cc(NC(=O)c4cnn5cccnc45)c(-c4cc(Cl)ccc4OC(F)F)n3)CC2)CC1]

N-[3-[5-chloro-2-(difluoromethoxy)phenyl]-1-[2-[4-(4-methylpiperazin-1-yl)piperidin-1-yl]-2-oxoethyl]-1H-pyrazol-4-yl]pyrazolo[1,5-a]pyrimidine-3-carboxamide To a solution of tert-butyl 4-oxopiperidine-1-carboxylate (1.00 g, 5.02 mmol) in MeOH (50 mL) was added 1-methylpiperazine (1.0 g, 9.98 mmol) and AcOH (0.1 mL, 1.75 mmol). The reaction was stirred 3 h and $NaBH_3CN$ (378 mg, 6.02 mmol) was added. The resulting solution was stirred at room temperature for 12 h. The reaction was then and quenched with saturated $NH_4Cl$ (2 mL). The resulting mixture was concentrated under vacuum. The residue was purified by flash chromatography on silica gel eluting with 8% MeOH in DCM. This resulted in 800 mg (39%) of tert-butyl 4-(4-methylpiperazin-1-yl)piperidine-1-carboxylate as light yellow oil. LCMS (Method 20) $[M+H]^+$=284.0, $R_T$=0.97 min.

A solution of tert-butyl 4-(4-methylpiperazin-1-yl)piperazine-1-carboxylate (800 mg, 1.97 mmol) and saturated HCl dioxane solution (15 mL) was stirred at room temperature for 3 h. The solids were collected by filtration and dried. This resulted in 600 mg (83%) of 1-methyl-4-(piperazin-1-yl)piperazine hydrochloride as a white solid. LCMS (Method 20) $[M+H]^+$=184.0, $R_T$=0.32 min.

To a solution of {3-(5-Chloro-2-difluoromethoxyphenyl)-4-[(pyrazolo[1,5-a]pyrimidine-3-carbonyl)amino]pyrazol-1-yl}acetic acid (200 mg, 0.35 mmol) in DMF (4 mL) was added 1-methyl-4-(piperidin-4-yl)piperazine hydrochloride (170 mg, 0.77 mmol), DIEA (134.4 mg, 1.04 mmol), HATU (160 mg, 0.42 mmol). The resulting solution was stirred at room temperature overnight. The resulting mixture was concentrated under vacuum. The crude product was purified by Prep-HPLC with the following conditions (Prep-HPLC-005): Column, XBridge Prep C18 OBD Column, 5 um, 19*150 mm; mobile phase, water with 0.05% FA and MeCN (25.0% up to 34.0% in 10 min, up to 95.0% in 1 min, hold 95.0% in 1 min, down to 25.0% in 2 min); Detector, UV 254/220 nm. This resulted in 74.3 mg (32%) of N-[3-[5-chloro-2-(difluoromethoxy)phenyl]-1-[2-[4-(4-methylpiperazin-1-yl)piperidin-1-yl]-2-oxoethyl]-1H-pyrazol-4-yl]pyrazolo[1,5-a]pyrimidine-3-carboxamide formate as an off-white solid. LCMS (Method 20) $[M+H]^+$=628.2, $R_T$=2.20 min. $^1$H NMR (400 MHz, DMSO-$d_6$) δ: (ppm) 9.76 (s, 1H), 9.36-9.34 (dd, 1H, J=1.6, 7.2 Hz), 8.69-8.68 (m, 2H), 8.31 (s, 1H), 7.63 (dd, 1H, J=2.4, 8.8 Hz), 7.55 (d, 1H, J=2.4 Hz), 7.46 (d, 1H, J=9.2 Hz), 7.29 (dd, 1H, J=4.0, 6.8 Hz), 7.09 (t, 1H, J=73.2 Hz), 5.25-5.21 (m, 2H), 4.36-4.29 (m, 1H), 3.98-3.79 (m, 1H), 3.10-3.00 (m, 1H), 2.69-2.51 (m, 1H), 2.49-2.32 (m, 8H), 2.18 (s, 3H), 1.91-1.86 (m, 2H), 1.47-1.41 (m, 1H), 1.39-1.25 (m, 1H).

Example 350

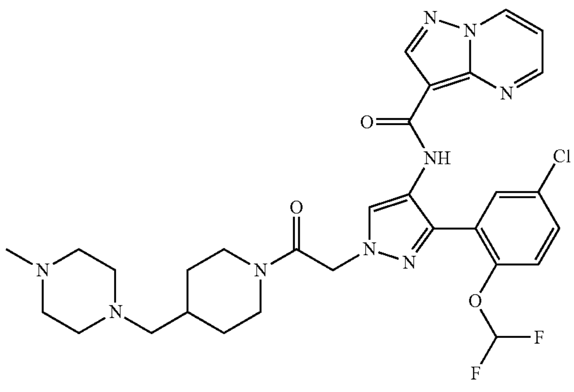 [SMILES: CN1CCN(CC2CCN(C(=O)Cn3cc(NC(=O)c4cnn5cccnc45)c(-c4cc(Cl)ccc4OC(F)F)n3)CC2)CC1]

N-[3-[5-chloro-2-(difluoromethoxy)phenyl]-1-(2-[4-[(4-methylpiperazin-1-yl)methyl]piperidin-1-yl]-2-oxoethyl)-1H-pyrazol-4-yl]pyrazolo[1,5-a]pyrimidine-3-carboxamide A solution of tert-butyl 4-formylpiperidine-1-carboxylate (1 g, 4.69 mmol) and 1-methylpiperazine (703 mg, 7.02 mmol) in methanol (10 mL) was stirred for 6 h, then $NaBH_3CN$ (444 mg, 7.07 mmol) was added. The resulting solution was stirred at room temperature overnight and quenched with water (1 mL). The resulting mixture was concentrated under vacuum. The residue was purified by flash chromatography on silica gel eluting with 5% MeOH in DCM. This resulted in 1.1 g (79%) of tert-butyl 4-[(4-methylpiperazin-1-yl)methyl]piperidine-1-carboxylate as yellow oil. LCMS (Method 28) $[M+H]^+$=298.0, $R_T$=0.46 min.

A mixture of tert-butyl 4-[(4-methylpiperazin-1-yl)methyl]piperidine-1-carboxylate (1.1 g, 3.70 mmol) and saturated HCl dioxane solution (20 mL) was stirred at room temperature overnight. The solids were collected by filtration. This resulted in 560 mg (65%) of 1-methyl-4-(piperidin-4-ylmethyl)piperazinehydrochloride as a white solid. LCMS (Method 20) $[M+H]^+$=198.0, $R_T$=0.32 min.

To a solution of {3-(5-Chloro-2-difluoromethoxyphenyl)-4-[(pyrazolo[1,5-a]pyrimidine-3-carbonyl)amino]pyrazol-1-yl}acetic acid (100 mg) in DMF (2 mL) was added 1-methyl-4-(piperidin-4-ylmethyl)piperazine hydrochloride (49 mg, 0.21 mmol), DIEA (67.2 mg, 0.52 mmol), HATU (79.2 mg, 0.21 mmol). The resulting solution was stirred at room temperature overnight and concentrated under vacuum. The crude product was purified by Prep-HPLC with the following conditions (Prep-HPLC-005): Column, XBridge Prep C18 OBD Column, 5 um, 19*150 mm; mobile phase, water with 10 mmol $NH_4HCO_3$ and MeCN (20.0% MeCN up to 30.0% in 10 min, up to 95.0% in 1 min, hold 95.0% in 1 min, down to 20.0% in 2 min); Detector, UV 254/220 nm. This resulted in 52.7 mg (47%) of N-[3-[5-chloro-2-(difluoromethoxy)phenyl]-1-(2-[4-[(4-methylpiperazin-1-yl)methyl]piperidin-1-yl]-2-oxoethyl)-1H-pyrazol-4-yl]pyrazolo[1,5-a]pyrimidine-3-carboxamide as an off-white solid. LCMS (Method 24) $[M+H]^+$=642.2, $R_T$=1.55 min. $^1$H NMR (400 MHz, DMSO-$d_6$) δ: (ppm) 9.76 (s, 1H), 9.34 (dd, 1H, J=1.6, 7.2 Hz), 8.69-8.68 (m, 2H), 8.30 (s, 1H), 7.62 (dd, 1H, J=2.4, 8.8 Hz), 7.54 (d, 1H, J=2.8 Hz), 7.45 (d, 1H, J=8.8 Hz), 7.28 (dd, 1H, J=4.4, 6.8 Hz), 7.08 (t, 1H, J=73.2 Hz), 5.26-5.16 (m, 2H), 4.37-4.30 (m, 1H), 3.93-3.87 (m, 1H), 3.11-3.05 (m, 1H), 2.67-2.59 (m, 1H), 2.49-2.23 (m, 8H), 2.16-2.12 (m, 5H), 1.83-1.71 (m, 3H), 1.10-1.07 (m, 1H), 0.97-0.88 (m, 1H).

Example 351

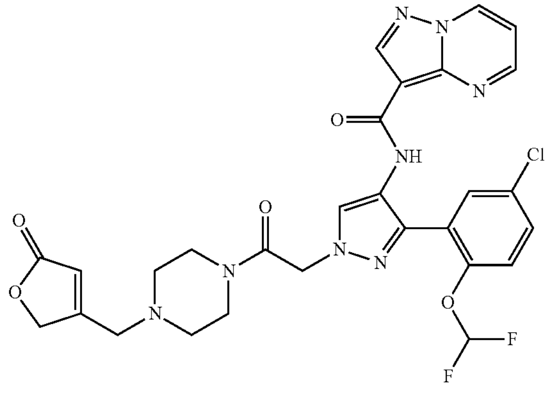 [SMILES: O=C1C=C(CN2CCN(C(=O)Cn3cc(NC(=O)c4cnn5cccnc45)c(-c4cc(Cl)ccc4OC(F)F)n3)CC2)CO1]

N-[3-[5-chloro-2-(difluoromethoxy)phenyl]-1-(2-oxo-2-[4-[(5-oxo-2,5-dihydrofuran-3-yl)methyl]piperazin-1-yl]ethyl)-1H-pyrazol-4-yl]pyrazolo[1,5-a]pyrimidine-3-carboxamide To a solution of N-[3-[5-chloro-2-(difluoromethoxy)phenyl]-1-[2-oxo-2-(piperazin-1-yl)ethyl]-1H-pyrazol-4-yl]pyrazolo[1,5-a]pyrimidine-3-carboxamide (100 mg, 0.19 mmol) in DMF (3 mL) was added DIEA (48.8 mg, 0.38 mmol), 4-(bromomethyl)-2,5-dihydrofuran-2-one (66.4 mg, 0.38 mmol). The resulting solution was stirred at room temperature for 4 h and concentrated under vacuum. The crude product was purified by Prep-HPLC with the following conditions (Prep-HPLC-005): Column, XBridge Prep C18 OBD Column, 5 um, 19*150 mm; mobile phase, water with 0.05% FA and MeCN (34.0% up to 39.0% in 10 min, up to 95.0% in 1 min, hold 95.0% in 1 min, down to 34.0% in 2 min); Detector, UV 254/220 nm. This resulted in 53.4 mg (45%) of N-[3-[5-chloro-2-(difluoromethoxy)phenyl]-1-(2-oxo-2-[4-[(5-oxo-2,5-dihydrofuran-3-yl)methyl]piperazin-1-yl]ethyl)-1H-pyrazol-4-yl]pyrazolo[1,5-a]pyrimidine-3-carboxamide as a light yellow solid. LCMS (Method 24) $[M+H]^+=627.1$, $R_T=1.55$ min. $^1H$ NMR (400 MHz, DMSO-$d_6$) δ: (ppm) 9.76 (s, 1H), 9.35 (d, 1H, J=6.8 Hz), 8.69-8.68 (m, 2H), 8.31 (s, 1H), 7.63 (dd, 1H, J=2.4, 8.8 Hz), 7.55 (d, 1H, J=2.4 Hz), 7.46 (d, 1H, J=9.2 Hz), 7.29 (dd, 1H, J=4.2, 7.0 Hz), 7.09 (t, 1H, J=73.2 Hz), 6.12 (s, 1H), 5.25 (s, 2H), 4.91 (s, 2H), 3.51 (t, 4H, J=5.4 Hz), 3.41 (s, 2H), 2.50-2.40 (m, 4H).

Example 352

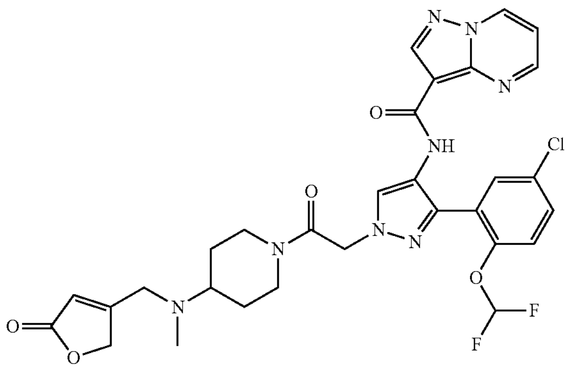 [SMILES: CN(CC1=CC(=O)OC1)C1CCN(C(=O)Cn2cc(NC(=O)c3cnn4cccnc34)c(-c3cc(Cl)ccc3OC(F)F)n2)CC1]

N-[3-[5-chloro-2-(difluoromethoxy)phenyl]-1-[2-(4-[methyl[(5-oxo-2,5-dihydrofuran-3-yl)methyl]amino]piperidin-1-yl)-2-oxoethyl]-1H-pyrazol-4-yl]pyrazolo[1,5-a]pyrimidine-3-carboxamide To a solution of N-[3-[5-chloro-2-(difluoromethoxy)phenyl]-1-[2-[4-(methylamino)piperidin-1-yl]-2-oxoethyl]-1H-pyrazol-4-yl]pyrazolo[1,5-a]pyrimidine-3-carboxamide (100 mg, 0.18 mmol) in DMF (4 mL) was added DIEA (46 mg, 0.36 mmol), 4-(bromomethyl)-2,5-dihydrofuran-2-one (63 mg, 0.36 mmol). The resulting solution was stirred at room temperature overnight. The resulting mixture was concentrated under vacuum. The crude product was purified by Prep-HPLC with the following conditions (Prep-HPLC-005): Column, XBridge Prep C18 OBD Column, 5 um, 19*150 mm; mobile phase, water with 0.05% FA and MeCN (40.0% up to 48.0% in 10 min, up to 95.0% in 1 min, hold 95.0% in 1 min, down to 40.0% in 2 min); Detector, UV 254/220 nm. This resulted in 15.5 mg (13%) of N-[3-[5-chloro-2-(difluoromethoxy)phenyl]-1-[2-(4-[methyl[(5-oxo-2,5-dihydrofuran-3-yl)methyl]amino]piperidin-1-yl)-2-oxoethyl]-1H-pyrazol-4-yl]pyrazolo[1,5-a]pyrimidine-3-carboxamide as a white solid. LCMS (Method 20) $[M+H]^+=655.2$, $R_T=1.91$ min. $^1H$ NMR (400 MHz, DMSO-$d_6$) δ: (ppm) 9.76 (s, 1H), 9.34 (dd, 1H, J=1.6, 7.2 Hz), 8.69-8.68 (m, 2H), 8.31 (s, 1H), 7.62 (dd, 1H, J=2.8, 8.8 Hz), 7.55 (d, 1H, J=2.8 Hz), 7.46 (d, 1H, J=9.2 Hz), 7.28 (dd, 1H, J=4.4, 7.2 Hz), 7.09 (t, 1H, J=73.2 Hz), 6.04 (s, 1H), 5.24-5.22 (m, 2H), 4.86 (d, 2H, J=1.2 Hz), 4.39-3.37 (m, 1H), 4.01-3.93 (m, 1H), 3.47 (s, 2H), 3.10-3.01 (m, 1H), 2.67-2.62 (m, 2H), 2.20 (s, 3H), 1.76-1.73 (m, 2H), 1.56-1.42 (m, 1H), 1.40-1.29 (m, 1H).

Example 353

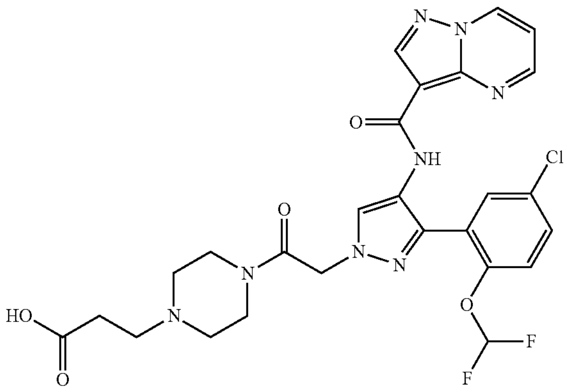 [SMILES: O=C(O)CCN1CCN(C(=O)Cn2cc(NC(=O)c3cnn4cccnc34)c(-c3cc(Cl)ccc3OC(F)F)n2)CC1]

3-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]propanoic acid To a solution of {3-(5-Chloro-2-difluoromethoxyphenyl)-4-[(pyrazolo[1,5-a]pyrimidine-3-carbonyl)amino]pyrazol-1-yl}acetic acid (200 mg, 0.35 mmol) in DMF (4 mL) was added ethyl 3-(piperazin-1-yl)propanoate hydrochloride (90 mg, 0.40 mmol), DIEA (179.25 mg, 1.39 mmol), HATU (158.20 mg, 0.42 mmol). The resulting solution was stirred at room temperature for 6 h. The resulting mixture was concentrated under vacuum. The residue was purified by flash chromatography on silica gel eluting with 10% MeOH in DCM. This resulted in 270 mg (crude) of ethyl 3-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]propanoate as a yellow solid. LCMS (Method 28) $[M+H]^+=631.2$, $R_T=0.66$ min.

To a solution of ethyl 3-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]propanoate (270 mg, 0.43 mmol) in ethanol (10 mL) was added KOH (200 mg, 3.56 mmol) and water (4 mL). The resulting solution was stirred at room temperature for 1 h and neutralized with 1 N HCl solution. The resulting mixture was concentrated under vacuum. The crude product was purified by Prep-HPLC with the following conditions (Prep-HPLC-005): Column, XBridge Prep C18 OBD Column, 5 um, 19*150 mm; mobile phase, water with 0.05% FA and MeCN (27.0% up to 35.0% in 10 min, up to 95.0% in 1 min, hold 95.0% in 1 min, down to 27.0% in 2 min); Detector, UV 254/220 nm. This resulted in 31.5 mg (11%) of the formic acid salt of 3-[4-(2-[3-[5-chloro-2-(difluoromethoxy)phenyl]-4-[pyrazolo[1,5-a]pyrimidine-3-amido]-1H-pyrazol-1-yl]-acetyl)piperazin-1-yl]propanoic acid as a off-white solid. LCMS (Method 28) $[M+H]^+$=603.1, $R_T$=0.81 min. $^1$H NMR (400 MHz, DMSO-$d_6$) δ: (ppm) 9.76 (s, 1H), 9.34 (dd, 1H, J=1.4, 7.0 Hz), 8.69-8.67 (m, 2H), 8.31 (s, 1H), 7.62 (dd, 1H, J=2.8, 8.8 Hz), 7.55 (d, 1H, J=2.4 Hz), 7.46 (d, 1H, J=8.4 Hz), 7.28 (dd, 1H, J=4.2, 7.0 Hz), 7.08 (t, 1H, J=73.6 Hz), 5.24 (s, 1H), 3.50-3.47 (m, 4H), 2.57 (t, 2H, J=7.2 Hz), 2.49-2.39 (m, 6H).

Example 354

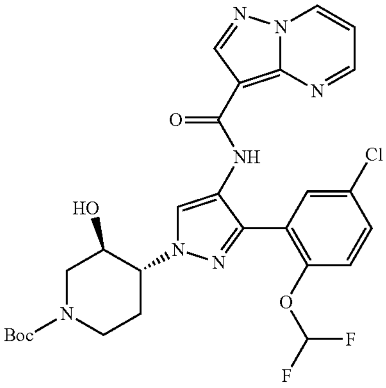

Assumed tert-butyl (3R,4R)-4-[3-[5-chloro-2-(difluoromethoxy)phenyl]-4-[pyrazolo[1,5-a]pyrimidine-3-amido]-1H-pyrazol-1-yl]-3-hydroxypiperidine-1-carboxylate To a solution of N-[3-[5-chloro-2-(difluoromethoxy)phenyl]-1H-pyrazol-4-yl]-pyrazolo[1,5-a]pyrimidine-3-carboxamide (600 mg, 1.482 mmol) in 1,2-dichloroethane (15 mL) was added $Yb(OTf)_3$ (300 mg, 0.484 mmol), tert-butyl 7-oxa-3-azabicyclo [4.1.0]heptane-3-carboxylate (1.20 g, 6.02 mmol). The resulting mixture was stirred t at 65° C. overnight and concentrated under vacuum. The residue was purified by flash chromatography on silica gel eluting with ethyl acetate/petroleum ether (4/1). The regioisomeric/enantiomeric mixtures (500 mg) were separated by Chiral-Prep-HPLC with the following conditions: Column, Phenomenex Lux 5u Cellulose-4££¬AXIA Packed 250*21.2 mm, 5 um; mobile phase, Mobile Phase A: Hexane, Mobile Phase B: Ethanol; Flow rate: 20 mL/min; Gradient: 35 B to 35 B in 28 min; RT 1:10; RT 2:13; Detector, 254/220 nm. 30 mg product was obtained which Alpha (25 degree C., Hex:EtOH=60:40) to give 31.3 mg (3.5%) of tert-butyl (3R,4R)-4-[3-[5-chloro-2-(difluoromethoxy)phenyl]-4-[pyrazolo[1,5-a]pyrimidine-3-amido]-1H-pyrazol-1-yl]-3-hydroxypiperidine-1-carboxylate as a solid. (This single isomer is the first peak in Chiral-HPLC with the above condition). LCMS (Method 20) $[M+H]^+$=604.3, $R_T$=2.08 min. $^1$H NMR (300 MHz, $CD_3OD$-$d_4$) δ: (ppm) 9.10 (dd, 1H, J=1.4, 6.9 Hz), 8.69-8.66 (m, 2H), 8.40 (s, 1H), 7.70 (d, 1H, J=2.4 Hz), 7.55 (dd, 1H, J=2.7, 8.7 Hz), 7.40 (d, 1H, J=8.7 Hz), 7.21 (dd, 1H, J=4.2, 6.9 Hz), 6.59 (t, 1H, J=73.7 Hz), 4.37-4.03 (m, 4H), 3.03 (m, 1H), 2.15 (m, 1H), 1.59 (m, 2H), 1.52 (m, 9H).

Example 355

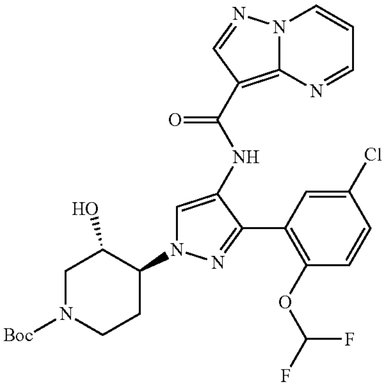

assumed tert-butyl (3S,4S)-4-[3-[5-chloro-2-(difluoromethoxy)phenyl]-4-[pyrazolo[1,5-a]pyrimidine-3-amido]-1H-pyrazol-1-yl]-3-hydroxypiperidine-1-carboxylate (This single isomer is the second peak in Chiral-HPLC with the above condition) to give 30.5 mg (3.5%) of tert-butyl (3S,4S)-4-[3-[5-chloro-2-(difluoromethoxy)phenyl]-4-[pyrazolo[1,5-a]pyrimidine-3-amido]-1H-pyrazol-1-yl]-3-hydroxypiperidine-1-carboxylate as a solid. LCMS (Method 20) $[M+H]^+$=604.3, $R_T$=2.08 min. $^1$H NMR (300 MHz, $CD_3OD$-$d_4$) δ: (ppm) 9.10 (dd, 1H, J=1.2, 6.9 Hz), 8.69-8.66 (m, 2H), 8.40 (s, 1H), 7.71 (s, 1H), 7.55 (d, 1H, J=8.4 Hz), 7.40 (d, 1H, J=8.4 Hz), 7.26-7.22 (m, 1H), 6.59 (t, 1H, J=73.5 Hz), 4.37-4.03 (m, 4H), 3.03 (m, 1H), 2.15 (m, 1H), 1.59 (m, 2H), 1.52 (m, 9H).

Example 356

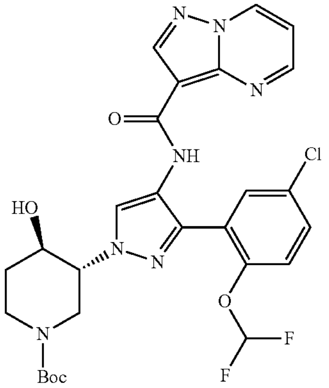

assumed tert-butyl (3R,4R)-3-[3-[5-chloro-2-(difluoromethoxy)phenyl]-4-[pyrazolo[1,5-a]pyrimidine-3-amido]-1H-pyrazol-1-yl]-4-hydroxypiperidine-1-carboxylate (This single isomer is the third peak in Chiral-HPLC with the above condition) to give 24.8 mg (2.8%) of tert-butyl (3R,4R)-3-[3-[5-chloro-2-(difluoromethoxy)phenyl]-4-[pyrazolo[1,5-a]pyrimidine-3-amido]-1H-pyrazol-1-yl]-4-hydroxypiperidine-1-carboxylate as a solid. LCMS (Method 20) $[M+H]^+$=604.3, $R_T$=2.08 min. $^1H$ NMR (300 MHz, $CD_3OD-d_4$) δ: (ppm) 9.10 (dd, 1H, J=1.2, 6.9 Hz), 8.69-8.65 (m, 2H), 8.38 (s, 1H), 7.69 (s, 1H), 7.55 (d, 1H, J=7.8 Hz), 7.39 (d, 1H, J=8.7 Hz), 7.25-7.22 (m, 1H), 6.83 (t, 1H, J=73.5 Hz), 4.38-4.35 (m, 1H), 4.25-4.15 (m, 2H), 4.01-3.93 (m, 1H), 2.97 (m, 1H), 2.77 (m, 1H), 2.17-2.13 (m, 2H), 1.53 (m, 9H).

Example 357

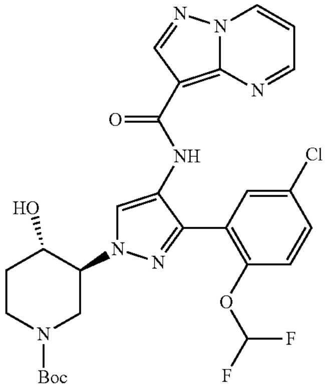

assumed tert-butyl (3S,4S)-3-[3-[5-chloro-2-(difluoromethoxy)phenyl]-4-[pyrazolo[1,5-a]pyrimidine-3-amido]-1H-pyrazol-1-yl]-4-hydroxypiperidine-1-carboxylate (This single isomer is the fourth peak in Chiral-HPLC with the above condition) to give 24.9 mg (2.8%) of tert-butyl (3S,4S)-3-[3-[5-chloro-2-(difluoromethoxy)phenyl]-4-[pyrazolo[1,5-a]pyrimidine-3-amido]-1H-pyrazol-1-yl]-4-hydroxypiperidine-1-carboxylate as a solid. LCMS (Method 20) $[M+H]^+$=604.3, $R_T$=2.08 min. $^1H$ NMR (300 MHz, $CD_3OD-d_4$) δ: (ppm) 9.10 (dd, 1H, J=1.2, 6.9 Hz), 8.69-8.65 (m, 2H), 8.38 (s, 1H), 7.69 (s, 1H), 7.55 (d, 1H, J=8.4 Hz), 7.42-7.39 (d, 1H, J=8.1 Hz), 7.25-7.22 (m, 1H), 6.58 (t, 1H, J=73.5 Hz), 4.38-4.35 (m, 1H), 4.25-4.15 (m, 2H), 4.01-3.93 (m, 1H), 2.97 (m, 1H), 2.77 (m, 1H), 2.15-2.14 (m, 2H), 1.53 (m, 9H).

Example 358

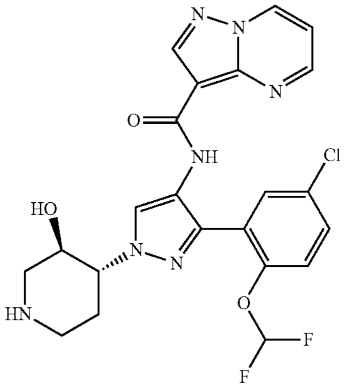 [SMILES: O=C(Nc1cn([C@@H]2CCNC[C@H]2O)nc1-c1cc(Cl)ccc1OC(F)F)c1cnn2cccnc12]

N-[3-[5-chloro-2-(difluoromethoxy)phenyl]-1-[(3R,4R)-3-hydroxypiperidin-4-yl]-1H-pyrazol-4-yl]pyrazolo[1,5-a]pyrimidine-3-carboxamide (Assumed)

A mixture of the first peak from Example 357 chiral separation (20 mg, 0.033 mmol) and saturated HCl dioxane solution (4 m) was stirred at room temperature for 2 h. The resulting mixture was concentrated under vacuum. This resulted in 18 mg (100%) of N-[3-[5-chloro-2-(difluoromethoxy)phenyl]-1-[(3R,4R)-3-hydroxypiperidin-4-yl]-1H-pyrazol-4-yl]pyrazolo[1,5-a]pyrimidine-3-carboxamide hydrochloride (assumed) as a solid. LCMS (Method 20) $[M+H]^+$=504.2, $R_T$=1.38 min. $^1H$ NMR (300 MHz, $CD_3OD-d4$) δ: (ppm) 9.10 (dd, 1H, J=1.5, 6.9 Hz), 8.67-8.65 (m, 2H), 8.44 (s, 1H), 7.71 (d, 1H, J=2.4 Hz), 7.56 (dd, 1H, J=2.5, 8.8 Hz), 7.40 (d, 1H, J=9 Hz), 7.21 (dd, 1H, J=4.4, 7.1 Hz), 6.85 (t, 1H, J=73.4 Hz), 4.45-4.43 (m, 1H), 4.28-4.23 (m, 1H), 3.77-3.50 (m, 4H), 2.32-2.27 (m, 1H), 1.91-1.86 (m, 1H).

Example 359

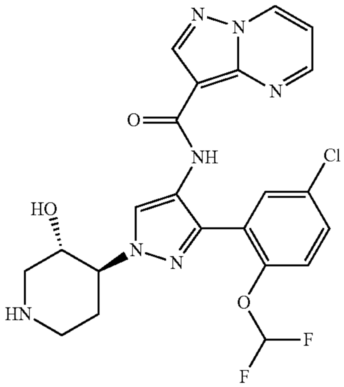 [SMILES: O=C(Nc1cn([C@H]2CCNC[C@@H]2O)nc1-c1cc(Cl)ccc1OC(F)F)c1cnn2cccnc12]

N-[3-[5-chloro-2-(difluoromethoxy)phenyl]-1-[(3S,4S)-3-hydroxypiperidin-4-yl]-1H-pyrazol-4-yl]pyrazolo[1,5-a]pyrimidine-3-carboxamide (Assumed)

A mixture of the second peak from Example 357 chiral separation (Example 358) and saturated HCl dioxane solution (4 mL) was stirred at room temperature for 2 h. The resulting mixture was concentrated under vacuum. This resulted in 20 mg (86%) of N-[3-[5-chloro-2-(difluoromethoxy)phenyl]-1-[(3S,4S)-3-hydroxypiperidin-4-yl]-1H-pyrazol-4-yl]pyrazolo[1,5-a]pyrimidine-3-carboxamide hydrochloride (assumed) as a yellow solid. LCMS (Method 20) $[M+H]^+$=504.2, $R_T$=1.71 min. $^1$H NMR (300 MHz, $CD_3OD-d_4$) δ: (ppm) 9.10 (d, 1H, J=6.9 Hz), 8.66-8.64 (m, 2H), 8.43 (s, 1H), 7.71 (d, 1H, J=2.7 Hz), 7.55 (dd, 1H, J=2.7, 8.7 Hz), 7.39 (d, 1H, J=9.0 Hz), 7.21 (dd, 1H, J=4.1, 6.9 Hz), 6.60 (t, 1H, J=73.4 Hz), 4.47-4.44 (m, 1H), 4.28-4.21 (m, 1H), 3.77-3.50 (m, 4H), 2.31-2.26 (m, 1H), 1.93-1.82 (m, 1H).

Example 360

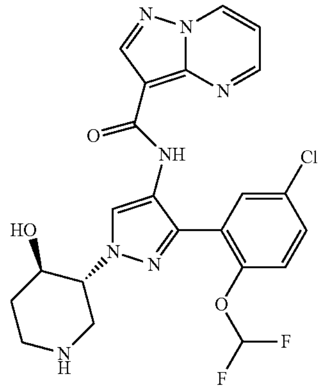 [SMILES: O=C(Nc1cn([C@@H]2CNCC[C@H]2O)nc1-c1cc(Cl)ccc1OC(F)F)c1cnn2cccnc12]

N-[3-[5-chloro-2-(difluoromethoxy)phenyl]-1-[(3R,4R)-4-hydroxypiperidin-3-yl]-1H-pyrazol-4-yl]pyrazolo[1,5-a]pyrimidine-3-carboxamide (Assumed Absolute)

A mixture of the third peak from Example 357 chiral separation (Example 359) (20 mg, 0.033 mmol) and saturated HCl dioxane solution was stirred room temperature for 2 h. The resulting mixture was concentrated under vacuum. This resulted in 11.3 mg (63%) of N-[3-[5-chloro-2-(difluoromethoxy)phenyl]-1-[(3R,4R)-4-hydroxypiperidin-3-yl]-1H-pyrazol-4-yl]pyrazolo[1,5-a]pyrimidine-3-carboxamide hydrochloride as a solid. LCMS (Method 20) $[M+H]^+$=504.2, $R_T$=1.38 min. $^1$H NMR (300 MHz, $CD_3OD-d_4$) δ: (ppm) 9.12 (d, 1H, J=6.0 Hz), 8.73-8.66 (m, 2H), 8.41 (s, 1H), 7.69 (d, 1H, J=1.5 Hz), 7.57 (dd, 1H, J=2.4, 8.7 Hz), 7.42 (d, 1H, J=5.7 Hz), 7.23 (dd, 1H, J=4.4, 7.1 Hz), 6.62 (t, 1H, J=73.4 Hz), 4.46-4.4.28 (m, 2H), 3.69-3.61 (m, 2H), 3.26 (m, 1H), 3.11-3.04 (m, 1H), 2.72-2.24 (m, 2H).

Example 361

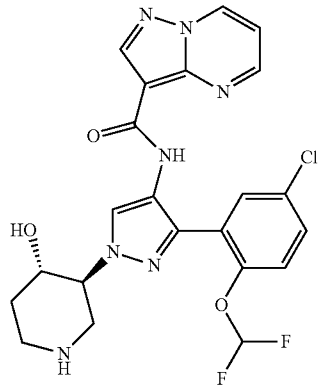 [SMILES: O=C(Nc1cn([C@H]2CNCC[C@@H]2O)nc1-c1cc(Cl)ccc1OC(F)F)c1cnn2cccnc12]

N-[3-[5-chloro-2-(difluoromethoxy)phenyl]-1-[(3S,4S)-4-hydroxypiperidin-3-yl]-1H-pyrazol-4-yl]pyrazolo[1,5-a]pyrimidine-3-carboxamide A mixture of fourth peak from Example 357 (Example 360) (26 mg) and saturated HCl dioxane solution (4 mL) was stirred at room temperature for 2 h. The resulting mixture was concentrated under vacuum. This resulted in 22.4 mg (96%) of N-[3-[5-chloro-2-(difluoromethoxy)phenyl]-1-[(3S,4S)-4-hydroxypiperidin-3-yl]-1H-pyrazol-4-yl]pyrazolo[1,5-a]pyrimidine-3-carboxamide hydrochloride as a yellow solid. LCMS (Method 20) $[M+H]^+$=504.2, $R_T$=1.73 min. $^1$H NMR (300 MHz, $CD_3OD-d_4$) δ: (ppm) 9.08 (d, 1H, J=7.2 Hz), 8.64-8.63 (m, 2H), 8.37 (s, 1H), 7.65 (d, 1H, J=2.1 Hz), 7.53 (dd, 1H, J=2.1, 9.0 Hz), 7.37 (d, 1H, J=8.7 Hz), 7.19 (dd, 1H, J=4.8, 6.3 Hz), 6.58 (t, 1H, J=73.5 Hz), 4.39-4.4.27 (m, 2H), 3.74-3.40 (m, 2H), 3.31 (m, 1H), 3.07-3.00 (m, 1H), 2.44-2.43 (m, 2H).

Example 362

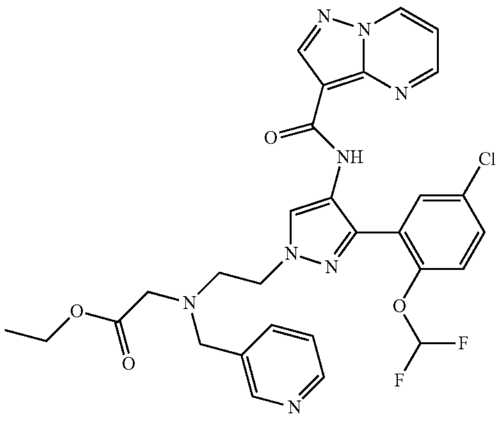 [SMILES: CCOC(=O)CN(CCn1cc(NC(=O)c2cnn3cccnc23)c(-c2cc(Cl)ccc2OC(F)F)n1)Cc1cccnc1]

ethyl 2-[(2-[3-[5-chloro-2-(difluoromethoxy)phenyl]-4-[pyrazolo[1,5-a]pyrimidine-3-amido]-1H-pyrazol-1-yl]ethyl)(pyridin-3-ylmethyl)amino]acetate To a solution of N-[1-(2-bromoethyl)-3-[5-chloro-2-(difluoromethoxy)phenyl]-1H-pyrazol-4-yl]pyrazolo[1,5-a]pyrimidine-3-carboxamide (510 mg, 1.00 mmol) in EtOH (30 mL) was added, triethylamine (1.01 g, 9.98 mmol) and ethyl 2-aminoacetate hydrochloride (681 mg, 4.88 mmol). The resulting solution was stirred at 80° C. for 24 h. The resulting mixture was concentrated under vacuum. The residue was purified by flash chromatography on silica gel eluting with 3% MeOH in DCM. This resulted in 420 mg (79%) of ethyl 2-[(2-[3-[5-chloro-2-(difluoromethoxy)phenyl]-4-[pyrazolo[1,5-a]pyrimidine-3-amido]-1H-pyrazol-1-yl]ethyl)amino]acetate as light yellow oil. LCMS (Method 20) $[M+H]^+$=534.0, $R_T$=1.18 min.

To a solution of ethyl 2-[(2-[3-[5-chloro-2-(difluoromethoxy)phenyl]-4-[pyrazolo[1,5-a]pyrimidine-3-amido]-1H-pyrazol-1-yl]ethyl)amino]acetate (420 mg, 0.79 mmol) in EtOH (30 mL) was added AcOH (0.1 mL, 1.75 mmol), pyridine-3-carbaldehyde (126 mg, 1.18 mmol). The mixture was stirred at room temperature for 3 h and $NaBH_3CN$ (99 mg, 1.58 mmol) was added. The resulting solution was stirred at 60° C. for 12 h. The solids were filtered out. The resulting mixture was concentrated under vacuum. The residue was purified by flash chromatography on silica gel eluting with 3% MeOH in DCM. The crude product (100 mg) was purified by Flash-Prep-HPLC with the following conditions (IntelFlash-2): Column, $C_{18}$ silica gel; mobile phase, $CH_3CN:H_2O=5:95$ increasing to $CH_3CN:H_2O=24:40$ within 12 min; Detector, UV 254 nm. 26 mg product was obtained. This resulted in 25.6 mg (5%) of ethyl 2-[(2-[3-[5-chloro-2-(difluoromethoxy)phenyl]-4-[pyrazolo[1,5-a]pyrimidine-3-amido]-1H-pyrazol-1-yl]-ethyl)(pyridin-3-ylmethyl)amino]acetate as an off-white solid. LCMS (Method 20) $[M+H]^+=625.3$, $R_T=1.68$ min. $^1H$ NMR (400 MHz, DMSO-$d_6$) δ: (ppm) 9.73 (s, 1H), 9.35 (d, 1H, J=6.8 Hz), 8.69-8.68 (m, 2H), 8.39-8.37 (m, 3H), 7.63-7.61 (m, 2H), 7.51 (s, 1H), 7.43 (d, 1H, J=8.8 Hz), 7.31-7.25 (m, 2H), 7.04 (t, 1H, J=73.6 Hz), 4.30-4.27 (m, 2H), 4.07 (q, 2H, J=6.8 Hz), 3.82 (s, 2H), 3.44 (s, 2H), 3.15-3.11 (m, 2H), 1.17 (t, 3H, J=7.2 Hz).

Example 363

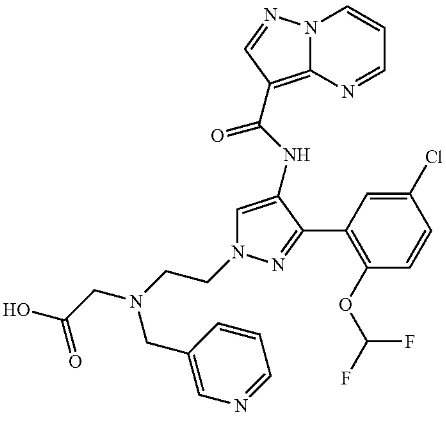 [SMILES: O=C(O)CN(CCn1cc(NC(=O)c2cnn3cccnc23)c(-c2cc(Cl)ccc2OC(F)F)n1)Cc1cccnc1]

2-[(2-[3-[5-chloro-2-(difluoromethoxy)phenyl]-4-[pyrazolo[1,5-a]pyrimidine-3-amido]-1H-pyrazol-1-yl]ethyl)(pyridin-3-ylmethyl)amino]acetic acid A mixture of ethyl 2-[(2-[3-[5-chloro-2-(difluoromethoxy)phenyl]-4-[pyrazolo[1,5-a]pyrimidine-3-amido]-1H-pyrazol-1-yl]ethyl)(pyridin-3-ylmethyl)amino] acetate (180 mg, 0.29 mmol), ethanol (10 mL) and 1 N sodium hydroxide (2 mL) was stirred at room temperature for 30 min. The mixture was acidified with 1 HCl to pH 5. The resulting mixture was concentrated under vacuum. The crude product (200 mg) was purified by Flash-Prep-HPLC with the following conditions (IntelFlash-1): Column, C18 silica gel; mobile phase, CH3CN:H2O=5:95 increasing to $CH_3CN:H_2O=24:40$ within 12 min; Detector, UV 254 nm. 8.6 mg product was obtained. This resulted in 8.6 mg (5%) of 2-[(2-[3-[5-chloro-2-(difluoromethoxy)phenyl]-4-[pyrazolo[1,5-a]pyrimidine-3-amido]-1H-pyrazol-1-yl]ethyl) (pyridin-3-ylmethyl)amino]acetic acid formate as a white solid. LCMS (Method 20) $[M+H]^+=597.2$, $R_T=2.72$ min. $^1H$ NMR (300 MHz, DMSO-$d_6$) δ: (ppm) 9.72 (s, 1H), 9.34 (d, 1H, J=7.2 Hz), 8.69-8.68 (m, 2H), 8.39-8.37 (m, 3H), 7.63-7.60 (m, 2H), 7.51 (d, 1H, J=2.1 Hz), 7.43 (d, 1H, J=9.0 Hz), 7.32-7.22 (m, 2H), 6.99 (t, 1H, J=73.2 Hz), 4.33-4.22 (m, 2H), 3.83 (s, 2H), 3.334 (s, 2H), 3.15-3.07 (m, 2H).

Example 364

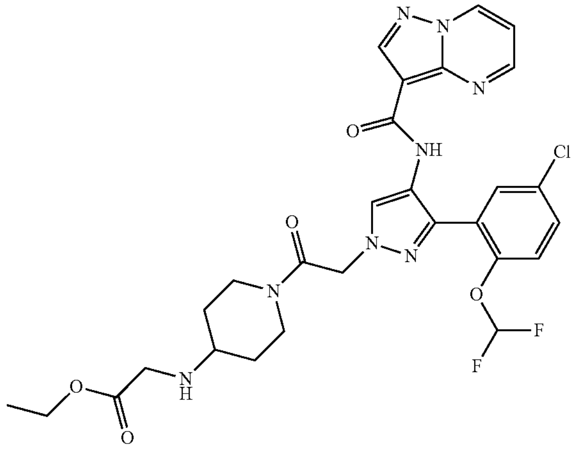 [SMILES: CCOC(=O)CNC1CCN(C(=O)Cn2cc(NC(=O)c3cnn4cccnc34)c(-c3cc(Cl)ccc3OC(F)F)n2)CC1]

ethyl 2-[[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl]amino]acetate To a solution of {3-(5-Chloro-2-difluoromethoxyphenyl)-4-[(pyrazolo[1,5-a]pyrimidine-3-carbonyl)amino]pyrazol-1-yl}acetic acid (665 mg, 1.44 mmol) in DMF (7 mL) was added tert-butyl N-(piperidin-4-yl)carbamate (300 mg, 1.50 mmol), triethylamine (700 mg, 6.92 mmol), HATU (670 g, 2.78 mol). The resulting solution was stirred at room temperature for 1.5 h. EtOAc (100 mL) and water (50 mL) was added. Phases were separated. The organic layer was, washed with brine, dried over anhydrous sodium sulfate and concentrated under vacuum. The residue was purified by flash chromatography on silica gel eluting with ethyl acetate/hexane (1/1). This resulted in 600 mg (65%) of tert-butyl N-[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl]carbamate as a yellow solid. TLC: $R_f=0.3$; ethyl acetate/petroleum ether=1/1.

TFA (2.0 mL, 26.93 mmol) was added to a solution of tert-butyl N-[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl]carbamate (600 mg, 0.93 mmol) in dichloromethane (8 mL). The resulting solution was stirred room temperature for 2 h and concentrated under vacuum. The residue was dissolved in ethyl acetate (100 mL), and saturated $NaHCO_3$ (50 mL) was added. Phases were separated. The organic layer was washed with saturated $NaHCO_3$, brine, dried over anhydrous sodium sulfate and concentrated under vacuum. This resulted in 450 mg (89%) of N-[1-[2-(4-aminopiperidin-1-yl)-2-oxoethyl]-3-[5-chloro-2-(difluoromethoxy)phenyl]-1H-pyrazol-4-yl]pyrazolo[1,5-a]pyrimidine-3-carboxamide as a yellow solid. TLC: $R_f=0.3$; MeOH/DCM=1/5.

To a solution of N-[1-[2-(4-aminopiperidin-1-yl)-2-oxoethyl]-3-[5-chloro-2-(difluoromethoxy)phenyl]-1H-pyrazol-4-yl]pyrazolo[1,5-a]pyrimidine-3-carboxamide (126 mg, 0.24 mmol) in DMF (3 mL) was added potassium carbonate (76 mg, 0.55 mmol), ethyl 2-bromoacetate (0.03 mL, 0.27 mmol). The resulting mixture was stirred at 25° C. for 1 h and diluted with 100 mL of ethyl acetate. Water (50 mL) was added. Phases were separated. The organic phase was washed with brine, dried over anhydrous sodium sulfate and concentrated under vacuum. The crude product was purified by Flash-Prep-HPLC with the following conditions (IntelFlash-1): Column: Xbridge C18, 19*150 mm, 5 um; Mobile Phase A: Water/0.05% $NH_4HCO_3$, Mobile Phase B: ACN; Flow rate: 30 mL/min; Gradient: 20% B to 85% B in 10 min; 254 nm. This resulted in 29.3 mg (98%) of ethyl 2-[[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl]amino]acetate as a white solid. LCMS (Method 25) $[M+H]^+$=631.2, $R_T$=1.89 min. $^1$H NMR (400 MHz, $CD_3OD-d_4$) δ: (ppm) 8.98 (d, 1H, J=6.8 Hz), 8.53-8.52 (m, 2H), 8.25 (s, 1H), 7.58 (d, 1H, J=2.4 Hz), 7.44 (dd, 1H, J=2.4, 8.8 Hz), 7.29 (d, 1H, J=8.8 Hz), 7.09 (dd, 1H, J=4.4, 6.8 Hz), 6.51 (t, 1H, J=73.6 Hz), 5.20-5.13 (m, 2H), 4.32 (d, 1H, J=13.2 Hz), 4.07 (q, 2H, J=7.2 Hz), 3.91 (d, 1H, J=13.2 Hz), 3.36 (s, 2H), 3.21-3.09 (m, 1H), 2.78-2.68 (m, 2H), 1.94-1.83 (m, 2H), 1.34-1.22 (m, 2H), 1.16 (t, 3H, J=7.2 Hz).

Example 365

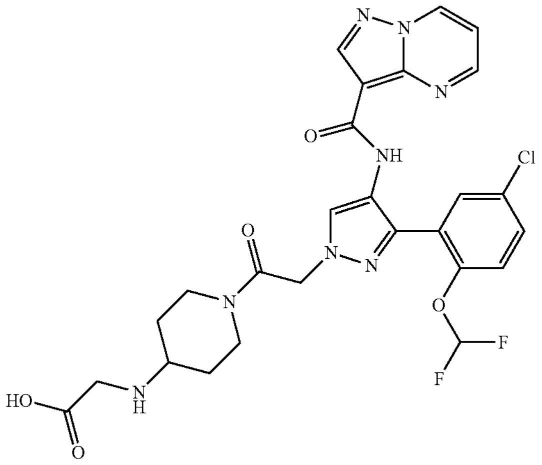 [SMILES: O=C(O)CNC1CCN(C(=O)Cn2cc(NC(=O)c3cnn4cccnc34)c(-c3cc(Cl)ccc3OC(F)F)n2)CC1]

2-[[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl]amino]acetic acid A mixture of ethyl 2-[[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl]amino]-acetate (200 mg, 0.32 mmol), KOH (100 mg, 1.78 mmol) in methanol (5 mL) was stirred at 25° C. for 12 h. The crude product was purified by Flash-Prep-HPLC with the following conditions (IntelFlash-1): Column: Xbridge $C_{18}$, 19*150 mm, 5 um; Mobile Phase A: Water/0.05% $NH_4HCO_3$, Mobile Phase B: ACN; Flow rate: 30 mL/min; Gradient: 20% B to 85% B in 10 min; 254 nm. This resulted in 28.5 mg (15%) of 2-[[1-(2-[3-[5-chloro-2-(difluoromethoxy)phenyl]-4-[pyrazolo[1,5-a]pyrimidine-3-amido]-1H-pyrazol-1-yl]-acetyl)piperidin-4-yl]amino]acetic acid as a white solid. LCMS (Method 25) $[M+H]^+$=603.1, $R_T$=1.39 min. $^1$H NMR (400 MHz, CD3OD-$d_4$) δ: (ppm) 8.98 (dd, 1H, J=1.2, 6.8 Hz), 8.54-8.53 (m, 2H), 8.24 (s, 1H), 7.57 (d, 1H, J=2.4 Hz), 7.45 (dd, 1H, J=2.8, 8.8 Hz), 7.30 (d, 1H, J=8.8 Hz), 7.09 (dd, 1H, J=4.4, 6.8 Hz), 6.70 (t, 1H, J=73.4 Hz), 5.23-5.10 (m, 2H), 4.54 (d, 1H, J=13.2 Hz), 4.05 (d, 1H, J=13.6 Hz), 3.45 (s, 2H), 3.30-3.11 (m, 4H), 2.71-2.65 (m, 1H), 2.11-2.05 (m, 1H), 1.58-1.43 (m, 2H).

Example 366

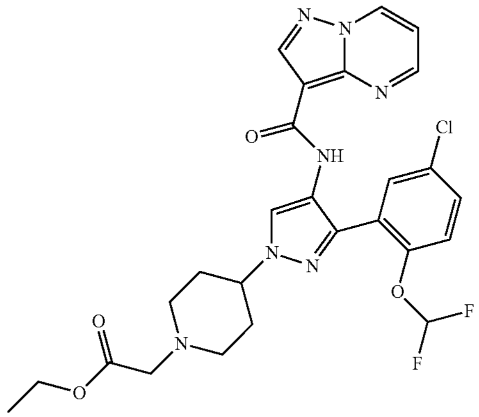 [SMILES: CCOC(=O)CN1CCC(n2cc(NC(=O)c3cnn4cccnc34)c(-c3cc(Cl)ccc3OC(F)F)n2)CC1]

ethyl 2-(4-[3-[5-chloro-2-(difluoromethoxy)phenyl]-4-[pyrazolo[1,5-a]pyrimidine-3-amido]-1H-pyrazol-1-yl]piperidin-1-yl)acetate To a solution of tert-butyl 4-hydroxypiperidine-1-carboxylate (1 g, 4.97 mmol) in DCM (50 mL) was added DIEA (2.00 g, 15.47 mmol), 4-dimethylaminopyridine (10 mg, 0.08 mmol) and MsCl (862 mg, 7.53 mmol). The resulting solution was stirred at room temperature for 12 h, washed with water and brine. The organic layer was dried over anhydrous sodium sulfate and concentrated under vacuum. The residue was purified by flash chromatography on silica gel eluting with ethyl acetate/petroleum ether (1/1). This resulted in 860 mg (62%) of tert-butyl 4-(methanesulfonyloxy)piperidine-1-carboxylate as a light yellow solid. LCMS (Method 20) $[M+H]^+$=224.0, $R_T$=1.42 min.

To a solution of N-[3-[5-chloro-2-(difluoromethoxy)phenyl]-1H-pyrazol-4-yl]pyrazolo[1,5-a]pyrimidine-3-carboxamide (500 mg, 1.24 mmol) in MeCN (50 mL) was added $Cs_2CO_3$ (1.21 g, 3.71 mmol), tert-butyl 4-(methanesulfonyloxy)piperidine-1-carboxylate (828 mg, 2.96 mmol). The resulting solution was stirred at 80° C. for 18 h. The solids were filtered out. The filtrate was concentrated under vacuum. The residue was purified by flash chromatography on silica gel eluting with 2% MeOH in DCM. This resulted in 1.1 g (crude) of tert-butyl 4-[3-[5-chloro-2-(difluoromethoxy)phenyl]-4-[pyrazolo[1,5-a]pyrimidine-3-amido]-1H-pyrazol-1-yl]piperidine-1-carboxylate as a yellow solid. LCMS (Method 25) $[M+H]^+$=588.0, $R_T$=1.17 min.

A mixture of crude product from previous step tert-butyl 4-[3-[5-chloro-2-(difluoromethoxy)phenyl]-4-[pyrazolo[1,5-a]pyrimidine-3-amido]-1H-pyrazol-1-yl]-piperidine-1-carboxylate (1.1 g) and saturated HCl dioxane solution (20 mL) was stirred at room temperature for 8 h. The resulting mixture was concentrated under vacuum. The residue was dissolved in ethanol (20 mL) and neutralized with 2 N NaOH to pH-8. The resulting mixture was concentrated under vacuum. The residue was purified by flash chromatography on silica gel eluting with 15% MeOH in DCM.

This resulted in 320 mg (35%) of N-[3-[5-chloro-2-(difluoromethoxy)phenyl]-1-(piperidin-4-yl)-1H-pyrazol-4-yl]pyrazolo[1,5-a]pyrimidine-3-carboxamide as a yellow solid.

To a solution of N-[3-[5-chloro-2-(difluoromethoxy)phenyl]-1-(piperidin-4-yl)-1H-pyrazol-4-yl]pyrazolo[1,5-a]pyrimidine-3-carboxamide (320 mg, 0.66 mmol) in ethanol (20 mL) was added 50% ethyl 2-oxoacetate hydrate (268 mg, 1.31 mmol), AcOH (0.1 mL, 1.75 mmol) and $NaBH_3CN$ (83 mg, 1.32 mmol). The resulting solution was stirred at 60° C. for 12 h and concentrated under vacuum. The residue was passed through a short pad of silica gel eluting with 2% MeOH in DCM. The crude product (100 mg) was purified by Flash-Prep-HPLC with the following conditions (IntelFlash-1): Column, silica gel; mobile phase, $CH_3CN$:$H_2O$=5:95 increasing to $CH_3CN$:$H_2O$=55:75 within 12 min; Detector, UV 254 nm. 25.3 mg product was obtained. This resulted in 25.3 mg (7%) of ethyl 2-(4-[3-[5-chloro-2-(difluoromethoxy)phenyl]-4-[pyrazolo[1,5-a]pyrimidine-3-amido]-1H-pyrazol-1-yl]piperidin-1-yl)acetate as an off-white solid. LCMS (Method 20) $[M+H]^+$=574.2, $R_T$=2.70 min. $^1H$ NMR (300 MHz, DMSO-$d_6$) δ: (ppm) 9.73 (s, 1H), 9.36 (s, 1H), 8.69-8.67 (m, 2H), 8.36 (s, 1H), 7.63-7.25 (m, 5H), 4.25-4.23 (m, 1H), 4.13-4.10 (m, 2H), 3.28-3.27 (m, 2H), 3.01-2.98 (m, 2H), 2.42-2.40 (m, 2H), 2.12-1.98 (m, 4H), 1.25-1.20 (m, 3H).

Example 367

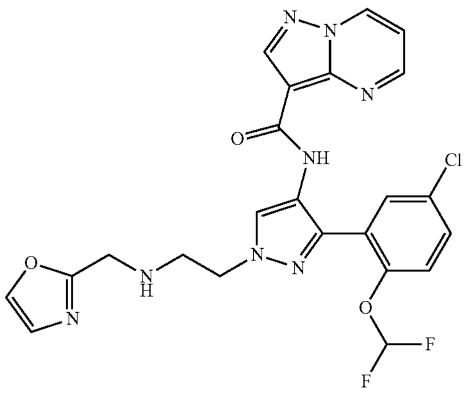 [SMILES: O=C(Nc1cn(CCNCc2ncco2)nc1-c1cc(Cl)ccc1OC(F)F)c1cnn2cccnc12]

N-[3-[5-chloro-2-(difluoromethoxy)phenyl]-1-[2-[(1,3-oxazol-2-ylmethyl)amino]ethyl]-1H-pyrazol-4-yl]pyrazolo[1,5-a]pyrimidine-3-carboxamide To a solution of N-[1-(2-aminoethyl)-3-[5-chloro-2-(difluoromethoxy)phenyl]-1H-pyrazol-4-yl]pyrazolo[1,5-a]pyrimidine-3-carboxamide (100 mg, 0.22 mmol) in MeOH (15 mL) was added 1,3-oxazole-2-carbaldehyde (21.7 mg, 0.22 mmol), followed by $NaBH_3CN$ (16 mg, 0.25 mmol). The resulting solution was stirred at room temperature for 12 h. The resulting mixture was concentrated under vacuum. The residue was passed through a short pad of silica gel eluting with 5% MeOH in DCM. The crude product was purified by Prep-HPLC with the following conditions (2#-AnalyseHPLC-SHIMADZU(HPLC-10)): Column, XBridge BEH130 Prep C18 OBD Column, 19� 100 mm 5 um 13 nm; mobile phase, Water with 10 mM NH4CO3 and ACN (20% ACN up to 50% in 6 min); Detector, UV 254/220 nm. 52.7 mg product was obtained. This resulted in 52.7 mg (45%) of N-[3-[5-chloro-2-(difluoromethoxy)phenyl]-1-[2-[(1,3-oxazol-2-ylmethyl)amino]ethyl]-1H-pyrazol-4-yl]pyrazolo[1,5-a]pyrimidine-3-carboxamide as a light yellow solid.

LCMS (Method 20) $[M+H]^+$=529.2, $R_T$=2.42 min. $^1H$ NMR (300 MHz, $CD_3OD$-$d_4$) δ: (ppm) 9.08 (dd, 1H, J=1.7, 7.1 Hz), 8.66-8.63 (m, 2H), 8.34 (s, 1H), 7.87 (d, 1H, J=0.6 Hz), 7.67 (d, 1H, J=2.7 Hz), 7.53 (dd, 1H, J=2.4, 8.7 Hz), 7.38 (d, 1H, J=8.7 Hz), 7.19 (dd, 1H, J=4.2, 7.2 Hz), 7.13 (d, 1H, J=0.6 Hz), 6.55 (t, 1H, J=73.5 Hz), 4.33 (t, 2H, J=6.0 Hz), 3.95 (s, 2H), 3.14 (t, 2H, J=6.0 Hz).

Example 368

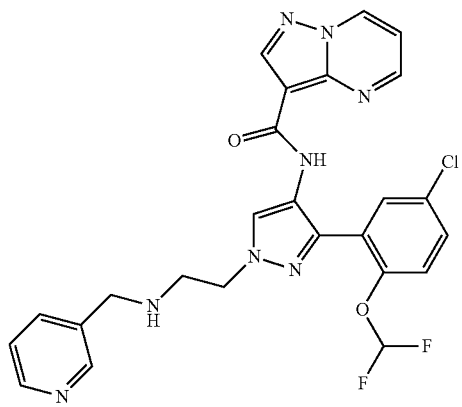 [SMILES: O=C(Nc1cn(CCNCc2cccnc2)nc1-c1cc(Cl)ccc1OC(F)F)c1cnn2cccnc12]

N-[3-[5-chloro-2-(difluoromethoxy)phenyl]-1-[2-[(pyridin-3-ylmethyl)amino]ethyl]-1H-pyrazol-4-yl]pyrazolo[1,5-a]pyrimidine-3-carboxamide A mixture of N-[1-(2-bromoethyl)-3-[5-chloro-2-(difluoromethoxy)phenyl]-1H-pyrazol-4-yl]pyrazolo[1,5-a]pyrimidine-3-carboxamide (150 mg, 0.29 mmol) and pyridin-3-ylmethanamine (158 mg, 1.46 mmol) in MeCN (3 mL) was stirred at 70° C. for 12 h. The resulting mixture was concentrated under vacuum. The crude product was purified by Flash-Prep-HPLC with the following conditions (IntelFlash-2): Column, $C_{18}$ silica gel; mobile phase, $CH_3CN$:$H_2O$=5:95 increasing to $CH_3CN$:$H_2O$=30:42 within 12 min; Detector, UV 254 nm. This resulted in 57.7 mg (37%) of N-[3-[5-chloro-2-(difluoromethoxy)phenyl]-1-[2-[(pyridin-3-ylmethyl)amino]ethyl]-1H-pyrazol-4-yl]pyrazolo[1,5-a]pyrimidine-3-carboxamide as a white solid. LCMS (Method 25) $[M+H]^+$=539.1, $R_T$=0.87 min. $^1H$ NMR (300 MHz, DMSO-$d_6$) δ: (ppm) 9.76 (s, 1H), 9.33 (dd, 1H, J=1.5, 6.9 Hz), 8.69-8.67 (m, 2H), 8.50 (d, 1H, J=1.8 Hz), 8.41 (dd, 1H, J=1.5, 4.8 Hz), 8.38 (s, 1H), 7.73-7.70 (m, 1H), 7.61 (dd, 1H, J=2.7, 8.7 Hz), 7.59 (d, 1H, J=2.4 Hz), 7.43 (d, 1H, J=8.7 Hz), 7.33-7.28 (m, 2H), 6.99 (t, 1H, J=73.2 Hz), 4.24 (t, 2H, J=6.0 Hz), 3.75-3.72 (m, 2H), 3.01-2.94 (m, 2H), 2.27 (br, 1H).

Example 369

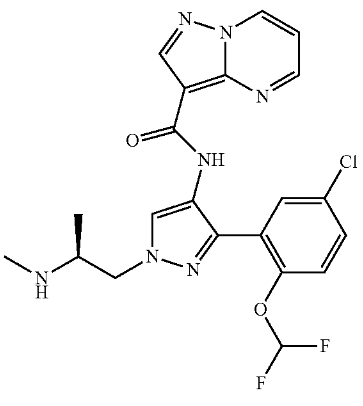 [SMILES: CN[C@@H](C)Cn1cc(NC(=O)c2cnn3cccnc23)c(-c2cc(Cl)ccc2OC(F)F)n1]

N-[3-[5-chloro-2-(difluoromethoxy)phenyl]-1-[(2S)-2-(methylamino)propyl]-1H-pyrazol-4-yl]pyrazolo[1,5-a]pyrimidine-3-carboxamide To a solution of (2S)-2-aminopropan-1-ol (1.0 g, 13.31 mmol) in MeOH (30 mL) was added, 4-methoxybenzaldehyde (1.8 g, 13.22 mmol). $NaBH_3CN$ (600 mg) was then added. The resulting solution was stirred at room temperature for 12 h. The solids were filtered out. The resulting mixture was concentrated under vacuum. This resulted in 2.1 g (crude) of (2S)-2-[[(4-methoxyphenyl)methyl]amino]propan-1-ol as light yellow oil. LCMS (Method 27) $[M+H]^+$= 196.0, $R_T$=0.95 min.

To a solution of (2S)-2-[[(4-methoxyphenyl)methyl]amino]propan-1-ol (2.1 g, 10.75 mmol) and 37% formaldehyde (900 mg) in methanol (50 mL) was added AcOH (0.1 mL, 1.75 mmol) and $NaBH_3CN$ (1.8 g, 28.64 mmol). The resulting solution was stirred at room temperature for 5 h, quenched with water (10 mL) and concentrated under vacuum. The residue was dissolved in dichloromethane (100 mL), washed with water and brine. The organic phase was dried over anhydrous sodium sulfate and concentrated under vacuum. The residue was purified by flash chromatography on silica gel eluting with 10% MeOH in DCM. This resulted in 1.0 g (44%) of (2S)-2-[[(4-methoxyphenyl)methyl](methyl)amino]propan-1-ol as colorless oil. LCMS (Method 21) $[M+H]^+$=210.0, $R_T$=0.92 min.

MsCl (250 mg, 2.18 mmol) was added dropwise to a stirring solution of (2S)-2-[[(4-methoxyphenyl)methyl](methyl)amino]propan-1-ol (400 mg, 1.91 mmol) and DIEA (516 mg, 3.99 mmol) in DCM (15 mL) at 0° C. The resulting solution was stirred at room temperature for 5 h and quenched water (50 mL). Phases were separated. The aqueous phase was extracted with DCM (×2) and the organic layers combined. The organic phases were washed with brine, dried over anhydrous sodium sulfate and concentrated under vacuum. This resulted in 510 mg (crude) of [(2S)-1-chloropropan-2-yl][(4-methoxyphenyl)methyl]methylamine as light red oil. LCMS (Method 25) $[M+H]^+$=228.0, $R_T$=0.55 min.

A 20-mL microwave vial was charged with N-[3-[5-chloro-2-(difluoromethoxy)phenyl]-1H-pyrazol-4-yl]pyrazolo[1,5-a]-pyrimidine-3-carboxamide (400 mg, 0.99 mmol), $Cs_2CO_3$ (652 mg, 2.00 mmol), DMF (10 mL) and [(2S)-1-chloropropan-2-yl][(4-methoxyphenyl)methyl]methylamine (454 mg, 1.99 mmol). The vessel was evacuated and refilled with nitrogen 3 times. The final reaction mixture was irradiated with microwave radiation for 30 min at 120° C. The reaction was then quenched by the addition of 50 mL of water. The resulting solution was extracted with dichloromethane (×2) and the organic layers combined and the organic layers were washed with brine, dried over anhydrous sodium sulfate and concentrated under vacuum. The residue was purified by flash chromatography on silica gel eluting with dichloromethane/ethyl acetate (1:1). This resulted in 420 m of N-[3-[5-chloro-2-(difluoromethoxy)phenyl]-1-[(2S)-2-[[(4-methoxyphenyl)methyl](methyl)amino]propyl]-1H-pyrazol-4-yl]pyrazolo[1,5-a]pyrimidine-3-carboxamide and N-[5-[5-chloro-2-(difluoromethoxy)phenyl]-1-[(2S)-2-[[(4-methoxyphenyl)methyl](methyl)amino]propyl]-1H-pyrazol-4-yl]pyrazolo[1,5-a]pyrimidine-3-carboxamide mixture. LCMS (Method 25) $[M+H]^+$= 596.0, $R_T$=0.81 min.

To the regioisomeric mixture from previous step (200 mg) in $CH_3CN$ (20 mL) was added chloro(1-chloroethoxy)methanone (240 mg, 1.68 mmol). The resulting solution was stirred at 80° C. for 5 h. The resulting mixture was concentrated under vacuum and dissolved with 20 mL of methanol. The resulting solution was stirred at 80° C. for 12 h and concentrated under vacuum. The residue was passed through a short pad of silica gel eluting with 5% MeOH in DCM. The crude product (120 mg) was purified by Prep-HPLC with the following conditions (3#-Pre-HPLC-006(Waters)): Column, XSelect CSH Prep $C_{18}$ OBD Column, 5 um, 19*150 mm; mobile phase, Water with 10 mmol NH4HCO3 and MeCN (26.0% MeCN up to 40.0% in 8 min); Detector, 254/220. Two fractions were obtained with the major isomer (36.3 mg) as the title compound. LCMS (Method 20) $[M+H]^+$= 476.2, $R_T$=2.53 min. $^1H$ NMR (300 MHz, DMSO-$d_6$) δ: (ppm) 9.73 (s, 1H), 9.33 (dd, 1H, J=1.2, 6.9 Hz), 8.68-8.66 (m, 2H), 8.33 (s, 1H), 7.65-7.61 (m, 2H), 7.43 (d, 1H, J=7.2 Hz), 7.27 (dd, 1H, J=4.5, 7.2 Hz), 6.97 (t, 1H, J=73.5 Hz), 4.11 (dd, 1H, J=6.3, 13.5 Hz), 4.01 (dd, 1H, J=6.0, 13.5 Hz), 2.97-2.91 (m, 1H), 2.29 (s, 3H), 1.76 (br, 1H), 0.95 (d, 3H, J=6.3 Hz).

Example 370

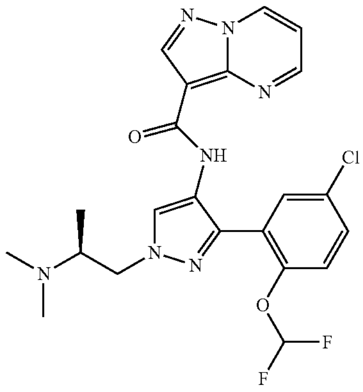 [SMILES: C[C@@H](Cn1cc(NC(=O)c2cnn3cccnc23)c(-c2cc(Cl)ccc2OC(F)F)n1)N(C)C]

N-[3-[5-chloro-2-(difluoromethoxy)phenyl]-1-[(2S)-2-(dimethylamino)propyl]-1H-pyrazol-4-yl]pyrazolo[1,5-a]pyrimidine-3-carboxamide To a solution of N-[1-[(2S)-2-aminopropyl]-3-[5-chloro-2-(difluoromethoxy)phenyl]-1H-pyrazol-4-yl]pyrazolo[1,5-a]pyrimidine-3-carboxamide (170 mg, 0.37 mmol) in MeOH (15 mL) was added 37% formaldehyde solution (16.6 mg, 0.55 mmol), $NaBH_3CN$ (23.3 mg, 0.37 mmol). The resulting solution was stirred at room temperature for 12 h and concentrated under vacuum. The residue was passed through a short pad of silica gel eluting with 10% MeOH in DCM. The crude product (80 mg) was purified by Prep-HPLC with the following conditions (1#-Pre-HPLC-006 (Waters)): Column, XSelect CSH Prep C18 OBD Column, 5 um, 19*150 mm; mobile phase, Water with 10 mM NH4CO3 and MeCN (20.0% MeCN up to 35.0% in 8 min); Detector, 254/220. This resulted in 29 mg (16%) of N-[3-[5-chloro-2-(difluoromethoxy)phenyl]-1-[(2S)-2-(dimethylamino)propyl]-1H-pyrazol-4-yl]pyrazolo[1,5-a]pyrimidine-3-carboxamide as an off-white solid. LCMS (Method 10) $[M+H]^+$=490.1, $R_T$=0.84 min. $^1H$ NMR (300 MHz, DMSO-$d_6$) δ: (ppm) 9.73 (s, 1H), 9.34 (dd, 1H, J=1.5, 6.9 Hz), 8.69-8.66 (m, 2H), 8.34 (s, 1H), 7.61 (dd, 1H, J=2.7, 8.7 Hz), 7.60 (d, 1H, J=2.1 Hz), 7.44 (d, 1H, J=8.4 Hz), 7.28 (dd, 1H, J=4.5, 7.2 Hz), 6.99 (t, 1H, J=73.5 Hz), 4.22 (dd, 1H, J=7.2, 13.8 Hz), 4.02 (dd, 1H, J=6.9, 13.8 Hz), 3.20-3.18 (m, 1H), 2.22 (s, 6H), 0.88 (d, 3H, J=6.6 Hz).

Example 371

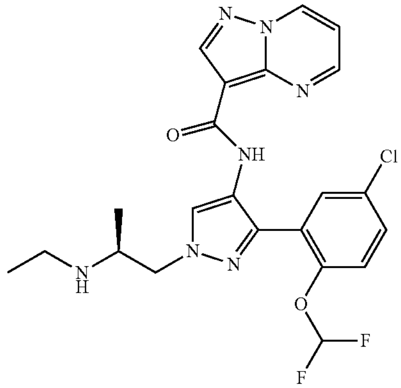 [SMILES: CCN[C@@H](C)Cn1cc(NC(=O)c2cnn3cccnc23)c(-c2cc(Cl)ccc2OC(F)F)n1]

N-[3-[5-chloro-2-(difluoromethoxy)phenyl]-1-[(2S)-2-(ethylamino)propyl]-1H-pyrazol-4-yl]pyrazolo[1,5-a]pyrimidine-3-carboxamide To a solution of N-[1-[(2S)-2-aminopropyl]-3-[5-chloro-2-(difluoromethoxy)phenyl]-1H-pyrazol-4-yl]pyrazolo[1,5-a]pyrimidine-3-carboxamide (200 mg, 0.43 mmol) in EtOH (20 mL) was added acetaldehyde (48 mg, 40% aqueous solution) and $NaBH_3CN$ (32.7 mg, 0.52 mmol). The resulting solution was stirred at room temperature for 12 h and concentrated under vacuum. The residue was passed through a short pad of silica gel eluting with 5% MeOH in DCM. The crude product (60 mg) was purified by Prep-HPLC with the following conditions (3#-Pre-HPLC-006(Waters)): Column, XSelect CSH Prep $C_{18}$ OBD Column, 5 um, 19*150 mm; mobile phase, Water with 10 mM NH4CO3 and MeCN (26.0% MeCN up to 40.0% in 8 min); Detector, 254/220. 24.2 mg product was obtained. This resulted in 24.2 mg (11%) of N-[3-[5-chloro-2-(difluoromethoxy)phenyl]-1-[(2S)-2-(ethylamino)propyl]-1H-pyrazol-4-yl]pyrazolo[1,5-a]pyrimidine-3-carboxamide as a light yellow solid. LCMS (Method 28) $[M+H]^+$=490.1, $R_T$=0.86 min. $^1H$ NMR (400 MHz, DMSO-$d_6$) δ: (ppm) 9.74 (s, 1H), 9.34 (dd, 1H, J=1.6, 7.2 Hz), 8.68-8.67 (m, 2H), 8.34 (s, 1H), 7.64 (d, 1H, J=2.1 Hz), 7.60 (dd, 1H, J=2.8, 8.4 Hz), 7.44 (d, 1H, J=8.4 Hz), 7.28 (dd, 1H, J=4.0, 7.2 Hz), 7.04 (t, 1H, J=73.2 Hz), 4.11 (dd, 1H, J=6.0, 13.6 Hz), 4.01 (dd, 1H, J=6.2, 13.6 Hz), 3.08-3.00 (m, 1H), 2.68-2.50 (m, 2H), 1.52 (br, 1H), 0.97 (t, 3H, J=7.0 Hz), 0.95 (d, 3H, J=6.4 Hz).

Example 372

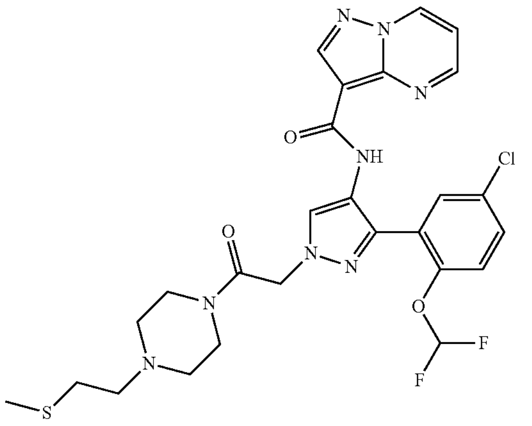 [SMILES: CSCCN1CCN(C(=O)Cn2cc(NC(=O)c3cnn4cccnc34)c(-c3cc(Cl)ccc3OC(F)F)n2)CC1]

N-[3-[5-chloro-2-(difluoromethoxy)phenyl]-1-(2-[4-[2-(methylsulfanyl)ethyl]piperazin-1-yl]-2-oxo-ethyl)-1H-pyrazol-4-yl]pyrazolo[1,5-a]pyrimidine-3-carboxamide To a solution of tert-butyl piperazine-1-carboxylate (1.00 g, 5.37 mmol) in DMF (30 mL) was added 1-chloro-2-(methylsulfanyl)ethane (710 mg, 6.42 mmol), $Cs_2CO_3$ (2.6 g, 7.98 mmol). The resulting mixture was stirred at 50° C. for 12 h. Water (50 mL) and EtOAc (30 mL) was added. Phases were separated. The aqueous phase was extracted with ethyl acetate (×2) and the organic layers combined. The organic phases were washed with brine, dried over anhydrous sodium sulfate and concentrated under vacuum. The residue was purified by flash chromatography on silica gel eluting with ethyl acetate/petroleum ether (1:2). This resulted in 180 mg (13%) of tert-butyl 4-[2-(methylsulfanyl)ethyl]piperazine-1-carboxylate as light yellow oil. LCMS (Method 25) $[M+H]^+$=261, $R_T$=0.63 min.

A mixture of tert-butyl 4-[2-(methyl sulfanyl)ethyl]piperazine-1-carboxylate (180 mg, 0.69 mmol) in DCM (5 mL) and trifluoroacetic acid (10 mL) was stirred at room temperature for 12 h. The resulting mixture was concentrated under vacuum. The residue was dissolved in 5 mL of dioxane-HCl. The resulting mixture was concentrated under vacuum. This resulted in 120 mg (88%) of 1-[2-(methylsulfanyl)ethyl]piperazine hydrochloride as a light yellow solid. LCMS (Method 25) $[M+H]^+$=161.1, $R_T$=0.21 min.

To a solution of {3-(5-Chloro-2-difluoromethoxyphenyl)-4-[(pyrazolo[1,5-a]pyrimidine-3-carbonyl)amino]pyrazol-1-yl}acetic acid (120 mg, 0.26 mmol) in DMF (10 mL) was added, 1-[2-(methylsulfanyl)ethyl]piperazine hydrochloride (102 mg, 0.52 mmol), HATU (119 mg, 0.31 mmol), DIEA (168 mg, 1.30 mmol). The resulting solution was stirred at room temperature for 12 h. Water (50 mL) was added. The resulting solution was extracted with DCM (×3) and the organic layers combined. The combined organic layers were washed with brine, dried over sodium sulfate and concentrated under vacuum. The crude product (150 mg) was purified by Prep-HPLC with the following conditions (1#-Pre-HPLC-006(Waters)): Column, XSelect CSH Prep C18 OBD Column, 5 um, 19*150 mm; mobile phase, Water with 10 mmol NH4HCO3 and MeCN (20.0% MeCN up to 35.0% in 8 min); Detector, 254/220. This resulted in 44.2 mg (28%) of N-[3-[5-chloro-2-(difluoromethoxy)phenyl]-1-(2-[4-[2-(methylsulfanyl)ethyl]-piperazin-1-yl]-2-oxoethyl)-1H-pyrazol-4-yl]-pyrazolo[1,5-a]pyrimidine-3-carboxamide as a white solid. LCMS (Method 20) $[M+H]^+$=605.2, $R_T$=1.61 min. $^1H$ NMR (400 MHz, DMSO-$d_6$) δ: (ppm) 9.75 (s, 1H), 9.34 (dd, 1H, J=1.6, 7.2 Hz), 8.69-8.68 (m, 2H), 8.31 (s, 1H), 7.62 (dd, 1H, J=2.4, 8.8 Hz), 7.55 (d, 1H, J=2.4 Hz), 7.45 (d, 1H, J=8.8 Hz), 7.28 (dd, 1H, J=4.4, 6.8 Hz), 7.08 (t, 1H, J=73.2 Hz), 5.23 (s, 2H), 3.50-3.47 (m, 4H), 2.67-2.56 (m, 4H), 2.2.47-2.33 (m, 4H), 2.08 (s, 3H).

Example 373

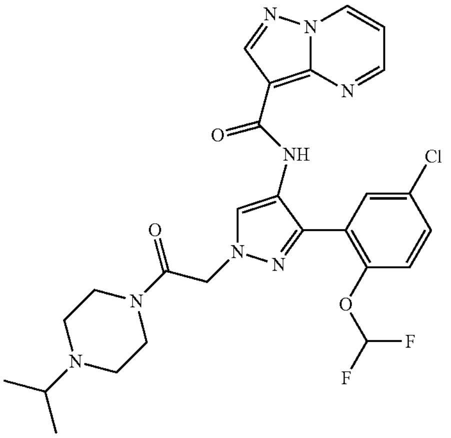 [SMILES: CC(C)N1CCN(C(=O)Cn2cc(NC(=O)c3cnn4cccnc34)c(-c3cc(Cl)ccc3OC(F)F)n2)CC1]

N-[3-[5-chloro-2-(difluoromethoxy)phenyl]-1-[2-oxo-2-[4-(propan-2-yl)piperazin-1-yl]ethyl]-1H-pyrazol-4-yl]pyrazolo[1,5-a]pyrimidine-3-carboxamide To a solution of {3-(5-Chloro-2-difluoromethoxyphenyl)-4-[(pyrazolo[1,5-a]pyrimidine-3-carbonyl)amino]pyrazol-1-yl}acetic acid (150 mg, 0.32 mmol) in DMF (10 mL) was added DIEA (126 mg, 0.97 mmol), 1-(propan-2-yl)piperazine (126 mg, 0.98 mmol) and HATU (185 mg, 0.49 mmol). The resulting solution was stirred at room temperature overnight and concentrated under vacuum. The crude product (200 mg) was purified by Flash-Prep-HPLC with the following conditions (IntelFlash-1): Column, C18 silica gel; mobile phase, CH3CN:H2O=5:95 increasing to $CH_3CN$:$H_2O$=40:60 within 14 min; Detector, UV 254 nm. This resulted in 51.6 mg (28%) of N-[3-[5-chloro-2-(difluoromethoxy)phenyl]-1-[2-oxo-2-[4-(propan-2-yl)piperazin-1-yl]ethyl]-1H-pyrazol-4-yl]pyrazolo[1,5-a]pyrimidine-3-carboxamide as a white solid. LCMS (Method 20) $[M+H]^+$=573.2, $R_T$=1.80 min. $^1$H NMR (300 MHz, DMSO-$d_6$) δ: (ppm) 9.76 (s, 1H), 9.34 (dd, 1H, J=1.2, 6.9 Hz), 8.69-8.67 (m, 2H), 8.31 (s, 1H), 7.62 (dd, 1H, J=2.7, 9.0 Hz), 7.55 (d, 1H, J=2.7 Hz), 7.45 (d, 1H, J=8.7 Hz), 7.28 (dd, 1H, J=4.2, 6.9 Hz), 7.02 (t, 1H, J=73.2 Hz), 5.23 (s, 2H), 3.52-3.48 (m, 4H), 2.78-2.65 (m, 1H), 2.46-2.39 (m, 4H), 1.09-0.97 (d, 6H, J=6.6 Hz).

Example 374

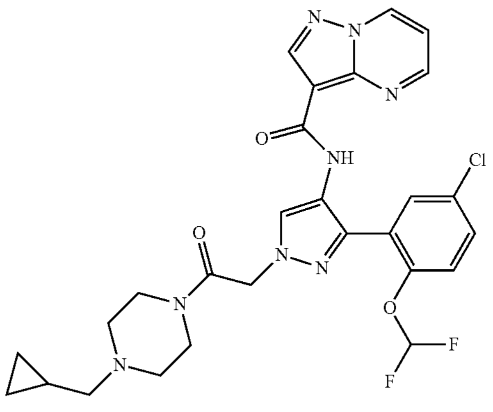 [SMILES: O=C(Nc1cn(CC(=O)N2CCN(CC3CC3)CC2)nc1-c1cc(Cl)ccc1OC(F)F)c1cnn2cccnc12]

N-[3-[5-chloro-2-(difluoromethoxy)phenyl]-1-[2-[4-(cyclopropylmethyl)piperazin-1-yl]-2-oxoethyl]-1H-pyrazol-4-yl]pyrazolo[1,5-a]pyrimidine-3-carboxamide To a solution of {3-(5-Chloro-2-difluoromethoxyphenyl)-4-[(pyrazolo[1,5-a]pyrimidine-3-carbonyl)amino]pyrazol-1-yl}acetic acid (100 mg) in DMF (10 mL) was added DIEA (83 mg, 0.64 mmol), 1-(cyclopropylmethyl)piperazine (60.6 mg, 0.43 mmol) and HATU. The resulting solution was stirred at room temperature overnight and concentrated under vacuum. The crude product (120 mg) was purified by Flash-Prep-HPLC with the following conditions (IntelFlash-1): Column, $C_{18}$ silica gel; mobile phase, $CH_3CN$:$H_2O$=5:95 increasing to $CH_3CN$:$H_2O$=24:40 within 14 min; Detector, UV 254 nm. This resulted in 47.6 mg (38%) of N-[3-[5-chloro-2-(difluoromethoxy)phenyl]-1-[2-[4-(cyclopropylmethyl)piperazin-1-yl]-2-oxoethyl]-1H-pyrazol-4-yl]pyrazolo[1,5-a]pyrimidine-3-carboxamide as a white solid. LCMS (Method 20) $[M+H]^+$=585.2, $R_T$=2.40 min. $^1$H NMR (300 MHz, DMSO-$d_6$) δ: (ppm) 9.75 (s, 1H), 9.34 (dd, 1H, J=1.5, 6.9 Hz), 8.69-8.67 (m, 2H), 8.31 (s, 1H), 7.62 (dd, 1H, J=2.7, 8.7 Hz), 7.55 (d, 1H, J=2.7 Hz), 7.45 (d, 1H, J=8.7 Hz), 7.28 (dd, 1H, J=4.2, 6.9 Hz), 7.02 (t, 1H, J=73.2 Hz), 5.23 (s, 2H), 3.51-3.49 (m, 4H), 2.49-2.41 (m, 4H), 2.23-2.21 (m, 2H), 0.87-0.82 (m, 1H), 0.50-0.44 (m, 2H), 0.13-0.08 (m, 2H).

Example 375

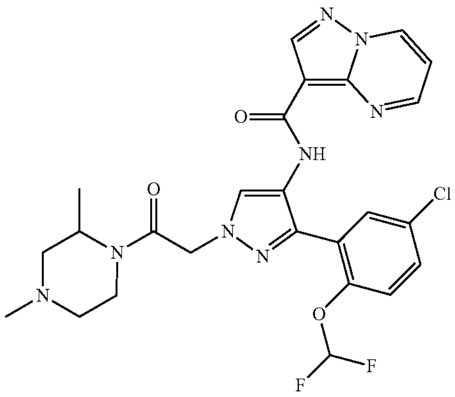 [SMILES: CC1CN(C)CCN1C(=O)Cn1cc(NC(=O)c2cnn3cccnc23)c(-c2cc(Cl)ccc2OC(F)F)n1]

N-[3-[5-chloro-2-(difluoromethoxy)phenyl]-1-[2-(2,4-dimethylpiperazin-1-yl)-2-oxoethyl]-1H-pyrazol-4-yl]pyrazolo[1,5-a]pyrimidine-3-carboxamide To a solution of tert-butyl 2-methylpiperazine-1-carboxylate (500 mg, 2.50 mmol) in EtOH (20 mL) was added 37% formaldehyde aqueous solution (405 mg) and AcOH (0.02 mL, 0.35 mmol). The mixture was stirred for 2 hand $NaBH_3CN$ (315 mg, 5.01 mmol) was added. The resulting solution was stirred at room temperature overnight and concentrated under vacuum. The residue was purified by flash chromatography on silica gel eluting with 4% MeOH in DCM. This resulted in 430 mg (80%) of tert-butyl 2,4-dimethylpiperazine-1-carboxylate as colorless oil. LCMS (Method 25) $[M+H]^+$=215.0, $R_T$=1.45 min.

A mixture of tert-butyl 2-methylpiperazine-1-carboxylate (430 mg, 2.15 mmol), and saturated HCl dioxane solution (15 mL) was stirred at room temperature for 2 h. The resulting mixture was concentrated under vacuum. This resulted in 520 mg (crude) of 1,3-dimethylpiperazine hydrochloride as a light yellow solid. LCMS (Method 24) $[M+H]^+$= 115.0, $R_T$=0.25 min.

To a solution of {3-(5-Chloro-2-difluoromethoxyphenyl)-4-[(pyrazolo[1,5-a]pyrimidine-3-carbonyl)amino]pyrazol-1-yl}acetic acid (150 mg, 0.32 mmol) in DMF (10 mL) was added DIEA (209 mg, 1.62 mmol), 1,3-dimethylpiperazine hydrochloride (146 mg, 0.97 mmol) and HATU (16 mg, 0.04 mmol). The resulting solution was stirred at room temperature overnight. Water (50 mL) and DCM (30 mL) was added. Phases were separated. The aqueous phase was extracted with DCM and the organic layers combined. The combined organic layers were washed with brine, dried over sodium sulfate and concentrated under vacuum. The residue was purified by Flash-Prep-HPLC with the following conditions (IntelFlash-2): Column, C18 silica gel; mobile phase, $CH_3CN:H_2O$=5:95 increasing to $CH_3CN:H_2O$=24:40 within 12 min; Detector, UV 254 nm. This resulted in 59.1 mg (33%) of N-[3-[5-chloro-2-(difluoromethoxy)phenyl]-1-[2-(2,4-dimethylpiperazin-1-yl)-2-oxoethyl]-1H-pyrazol-4-yl]pyrazolo[1,5-a]pyrimidine-3-carboxamide as a yellow solid. LCMS (Method 25) $[M+H]^+$=559.2, $R_T$=1.63 min. $^1$H NMR (300 MHz, DMSO-$d_6$) δ: (ppm) 9.75 (s, 1H), 9.34 (dd, 1H, J=1.5, 7.2 Hz), 8.69-8.67 (m, 2H), 8.34-8.31 (m, 1H), 7.62 (dd, 1H, J=2.7, 8.7 Hz), 7.55 (d, 1H, J=2.7 Hz), 7.45 (d, 1H, J=8.7 Hz), 7.28 (dd, 1H, J=4.2, 7.2 Hz), 7.02 (t, 1H, J=73.2 Hz), 5.31-5.11 (m, 2H), 4.52-4.47 (m, 0.5H), 4.20-4.11 (m, 1H), 3.78-3.69 (m, 0.5H), 3.32-3.21 (m, 0.5H), 2.97-2.83 (m, 0.5H), 2.75 (d, 1H, J=11.1 Hz), 2.63 (d, 1H, J=11.4 Hz), 2.20-1.71 (m, 5H), 1.38-1.12 (m, 3H).

Example 376

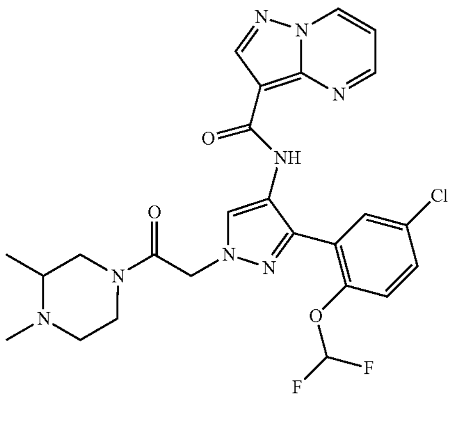 [SMILES: CC1CN(C(=O)Cn2cc(NC(=O)c3cnn4cccnc34)c(-c3cc(Cl)ccc3OC(F)F)n2)CCN1C]

N-[3-[5-chloro-2-(difluoromethoxy)phenyl]-1-[2-(3,4-dimethylpiperazin-1-yl)-2-oxoethyl]-1H-pyrazol-4-yl]pyrazolo[1,5-a]pyrimidine-3-carboxamide Using synthetic method analoguous that of N-[3-[5-chloro-2-(difluoromethoxy)phenyl]-1-[2-(2,4-dimethylpiperazin-1-yl)-2-oxoethyl]-1H-pyrazol-4-yl]pyrazolo[1,5-a]pyrimidine-3-carboxamide, the title compound was prepared from tert-butyl 3-methylpiperazine-1-carboxylate. LCMS (Method 20) $[M+H]^+$=559.2, $R_T$=2.23 min. $^1$H NMR (300 MHz, DMSO-$d_6$) δ: (ppm) 9.75 (s, 1H), 9.34 (dd, 1H, J=1.5 Hz, 7.2 Hz), 8.69-8.67 (m, 2H), 8.31 (s, 1H), 7.62 (dd, 1H, J=2.7, 8.7 Hz), 7.55 (d, 1H, J=2.7 Hz), 7.45 (d, 1H, J=8.7 Hz), 7.28 (dd, 1H, J=4.2, 6.9 Hz), 7.02 (t, 1H, J=73.2 Hz), 5.35-5.13 (m, 2H), 4.18-4.02 (m, 1H), 3.86-3.78 (m, 1H), 3.26-3.10 (m, 1H), 2.84-2.73 (m, 2H), 2.26-1.91 (m, 5H), 1.01 (d, 3H, J=6.0 Hz).

Example 377

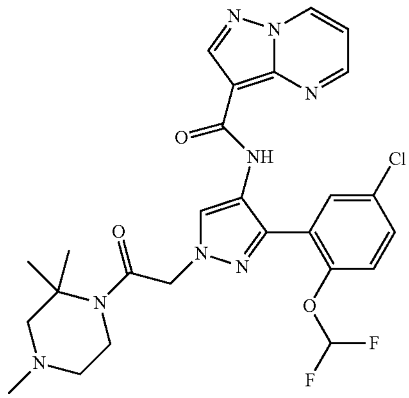 [SMILES: CN1CCN(C(=O)Cn2cc(NC(=O)c3cnn4cccnc34)c(-c3cc(Cl)ccc3OC(F)F)n2)C(C)(C)C1]

N-[3-[5-chloro-2-(difluoromethoxy)phenyl]-1-[2-oxo-2-(2,2,4-trimethylpiperazin-1-yl)ethyl]-1H-pyrazol-4-yl]pyrazolo[1,5-a]pyrimidine-3-carboxamide Using synthetic method analoguous to that of N-[3-[5-chloro-2-(difluoromethoxy)phenyl]-1-[2-(2,4-dimethylpiperazin-1-yl)-2-oxoethyl]-1H-pyrazol-4-yl]pyrazolo[1,5-a]pyrimidine-3-carboxamide, the title compound was prepared from tert-butyl 2,2-dimethylpiperazine-1-carboxylate. LCMS (Method 25) $[M+H]^+$=573.2, $R_T$=0.97 min. $^1$H NMR (300 MHz, DMSO-$d_6$) δ: (ppm) 9.75 (s, 1H), 9.34 (dd, 1H, J=1.2, 6.9 Hz), 8.69-8.68 (m, 2H), 8.27 (s, 1H), 7.62 (dd, 1H, J=2.7, 8.7 Hz), 7.56 (d, 1H, J=2.4 Hz), 7.45 (d, 1H, J=8.7 Hz), 7.28 (dd, 1H, J=4.5, 6.9 Hz), 7.03 (t, 1H, 73.1 Hz), 5.17 (s, 2H), 3.48-3.42 (m, 2H), 2.28-2.22 (m, 2H), 2.17 (s, 3H), 2.08 (s, 2H), 1.39 (s, 6H).

Example 378

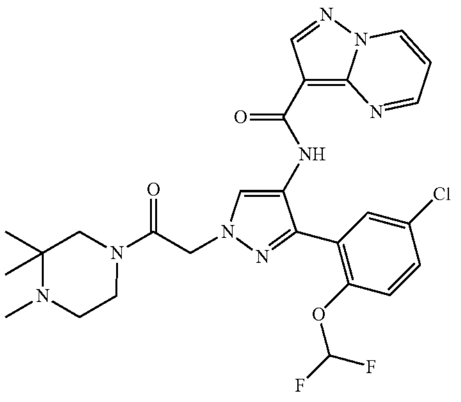 [SMILES: CN1CCN(C(=O)Cn2cc(NC(=O)c3cnn4cccnc34)c(-c3cc(Cl)ccc3OC(F)F)n2)CC1(C)C]

N-[3-[5-chloro-2-(difluoromethoxy)phenyl]-1-[2-oxo-2-(3,3,4-trimethylpiperazin-1-yl)ethyl]-1H-pyrazol-4-yl]pyrazolo[1,5-a]pyrimidine-3-carboxamide Using synthetic method analoguous to that of N-[3-[5-chloro-2-(difluoromethoxy)phenyl]-1-[2-(2,4-dimethylpiperazin-1-yl)-2-oxoethyl]-1H-pyrazol-4-yl]pyrazolo[1,5-a]pyrimidine-3-carboxamide, the title compound was prepared from tert-butyl 3,3-dimethylpiperazine-1-carboxylate. LCMS (Method 20) $[M+H]^+$=573.2, $R_T$=2.51 min. $^1H$ NMR (300 MHz, DMSO-$d_6$) δ: (ppm) 9.76 (s, 1H), 9.34 (dd, 1H, J=1.5, 7.2 Hz), 8.69-8.67 (m, 2H), 8.33 (s, 1H), 7.62 (dd, 1H, J=2.7, 8.7 Hz), 7.55 (d, 1H, J=2.1 Hz), 7.45 (d, 1H, J=9.0 Hz), 7.28 (dd, 1H, J=4.2, 6.9 Hz), 7.02 (t, 1H, J=73.2 Hz), 5.26 (s, 1H), 5.17 (s, 1H), 3.51-3.48 (m, 2H), 3.22 (d, 2H, J=11.4 Hz), 2.45-2.36 (m, 2H), 2.13 (s, 3H), 0.99 (s, 3H), 0.92 (s, 3H).

Example 379

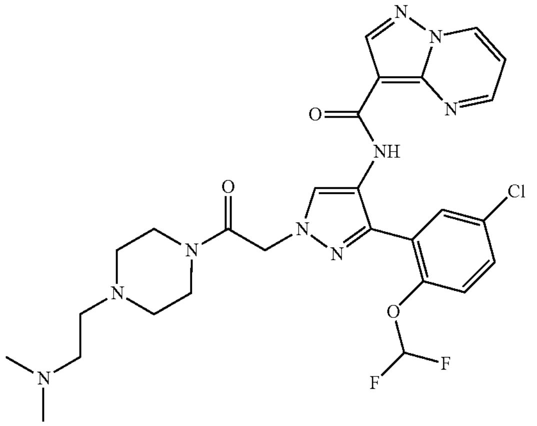 [SMILES: CN(C)CCN1CCN(C(=O)Cn2cc(NC(=O)c3cnn4cccnc34)c(-c3cc(Cl)ccc3OC(F)F)n2)CC1]

N-[3-[5-chloro-2-(difluoromethoxy)phenyl]-1-(2-[4-[2-(dimethylamino)ethyl]piperazin-1-yl]-2-oxoethyl)-1H-pyrazol-4-yl]pyrazolo[1,5-a]pyrimidine-3-carboxamide To a solution of 2-[3-[5-chloro-2-(difluoromethoxy)phenyl]-4-[pyrazolo[1,5-a]-pyrimidine-3-amido]-1H-pyrazol-1-yl]acetic acid (100 mg, 0.22 mmol) in DMF (10 mL) was added dimethyl[2-(piperazin-1-yl)ethyl]amine (68 mg, 0.43 mmol), DIEA (125 mg, 0.97 mmol) and HATU (123 mg, 0.32 mmol). The resulting solution was stirred at room temperature overnight and concentrated under vacuum. The crude product was purified by Prep-HPLC with the following conditions (2#-AnalyseHPLC-SHIMADZU(HPLC-10)): Column, XBridge BEH130 Prep C18 OBD Column, 19� 100 mm 5 um 13 nm; mobile phase, Water with 10 mM NH4CO3 and ACN (15% ACN up to 40% in 6 min); Detector, UV 254/220 nm. This resulted in 79.1 mg (61%) of N-[3-[5-chloro-2-(difluoromethoxy)phenyl]-1-(2-[4-[2-(dimethylamino)ethyl]piperazin-1-yl]-2-oxoethyl)-1H-pyrazol-4-yl]pyrazolo[1,5-a]pyrimidine-3-carboxamide as a light yellow solid. LCMS (Method 25) $[M+H]^+$=602.2, $R_T$=0.89 min. $^1H$ NMR (300 MHz, DMSO-$d_6$) δ: (ppm) 9.75 (s, 1H), 9.34 (dd, 1H, J=1.7, 7.1 Hz), 8.69-8.67 (m, 2H), 8.30 (s, 1H), 7.62 (dd, 1H, J=2.7, 8.7 Hz), 7.55 (d, 1H, J=2.7 Hz), 7.45 (d, 1H, J=9.0 Hz), 7.28 (dd, 1H, J=4.2, 6.9 Hz), 7.02 (t, 1H, J=73.2 Hz), 5.23 (s, 2H), 3.48-3.42 (m, 4H), 2.45-2.32 (m, 8H), 2.13 (s, 6H).

Example 380

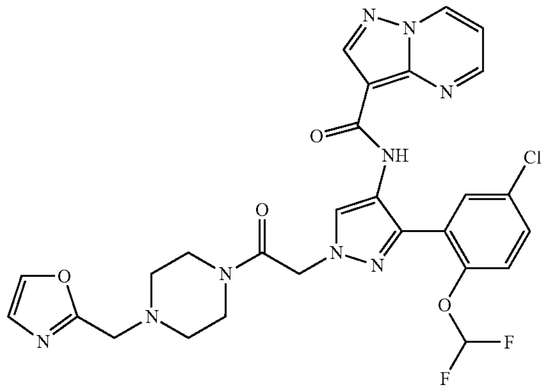 [SMILES: O=C(Nc1cn(CC(=O)N2CCN(Cc3ncco3)CC2)nc1-c1cc(Cl)ccc1OC(F)F)c1cnn2cccnc12]

N-[3-[5-chloro-2-(difluoromethoxy)phenyl]-1-[2-[4-(1,3-oxazol-2-ylmethyl)piperazin-1-yl]-2-oxoethyl]-1H-pyrazol-4-yl]pyrazolo[1,5-a]pyrimidine-3-carboxamide To a solution of tert-butyl piperazine-1-carboxylate (300 mg, 1.61 mmol) in MeOH (15 mL) was added 1,3-oxazole-2-carbaldehyde (172 mg, 1.77 mmol), AcOH (0.01 mL, 0.17 mmol), and $NaBH_3CN$ (152 mg, 2.42 mmol). The resulting solution was stirred at room temperature overnight and concentrated under vacuum. The residue was purified by flash chromatography on silica gel eluting with 5% MEOH in DCM. This resulted in 480 mg (89%) of tert-butyl 4-(1,3-oxazol-2-ylmethyl) piperazine-1-carboxylate as colorless oil. TLC: $R_f$=0.4; MeOH/DCM=1/10.

A mixture of tert-butyl 4-(1,3-oxazol-2-ylmethyl)piperazine-1-carboxylate (480 mg, 1.44 mmol) saturated HCl dioxane solution (15 mL) was stirred at room temperature for 3 h. This resulted in 300 mg (82%) of 1-(1,3-oxazol-2-ylmethyl)piperazine hydrochloride as a white solid. LCMS (Method 20) $[M+H]^+$=168.0, $R_T$=0.32 min.

To a solution of 2-[3-[5-chloro-2-(difluoromethoxy)phenyl]-4-[pyrazolo[1,5-a]-pyrimidine-3-amido]-1H-pyrazol-1-yl]acetic acid (100 mg, 0.22 mmol) in DMF (10 mL) was added 1-(1,3-oxazol-2-ylmethyl)piperazine hydrochloride (132 mg, 0.65 mmol), HATU (123 mg, 0.32 mmol), DIEA (139 mg, 1.08 mmol). The resulting solution was stirred at room temperature overnight. Water (50 mL) and DCM (30 mL) was added. Phases were separated. The aqueous phase was extracted with DCM (×2) and the organic layers combined. The organic layers were washed with brine, dried over $Na_2SO_4$ and concentrated under vacuum. The crude product (150 mg) was purified by Prep-HPLC with the following conditions (2#-AnalyseHPLC-SHIMADZU (HPLC-10)): Column, XBridge BEH130 Prep C18 OBD Column, 19� 100 mm 5 um 13 nm; mobile phase, Water with 10 mM NH4HCO3 and ACN (28% ACN up to 38% in 6 min); Detector, UV 254/220 nm. This resulted in 68.2 mg (52%) of N-[3-[5-chloro-2-(difluoromethoxy)phenyl]-1-[2-[4-(1,3-oxazol-2-ylmethyl)piperazin-1-yl]-2-oxoethyl]-1H-pyrazol-4-yl]pyrazolo[1,5-a]pyrimidine-3-carboxamide as an off-white solid. LCMS (Method 25) $[M+H]^+$= 612.1, $R_T$=1.70 min. $^1H$ NMR (300 MHz, DMSO-$d_6$) δ: (ppm) 9.75 (s, 1H), 9.34 (dd, 1H, J=1.7, 7.1 Hz), 8.69-8.67 (m, 2H), 8.30 (s, 1H), 8.09 (d, 1H, J=0.6 Hz), 7.62 (dd, 1H, J=2.7, 8.7 Hz), 7.55 (d, 1H, J=2.7 Hz), 7.45 (d, 1H, J=9.0 Hz), 7.28 (dd, 1H, J=4.2, 7.2 Hz), 7.18 (d, 1H, J=0.6 Hz), 7.01 (t, 1H, J=73.2 Hz), 5.23 (s, 2H), 3.76 (s, 2H), 3.54-3.48 (m, 4H), 2.45-2.42 (m, 4H).

Example 381

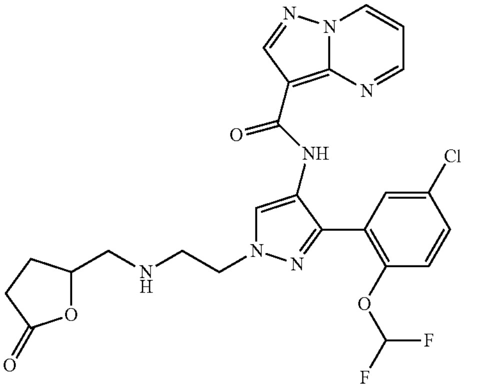 [SMILES: O=C1CCC(CNCCn2cc(NC(=O)c3cnn4cccnc34)c(-c3cc(Cl)ccc3OC(F)F)n2)O1]

N-[3-[5-chloro-2-(difluoromethoxy)phenyl]-1-(2-[[(5-oxooxolan-2-yl)methyl]amino]ethyl)-1H-pyrazol-4-yl]pyrazolo[1,5-a]pyrimidine-3-carboxamide Methanesulfonyl chloride (2.5 g, 21.8 mmol) was added dropwise to a stirring solution of tert-butyl N-(2-hydroxyethyl)carbamate (3.0 g, 18.61 mmol) and DIEA (7.2 g, 55.71 mmol) in DCM (50 mL) at 0° C. The resulting solution was stirred at room temperature for 8 h. The reaction was then quenched by the addition of 100 mL of sodium bicarbonate. Phases were separated. The aqueous phase was extracted with DCM (×2) and the organic layers combined. The combined organic layers were washed with brine, dried over anhydrous sodium sulfate and concentrated under vacuum. The residue was purified by flash chromatography on silica gel eluting with ethyl acetate/petroleum ether (1:2). This resulted in 3.4 g (76%) of tert-butyl N-[2-(methanesulfonyloxy)-ethyl]carbamate as a red solid. LCMS (Method 25) $[M+H]^+$=225.0, $R_T$=0.77 min.

To a solution of N-[3-[5-chloro-2-(difluoromethoxy)phenyl]-1H-pyrazol-4-yl]pyrazolo[1,5-a]pyrimidine-3-carboxamide (1.00 g, 2.47 mmol) in $CH_3CN$ (30 mL) was added $Cs_2CO_3$ (2.00 g, 6.14 mmol) and tert-butyl N-[2-(methanesulfonyloxy)-ethyl]carbamate (1.20 g, 5.01 mmol). The resulting solution was stirred at 70° C. overnight. The solids were filtered out. The filtrate was concentrated under vacuum. The residue was purified by flash chromatography on silica gel eluting with DCM/EtOAc (3:1). This resulted in 680 mg (50%) of tert-butyl N-(2-[3-[5-chloro-2-(difluoromethoxy)pyridin-3-yl]-4-[pyrazolo[1,5-a]pyrimidine-3-amido]-1H-pyrazol-1-yl]ethyl)carbamate as yellow oil. LCMS (Method 28) $[M+H]^+$=548.0, $R_T$=1.33 min A mixture of tert-butyl N-(2-[3-[5-chloro-2-(difluoromethoxy)phenyl]-4-[pyrazolo[1,5-a]pyrimidine-3-amido]-1H-pyrazol-1-yl]ethyl)carbamate (420 mg, 0.77 mmol) and saturated HCl dioxane solution (10 mL) was stirred at room temperature for 3 h. The resulting mixture was concentrated under vacuum. The residue was dissolved in 15 mL of ethanol. The pH value of the solution was adjusted to 8 with sodium hydroxide (2 mol/L). The resulting mixture was concentrated under vacuum. The residue was applied onto a silica gel column with dichloromethane/methanol (85/15). This resulted in 260 mg (76%) of N-[1-(2-aminoethyl)-3-[5-chloro-2-(difluoromethoxy)phenyl]-1H-pyrazol-4-yl]pyrazolo[1,5-a]pyrimidine-3-carboxamide as a light yellow solid. LCMS (Method 20) $[M+H]^+$=448.0, $R_T$=0.76 min.

To a solution of N-[1-(2-aminoethyl)-3-[5-chloro-2-(difluoromethoxy)phenyl]-1H-pyrazol-4-yl]pyrazolo[1,5-a]pyrimidine-3-carboxamide (200 mg, 0.45 mmol) in CH3CN (20 mL) was added (5-oxooxolan-2-yl)methyl trifluoromethanesulfonate (166 mg, 0.67 mmol) and DIEA (173 mg, 1.34 mmol). The resulting solution was stirred at room temperature overnight and concentrated under vacuum. The residue was passed through a short pad of silica gel eluting with 5% MeOH in DCM. The crude product (100 mg) was purified by Prep-HPLC with the following conditions (1#-Pre-HPLC-006(Waters)): Column, XSelect CSH Prep $C_{18}$ OBD Column, 5 um, 19*150 mm; mobile phase, Water with 0.05% FA and MeCN (24.0% MeCN up to 40.0% in 8 min); Detector, 254/220. 31.6 mg product was obtained. This resulted in 32 mg (12%) of the formic acid salt of N-[3-[5-chloro-2-(difluoromethoxy)phenyl]-1-(2-[[(5-oxooxolan-2-yl)methyl]-amino]ethyl)-1H-pyrazol-4-yl]pyrazolo[1,5-a]pyrimidine-3-carboxamide as an off-white solid. LCMS (Method 28) $[M+H]^+$=546.1, $R_T$=0.82 min. $^1H$ NMR (400 MHz, DMSO-$d_6$) δ: (ppm) 9.76 (s, 1H), 9.34 (dd, 1H, J=1.6, 7.2 Hz), 8.68-8.66 (m, 2H), 8.31 (s, 1H), 7.64-7.62 (m, 2H), 7.44 (d, 1H, J=8.8 Hz), 7.28 (dd, 1H, J=4.4, 6.8 Hz), 7.06 (t, 1H, J=73.2 Hz), 4.56-4.53 (m, 1H), 4.23 (t, 2H, J=6.4 Hz), 3.01 (t, 2H, J=6.0 Hz), 2.77-2.75 (m, 2H), 2.48-2.44 (m, 2H), 2.19-2.16 (m, 1H), 1.92-1.88 (m, 1H).

Example 382

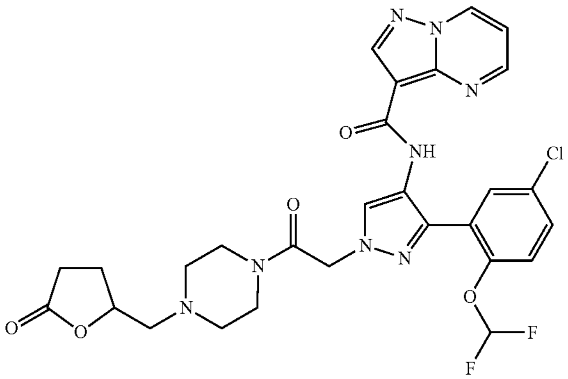 [SMILES: O=C1CCC(CN2CCN(C(=O)Cn3cc(NC(=O)c4cnn5cccnc45)c(-c4cc(Cl)ccc4OC(F)F)n3)CC2)O1]

N-[3-[5-chloro-2-(difluoromethoxy)phenyl]-1-(2-oxo-2-[4-[(5-oxooxolan-2-yl)methyl]piperazin-1-yl]ethyl)-1H-pyrazol-4-yl]pyrazolo[1,5-a]pyrimidine-3-carboxamide Neat triflic anhydride $Tf_2O$ (486 mg, 1.72 mmol) was added dropwise a solution of 5-(hydroxymethyl)oxolan-2-one (200 mg, 1.72 mmol) and DIEA (665 mg, 5.15 mmol) in DCM (20 mL) under stirring at −5° C. The resulting solution was stirred at room temperature for 3 h and quenched by saturated $NaHCO_3$ solution (50 mL). The resulting solution was extracted with DCM (×2) and the organic layers combined. The combined organic layers were washed with brine, dried over anhydrous sodium sulfate and concentrated under vacuum. This resulted in 280 mg (crude)

of (5-oxooxolan-2-yl)methyl trifluoromethanesulfonate as a yellow liquid. TLC: $R_f$=0.5; ethyl acetate/petroleum ether=1/2.

To a solution of N-[3-[5-chloro-2-(difluoromethoxy)phenyl]-1-[2-oxo-2-(piperazin-1-yl)ethyl]-1H-pyrazol-4-yl]pyrazolo[1,5-a]pyrimidine-3-carboxamide (100 mg, 0.19 mmol) in $CH_3CN$ (15 mL) was added DIEA (73.03 mg, 0.57 mmol), and (5-oxooxolan-2-yl)methyl trifluoromethanesulfonate (93.49 mg, 0.38 mmol). The resulting solution was stirred for 12 h at room temperature for 3 h and concentrated under vacuum. The crude product (180 mg) was purified by Prep-HPLC with the following conditions (2#-AnalyseHPLC-SHIMADZU(HPLC-10)): Column, XBridge BEH130 Prep C18 OBD Column, 19� 100 mm 5 um 13 nm; mobile phase, Water with 10 mM NH4CO3 and ACN (30% ACN up to 40% in 6 min); Detector, UV 254/220 nm. 65 mg product was obtained. The residue was applied onto a silica gel column with 5% MeOH in DCM. This resulted in 29.5 mg of N-[3-[5-chloro-2-(difluoromethoxy)phenyl]-1-(2-oxo-2-[4-[(5-oxooxolan-2-yl)methyl]piperazin-1-yl]ethyl)-1H-pyrazol-4-yl]pyrazolo[1,5-a]-pyrimidine-3-carboxamide as a white solid. LCMS (Method 28) $[M+H]^+$=629.1, $R_T$=0.81 min. $^1$H NMR (300 MHz, DMSO-$d_6$) δ: (ppm) 9.76 (s, 1H), 9.34 (dd, 1H, J=1.5, 6.9 Hz), 8.69-8.67 (m, 2H), 8.31 (s, 1H), 7.62 (dd, 1H, J=2.7, 8.7 Hz), 7.55 (d, 1H, J=2.7 Hz), 7.45 (d, 1H, J=9.0 Hz), 7.28 (dd, 1H, J=4.2, 6.9 Hz), 7.02 (t, 1H, J=73.2 Hz), 5.24 (s, 2H), 4.71-4.66 (m, 1H), 3.50-3.33 (m, 4H), 2.58 (d, 2H, J=5.4 Hz), 2.60-2.46 (m, 6H), 2.48-2.42 (m, 4H), 2.30-2.21 (m, 1H), 1.90-1.83 (m, 1H).

Example 383

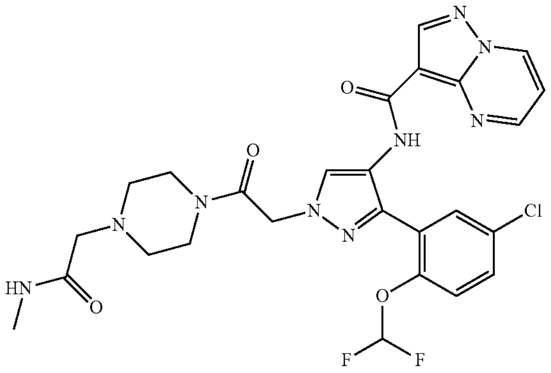 [SMILES: CNC(=O)CN1CCN(C(=O)Cn2cc(NC(=O)c3cnn4cccnc34)c(-c3cc(Cl)ccc3OC(F)F)n2)CC1]

N-[3-[5-chloro-2-(difluoromethoxy)phenyl]-1-(2-[4-[(methylcarbamoyl)methyl]piperazin-1-yl]-2-oxo-ethyl)-1H-pyrazol-4-yl]pyrazolo[1,5-a]pyrimidine-3-carboxamide To a solution of 2-[4-[(tert-butoxy)carbonyl]piperazin-1-yl]acetic acid (500 mg, 2.05 mmol) in DMF (20 mL) was added methanamine hydrochloride (406 mg, 6.01 mmol), DIEA (793 mg, 6.14 mmol) and HATU (1.17 g, 3.08 mmol). The resulting solution was stirred for 12 h at room temperature for 12 h. Water (50 mL) was added. The resulting solution was extracted with DCM (×3) and the organic layers combined. The combined organic layers were washed with brine, dried over anhydrous sodium sulfate and concentrated under vacuum. The residue was purified by flash chromatography on silica gel eluting with 5% MeOH in DCM. This resulted in 500 mg of tert-butyl 4-[(methylcarbamoyl)methyl]piperazine-1-carboxylate as yellow oil. LCMS (Method 25) $[M+H]^+$=258.0, $R_T$=0.52 min.

A mixture of tert-butyl 4-[(methylcarbamoyl)methyl]piperazine-1-carboxylate (500 mg, 1.94 mmol) and saturated HCl dioxane solution was stirred at room temperature for 3 h. The resulting solution was concentrated under vacuum. This resulted in 300 mg (crude) of N-methyl-2-(piperazin-1-yl)acetamide hydrochloride. LCMS (Method 20) $[M+H]^+$= 158.0, $R_T$=0.37 min.

To a solution of {3-(5-Chloro-2-difluoromethoxyphenyl)-4-[(pyrazolo[1,5-a]pyrimidine-3-carbonyl)amino]pyrazol-1-yl}acetic acid (150 mg, 0.32 mmol) in DMF (10 mL) was added N-methyl-2-(piperazin-1-yl)acetamide hydrochloride (125 mg, 0.65 mmol), HATU (185 mg, 0.49 mmol), DIEA (126 mg, 0.97 mmol). The resulting solution was stirred at room temperature for 12 h and concentrated under vacuum. The residue was passed through a short pad of silica gel eluting with 8% MeOH in DCM. The crude product (180 mg) was purified by Prep-HPLC with the following conditions (3#-Pre-HPLC-006(Waters)): Column, XSelect CSH Prep C18 OBD Column, 5 um, 19*150 mm; mobile phase, Water with 10 mM NH4CO3 and MeCN (26.0% MeCN up to 40.0% in 8 min); Detector, 254/220. This resulted in 73.9 mg (38%) of N-[3-[5-chloro-2-(difluoromethoxy)phenyl]-1-(2-[4-[(methylcarbamoyl)methyl]piperazin-1-yl]-2-oxo-ethyl)-1H-pyrazol-4-yl]pyrazolo[1,5-a]pyrimidine-3-carboxamide as a white solid. LCMS (Method 20) $[M+H]^+$= 602.2, $R_T$=3.66 min. $^1$H NMR (400 MHz, DMSO-$d_6$) δ: (ppm) 9.76 (s, 1H), 9.34 (dd, 1H, J=1.6, 6.8 Hz), 8.69-8.68 (m, 2H), 8.32 (s, 1H), 7.75 (q, 1H, J=4.8 Hz), 7.63 (dd, 1H, J=2.6, 8.6 Hz), 7.56 (d, 1H, J=2.8 Hz), 7.46 (d, 1H, J=8.8 Hz), 7.29 (dd, 1H, J=4.4, 7.2 Hz), 7.08 (t, 1H, J=73.2 Hz), 5.24 (s, 2H), 3.54 (t, 4H, J=5.0 Hz), 2.95 (s, 2H), 2.63 (d, 3H, J=4.8 Hz), 2.48-2.45 (m, 2H), 2.44-2.41 (m, 2H).

Example 384

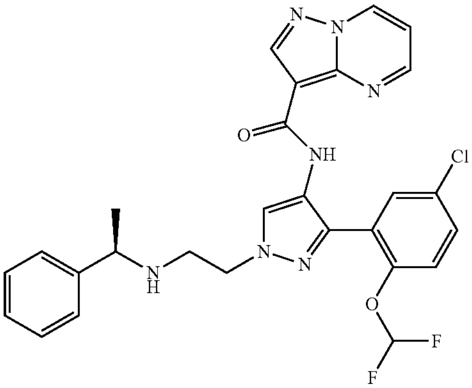 [SMILES: C[C@@H](NCCn1cc(NC(=O)c2cnn3cccnc23)c(-c2cc(Cl)ccc2OC(F)F)n1)c1ccccc1]

N-[3-[5-chloro-2-(difluoromethoxy)phenyl]-1-(2-[[(1R)-1-phenylethyl]amino]ethyl)-1H-pyrazol-4-yl]pyrazolo[1,5-a]pyrimidine-3-carboxamide A mixture of N-[1-(2-bromoethyl)-3-[5-chloro-2-(difluoromethoxy)phenyl]-1H-pyrazol-4-yl]pyrazolo[1,5-a]pyrimidine-3-carboxamide (100 mg, 0.20 mmol) and (1R)-1-phenylethan-1-amine (242 mg, 2.00 mmol) in MeCN (3 mL, 57.07 mmol) was stirred at 80° C. for 12 h. The crude product (120 mg) was purified by Prep-HPLC with the following conditions (2#-Analyse HPLC-SHIMADZU (HPLC-10)): Column, XBridge BEH130 Prep C18 OBD Column, 19� 100 mm 5 um 13 nm; mobile phase, Water with 10 mM NH4CO3 and ACN (40% ACN up to 58% in 6 min); Detector, UV 254/220 nm. This resulted in 38 mg of N-[3-[5-chloro-2-(difluoromethoxy)phenyl]-1-(2-[[(1R)-1-phenylethyl]amino]ethyl)-1H-pyrazol-4-yl]pyrazolo[1,5-a]pyrimidine-3-carboxamide as a off-white solid. LCMS (Method 25) $[M+H]^+$=552.1, $R_T$=1.16 min. $^1H$ NMR (300 MHz, DMSO-$d_6$) δ: (ppm) 9.72 (s, 1H), 9.34 (dd, 1H, J=1.5, 6.9 Hz), 8.69-8.67 (m, 2H), 8.34 (s, 1H), 7.60 (dd, 1H, J=2.7, 9.0 Hz), 7.55 (d, 1H, J=2.7 Hz), 7.43 (d, 1H, J=8.7 Hz), 7.31-7.17 (m, 6H), 6.98 (t, 1H, J=73.2 Hz), 4.18 (t, 2H, J=6.0 Hz), 3.70 (q, 1H, J=6.6 Hz), 2.83-2.73 (m, 2H), 1.22 (d, 3H, J=6.6 Hz).

Example 385

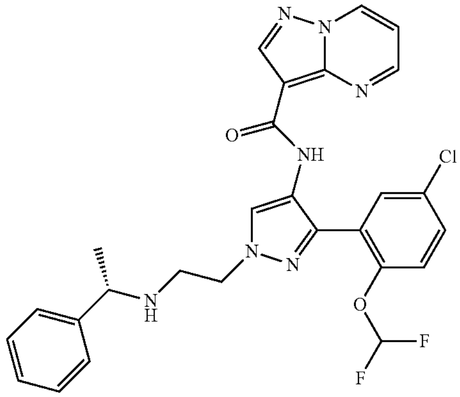 [SMILES: C[C@H](NCCn1cc(NC(=O)c2cnn3cccnc23)c(-c2cc(Cl)ccc2OC(F)F)n1)c1ccccc1]

N-[3-[5-chloro-2-(difluoromethoxy)phenyl]-1-(2-[[(1S)-1-phenyl ethyl]amino]ethyl)-1H-pyrazol-4-yl] pyrazolo[1,5-a]pyrimidine-3-carboxamide Using synthetic method analoguous to that of N-[3-[5-chloro-2-(difluoromethoxy)phenyl]-1-(2-[[(1R)-1-phenyl ethyl]amino]ethyl)-1H-pyrazol-4-yl]pyrazolo[1,5-a]pyrimidine-3-carboxamide, the title compound was prepared from (1S)-1-phenylethan-1-amine. LCMS (Method 25) $[M+H]^+$=552.1, $R_T$=1.15 min. $^1H$ NMR (300 MHz, DMSO-$d_6$) δ: (ppm) 9.72 (s, 1H), 9.33 (dd, 1H, J=1.5, 6.9 Hz), 8.69-8.67 (m, 2H), 8.34 (s, 1H), 7.60 (dd, 1H, J=2.9, 8.9 Hz), 7.55 (d, 1H, J=2.7 Hz), 7.43 (d, 1H, J=8.7 Hz), 7.31-7.16 (m, 6H), 6.98 (t, 1H, J=73.2 Hz), 4.18 (t, 2H, J=6.0 Hz), 3.70 (q, 1H, J=6.6 Hz), 2.83-2.73 (m, 2H), 1.22 (d, 3H, J=6.6 Hz).

Example 386

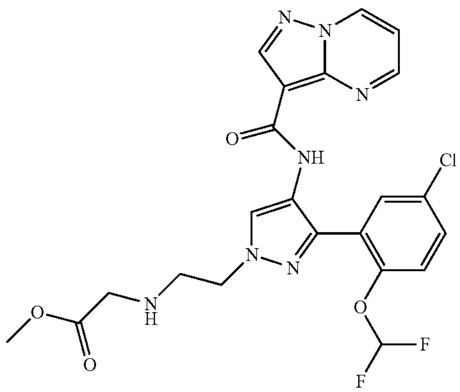 [SMILES: COC(=O)CNCCn1cc(NC(=O)c2cnn3cccnc23)c(-c2cc(Cl)ccc2OC(F)F)n1]

methyl 2-[(2-[3-[5-chloro-2-(difluoromethoxy)phenyl]-4-[pyrazolo[1,5-a]pyrimidine-3-amido]-1H-pyrazol-1-yl]ethyl)amino]acetate Using synthetic method analoguous to that of N-[3-[5-chloro-2-(difluoromethoxy)phenyl]-1-(2-[[(1R)-1-phenylethyl]amino]ethyl)-1H-pyrazol-4-yl]pyrazolo[1,5-a]pyrimidine-3-carboxamide, the title compound was prepared from methyl 2-aminoacetate hydrochloride and DIEA. LCMS (Method 28) $[M+H]^+$=520.1, $R_T$=0.85 min. $^1H$ NMR (300 MHz, DMSO-$d_6$) δ: (ppm) 9.73 (s, 1H), 9.33 (dd, 1H, J=1.8, 6.9 Hz), 8.69-8.67 (m, 2H), 8.36 (s, 1H), 7.65-7.61 (m, 2H), 7.44 (d, 1H, J=9.3 Hz), 7.28 (dd, 1H, J=4.2, 7.2 Hz), 7.00 (t, 1H, J=73.5 Hz), 4.22 (t, 2H, J=6.0 Hz), 3.62 (s, 3H), 3.37 (s, 2H), 2.98 (t, 2H, J=6.0 Hz), 2.27 (br, 1H).

Example 387

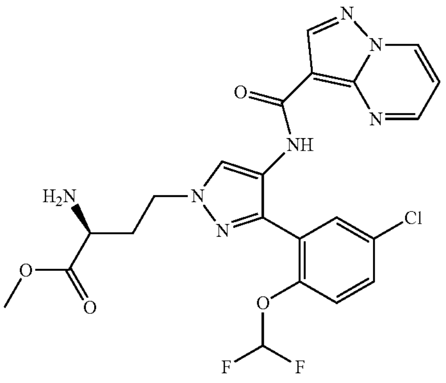 [SMILES: COC(=O)[C@@H](N)CCn1cc(NC(=O)c2cnn3cccnc23)c(-c2cc(Cl)ccc2OC(F)F)n1]

methyl (2S)-2-amino-4-[3-[5-chloro-2-(difluoromethoxy)phenyl]-4-[pyrazolo[1,5-a]pyrimidine-3-amido]-1H-pyrazol-1-yl]butanoate To a solution of (2S)-2-[[(tert-butoxy)carbonyl]amino]-4-hydroxybutanoic acid (2.20 g, 10.03 mmol) in DCM (80 mL) was added DIEA (2.58 g, 19.96 mmol), followed by TBDMS-Cl (1.65 g, 10.95 mmol) batchwise at 0° C. The resulting solution was stirred at room temperature for 12 h. Water (100 mL) was added. Phases were separated. The aqueous phase was extracted with DCM (×2) and the organic layers combined. The combined organic layers were washed with brine, dried over anhydrous sodium sulfate and concentrated under vacuum. The residue was purified by flash chromatography on silica gel eluting with ethyl acetate/petroleum ether (4:1). This resulted in 800 mg of (2S)-2-[[(tert-butoxy)carbonyl]amino]-4-[(tert-butyl dimethyl silyl)oxy]butanoic acid as light yellow oil. LCMS (Method 28) $[M+H]^+$=275.0, $R_T$=1.16 min.

To a solution of (2S)-2-[[(tert-butoxy)carbonyl]amino]-4-[(tert-butyldimethylsilyl)oxy]butanoic acid (800 mg, 2.40 mmol) in DCM (30 mL) was added 4-dimethylaminopyridine (29 mg, 0.24 mmol), EDC.HCl (550 mg, 2.87 mmol) and methanol (5 mL). The resulting solution was stirred at room temperature overnight and concentrated under vacuum. The residue was purified by flash chromatography on silica gel eluting with ethyl acetate/petroleum ether (1:4). This resulted in 600 mg (72%) of methyl (2S)-2-[[(tert-butoxy)carbonyl]amino]-4-[(tert-butyldimethylsilyl)oxy] butanoate as light yellow oil. LCMS (Method 25) $[M+H]^+$=348.0, $R_T$=1.21 min.

A solution of methyl 2-[[(tert-butoxy)carbonyl]amino]-4-[(tert-butyldimethylsilyl)oxy]butanoate (600 mg, 1.73 mmol) in THF (2 mL), water (2 mL) and AcOH (8 mL, 139.61 mmol, 80.90 equiv) was stirred at for 2 h. The reaction mixture was neutralized with saturated sodium bicarbonate solution, extracted with DCM (×3) and the organic layers combined. The combined organic layers were washed with brine, dried over anhydrous sodium sulfate and concentrated under vacuum. This resulted in 400 mg of methyl 2-[[(tert-butoxy)carbonyl]amino]-4-hydroxybutanoate as light yellow oil. LCMS (Method 28) $[M+H]^+$=175, $R_T$=0.65 min.

To a stirring solution of crude methyl 2-[[(tert-butoxy)carbonyl]amino]-4-hydroxybutanoate (400 mg) in DCM (20 mL) was added DIEA (387 mg, 2.99 mmol), followed by MsCl (114 mg, 1.00 mmol) dropwise with stirring at 0° C. The resulting solution was stirred at room temperature for 3 h. Saturated $NaHCO_3$ (50 mL) was added. The resulting solution was extracted with DCM (×2) and the organic layers combined. The combined organic layers were washed with brine, dried over anhydrous sodium sulfate and concentrated under vacuum. This resulted in 510 mg (80%) of methyl 2-[[(tert-butoxy)carbonyl]amino]-4-(methanesulfonyloxy) butanoate as yellow oil. LCMS (Method 25) $[M+H]^+$=212.0, $R_T$=0.76 min.

To a solution of N-[3-[5-chloro-2-(difluoromethoxy)phenyl]-1H-pyrazol-4-yl]pyrazolo[1,5-a]pyrimidine-3-carboxamide (200 mg, 0.49 mmol) in $CH_3CN$ (30 mL) was added $Cs_2CO_3$ (326 mg, 1.00 mmol), and methyl (2S)-2-[[(tert-butoxy)carbonyl]amino]-4-(methanesulfonyloxy)butanoate (400 mg, crude). The resulting solution was stirred at room temperature overnight. The solids were filtered out. The filtrate was concentrated under vacuum. The residue was purified by flash chromatography on silica gel eluting with dichloromethane/ethyl acetate (70/30). This resulted in 280 mg (73%) of methyl 2-[[(tert-butoxy)carbonyl]amino]-4-[3-[5-chloro-2-(difluoromethoxy)phenyl]-4-[pyrazolo[1,5-a]pyrimidine-3-amido]-1H-pyrazol-1-yl]butanoate as an off-white solid. LCMS (Method 25) $[M+H]^+$=620.0, $R_T$=0.98 min.

The mixture of methyl (2S)-2-[[(tert-butoxy)carbonyl]amino]-4-[3-[5-chloro-2-(difluoromethoxy)phenyl]-4-[pyrazolo[1,5-a]pyrimidine-3-amido]-1H-pyrazol-1-yl]-butanoate (280 mg), in DCM/TFA (15 mL, 2:1) was stirred at room temperature overnight. The resulting mixture was concentrated under vacuum. The crude product (200 mg) was purified by Prep-HPLC with the following conditions (1#-Pre-HPLC-006(Waters)): Column, XSelect CSH Prep C18 OBD Column, 5 um, 19*150 mm; mobile phase, Water with 0.05% FA and MeCN (24.0% MeCN up to 40.0% in 8 min); Detector, 254/220. 150 mg product was obtained. This resulted in 148.4 mg (73%) of methyl (2S)-2-amino-4-[3-[5-chloro-2-(difluoromethoxy)phenyl]-4-[pyrazolo[1,5-a]pyrimidine-3-amido]-1H-pyrazol-1-yl]butanoate formate as an off-white solid. LCMS (Method 28) $[M+H]^+$=520.1, $R_T$=0.82 min. $^1H$ NMR (300 MHz, DMSO-$d_6$) δ: (ppm) 9.75 (s, 1H), 9.34 (dd, 1H, J=1.5, 6.9 Hz), 8.69-8.68 (m, 2H), 8.36 (s, 1H), 7.65-7.61 (m, 2H), 7.45 (d, 1H, J=8.4 Hz), 7.28 (dd, 1H, J=4.2, 7.2 Hz), 7.01 (t, 1H, J=73.2 Hz), 4.40-4.26 (m, 2H), 3.64 (s, 3H), 3.50-3.43 (m, 1H), 2.32-2.18 (m, 1H), 2.11-1.99 (m, 1H).

Example 388

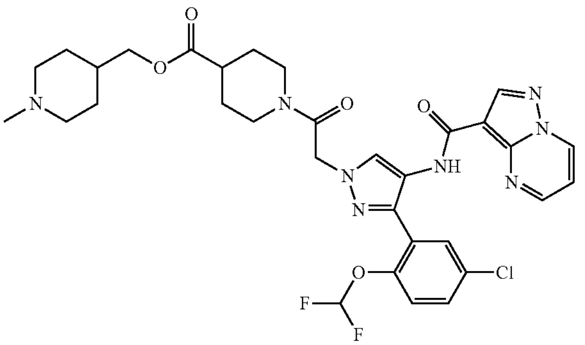 [SMILES: CN1CCC(COC(=O)C2CCN(C(=O)Cn3cc(NC(=O)c4cnn5cccnc45)c(-c4cc(Cl)ccc4OC(F)F)n3)CC2)CC1]

(1-methylpiperidin-4-yl)methyl 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylate To a solution of 1-[(tert-butoxy)carbonyl]piperidine-4-carboxylic acid (1.00 g, 4.36 mmol) in DCM (50 mL) was added (1-methylpiperidin-4-yl)methanol (1.13 g, 8.75 mmol), EDC.HCl (1.0 g, 5.22 mmol), 4-dimethylaminopyridine (54 mg, 0.44 mmol), The resulting solution was stirred at room temperature overnight. Water (50 mL) was added. Phases were separated. The aqueous phase was extracted with DCM (×2) and the organic layers combined. The organic layers were dried over anhydrous sodium sulfate and concentrated under vacuum. The residue was purified by flash chromatography on silica gel eluting with 6% MeOH in DCM. This resulted in 1.2 g of 1-tert-butyl 4-(1-methylpiperidin-4-yl)methyl piperidine-1,4-dicarboxylate as light yellow oil. LCMS (Method 28) $[M+H]^+$=341.0, $R_T$=0.58 min.

A mixture of 1-tert-butyl 4-(1-methylpiperidin-4-yl)methyl piperidine-1,4-dicarboxylate (1.2 g, 3.52 mmol) and saturated HCl dioxane solution (15 mL) was stirred at room temperature overnight. The resulting solution was concentrated under vacuum. This resulted in 1.5 g (crude) of (1-methylpiperidin-4-yl)methyl piperidine-4-carboxylate hydrochloride as a white solid. LCMS (Method 25) $[M+H]^+$= 241.0, $R_T$=0.19 min.

To a solution of {3-(5-Chloro-2-difluoromethoxyphenyl)-4-[(pyrazolo[1,5-a]pyrimidine-3-carbonyl)amino]pyrazol-1-yl}acetic acid (150 mg, 0.32 mmol) in DMF (10 mL) was added (1-methylpiperidin-4-yl)methyl piperidine-4-carboxylate hydrochloride (178 mg, 0.64 mmol), DIEA (126 mg, 0.97 mmol), HATU (160 mg, 0.42 mmol). The resulting solution was stirred at room temperature overnight. Water (50 mL) was added. The resulting solution was extracted with DCM (×3) and the organic layers combined. The combined organic layers were washed with brine, dried over anhydrous sodium sulfate and concentrated under vacuum. The residue was passed through a short pad of silica gel eluting with 8% MeOH in DCM. The crude product (80 mg) was purified by Prep-HPLC with the following conditions (3#-Pre-HPLC-006(Waters)): Column, XSelect CSH Prep $C_{18}$ OBD Column, 5 um, 19*150 mm; mobile phase, Water with 0.05% FA and MeCN (32.0% MeCN up to 50.0% in 8 min); Detector, 254/220. This resulted in 37 mg (16%) of the formic acid salt of (1-methylpiperidin-4-yl)methyl 1-(2-[3-

[5-chloro-2-(difluoromethoxy)phenyl]-4-[pyrazolo[1,5-a]pyrimidine-3-amido]-1H-pyrazol-1-yl]acetyl)piperidine-4-carboxylate as an off-white solid. LCMS (Method 25) $[M+H]^+$=685.2, $R_T$=1.05 min. $^1H$ NMR (400 MHz, DMSO-d6) δ: (ppm) 9.75 (s, 1H), 9.35 (dd, 1H, J=1.2, 6.8 Hz), 8.69-8.68 (m, 2H), 8.32 (s, 1H), 7.63 (dd, 1H, J=2.8, 8.8 Hz), 7.55 (d, 1H, J=2.4 Hz), 7.46 (d, 1H, J=8.8 Hz), 7.29 (dd, 1H, J=4.4, 7.2 Hz), 7.08 (t, 1H, J=73.2 Hz), 5.36-5.18 (m, 2H), 4.28-4.21 (m, 1H), 3.96-3.88 (m, 3H), 3.25-3.12 (m, 1H), 2.86-2.74 (m, 3H), 2.73-2.66 (m, 1H), 2.15 (s, 3H), 1.92-1.83 (m, 4H), 1.65-1.52 (m, 4H), 1.48-1.38 (m, 1H), 1.29-1.16 (m, 2H).

Example 389

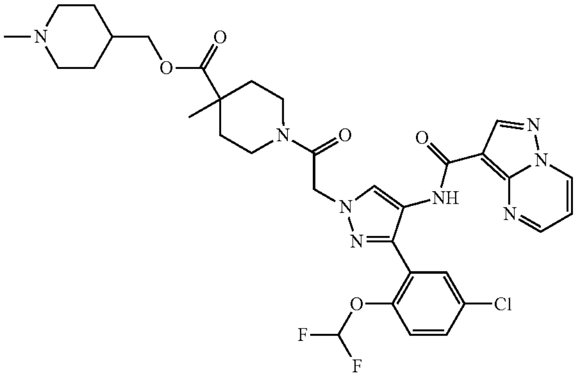 [SMILES: CN1CCC(COC(=O)C2(C)CCN(C(=O)Cn3cc(NC(=O)c4cnn5cccnc45)c(-c4cc(Cl)ccc4OC(F)F)n3)CC2)CC1]

(1-methylpiperidin-4-yl)methyl 1-(2-[3-[5-chloro-2-(difluoromethoxy)phenyl]-4-[pyrazolo[1,5-a]pyrimidine-3-amido]-1H-pyrazol-1-yl]acetyl)-4-methylpiperidine-4-carboxylate Using synthetic method analoguous to that of (1-methylpiperidin-4-yl)methyl 1-(2-[3-[5-chloro-2-(difluoromethoxy)phenyl]-4-[pyrazolo[1,5-a]pyrimidine-3-amido]-1H-pyrazol-1-yl]acetyl)piperidine-4-carboxylate, the title compound was prepared from 1-[(tert-butoxy)carbonyl]-4-methylpiperidine-4-carboxylic acid. LCMS (Method 28) $[M+H]^+$=699.2, $R_T$=0.95 min. $^1H$ NMR (400 MHz, DMSO-$d_6$) δ: (ppm) 9.75 (s, 1H), 9.34 (dd, 1H, J=1.6, 7.2 Hz), 8.69-8.68 (m, 2H), 8.31 (s, 1H), 7.63 (dd, 1H, J=2.4, 8.8 Hz), 7.55 (d, 1H, J=2.8 Hz), 7.46 (d, 1H, J=8.8 Hz), 7.29 (dd, 1H, J=4.0, 6.8 Hz), 7.08 (t, 1H, J=73.2 Hz), 5.24 (s, 2H), 3.99-3.96 (m, 2H), 3.94-3.88 (m, 1H), 3.78-3.71 (m, 1H), 3.26-3.20 (m, 1H), 3.08-3.00 (m, 1H), 2.85-2.80 (m, 2H), 2.20 (s, 3H), 2.02-1.94 (m, 4H), 1.68-1.59 (m, 4H), 1.54-1.48 (m, 1H), 1.41-1.34 (m, 1H), 1.28-1.23 (m, 2H), 1.18 (s, 3H).

Example 390

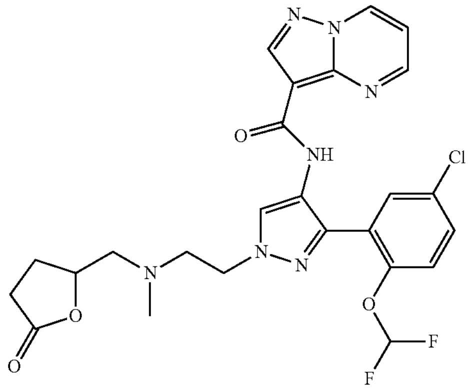 [SMILES: CN(CCn1cc(NC(=O)c2cnn3cccnc23)c(-c2cc(Cl)ccc2OC(F)F)n1)CC1CCC(=O)O1]

N-[3-[5-chloro-2-(difluoromethoxy)phenyl]-1-(2-[methyl[(5-oxooxolan-2-yl)methyl]amino]ethyl)-1H-pyrazol-4-yl]pyrazolo[1,5-a]pyrimidine-3-carboxamide To a solution of N-[3-[5-chloro-2-(difluoromethoxy)phenyl]-1-(2-[[(5-oxooxolan-2-yl)methyl]amino]ethyl)-1H-pyrazol-4-yl]pyrazolo[1,5-a]pyrimidine-3-carboxamide (140 mg, 0.26 mmol) in MeOH (20 mL) was added 37% formaldehyde in water (23 mg), followed by $NaBH_3CN$ (24.6 mg, 0.39 mmol). The resulting solution was stirred at room temperature for 3 h. The resulting mixture was concentrated under vacuum. The residue was passed through a short pad of silica gel eluting with 8% MeOH in DCM. The crude product (60 mg) was purified by Prep-HPLC with the following conditions (1#-Pre-HPLC-006(Waters)): Column, XSelect CSH Prep C18 OBD Column, 5 um, 19*150 mm; mobile phase, Water with 0.05% FA and MeCN (18.0% MeCN up to 36.0% in 8 min); Detector, 254/220. This resulted in 22.4 mg of the formic acid salt of N-[3-[5-chloro-2-(difluoromethoxy)phenyl]-1-(2-[methyl[(5-oxooxolan-2-yl)methyl]amino]ethyl)-1H-pyrazol-4-yl]pyrazolo[1,5-a]pyrimidine-3-carboxamide as a white solid. LCMS (Method 28) $[M+H]^+$=560.2, $R_T$=0.94 min. $^1H$ NMR (400 MHz, DMSO-$d_6$) δ: (ppm) 9.76 (s, 1H), 9.34 (dd, 1H, J=1.6, 7.2 Hz), 8.69-8.67 (m, 2H), 8.38 (s, 1H), 7.62 (dd, 1H, J=2.8, 8.8 Hz), 7.60 (d, 1H, J=2.4 Hz), 7.45 (d, 1H, J=8.8 Hz), 7.29 (dd, 1H, J=4.0, 6.8 Hz), 7.08 (t, 1H, J=73.2 Hz), 4.59-4.55 (m, 1H), 4.30-4.27 (m, 2H), 2.94-2.88 (m, 2H), 2.62 (d, 2H, J=5.6 Hz), 2.44-2.41 (m, 2H), 2.32 (s, 3H), 2.14-2.11 (m, 1H), 1.83-1.77 (m, 1H).

Example 391

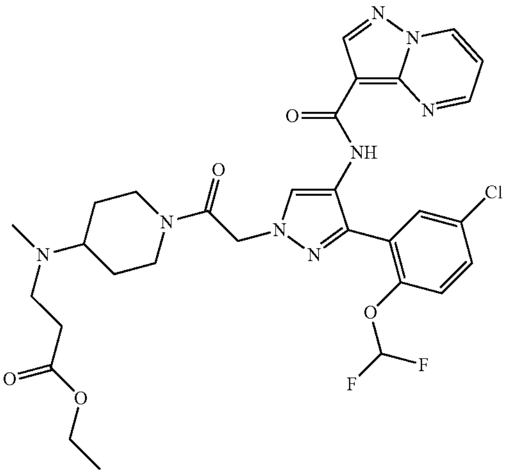 [SMILES: CCOC(=O)CCN(C)C1CCN(C(=O)Cn2cc(NC(=O)c3cnn4cccnc34)c(-c3cc(Cl)ccc3OC(F)F)n2)CC1]

ethyl 3-[[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl](methyl)amino]propanoate To a solution of tert-butyl 4-(methylamino)piperidine-1-carboxylate (1.00 g, 4.67 mmol) in ethanol (50 mL) was added AcOH (0.1 mL, 1.75 mmol) and ethyl 3-oxopropanoate (1.63 g, 14.04 mmol). The mixture was stirred at room temperature for 5 h and $NaBH_3CN$ (882 mg, 14.04 mmol) was added. The resulting solution was stirred at room temperature overnight and concentrated under vacuum. The residue was purified by flash chromatography on silica gel eluting with 4% MeOH in DCM. This resulted in 580 mg of tert-butyl 4-[(3-ethoxy-3-oxopropyl)(methyl)amino]piperidine-1-carboxylate as colorless oil. LCMS (Method 20) $[M+H]^+$=315.0, $R_T$=1.14 min.

A mixture of tert-butyl 4-[(3-ethoxy-3-oxopropyl)(methyl)amino]piperidine-1-carboxylate (580 mg, 1.84 mmol) and saturated HCl dioxane solution was stirred at room temperature for 3 h. The resulting mixture was concentrated under vacuum. The residue was titrated with EtOAc. The solids were collected by filtration. This resulted in 200 mg (crude) of ethyl 3-[methyl(piperidin-4-yl)amino]propanoate hydrochloride as an off-white solid. LCMS (Method 20) $[M+H]^+$=215.0, $R_T$=0.45 min.

To a solution of {3-(5-Chloro-2-difluoromethoxyphenyl)-4-[(pyrazolo[1,5-a]pyrimidine-3-carbonyl)amino]pyrazol-1-yl}acetic acid (100 mg, 0.22 mmol) in DMF (10 mL) was added HATU (123 mg, 0.32 mmol), DIEA (83 mg, 0.64 mmol), and ethyl 3-[methyl(piperidin-4-yl)amino]propanoate hydrochloride (200 mg). The resulting solution was stirred at room temperature overnight. Water (50 mL) was added. The resulting mixture was extracted with DCM (×3) and the organic layers combined. The combined organic layers were washed brine, dried over anhydrous sodium sulfate and concentrated under vacuum. The crude product (82 mg) was purified by Prep-HPLC with the following conditions (1#-Pre-HPLC-006(Waters)): Column, XSelect CSH Prep C18 OBD Column, 5 um, 19*150 mm; mobile phase, Water with 0.05% FA and MeCN (18.0% MeCN up to 36.0% in 8 min); Detector, 254/220. 20.3 mg product was obtained. This resulted in 20.3 mg (13%) of the formic acid salt of ethyl 3-[[1-(2-[3-[5-chloro-2-(difluoromethoxy)phenyl]-4-[pyrazolo[1,5-a]pyrimidine-3-amido]-1H-pyrazol-1-yl]acetyl)piperidin-4-yl](methyl)amino]propanoate as an off-white solid. LCMS (Method 28) $[M+H]^+$=659.2, $R_T$=0.90 min. $^1$HNMR (300 MHz, DMSO-$d_6$) δ: (ppm) 9.76 (s, 1H), 9.34 (dd, 1H, J=1.5, 7.2 Hz), 8.68-8.66 (m, 2H), 8.31 (s, 1H), 7.62 (dd, 1H, J=2.7, 8.7 Hz), 7.55 (d, 1H, J=2.4 Hz), 7.45 (d, 1H, J=8.7 Hz), 7.28 (dd, 1H, J=4.2, 7.2 Hz), 7.03 (t, 1H, J=73.2 Hz), 5.36-5.15 (m, 2H), 4.48-4.33 (m, 1H), 4.02 (q, 2H, J=7.2 Hz), 4.00-3.96 (m, 1H), 3.18-3.00 (m, 1H), 2.89-2.80 (m, 3H), 2.68-2.54 (m, 3H), 2.31 (s, 3H), 1.85-1.76 (m, 2H), 1.61-1.25 (m, 2H), 1.19 (t, 3H, J=6.9 Hz).

Example 392

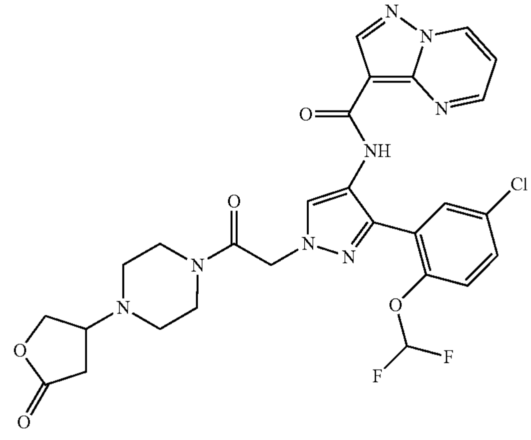 [SMILES: O=C1CC(N2CCN(C(=O)Cn3cc(NC(=O)c4cnn5cccnc45)c(-c4cc(Cl)ccc4OC(F)F)n3)CC2)CO1]

N-[3-[5-chloro-2-(difluoromethoxy)phenyl]-1-[2-oxo-2-[4-(5-oxooxolan-3-yl)piperazin-1-yl]ethyl]-1H-pyrazol-4-yl]pyrazolo[1,5-a]pyrimidine-3-carboxamide A mixture of tert-butyl piperazine-1-carboxylate (1.0 g, 5.37 mmol), oxolane-2,4-dione (1.07 g, 10.69 mmol) and AcOH (0.2 mL) in THF (50 mL) was stirred at room temperature for 3 h. $NaBH_3CN$ (508 mg, 8.08 mmol) was added. The resulting solution was stirred at room temperature overnight. The resulting mixture was concentrated under vacuum. The residue was passed through a short pad of silica gel eluting with dichloromethane/ethyl acetate (1/4). This resulted in 400 mg (28%) of tert-butyl 4-(5-oxooxolan-3-yl)piperazine-1-carboxylate as light yellow oil. LCMS (Method 10) $[M+H]^+$=271.0, $R_T$=0.56 min.

A mixture of tert-butyl 4-(5-oxooxolan-3-yl)piperazine-1-carboxylate (400 mg, 1.48 mmol) and saturated HCl dioxane solution (15 mL) was stirred at room temperature for 3 h. The solids were collected by filtration. This resulted in 380 mg (crude) of 4-(piperazin-1-yl)oxolan-2-one hydrochloride as a white solid. LCMS (Method 22) $[M+H]^+$=171.0, $R_T$=0.38 min.

To a solution of {3-(5-Chloro-2-difluoromethoxyphenyl)-4-[(pyrazolo[1,5-a]pyrimidine-3-carbonyl)amino]pyrazol-1-yl}acetic acid (200 mg, 0.43 mmol) in DMF (10 mL) was added 4-(piperazin-1-yl)oxolan-2-one hydrochloride (250 mg, 1.21 mmol), HATU (247 mg, 0.65 mmol), DIEA (167 mg, 1.29 mmol)., The resulting solution was stirred at room temperature overnight. Water (50 mL) was added. The resulting solution was extracted with DCM (×3) and the organic layers combined. The combined organic layers were washed with brine, dried over anhydrous sodium sulfate and concentrated under vacuum. The residue was passed through a short pad of silica gel eluting with 8% MeOH in DCM. The crude product (80 mg) was purified by Prep-HPLC with the following conditions (1#-Pre-HPLC-006(Waters)): Column, XSelect CSH Prep C18 OBD Column, 5 um, 19*150 mm; mobile phase, Water with 0.05% FA and MeCN (32.0% MeCN up to 60.0% in 10 min); Detector, 254/220. 37 mg product was obtained. This resulted in 36.7 mg (14%) of N-[3-[5-chloro-2-(difluoromethoxy)phenyl]-1-[2-oxo-2-[4-(5-oxooxolan-3-yl)piperazin-1-yl]ethyl]-1H-pyrazol-4-yl]pyrazolo[1,5-a]pyrimidine-3-carboxamide as a white solid. LCMS (Method 28) $[M+H]^+$=615.0, $R_T$=0.99 min. $^1$H NMR (300 MHz, DMSO-$d_6$) δ: (ppm) 9.76 (s, 1H), 9.34 (d, 1H, J=6.9 Hz), 8.69-8.67 (m, 2H), 8.30 (s, 1H), 7.62 (dd, 1H, J=2.4, 9.0 Hz), 7.56 (s, 1H), 7.45 (d, 1H, J=8.7 Hz), 7.28 (dd, 1H, J=4.2, 6.9 Hz), 7.02 (t, 1H, J=73.2 Hz), 5.24 (s, 2H), 4.44-4.38 (m, 1H), 4.26-4.18 (m, 1H), 3.49 (t, 4H, J=5.1 Hz), 3.40-3.37 (m, 1H), 2.78-2.68 (m, 1H), 2.60-2.55 (m, 1H), 2.47-2.35 (m, 4H).

Example 393

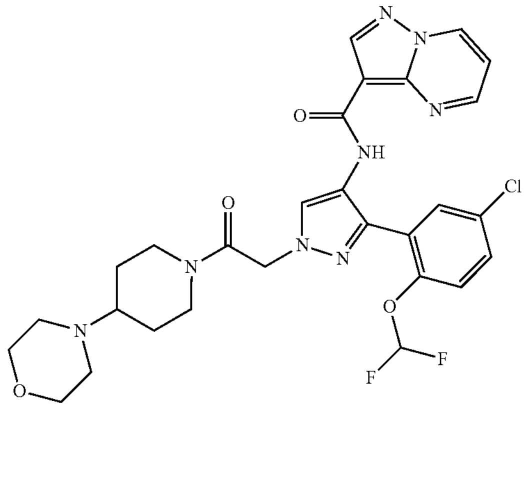 [SMILES: O=C(Nc1cn(CC(=O)N2CCC(N3CCOCC3)CC2)nc1-c1cc(Cl)ccc1OC(F)F)c1cnn2cccnc12]

N-[3-[5-chloro-2-(difluoromethoxy)phenyl]-1-[2-[4-(morpholin-4-yl)piperidin-1-yl]-2-oxoethyl]-1H-pyrazol-4-yl]pyrazolo[1,5-a]pyrimidine-3-carboxamide To a solution of {3-(5-Chloro-2-difluoromethoxyphenyl)-4-[(pyrazolo[1,5-a]pyrimidine-3-carbonyl)amino]pyrazol-1-yl}acetic acid (100 mg) in DMF (2 mL) was added HATU (100 mg, 0.26 mmol), DIEA (85 mg, 0.66 mmol), and 4-(piperidin-4-yl)morpholine hydrochloride (67 mg, 0.32 mmol). The resulting solution was stirred at room temperature overnight. The crude product (60 mg) was purified by Prep-HPLC with the following conditions (1#-Pre-HPLC-006(Waters)): Column, XSelect CSH Prep C18 OBD Column, 5 um, 19*150 mm; mobile phase, Water with 10 mM NH4CO3 and MeCN (20.0% MeCN up to 35.0% in 8 min); Detector, 254/220. This resulted in 28.3 mg (21%) of N-[3-[5-chloro-2-(difluoromethoxy)phenyl]-1-[2-[4-(morpholin-4-yl)piperidin-1-yl]-2-oxoethyl]-1H-pyrazol-4-yl]pyrazolo[1,5-a]pyrimidine-3-carboxamide as a yellow solid. LCMS (Method 20) $[M+H]^+$=615.2, $R_T$=1.84 min. $^1H$ NMR (300 MHz, DMSO-$d_6$) δ: (ppm) 9.75 (s, 1H), 9.34 (dd, 1H, J=1.5, 6.9 Hz), 8.69-8.67 (m, 2H), 8.31 (s, 1H), 7.62 (dd, 1H, J=2.7, 8.7 Hz), 7.55 (d, 1H, J=2.7 Hz), 7.45 (d, 1H, J=8.7 Hz), 7.28 (dd, 1H, J=4.2, 6.9 Hz), 7.02 (t, 1H, J=73.2 Hz), 5.24-5.21 (m, 2H), 4.42-4.31 (m, 1H), 4.02-3.95 (m, 1H), 3.55 (t, 4H, J=4.5 Hz), 3.16-3.02 (m, 1H), 2.78-2.64 (m, 1H), 2.49-2.45 (m, 5H), 1.90-1.76 (m, 2H), 1.54-1.21 (m, 2H).

Example 394

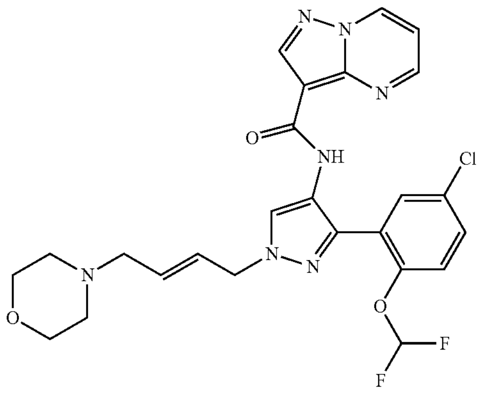 [SMILES: O=C(Nc1cn(C/C=C/CN2CCOCC2)nc1-c1cc(Cl)ccc1OC(F)F)c1cnn2cccnc12]

N-[3-[5-chloro-2-(difluoromethoxy)phenyl]-1-[(2E)-4-(morpholin-4-yl)but-2-en-1-yl]-1H-pyrazol-4-yl]pyrazolo[1,5-a]pyrimidine-3-carboxamide A mixture of N-[3-[5-chloro-2-(difluoromethoxy)phenyl]-1H-pyrazol-4-yl]pyrazolo[1,5-a]pyrimidine-3-carboxamide (400 mg, 0.99 mmol), (2E)-1,4-dichlorobut-2-ene (370 mg, 2.96 mmol) and cesium carbonate (1 g, 3.07 mmol) was stirred at 65° C. for 20 h. The reaction mixture was cooled. The resulting solution was diluted with ethyl acetate (100 mL), and washed $H_2O$ (×3). The organic layer was dried over sodium sulfate and concentrated under vacuum. The residue was purified by flash chromatography on silica gel eluting with ethyl acetate/hexane (1:1). The appropriate fractions were combined and concentrated under vacuum.

This resulted in 320 mg (66%) of N-[3-[5-chloro-2-(difluoromethoxy)phenyl]-1-[(2E)-4-chlorobut-2-en-1-yl]-1H-pyrazol-4-yl]pyrazolo[1,5-a]pyrimidine-3-carboxamide as a light yellow solid. TLC: $R_f$=0.4; ethyl acetate/petroleum ether=1:1.

A solution of N-[3-[5-chloro-2-(difluoromethoxy)phenyl]-1-[(2E)-4-chlorobut-2-en-1-yl]-1H-pyrazol-4-yl]pyrazolo[1,5-a]pyrimidine-3-carboxamide (160 mg, 0.324 mmol) and morpholine (0.5 mL) in DMF (4 mL) was stirred at room temperature for 2 h. The resulting mixture was concentrated under vacuum. The crude product (200 mg) was purified by Flash-Prep-HPLC with the following conditions (IntelFlash-1): Column, silica gel; mobile phase, $CH_3CN/H_2O$=20% increasing to $CH_3CN/H_2O$=50% within 20 min; Detector, UV 254 nm. 35.4 mg product was obtained. This resulted in 35.4 mg (20%) of N-[3-[5-chloro-2-(difluoromethoxy)phenyl]-1-[(2E)-4-(morpholin-4-yl)but-2-en-1-yl]-1H-pyrazol-4-yl]pyrazolo[1,5-a]pyrimidine-3-carboxamide as a off-white solid. LCMS (Method 23) $[M+H]^+$=544.0, $R_T$=2.37 min. $^1H$ NMR (400 MHz, DMSO-$d_6$) δ: (ppm) 9.74 (s, 1H), 9.34 (dd, 1H, J=1.6, 6.8 Hz), 8.68-8.66 (m, 2H), 8.31 (s, 1H), 7.62 (dd, 1H, J=2.8, 8.8 Hz), 7.58 (d, 1H, J=2.8 Hz), 7.44 (d, 1H, J=8.8 Hz), 7.28 (dd, 1H, J=4.4, 6.8 Hz), 7.06 (t, 1H, J=73.2 Hz), 5.94-5.84 (m, 1H), 5.79-5.69 (m, 1H), 4.82 (d, 2H, J=6.0 Hz), 3.56 (t, 4H, J=4.6 Hz), 2.96 (d, 2H, J=6.4 Hz), 2.40-2.30 (m, 4H).

Example 395

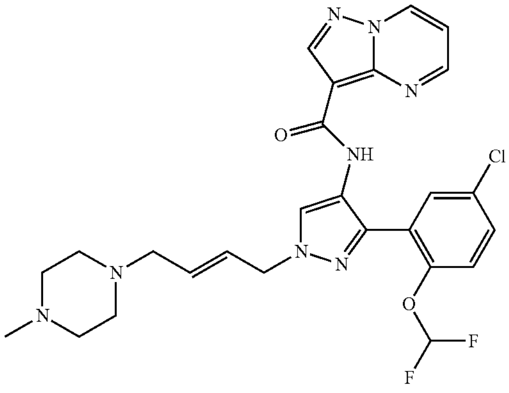 [SMILES: CN1CCN(C/C=C/Cn2cc(NC(=O)c3cnn4cccnc34)c(-c3cc(Cl)ccc3OC(F)F)n2)CC1]

N-[3-[5-chloro-2-(difluoromethoxy)phenyl]-1-[(2E)-4-(4-methylpiperazin-1-yl)but-2-en-1-yl]-1H-pyrazol-4-yl]pyrazolo[1,5-a]pyrimidine-3-carboxamide Using synthetic method analoguous to that of N-[3-[5-chloro-2-(difluoromethoxy)phenyl]-1-[(2E)-4-(morpholin-4-yl)but-2-en-1-yl]-1H-pyrazol-4-yl]pyrazolo[1,5-a]pyrimidine-3-carboxamide, the title compound was prepared from 1-methylpiperazine. LCMS (Method 23) $[M+H]^+$=557.1, $R_T$=1.76 min. $^1H$ NMR (400 MHz, DMSO-$d_6$) δ: (ppm) 9.74 (s, 1H), 9.34 (d, 1H, J=5.2 Hz), 8.68-8.66 (m, 2H), 8.31 (s, 1H), 7.62 (d, 1H, J=8.8 Hz), 7.58 (d, 1H, J=2.4 Hz), 7.47 (d, 1H, J=8.8 Hz), 7.28 (dd, 1H, J=4.0, 6.8 Hz), 7.06 (t, 1H, J=73.2 Hz), 5.92-5.80 (m, 1H), 5.78-5.66 (m, 1H), 4.81 (d, 2H, J=6.0 Hz), 2.94 (d, 2H, J=6.4 Hz), 2.45-2.20 (m, 8H), 2.13 (s, 3H).

Example 396

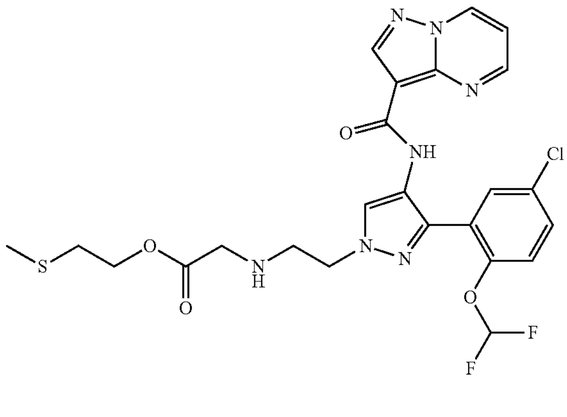 [SMILES: CSCCOC(=O)CNCCn1cc(NC(=O)c2cnn3cccnc23)c(-c2cc(Cl)ccc2OC(F)F)n1]

2-(methylthio)ethyl 2-(2-(3-(5-chloro-2-(difluoromethoxy)phenyl)-4-(pyrazolo[1,5-a]pyrimidine-3-carboxamido)-1H-pyrazol-1-yl)ethylamino)acetate To a solution of 2-(methylsulfanyl)ethan-1-ol (2.40 g, 26.04 mmol) in DMF (15 mL) was added 2-[(tert-butoxy)carbonyl]aminoacetic acid (3.19 g, 18.21 mmol), HOBt (2.82 g, 20.87 mmol), EDC.HCl (3.99 g, 20.81 mmol) and DIEA (2 mL). The resulting solution was stirred overnight at room temperature. The mixture was partitioned between ethyl acetate and water. The organic layer was washed with brine, dried over $Na_2SO_4$ and concentrated under vacuum. The residue was purified by flash chromatography on silica gel eluting with ethyl acetate/petroleum ether (3/1). This resulted in 2.00 g (31%) of 2-(methylsulfanyl)ethyl 2-[[(tert-butoxy)carbonyl]amino]acetate as light yellow oil. LCMS (Method 21): $[M+H]^+$=250, $R_T$=1.37 min.

To a solution of 2-(methylsulfanyl)ethyl 2-[[(tert-butoxy)carbonyl]amino]acetate (2.00 g, 8.02 mmol) in dioxane (5 mL) was added saturated HCl dioxane solution (10 mL) at room temperature. The resulting solution was stirred at room temperature for 2 h. The solids were collected by filtration. This resulted in 1.2 g of 2-(methylsulfanyl)ethyl 2-aminoacetate HCl salt as a white solid. LCMS (Method 25): $[M+H]^+$=150, $R_T$=0.28 min.

To a solution of 2-(methylsulfanyl)ethyl 2-aminoacetate HCl salt (792 mg, 3.57 mmol) in $CH_3CN$ was added N-[1-(2-bromoethyl)-3-[5-chloro-2-(difluoromethoxy)phenyl]-1H-pyrazol-4-yl]pyrazolo[1,5-a]pyrimidine-3-carboxamide (364 mg, 0.71 mmol) and DIEA (1.57 g, 12.15 mmol). The resulting solution was stirred at 75° C. overnight and concentrated under vacuum. The crude product was purified by Prep-HPLC with the following conditions (2#-Waters 2767-2 (HPLC-08)): Column, Xbridge Prep Phenyl, 5 um, 19×150 mm; mobile phase, Water with 50 mmol ammonium bicarbonate and acetonitrile (10.0% acetonitrile up to 33.0% in 2 min, up to 53.0% in 8 min, up to 100.0% in 1 min, down to 10.0% in 1 min); Detector, UV 220 nm. This resulted in 53.1 mg (2%) of the formic acid salt of 2-(methylsulfanyl)ethyl 2-[(2-[3-[5-chloro-2-(difluoromethoxy)phenyl]-4-[pyrazolo[1,5-a]pyrimidine-3-amido]-1H-pyrazol-1-yl]ethyl)amino]acetate as light yellow oil. LCMS (Method 20): $[M+H]^+$=580.15, $R_T$=2.76 min. $^1H$ NMR (300 MHz, DMSO-$d_6$) δ: (ppm) 9.73 (s, 1H), 9.33 (dd, 1H, J=1.5, 6.9 Hz), 8.67 (dd, 1H, J=1.5, 4.2 Hz), 8.66 (s, 1H), 8.36 (s, 1H), 7.65-7.61 (m, 2H), 7.44 (d, 1H, J=9.3 Hz), 7.23 (dd, 1H, J=4.5, 7.2 Hz), 6.99 (t, 1H, J=73.5 Hz), 4.27-4.18 (m, 4H), 3.38 (s, 2H), 2.99 (t, 2H, J=6.0 Hz), 2.67 (t, 2H, J=6.6 Hz), 2.07 (s, 3H).

Example 397

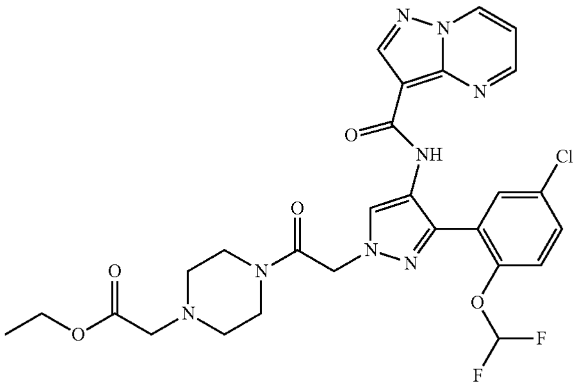 [SMILES: CCOC(=O)CN1CCN(C(=O)Cn2cc(NC(=O)c3cnn4cccnc34)c(-c3cc(Cl)ccc3OC(F)F)n2)CC1]

ethyl 2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]acetate To a solution of ethyl 2-(piperazin-1-yl)acetate hydrochloride (400 mg, 1.92 mmol) in DMF (10 mL) was added {3-(5-Chloro-2-difluoromethoxyphenyl)-4-[(pyrazolo[1,5-a]pyrimidine-3-carbonyl)amino]pyrazol-1-yl}acetic acid (500 mg), DIEA (440 mg, 3.40 mmol), HATU (460 mg, 1.21 mmol). The resulting solution was stirred at room temperature overnight and concentrated under vacuum. The residue was purified by flash chromatography on silica eluting with 4.5% MeOH in DCM to afford 59.4 mg (11%) of ethyl 2-[4-(2-[3-[5-chloro-2-(difluoromethoxy)phenyl]-4-[pyrazolo[1,5-a]pyrimidine-3-amido]-1H-pyrazol-1-yl]acetyl)piperazin-1-yl]acetate as a white solid. LCMS (Method 20) $[M+H]^+$=617.2, $R_T$=2.68 min. $^1H$ NMR (400 MHz, DMSO-$d_6$) δ: (ppm) 9.75 (s, 1H), 9.34 (dd, 1H, J=1.6, 6.8 Hz), 8.69-8.67 (m, 2H), 8.31 (s, 1H), 7.62 (dd, 1H, J=2.4, 8.8 Hz), 7.56 (d, 1H, J=2.8 Hz), 7.45 (d, 1H, J=8.8 Hz), 7.28 (dd, 1H, J=4.4, 6.8 Hz), 7.07 (t, 1H, J=73.2 Hz), 5.24 (s, 2H), 4.07 (q, 2H, J=7.2 Hz), 3.52-3.49 (m, 4H), 3.28 (s, 2H), 3.17-3.16 (m, 1H), 2.59-2.50 (m, 4H), 1.18 (t, 3H, J=7.2 Hz).

Example 403

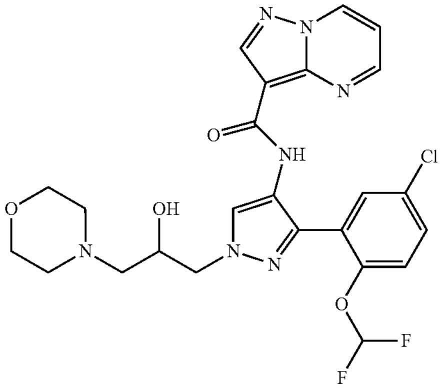 [SMILES: O=C(Nc1cn(CC(O)CN2CCOCC2)nc1-c1cc(Cl)ccc1OC(F)F)c1cnn2cccnc12]

N-(3-(5-chloro-2-(difluoromethoxy)phenyl)-1-(2-hydroxy-3-morpholinopropyl)-1H-pyrazol-4-yl)pyrazolo[1,5-a]pyrimidine-3-carboxamide To a solution of N-[3-[5-chloro-2-(difluoromethoxy)phenyl]-1H-pyrazol-4-yl]pyrazolo[1,5-a]pyrimidine-3-carboxamide (1.00 g, 2.47 mmol) in N,N-dimethylformamide (10 mL), $Cs_2CO_3$ (970 mg, 2.977 mmol) was added and stirred for 10 minutes at room temperature. Then 2-(chloromethyl)oxirane (2.28 g, 24.64 mmol) was added dropwise at room temperature. The resulting mixture was stirred for 14 hour at room temperature and diluted with ethyl acetate (100 mL), washed with water and brine. The organic layer was dried over anhydrous sodium sulfate and concentrated under vacuum. The residue was purified by flash chromatography on silica gel eluting with ethyl acetate/petroleum ether (60/40) to give 500 mg (44%) of N-[3-[5-chloro-2-(difluoromethoxy)phenyl]-1-(oxiran-2-ylmethyl)-1H-pyrazol-4-yl]pyrazolo[1,5-a]pyrimidine-3-carboxamide as a light yellow solid. LCMS (Method 24), $[M+H]^+$=461.1, $R_T$=1.30 min.

To a solution of N-[3-[5-chloro-2-(difluoromethoxy)phenyl]-1-(oxiran-2-ylmethyl)-1H-pyrazol-4-yl]pyrazolo[1,5-a]pyrimidine-3-carboxamide (50 mg, 0.11 mmol) in N,N-dimethylformamide (1 mL), DIEA (67 mg, 0.518 mmol) and morpholine (14 mg, 0.161 mmol) was added at room temperature. The resulting solution was stirred at 60° C. overnight, cooled, diluted with 30 mL of ethyl acetate, washed with 2×10 mL of water and 2×10 mL of brine. The organic layer was dried over anhydrous sodium sulfate and concentrated under vacuum. The residue was purified by flash chromatography on silica gel eluting with dichloromethane/methanol (95/5). This resulted in 50 mg of crude product, which was purified by Flash-Prep-HPLC with the following conditions (IntelFlash-1): Column: X Bridge C18, 19*150 mm, 5 um; Mobile Phase A:Water/0.05% $NH_4HCO_3$, Mobile Phase B: ACN; Flow rate: 20 mL/min; Gradient: 30% B to 70% B in 10 min; 254 nm to obtain 40 mg (67%) of N-[3-[5-chloro-2-(difluoromethoxy)phenyl]-1-[2-hydroxy-3-(morpholin-4-yl)propyl]-1H-pyrazol-4-yl]pyrazolo[1,5-a]pyrimidine-3-carboxamide as a white solid. LCMS (Method 35) $[M+H]^+$=548.2, $R_T$=2.28 min. $^1$H-NMR (300 MHz, DMSO-$d_6$): δ (ppm) 9.73 (s, 1H), 9.33 (dd, 1H, J=1.5, 7.2 Hz), 8.68-8.67 (m, 2H), 8.34 (s, 1H), 7.65 (d, 1H, J=2.7 Hz), 7.61 (s, 1H), 7.44 (d, 1H, J=8.7 Hz), 7.27 (dd, 1H, J=4.2, 6.9 Hz), 7.00 (t, 1H, J=73.5 Hz), 4.99 (d, 1H, J=4.5 Hz), 4.31-4.28 (m, 1H), 4.13-4.07 (m, 2H), 3.56 (t, 4H, J=4.5 Hz), 2.42 (t, 4H, J=4.5 Hz), 2.32 (d, 2H, J=4.8 Hz).

Example 414

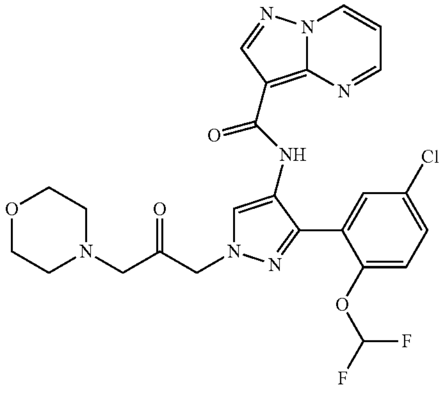 [SMILES: O=C(CN1CCOCC1)Cn1cc(NC(=O)c2cnn3cccnc23)c(-c2cc(Cl)ccc2OC(F)F)n1]

N-(3-(5-chloro-2-(difluoromethoxy)phenyl)-1-(2-oxo-3-(piperidin-1-yl)propyl)-1H-pyrazol-4-yl)pyrazolo[1,5-a]pyrimidine-3-carboxamide To a stirring solution of oxalyl dichloride (0.46 mL, 0.923 mmol, 2 M) in dichloromethane (6 mL) at −78° C., a solution of DMSO (144 mg) in dichloromethane (1 mL) was added dropwise in 10 min. The mixture was stirred for an additional 10 minutes at this temperature and a solution of N-(3-(5-chloro-2-(difluoromethoxy)phenyl)-1-(2-hydroxy-3-morpholinopropyl)-1H-pyrazol-4-yl)pyrazolo[1,5-a]pyrimidine-3-carboxamide (253 mg, 0.461 mmol) in 2 mL of dichloromethane was added dropwise at this temperature. The mixture was stirred for another 30 min at this temperature. Then DIEA (476 mg, 3.683 mmol) was added dropwise at this temperature. The resulting solution was stirred for 0.5 h at −78° C. and then allowed warm to room temperature and stirred for another 30 min. The resulting solution was diluted with 50 mL of ethyl acetate, washed with 2×20 mL of water and 2×20 mL of brine. The organic layer was dried over sodium sulfate and concentrated under vacuum. The crude product (200 mg) was purified by Flash-Prep-HPLC with the following conditions: Column: X Bridge RP, 19*150 mm, 5 um; Mobile Phase A:Water/0.05% $NH_4HCO_3$, Mobile Phase B: ACN; Flow rate: 30 mL/min; Gradient: 25% B to 44% B in 10 min; 254 nm to give 108.6 mg (43%) of -(3-(5-chloro-2-(difluoromethoxy)phenyl)-1-(2-oxo-3-(piperidin-1-yl)propyl)-1H-pyrazol-4-yl)pyrazolo[1,5-a]pyrimidine-3-carboxamide as a white solid. LCMS (Method 24) $[M+H]^+$=546.2, $R_T$=1.68 min. $^1$H-NMR (300 MHz, $CDCl_3$-d): δ (ppm) 9.89 (s, 1H), 8.77 (dd, 1H, J=1.5, 6.9 Hz), 8.72 (s, 1H), 8.55 (dd, 1H, J=1.5, 4.2 Hz), 8.40 (s, 1H), 7.68 (d, 1H, J=2.4 Hz), 7.42 (dd, 1H, J=2.4, 8.7 Hz), 7.28 (d, 1H, J=8.7 Hz), 6.99 (dd, 1H, J=4.2, 7.2 Hz), 6.47 (t, 1H, J=73.8 Hz), 5.07 (s, 1H), 3.76 (t, 4H, J=4.5 Hz), 3.26 (s, 2H), 2.56 (t, 4H, J=4.8 Hz).

Example 415

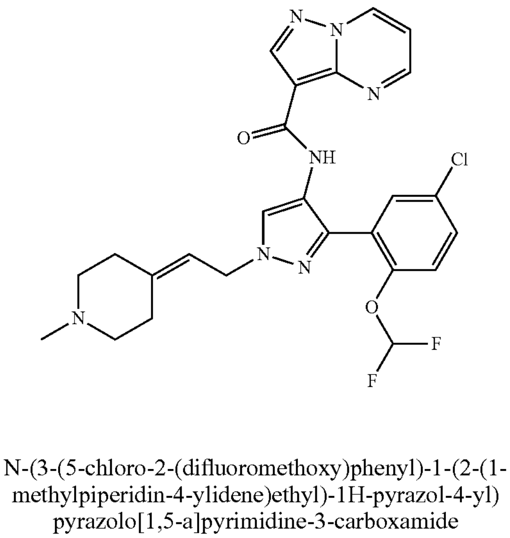

N-(3-(5-chloro-2-(difluoromethoxy)phenyl)-1-(2-(1-methylpiperidin-4-ylidene)ethyl)-1H-pyrazol-4-yl)pyrazolo[1,5-a]pyrimidine-3-carboxamide To a mixture of N-[3-[5-chloro-2-(difluoromethoxy)phenyl]-1H-pyrazol-4-yl]pyrazolo[1,5-a]pyrimidine-3-carboxamide (215.20 mg, 0.532 mmol), $Cs_2CO_3$ (694.8 mg, 2.132 mmol) in N,N-dimethylformamide (15 mL) was added tert-butyl 4-[2-(methanesulfonyloxy)ethylidene]piperidine- 1-carboxylate (650 mg, 2.128 mmol). The resulting mixture was stirred at 60° C. overnight, and concentrated under vacuum. The residue was purified by flash chromatography on silica gel eluting with ethyl acetate/petroleum ether (9/1). This resulted in 310 mg (95%) of tert-butyl 4-(2-[3-[5-chloro-2-(difluoromethoxy)phenyl]-4-[pyrazolo[1,5-a]pyrimidine-3-amido]-1H-pyrazol-1-yl]ethylidene)piperidine-1-carboxylate as yellow oil. LCMS (Method 25) $[M+H]^+$=614.2, $R_T$=1.11 min.

To a solution of tert-butyl 4-(2-[3-[5-chloro-2-(difluoromethoxy)phenyl]-4-[pyrazolo[1,5-a]pyrimidine-3-amido]-1H-pyrazol-1-yl]ethylidene)piperidine-1-carboxylate (310 mg, 0.505 mmol) in dichloromethane (10 mL) was added trifluoroacetic acid (6 mL) at room temperature. The resulting solution was stirred for 5 h at room temperature and concentrated under vacuum. The crude product was used without further purification. LCMS (Method 25) $[M+H]^+$=514.1, $R_T$=0.91 min.

An aqueous solution of 40% formaldehyde (210 mg) was added to solution of N-[3-[5-chloro-2-(difluoromethoxy)phenyl]-1-[2-(piperidin-4-ylidene)ethyl]-1H-pyrazol-4-yl]pyrazolo[1,5-a]pyrimidine-3-carboxamide (360.00 mg, 0.700 mmol) in methanol (30 mL). The resulting solution was stirred at ambient temperature for 2.5 h and $NaBH_3CN$ (44.02 mg, 0.700 mmol) was added. The resulting solution was stirred at this temperature for 3 h and concentrated under vacuum. The residue was applied onto a short pad of silica gel eluting with dichloromethane/MeOH (10/1). The crude product (60 mg) was purified by Flash-Prep-HPLC with the following conditions (IntelFlash-1): Column, silica gel; mobile phase, ACN/10 mmol $NH_4HCO_3$=40% increasing to ACN/10 mmol $NH_4HCO_3$=75% within 6 min; Detector, UV 254 nm to obtain 4.3 mg (1%) of N-[3-[5-chloro-2-(difluoromethoxy)phenyl]-1-[2-(1-methylpiperidin-4-ylidene)ethyl]-1H-pyrazol-4-yl]pyrazolo[1,5-a]pyrimidine-3-carboxamide as a light yellow solid. LCMS (Method 32): $[M+H]^+$=528.1, $R_T$=2.21 min. $^1H$ NMR (400 MHz, DMSO-$d_6$) δ: (ppm) 9.73 (s, 1H), 9.34 (dd, 1H, J=1.6, 6.8 Hz), 8.68-8.66 (m, 2H), 8.32 (s, 1H), 7.67-7.61 (m, 2H), 7.45 (d, 1H, J=8.4 Hz), 7.28 (dd, 1H, J=4.0, 6.8 Hz), 7.06 (t, 1H, J=73.2 Hz), 5.44 (t, 1H, J=6.8 Hz), 4.27 (d, 2H, J=6.8 Hz), 2.81-2.68 (m, 2H), 2.52-2.50 (m, 2H), 2.50-2.42 (m, 2H), 2.19 (s, 3H), 2.12-2.04 (m, 2H).

Example 421

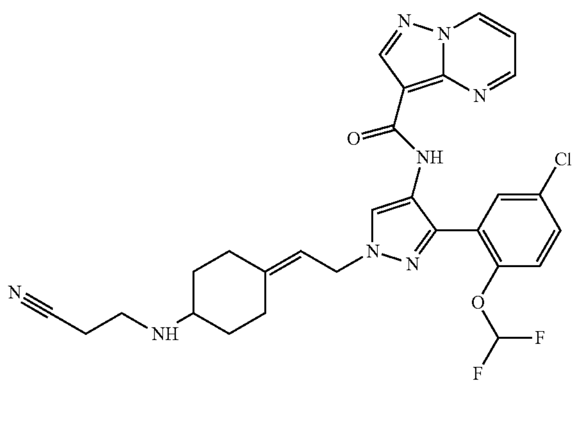 [SMILES: N#CCCNC1CCC(=CCn2cc(NC(=O)c3cnn4cccnc34)c(-c3cc(Cl)ccc3OC(F)F)n2)CC1]

N-(3-(5-chloro-2-(difluoromethoxy)phenyl)-1-(2-(4-(2-cyanoethylamino)cyclohexylidene)ethyl)-1H-pyrazol-4-yl)pyrazolo[1,5-a]pyrimidine-3-carboxamide Methanesulfonyl chloride (1.87 g, 16.325 mmol) was added dropwise to a solution of 2-[1,4-dioxaspiro[4.5]decan-8-ylidene]ethan-1-ol (2.00 g, 10.86 mmol) and DIEA (4.21 g, 32.57 mmol) in dichloromethane (100 mL) at room temperature. The resulting solution was stirred at room temperature overnight and concentrated under vacuum. The residue was purified by flash chromatography on silica gel eluting with ethyl acetate/petroleum ether (1/9). This resulted in 1.95 g (68%) of 2-[1,4-dioxaspiro[4.5]decan-8-ylidene]ethyl methanesulfonate as off-white oil. TLC: $R_f$=0.6; ethyl acetate/petroleum ether=1/2.

To a solution of N-[3-[5-chloro-2-(difluoromethoxy)phenyl]-1H-pyrazol-4-yl]pyrazolo[1,5-a]pyrimidine-3-carboxamide (1.50 g, 3.71 mmol) in N,N-dimethylformamide (120 mL) was added $Cs_2CO_3$ (3.62 g, 11.11 mmol) and 2-[1,4-dioxaspiro[4.5]decan-8-ylidene]ethyl methanesulfonate (1.94 g, 7.39 mmol) at room temperature. The resulting solution was stirred for 4 h at room temperature and concentrated under vacuum. The residue was purified by flash chromatography on silica gel eluting with ethyl acetate/petroleum ether (3/2) to give 1.59 g (75%) of N-[3-[5-chloro-2-(difluoromethoxy)phenyl]-1-(2-[1,4-dioxaspiro[4.5]decan-8-ylidene]ethyl)-1H-pyrazol-4-yl]pyrazolo[1,5-a]pyrimidine-3-carboxamide as a light yellow solid. LCMS (Method 31) $[M+H]^+$=571.4, $R_T$=1.21 min.

Concentrated HCl aqueous solution (16 mL) was added to a solution of N-[3-[5-chloro-2-(difluoromethoxy)phenyl]-1-(2-[1,4-dioxaspiro[4.5]decan-8-ylidene]ethyl)-1H-pyrazol-4-yl]pyrazolo[1,5-a]pyrimidine-3-carboxamide (1.59 g, 2.785 mmol) in 1,4-dioxane (160 mL). The resulting solution was stirred at room temperature for 3 h and neutralized with saturated sodium bicarbonate solution. The resulting mixture was concentrated under vacuum. The residue was dissolved in dichloromethane, washed with water, brine. The organic layer was dried, and concentrated under vacuum. The residue was purified by flash chromatography on silica gel eluting with ethyl acetate/petroleum ether (3/2). This resulted in 930 mg (63%) of N-[3-[5-chloro-2-(difluoromethoxy)phenyl]-1-[2-(4-oxocyclohexylidene)ethyl]-1H-pyrazol-4-yl]pyrazolo[1,5-a]pyrimidine-3-carboxamide as a light yellow solid. LCMS (Method 25) $[M+H]^+$=527.1, $R_T$=0.94 min.

To solution of N-[3-[5-chloro-2-(difluoromethoxy)phenyl]-1-[2-(4-oxocyclohexylidene)ethyl]-1H-pyrazol-4-yl]pyrazolo[1,5-a]pyrimidine-3-carboxamide (300.0 mg, 0.569 mmol) in methanol (30 mL) was added 3-aminopropanenitrile (199.5 mg, 2.85 mmol). The resulting solution was stirred at room temperature for 3. Then $NaBH_3CN$ (71.56 mg, 1.14 mmol) was added. The resulting solution was stirred at room temperature overnight and concentrated under vacuum. The residue was applied onto a short pad of silica gel eluting with ethyl acetate. The crude product (60 mg) was purified by Flash-Prep-HPLC with the following conditions (IntelFlash-1): Column, silica gel; mobile phase, ACN/0.05% $NH_4HCO_3$=30% increasing to ACN/0.05% $NH_4HCO_3$=55% within 8 min; Detector, UV 254 nm. 6.7 mg product was obtained. This resulted in 6.7 mg (2%) of N-[3-[5-chloro-2-(difluoromethoxy)phenyl]-1-(2-[4-[(2-cyanoethyl)amino]cyclohexylidene]ethyl)-1H-pyrazol-4-yl]pyrazolo[1,5-a]pyrimidine-3-carboxamide as a off-white solid. LCMS (Method 34) $[M+H]^+$=581.4, $R_T$=2.44 min. $^1H$ NMR (300 MHz, DMSO-$d_6$) δ: (ppm) 9.73 (s, 1H), 9.33 (dd, 1H, J=1.5, 6.9 Hz), 8.68-8.66 (m, 2H), 8.27 (s, 1H), 7.64-7.60 (m, 2H), 7.43 (d, 1H, J=8.1 Hz), 7.27 (dd, 1H, J=4.2, 6.9 Hz), 7.00 (t, 1H, J=73.5 Hz), 5.45 (t, 1H, J=6.9 Hz), 4.80 (d, 2H, J=7.2 Hz), 2.79-2.72 (m, 3H), 2.71-2.57 (m, 5H), 2.10-1.97 (m, 2H), 1.94-1.86 (m, 2H), 1.23-1.16 (m, 2H).

Example 420

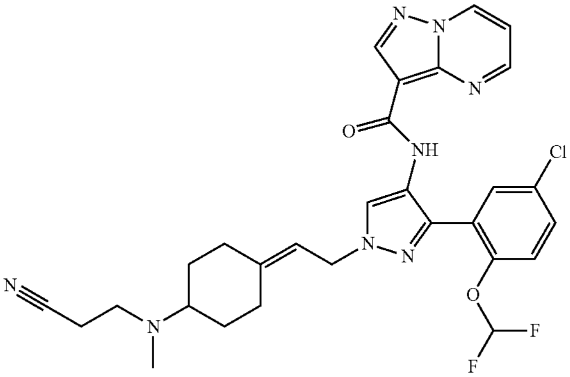 [SMILES: CN(CCC#N)C1CCC(=CCn2cc(NC(=O)c3cnn4cccnc34)c(-c3cc(Cl)ccc3OC(F)F)n2)CC1]

N-(3-(5-chloro-2-(difluoromethoxy)phenyl)-1-(2-(4-((2-cyanoethyl)(methyl)amino)cyclohexylidene)ethyl)-1H-pyrazol-4-yl)pyrazolo[1,5-a]pyrimidine-3-carboxamide To a solution of N-[3-[5-chloro-2-(difluoromethoxy)phenyl]-1-(2-[4-[(2-cyanoethyl)amino]cyclohexylidene]ethyl)-1H-pyrazol-4-yl]pyrazolo[1,5-a]pyrimidine-3-carboxamide (140.0 mg, 0.241 mmol) in methanol (20 mL) was added 40% HCHO aqueous solution (75 mg, 0.96 mmol). The resulting solution was stirred at room temperature overnight. Then $NaBH_3CN$ (15.14 mg, 0.241 mmol) was added. The resulting solution was stirred at room temperature for 4 h and concentrated under vacuum. The residue was purified by flash chromatography on silica gel eluting with dichloromethane/MeOH (10/1). This resulted in 34.7 mg (24%) of N-[3-[5-chloro-2-(difluoromethoxy)phenyl]-1-(2-[4-[(2-cyanoethyl)(methyl)amino]cyclohexylidene]ethyl)-1H-pyrazol-4-yl]pyrazolo[1,5-a]pyrimidine-3-carboxamide as a light yellow solid. LCMS (Method 33) $[M+H]^+$=595.4, $R_T$=1.43 min. $^1$H NMR (300 MHz, DMSO-$d_6$) δ: (ppm) 9.73 (s, 1H), 9.33 (dd, 1H, J=1.5, 6.9 Hz), 8.69-8.66 (m, 2H), 8.28 (s, 1H), 7.64-7.60 (m, 2H), 7.43 (d, 1H, J=8.4 Hz), 7.27 (dd, 1H, J=4.5, 7.5 Hz), 7.00 (t, 1H, J=73.5 Hz), 5.43 (t, 1H, J=7.2 Hz), 4.81 (d, 2H, J=6.9 Hz), 2.88-2.82 (m, 1H), 2.66-2.59 (m, 5H), 2.33-2.29 (m, 1H), 2.22 (s, 3H), 2.10-2.05 (m, 1H), 1.93-1.80 (m, 3H), 1.37-1.25 (m, 2H).

Example 452

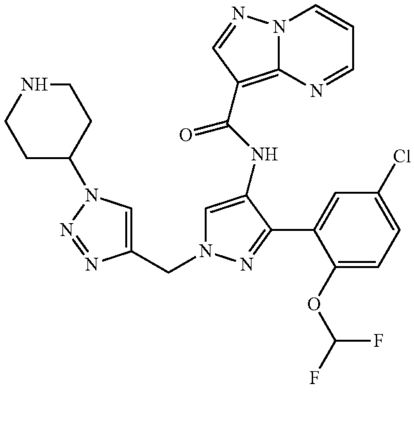 [SMILES: O=C(Nc1cn(Cc2cn(C3CCNCC3)nn2)nc1-c1cc(Cl)ccc1OC(F)F)c1cnn2cccnc12]

N-(3-(5-chloro-2-(difluoromethoxy)phenyl)-1-((1-(piperidin-4-yl)-1H-1,2,3-triazol-4-yl)methyl)-1H-pyrazol-4-yl)pyrazolo[1,5-a]pyrimidine-3-carboxamide Sodium azide (246 mg, 2.79 mmol) was added to a solution of tert-butyl 4-bromopiperidine-1-carboxylate (1.00 g, 3.79 mmol) and sodium iodide (113 mg, 0.753 mmol) in N,N-dimethylformamide (20 mL) at room temperature. The resulting solution was stirred at 60° C. overnight, allowed cool to cool to room temperature. Caution: the reaction should be conducted behind a blast shield. The reaction was then quenched by the addition of 10 mL of saturated sodium bicarbonate aqueous solution. The resulting solution was extracted with 2×50 mL of ethyl acetate and the organic layers combined and concentrated under vacuum. The residue was applied onto a silica gel column with ethyl acetate/petroleum ether (1/4). This resulted in 800 mg (93%) of tert-butyl 4-azidopiperidine-1-carboxylate as colorless oil. TLC: $R_f$=0.6; ethyl acetate/petroleum ether=1/4.

To a solution of N-[3-[5-chloro-2-(difluoromethoxy)phenyl]-1H-pyrazol-4-yl]pyrazolo[1,5-a]pyrimidine-3-carboxamide (2 g, 4.941 mmol) in N,N-dimethylformamide (50 mL) was added $Cs_2CO_3$ (3.23 g, 9.913 mmol) and 3-chloroprop-1-yne (720 mg, 9.663 mmol). The resulting mixture was stirred at 50° C. for 5 h and concentrated under vacuum. The residue was purified by flash chromatography on silica gel eluting with ethyl acetate. This resulted in 1.74 g (80%) of N-[3-[5-chloro-2-(difluoromethoxy)phenyl]-1-(prop-2-yn-1-yl)-1H-pyrazol-4-yl]pyrazolo[1,5-a]pyrimidine-3-carboxamide as a light yellow solid. LCMS (Method 23) $[M+H]^+$=443.0, $R_T$=1.45 min.

To a solution of N-[3-[5-chloro-2-(difluoromethoxy)phenyl]-1-(prop-2-yn-1-yl)-1H-pyrazol-4-yl]pyrazolo[1,5-a]pyrimidine-3-carboxamide (1.68 g, 3.794 mmol) in N,N-dimethylformamide (40 mL) was added DIEA (980.6 mg, 7.587 mmol), CuI (143.7 mg, 0.755 mmol), tert-butyl 4-azidopiperidine-1-carboxylate (858.8 mg, 3.795 mmol). The resulting solution was stirred at room temperature for 7 h and concentrated under vacuum. The residue was purified by flash chromatography on silica gel eluting with ethyl acetate. This resulted in 1.98 g (78%) of tert-butyl 4-[4-([3-[5-chloro-2-(difluoromethoxy)phenyl]-4-[pyrazolo[1,5-a]pyrimidine-3-amido]-1H-pyrazol-1-yl]methyl)-1H-1,2,3-triazol-1-yl]piperidine-1-carboxylate as a light yellow solid. LCMS (Method 24) $[M+H]^+$=669.2, $R_T$=1.34 min.

To a solution of tert-butyl 4-[4-([3-[5-chloro-2-(difluoromethoxy)phenyl]-4-[pyrazolo[1,5-a]pyrimidine-3-amido]-1H-pyrazol-1-yl]methyl)-1H-1,2,3-triazol-1-yl]piperidine-1-carboxylate (1.98 g, 2.96 mmol) in methanol (30 mL) was added concentrated HCl aqueous solution (15 mL). The resulting solution was stirred for 5 h at room temperature. The resulting mixture was concentrated under vacuum. This resulted in 1.85 g crude product, which was sufficient for next step without further purification. A small portion was purified for characterization and biological submission. The crude product (100 mg) was purified by Flash-Prep-HPLC with the following conditions (IntelFlash-1): Column, silica gel; mobile phase, $ACN/H_2O$ (10 mmol $NH_4HCO_3$)=18% increasing to $ACN/H_2O$ (10 mmol $NH_4HCO_3$)=49% within 9 min; Detector, UV 254 nm. 42.1 mg product was obtained. This resulted in 42.0 mg of N-[3-[5-chloro-2-(difluoromethoxy)phenyl]-1-[[1-(piperidin-4-yl)-1H-1,2,3-triazol-4-yl]methyl]-1H-pyrazol-4-yl]pyrazolo[1,5-a]pyrimidine-3-carboxamide as a light yellow solid. LCMS (Method 36) $[M+H]^+$=569.2, $R_T$=2.59 min. $^1$H NMR (400 MHz, DMSO-$d_6$) δ: (ppm) 9.69 (s, 1H), 9.34 (d, 1H, J=6.4 Hz), 8.68-8.64 (m, 2H), 8.40 (s, 1H), 8.22 (s, 1H), 7.67-7.61 (m, 2H), 7.45 (d, 1H, J=8.4 Hz), 7.28 (dd, 1H, J=4.2, 7.0 Hz), 7.06 (t, 1H, J=73.4 Hz), 5.49 (s, 2H), 4.58-4.51 (m, 1H), 3.05-3.02 (m, 2H), 2.62-2.57 (m, 1H), 2.30-2.25 (br, 1H), 2.01-1.98 (m, 2H), 1.87-1.73 (m, 2H).

Example 457

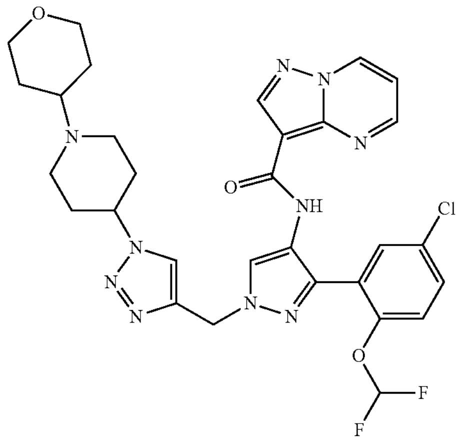 [SMILES: O=C(Nc1cn(Cc2cn(C3CCN(C4CCOCC4)CC3)nn2)nc1-c1cc(Cl)ccc1OC(F)F)c1cnn2cccnc12]

N-(3-(5-chloro-2-(difluoromethoxy)phenyl)-1-((1-(1-(tetrahydro-2H-pyran-4-yl)piperidin-4-yl)-1H-1,2,3-triazol-4-yl)methyl)-1H-pyrazol-4-yl)pyrazolo[1,5-a]pyrimidine-3-carboxamide To a solution of N-[3-[5-chloro-2-(difluoromethoxy)phenyl]-1-[[1-(piperidin-4-yl)-1H-1,2,3-triazol-4-yl]methyl]-1H-pyrazol-4-yl]pyrazolo[1,5-a]pyrimidine-3-carboxamide hydrochloride (200 mg, 0.330 mmol) in dichloromethane (30 mL) was added oxan-4-one (264.9 mg, 2.646 mmol). The resulting solution was stirred at room temperature overnight. Then $NaBH(OAc)_3$ (280.8 mg, 1.325 mmol) was added. The resulting solution was stirred at room temperature for 6 h and concentrated under vacuum. The residue was applied onto a silica gel column eluting with DCM/MeOH (80:20). The crude product (150 mg) was purified by Flash-Prep-HPLC with the following conditions (IntelFlash-1): Column, silica gel; mobile phase, $ACN/H_2O$ (10 mmol $NH_4HCO_3$)=20% increasing to $ACN/H_2O$ (10 mmol $NH_4HCO_3$)=49% within 8 min; Detector, UV 254 nm. 56.9 mg product was obtained. This resulted in 56.9 mg (26%) of N-[3-[5-chloro-2-(difluoromethoxy)phenyl]-1-([1-[1-(oxan-4-yl)piperidin-4-yl]-1H-1,2,3-triazol-4-yl]methyl)-1H-pyrazol-4-yl]pyrazolo[1,5-a]pyrimidine-3-carboxamide as a light yellow solid. LCMS (Method 20) $[M+H]^+$=653.3, $R_T$=1.74 min. $^1H$ NMR (400 MHz, DMSO-$d_6$) δ: (ppm) 9.73 (s, 1H), 9.34 (dd, 1H, J=1.6, 7.2 Hz), 8.67-8.66 (m, 2H), 8.39 (s, 1H), 8.26 (s, 1H), 7.65-7.62 (m, 2H), 7.44 (d, 1H, J=8.4 Hz), 7.28 (dd, 1H, J=4.0, 6.8 Hz), 7.06 (t, 1H, J=73.4 Hz), 5.48 (s, 2H), 4.58-4.45 (m, 1H), 3.90-3.87 (m, 2H), 3.32-3.25 (m, 2H), 3.04-2.98 (m, 2H), 2.51-2.33 (m, 1H), 2.30-2.24 (m, 2H), 2.09-2.06 (m, 2H), 1.99-1.91 (m, 2H), 1.70-1.67 ((m, 2H), 1.49-1.40 (m, 2H).

Example 468

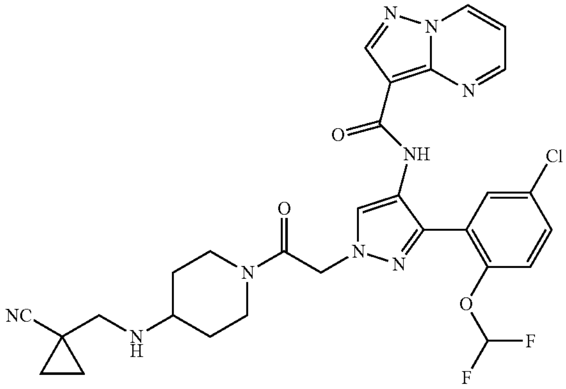

N-(3-(5-chloro-2-(difluoromethoxy)phenyl)-1-(2-(4-(((1-cyanocyclopropyl)methyl)amino)piperidin-1-yl)-2-oxoethyl)-1H-pyrazol-4-yl)pyrazolo[1,5-a]pyrimidine-3-carboxamide To a solution of 1,4-dioxa-8-azaspiro[4,5]decane (9.80 g, 67.1 mmol) in dichloromethane (150 mL) under nitrogen was added triethylamine (11.2 mL, 80.5 mmol. This was then cooled to 0° C. and to this was added dropwise with stirring 2-chloroacetyl chloride (6.53 mL, 80.5 mmol) in dichloromethane (50 mL) over 1 and a half hours. This was then stirred overnight warming to room temperature in the process. The reaction was then quenched by adding 1 N HCl (100 mL). This was then extracted with ethyl acetate and the ethyl acetate layers were dried with solid anhydrous magnesium sulfate powder, filtered and concentrated to give 2-Chloro-1-(1,4-dioxa-8-azaspiro[4,5]decan-8-yl)ethan-1-one as a brown oil (15.44 g). This was used without purification for the next step.

To N-[3-[5-chloro-2-(difluoromethoxy)phenyl]-1H-pyrazol-4-yl]pyrazolo[1,5-a]pyrimidine-3-carboxamide (4.65 g, 11.5 mmol) and cesium carbonate (10.08 g, 30.94 mmol) was added N,N-Dimethylformamide (40 mL) and stirred at room temperature for 5 minutes. To this was added 2-Chloro-1-(1,4-dioxa-8-azaspiro[4,5]decan-8-yl)ethan-1-one (5.34 g, 20.2 mmol) in N,N-Dimethylformamide (4.5 mL) and stirred at room temperature for 3 and a half hours. LC/MS (method 31) shows reaction complete. The reaction was then filtered and the filtrate was concentrated under reduced pressure to give a red oil. This was then dissolved in 30 mL dichloromethane and purified by ISCO using a silica column and eluting with 0-100% Ethyl acetate in heptane in 5 minutes followed by 0-15% Methanol in dichloromethane to give 5.16 g (8.78 mmol) of N-[3-[5-chloro-2-(difluoromethoxy)phenyl]-1-[2-(1,4-dioxa-8-azaspiro[4,5]decan-8-yl)-2-oxo-ethyl]pyrazol-4-yl]pyrazolo[1,5-a]pyrimidine-3-carboxamide as a yellow foamy solid. LC/MS (method 39) $[M+H]^+$=589.2, $R_T$=1.91 min.

To a solution of N-[3-[5-chloro-2-(difluoromethoxy)phenyl]-1-[2-(1,4-dioxa-8-azaspiro[4,5]decan-8-yl)-2-oxo-ethyl]pyrazol-4-yl]pyrazolo[1,5-a]pyrimidine-3-carboxamide (1.01 g, 1.72 mmol) in acetone (20 mL) was added p-toluenesulfonic acid (359 mg, 2.06 mmol) and refluxed for 6 hours. LC/MS (method 31) shows product and presence of minor amounts of starting material. The reaction was cooled to room temperature and quenched with water. This was then extracted with ethyl acetate, dried with solid anhydrous magnesium sulfate powder and filtered to give a red oil. This was then purified by ISCO with a silica column and eluted with 0-15% methanol in dichloromethane to afford 0.43 g (0.78 mmol) of N-[3-[5-chloro-2-(difluoromethoxy)phenyl]-1-[2-oxo-2-(4-oxo-1-piperidyl)ethyl]pyrazol-4-yl]pyrazolo[1,5-a]pyrimidine-3-carboxamide as a foamy off white solid. LC/MS (method 39) $[M+H]^+$=544.1, $R_T$=1.91 min.

To a solution of N-[3-[5-chloro-2-(difluoromethoxy)phenyl]-1-[2-oxo-2-(4-oxo-1-piperidyl)ethyl]pyrazol-4-yl]pyrazolo[1,5-a]pyrimidine-3-carboxamide (201.7 mg 0.38 mmol) in dichloromethane (1.0 mL) was added acetic acid (0.3 mL, 5.24 mmol). To this was then added 1-(aminomethyl)cyclopropanecarbonitrile (47.2 mg, 0.466 mmol). This was then stirred at room temperature for 5 minutes. The reaction was then cooled to 0° C. and to this was added sodium triacetyoxyborohydride (124.1 mg, 0.56 mmol) and stirred for 3 hours and let warm to room temperature in the process. LC/MS (method 31) shows product as a major peak. The reaction was quenched by adding 2 mL water followed by 10 mL saturated sodium bicarbonate solution. This was the extracted with dichloromethane and the organic layers were dried with solid anhydrous magnesium sulfate powder, filtered and concentrated to give a white solid. 20.6 mg was then purified by reverse phase HPLC purification to afford 10.2 mg of N-(3-(5-chloro-2-(difluoromethoxy)phenyl)-1-(2-(4-(((1-cyanocyclopropyl)methyl)amino)piperidin-1-yl)-2-oxoethyl)-1H-pyrazol-4-yl)pyrazolo[1,5-a]pyrimidine-3-carboxamide. LC/MS (method 38) $[M+H]^+$=624.2, $R_T$=2.80 min. 1H NMR (400 MHz, DMSO-d6) 9.75 (s, 1H), 9.34 (dd, J=7.0, 1.7 Hz, 1H), 8.68 (dd, J=4.3, 1.6 Hz, 1H), 8.67 (s, 1H), 8.30 (s, 1H), 7.63 (dd, J=8.8, 2.7 Hz, 1H), 7.56 (d, J=2.7 Hz, 1H), 7.46 (d, J=8.8 Hz, 1H), 7.29 (dd, J=7.0, 4.2 Hz, 1H), 7.25 (t, J=73.0 Hz, 1H), 5.23 (d, J=4.7 Hz, 2H), 4.12 (d, J=12.7 Hz, 1H), 3.84 (d, J=13.7 Hz, 1H), 3.14 (t, J=11.9 Hz, 1H), 2.85 (t, J=11.9 Hz, 1H), 2.71-2.65 (m, 3H), 2.02 (s, 1H), 1.83 (t, J=16.2 Hz, 2H), 1.33-1.12 (m, 4H), 0.94 (m, 2H).

Enzymatic Assays

JAK Enzyme Assays were carried out as follows:

The activity of the isolated recombinant JAK1 and JAK2 kinase domain was measured by monitoring phosphorylation of a peptide derived from JAK3 (Val-Ala-Leu-Val-Asp-Gly-Tyr-Phe-Arg-Leu-Thr-Thr, fluorescently labeled on the N-terminus with 5-carboxyfluorescein) using the Caliper LabChip® technology (Caliper Life Sciences, Hopkinton, Mass.). To determine inhibition constants ($K_i$), compounds were diluted serially in DMSO and added to 50 μL kinase reactions containing purified enzyme (1.5 nM JAK1, or 0.2 nM JAK2), 100 mM HEPES buffer (pH 7.2), 0.015% Brij-35, 1.5 μM peptide substrate, ATP (25 μM), 10 mM $MgCl_2$, 4 mM DTT at a final DMSO concentration of 2%. Reactions were incubated at 22° C. in 384-well polypropylene microtiter plates for 30 minutes and then stopped by addition of 25 μL of an EDTA containing solution (100 mM HEPES buffer (pH 7.2), 0.015% Brij-35, 150 mM EDTA), resulting in a final EDTA concentration of 50 mM. After termination of the kinase reaction, the proportion of phosphorylated product was determined as a fraction of total peptide substrate using the Caliper LabChip® 3000 according to the manufacturer's specifications. $K_i$ values were then determined using the Morrison tight binding model (Morrison, J. F., Biochim. Biophys. Acta. 185:269-296 (1969); William, J. W. and Morrison, J. F., Meth. Enzymol., 63:437-467 (1979)) modified for ATP-competitive inhibition $[K_i=K_{i,app}/(1+[ATP]/K_{m,app})]$.

JAK1 Pathway Assay in Cell Lines was carried out as follows:

Inhibitor potency ($EC_{50}$) was determined in cell-based assays designed to measure JAK1 dependent STAT phosphorylation. As noted above, inhibition of IL-4, IL-13, and IL-9 signaling by blocking the Jak/Stat signaling pathway can alleviate asthmatic symptoms in pre-clinical lung inflammation models (Mathew et al., 2001, J Exp Med 193(9): 1087-1096; Kudlacz et. al., 2008, Eur J. Pharmacol 582(1-3): 154-161).

In one assay approach, TF-1 human erythroleukemia cells obtained from the American Type Culture Collection (ATCC; Manassas, Va.) were used to measure JAK1-dependent STAT6 phosphorylation downstream of IL-13 stimulation. Prior to use in the assays, TF-1 cells were starved of GM-CSF overnight in OptiMEM medium (Life Technologies, Grand Island, N.Y.) supplemented with 0.5% charcoal/dextran stripped fetal bovine serum (FBS), 0.1 mM non-essential amino acids (NEAA), and 1 mM sodium pyruvate. The assays were run in 384-well plates in serum-free OptiMEM medium using 300,000 cells per well. In a second assay approach, BEAS-2B human bronchial epithelial cells obtained from ATCC were plated at 100,000 cells per well of a 96-well plate one day prior to the experiment. The BEAS-2B assay was run in complete growth medium (bronchial epithelial basal medium plus bulletkit; Lonza; Basel, Switzerland).

Test compounds were serially diluted 1:2 in DMSO and then diluted 1:50 in medium just before use. Diluted compounds were added to the cells, for a final DMSO concentration of 0.2%, and incubated for 30 min (for the TF-1 assay) or 1 hr (for the BEAS-2B assay) at 37° C. Then, cells were stimulated with human recombinant cytokine at their respective $EC_{90}$ concentrations, as previously determined for each individual lot. Cells were stimulated with IL-13 (R&D Systems, Minneapolis, Minn.) for 15 min at 37° C. The TF-1 cell reactions were stopped by the direct addition of 10× lysis buffer (Cell Signaling Technologies, Danvers, Mass.), whereas the BEAS-2B cell incubations were halted by the removal of medium and addition of 1× lysis buffer. The resultant samples were frozen in the plates at −80° C. Compound mediated inhibition of STAT6 phosphorylation was measured in the cell lysates using MesoScale Discovery (MSD) technology (Gaithersburg, Md.). $EC_{50}$ values were determined as the concentration of compound required for 50% inhibition of STAT phosphorylation relative to that measured for the DMSO control.

Table 2 provides JAK1 $K_i$, JAK2 $K_i$ and IL-13-pSTAT6 $IC_{50}$ information for the noted Examples of the indicated Tables as well as LCMS (ESI) information.

TABLE 2

| Ex # | LCMS (ESI) m/z [M + H]+ | LCMS Method | LCMS RT (Min) | JAK1 Ki (uM) | JAK2 Ki (uM) | IL13-pSTAT6 EC50_TF-1 (uM) | IL13-pSTAT6 EC50 (uM)_BEAS-2B |
|---|---|---|---|---|---|---|---|
| 1 | 488.0 | 5 | 2.93 | 0.00162 | 0.00046 | 0.0211 | |
| 2 | 503.3 | 5 | 2.32 | 0.00072 | 0.00019 | 0.0052 | 0.0195 |
| 3 | 570.9 | 5 | 2.82 | 0.00079 | 0.00081 | 0.0167 | 0.0324 |
| 4 | 556.9 | 5 | 2.83 | 0.00066 | 0.00080 | 0.5473 | |
| 5 | 585.0 | 5 | 2.88 | 0.00084 | 0.00078 | 0.0111 | |
| 6 | 611.1 | 5 | 3.02 | 0.00071 | 0.00075 | 0.0059 | |
| 7 | 586.0 | 5 | 2.58 | 0.00110 | 0.00096 | 1.0402 | |
| 8 | 585.0 | 5 | 3.03 | 0.09634 | 0.11951 | 0.7456 | |
| 9 | 586.0 | 11 | 0.90 | 0.00071 | 0.00028 | 0.0156 | 0.5543 |
| 10 | 571.9 | 11 | 0.90 | 0.00065 | 0.00032 | | |
| 11 | 600.1 | 11 | 0.93 | 0.00105 | 0.00030 | 0.0118 | |
| 12 | 599.1 | 5 | 2.96 | 0.00130 | 0.00117 | 0.0150 | |
| 13 | 661.1 | 5 | 3.38 | 0.00073 | 0.00066 | 0.0220 | |
| 14 | 615.0 | 5 | 2.86 | 0.00114 | 0.00113 | 0.3348 | |
| 15 | 659.0 | 5 | 3.58 | 0.00053 | 0.00093 | 0.3345 | |
| 16 | 647.0 | 5 | 3.24 | 0.00062 | 0.00056 | 0.0081 | |
| 17 | 788.3 | 5 | 3.57 | 0.00071 | 0.00085 | 0.0809 | |
| 18 | 682.1 | 5 | 2.91 | 0.00056 | 0.00056 | 0.2743 | |
| 19 | 684.2 | 5 | 2.85 | 0.00072 | 0.00071 | 0.3792 | |
| 20 | 570.9 | 5 | 2.87 | 0.00051 | 0.00121 | 0.3435 | |
| 21 | 570.9 | 5 | 2.90 | 0.00047 | 0.00116 | 3.0382 | |
| 22 | 696.1 | 5 | 2.87 | 0.00094 | 0.00095 | 0.1575 | |
| 23 | 726.2 | 5 | 3.20 | 0.00070 | 0.00081 | 0.0086 | |
| 24 | 584.9 | 5 | 2.88 | 0.00078 | 0.00202 | 0.0049 | |
| 25 | 585.0 | 5 | 2.90 | 0.00066 | 0.00161 | 0.1214 | |
| 26 | 655.1 | 5 | 2.93 | 0.00077 | 0.00094 | 0.0062 | |
| 27 | 677.0 | 5 | 2.84 | 0.00046 | 0.00055 | 0.1444 | |
| 28 | 613.1 | 5 | 3.06 | 0.00082 | 0.00084 | 0.0035 | 0.1770 |
| 29 | 584.9 | 5 | 2.85 | 0.00101 | 0.00176 | 0.0056 | |
| 30 | 584.9 | 5 | 2.85 | 0.00070 | 0.00169 | | |
| 31 | 663.1 | 5 | 2.84 | 0.00037 | 0.00053 | 0.1024 | |
| 32 | 684.4 | 5 | 2.87 | 0.00046 | 0.00050 | 0.0985 | |
| 33 | 689.3 | 5 | 3.29 | 0.00066 | 0.00049 | 0.0062 | 0.0485 |
| 34 | 732.2 | 5 | 3.00 | 0.00047 | 0.00046 | | |
| 35 | 766.4 | 5 | 2.94 | 0.00051 | 0.00073 | 0.2346 | |
| 36 | 725.3 | 5 | 2.99 | 0.00084 | 0.00062 | 0.0576 | |
| 37 | 677.2 | 5 | 3.26 | 0.00110 | 0.00078 | 0.0118 | |
| 38 | 629.2 | 5 | 2.94 | 0.00088 | 0.00078 | 0.0085 | |
| 39 | 641.2 | 5 | 2.86 | 0.00055 | 0.00087 | 0.0066 | |
| 40 | 625.2 | 5 | 3.13 | 0.00065 | 0.00061 | 0.0038 | 0.1280 |
| 41 | 585.2 | 5 | 2.86 | 0.00091 | 0.00147 | 0.0080 | |
| 42 | 585.2 | 5 | 2.86 | 0.00069 | 0.00067 | 0.0031 | |
| 43 | 647.2 | 5 | 3.24 | 0.00066 | 0.00036 | 0.0150 | |
| 44 | 647.2 | 5 | 3.24 | 0.00054 | 0.00022 | 0.0067 | |
| 45 | 585.2 | 5 | 2.87 | 0.00074 | 0.00178 | 0.0071 | 0.0245 |
| 46 | 669.3 | 5 | 3.14 | 0.00058 | 0.00070 | 0.0082 | |
| 47 | 678.3 | 5 | 3.39 | 0.00033 | 0.00054 | 0.0110 | |
| 48 | 585.2 | 5 | 2.87 | 0.00094 | 0.00185 | 0.0137 | 0.0594 |
| 49 | 585.2 | 5 | 2.86 | 0.00050 | 0.00096 | 0.0113 | |
| 50 | 643.2 | 5 | 2.93 | 0.00099 | 0.00074 | 0.0320 | |
| 51 | 728.3 | 5 | 2.99 | 0.00109 | 0.00106 | 0.0779 | |
| 52 | 653.4 | 5 | 3.39 | 0.00065 | 0.00062 | 0.0054 | 0.0388 |
| 53 | 585.2 | 5 | 2.85 | 0.00061 | 0.00122 | 0.0109 | |
| 54 | 730.4 | 5 | 3.23 | 0.00076 | 0.00067 | 0.0151 | |
| 55 | 697.3 | 5 | 3.29 | 0.00085 | 0.00072 | 0.0210 | |
| 56 | 600.1 | 5 | 2.90 | 0.00074 | 0.00026 | 0.0069 | |
| 57 | 626.2 | 5 | 3.07 | 0.00059 | 0.00013 | 0.0150 | |
| 58 | 704.2 | 5 | 3.34 | 0.00060 | 0.00033 | 0.0256 | |
| 59 | 639.2 | 5 | 4.10 | 0.00050 | 0.00080 | 0.0037 | |
| 60 | 725.2 | 5 | 3.62 | 0.00110 | 0.00070 | 0.0462 | |
| 61 | 585.2 | 5 | 2.91 | 0.00023 | 0.00068 | 0.0275 | 0.0324 |
| 62 | 585.2 | 5 | 2.91 | 0.00207 | 0.00268 | 0.0558 | 0.0892 |
| 63 | 612.2 | 5 | 2.84 | 0.00034 | 0.00070 | 0.0057 | 0.0122 |
| 64 | 545.0 | 5 | 2.81 | 0.00066 | 0.00084 | | |
| 65 | 559.0 | 5 | 2.89 | 0.00054 | 0.00069 | 0.0094 | |
| 66 | 545.0 | 5 | 2.84 | 0.00058 | 0.00178 | 0.0356 | 0.3345 |
| 67 | 573.0 | 5 | 2.88 | 0.00089 | 0.00187 | 0.0146 | 0.0715 |
| 68 | 617.0 | 5 | 2.98 | 0.00074 | 0.00168 | 0.0134 | |
| 69 | 599.1 | 5 | 2.95 | 0.00086 | 0.00245 | 0.0204 | |
| 70 | 587.0 | 5 | 2.94 | 0.00067 | 0.00238 | 0.0161 | |
| 71 | 587.0 | 5 | 3.01 | 0.00106 | 0.00466 | | |
| 72 | 587.1 | 5 | 3.01 | 0.00117 | 0.00407 | 0.0072 | |
| 73 | 617.1 | 5 | 3.01 | 0.00071 | 0.00171 | | |
| 74 | 603.1 | 5 | 2.87 | 0.00097 | 0.00242 | 0.0385 | |

TABLE 2-continued

| Ex # | LCMS (ESI) m/z [M + H]+ | LCMS Method | LCMS RT (Min) | JAK1 Ki (uM) | JAK2 Ki (uM) | IL13-pSTAT6 EC50_TF-1 (uM) | IL13-pSTAT6 EC50 (uM)_BEAS-2B |
|---|---|---|---|---|---|---|---|
| 75 | 587.9 | 11 | 0.91 | 0.00066 | 0.00061 | 0.0787 | |
| 76 | 630.2 | 11 | 0.89 | 0.00050 | 0.00052 | | |
| 77 | 630.2 | 11 | 0.88 | 0.00060 | 0.00051 | 0.2095 | |
| 78 | 587.9 | 12 | 1.18 | 0.00208 | 0.00138 | 0.0524 | |
| 79 | 587.9 | 12 | 1.18 | 0.00454 | 0.00211 | 0.1582 | |
| 80 | 663.2 | 5 | 3.26 | 0.00043 | 0.00087 | 0.0049 | |
| 81 | 545.1 | 5 | 2.92 | 0.00535 | 0.00324 | 0.2532 | |
| 82 | 602.2 | 5 | 3.01 | 0.00117 | 0.00053 | 0.0087 | |
| 83 | 559.2 | 5 | 2.84 | 0.00107 | 0.00159 | 0.0423 | 0.1425 |
| 84 | 599.2 | 5 | 3.02 | 0.00091 | 0.00147 | 0.0246 | |
| 85 | 663.3 | 5 | 3.37 | 0.00086 | 0.00166 | 0.0153 | 0.1003 |
| 86 | 664.3 | 5 | 3.10 | 0.00072 | 0.00160 | 0.0252 | |
| 87 | 598.2 | 5 | 2.97 | 0.00040 | 0.00073 | 0.0154 | 0.0140 |
| 88 | 672.2 | 5 | 3.03 | 0.00172 | 0.00191 | 0.2987 | |
| 89 | 649.2 | 5 | 3.38 | 0.00088 | 0.00145 | 0.0227 | |
| 90 | 679.3 | 5 | 3.12 | 0.00095 | 0.00131 | 0.0233 | |
| 91 | 665.2 | 5 | 3.10 | 0.00075 | 0.00115 | 0.1487 | |
| 92 | 683.2 | 5 | 3.50 | 0.00092 | 0.00203 | 0.0556 | |
| 93 | 717.3 | 5 | 3.63 | 0.00128 | 0.00258 | 0.0959 | |
| 94 | 697.3 | 5 | 3.57 | 0.00120 | 0.00207 | 0.0424 | 0.0931 |
| 95 | 693.3 | 5 | 3.38 | 0.00080 | 0.00260 | 0.0173 | |
| 96 | 643.3 | 5 | 2.90 | 0.00063 | 0.00140 | 0.0041 | |
| 97 | 731.3 | 5 | 3.70 | 0.00116 | 0.00197 | 0.1869 | |
| 98 | 649.3 | 5 | 3.22 | 0.00079 | 0.00181 | 0.0038 | 0.0381 |
| 99 | 641.2 | 5 | 4.39 | 0.00040 | 0.00076 | 0.0017 | 0.0305 |
| 100 | 679.3 | 5 | 3.35 | 0.00084 | 0.00201 | 0.0054 | |
| 101 | 669.3 | 5 | 3.63 | 0.00067 | 0.00177 | 0.0165 | |
| 102 | 699.2 | 5 | 3.71 | 0.00062 | 0.00110 | 0.0085 | 0.0347 |
| 103 | 731.3 | 5 | 5.49 | 0.00398 | 0.00795 | 0.2649 | |
| 104 | 757.2 | 5 | 3.65 | 0.00093 | 0.00211 | 0.0202 | |
| 105 | 757.2 | 5 | 3.52 | 0.00145 | 0.00317 | 0.0500 | |
| 106 | 713.3 | 5 | 3.48 | 0.00109 | 0.00229 | 0.0155 | |
| 107 | 713.2 | 5 | 3.55 | 0.00097 | 0.00249 | 0.0176 | |
| 108 | 735.4 | 5 | 3.81 | 0.00247 | 0.00366 | 0.0431 | |
| 109 | 719.5 | 5 | 3.64 | 0.00322 | 0.00730 | 0.0429 | |
| 110 | 693.5 | 5 | 3.51 | 0.00104 | 0.00203 | 0.0089 | 0.0875 |
| 111 | 739.4 | 5 | 4.00 | 0.00310 | 0.01061 | 0.2030 | |
| 112 | 693.4 | 5 | 3.38 | 0.00045 | 0.00101 | 0.0963 | |
| 113 | 741.4 | 5 | 3.74 | 0.00119 | 0.00215 | 0.0306 | |
| 114 | 680.4 | 5 | 3.43 | 0.00052 | 0.00134 | 0.0153 | |
| 115 | 683.3 | 5 | 5.43 | 0.00128 | 0.00248 | 0.0577 | |
| 116 | 717.3 | 5 | 5.38 | 0.00376 | 0.00704 | 0.0233 | |
| 117 | 725.4 | 5 | 3.97 | 0.00051 | 0.00113 | 0.0086 | 0.0546 |
| 118 | 731.4 | 5 | 4.01 | 0.00257 | 0.00445 | 0.1001 | 0.3030 |
| 119 | 727.2 | 5 | 3.45 | 0.00121 | 0.00051 | 0.0208 | |
| 120 | 705.4 | 5 | 3.78 | 0.00030 | 0.00023 | 0.1179 | |
| 121 | 717.3 | 5 | 3.56 | 0.00024 | 0.00031 | 0.1397 | |
| 122 | 727.3 | 5 | 3.43 | 0.00027 | 0.00017 | 0.0249 | |
| 123 | 677.3 | 5 | 3.49 | 0.00223 | 0.00163 | 0.0076 | 0.0487 |
| 124 | 691.3 | 5 | 3.48 | 0.00121 | 0.00290 | 0.0879 | 0.5355 |
| 125 | 707.4 | 5 | 3.55 | 0.00061 | 0.00220 | 0.0117 | |
| 126 | 683.3 | 5 | 3.40 | 0.00063 | 0.00180 | 0.0149 | |
| 127 | 721.4 | 5 | 3.80 | 0.00078 | 0.00244 | 0.0724 | |
| 128 | 717.3 | 5 | 3.51 | 0.00112 | 0.00309 | 0.0425 | |
| 129 | 677.3 | 5 | 3.46 | 0.00114 | 0.00333 | 0.0142 | |
| 130 | 699.3 | 5 | 3.50 | 0.00110 | 0.00291 | 0.0323 | |
| 131 | 745.3 | 5 | 3.46 | 0.00107 | 0.00268 | 0.0237 | |
| 132 | 703.3 | 5 | 4.87 | 0.00057 | 0.00127 | 0.0031 | 0.0973 |
| 133 | 731.3 | 5 | 5.56 | 0.00651 | 0.00833 | | |
| 134 | 637.2 | 5 | 3.09 | 0.00033 | 0.00069 | 0.0023 | 0.0118 |
| 135 | 681.3 | 5 | 3.32 | 0.00052 | 0.00115 | 0.0269 | |
| 136 | 574.0 | 12 | 1.18 | 0.00064 | 0.00025 | 0.0367 | |
| 137 | 632.0 | 11 | 0.94 | 0.00053 | 0.00072 | | |
| 138 | 560.2 | 11 | 0.87 | 0.00052 | 0.00026 | | |
| 139 | 588.2 | 5 | 2.93 | 0.00078 | 0.00036 | 0.0402 | |
| 140 | 617.9 | 11 | 0.88 | 0.00046 | 0.00039 | 0.0293 | |
| 141 | 632.1 | 11 | 0.90 | 0.00068 | 0.00059 | 0.0150 | |
| 142 | 587.0 | 5 | 2.91 | 0.00165 | 0.00038 | 0.0363 | |
| 143 | 656.1 | 5 | 3.47 | 0.00076 | 0.00018 | 0.0204 | |
| 144 | 628.0 | 7 | 0.98 | 0.00054 | 0.00017 | 0.0128 | 0.0213 |
| 145 | 664.0 | 9 | 1.26 | 0.00057 | 0.00016 | 0.0148 | |
| 146 | 628.0 | 9 | 1.20 | 0.00045 | 0.00013 | 0.0039 | |
| 147 | 658.0 | 9 | 1.19 | 0.00055 | 0.00014 | 0.0118 | |
| 148 | 616.0 | 11 | 0.99 | 0.00064 | 0.00010 | 0.0094 | |

TABLE 2-continued

| Ex # | LCMS (ESI) m/z [M + H]+ | LCMS Method | LCMS RT (Min) | JAK1 Ki (uM) | JAK2 Ki (uM) | IL13-pSTAT6 EC50_TF-1 (uM) | IL13-pSTAT6 EC50 (uM)_BEAS-2B |
|---|---|---|---|---|---|---|---|
| 149 | 601.9 | 13 | 1.75 | 0.00081 | 0.00020 | 0.0083 | 0.0198 |
| 150 | 602.0 | 11 | 0.98 | 0.00073 | 0.00017 | 0.0201 | |
| 151 | 678.0 | 11 | 1.04 | 0.00200 | 0.00042 | 0.0938 | |
| 152 | 657.3 | 5 | 3.03 | 0.00108 | 0.00019 | 0.0119 | |
| 153 | 629.2 | 5 | 2.91 | 0.00155 | 0.00027 | 0.0365 | |
| 154 | 628.3 | 5 | 3.06 | 0.00142 | 0.00023 | 0.0027 | |
| 155 | 613.2 | 5 | 3.01 | 0.00156 | 0.00024 | 0.0051 | |
| 156 | 601.2 | 5 | 3.05 | 0.00153 | 0.00019 | 0.0318 | |
| 157 | 559.1 | 5 | 2.93 | 0.00132 | 0.00075 | 0.0092 | |
| 158 | 615.3 | 5 | 2.47 | 0.00212 | 0.00026 | 0.0388 | |
| 159 | 631.2 | 5 | 2.53 | 0.00232 | 0.00024 | 0.0578 | |
| 160 | 573.3 | 5 | 2.90 | 0.00302 | 0.00039 | 0.0193 | |
| 161 | 663.3 | 5 | 2.92 | 0.00123 | 0.00013 | 0.0223 | |
| 162 | 588.1 | 5 | 2.93 | 0.00059 | 0.00018 | 0.0154 | |
| 163 | 629.1 | 5 | 2.99 | 0.00069 | 0.00019 | 0.0073 | |
| 164 | 643.1 | 5 | 3.13 | 0.00044 | 0.00006 | 0.0056 | |
| 165 | 574.2 | 5 | 2.88 | 0.00038 | 0.00015 | 0.0069 | |
| 166 | 719.4 | 5 | 3.60 | 0.00091 | 0.00026 | 0.0229 | |
| 167 | 678.3 | 5 | 3.49 | 0.00053 | 0.00018 | 0.0197 | |
| 168 | 587.3 | 5 | 3.03 | 0.00147 | 0.00029 | 0.0077 | |
| 169 | 643.2 | 5 | 3.03 | 0.00116 | 0.00022 | 0.0068 | |
| 170 | 573.3 | 5 | 2.86 | 0.00167 | 0.00025 | 0.0114 | |
| 171 | 516.9 | 11 | 0.98 | 0.00072 | 0.00017 | 0.0219 | |
| 172 | 530.9 | 11 | 0.99 | 0.00088 | 0.00015 | 0.0159 | |
| 173 | 642.3 | 5 | 3.00 | 0.00058 | 0.00013 | 0.0048 | |
| 174 | 559.1 | 5 | 3.27 | 0.00067 | 0.00009 | 0.0123 | |
| 175 | 617.2 | 5 | 3.32 | 0.00078 | 0.00013 | 0.0134 | |
| 176 | 561.2 | 5 | 2.96 | 0.00068 | 0.00012 | 0.0127 | |
| 177 | 623.2 | 5 | 3.02 | 0.00045 | 0.00009 | 0.0150 | |
| 178 | 593.2 | 5 | 3.43 | 0.00123 | 0.00043 | 0.0839 | |
| 179 | 635.2 | 5 | 3.79 | 0.00304 | 0.00090 | 0.1302 | |
| 180 | 637.3 | 5 | 3.65 | 0.00125 | 0.00035 | 0.0384 | |
| 181 | 679.3 | 5 | 3.79 | 0.00199 | 0.00048 | 0.0956 | |
| 182 | 502.9 | 12 | 1.23 | 0.00049 | 0.00020 | 0.0089 | |
| 183 | 502.9 | 11 | 1.00 | 0.00049 | 0.00023 | 0.0068 | |
| 184 | 547.3 | 11 | 1.00 | 0.00076 | 0.00018 | 0.0035 | |
| 185 | 489.1 | 11 | 0.91 | 0.00059 | 0.00031 | | |
| 186 | 488.9 | 12 | 1.10 | 0.00071 | 0.00020 | 0.0123 | |
| 187 | 742.4 | 5 | 3.94 | 0.00705 | 0.00903 | | |
| 188 | 548.1 | 5 | 3.20 | 0.00126 | 0.00084 | 0.0058 | 0.0349 |
| 189 | 587.2 | 5 | 3.19 | 0.00259 | 0.00161 | 0.0053 | 0.0200 |
| 190 | 562.1 | 5 | 3.18 | 0.00269 | 0.00202 | 0.0146 | 0.0098 |
| 191 | 576.1 | 5 | 3.29 | 0.00293 | 0.00292 | 0.0105 | |
| 192 | 638.2 | 5 | 3.73 | 0.00500 | 0.00372 | 0.2723 | |
| 193 | 619.1 | 5 | 3.03 | 0.00223 | 0.00146 | 0.0235 | |
| 194 | 587.2 | 5 | 3.15 | 0.00228 | 0.00144 | 0.0174 | |
| 195 | 560.1 | 5 | 3.07 | 0.00136 | 0.00086 | 0.0165 | |
| 196 | 596.1 | 5 | 3.71 | 0.00174 | 0.00105 | 0.0174 | |
| 197 | 586.3 | 5 | 3.10 | 0.00089 | 0.00086 | 0.0062 | |
| 198 | 616.1 | 5 | 5.36 | 0.00272 | 0.00217 | 0.0291 | |
| 199 | 590.3 | 5 | 3.51 | 0.00122 | 0.00107 | 0.0073 | |
| 200 | 618.2 | 5 | 3.17 | 0.00124 | 0.00107 | 0.0059 | 0.0254 |
| 201 | 624.2 | 5 | 3.55 | 0.00505 | 0.00376 | 0.1837 | |
| 202 | 727.4 | 5 | 4.89 | 0.00110 | 0.00182 | 0.0158 | |
| 203 | 655.3 | 5 | 3.96 | 0.00548 | 0.00415 | | |
| 204 | 766.4 | 5 | 3.77 | 0.00200 | 0.00141 | 0.0079 | 0.1715 |
| 205 | 520.2 | 5 | 3.02 | 0.00080 | 0.00058 | 0.0044 | 0.0338 |
| 206 | 610.2 | 5 | 3.64 | 0.01404 | 0.00867 | | |
| 207 | 560.1 | 5 | 3.26 | 0.00101 | 0.00069 | 0.0236 | |
| 208 | 588.0 | 5 | 5.29 | 0.00138 | 0.00108 | 0.0335 | |
| 209 | 503.0 | 5 | 3.16 | 0.00078 | 0.00028 | 0.0074 | 0.0415 |
| 210 | 545.1 | 5 | 3.48 | 0.00016 | 0.00010 | 0.2397 | |
| 211 | 570.9 | 5 | 2.86 | 0.00110 | 0.00138 | 0.0209 | |
| 212 | 585.1 | 5 | 2.92 | 0.00091 | 0.00193 | 0.0306 | |
| 213 | 615.2 | 5 | 2.97 | 0.00149 | 0.00234 | | |
| 214 | 556.9 | 5 | 2.82 | 0.00117 | 0.00129 | | |
| 215 | 630.2 | 12 | 1.12 | 0.00133 | 0.00126 | | |
| 216 | 585.0 | 5 | 2.87 | 0.00113 | 0.00182 | 0.0125 | |
| 217 | 570.9 | 5 | 2.87 | 0.00107 | 0.00137 | | |
| 218 | 585.0 | 5 | 2.92 | 0.00101 | 0.00308 | 0.0756 | |
| 219 | 556.9 | 5 | 2.87 | 0.00056 | 0.00128 | 1.0320 | |
| 220 | 556.9 | 5 | 2.84 | 0.00122 | 0.00271 | 1.1706 | |
| 221 | 570.9 | 5 | 2.88 | 0.00092 | 0.00168 | 0.1305 | |
| 222 | 599.0 | 5 | 2.94 | 0.00054 | 0.00159 | 0.0289 | |

TABLE 2-continued

| Ex # | LCMS (ESI) m/z [M + H]+ | LCMS Method | LCMS RT (Min) | JAK1 Ki (uM) | JAK2 Ki (uM) | IL13-pSTAT6 EC50_TF-1 (uM) | IL13-pSTAT6 EC50 (uM)_BEAS-2B |
|---|---|---|---|---|---|---|---|
| 223 | 584.9 | 5 | 2.94 | 0.00044 | 0.00072 | 0.1867 | |
| 224 | 599.0 | 5 | 2.96 | 0.00056 | 0.00147 | 0.0193 | |
| 225 | 641.3 | 5 | 3.15 | 0.00039 | 0.00129 | 0.0050 | 0.0423 |
| 226 | 816.4 | 5 | 3.59 | 0.00041 | 0.00111 | 0.0415 | |
| 227 | 545.1 | 5 | 2.89 | 0.00055 | 0.00093 | 0.0036 | 0.0271 |
| 228 | 575.1 | 5 | 2.84 | 0.00047 | 0.00089 | 0.0111 | 0.0655 |
| 229 | 589.1 | 5 | 2.98 | 0.00038 | 0.00084 | 0.0033 | 0.0516 |
| 230 | 589.1 | 5 | 2.84 | 0.00061 | 0.00071 | | |
| 231 | 619.2 | 5 | 2.85 | 0.00054 | 0.00118 | | |
| 232 | 637.1 | 5 | 3.05 | 0.00074 | 0.00146 | | |
| 233 | 559.1 | 5 | 2.89 | 0.00078 | 0.00143 | 0.0100 | 0.0181 |
| 234 | 575.0 | 5 | 2.83 | 0.00058 | 0.00122 | | |
| 235 | 575.1 | 5 | 2.82 | 0.00058 | 0.00108 | 0.0213 | 0.1140 |
| 236 | 607.0 | 5 | 4.68 | 0.00041 | 0.00074 | | |
| 237 | 632.1 | 5 | 4.47 | 0.00032 | 0.00076 | | |
| 238 | 646.1 | 5 | 3.32 | 0.00045 | 0.00055 | | 0.0218 |
| 239 | 559.1 | 5 | 2.87 | 0.00155 | 0.00238 | 0.0086 | |
| 240 | 589.1 | 5 | 2.88 | 0.00100 | 0.00168 | | |
| 241 | 585.1 | 5 | 2.98 | 0.00087 | 0.00125 | | |
| 242 | 571.0 | 5 | 2.89 | 0.00095 | 0.00103 | | |
| 243 | 560.0 | 5 | 2.88 | 0.00049 | 0.00036 | | |
| 244 | 589.9 | 11 | 0.90 | 0.00049 | 0.00024 | | |
| 245 | 604.0 | 11 | 0.94 | 0.00035 | 0.00022 | | |
| 246 | 573.9 | 11 | 0.91 | 0.00108 | 0.00057 | 0.0488 | |
| 247 | 574.1 | 11 | 0.91 | 0.00055 | 0.00030 | | |
| 248 | 600.2 | 11 | 0.94 | 0.00062 | 0.00039 | | |
| 249 | 545.9 | 12 | 1.09 | 0.00073 | 0.00044 | 0.0323 | |
| 250 | 572.0 | 11 | 0.89 | 0.00139 | 0.00048 | | |
| 251 | 574.0 | 11 | 1.01 | 0.00083 | 0.00046 | | |
| 252 | 571.9 | 11 | 0.99 | 0.00081 | 0.00015 | 0.0430 | |
| 253 | 652.3 | 5 | 3.35 | 0.00056 | 0.00041 | 0.0183 | |
| 254 | 499.0 | 5 | 3.87 | 0.00163 | 0.00077 | 0.1174 | |
| 255 | 555.1 | 5 | 3.39 | 0.00056 | 0.00040 | 0.0862 | |
| 256 | 585.2 | 5 | 3.45 | 0.00131 | 0.00095 | 0.0920 | |
| 257 | 603.1 | 5 | 4.28 | 0.00293 | 0.00210 | 1.0000 | |
| 258 | 596.1 | 5 | 3.46 | 0.00117 | 0.00072 | 0.0710 | |
| 259 | 624.2 | 5 | 3.29 | 0.00093 | 0.00056 | 0.0130 | |
| 260 | 562.1 | 5 | 2.56 | 0.00774 | 0.00265 | 0.0685 | |
| 261 | 569.1 | 5 | 3.62 | 0.01790 | 0.01024 | | |
| 262 | 560.1 | 5 | 2.85 | 0.00584 | 0.00173 | 0.0627 | |
| 263 | 519.0 | 5 | 3.23 | 0.00150 | 0.00203 | 0.0192 | |
| 264 | 574.1 | 5 | 3.06 | 0.00269 | 0.00238 | 0.0198 | |
| 265 | 576.1 | 5 | 3.09 | 0.00363 | 0.00429 | 0.0228 | |
| 266 | 575.2 | 5 | 3.64 | 0.00024 | 0.00010 | 0.0059 | |
| 267 | 576.1 | 5 | 3.50 | 0.00066 | 0.00062 | 0.0358 | |
| 268 | 546.1 | 5 | 3.68 | 0.00049 | 0.00046 | 0.0055 | |
| 269 | 545.9 | 5 | 3.55 | 0.00033 | 0.00083 | | |
| 270 | 547.0 | 11 | 1.01 | 0.00024 | 0.00020 | | |
| 271 | 517.2 | 11 | 1.06 | 0.00021 | 0.00013 | | |
| 272 | 576.0 | 5 | 3.30 | 0.00033 | 0.00078 | | |
| 273 | 577.1 | 12 | 1.17 | 0.00049 | 0.00023 | | |
| 274 | 560.0 | 5 | 3.58 | 0.00034 | 0.00091 | 0.0032 | 0.0131 |
| 275 | 590.1 | 5 | 3.54 | 0.00031 | 0.00089 | | |
| 276 | 623.1 | 5 | 3.05 | 0.00023 | 0.00018 | | |
| 277 | 562.0 | 5 | 3.43 | 0.00051 | 0.00083 | | |
| 278 | 546.0 | 5 | 3.51 | 0.00024 | 0.00063 | | 0.0050 |
| 279 | 651.2 | 12 | 1.35 | 0.00039 | 0.00022 | | |
| 280 | 560.0 | 5 | 3.69 | 0.00039 | 0.00081 | 0.0043 | 0.0215 |
| 281 | 631.0 | 5 | 4.75 | 0.00048 | 0.00045 | 0.0022 | |
| 282 | 567.0 | 11 | 1.10 | 0.00017 | 0.00012 | | |
| 283 | 646.1 | 11 | 1.19 | 0.00055 | 0.00029 | | |
| 284 | 528.0 | 5 | 4.28 | 0.00015 | 0.00037 | 0.0016 | 0.0125 |
| 285 | 637.1 | 11 | 1.20 | 0.00061 | 0.00047 | | |
| 286 | 637.0 | 11 | 1.23 | 0.00054 | 0.00026 | | |
| 287 | 552.0 | 5 | 4.22 | 0.00035 | 0.00065 | | |
| 288 | 532.0 | 5 | 3.77 | 0.00058 | 0.00111 | 0.0028 | 0.0363 |
| 289 | 622.0 | 5 | 4.22 | 0.00030 | 0.00038 | | |
| 290 | 547.0 | 11 | 1.04 | 0.00024 | 0.00011 | | |
| 291 | 546.0 | 5 | 3.69 | 0.00054 | 0.00055 | 0.0036 | 0.0317 |
| 292 | 503.0 | 5 | 4.52 | 0.00039 | 0.00040 | 0.0014 | 0.0210 |
| 293 | 546.0 | 5 | 3.83 | 0.00029 | 0.00038 | 0.0030 | 0.0081 |
| 294 | 506.0 | 5 | 3.00 | 0.00089 | 0.00057 | 0.0062 | 0.0367 |
| 295 | 463.0 | 5 | 2.81 | 0.00049 | 0.00021 | 0.0055 | 0.0345 |
| 296 | 531.2 | 5 | 3.10 | 0.00026 | 0.00021 | 0.0056 | 0.0283 |

TABLE 2-continued

| Ex # | LCMS (ESI) m/z [M + H]+ | LCMS Method | LCMS RT (Min) | JAK1 Ki (uM) | JAK2 Ki (uM) | IL13-pSTAT6 EC50_TF-1 (uM) | IL13-pSTAT6 EC50 (uM)_BEAS-2B |
|---|---|---|---|---|---|---|---|
| 297 | 489.1 | 5 | 2.87 | 0.00032 | 0.00007 | 0.0071 | 0.0308 |
| 298 | 503.2 | 5 | 2.93 | 0.00052 | 0.00018 | 0.0044 | 0.0215 |
| 299 | 595.2 | 5 | 3.08 | 0.00038 | 0.00039 | 0.0041 | 0.0104 |
| 300 | 615.0 | 5 | 4.42 | 0.00028 | 0.00018 | 0.0040 | 0.0142 |
| 301 | 581.2 | 5 | 3.22 | 0.00033 | 0.00036 | 0.0034 | 0.0095 |
| 302 | 635.2 | 5 | 3.27 | 0.00060 | 0.00111 | 0.0162 | |
| 303 | 703.3 | 5 | 5.09 | 0.00190 | 0.00328 | 0.0784 | |
| 304 | 475.1 | 17 | 6.52 | 0.00078 | 0.00039 | 0.0059 | 0.0469 |
| 305 | 489.1 | 18 | 7.75 | 0.00061 | 0.00032 | 0.0109 | 0.0426 |
| 306 | 534.2 | 14 | 1.13 | 0.00115 | 0.00054 | 0.0062 | 0.0659 |
| 307 | 574.2 | 15 | 2.23 | 0.00145 | 0.00059 | 0.0061 | 0.0250 |
| 308 | 530.1 | 5 | 4.27 | 0.00024 | 0.00055 | 0.0015 | 0.0236 |
| 309 | 534.1 | 16 | 2.68 | 0.00134 | 0.00047 | 0.0163 | 0.0490 |
| 310 | 589.2 | 26 | 0.82 | 0.00052 | 0.00059 | | 8.8300 |
| 311 | 589.1 | 25 | 0.85 | 0.00125 | 0.00073 | | 2.6000 |
| 312 | 522.2 | 20 | 2.5 | 0.00040 | 0.00032 | | 0.0719 |
| 313 | 538.2 | 20 | 2.7 | 0.00021 | 0.00021 | | 0.0218 |
| 314 | 539.2 | 20 | 2.53 | 0.00062 | 0.00039 | | 0.0995 |
| 315 | 539.1 | 25 | 1.45 | 0.00072 | 0.00040 | | 0.0823 |
| 316 | 635 | 21 | 1.56 | 0.00048 | 0.00104 | | 0.1420 |
| 317 | 587.1 | 25 | 1.8 | 0.00064 | 0.00116 | | 0.0229 |
| 318 | 615.2 | 25 | 0.93 | 0.00056 | 0.00111 | | 0.0283 |
| 319 | 573.2 | 20 | 2.86 | 0.00050 | 0.00086 | | 0.0577 |
| 320 | 621 | 21 | 1.53 | 0.00031 | 0.00060 | | 0.0473 |
| 321 | 644.2 | 20 | 2.34 | 0.00040 | 0.00090 | | 0.0133 |
| 322 | 603.2 | 20 | 2.83 | 0.00031 | 0.00080 | | 0.0411 |
| 323 | 503.1 | 20 | 1.65 | 0.00068 | 0.00033 | | 0.0209 |
| 324 | 531.2 | 20 | 2.67 | 0.00095 | 0.00161 | | 0.0566 |
| 325 | 616.3 | 20 | 2.41 | 0.00041 | 0.00103 | | 0.0651 |
| 326 | 554.2 | 20 | 2.79 | 0.00021 | 0.00028 | | 0.0070 |
| 327 | 554.2 | 20 | 1.58 | 0.00025 | 0.00020 | | 0.0077 |
| 328 | 554.2 | 20 | 1.58 | 0.00021 | 0.00023 | | 0.0102 |
| 329 | 617.2 | 24 | 1.53 | 0.00030 | 0.00076 | | 0.0115 |
| 330 | 643.2 | 25 | 1.49 | 0.00039 | 0.00088 | | 0.0343 |
| 331 | 617.1 | 25 | 1.51 | 0.00039 | 0.00077 | | 0.0176 |
| 332 | 631.2 | 28 | 0.89 | 0.00049 | 0.00091 | | 0.0692 |
| 333 | 700.2 | 24 | 2.21 | 0.00069 | 0.00196 | | 0.0065 |
| 334 | 714.2 | 24 | 2.42 | 0.00069 | 0.00181 | | 0.0061 |
| 335 | 714.2 | 24 | 1.94 | 0.00084 | 0.00222 | | 0.0121 |
| 336 | 687.2 | 28 | 0.86 | 0.00049 | 0.00105 | | 0.0145 |
| 337 | 728.2 | 24 | 1.87 | 0.00083 | 0.00252 | | 0.0232 |
| 338 | 645.2 | 24 | 2.97 | 0.00036 | 0.00116 | | 0.0177 |
| 339 | 701.2 | 20 | 0.92 | 0.00041 | 0.00101 | | 0.0094 |
| 340 | 659.2 | 28 | 1.23 | 0.00044 | 0.00179 | | 0.0090 |
| 341 | 671.3 | 20 | 1.58 | 0.00053 | 0.00262 | | 0.5340 |
| 342 | 574.1 | 28 | 1.11 | 0.00019 | 0.00020 | | 1.8100 |
| 343 | 588.2 | 20 | 2.79 | | | | |
| 344 | 657.2 | 24 | 1.68 | 0.00070 | 0.00190 | | 0.0484 |
| 345 | 645.2 | 24 | 1.64 | 0.00059 | 0.00147 | | 0.0166 |
| 346 | 584.2 | 20 | 2.23 | 0.00037 | 0.00031 | | 0.1150 |
| 347 | 629.1 | 28 | 1.44 | 0.00039 | 0.00076 | | 0.0307 |
| 348 | 629.2 | 20 | 1.55 | 0.00040 | 0.00102 | | 0.0120 |
| 349 | 628.2 | 20 | 2.2 | 0.00055 | 0.00165 | | 0.0155 |
| 350 | 642.2 | 24 | 1.55 | 0.00043 | 0.00142 | | 0.0094 |
| 351 | 627.1 | 24 | 1.55 | 0.00046 | 0.00094 | | 0.0365 |
| 352 | 655.2 | 20 | 1.91 | 0.00033 | 0.00075 | | 0.0124 |
| 353 | 603.1 | 28 | 0.81 | 0.00032 | 0.00036 | | 3.6100 |
| 354 | 604.3 | 20 | 2.08 | 0.00072 | 0.00105 | | 0.0240 |
| 355 | 604.3 | 20 | 2.08 | 0.00332 | 0.00372 | | 0.0678 |
| 356 | 604.3 | 20 | 2.08 | 0.00264 | 0.00237 | | 0.0396 |
| 357 | 604.3 | 20 | 2.08 | 0.00122 | 0.00106 | | 0.0216 |
| 358 | 504.2 | 20 | 1.38 | 0.00093 | 0.00066 | | 0.0133 |
| 359 | 504.2 | 20 | 1.71 | 0.00385 | 0.00270 | | 0.0309 |
| 360 | 504.2 | 20 | 1.38 | 0.00469 | 0.00170 | | 0.0366 |
| 361 | 504.2 | 20 | 1.71 | 0.00294 | 0.00205 | | 0.0273 |
| 362 | 625.3 | 20 | 1.68 | 0.00504 | 0.00327 | | |
| 363 | 597.2 | 20 | 2.72 | 0.00415 | 0.00121 | | 3.7800 |
| 364 | 631.2 | 25 | 1.89 | 0.00077 | 0.00160 | | 0.0952 |
| 365 | 603.1 | 25 | 1.39 | 0.00041 | 0.00055 | | 7.5600 |
| 366 | 574.2 | 20 | 2.7 | 0.00107 | 0.00099 | | 0.3120 |
| 367 | 529.2 | 20 | 2.42 | 0.00083 | 0.00050 | | 0.0352 |
| 368 | 539.1 | 25 | 0.87 | 0.00072 | 0.00051 | | 0.0560 |
| 369 | 476.2 | 20 | 2.53 | 0.00113 | 0.00125 | | 0.0093 |
| 370 | 490.1 | 28 | 0.84 | 0.00137 | 0.00137 | | 0.0402 |

TABLE 2-continued

| Ex # | LCMS (ESI) m/z [M + H]+ | LCMS Method | LCMS RT (Min) | JAK1 Ki (uM) | JAK2 Ki (uM) | IL13-pSTAT6 EC50_TF-1 (uM) | IL13-pSTAT6 EC50 (uM)_BEAS-2B |
|---|---|---|---|---|---|---|---|
| 371 | 490.1 | 28 | 0.86 | 0.00114 | 0.00119 | | 0.0146 |
| 372 | 605.2 | 20 | 1.61 | 0.00025 | 0.00051 | | 0.0197 |
| 373 | 573.2 | 20 | 1.8 | 0.00070 | 0.00124 | | 0.0342 |
| 374 | 585.2 | 20 | 2.4 | 0.00045 | 0.00088 | | 0.0295 |
| 375 | 559.2 | 25 | 1.63 | 0.00075 | 0.00154 | | 0.0716 |
| 376 | 559.2 | 20 | 2.23 | 0.00066 | 0.00103 | | 0.0325 |
| 377 | 573.2 | 25 | 0.97 | 0.00056 | 0.00130 | | 0.0528 |
| 378 | 573.2 | 20 | 2.51 | 0.00093 | 0.00160 | | 0.0874 |
| 379 | 602.2 | 25 | 0.89 | 0.00086 | 0.00233 | | 0.0755 |
| 380 | 612.1 | 25 | 1.7 | 0.00030 | 0.00068 | | 0.0481 |
| 381 | 546.1 | 28 | 0.82 | 0.00107 | 0.00055 | | 0.0298 |
| 382 | 629.1 | 28 | 0.81 | 0.00034 | 0.00075 | | 0.0257 |
| 383 | 602.2 | 20 | 3.66 | 0.00039 | 0.00066 | | 0.2770 |
| 384 | 552.1 | 25 | 1.16 | 0.00030 | 0.00023 | | 0.1390 |
| 385 | 552.1 | 25 | 1.15 | 0.00045 | 0.00030 | | 0.1630 |
| 386 | 520.1 | 28 | 0.85 | 0.00106 | 0.00056 | | 0.0297 |
| 387 | 520.1 | 28 | 0.82 | 0.00124 | 0.00046 | | 0.0107 |
| 388 | 685.2 | 25 | 1.05 | 0.00051 | 0.00242 | | 0.0241 |
| 389 | 699.2 | 28 | 0.95 | 0.00040 | 0.00216 | | 0.0175 |
| 390 | 560.2 | 28 | 0.94 | 0.00128 | 0.00084 | | 0.0424 |
| 391 | 659.2 | 28 | 0.9 | 0.00091 | 0.00249 | | 0.0206 |
| 392 | 615 | 28 | 0.99 | 0.00040 | 0.00077 | | 0.0261 |
| 393 | 615.2 | 20 | 1.84 | 0.00038 | 0.00089 | | 0.0115 |
| 394 | 544 | 23 | 2.37 | 0.00087 | 0.00061 | | 0.0311 |
| 395 | 557.1 | 23 | 1.76 | 0.00129 | 0.00096 | | 0.0224 |
| 396 | 580.1 | 20 | 2.76 | 0.00329 | 0.00129 | | 0.0382 |
| 397 | 617.2 | 20 | 2.68 | 0.00028 | 0.00077 | | 0.0270 |
| 398 | 656.4 | 20 | 1.45 | 0.00050 | 0.00145 | | 0.0183 |
| 399 | 518.1 | 23 | 1.46 | 0.00090 | 0.00039 | | 0.0232 |
| 400 | 644.3 | 20 | 2.38 | 0.00058 | 0.00173 | | 0.0309 |
| 401 | 630.2 | 20 | 2.34 | 0.00075 | 0.00203 | | 0.1520 |
| 402 | 518.2 | 20 | 1.45 | 0.00083 | 0.00040 | | 0.0187 |
| 403 | 548.2 | 35 | 2.28 | 0.00146 | 0.00071 | | 0.0283 |
| 404 | 506.1 | 24 | 2.41 | 0.00168 | 0.00061 | | 0.0078 |
| 405 | 546.2 | 24 | 1.96 | 0.00173 | 0.00068 | | 0.0257 |
| 406 | 584.3 | 20 | 2.32 | 0.00046 | 0.00099 | | 0.0333 |
| 407 | 628.3 | 20 | 1.41 | 0.00036 | 0.00071 | | 0.1720 |
| 408 | 642.2 | 30 | 0.93 | 0.00059 | 0.00229 | | 0.1210 |
| 409 | 624.1 | 32 | 1.65 | 0.00036 | 0.00089 | | 0.0196 |
| 410 | 629.3 | 20 | 1.46 | 0.00060 | 0.00125 | | 0.0183 |
| 411 | 504.2 | 24 | 2.57 | 0.00170 | 0.00043 | | 0.0228 |
| 412 | 546.2 | 24 | 1.68 | 0.00170 | 0.00096 | | 0.0395 |
| 413 | 626.4 | 33 | 1.24 | 0.00025 | 0.00074 | | 0.0209 |
| 414 | 638.3 | 29 | 1.56 | 0.00030 | 0.00076 | | 0.0182 |
| 415 | 528.1 | 32 | 2.21 | 0.00299 | 0.00209 | | 0.0460 |
| 416 | 642.5 | 31 | 1.35 | 0.00041 | 0.00084 | | 0.0316 |
| 417 | 531.2 | 35 | 2.3 | 0.00291 | 0.00137 | | 0.0934 |
| 418 | 544.2 | 24 | 2.36 | 0.00243 | 0.00080 | | 0.0609 |
| 419 | 612.4 | 33 | 1.23 | 0.00041 | 0.00106 | | 0.0313 |
| 420 | 595.4 | 33 | 1.43 | 0.00057 | 0.00081 | | 0.0301 |
| 421 | 581.4 | 34 | 2.44 | 0.00065 | 0.00089 | | 0.0498 |
| 422 | 528.2 | 20 | 1.59 | 0.00089 | 0.00177 | | 0.0610 |
| 423 | 684.4 | 19 | 1.86 | 0.00073 | 0.00279 | | 0.0312 |
| 424 | 670.3 | 20 | 1.5 | 0.00112 | 0.00344 | | 0.0987 |
| 425 | 670.4 | 20 | 2.51 | 0.00060 | 0.00164 | | 0.0411 |
| 426 | 656.3 | 20 | 1.46 | 0.00053 | 0.00125 | | 0.0394 |
| 427 | 713.3 | 25 | 0.95 | 0.00042 | 0.00125 | | 0.0224 |
| 428 | 713.3 | 25 | 0.9 | 0.00079 | 0.00251 | | 0.0453 |
| 429 | 615.2 | 20 | 1.45 | 0.00048 | 0.00099 | | 0.0074 |
| 430 | 571.2 | 25 | 1.11 | 0.00051 | 0.00077 | | 0.0058 |
| 431 | 624.2 | 24 | 1.76 | 0.00029 | 0.00074 | | 0.0029 |
| 432 | 629.2 | 20 | 2.68 | 0.00040 | 0.00120 | | 0.0326 |
| 433 | 645.2 | 24 | 1.58 | 0.00042 | 0.00116 | | 0.0360 |
| 434 | 631.2 | 20 | 1.52 | 0.00031 | 0.00067 | | 0.0187 |
| 435 | 652.2 | 24 | 2.9 | 0.00034 | 0.00098 | | 0.0074 |
| 436 | 610.1 | 24 | 2.73 | 0.00025 | 0.00075 | | 0.0103 |
| 437 | 601.2 | 24 | 1.46 | 0.00038 | 0.00088 | | 0.0126 |
| 438 | 659.1 | 25 | 1.06 | 0.00059 | 0.00192 | | 0.0150 |
| 439 | 571.2 | 20 | 1.49 | 0.00071 | 0.00078 | | 0.0353 |
| 440 | 585.2 | 24 | 1.59 | 0.00046 | 0.00054 | | 0.0068 |
| 441 | 629.4 | 20 | 2.54 | 0.00052 | 0.00148 | | 0.0084 |
| 442 | 629.2 | 20 | 2.68 | 0.00033 | 0.00084 | | 0.0194 |
| 443 | 647.1 | 24 | 1.34 | 0.00023 | 0.00063 | | 0.0663 |
| 444 | 557.2 | 20 | 1.45 | 0.00076 | 0.00089 | | 0.0540 |

TABLE 2-continued

| Ex # | LCMS (ESI) m/z [M + H]+ | LCMS Method | LCMS RT (Min) | JAK1 Ki (uM) | JAK2 Ki (uM) | IL13-pSTAT6 EC50_TF-1 (uM) | IL13-pSTAT6 EC50 (uM)_BEAS-2B |
|---|---|---|---|---|---|---|---|
| 445 | 628.4 | 20 | 1.43 | 0.00035 | 0.00087 | | 0.3000 |
| 446 | 610.3 | 20 | 2.46 | 0.00045 | 0.00130 | | 0.0121 |
| 447 | 627.2 | 25 | 0.96 | 0.00049 | 0.00125 | | 0.0161 |
| 448 | 642.2 | 24 | 1.43 | 0.00036 | 0.00088 | | 0.0425 |
| 449 | 629.3 | 20 | 1.46 | 0.00038 | 0.00110 | | 0.0136 |
| 450 | 627.2 | 25 | 0.97 | 0.00037 | 0.00097 | | 0.0126 |
| 451 | 629.3 | 20 | 2.29 | 0.00045 | 0.00156 | | 0.0201 |
| 452 | 569.2 | 36 | 2.59 | 0.00071 | 0.00065 | | 0.0809 |
| 453 | 673.3 | 25 | 1.14 | 0.00041 | 0.00130 | | 0.0304 |
| 454 | 583.2 | 24 | 1.58 | 0.00040 | 0.00023 | | 0.0235 |
| 455 | 639.2 | 24 | 2.47 | 0.00030 | 0.00015 | | 0.0210 |
| 456 | 612.2 | 20 | 1.49 | 0.00049 | 0.00111 | | 0.0410 |
| 457 | 653.3 | 20 | 1.74 | 0.00045 | 0.00026 | | 0.0156 |
| 458 | 629.2 | 20 | 2.53 | 0.00047 | 0.00090 | | 0.0081 |
| 459 | 615.2 | 20 | 1.46 | 0.00030 | 0.00072 | | 0.0075 |
| 460 | 660.2 | 24 | 1.63 | 0.00039 | 0.00110 | | 0.0068 |
| 461 | 598.2 | 20 | 2.34 | 0.00040 | 0.00084 | | 0.0117 |
| 462 | 638.1 | 23 | 2.55 | 0.00038 | 0.00086 | | 0.0108 |
| 463 | 623.1 | 25 | 1.28 | 0.00031 | 0.00070 | | 0.0070 |
| 464 | 626.3 | 20 | 2.41 | 0.00049 | 0.00141 | | 0.0095 |
| 465 | 640.2 | 25 | 2.94 | 0.00024 | 0.00056 | | 0.0114 |
| 466 | 626.2 | 24 | 1.85 | 0.00027 | 0.00074 | | 0.0140 |
| 467 | 639.2 | 37 | 3.15 | 0.00024 | 0.00064 | | 0.0075 |
| 468 | 624.2 | 38 | 2.8 | 0.00036 | 0.00092 | | 0.0060 |

Blank: Not determined

Clearance Assay

In certain instances high systemic clearance of a drug substance may be of benefit. For example, in the treatment of pulmonary diseases it may be beneficial to have high drug concentrations in the lung, with lower concentrations in the bloodstream or peripheral organs. In such cases, it may be advantageous to administer a drug substance with high systemic clearance via the inhaled delivery route. This approach may maximize pharmacologic activity of the drug substance in the lung while minimizing the possibility of on-target toxicity elsewhere in the body. The functional groups appended to the 5-chloro-2-difluoromethoxyphenyl pyrazolopyrimidine scaffold affect systemic clearance. For example, compound i exhibits a mouse intravenous (IV) clearance value of 5.3 mL/min/kg, or 6% of mouse liver blood flow. Representative mouse IV clearance values for examples in the present invention are shown in Table 3.

Compound i

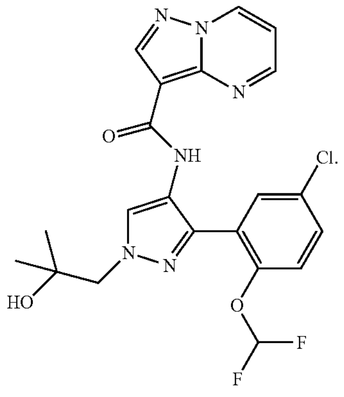

TABLE 3

Mouse IV clearance values for compounds in the present invention.

| Ex # | IV Mouse CL, mL/min/kg | IV Mouse CL, % of liver blood flow |
|---|---|---|
| 2 | 580 | >100% |
| 3 | 216 | >100% |
| 59 | 39 | 43% |
| 63 | 139 | >100% |
| 67 | 205 | >100% |
| 85 | 55 | 61% |
| 98 | 178 | >100% |
| 99 | 234 | >100% |
| 102 | 140 | >100% |
| 134 | 222 | >100% |
| 198 | 326 | >100% |
| 205 | 46 | 51% |
| 209 | 64 | 71% |
| 233 | 153 | >100% |
| 278 | 133 | >100% |
| 284 | 219 | >100% |
| 294 | 95 | >100% |
| 313 | 51 | 57% |
| 338 | >200 | >100% |
| 348 | 143 | >100% |
| 372 | 93 | >100% |
| 397 | 141 | >100% |
| 466 | 72 | 80% |
| 468 | 140 | >100% |

Female BALB/c mice were obtained from Charles River Labs (Hollister, Calif. USA). Twelve animals were given a single IV dose of 1 mg/kg of compounds via the tail vein. A representative dose solution was prepared as follows: the compound was dissolved in a mixture of 5% dimethylsulfoxide (DMSO), 35% polyethylene glycol (PEG 400), and 60% water (v/v/v), respectively, and administered at a dosing volume of 5 mL/kg. Mice weighed approximately 20-25 g at the start of the study. After intravenous administration of compounds, each animal was bled twice via retro-orbital and cardiac puncture. PK time points were collected at 2 min, 5 min, 15 min, 30 min, 1 hr, 2 hr, 4 hr, and 8 hr post-dose. Plasma samples were stored at approximately −80° C. until thawed for LC-MS/MS analysis. PK data analysis was performed on mean plasma concentration-time data and PK parameters were determined by non compartmental methods using WinNonlin® Enterprise, version 5.2.1 (Pharsight Corporation; Mountain View, Calif.).

What is claimed is:

1. A compound of Formula (00A):

(00A)

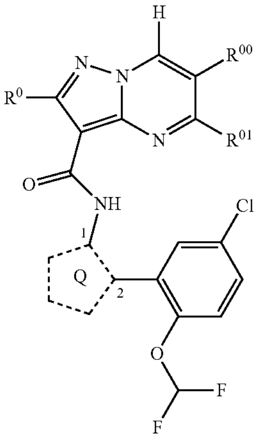

or a stereoisomer or salt thereof, wherein: $R^{00}$ is H or $CH_3$; $R^{01}$ is H or $NH_2$; $R^0$ is H or $NH_2$; and Ring Q is (ii):

(ii)

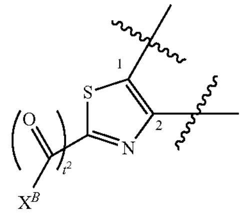

wherein: $t^2$ is 0 or 1; $X^B$ is selected from the group consisting of H, $C_1$-$C_6$ alkyl, $C_2$-$C_4$ alkenyl, —$NR^aR^b$, $C_2$-$C_5$ alkynyl, 3-6-membered cycloalkyl, 6-10 membered aryl, 3-11 membered heterocycloalkyl, 5-6 membered heterocycloalkenyl, and 5-10 membered heteroaryl; wherein when $X^B$ is $C_1$-$C_6$ alkyl, $C_2$-$C_4$ alkenyl, $C_2$-$C_5$ alkynyl, 3-6-membered cycloalkyl, 6-10 membered aryl, 3-11 membered heterocycloalkyl, 5-6 membered heterocycloalkenyl, or 5-10 membered heteroaryl, $X^B$ is optionally substituted by $Y^1$, wherein $Y^1$ is selected from:

(a) $C_1$-$C_6$ alkyl optionally substituted by $T^1$, wherein $T^1$ is selected from the group consisting of OH, halo, CN, imino, 3-6 membered cycloalkyl, 3-11 membered heterocycloalkyl, 3-11 membered heterocycloalkenyl, 5-10 membered heteroaryl, —O—($C_1$-$C_6$ alkyl), C(O)OH, oxetan-3-ylmethyl, —C(O)O—($C_1$-$C_6$ alkyl), —S—($C_1$-$C_6$ alkyl), —$SO_2$—($C_1$-$C_6$ alkyl), —$NR^aR^b$, —C(O)$NR^aR^b$, -(2-oxoindolin-1-yl), —OC(O)-3-6 membered cycloalkyl, and phenyl, wherein each alkyl, cycloalkyl, heterocycloalkyl, heterocycloalkenyl, heteroaryl, and phenyl of $T^1$ is optionally substituted by OH, —C(O)O—($C_1$-$C_6$ alkyl), $C_1$-$C_6$ alkyl, halo, CN, oxo, —($C_1$-$C_6$ alkyl) $CONR^aR^b$, —$NR^aR^b$, phenyl, or —O—($C_1$-$C_6$ alkyl) optionally substituted by OH;

(b) 3-11 membered heterocycloalkyl, —($C_1$-$C_6$ alkylene)-3-11 membered heterocycloalkyl, —C(O)-3-11 membered heterocycloalkyl, —($C_1$-$C_6$ alkylene) C(O)-3-11 membered heterocycloalkyl, or —OC(O)-4-6 membered heterocycloalkyl; wherein the heterocycloalkyl is optionally substituted by OH, halo, CN, $C_1$-$C_6$ alkyl, —($C_1$-$C_6$ alkylene)-$CF_3$, oxo, —C(O)—($C_1$-$C_6$ alkyl), —C(O)O—($C_1$-$C_6$ alkyl), —C(O)O—($C_1$-$C_6$ alkylene)-phenyl, —$SO_2$—($C_1$-$C_6$ alkyl), —C(O)$NR^aR^b$, —$NR^aR^b$, ($C_1$-$C_6$ alkylene)-phenyl, or —C(O)-4-6 membered heterocycloalkyl optionally substituted by —$NR^aR^b$;

(c) $N(+)(AA)_3$, wherein each AA is independently $C_1$-$C_6$ alkyl optionally substituted by phenyl;

(d) 3-6 membered cycloalkyl optionally substituted by OH, halo, $NR^aR^b$, or CN;

(e) CN, halo, or oxo;

(f) —C(O)—($C_1$-$C_6$ alkyl), —C(O)OH, —C(O)O—($C_1$-$C_6$ alkylene)-phenyl, —$SO_2$—($C_1$-$C_6$ alkyl), —C(O)$NR^aR^b$, or —C(O)-4-6 membered heterocycloalkyl optionally substituted by —($C_1$-$C_6$ alkyl) or —$NR^aR^b$, or —C(O)O—($C_1$-$C_6$ alkyl) optionally substituted by OH, $NR^aR^b$, or 3-11 membered heterocycloalkyl wherein said heterocycloalkyl is optionally substituted by $C_1$-$C_6$ alkyl;

(g) OH, —O-phenyl, or —O—($C_1$-$C_6$ alkyl), wherein the alkyl is optionally substituted by OH or —$NR^aR^b$;

(h) phenyl optionally substituted by OH, halo, $C_1$-$C_6$ alkyl, $CF_3$, or CN;

(i) 5-6 membered heteroaryl optionally substituted by OH, halo, $C_1$-$C_6$ alkyl, $CF_3$, CN, or 3-11 membered heterocycloalkyl optionally substituted by $C_1$-$C_6$ alkyl or 3-11 membered heterocycloalkyl;

(j) isoindolin-2-yl optionally substituted by halo;

(k) —$NR^aR^b$, and (l) —O—$CH_2$C(O)-3-11 membered heterocycloalkyl;

wherein $R^a$ and $R^b$ are independently selected from:

(a) H, (b) $C_1$-$C_6$ alkyl optionally substituted by OH, halo, CN, —C(O)OH, —C(O)O—($C_1$-$C_6$alkyl), —C(O)O-(3-11 membered heterocycloalkyl), —C(O)O—($C_1$-$C_6$ alkyl)-S—($C_1$-$C_6$ alkyl), —S—($C_1$-$C_6$ alkyl), naphthylenyl, —$NR^{az}R^{bz}$, —C(O)$NR^{az}R^{bz}$, oxo, —O—($C_1$-$C_6$ alkyl), 5-6 membered heteroaryl optionally substituted by $C_1$-$C_6$ alkyl or halo, or benzo[1,3]dioxol-2-yl, or 3-11 membered heterocycloalkenyl optionally substituted by oxo;

(c) —($C_1$-$C_6$ alkylene)-3-6 membered cycloalkyl wherein the alkylene is optionally substituted by OH, halo, or CN;

(d) —($C_1$-$C_6$ alkylene)-phenyl wherein alkylene is optionally substituted by halo and the phenyl is optionally substituted by OH, halo, $CF_3$, $C_1$-$C_6$ alkyl, —O—($C_1$-$C_6$ alkyl), —S—($C_1$-$C_6$ alkyl, or —O-phenyl;

(e) —($C_1$-$C_6$ alkylene)-4-6 membered heterocycloalkyl wherein the heterocycloalkyl is optionally substituted by halo, oxo, or $C_1$-$C_6$ alkyl;

(f) —($C_1$-$C_6$ alkylene)-O-phenyl wherein the phenyl is optionally substituted by halo, $C_1$-$C_6$ alkyl, or —O-phenyl;

(g) —($C_1$-$C_6$ alkyl)3-6 membered cycloalkyl optionally substituted by OH, halo, CN, or $C_1$-$C_6$ alkyl optionally substituted by OH or CN;

(h) $C_2$-$C_5$ alkenyl;

(i) 4-6 membered heterocycloalkyl optionally substituted by halo, (j) —($C_1$-$C_6$ alkylene)-3-6 membered cycloalkyl substituted by hydroxymethyl, (k) phenyl, (l) —C(O)($C_1$-$C_6$ alkyl), (m) —C(O)O($C_1$-$C_6$ alkyl), (n) —C(O)O(3-6 membered cycloalkyl), and (o) —C(O)-phenyl, wherein $R^{az}$ and $R^{bz}$ are each independently selected from (a) H, (b) $C_1$-$C_6$ alkyl optionally substituted by OH, halo, CN, —C(O)OH, —C(O)O—($C_1$-$C_6$alkyl), —C(O)O-(3-11 membered heterocycloalkyl), —C(O)O—($C_1$-$C_6$ alkyl)-S—($C_1$-$C_6$ alkyl), —S—($C_1$-$C_6$ alkyl), naphthylenyl, -oxo, —O—($C_1$-$C_6$ alkyl), 5-6 membered heteroaryl optionally substituted by $C_1$-$C_6$ alkyl or halo, or benzo[1,3]dioxol-2-yl, or 3-11 membered heterocycloalkenyl optionally substituted by oxo;

(c) —($C_1$-$C_6$ alkylene)-3-6 membered cycloalkyl wherein the alkylene is optionally substituted by OH, halo, or CN;

(d) —($C_1$-$C_6$ alkylene)-phenyl wherein alkylene is optionally substituted by halo and the phenyl is optionally substituted by OH, halo, $CF_3$, $C_1$-$C_6$ alkyl, —O—($C_1$-$C_6$ alkyl), —S—($C_1$-$C_6$ alkyl, or —O-phenyl;

(e) —($C_1$-$C_6$ alkylene)-4-6 membered heterocycloalkyl wherein the heterocycloalkyl is optionally substituted by halo, oxo, or $C_1$-$C_6$ alkyl;

(f) —($C_1$-$C_6$ alkylene)-O-phenyl wherein the phenyl is optionally substituted by halo, $C_1$-$C_6$ alkyl, or —O-phenyl;

(g) —($C_1$-$C_6$ alkyl)3-6 membered cycloalkyl optionally substituted by OH, halo, CN, or $C_1$-$C_6$ alkyl optionally substituted by OH or CN;

(h) $C_2$-$C_5$ alkenyl;

(i) 4-6 membered heterocycloalkyl optionally substituted by halo, (j) —($C_1$-$C_6$ alkylene)-3-6 membered cycloalkyl substituted by hydroxymethyl, (k) phenyl, (l) —C(O)($C_1$-$C_6$ alkyl), (m) —C(O)O($C_1$-$C_6$ alkyl), (n) —C(O)O(3-6 membered cycloalkyl), and (o) —C(O)-phenyl.

2. The compound of claim 1, further defined as a compound of Formula (IV):

(IV)

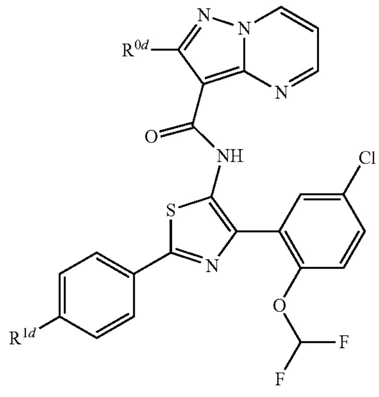

wherein:

$R^{0d}$ is H or $NH_2$;

$R^{1d}$ is 3-11 membered heterocycloalkyl or —C(O)-3-11 membered heterocycloalkyl, wherein the heterocycloalkyl is optionally substituted $C_1$-$C_6$ alkyl, $CF_3$, or fluoro, or $R^{1d}$ is —($C_1$-$C_6$ alkylene)-$NR^vR^w$, wherein $R^v$ and $R^w$ are independently H or $C_1$-$C_6$ alkyl optionally substituted by halo.

3. The compound of claim 1, further defined as a compound of Formula (V):

(V)

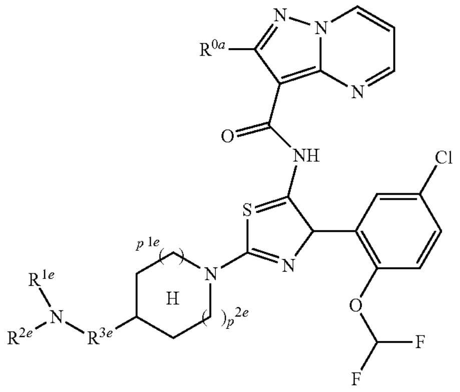

wherein:

$R^{0e}$ is H or $NH_2$;

$R^{1e}$ is selected from the group consisting of a. H, b. $C_1$-$C_6$ alkyl optionally substituted by halo, CN, or phenyl, c. —($C_1$-$C_6$ alkylene)-3-6 membered cycloalkyl wherein the cycloalkyl is optionally substituted by CN, d. —($C_1$-$C_6$ alkylene)-4-6 membered heterocycloalkyl wherein the heterocycloalkyl is optionally substituted by $C_1$-$C_6$ alkyl;

$R^{2e}$ is H or $C_1$-$C_6$ alkyl;

or $R^{1e}$ and $R^{2e}$ together form a 3-11 membered heterocycloalkyl optionally substituted by halo or —$NR^vR^w$, wherein $R^v$ and $R^w$ are independently H or $C_1$-$C_6$ alkyl optionally substituted by halo;

$R^{3e}$ is a bond or $C_1$-$C_6$ alkylene optionally substituted by oxo; and

Ring H is a 3-7 membered heterocycloalkyl wherein $p^{1e}$ is 0, 1 or 2 and $p^{2e}$ is 0, 1 or 2.

4. The compound of claim 1, further defined as a compound of Formula (VI):

(VI)

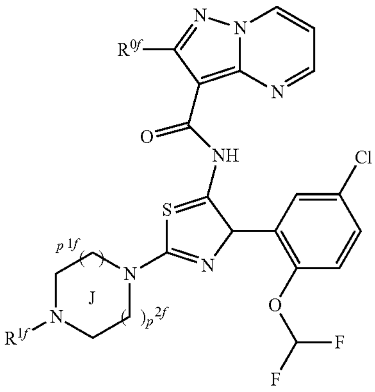

wherein:

$R^{0f}$ is H or $NH_2$;

$R^{1f}$ is selected from the group consisting of $C_1$-$C_6$ alkyl optionally substituted by halo, 3-6 membered cycloalkyl, or phenyl; and Ring J is a 6-7 membered heterocycloalkyl wherein $p^{1f}$ is 1 or 2 and $p^{2f}$ is 1 or 2.

5. The compound of claim 1, further defined as a compound of Formula (VII):

(VII)

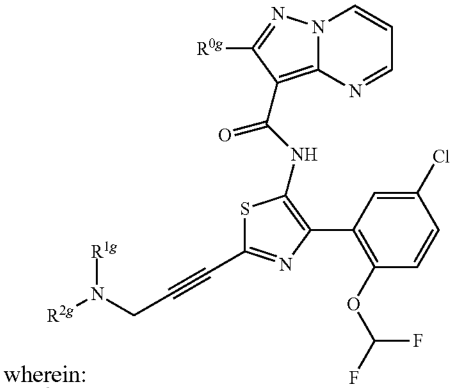

wherein:

$R^{0g}$ is H or $NH_2$;

$R^{1g}$ is selected from the group consisting of $C_1$-$C_6$ alkyl;

$R^{2g}$ is selected from the group consisting of $C_1$-$C_6$ alkyl.

6. The compound of claim 1, further defined as a compound of Formula (X):

(X)

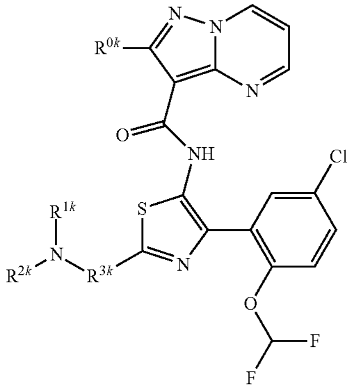

wherein:

$R^{0k}$ is H or $NH_2$;

$R^{1k}$ is selected from the group consisting of a. H, b. $C_1$-$C_6$ alkyl optionally substituted by halo, CN, or phenyl, c. —($C_1$-$C_6$ alkylene)-3-6 membered cycloalkyl wherein the cycloalkyl is optionally substituted by CN, d. —($C_1$-$C_6$ alkylene)-4-6 membered heterocycloalkyl wherein the heterocycloalkyl is optionally substituted by $C_1$-$C_6$ alkyl;

$R^{2k}$ is selected from the group consisting of H and $C_1$-$C_6$ alkyl;

or $R^{1k}$ and $R^{2k}$ together form a 3-11 membered heterocycloalkyl optionally substituted by halo; $C_1$-$C_6$ alkyl optionally substituted by OH; or —$NR^vR^w$, wherein $R^v$ and $R^w$ are independently H or $C_1$-$C_6$ alkyl optionally substituted by halo; and $R^{3k}$ is a bond, methylene, or —C(═O)—.

7. The compound of claim 1, wherein $X^B$ is selected from the group consisting of 3-6-membered cycloalkyl, 6-10 membered aryl, 5-6 membered heterocycloalkenyl, and 5-10 membered heteroaryl, wherein $X^B$ is optionally substituted by $Y^1$.

8. The compound of claim 1, wherein either $X^B$ is a 3-11 membered heterocycloalkyl optionally substituted by $Y^1$.

9. The compound of claim 1, wherein $t^2$ is 0.

10. The compound of claim 1, wherein $t^2$ is 1.

11. The compound of claim 1, wherein $R^0$, $R^{00}$ and $R^{01}$ are each H.

12. The compound of claim 1, wherein $R^0$ is $NH_2$.

13. The compound of claim 1, selected from the group consisting of:

N-[4-[5-chloro-2-(difluoromethoxy)phenyl]-2-[4-(dimethylamino)-1-piperidyl]thiazol-5-yl]pyrazolo[1,5-a]pyrimidine-3-carboxamide;

N-[4-[5-chloro-2-(difluoromethoxy)phenyl]-2-[4-[2-cyanoethyl(methyl)amino]-1-piperidyl]thiazol-5-yl]pyrazolo[1,5-a]pyrimidine-3-carboxamide;

N-[4-[5-chloro-2-(difluoromethoxy)phenyl]-2-[4-[(dimethylamino)methyl]-1-piperidyl]thiazol-5-yl]pyrazolo[1,5-a]pyrimidine-3-carboxamide;

N-[4-[5-chloro-2-(difluoromethoxy)phenyl]-2-[4[2-(dimethylamino)ethyl]-1-piperidyl]thiazol-5-yl]pyrazolo[1,5-a]pyrimidine-3-carboxamide;

N-[4-[5-chloro-2-(difluoromethoxy)phenyl]-2-[4-[methyl(2-phenylethyl)amino]-1-piperidyl]thiazol-5-yl]pyrazolo[1,5-a]pyrimidine-3-carboxamide;

N-[2-[4-[(4-amino-4-oxo-butyl)-methyl-amino]-1-piperidyl]-4-[5-chloro-2-(difluoromethoxy)phenyl]thiazol-5-yl]pyrazolo[1,5-a]pyrimidine-3-carboxamide;

N-[4-[5-chloro-2-(difluoromethoxy)phenyl]-2-[4-(3-fluoroazetidin-1-yl)-1-piperidyl]thiazol-5-yl]pyrazolo[1,5-a]pyrimidine-3-carboxamide;

N-[4-[5-chloro-2-(difluoromethoxy)phenyl]-2-[3-(1-piperidyl)azetidin-1-yl]thiazol-5-yl]pyrazolo[1,5-a]pyrimidine-3-carboxamide;

N-[4-[5-chloro-2-(difluoromethoxy)phenyl]-2-[4-(3,3-difluoroazetidin-1-yl)-1-piperidyl]thiazol-5-yl]pyrazolo[1,5-a]pyrimidine-3-carboxamide;

N-[4-[5-chloro-2-(difluoromethoxy)phenyl]-2-[4-[4-(dimethylamino)piperidine-1-carbonyl]-1-piperidyl]thiazol-5-yl]pyrazolo[1,5-a]pyrimidine-3-carboxamide;

N-[4-[5-chloro-2-(difluoromethoxy)phenyl]-2-[4-[methyl(2,2,2-trifluoroethyl)amino]-1-piperidyl]thiazol-5-yl]pyrazolo[1,5-a]pyrimidine-3-carboxamide;

N-[2-[4-[butyl(methyl)amino]-1-piperidyl]-4-[5-chloro-2-(difluoromethoxy)phenyl]thiazol-5-yl]pyrazolo[1,5-a]pyrimidine-3-carboxamide;

N-[4-[5-chloro-2-(difluoromethoxy)phenyl]-2-[4-[methyl-[(3-methyloxetan-3-yl)methyl]amino]-1-piperidyl]thiazol-5-yl]pyrazolo[1,5-a]pyrimidine-3-carboxamide;

N-[2-[4-[benzyl(methyl)amino]-1-piperidyl]-4-[5-chloro-2-(difluoromethoxy)phenyl]thiazol-5-yl]pyrazolo[1,5-a]pyrimidine-3-carboxamide;

N-[4-[5-chloro-2-(difluoromethoxy)phenyl]-2-[4-[4-[methyl(2,2,2-trifluoroethyl)amino]piperidine-1-carbonyl]-1-piperidyl]thiazol-5-yl]pyrazolo[1,5-a]pyrimidine-3-carboxamide;

N-[4-[5-chloro-2-(difluoromethoxy)phenyl]-2-[4-(1-cyanocyclohexyl)methyl-methyl-aminol-1-piperidyl]thiazol-5-yl]pyrazolo[1,5-a]pyrimidine-3-carboxamide;

N-[4-[5-chloro-2-(difluoromethoxy)phenyl]-2-[4-[4-[(1-cyanocyclohexyl)methyl-methyl-amino]piperidine-1-carbonyl]-1-piperidyl]thiazol-5-yl]pyrazolo[1,5-a]pyrimidine-3-carboxamide;

N-[4-[5-chloro-2-(difluoromethoxy)phenyl]-2-(4-methylpiperazin-1-yl)thiazol-5-yl]pyrazolo[1,5-a]pyrimidine-3-carboxamide;

N-[4-[5-chloro-2-(difluoromethoxy)phenyl]-2-[4-(2-phenylethyl)piperazin-1-yl]thiazol-5-yl]pyrazolo[1,5-a]pyrimidine-3-carboxamide;

N-[4-[5-chloro-2-(difluoromethoxy)phenyl]-2-[4-(cyclopropylmethyl)piperazin-1-yl]thiazol-5-yl]pyrazolo[1,5-a]pyrimidine-3-carboxamide;

N-[4-[5-chloro-2-(difluoromethoxy)phenyl]-2-[4-(2,2,2-trifluoroethyl)piperazin-1-yl]thiazol-5-yl]pyrazolo[1,5-a]pyrimidine-3-carboxamide;

N-[4-[5-chloro-2-(difluoromethoxy)phenyl]-2-[3-(dimethylamino)prop-1-ynyl]thiazol-5-yl]pyrazolo[1,5-a]pyrimidine-3-carboxamide;

N-[2-[3-[butyl(methyl)amino]prop-1-ynyl]-4-[5-chloro-2-(difluoromethoxy)phenyl]thiazol-5-yl]pyrazolo[1,5-a]pyrimidine-3-carboxamide;

N-[4-[5-chloro-2-(difluoromethoxy)phenyl]-2-[4-[4-(dimethylamino)piperidine-1-carbonyl]phenyl]thiazol-5-yl]pyrazolo[1,5-a]pyrimidine-3-carboxamide;

N-[4-[5-chloro-2-(difluoromethoxy)phenyl]-2-(4-pyridyl)thiazol-5-yl]pyrazolo[1,5-a]pyrimidine-3-carboxamide;

N-[4-[5-chloro-2-(difluoromethoxy)phenyl]-2-[4-[(dimethylamino)methyl]phenyl]thiazol-5-yl]pyrazolo[1,5-a]pyrimidine-3-carboxamide;

N-[4-[5-chloro-2-(difluoromethoxy)phenyl]-2-[4-[(3-fluoroazetidin-1-yl)methyl]phenyl]thiazol-5-yl]pyrazolo[1,5-a]pyrimidine-3-carboxamide;

N-[4-[5-chloro-2-(difluoromethoxy)phenyl]-2-[4-[(3,3-difluoroazetidin-1-yl)methyl]phenyl]thiazol-5-yl]pyrazolo[1,5-a]pyrimidine-3-carboxamide;

N-[4-[5-chloro-2-(difluoromethoxy)phenyl]-2-[4-(4-methylpiperazin-1-yl)phenyl]thiazol-5-yl]pyrazolo[1,5-a]pyrimidine-3-carboxamide;

N-[4-[5-chloro-2-(difluoromethoxy)phenyl]-2-[4-(4-methylpiperazine-1-carbonyl)phenyl]thiazol-5-yl]pyrazolo[1,5-a]pyrimidine-3-carboxamide;

N-[4-[5-chloro-2-(difluoromethoxy)phenyl]-2-[[4-(dimethylamino)-1-piperidyl]methyl]thiazol-5-yl]pyrazolo[1,5-a]pyrimidine-3-carboxamide;

N-[4-[5-chloro-2-(difluoromethoxy)phenyl]-2-[[methyl(2-phenylethyl)amino]methyl]thiazol-5-yl]pyrazolo[1,5-a]pyrimidine-3-carboxamide;

N-[2-[[(3aR,6aS)-2-methyl-1,3,3a,4,6,6a-hexahydropyrrolo[3,4-c]pyrrol-5-yl]methyl]-4-[5-chloro-2-(difluoromethoxy)phenyl]thiazol-5-yl]pyrazolo[1,5-a]pyrimidine-3-carboxamide;

N-[4-[5-chloro-2-(difluoromethoxy)phenyl]-2-(1-piperidylmethyl)thiazol-5-yl]pyrazolo[1,5-a]pyrimidine-3-carboxamide;

N-[2-[(3aR,6aS)-2-methyl-1,3,3a,4,6,6a-hexahydropyrrolo[3,4-c]pyrrole-5-carbonyl]-4-[5-chloro-2-(difluoromethoxy)phenyl]thiazol-5-yl]pyrazolo[1,5-a]pyrimidine-3-carboxamide; and N-[4-[5-chloro-2-(difluoromethoxy)phenyl]-2-[4-(dimethylamino)piperidine-1-carbonyl]thiazol-5-yl]pyrazolo[1,5-a]pyrimidine-3-carboxamide.

14. A pharmaceutical composition comprising a compound of claim 1 and a pharmaceutically acceptable carrier, diluent or excipient.

15. A method of treating a disease or condition responsive to the inhibition of a Janus kinase activity in a patient, wherein the disease or condition is asthma, comprising administering to the patient a therapeutically effective amount of a compound of claim 1.

16. The method of claim 15, wherein the Janus kinase is JAK1.

17. A compound selected from the group consisting of:

N-[4-[5-chloro-2-(difluoromethoxy)phenyl]-2-[4-[2-cyanoethyl(methyl)amino]-1-piperidyl]thiazol-5-yl]pyrazolo[1,5-a]pyrimidine-3-carboxamide;

N-[4-[5-chloro-2-(difluoromethoxy)phenyl]-2-[4-[methyl(2-phenylethyl)amino]-1-piperidyl]thiazol-5-yl]pyrazolo[1,5-a]pyrimidine-3-carboxamide;

N-[2-[4-[(4-amino-4-oxo-butyl)-methyl-amino]-1-piperidyl]-4-[5-chloro-2-(difluoromethoxy)phenyl]thiazol-5-yl]pyrazolo[1,5-a]pyrimidine-3-carboxamide;

N-[4-[5-chloro-2-(difluoromethoxy)phenyl]-2-[4-(3-fluoroazetidin-1-yl)-1-piperidyl]thiazol-5-yl]pyrazolo[1,5-a]pyrimidine-3-carboxamide;

N-[4-[5-chloro-2-(difluoromethoxy)phenyl]-2-[3-(1-piperidyl)azetidin-1-yl]thiazol-5-yl]pyrazolo[1,5-a]pyrimidine-3-carboxamide;

N-[4-[5-chloro-2-(difluoromethoxy)phenyl]-2-[4-[4-[(1-cyanocyclohexyl)methyl-methyl-amino]piperidine-1-carbonyl]-1-piperidyl]thiazol-5-yl]pyrazolo[1,5-a]pyrimidine-3-carboxamide;

N-[4-[5-chloro-2-(difluoromethoxy)phenyl]-2-[4-(2-phenylethyl)piperazin-1-yl]thiazol-5-yl]pyrazolo[1,5-a]pyrimidine-3-carboxamide;

N-[4-[5-chloro-2-(difluoromethoxy)phenyl]-2-[4-[(3,3-difluoroazetidin-1-yl)methyl]phenyl]thiazol-5-yl]pyrazolo[1,5-a]pyrimidine-3-carboxamide; and N-[4-[5-chloro-2-(difluoromethoxy)phenyl]-2-[4-(dimethylamino)piperidine-1-carbonyl]thiazol-5-yl]pyrazolo[1,5-a]pyrimidine-3-carboxamide.

18. A compound, which is N-[4-[5-chloro-2-(difluoromethoxy)phenyl]-2-[4-[2-cyanoethyl(methyl)amino]-1-piperidyl]thiazol-5-yl]pyrazolo[1,5-a]pyrimidine-3-carboxamide.

19. A compound, which is N-[2-[4-[(4-amino-4-oxo-butyl)-methyl-amino]-1-piperidyl]-4-[5-chloro-2-(difluoromethoxy)phenyl]thiazol-5-yl]pyrazolo[1,5-a]pyrimidine-3-carboxamide.

20. A compound, which is N-[4-[5-chloro-2-(difluoromethoxy)phenyl]-2-[4-[4-[(1-cyanocyclohexyl)methyl-methyl-amino]piperidine-1-carbonyl]-1-piperidyl]thiazol-5-yl]pyrazolo[1,5-a]pyrimidine-3-carboxamide.

21. A compound, which is N-[4-[5-chloro-2-(difluoromethoxy)phenyl]-2-[4-[(3,3-difluoroazetidin-1-yl) methyl]phenyl]thiazol-5-yl]pyrazolo[1,5-a]pyrimidine-3-carboxamide.

* * * * *

UNITED STATES PATENT AND TRADEMARK OFFICE

CERTIFICATE OF CORRECTION

PATENT NO. : 9,604,984 B2
APPLICATION NO. : 15/139164
DATED : March 28, 2017
INVENTOR(S) : Mark Edward Zak et al.

It is certified that error appears in the above-identified patent and that said Letters Patent is hereby corrected as shown below:

In the Specification

At Column 45, Line 55, delete "$R^1$" and insert therefor -- $R^{01}$ --.

At Column 45, Line 60, delete "$R^1$" and insert therefor -- $R^{01}$ --.

At Column 470, Line 24, delete "pyrazzolo" and insert therefor -- pyrazolo --.

At Column 478, Line 59, delete "2-oxo-ethyl)}" and insert therefor -- 2-oxo-ethyl} --.

At Column 479, Line 6, delete "2-oxo-ethyl)}" and insert therefor -- 2-oxo-ethyl} --.

At Column 585, Example #194, delete "587.2" and insert therefor -- 578.2 --.

Signed and Sealed this
Twenty-third Day of January, 2018

Joseph Matal

*Performing the Functions and Duties of the*
*Under Secretary of Commerce for Intellectual Property and*
*Director of the United States Patent and Trademark Office*